(12) United States Patent
Otte et al.

(10) Patent No.: US 11,214,818 B2
(45) Date of Patent: Jan. 4, 2022

(54) SEMI-BIOSYNTHETIC PRODUCTION OF FATTY ALCOHOLS AND FATTY ALDEHYDES

(71) Applicant: Provivi, Inc., Santa Monica, CA (US)

(72) Inventors: Konrad B. Otte, Stuttgart (DE); Micah Sheppard, Los Angeles, CA (US); Vu Bui, Santa Monica, CA (US); Keith M. Wampler, Santa Monica, CA (US); Effendi Leonard, Anaheim Hills, CA (US)

(73) Assignee: Provivi, Inc., Santa Monica, CA (US)

( * ) Notice: Subject to any disclaimer, the term of this patent is extended or adjusted under 35 U.S.C. 154(b) by 0 days.

(21) Appl. No.: 16/307,282

(22) PCT Filed: Jun. 6, 2017

(86) PCT No.: PCT/US2017/036136
§ 371 (c)(1),
(2) Date: Dec. 5, 2018

(87) PCT Pub. No.: WO2017/214133
PCT Pub. Date: Dec. 14, 2017

(65) Prior Publication Data
US 2019/0136272 A1    May 9, 2019

Related U.S. Application Data

(60) Provisional application No. 62/346,335, filed on Jun. 6, 2016.

(51) Int. Cl.
| C12P 7/64 | (2006.01) |
| C07C 29/136 | (2006.01) |
| C12N 1/14 | (2006.01) |
| C12N 9/02 | (2006.01) |
| C12N 15/52 | (2006.01) |
| C12R 1/645 | (2006.01) |

(52) U.S. Cl.
CPC .......... *C12P 7/6409* (2013.01); *C07C 29/136* (2013.01); *C12N 1/145* (2021.05); *C12N 9/004* (2013.01); *C12N 9/0042* (2013.01); *C12N 15/52* (2013.01); *C12P 7/649* (2013.01); *C12P 7/6436* (2013.01); *C12R 2001/645* (2021.05); *C12Y 106/02002* (2013.01); *C12Y 106/02004* (2013.01)

(58) Field of Classification Search
None
See application file for complete search history.

(56) References Cited

U.S. PATENT DOCUMENTS

| 4,231,947 A | 11/1980 | Schrock |
| 4,245,131 A | 1/1981 | Schrock |
| 4,427,595 A | 1/1984 | Schrock |
| 4,681,956 A | 7/1987 | Schrock |
| 4,727,215 A | 2/1988 | Schrock |
| 5,087,710 A | 2/1992 | Schrock et al. |
| 5,124,491 A | 6/1992 | Fleckenstein et al. |
| 5,142,073 A | 8/1992 | Schrock et al. |
| 5,146,033 A | 9/1992 | Schrock et al. |
| 6,121,473 A | 9/2000 | Schrock et al. |
| 6,291,742 B1 | 9/2001 | Somerville et al. |
| 6,346,652 B1 | 2/2002 | Schrock et al. |
| 7,169,959 B2 | 1/2007 | Heck et al. |
| 7,700,833 B2 | 4/2010 | Renz et al. |
| 8,110,093 B2 | 2/2012 | Friedman et al. |
| 8,110,670 B2 | 2/2012 | Hu et al. |
| 8,268,599 B2 | 9/2012 | Schirmer et al. |
| 8,283,143 B2 | 10/2012 | Hu et al. |
| 8,535,916 B2 | 9/2013 | Del Cardayre et al. |
| 8,658,404 B2 | 2/2014 | Schirmer et al. |

(Continued)

FOREIGN PATENT DOCUMENTS

| CN | 1656226 A | 8/2005 |
| CN | 101490241 A | 7/2009 |

(Continued)

OTHER PUBLICATIONS

Q. Zhu et al. "Metabolic engineering of Yarrowia lipolytica for industrial applications", Current Opinion in Biotechnology 36:65-72. (Year: 2015).*

S. Mausberger. "Cytochromes P450 of the Alkane-Utilising Yeast *Yarrowia lipolytica*", pp. 227-262 in G. Barth (ed.), Yarrowia lipolytica, Microbiology Monographs 25, Springer-Verlag Berlin Heidelberg 2013 (Year: 2013).*

Chandrasekhar, et al., "One pot conversion of carboxylic acids to aldehydes with DIBAL-H". Tetrahedron Letters (Feb. 19, 1998); 39(8): 909-910.

Extended European Search Report for Application No. EP 17810850.2 dated Feb. 18, 2020, 9 pages.

Kuemmel and Chapman, "The 9-hexadecenoic and 11-octadecenoic acid content of natural fats and oils". Lipids (1968); 3(4): 313-316.

(Continued)

*Primary Examiner* — Rebecca E Prouty
(74) *Attorney, Agent, or Firm* — Cooley LLP

(57) ABSTRACT

The present application relates to methods of producing one or more fatty alcohols and/or one or more fatty aldehydes from one or more unsaturated lipid moieties by combining the obtainment or production of the one or more unsaturated lipid moieties from a biological source with conversion by non-biological means of the one or more unsaturated lipid moieties to one or more fatty alcohols and/or one or more fatty aldehydes. The present application also relates to recombinant microorganisms having a biosynthesis pathway for the production of one or more unsaturated lipid moieties. The one or more fatty alcohols can further be chemically converted to one or more corresponding fatty acetates. The one or more fatty alcohols, one or more fatty aldehydes and/or one or more fatty acetates produced by the methods described herein may be one or more insect pheromones, one or more fragrances, one or more flavoring agents, or one or more polymer intermediates.

13 Claims, 37 Drawing Sheets
Specification includes a Sequence Listing.

(56) References Cited

U.S. PATENT DOCUMENTS

| | | |
|---|---|---|
| 8,987,531 B2 | 3/2015 | Grubbs et al. |
| 9,017,984 B2 | 4/2015 | Hu et al. |
| 9,068,201 B2 | 6/2015 | Hu et al. |
| 9,200,299 B2 | 12/2015 | Friedman et al. |
| 9,598,706 B2 | 3/2017 | Keasling et al. |
| 9,776,179 B2 | 10/2017 | Wampler et al. |
| 10,017,455 B2 | 7/2018 | Hu et al. |
| 10,093,950 B2 | 10/2018 | Gatter et al. |
| 10,308,962 B1 | 6/2019 | Leonard et al. |
| 2006/0078973 A1 | 4/2006 | Renz et al. |
| 2007/0282148 A1 | 12/2007 | Berlin et al. |
| 2008/0009598 A1 | 1/2008 | Herrmann et al. |
| 2008/0119678 A1 | 5/2008 | Hock et al. |
| 2008/0207911 A1 | 8/2008 | Herrmann et al. |
| 2008/0221345 A1 | 9/2008 | Winde et al. |
| 2008/0275247 A1 | 11/2008 | Kadyrov et al. |
| 2010/0087644 A1 | 4/2010 | Mauduit et al. |
| 2010/0113795 A1 | 5/2010 | Arlt et al. |
| 2010/0170826 A1 | 7/2010 | Friedman et al. |
| 2010/0174068 A1 | 7/2010 | Grela et al. |
| 2010/0199548 A1 | 8/2010 | Del Cardayre et al. |
| 2010/0235934 A1 | 9/2010 | Friedman et al. |
| 2010/0242345 A1 | 9/2010 | Keasling et al. |
| 2010/0251601 A1 | 10/2010 | Hu et al. |
| 2011/0015430 A1 | 1/2011 | Schrock et al. |
| 2011/0282068 A1 | 1/2011 | Herrmann et al. |
| 2011/0040099 A1 | 2/2011 | Kadyrov et al. |
| 2011/0065915 A1 | 3/2011 | Malcolmson et al. |
| 2011/0077421 A1 | 3/2011 | Schrock |
| 2011/0097769 A1 | 4/2011 | Del Cardayre et al. |
| 2011/0237815 A1 | 9/2011 | Hock et al. |
| 2011/0256599 A1 | 10/2011 | Hu et al. |
| 2012/0123133 A1 | 5/2012 | Berlin et al. |
| 2012/0142979 A1 | 6/2012 | Keasling et al. |
| 2012/0156249 A1 | 6/2012 | Lang et al. |
| 2012/0264983 A1 | 10/2012 | Hu et al. |
| 2012/0302710 A1 | 11/2012 | Hoveyda et al. |
| 2012/0316235 A1 | 12/2012 | Ogawa et al. |
| 2012/0323000 A1 | 12/2012 | Hoveyda et al. |
| 2013/0079515 A1 | 3/2013 | Grela et al. |
| 2013/0116434 A1 | 5/2013 | Schrock et al. |
| 2013/0144060 A1 | 6/2013 | Mauduit et al. |
| 2013/0211096 A1 | 8/2013 | Arlt et al. |
| 2013/0245339 A1 | 9/2013 | Keasling et al. |
| 2013/0261312 A1 | 10/2013 | Allen et al. |
| 2013/0274482 A1 | 10/2013 | Schrock et al. |
| 2013/0281688 A1 | 10/2013 | Di Biase et al. |
| 2013/0281706 A1 | 10/2013 | Hock et al. |
| 2013/0296511 A1 | 11/2013 | Ung et al. |
| 2014/0171607 A1 | 6/2014 | Grela et al. |
| 2014/0330018 A1 | 11/2014 | Czirok et al. |
| 2014/0378637 A1 | 12/2014 | Schrock et al. |
| 2015/0018557 A1 | 1/2015 | Nolan et al. |
| 2015/0038723 A1 | 2/2015 | Herrmann et al. |
| 2015/0045558 A1 | 2/2015 | Plenio et al. |
| 2015/0125933 A1 | 5/2015 | Groban et al. |
| 2015/0166465 A1 | 6/2015 | Chen et al. |
| 2015/0275188 A1 | 10/2015 | Hu et al. |
| 2016/0046914 A1 | 2/2016 | Hom et al. |
| 2016/0076058 A1 | 3/2016 | Friedman et al. |
| 2016/0108436 A1 | 4/2016 | Coelho et al. |
| 2016/0222419 A1 | 8/2016 | Stuart |
| 2016/0304913 A1 | 10/2016 | Gatter et al. |
| 2017/0275651 A1 | 9/2017 | Keasling et al. |
| 2017/0327799 A1 | 11/2017 | Hu et al. |
| 2018/0162916 A1 | 6/2018 | Borodina et al. |
| 2018/0371510 A1 | 12/2018 | Gatter et al. |
| 2019/0031594 A1 | 1/2019 | Hu et al. |
| 2019/0338317 A1 | 11/2019 | Leonard et al. |
| 2019/0376094 A1 | 12/2019 | Friedman et al. |
| 2020/0017890 A1 | 1/2020 | Sanchez-Riera et al. |
| 2020/0140902 A1 | 5/2020 | Sheppard et al. |

FOREIGN PATENT DOCUMENTS

| | | |
|---|---|---|
| CN | 102264910 A | 11/2011 |
| CN | 102807470 A | 12/2012 |
| CN | 104370701 A | 2/2015 |
| CN | 104781411 A | 7/2015 |
| CN | 104968672 A | 10/2015 |
| CN | 108138202 A | 6/2018 |
| JP | S61-254193 A | 11/1986 |
| JP | S64-47726 A | 2/1989 |
| JP | H10-506783 A | 7/1998 |
| WO | WO 1991/009825 A1 | 7/1991 |
| WO | WO 1992/019631 A1 | 11/1992 |
| WO | WO 2007/075427 A1 | 7/2007 |
| WO | WO 2007/136762 A2 | 11/2007 |
| WO | WO 2007/140954 A1 | 12/2007 |
| WO | WO 2008/066754 A1 | 6/2008 |
| WO | WO 2008/100251 A1 | 8/2008 |
| WO | WO 2008/113041 A2 | 9/2008 |
| WO | WO 2008/119082 A2 | 10/2008 |
| WO | WO 2008/147781 A2 | 12/2008 |
| WO | WO 2009/094201 A3 | 7/2009 |
| WO | WO 2009/126831 A1 | 10/2009 |
| WO | WO 2010/037550 A1 | 4/2010 |
| WO | WO 2010/144296 A2 | 12/2010 |
| WO | WO 2011/040963 A1 | 4/2011 |
| WO | WO 2011/069134 A3 | 6/2011 |
| WO | WO 2011/091980 A1 | 8/2011 |
| WO | WO 2011/097642 A1 | 8/2011 |
| WO | WO 2012/087964 A1 | 6/2012 |
| WO | WO 2012/167171 A3 | 12/2012 |
| WO | WO 2012/168183 A1 | 12/2012 |
| WO | WO 2013/019647 A1 | 2/2013 |
| WO | WO 2013/135776 A1 | 3/2013 |
| WO | WO 2013/070725 A1 | 5/2013 |
| WO | WO 2014/001291 A1 | 1/2014 |
| WO | WO 2014/008054 A2 | 1/2014 |
| WO | WO 2014/067767 A1 | 5/2014 |
| WO | WO 2014/134333 A1 | 9/2014 |
| WO | WO 2014/139679 A3 | 9/2014 |
| WO | WO 2014/155185 A1 | 10/2014 |
| WO | WO 2014/169014 A1 | 10/2014 |
| WO | WO 2014/172534 A1 | 10/2014 |
| WO | WO 2014/207113 A1 | 12/2014 |
| WO | WO 2015/003814 A1 | 1/2015 |
| WO | WO 2015/003815 A1 | 1/2015 |
| WO | WO 2015/042306 A1 | 3/2015 |
| WO | WO 2015/077752 A1 | 5/2015 |
| WO | WO 2015/086684 A1 | 6/2015 |
| WO | WO 2015/171057 A1 | 11/2015 |
| WO | WO 2016/099568 A1 | 6/2016 |
| WO | WO 2016/159869 A1 | 10/2016 |
| WO | WO 2016/207339 A1 | 12/2016 |
| WO | WO 2017/087846 A1 | 5/2017 |
| WO | WO 2017/214133 A2 | 12/2017 |
| WO | WO 2018/213554 A1 | 11/2018 |

OTHER PUBLICATIONS

Vickery, J.R., "The fatty acid composition of the seed oils of proteaceae: A chemotaxonomic study". Phytochemistry (Jan. 1971); 10(1): 123-130.

Wang, et al., "Comparative study of sex pheromone composition and biosynthesis in Helicoverpa armigera, H. assulta and their hybrid". Insect Biochemistry and Molecular Biology (Jun. 2005); 35(6): 575-583. Epub Mar. 16, 2005.

[Author Unknown] "NP 001037017: (11Z)-hexadec-11-enoyl-CoA conjugase [Bombyx mori]," NCBI Protein, Jul. 5, 2004 (Jul. 5, 2004), pp. 1-4. Retrieved from the Internet: <https://www.ncbi.nlm.nih.gov/protein/162809332> on Jan. 18, 2017 (Jan. 18, 2017). Entire document.

Ayciriex, et al., "YPR139c/LOA1 encodes a novel lysophosphatidic acid acyltransferase associated with lipid droplets and involved in TAG homeostasis." Mol Biol Cell (2012); 23 (2): 233-246.

Baba, et al., "Construction of Escherichia coli K-12 in-frame, single-gene knockout mutants: the Keio collection." Molecular Systems Biology (2006); 2 (1): 1-11.

(56) References Cited

OTHER PUBLICATIONS

Beisson, et al., "The acyltransferase GPAT5 is required for the synthesis of suberin in seed coat and root of *Arabidopsis*." Plant Cell (2007); 19 (1): 351-368.
Benghezal, et al., "SLC1 and SLC4 Encode Partially Redundant Acyl-Coenzyme A 1-Acylglycerol-3-phosphate O-Acyltransferases of Budding Yeast." The Journal of Biological Chemistry (2007); 282 (42): 30845-30855.
Blom, et al., "Sequence and structure-based prediction of eukaryotic protein phosphorylation sites." J. Mol. Biol. (1999); 294 (5): 1351-1362.
Bredeweg, et al., "A molecular genetic toolbox for Yarrowia lipolytica." Biotechnol Biofuels (2017); 10: 2, pp. 1-22, ePub Jan. 3, 2017.
Broun, et al., "Catalytic plasticity of fatty acid modification enzymes underlying chemical diversity of plant lipids." Science (1998); 282 (5392): 1315-1317.
Brown, et al., "Limnanthes douglasii lysophosphatidic acid acyltransferases: immunological quantification, acyl selectivity and functional replacement of the *Escherichia coli* plsC gene." Biochemical Journal (2002); 364 (3): 795-805.
Chen, et al., "The yeast acylglycerol acyltransferase LCA1 is a key component of Lands cycle for phosphatidylcholine turnover." FEBS Letters (2007); 581 (28): 5511-5516.
Choi, et al., "Regulatory elements that control transcription activation and unsaturated fatty acid-mediated repression of the *Saccharomyces cerevisiae* OLE1 gene." J Biol. Chem. (1996); 271 (7): 3581-3589.
Colby, et al., "Calculating synergistic and antagonistic responses of herbicide combinations." Weeds, (1967); 15 (1): 20-22.
Dahlqvist, et al., "Phospholipid:diacylglycerol acyltransferase: An enzyme that catalyzes the acyl-CoA-independent formation of triacylglycerol in yeast and plants." Proc Natl Acad Sci USA (2000); 97 (12): 6487-6492.
Devos and Valencia. "Practical limits of function prediction." Proteins: Structure, Function, and Genetics (2000); 41 (1): 98-107.
Ding, et al., "Analysis of the Agrotis segetum pheromone gland transcriptome in the light of sex pheromone biosynthesis" BMC Genomics (2015); 16 (711): 1-21.
EBI Accession EAY76846. Oryza sativa triacylglycerol lipase, Dec. 29, 2008 [online]. [Retrieved Sep. 21, 2008]. 3 Pages, Retrieved from the internet: <URL: https:/lwww.ebi.ac.uk/ena/data/view/EAY76846&display=text>.
Endo, et al., "Chelated ruthenium catalysts for Z-selective olefin metathesis" J Am Chem Soc. (2011); 133 (22): 8525-8527.
Extended European Search Report for Application No. EP 16867255.8 dated Feb. 5, 2019, 12 pages.
Flook, et al. "Z-Selective and Syndioselective Ring-Opening Metathesis Polymerization (ROMP) Initiated by MonoAryloxidePyrrolide (MAP) Catalysts" Macromolecules (2010) 43(18):7515-7522.
Gatter, et al., "A newly identified fatty alcohol oxidase gene is mainly responsible for the oxidation of long-chain ω-hydroxy fatty acids in Yarrowia lipolytica." FEMS Yeast Res. (Sep. 2014); 14(6): 858-872. Epub Jul. 2, 2014.
GenBank Accession AAL49962.1. Diacylglycerol acyltransferase 1 [Bos Taurus], Feb. 11, 2002 [online]. [Retrieved Sep. 21, 2002]. 2 pages, Retrieved from the internets URL: https://www.ncbi.nlm.nih.gov/protein/AAL49962.1/>.
GenBank Accession KTA99184.1 Alcohol O-acetyltransferase 2 [Candida] glabrata]. Feb. 9, 2016 [online]. [Retrieved Sep. 21, 2018]. 1 page, Retrieved from the internets URL: https://www.ncbi.nlm.nih.gov/protein/KTA99184.1/>.
GenBank Accession AKD01723.1 Alcohol dehydrogenase 12 [Helicoverpa armigera], Apr. 25, 2015 [online]. [retrieved Sep. 21, 2018]. 1 page, Retrieved from the internets URL: https://www.ncbi.nlm.nih.gov/protein/AKD01723.1/>.
Goelz and Cronan Jr., "The positional distribution of fatty acids in *Escherichia coli* phospholipids is not regulated by sn-glycerol 3-phosphate levels." J Bacteriol (1980); 144 (1): 462-464.
Gonzalez, et al., "Fatty acid-responsive control of mRNA stability. Unsaturated fatty acid-induced degradation of the *Saccharomyces* OLEI transcript" J. Biol. Chem. (1996); 271 (42): 25801-25809.
Greenway and Silbert, "Altered acyltransferase activity in *Escherichia coli* associated with mutations in acyl coenzyme A synthetase." The Journal of Biological Chemistry (1983); 258 (21): 13034-13042.
Groot, et al., "The Genetic Basis of Pheromone Evolution in Moths." Annu Rev Entomol. (2016); 61: 99-117. Epub Nov. 4, 2015.
Hagström, et al., "A moth pheromone brewery: production of (Z)-11-hexadecenol by heterologous co-expression of two biosynthetic genes from a noctuid moth in a yeast cell factory" Microb. Cell Fact. (2013); 12: 125, pp. 1-11.
Hagstrom, et al., "Semi-selective fatty acyl reductases from four heliothine moths influence the specific pheromone composition" PLoS One (2012); 7 (5): e37230: 1-11.
Halford, B. "Olefin Metathesis for Macrocycles—Organic Synthesis: Tungsten catalysts make macrocyclic olefins with Z-selectivity" Chem. Eng. News (2011); 89 (45): 11.
Hartung, et al., "Highly Z-selective and enantioselective ring-opening/cross-metathesis catalyzed by a resolved stereogenic-at-Ru complex" J Am Chem Soc. (2013); 135 (28): 10183-10185.
Heier, et al., "Identification of Yju3p as functional orthologue of mammalian monoglyceride lipase in the yeast *Saccharomyces cerevisiae*." Biochimica et Biophysica Acta (2010); 1801 (9): 1063-1071.
Herbert, et al., "Concise syntheses of insect pheromones using Z-selective cross metathesis" Angew Chem Int Ed Engl. (2013); 52 (1): 310-314.
Hobbs, et al., "Cloning of a cDNA encoding diacylglycerol acyltransferase from *Arabidopsis thaliana* and its functional expression." FEBS Lett (1999); 452 (3): 145-149.
Ingrell, et al., "NetPhosYeast: prediction of protein phosphorylation sites in yeast." Bioinformatics (2007); 23 (7): 895-897.
Iwama, et al., "Alcohol dehydrogenases and an alcohol oxidase involved in the assimilation of exogenous fatty alcohols in Yarrowia lipolytica." FEMS Yeast Research (May 2015); 15(3): fov014, pp. 1-12.
Jain, et al., "Identification of a Novel Lysophospholipid Acyltransferase in *Saccharomyces cerevisiae*." The Journal of Biological Chemistry (2007); 282 (42): 30562-30569.
Jako, et al., "Seed-Specific Over-Expression of an *Arabidopsis* cDNA Encoding a Diacylglycerol Acyltransferase Enhances Seed Oil Content and Seed Weight." Plant Physiol (2001); 126 (2): 861-874.
Jurenka and Rafaeli, "Regulatory Role of PBAN in Sex Pheromone Biosynthesis of Heliothine Moths." Front. Endocrinol. (2011); 2 (46): 1-8.
Kajiwara, et al., "Molecular cloning and characterization of the Δ9 fatty acid desaturase gene and its promoter from *Saccharomyces kluyveri*" FEMS Yeast. Res. (2002); 2: 333-339.
Kalscheuer and Steinbüchel, "A Novel Bifunctional Wax Ester Synthase/Acyl-CoA:Diacylglycerol Acyltransferase Mediates Wax Ester and Triacylglycerol Biosynthesis in Acinetobacter calcoaceticus ADP1." The Journal of Biological Chemistry (2002); 278 (10): 8075-8082.
Keitz, et al., "Cis-selective ring-opening metathesis polymerization with ruthenium catalysts" J Am Chem Soc. (2012); 134 (4): 2040-2043.
Keitz, et al., "Improved ruthenium catalysts for Z-selective olefin metathesis" J Am Chem Soc. (2012); 134 (1): 693-699.
Kito, et al., "Inhibition of L-Glycerol 3-Phosphate Acyltransferase from *Escherichia coli* by cis-9, 10-Methylenehexadecanoic Acid." The Journal of Biochemistry (1972); 71 (1): 99-105.
Lardizabal, et al., "DGAT2 is a new diacylglycerol acyltransferase gene family: purification, cloning, and expression in insect cells of two polypeptides from Mortierella ramanniana with diacylglycerol acyltransferase activity." The Journal of Biological Chemistry (2001); 276 (42): 38862-38869.
Lassner, et al., "Lysophosphatidic Acid Acyltransferase from Meadowfoam Mediates Insertion of Erucic Acid at the sn-2 Position of Triacylglycerol in Transgenic Rapeseed Oil." Plant Physiol (1995); 109 (4): 1389-1394.

(56) References Cited

OTHER PUBLICATIONS

Lee, D. "Organic chemistry: Overcoming catalytic bias" Nature (2011) 471 (7339): 452-453.
Liénard, et al., "Sex pheromone biosynthetic pathways are conserved between moths and the butterfly *Bicyclus anynana*." Nature Communications (2014); 5: 3957, pp. 1-12.
Lewin, et al., "Analysis of Amino Acid Motifs Diagnostic for the sn-Glycerol-3-phosphate Acyltransferase Reaction." Biochemistry (1999); 38 (18): 5764-5771.
Li, et al., "Identification of acyltransferases required for cutin biosynthesis and production of cutin with suberin-like monomers." Proc Natl Acad Sci USA (2007); 104 (46): 18339-18344.
Liu, et al., "Functional and Topological Analysis of Yeast Acyl-CoA:Diacylglycerol Acyltransferase 2, an Endoplasmic Reticulum Enzyme Essential for Triacylglycerol Biosynthesis." The Journal of Biological Chemistry (2011); 286 (15): 13115-13126.
Lu, et al., "Acyl-phosphates initiate membrane phospholipid synthesis in Gram-positive pathogens." Mol Cell (2006); 23 (5): 765-772.
Maniatis, et al,. "Regulation of inducible and tissue-specific gene expression" Science (1987); 236 (4806): 1237-1245.
Marx, et al, "Stereoselective access to Z and E macrocycles by ruthenium-catalyzed Z-selective ring-closing metathesis and ethenolysis" J Am Chem Soc. (2013); 135 (1): 94-97.
Mauersberger, et al., "Insertional Mutagenesis in the n-Alkane-Assimilating Yeast *Yarrowia lipolytica*: Generation of Tagged Mutations in Genes Involved in Hydrophobic Substrate Utilization." J. Bacteriology (2001); 183 (17): 5102-5109.
Meek, et al. "Z-selective catalytic olefin cross-metathesis for natural product synthesis" Nature (2011); 471 (7339): 461-466.
Miller, W. T., "Tyrosine kinase signaling and the emergence of multicellularity" Biochimica et Biophysica Acta (BBA)—Molecular Cell Research (2012); 1823 (6): 1053-1057.
Moss, et al. "Determination of cellular fatty acid compositions of various yeasts by gas-liquid chromatography" J Clin Microbiol. (1982); 16 (6): 1073-1079.
Moto, et al., "Involvement of a bifunctional fatty-acyl desaturase in the biosynthesis of the silkmoth, *Bombyx mori*, sex pheromone." PNAS (2004); 101 (23): 8631-8636.
Murata, et al., "Modes of Fatty-Acid Desaturation in Cyanobacteria." Plant Cell Physiol (1992); 33(7): 933-941.
Nagiec, et al., "A suppressor gene that enables *Saccharomyces cerevisiae* to grow without making sphingolipids encodes a protein that resembles an *Escherichia coli* fatty acyltransferase." The Journal of Biological Chemistry (1993); 268 (29): 22156-22163.
Nishida, et al., "The gene and the RNA for the precursor to the plastid-located glycerol-3-phosphate acyltransferase of *Arabidopsis thaliana*." Plant Mol Biol. (1993); 21 (2): 267-277.
Oelkers, et al., "The DGA1 gene determines a second triglyceride synthetic pathway in yeast." The Journal of Biological Chemistry (2002); 277 (11): 8877-8881.
Okuyama and Wakil, "Positional Specificities of Acyl Coenzyme A:Glycerophosphate and Acyl Coenzyme A:Monoacylglycerophosphate Acyltransferases in *Escherichia coli*." The Journal of Biological Chemistry (1973); 248 (14): 5197-5205.
Ondi, et al. "High activity, stabilized formulations, efficient synthesis and industrial use of Mo-and W-based metathesis catalysts" XiMo Technology Updates, 2015: http://www.ximoinc.com/files/ximo/uploads/download/Summary_3.11.15.pdf.
PCT/US2016/062852, International Preliminary Reporton Patentability, dated May 22, 2018, 10 pages.
PCT/US2016/062852, International Search Report and Written Opinion, dated Feb. 7, 2017, 13 pages.
PCT/US2016/062852, Third Party Observation filed by Danmarks Tekniske Universitet on Oct. 5, 2017 with WIPO, 7 pages.
PCT/US2017/036136, Invitation to Pay Additional Fees, dated Sep. 20, 2017, 3 pages.
PCT/US2017/036136, International Search Report and Written Opinion, dated Nov. 17, 2017, 15 pages.
PCT/US2017/036136, International Preliminary Reporton Patentability, dated Dec. 11, 2018, 10 pages.
PCT/US2018/033151, Invitation to Pay Additional Fees, dated Aug. 14, 2018, 6 pages.
PCT/US2018/033151, International Search Report and Written Opinion, dated Oct. 15, 2018, 22 pages.
Peryshkov, et al. "B(C6F5)3 Activation of Oxo Tungsten complexes that are relevant to olefin metathesis" Organometallics (2013); 32 (19): 5256-5259.
Peryshkov, et al., "Z-Selective olefin metathesis reactions promoted by tungsten oxo alkylidene complexes" J Am Chem Soc. (2011); 133 (51): 20754-20757.
Riekhof, et al., "Identification and Characterization of the Major Lysophosphatidylethanolamine Acyltransferase in *Saccharomyces cerevisiae*." The Journal of Biological Chemistry (2007); 282 (39): 28344-28352.
Rock, et al., "Phospholipid synthesis in *Escherichia coli*. Characteristics of fatty acid transfer from acylacyl carrier protein to sn-glycerol 3-phosphate." The Journal of Biological Chemistry (1981); 256 (2): 736-742.
Rosenfeld, et al., "Structural and functional conservation and divergence among acyl-CoA desaturases of two noctuid species, the corn earworm, *Helicoverpa zea*, and the cabbage looper, *Trichoplusia ni*." Insect. Biochem. Mol. Biol. (2001); 31 (10): 949-964.
Sandager, et al., "Storage lipid synthesis is non-essential in yeast." J Biol Chem (2002); 277 (8): 6478-6482.
Schrock, et al. "Z-Selective and syndioselective ring-opening metathesis polymerization (ROMP) Initiated by monoaryloxidepyrrolide (MAP) catalysts" Macromolecules (2010); 43 (18): 7515-7522.
Seffernick, et al., "Melamine deaminase and Atrazine chlorohydrolase: 98 percent identical but functionally different." J. Bacteriol. (2001); 183 (8): 2405-2410.
Shi, et al., "Improving Production of Malonyl Coenzyme A-Derived Metabolites by Abolishing Snf1-Dependent Regulation of Acc1." mBio (2014); 5 (3): e01130-14: 1-8.
Sorger and Daum, "Synthesis of Triacylglycerols by the Acyl-Coenzyme A:Diacyl-Glycerol Acyltransferase Dga1p in Lipid Particles of the Yeast *Saccharomyces cerevisiae*." J Bacteriol (2002); 184 (2): 519-524.
Ståhl, et al., "Cloning and Functional Characterization of a Phospholipid:Diacylglycerol Acyltransferase from *Arabidopsis*." Plant Physiology (2004); 135 (3): 1324-1335.
Stöveken, et al., "The Wax Ester Synthase/Acyl Coenzyme A:Diacylglycerol Acyltransferase from *Acinetobacter* sp. Strain ADP1: Characterization of a Novel Type of Acyltransferase." J Bacteriol (2005); 187 (4): 1369-1376.
Takai et al. "Construction and characterization of a Yarrowia lipolytica mutant lacking genes encoding cytochromes P450 subfamily 52." Fungal Genet Biol. (2012); 49 (1): 58-64. Epub Nov. 17, 2011.
Townsend, et al. "Z-selective metathesis homocoupling of 1,3-dienes by molybdenum and tungsten monoaryloxide pyrrolide (MAP) complexes" J Am Chem Soc. (2012); 134 (28): 11334-11337.
UniProtKB-074934 (ACOX1_YARLI) 9 (nine) pages downloaded on Oct. 23, 2018 from https://www.uniprot.org/uniprot/074934.
Uniprot Accession A0A178WDE4. Acyl-coenzyme A oxidase, Apr. 12, 2017 [online]. [Retrieved on Aug. 10, 2018]. 1 page, Retrieved from the internet: <URL: https://www.uniprot.org/uniproVAOA178WDE4.txt?version=7>.
Uniprot Accession R8XW24. Acinetobacter calcoaceticus—Fatty acyl-CoA reductase, Apr. 13, 2013 [online]. [Retrieved Sep. 21, 2018]. 1 page, Retrieved from the internet: <URL: https://www.uniprot.org/uniprot/R8XW24.txt?version=14>.
Uthoff, et al., "Thio Wax Ester Biosynthesis Utilizing the Unspecific Bifunctional Wax Ester Synthase/Acyl Coenzyme A:Diacylglycerol Acyltransferase of *Acinetobacter* sp. Strain ADP1." Appl. Environ. Microbiol. (2005); 71 (2): 790-796.
Wahl, et al., "Antagonistic regulation of dgkA and plsB genes of phospholipid synthesis by multiple stress responses in *Escherichia coli*." Molecular Microbiology (2011); 80 (5): 1260-1275.
Wang, et al. "Efficient and selective formation of macrocyclic disubstituted Z alkenes by ring-closing metathesis (RCM) reactions catalyzed by Mo- or W-based monoaryloxide pyrrolide (MAP)

(56) References Cited

OTHER PUBLICATIONS complexes: applications to total syntheses of epilachnene, yuzu lactone, ambrettolide, epothilone C, and nakadomarin A" Chemistry (2013); 19 (8): 2726-2740.
Wang, et al., "Exploring fatty alcohol-producing capability of Yarrowia lipolytica." Biotechnology for Biofuels (2016); 9: 107, pp. 1-10.
Wang, et al., "Mo-Based Complexes with Two Aryloxides and a Pentafluoroimido Ligand: Catalysts for EfficientZ-Selective Synthesis of a Macrocyclic Trisubstituted Alkene by Ring-Closing Metathesis." Angew Chem Int Ed Engl., (2013); 52 (7): 1939-1943.
Whisstock and Lesk, "Prediction of protein function from protein sequence and structure." Q. Rev. Biophysics. (2003); 36 (3): 307-340.
Witkowski, et al., "Conversion of a ß-ketoacyl synthase to a malonyl decarboxylase by replacement of the active-site cysteine with glutamine." Biochemistry (1999); 38 (36): 11643-11650.
Xia, et al., "Large number of putative chemoreception and pheromone biosynthesis genes revealed by analyzing transcriptome from ovipositor-pheromone glands of Chilo suppressalis." Scientific Reports (Jan. 2015); 5: 7888. Epub Jan. 20, 2015.
Yoshimura, et al., "Involvement of the YneS/YgiH and PlsX proteins in phospholipid biosynthesis in both Bacillus subtilis and *Escherichia coli*." BMC Microbiology (2007); 7: 69, 13 pages.
Yousuf, et al., "Microbial conversion of olive oil mill wastewaters into lipids suitable for biodiesel production." J Agric. Food Chem. (2010); 58 (15): 8630-8635.
Yu, et al., "Enol Ethers as Substrates for Efficient Z- and Enantioselective Ring-Opening/Cross-Metathesis Reactions Promoted by Stereogenic-at-Mo Complexes: Utility in Chemical Synthesis and Mechanistic Attributes." J Am. Chem. Soc. (2012); 134(5): 2788-2799.
Yu, et al., "Synthesis of macrocyclic natural products by catalyst-controlled stereoselective ring-closing metathesis" Nature, (2011); 479 (7371): 88-93.
Zhao, et al. "Endo-selective enyne ring-closing metathesis promoted by stereogenic-at-W mono-pyrrolide complexes" Org Lett. (2011); 13 (4): 784-787.
Zheng and Zou, "The initial step of the glycerolipid pathway: identification of glycerol 3-phosphate/dihydroxyacetone phosphate dual substrate acyltransferases in *Saccharomyces cerevisiae*." The Journal of Biological Chemistry (2001); 276 (45): 417104-417116.
Zou, et al., "The *Arabidopsis thaliana* TAG1 mutant has a mutation in a diacylglycerol acyltransferase gene." The Plant Journal (1999); 19 (6): 645-653.
Ando, et al., "Lepidopteran Sex Pheromones". Topics in Current Chemistry (2004); 239: 51-96.
GenBank entry AF272342.1, Helicoverpa zea acyl-CoA delta-11 desaturase (PGDs1) mRNA, complete cds, Aug. 30, 2001, 2 pages, (https://www.ncbi.nlm.nih.gov/nuccore/AF272342.1), retrieved on Jan. 6, 2020.
Heath, et al., "Periodicity of Female Sex Pheromone Titer and Release in Heliothis subflexa and H. virescens (Lepidoptera: Noctuidae)". Annals of the Entomological Society of America (Mar. 1, 1991); vol. 84, Issue 2, pp. 182-189.
PCT/US2018/033151, International Preliminary Reporton Patentability, dated Nov. 19, 2019, 14 pages.
Rosenfield, et al., "Structural and functional conservation and divergence among acyl-CoA desaturases of two noctuid species, the corn earworm, *Helicoverpa zea*, and the cabbage looper, *Trichoplusia ni*." Insect. Biochem. Mol. Biol. (2001); 31 (10): 949-964.
Sheng and Feng, "Metabolic engineering of yeast to produce fatty acid-derived biofuels: bottlenecks and solutions". Frontiers in Microbiology (2015) vol. 6, art. 554, 11 pages.
Third Party Observations filed Jan. 8, 2020, in European Application No. 16867255.8, 19 pages.
European Patent Office Communication dated Jan. 13, 2020 transmitting Third Party Observations filed Jan. 8, 2020, in European Application No. 16867255.8, 1 page.
Adrio, J.L., "Oleaginous Yeasts: Promising Platforms for the Production of Oleochemicals and Biofuels". Biotechnol Bioeng. (Sep. 2017); 114(9): 1915-1920. Epub May 29, 2017.
Shi and Zhao, "Metabolic Engineering of Oleaginous Yeasts for Production of Fuels and Chemicals". Front Microbiol. (Nov. 8, 2017); 8: 2185. Published online Nov. 8, 2017.
U.S. Appl. No. 16/307,282, filed Dec. 5, 2018 (pending); and.
Chuang, et al., "Co-expression of heterologous desaturase genes in Yarrowia lipolytica". New Biotechnology (Sep. 30, 2010); 27(4): 277-282.
Extended European Search Report for Application No. EP 20216824.1 dated Jul. 21, 2021, 15 pages.
Holkenbrink, et al., "Production of moth sex pheromones for pest control by yeast fermentation". Metabolic Engineering (Nov. 1, 2020); 62: 312-321.
Petkevicius, K., et al., "Insect sex pheromone production in yeasts and plants". Current Opinion in Biotechnology (Oct. 1, 2020); 65: 259-267. Epub Aug. 28, 2020.
Petkevicius, K., et al., "Biotechnological production of the European corn borer sex pheromone in the yeast *Yarrowia lipolytica*". Biotechnology Journal (Jun. 2021); 16(6): 2100004.
Boettcher, et al., "Carbon Footprint of agricultural production and processing of tobacco (*Nicotiana tabacum*) in southern Brazil". Environmental Technology & Innovation (May 2020); 18: 100625, pp. 1-9.
Extended European Search Report for Application No. EP 18803040.7 dated Feb. 26, 2021, 7 pages.
Flock, et al., "Synthesis of cis,syndiotactic ROMP Polymers Containing Alternating Enantiomers", J. Am. Chem. Soc. (Jan. 25, 2011); 133(6): 1784-1786.
GenBank Accession No. AAD03775.1, "acyl-CoA delta11 desaturase [Trichoplusia ni]", Jan. 11, 1999.
GenBank Accession No. AAF81787.1, "acyl-CoA delta-11 desaturase [Helicoverpa zea]", Aug. 30, 2001, 1 page.
GenBank Accession No. AAF81790.2, "acyl-CoA delta-9 desaturase [Helicoverpa zea]", Aug. 30, 2001, 2 pages.
GenBank Accession No. AAM28480.2, "acyl-CoA desaturase HassGATD [Helicoverpa assulta]". May 22, 2003, 2 pages.
GenBank Accession No. AAM28481.2, "acyl-CoA desaturase HassKPSE [Helicoverpa assulta]", May 22, 2003, 1 page.
GenBank Accession No. AAM28483.2, "acyl-CoA desaturase HassLPAQ [Helicoverpa assulta]", May 22, 2003, 2 pages.
GenBank Accession No. AAM28484.2, "acyl-CoA desaturase HassNPVE [Helicoverpa assulta]", May 22, 2003, 1 page.
GenBank Accession No. AF416738.1, "Argyrotaenia velutinana acyl-CoA delta-11 desaturase mRNA, complete cds", Oct. 17, 2001, 2 pages.
GenBank Accession No. AF482906.2, "Helicoverpa assulta acyl-CoA desaturase HassKPSE mRNA, complete cds", May 22, 2003, 1 page.
GenBank Accession No. AF545481.1, "Choristoneura rosaceana acyl-CoA Z/E11 desaturase mRNA, complete cds", Mar. 8, 2005, 2 pages.
GenBank Accession No. AKU76402.1, "acyl-CoA desaturase 3 [Helicoverpa armigera]", Dec. 31, 2015, 2 pages.
GenBank Accession No. AKU76404.1, "acyl-CoA desaturase 5 [Helicoverpa armigera]", Dec. 31, 2015, 2 pages.
GenBank Accession No. AKU76405.1, "acyl-CoA desaturase 6 [Helicoverpa armigera]", Dec. 31, 2015, 1 page.
GenBank Accession No. AKU76408.1, "acyl-CoA desaturase 2 [Helicoverpa assulta]", Dec. 31, 2015, 1 page.
GenBank Accession No. AKU76409.1, "acyl-CoA desaturase 3 [Helicoverpa assulta]", Dec. 31, 2015, 1 page.
GenBank Accession No. AKU76410.1, "acyl-CoA desaturase 4 [Helicoverpa assulta]", Dec. 31, 2015, 1 page.
GenBank Accession No. AKU76411.1, "acyl-CoA desaturase 5 [Helicoverpa assulta]", Dec. 31, 2015, 1 page.
GenBank Accession No. AKU76412.1, "acyl-CoA desaturase 6 [Helicoverpa assulta]", Dec. 31, 2015, 2 pages.
GenBank Accession No. ATJ44449.1, "desaturase MPVE [Helicoverpa armigera]", Oct. 18, 2017, 1 page.
GenBank Accession No. ATJ44454.1, "desaturase LPAQ [Helicoverpa armigera]", Oct. 18, 2017, 2 pages.

(56) References Cited

OTHER PUBLICATIONS

GenBank Accession No. ATJ44456.1, "desaturase PDSN [Helicoverpa armigera]", Oct. 18, 2017, 1 page.
GenBank Accession No. ATJ44457.1, "desaturase IPAE [Helicoverpa armigera]", Oct. 18, 2017, 2 pages.
GenBank Accession No. ATJ44509.1, "desaturase KSVE [Helicoverpa assulta]", Oct. 18, 2017, 1 page.
GenBank Accession No. ATJ44511.1, "desaturase MPVE [Helicoverpa assulta]", Oct. 18, 2017, 1 page.
GenBank Accession No. ATJ44514.1, "desaturase PDSN [Helicoverpa assulta]", Oct. 18, 2017, 1 page.
GenBank Accession No. AY493438.1, "Thalassiosira pseudonana delta-11 fatty acid desaturase (desN) gene, complete cds", Apr. 6, 2004, 2 pages.
GenBank Accession No. EU152335.1, "Lampronia capitella acyl-CoA-delta11-desaturase mRNA, complete cds", Oct. 12, 2008, 2 pages.
GenBank Accession No. JX679209.1, "Agrotis segetum fatty acyl delta-11 desaturase (D11) mRNA, complete cds", Aug. 3, 2014, 1 page.
GenBank Accession No. JX964774.1, "Amyelois transitella delta 11 desaturase mRNA, complete cds", Sep. 3, 2014, 2 pages.
GenBank Accession No. PZC81408.1, "hypothetical protein B5X24_HaOG212613 [Helicoverpa armigera]", Jun. 15, 2018, 2 pages.
GenBank Accession No. PZC82682.1, "hypothetical protein B5X24_HaOG209780 [Helicoverpa armigera]", Jun. 15, 2018, 2 pages.
GenBank Accession No. PZC86045.1, "hypothetical protein B5X24_HaOG213003 [Helicoverpa armigera]", Jun. 15, 2018, 2 pages.
GenBank Accession No. PZC86046.1, "hypothetical protein B5X24_HaOG213004 [Helicoverpa armigera]", Jun. 15, 2018, 2 pages.
GenBank Accession No. XP_021183629.1, "acyl-CoA Delta(11) desaturase [Helicoverpa armigera]", Jun. 1, 2017, 2 pages.
GenBank Accession No. XP_021185492.1, "acyl-CoA Delta(11) desaturase-like [Helicoverpa armigera]", Jun. 1, 2017, 1 page.
GenBank Accession No. XP_021187735.1, "acyl-CoA Delta(11) desaturase-like [Helicoverpa armigera]", Jun. 1, 2017, 2 pages.
GenBank Accession No. XP_021182948.1, "acyl-CoA Delta(11) desaturase-like [Helicoverpa armigera]", Jun. 1, 2017, 2 pages.
GenBank Accession No. XP_021183600.1, "acyl-CoA Delta(11) desaturase-like isoform X1 [Helicoverpa armigera]", Jun. 1, 2017, 1 page.
GenBank Accession No. XP_021183601.1, "acyl-CoA Delta(11) desaturase-like isoform X2 [Helicoverpa armigera]", Jun. 1, 2017, 1 page.
GenBank Accession No. XP_021183624.1, "stearoyl-CoA desaturase 5 [Helicoverpa armigera]", Jun. 1, 2017, 2 pages.
GenBank Accession No. XP_021183628.1, "acyl-CoA Delta(11) desaturase [Helicoverpa armigera]", Jun. 1, 2017, 2 pages.
GenBank Accession No. XP_021183660.1, "acyl-CoA Delta(11) desaturase-like [Helicoverpa armigera]", Jun. 1, 2017, 1 page.
GenBank Accession No. XP_021183696.1, "acyl-CoA Delta(11) desaturase-like [Helicoverpa armigera]", Jun. 1, 2017, 1 page.
GenBank Accession No. XP_021190176.1, "acyl-CoA Delta(11) desaturase-like [Helicoverpa armigera]", Jun. 1, 2017, 1 page.
GenBank Accession No. XP021195328.1, "stearoyl-CoA desaturase 5-like [Helicoverpa armigera]", Jun. 1, 2017, 2 pages.
GenBank Accession No. XP_021195974.1, "Low Quality Protein: acyl-CoA Delta(11) desaturase-like [Helicoverpa armigera]", Jun. 1, 2017, 2 pages.
GenBank Accession No. XP_021200693.1, "acyl-CoA Delta(11) desaturase-like [Helicoverpa armigera]", Jun. 1, 2017, 1 page.
Gerber and Schrock, "Synthesis of methylidene complexes that contain a 2,6-dimesitylphenylimido ligand and ethenolysis of 2,3-dicarbomethoxynorbornadiene" Organometallics (2013); 32 (19): 5573-5580.
Lassance, et al., "Evolution of the codling moth pheromone via an ancient gene duplication". BMC Biology (2021); 19: 83, pp. 1-20.
Los and Murata, "Structure and expression of fatty acid desaturases", Biochimica et Biophysica Acta (Oct. 2, 1998); 1394(1): 3-15.
Marinescu, et al. "Synthesis of variations of Sterogenic-at-Metal Imido Alkylidene Complexes of Molybdenum" Organometallics (2012); 31: 6336-6343.
Shanklin, et al., "Eight Histidine Residues Are Catalytically Essential in a Membrane-Associated Iron Enzyme, Stearoyl-CoA Desaturase, and Are Conserved in Alkane Hydroxylase and Xylene Monooxygenase", Biochemistry (Jan. 1, 1994), 33 (43): 12787-12794.
Xia, et al., "Production of moth sex pheromone precursors in *Nicotiana* spp.: a worthwhile new approach to pest control". Journal of Pest Science (2020); 93: 1333-1346.

\* cited by examiner

FIG. 4

Table 1.3 Annual average production of 17 oils and fats in selected five-year periods from 1976/80 with forecasts up to 2016/20

|  | 1976/80 | 1986/90 | 1996/00 | 2006/10 | 2016/20 |
|---|---|---|---|---|---|
| World total | 52.65 | 75.66 | 105.06 | 165.65 | 184.77 |
| Soybean oil | 11.23 | 15.28 | 23.14 | 33.60 | 41.12 |
| Cottonseed oil | 2.83 | 3.64 | 4.00 | 5.35 | 6.51 |
| Groundnut oil | 3.01 | 3.70 | 4.55 | 5.72 | 6.38 |
| Sunflowerseed oil | 4.21 | 7.23 | 9.11 | 12.43 | 16.97 |
| Rapeseed oil | 3.01 | 7.51 | 12.64 | 17.72 | 22.69 |
| Sesameseed oil | 0.51 | 0.64 | 0.70 | 0.86 | 0.96 |
| Corn oil | 0.83 | 1.35 | 1.91 | 2.49 | 3.16 |
| Olive oil | 1.68 | 1.80 | 2.47 | 2.75 | 2.98 |
| Palm oil | 3.69 | 9.22 | 18.72 | 31.43 | 43.38 |
| Palmkernel oil | 0.46 | 1.21 | 2.34 | 3.84 | 5.28 |
| Coconut oil | 2.85 | 3.07 | 3.01 | 3.70 | 4.55 |
| Butter | 5.60 | 6.35 | 5.81 | 6.93 | 7.99 |
| Lard | 4.25 | 5.17 | 6.38 | 7.93 | 9.14 |
| Fish oil | 1.13 | 1.53 | 1.25 | 1.18 | 11.59 |
| Linseed oil | 0.79 | 0.73 | 0.70 | 0.81 | 0.97 |
| Castorseed oil | 0.32 | 0.40 | 0.46 | 0.71 | 0.78 |
| Tallow | 6.24 | 6.79 | 7.83 | 10.06 | 10.76 |

Source: Mielke 2002. The order of citation in the above Table is that used in the reference publication. This book does not include the four animal fats nor castor oil. The reference publication does not provide figures for cocoa butter but this has an annual production of about 1.7 million tonnes.

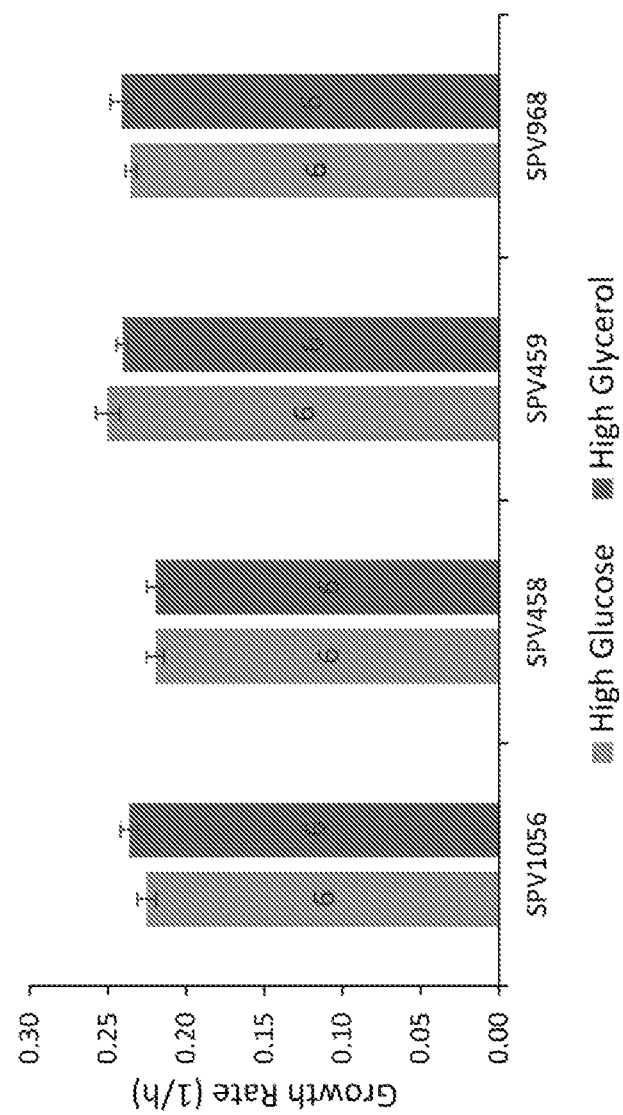

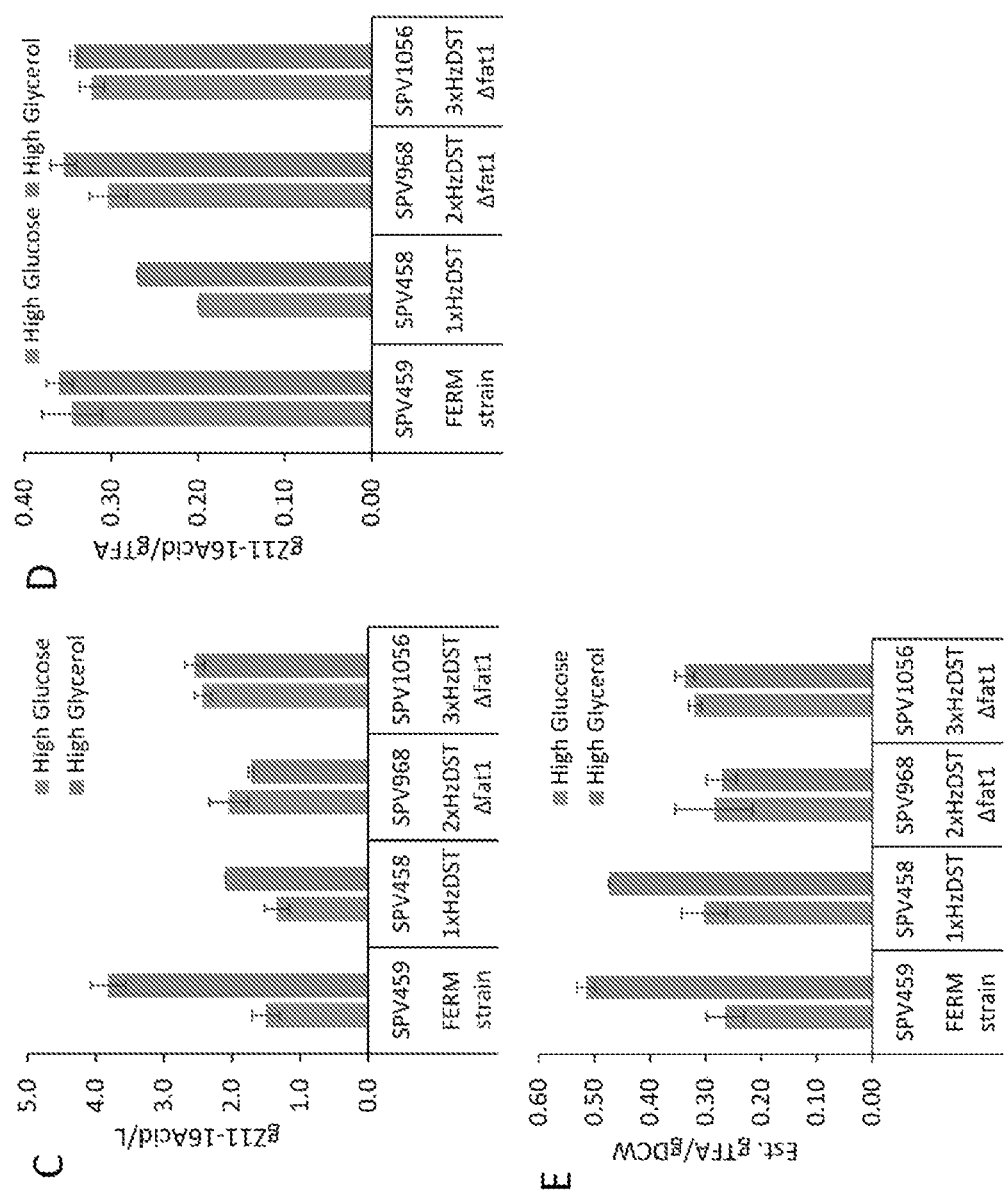

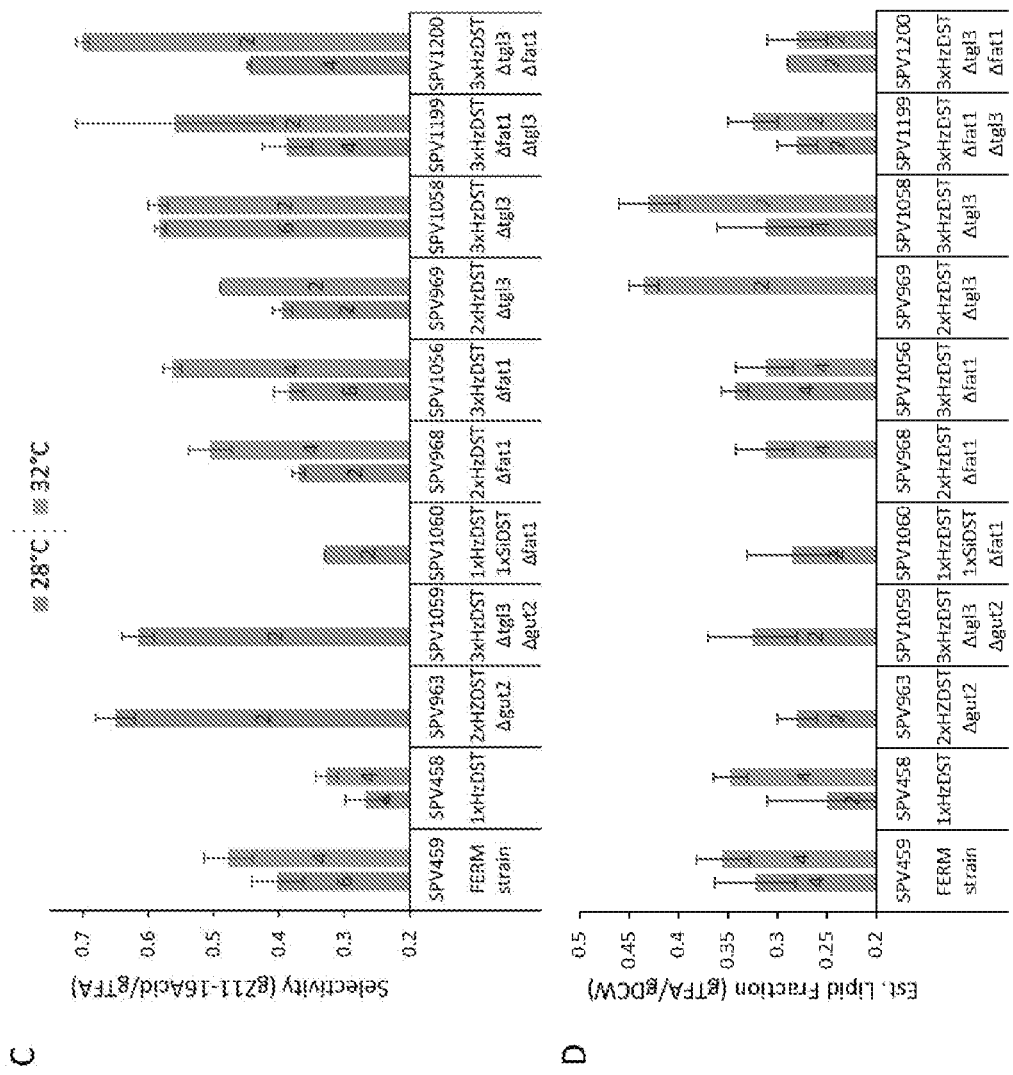

SEMI-BIOSYNTHETIC PRODUCTION OF FATTY ALCOHOLS AND FATTY ALDEHYDES

CROSS REFERENCE TO RELATED APPLICATIONS

The current application is a U.S. National Stage of PCT Application No. PCT/US2017/036136, filed on Jun. 6, 2017, which itself claims the benefit of priority to U.S. Provisional Application Ser. No. 62/346,335, filed Jun. 6, 2016, which is hereby incorporated by reference in its entirety.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is PRVI-017_01WO_SeqList_ST25.txt. The text file is about 103 KB, was created on Jun. 5, 2017, and is being submitted electronically via EFS-Web.

TECHNICAL FIELD

This application relates to methods of producing one or more fatty alcohols and/or one or more fatty aldehydes from one or more unsaturated lipid moieties by: obtaining one or more unsaturated lipid moieties from one or more naturally occurring organisms or producing the one or more unsaturated lipid moieties in one or more recombinant microorganisms manipulated to comprise a biosynthesis pathway for the production of the one or more unsaturated lipid moieties, chemically converting the one or more unsaturated lipid moieties to one or more free fatty acid (FFAs) and/or one or more fatty acid alkyl esters (FAAEs), and reducing the one or more FFAs and/or the one or more FAAEs, wherein the reduction produces one or more fatty alcohols and/or one or more fatty aldehydes. The one or more fatty alcohols can further be chemically converted to one or more corresponding fatty acetates. The one or more fatty alcohols, one or more fatty aldehydes and/or one or more fatty acetates may be useful as insect pheromones, fragrances, flavors, and polymer intermediates. The application further relates to recombinant microorganisms useful in the biosynthesis of unsaturated lipid moieties as well as compositions comprising one or more fatty alcohols and/or one or more fatty aldehydes.

BACKGROUND

As the global demand for food grows, there is an increasing need for effective pest control. Conventional insecticides are among the most popular chemical control agents because they are readily available, rapid acting, and highly reliable. However, the overuse, misuse, and abuse of these chemicals have led to resistant pests, alteration of the natural ecology, and in some cases, environmental damage.

The use of insect pheromones to control pest populations has gained increasing popularity as a viable, safe, and environmentally-friendly alternative to conventional insecticides. Since their discovery in the late 1950s, these molecules have shown efficacy in reducing insect populations through a variety of methods, including mass trappings, attract and kill, and mating disruption. The latter method in particular represents a non-toxic means of pest control and utilizes the ability of synthetic pheromones to mask naturally occurring pheromones, thereby causing confusion and mating disruption.

Although pheromones have significant potential in agricultural insect control, the cost of synthesizing pheromones using currently available techniques is very high, which prohibits widespread use of this sustainable technology beyond high-value crops. Thus, there is an existing need to develop novel technologies for the cost-efficient production of insect pheromones and related fragrances, flavors, and polymer intermediates. The present inventors address this need with the development of methods for the semi-biosynthesis production of fatty alcohols and/or fatty aldehydes including synthetic insect pheromones from low-cost feedstocks.

SUMMARY OF THE DISCLOSURE

The present application relates to methods of producing one or more fatty alcohols and/or one or more fatty aldehydes from one or more unsaturated lipid moieties by combining the obtainment or production of the one or more unsaturated lipid moieties from a biological source with conversion by non-biological means of the one or more unsaturated lipid moieties to one or more fatty alcohols and/or one or more fatty aldehydes. The present application also relates to recombinant microorganisms having a biosynthesis pathway for the production of one or more unsaturated lipid moieties. The one or more fatty alcohols and/or one or more fatty aldehydes produced by the methods described herein may be one or more insect pheromones, one or more fragrances, one or more flavoring agents, or one or more polymer intermediates.

In one aspect, a method of producing one or more fatty alcohols and/or one or more fatty aldehydes from one or more unsaturated lipid moieties comprise the steps of: obtaining the one or more unsaturated lipid moieties from one or more naturally occurring organisms; and reducing the one or more unsaturated lipid moieties directly, wherein the reduction produces one or more fatty alcohols and/or one or more fatty aldehydes.

In another aspect, a method of producing one or more fatty alcohols and/or one or more fatty aldehydes from one or more unsaturated lipid moieties comprises the steps of: obtaining the one or more unsaturated lipid moieties from one or more naturally occurring organisms; chemically converting the one or more unsaturated lipid moieties to one or more free fatty acids (FFAs); esterifying the one or more FFAs to one or more fatty acid alkyl esters (FAAEs); and reducing the one or more FFAs and/or the one or more FAAEs, wherein the reduction produces one or more fatty alcohols and/or one or more fatty aldehydes. In one embodiment, the FAAEs comprise fatty acid methyl esters (FAMEs).

In another aspect, a method of producing one or more fatty alcohols and/or one or more fatty aldehydes from one or more unsaturated lipid moieties comprises the steps of: obtaining the one or more unsaturated lipid moieties from one or more naturally occurring organisms; chemically converting the one or more unsaturated lipid moieties to one or more FAAEs; and reducing the one or more FAAEs, wherein the reduction produces one or more fatty alcohols and/or one or more fatty aldehydes. In one embodiment, the FAAEs comprise fatty acid methyl esters (FAMEs).

In one embodiment, the one or more naturally occurring organisms is an insect. In another embodiment, the one or more naturally occurring organisms is not an insect. In some embodiments, the one or more naturally occurring organisms is selected from the group consisting of plants, algae and bacteria. In some embodiments, the plants are from families selected from the group consisting of Proteaceae and Rhamnaceae. In certain embodiments, the plants comprise species from the genus *Gevuina, Calendula, Limnanthes, Lunaria, Carum, Daucus, Coriandrum, Macadamia, Myristica, Licania, Aleurites, Ricinus, Corylus, Kermadecia, Asclepias, Cardwellia, Grevillea, Orites, Ziziphus, Hicksbeachia, Hippophae, Ephedra, Placospermum, Xylomelum* and/or *Simmondsia*. In some embodiments, the plants are selected from the group consisting of *Gevuina avellana, Corylus avellana, Kermadecia sinuata, Asclepias syriaca, Cardwellia sublimis, Grevillea exul* var. *rubiginosa, Orites diversifolius, Orites revoluta, Ziziphus jujube, Hicksbeachia pinnatifolia,* and *Grevillea decora*. In some embodiments, the algae comprise green algae. In certain embodiments, the green algae comprise species from the genus *Pediastrum*. In some embodiments, the green algae comprise *Pediastrum simplex*. In some embodiments, the bacteria comprise gram-negative bacteria. In some embodiments, the gram-negative bacteria comprise species from the genus *Myxococcus*. In certain embodiments, the gram-negative bacteria comprise *Myxococcus xanthus*. In some embodiments, the bacteria comprise cyanobacteria. In some embodiments, the cyanobacteria comprise species from the genus *Synechococcus*. In certain embodiments, the cyanobacteria comprise *Synechococcus elongatus*.

In another aspect, a method of producing one or more fatty alcohols and/or one or more fatty aldehydes from one or more unsaturated lipid moieties comprises the steps of: producing the one or more unsaturated lipid moieties in one or more recombinant microorganisms manipulated to comprise a biosynthesis pathway for the production of one or more unsaturated lipid moieties; chemically converting the one or more unsaturated lipid moieties to one or more free fatty acid (FFAs) and/or one or more fatty acid methyl esters (FAAEs); and reducing the one or more FFAs and/or the one or more FAAEs, wherein the reduction produces one or more fatty alcohols and/or one or more fatty aldehydes. In one embodiment, the FAAEs comprise fatty acid methyl esters (FAMEs).

In one embodiment, the one or more recombinant microorganisms use one or more carbon sources for production of the one or more unsaturated lipid moieties. In another embodiment, the one or more carbon sources comprise sugars, glycerol, ethanol, organic acids, alkanes, and/or fatty acids. In certain embodiments, the one or more carbon sources is selected from the group consisting of alkanes and fatty acids. In some embodiments, the one or more recombinant microorganisms have high tolerance to alkanes and/or fatty acids. In some embodiments, the one or more recombinant microorganisms accumulate lipid. In other embodiments, the one or more recombinant microorganisms comprise one or more bacteria and/or fungi. In certain embodiments, the one or more fungi are oleaginous yeasts. In one embodiment, the oleaginous yeasts comprise species from the genus *Yarrowia* and/or *Candida*. In another embodiment, the oleaginous yeasts comprise *Yarrowia lipolytica* and/or *Candida viswanathii/tropicalis*.

In one embodiment, the one or more recombinant microorganisms manipulated to comprise a biosynthesis pathway for the production of one or more unsaturated lipid moieties comprise one or more exogenous biosynthetic enzymes selected from one or more desaturases, one or more acyl-CoA oxidases, one or more acylglycerol lipases, one or more flavoprotein pyridine nucleotide cytochrome reductases, one or more elongases, one or more thioesterases, one or more glycerol-3-phosphate acyltransferases, one or more lysophosphatidic acid acyltransferases, one or more diacylglycerol acyltransferases, and/or one or more lipid binding proteins. In another embodiment, the one or more desaturases is selected from the group consisting of a fatty acyl-CoA desaturase and a fatty acyl-ACP desaturase. In some embodiments, the one or more flavoprotein pyridine nucleotide cytochrome reductases is selected from the group consisting of a cytochrome-b5 reductase and a NADPH-dependent cytochrome P450 reductase. In some embodiments, the one or more elongases is selected from the group consisting of ELO1, ELO2, ELO3, or any combination thereof. In some embodiments, the one or more thioesterases is selected from the group consisting of an acyl-ACP thioesterase and an acyl-CoA thioesterase. In some embodiments, the one or more glycerol-3-phosphate acyltransferases is a dual glycerol-3-phosphate O-acyltransferase/dihydroxyacetone phosphate acyltransferase. In some embodiments, the one or more lysophosphatidic acid acyltransferases is selected from the group consisting of SLC1, ALE1 and LOA1, or any combination thereof. In some embodiments, the one or more diacylglycerol acyltransferases is selected from the group consisting of an acyl-CoA dependent acyltransferase and a phospholipid:diacylglycerol acyltransferase. In some embodiments, the one or more lipid binding proteins is sterol carrier protein 2 (SCP2). In some embodiments, the one or more exogenous biosynthetic enzymes are from a genus selected from the group consisting of *Saccharomyces, Yarrowia, Candida, Helicoverpa, Agrotis, Trichoplusia, Spodoptera, Ostrinia, Amyelois, Lobesia, Cydia, Grapholita, Lampronia, Sesamia, Plodia, Bombyx, Phoenix, Rattus, Arabidopsis, Plutella* and *Bicyclus*. In some embodiments, the one or more exogenous biosynthetic enzymes are from a species selected from the group consisting of *Saccharomyces cerevisiae, Yarrowia lipolytica, Candida albicans, Candida tropicalis, Candida viswanathii, Helicoverpa armigera, Helicoverpa zea, Agrotis segetum, Trichoplusia ni, Spodoptera littoralis, Spodoptera exigua, Amyelois transitella, Lobesia botrana, Cydia pomonella, Lampronia capitella, Grapholita molesta, Ostrinia scapulalis, Ostrinia furnacalis, Ostrinia nubilalis, Ostrinia latipennis, Ostrinia ovalipennis, Plodia interpunctella, Sesamia inferens, Bombyx mori, Phoenix dactylifera, Rattus norvegicus, Arabidopsis thaliana, Plutella xylostella* and *Bicyclus anynana*.

In some embodiments, the fatty-acyl desaturase is a desaturase capable of utilizing a fatty acyl-CoA as a substrate that has a chain length of 6, 7, 8, 9, 10, 11, 12, 13, 14, 15, 16, 17, 18, 19, 20, 21, 22, 23, or 24 carbon atoms.

In some embodiments, the fatty-acyl desaturase is capable of generating a double bond at position C5, C6, C7, C8, C9, C10, C11, C12, or C13 in the fatty acid or its derivatives, such as, for example, fatty acid CoA esters.

In one exemplary embodiment, the fatty-acyl desaturase is a Z11 desaturase. In various embodiments described herein, the Z11 desaturase, or the nucleic acid sequence that encodes it, can be isolated from organisms of the species *Agrotis segetum, Amyelois transitella, Argyrotaenia velutiana, Choristoneura rosaceana, Lampronia capitella, Trichoplusia ni, Helicoverpa zea,* or *Thalassiosira pseudonana*. Further Z11-desaturases, or the nucleic acid sequences encoding them, can be isolated from *Bombyx mori, Manduca sexta, Diatraea grandiosella, Earias insulana, Earias vittella, Plutella xylostella, Bombyx mori* or *Diaphania nitidalis*. In exemplary embodiments, the Z11 desaturase comprises a sequence selected from GenBank Accession Nos. JX679209, JX964774, AF416738, AF545481, EU152335, AAD03775, AAF81787, and AY493438. In some embodiments, a nucleic acid sequence encoding a Z11 desaturase from organisms of the species *Agrotis segetum, Amyelois transitella, Argyrotaenia velutiana, Choristoneura rosaceana, Lampronia capitella, Trichoplusia ni, Helicoverpa zea*, or *Thalassiosira pseudonana* is codon optimized. In some embodiments, the Z11 desaturase comprises a nucleotide sequence selected from SEQ ID NOs: 3, 11, 17 and 19 from *Trichoplusia ni*. In some embodiments, the Z11 desaturase comprises an amino acid sequence set forth in SEQ ID NO: 25 from *Trichoplusia ni*. In other embodiments, the Z11 desaturase comprises a nucleotide sequence selected from SEQ ID NOs: 4 and 9 from *Agrotis segetum*. In some embodiments, the Z11 desaturase comprises an amino acid sequence set forth in SEQ ID NO: 29 from *Agrotis segetum*. In some embodiments, the Z11 desaturase comprises a nucleotide sequence selected from SEQ ID NOs: 5 and 16 from *Thalassiosira pseudonana*. In some embodiments, the Z11 desaturase comprises an amino acid sequence selected from SEQ ID NOs: 26 and 27 from *Thalassiosira pseudonana*. In certain embodiments, the Z11 desaturase comprises a nucleotide sequence selected from SEQ ID NOs: 6, 10 and 23 from *Amyelois transitella*. In some embodiments, the Z11 desaturase comprises an amino acid sequence set forth in SEQ ID NO: 28 from *Amyelois transitella*. In further embodiments, the Z11 desaturase comprises a nucleotide sequence selected from SEQ ID NOs: 7, 12, 18, 20 and 24 from *Helicoverpa zea*. In some embodiments, the Z11 desaturase comprises an amino acid sequence set forth in SEQ ID NO: 1 from *Helicoverpa zea*. In some embodiments, the Z11 desaturase comprises an amino acid sequence set forth in SEQ ID NO: 2 from *S. inferens*. In some embodiments, the Z11 desaturase comprises an amino acid sequence set forth in GenBank Accession nos. AF416738, AGH12217.1, AII21943.1, CAJ43430.2, AF441221, AAF81787.1, AF545481, AJ271414, AY362879, ABX71630.1 and NP001299594.1, Q9N9Z8, ABX71630.1 and AIM40221.1. In some embodiments, the Z11 desaturase comprises a chimeric polypeptide. In some embodiments, a complete or partial Z11 desaturase is fused to another polypeptide. In certain embodiments, the N-terminal native leader sequence of a Z11 desaturase is replaced by an oleosin leader sequence from another species. In certain embodiments, the Z11 desaturase comprises a nucleotide sequence selected from SEQ ID NOs: 8, 21 and 22. In some embodiments, the Z11 desaturase comprises an amino acid sequence selected from SEQ ID NOs: 33, 34, 35, 36, 37 and 38.

In certain embodiments, the Z11 desaturase catalyzes the conversion of a fatty acyl-CoA into a mono- or polyunsaturated product selected from Z11-13:Acyl-CoA, E11-13:Acyl-CoA, (Z,Z)-7,11-13:Acyl-CoA, Z11-14:Acyl-CoA, E11-14:Acyl-CoA, (E,E)-9,11-14:Acyl-CoA, (E,Z)-9,11-14:Acyl-CoA, (Z,E)-9,11-14:Acyl-CoA, (Z,Z)-9,11-14:Acyl-CoA, (E,Z)-9,11-15:Acyl-CoA, (Z,Z)-9,11-15:Acyl-CoA, Z11-16:Acyl-CoA, E11-16:Acyl-CoA, (E,Z)-6,11-16:Acyl-CoA, (E,Z)-7,11-16:Acyl-CoA, (E,Z)-8,11-16:Acyl-CoA, (E,E)-9,11-16:Acyl-CoA, (E,Z)-9,11-16:Acyl-CoA, (Z,E)-9,11-16:Acyl-CoA, (Z,Z)-9,11-16:Acyl-CoA, (E,E)-11,13-16:Acyl-CoA, (E,Z)-11,13-16:Acyl-CoA, (Z,E)-11,13-16:Acyl-CoA, (Z,Z)-11,13-16:Acyl-CoA, (Z,E)-11,14-16:Acyl-CoA, (E,E,Z)-4,6,11-16:Acyl-CoA, (Z,Z,E)-7,11,13-16:Acyl-CoA, (E,E,Z,Z)-4,6,11,13-16:Acyl-CoA, Z11-17:Acyl-CoA, (Z,Z)-8,11-17:Acyl-CoA, Z11-18:Acyl-CoA, E11-18:Acyl-CoA, (Z,Z)-11,13-18:Acyl-CoA, (E,E)-11,14-18:Acyl-CoA, or combinations thereof.

In another exemplary embodiment, the fatty-acyl desaturase is a Z9 desaturase. In various embodiments described herein, the Z9 desaturase, or the nucleic acid sequence that encodes it, can be isolated from organisms of the species *Ostrinia furnacalis, Ostrinia nobilalis, Choristoneura rosaceana, Lampronia capitella, Helicoverpa assulta*, or *Helicoverpa zea*. In exemplary embodiments, the Z9 desaturase comprises a sequence selected from GenBank Accession Nos. AY057862, AF243047, AF518017, EU152332, AF482906, and AAF81788. In some embodiments, a nucleic acid sequence encoding a Z9 desaturase is codon optimized. In some embodiments, the Z9 desaturase comprises a nucleotide sequence set forth in SEQ ID NO: 13 from *Ostrinia furnacalis*. In some embodiments, the Z9 desaturase comprises an amino acid sequence set forth in SEQ ID NO: 30 from *Ostrinia furnacalis*. In other embodiments, the Z9 desaturase comprises a nucleotide sequence set forth in SEQ ID NO: 14 from *Lampronia capitella*. In some embodiments, the Z9 desaturase comprises an amino acid sequence set forth in SEQ ID NO: 31 from *Lampronia capitella*. In some embodiments, the Z9 desaturase comprises a nucleotide sequence set forth in SEQ ID NO: 15 from *Helicoverpa zea*. In some embodiments, the Z9 desaturase comprises an amino acid sequence set forth in SEQ ID NO: 32 from *Helicoverpa zea*.

In certain embodiments, the Z9 desaturase catalyzes the conversion of a fatty acyl-CoA into a monounsaturated or polyunsaturated product selected from Z9-11:Acyl-CoA, Z9-12:Acyl-CoA, E9-12:Acyl-CoA, (E,E)-7,9-12:Acyl-CoA, (E,Z)-7,9-12:Acyl-CoA, (Z,E)-7,9-12:Acyl-CoA, (Z,Z)-7,9-12:Acyl-CoA, Z9-13:Acyl-CoA, E9-13:Acyl-CoA, (E,Z)-5,9-13:Acyl-CoA, (Z,E)-5,9-13:Acyl-CoA, (Z,Z)-5,9-13:Acyl-CoA, Z9-14:Acyl-CoA, E9-14:Acyl-CoA, (E,Z)-4,9-14:Acyl-CoA, (E,E)-9,11-14:Acyl-CoA, (E,Z)-9,11-14:Acyl-CoA, (Z,E)-9,11-14:Acyl-CoA, (Z,Z)-9,11-14:Acyl-CoA, (E,E)-9,12-14:Acyl-CoA, (Z,E)-9,12-14:Acyl-CoA, (Z,Z)-9,12-14:Acyl-CoA, Z9-15:Acyl-CoA, E9-15:Acyl-CoA, (Z,Z)-6,9-15:Acyl-CoA, Z9-16:Acyl-CoA, E9-16:Acyl-CoA, (E,E)-9,11-16:Acyl-CoA, (E,Z)-9,11-16:Acyl-CoA, (Z,E)-9,11-16:Acyl-CoA, (Z,Z)-9,11-16:Acyl-CoA, Z9-17:Acyl-CoA, E9-18:Acyl-CoA, Z9-18:Acyl-CoA, (E,E)-5,9-18:Acyl-CoA, (E,E)-9,12-18:Acyl-CoA, (Z,Z)-9,12-18:Acyl-CoA, (Z,Z,Z)-3,6,9-18:Acyl-CoA, (E,E,E)-9,12,15-18:Acyl-CoA, (Z,Z,Z)-9,12,15-18:Acyl-CoA, or combinations thereof.

In some embodiments, the fatty acyl desaturase catalyzes the conversion of a fatty acyl-CoA into a mono- or polyunsaturated intermediate selected from E5-10:Acyl-CoA, E7-12:Acyl-CoA, E9-14:Acyl-CoA, E11-16:Acyl-CoA, E13-18:Acyl-CoA, Z7-12:Acyl-CoA, Z9-14:Acyl-CoA, Z11-16:Acyl-CoA, Z13-18:Acyl-CoA, Z8-12:Acyl-CoA, Z10-14:Acyl-CoA, Z12-16:Acyl-CoA, Z14-18:Acyl-CoA, Z7-10:Acyl-coA, Z9-12:Acyl-CoA, Z11-14:Acyl-CoA, Z13-16:Acyl-CoA, Z15-18:Acyl-CoA, E7-10:Acyl-CoA, E9-12:Acyl-CoA, E11-14:Acyl-CoA, E13-16:Acyl-CoA, E15-18:Acyl-CoA, E5Z7-12:Acyl-CoA, E7Z9-12:Acyl-CoA, E9Z11-14:Acyl-CoA, E11Z13-16:Acyl-CoA, E13Z15-18:Acyl-CoA, E6E8-10:Acyl-CoA, E8E10-12:Acyl-CoA, E10E12-14:Acyl-CoA, E12E14-16:Acyl-CoA, Z5E8-10:Acyl-CoA, Z7E10-12:Acyl-CoA, Z9E12-14:Acyl-CoA, Z11E14-16:Acyl-CoA, Z13E16-18:Acyl-CoA, Z3-10:Acyl-CoA, Z5-12:Acyl-CoA, Z7-14:Acyl-CoA, Z9-16:Acyl-CoA, Z11-18:Acyl-CoA, Z3Z5-10:Acyl-CoA, Z5Z7-12:Acyl-CoA, Z7Z9-14:Acyl-CoA, Z9Z11-16:Acyl-CoA, Z11Z13-16:Acyl-CoA, and Z13Z15-18:Acyl-CoA.

In some embodiments, the recombinant microorganism may express a bifunctional desaturase capable of catalyzing the subsequent desaturation of two double bonds.

In some embodiments, the recombinant microorganism may express more than one exogenous nucleic acid molecule encoding a fatty-acyl desaturase that catalyzes the conversion of a saturated C6-C24 fatty acyl-CoA to a corresponding mono- or poly-unsaturated C6-C24 fatty acyl-CoA. For instance, the recombinant microorganism may express an exogenous nucleic acid molecule encoding a Z11 desaturase and another exogenous nucleic acid molecule encoding a Z9 desaturase.

In some embodiments, the one or more recombinant microorganisms manipulated to comprise a biosynthesis pathway for the production of one or more unsaturated lipid moieties comprise at least one exogenous nucleic acid molecule encoding an acyl-CoA oxidase that catalyzes the conversion of a mono- or poly-unsaturated C6-C24 fatty acyl-CoA into a truncated mono- or poly-unsaturated fatty acyl-CoA after one or more successive cycle of acyl-CoA oxidase activity, with a given cycle producing a mono- or poly-unsaturated C4-C22 fatty acyl-CoA intermediate with a two carbon truncation relative to a starting mono- or poly-unsaturated C6-C24 fatty acyl-CoA substrate in that cycle. In some embodiments, the acyl-CoA oxidase is selected from Table 3a.

In some embodiments, the recombinant microorganism further comprises at least one endogenous or exogenous nucleic acid molecule encoding an acylglycerol lipase and/or sterol ester esterase enzyme that preferably hydrolyzes ester bonds of >C16, of >C14, of >C12 or of >C10 acylglycerol substrates. In some embodiments, the acylglycerol lipase and/or sterol ester esterase enzyme being expressed are selected from Table 3b.

In one embodiment, the one or more recombinant microorganisms manipulated to comprise a biosynthesis pathway for the production of one or more unsaturated lipid moieties are further manipulated to delete, disrupt, mutate, and/or reduce the activity of one or more endogenous proteins in a pathway that competes with the biosynthesis pathway for the production of one or more unsaturated lipid moieties. In some embodiments, the one or more endogenous proteins are from a genus selected from the group consisting of Saccharomyces, Yarrowia and Candida. In other embodiments, the one or more endogenous proteins are from a species selected from the group consisting of Saccharomyces cerevisiae, Yarrowia lipolytica, Candida albicans and Candida tropicalis/Candida viswanathii.

In some embodiments, the recombinant microorganism is manipulated to delete, disrupt, mutate, and/or reduce the activity of one or more endogenous proteins involved in one or more undesired fatty acid elongation pathways. In certain embodiments, the one or more endogenous proteins involved in one or more undesired fatty acid elongation pathways is selected from the group consisting of a β-ketoacyl-CoA reductase, a β-hydroxyacyl-CoA dehydratase, an enoyl-CoA reductase, or any combination thereof.

In other embodiments, the recombinant microorganism is manipulated to delete, disrupt, mutate, and/or reduce the activity of one or more endogenous proteins involved in one or more lipid body storage and/or recycling pathways. In certain embodiments, the one or more endogenous proteins involved in one or more lipid body storage and/or recycling pathways is selected from the group consisting of a triacylglycerol lipase, a lysophosphatidic acid acyltransferase, a steryl ester hydrolase, an acyl-CoA synthetase, or any combination thereof. In some embodiments, the triacylglycerol lipase to be deleted, disrupted, mutated and/or reduced in activity is YALI0D17534g (TGL3). In some embodiments, the fatty acyl-CoA synthetase (fatty acid transporter) to be deleted, disrupted, mutated and/or reduced in activity is YALI0E16016g (FAT1).

In some embodiments, the recombinant microorganism is manipulated to delete, disrupt, mutate, and/or reduce the activity of one or more endogenous proteins involved in one or more fatty acid degradation pathways. In certain embodiments, the fatty acid degradation pathway is a beta-oxidation pathway. In certain embodiments, the one or more endogenous proteins is selected from the group consisting of an acyl-CoA oxidase, a multifunctional enoyl-CoA hydratase-β-hydroxyacyl-CoA dehydrogenase, a β-ketoacyl-CoA thiolase, or any combination thereof. In some preferred embodiments, one or more genes of the microbial host encoding acyl-CoA oxidases are deleted or down-regulated to eliminate or reduce the truncation of desired fatty acyl-CoAs beyond a desired chain-length. In some embodiments, the recombinant microorganism comprises a deletion, disruption, mutation, and/or reduction in the activity of one or more endogenous acyl-CoA oxidase enzyme selected from the group consisting of Y. lipolytica POX1 (YALI0E32835g), Y. lipolytica POX2 (YALI0F10857g), Y. lipolytica POX3 (YALI0D24750g), Y. lipolytica POX4 (YALI0E27654g), Y. lipolytica POX5 (YALI0C23859g), Y. lipolytica POX6 (YALI0E06567g); S. cerevisiae POX1 (YGL205W); Candida POX2 (CaO19.1655, CaO19.9224, CTRG_02374, M18259), Candida POX4 (CaO19.1652, CaO19.9221, CTRG_02377, M12160), and Candida POX5 (CaO19.5723, CaO19.13146, CTRG_02721, M12161).

In some embodiments, one or more genes of the recombinant microorganism encoding glycerol-3-phosphate acyl transferases (GPATs), lysophosphatidic acid acyltransferases (LPAATs), glycerolphospholipid acyltransferase (GPLATs) and/or diacylglycerol acyltransferases (DGATs) are deleted or downregulated, and replaced with one or more heterologous GPAT, LPAAT, GPLAT, or DGAT variants. In some embodiments, the one or more acyltransferase variant is derived from one or more heterologous acyltransferase selected from Table 3c. In some embodiments, the recombinant microorganism comprises a deletion, disruption, mutation, and/or reduction in the activity of one or more endogenous acyltransferase enzyme selected from the group consisting of Y. lipolytica YALI0C00209g, Y. lipolytica YALI0E18964g, Y. lipolytica YALI0F19514g, Y. lipolytica YALI0C14014g, Y. lipolytica YALI0E16797g, Y. lipolytica YALI0E32769g, and Y. lipolytica YALI0D07986g, S. cerevisiae YBL011w, S. cerevisiae YDL052c, S. cerevisiae YOR175C, S. cerevisiae YPR139C, S. cerevisiae YNR008w, and S. cerevisiae YOR245c, and Candida 1503_02577, Candida CTRG_02630, Candida CaO19.250, Candida CaO19.7881, Candida CTRG_02437, Candida CaO19.1881, Candida CaO19.9437, Candida CTRG_01687, Candida CaO19.1043, Candida CaO19.8645, Candida CTRG_04750, Candida CaO19.13439, Candida CTRG_04390, Candida CaO19.6941, Candida CaO19.14203, and Candida CTRG_06209.

In certain embodiments, the fatty acid degradation pathway is an omega-oxidation pathway. In certain embodiments, the one or more endogenous proteins is selected from the group consisting of a monooxygenase (CYP52), a fatty alcohol oxidase, a fatty alcohol dehydrogenase, an alcohol dehydrogenase, a fatty aldehyde dehydrogenase, or any combination thereof. In some preferred embodiments, the recombinant microorganism comprises a deletion, disruption, mutation, and/or reduction in the activity of one or more endogenous cytochrome P450 monooxygenases selected from the group consisting of *Y. lipolytica* YALI0E25982g (ALK1), *Y. lipolytica* YALI0F01320g (ALK2), *Y. lipolytica* YALI0E23474g (ALK3), *Y. lipolytica* YALI0B13816g (ALK4), *Y. lipolytica* YALI0B13838g (ALK5), *Y. lipolytica* YALI0B01848g (ALK6), *Y. lipolytica* YALI0A15488g (ALK7), *Y. lipolytica* YALI0C12122g (ALK8), *Y. lipolytica* YALI0B06248g (ALK9), *Y. lipolytica* YALI0B20702g (ALK10), *Y. lipolytica* YALI0C10054g (ALK11) and *Y. lipolytica* YALI0A20130g (ALK12).

In other embodiments, the recombinant microorganism is manipulated to delete, disrupt, mutate, and/or reduce the activity of one or more endogenous proteins involved in peroxisome biogenesis. In certain embodiments, the one or more endogenous proteins involved in peroxisome biogenesis is selected from the group consisting of PEX1, PEX2, PEX3, PEX4, PEX5, PEX6, PEX7, PEX8, PEX10, PEX11, PEX12, PEX13, PEX14, PEX15, PEX17, PEX18, PEX19, PEX21, PEX22, PEX25, PEX27, PEX28, PEX29, PEX30, PEX31, PEX32 and PEX34, or any combination thereof.

In another embodiment, the one or more recombinant microorganisms are further manipulated to increase intracellular levels of a coenzyme. In certain embodiments, the coenzyme is NADH and/or NADPH. In some embodiments, the one or more recombinant microorganisms are further manipulated to express one or more endogenous or exogenous proteins selected from the group consisting of a glucose-6-phosphate dehydrogenase, a 6-phosphogluconolactonase, a 6-phosphogluconate dehydrogenase, a transaldolase, a transketolase, a ribose-5-phosphate ketolisomerase, a D-ribulose-5-phosphate 3-epimerase, an NADP+-dependent isocitrate dehydrogenase, an NAD+ or NADP+ dependent malate dehydrogenase, an alcohol dehydrogenase, an aldehyde dehydrogenase, a transhydrogenase, or any combination thereof. In another embodiment, the expression of one or more endogenous or exogenous proteins is coupled with supplementation of a co-substrate. In some embodiments, the one or more recombinant microorganisms are further manipulated to delete, disrupt, mutate, and/or reduce the activity of one or more endogenous proteins selected from the group consisting of a glucose-6-phosphate dehydrogenase, a 6-phosphogluconolactonase, a 6-phosphogluconate dehydrogenase, a transaldolase, a transketolase, a ribose-5-phosphate ketol-isomerase, a D-ribulose-5-phosphate 3-epimerase, or any combination thereof.

In some embodiments, the recombinant microorganism expresses one or more acyl-CoA oxidase enzymes and is manipulated to delete, disrupt, mutate, and/or reduce the activity of one or more endogenous acyl-CoA oxidase enzymes. In some embodiments, the one or more acyl-CoA oxidase enzymes being expressed are different from the one or more endogenous acyl-CoA oxidase enzymes being deleted or downregulated. In other embodiments, the one or more acyl-CoA oxidase enzymes that are expressed regulate chain length of the one or more unsaturated lipid moieties. In other embodiments, the one or more acyl-CoA oxidase enzymes being expressed are selected from Table 3a.

In another aspect, a recombinant microorganism used in any of the methods of producing one or more fatty alcohols and/or one or more fatty aldehydes from one or more unsaturated lipid moieties is disclosed herein.

In another aspect, a method of producing a recombinant microorganism used in any of the methods of producing one or more fatty alcohols and/or one or more fatty aldehydes from one or more unsaturated lipid moieties is disclosed herein.

In one embodiment, the one or more unsaturated lipid moieties are selected from (Z)-3-hexenoic acid, (Z)-3-nonenoic acid, (Z)-5-decenoic acid, (E)-5-decenoic acid, (Z)-7-dodecenoic acid, (E)-8-dodecenoic acid, (Z)-8-dodecenoic acid, (Z)-9-dodecenoic acid, (E,E)-8,10-dodecadienoic acid, (7E,9Z)-dodecadienoic acid, (Z)-9-tetradecenoic acid, (Z)-11-tetradecenoic acid, (E)-11-tetradecenoic acid, (Z)-7-hexadecenoic acid, (Z)-9-hexadecenoic acid, (Z)-11-hexadecenoic acid, (Z,Z)-11,13-hexadecadienoic acid, (11Z,13E)-hexadecadienoic acid, (9Z,11E)-hexadecadienoic acid, (Z)-13-octadecenoic acid, (Z,Z,Z,Z,Z)-3,6,9,12,15-tricosapentaenoic acid, or any combination thereof. In another embodiment, the one or more unsaturated lipid moieties are selected from the group consisting of (Z)-9-tetradecenoic acid (Z9-14:COOH), (Z)-11-hexadecenoic acid (Z11-16:COOH) and (Z)-11-octadecenoic acid (Z11-18:COOH). In another embodiment, the one or more fatty alcohols and/or one or more fatty aldehydes comprise one or more insect pheromones, fragrances, flavors and/or polymer intermediates. In certain embodiments, the one or more fatty alcohols and/or one or more fatty aldehydes comprise one or more insect pheromones.

Exemplary insect pheromones in the form of fatty alcohols, fatty aldehydes, or fatty acetates capable of being generated using the recombinant microorganisms and methods described herein include, but are not limited to, (Z)-11-hexadecenal, (Z)-11hexadecenyl acetate, (Z)-9-tetradecenyl acetate, (Z,Z)-11,13-hexadecadienal, (9Z,11E)-hexadecadienal, (E,E)-8,10-dodecadien-1-ol, (7E,9Z)-dodecadienyl acetate, (Z)-3-nonen-1-ol, (Z)-5-decen-1-ol, (Z)-5-decenyl acetate, (E)-5-decen-1-ol, (E)-5-decenyl acetate, (Z)-7-dodecen-1-ol, (Z)-7-dodecenyl acetate, (E)-8-dodecen-1-ol, (E)-8-dodecenyl acetate, (Z)-8-dodecen-1-ol, (Z)-8-dodecenyl acetate, (Z)-9-dodecen-1-ol, (Z)-9-dodecenyl acetate, (Z)-9-tetradecen-1-ol, (Z)-11-tetraceden-1-ol, (Z)-11-tetracedenyl acetate, (E)-11-tetradecen-1-ol, (E)-11-tetradecenyl acetate, (Z)-7-hexadecen-1-ol, (Z)-7-hexadecenal, (Z)-9-hexadecen-1-ol, (Z)-9-hexadecenal, (Z)-9-hexadecenyl acetate, (Z)-11-hexadecen-1-ol, (Z)-13-octadecen-1-ol, and (Z)-13-octadecenal.

In one embodiment of any of the methods of producing one or more fatty alcohols and/or one or more fatty aldehydes from one or more unsaturated lipid moieties disclosed herein comprising a chemical conversion step, the step of chemically converting the one or more unsaturated lipid moieties to one or more FFAs and/or one or more FAAEs further comprises the steps of: isolating the one or more unsaturated lipid moieties; optionally enriching for one or more unsaturated lipid moieties having specific chain lengths; and processing the one or more unsaturated lipid moieties to produce fatty acid derivatives. In some embodiments, the step of processing the one or more unsaturated lipid moieties comprises saponification of the one or more unsaturated lipid moieties to one or more FFAs. In some embodiments, the step of processing the one or more unsaturated lipid moieties comprises esterification of the one or more unsaturated lipid moieties to one or more FAAEs. In one embodiment, the optional step of enriching for one or more unsaturated lipid moieties having specific chain lengths comprises a separation method. In another embodiment, the separation method comprises distillation and/or chromatography. In one embodiment, the FAAEs comprise fatty acid methyl esters (FAMEs).

In one embodiment of any of the methods of producing one or more fatty alcohols and/or one or more fatty aldehydes from one or more unsaturated lipid moieties disclosed herein, the step of reducing the one or more unsaturated lipid moieties, the one or more FFAs and/or the one or more FAAEs to one or more fatty alcohols and/or one or more fatty aldehydes comprises contacting the one or more unsaturated lipid moieties, the one or more FFAs and/or the one or more FAAEs with one or more stoichiometric reducing agents. In some embodiments, the one or more stoichiometric reducing agents comprise sodium bis(2-methoxyethoxy)aluminum hydride Vitride (Red-Al, Vitride, SMEAH) and/or diisobutylaluminum hydride (DIBAL). In certain embodiments, the step of reducing the one or more unsaturated lipid moieties, the one or more FFAs and/or the one or more FAAEs comprises a bulky cyclic nitrogen Lewis base to modify the reducing agent. In one embodiment, the bulky cyclic nitrogen Lewis base allows selectivity of the reducing step for the production of one or more fatty aldehydes. In one embodiment, the FAAEs comprise fatty acid methyl esters (FAMEs).

In one embodiment of any of the methods of producing one or more fatty alcohols and/or one or more fatty aldehydes from one or more unsaturated lipid moieties disclosed herein, the step of reducing the one or more unsaturated lipid moieties, the one or more FFAs and/or the one or more FAAEs to one or more fatty alcohols comprises contacting the one or more unsaturated lipid moieties, the one or more FFAs and/or the one or more FAAEs with one or more transition metal catalysts. In certain embodiments, the one or more transition metal catalysts comprise one or more group VIII catalysts. In one embodiment, the FAAEs comprise fatty acid methyl esters (FAMEs).

In one embodiment of any of the methods of producing one or more fatty alcohols and/or one or more fatty aldehydes from one or more unsaturated lipid moieties disclosed herein, the fatty alcohols produced are further oxidized to fatty aldehydes by an oxidation step. In some embodiments, the oxidation step comprises one or more partial oxidation methods. In certain embodiments, the one or more partial oxidation methods comprise NaOCl/TEMPO. In other embodiments, the oxidation step comprises a copper-catalyzed aerobic oxidation.

In one embodiment of any of the methods of producing one or more fatty alcohols and/or one or more fatty aldehydes from one or more unsaturated lipid moieties disclosed herein, the one or more fatty alcohols produced are further chemically converted to one or more corresponding fatty acetate esters. In certain embodiments, the step of chemically converting the one or more fatty alcohols to one or more corresponding fatty acetate esters comprises contacting the one or more fatty alcohols with acetic anhydride.

In one embodiment of any of the methods of producing one or more fatty alcohols, one or more fatty aldehydes and/or one or more fatty acetates from one or more unsaturated lipid moieties disclosed herein, the one or more fatty alcohols, one or more fatty aldehydes and/or one or more fatty acetates are further enriched by a separation procedure.

In another aspect, one or more compositions produced by any of the methods of producing one or more fatty alcohols, one or more fatty aldehydes and/or one or more fatty acetates from one or more unsaturated lipid moieties disclosed herein are provided.

BRIEF DESCRIPTION OF DRAWINGS

Illustrative embodiments of the disclosure are illustrated in the drawings, in which:

FIG. 4 illustrates production of 17 commodity oils from 1976 with forecast to 2016 (Gunstone, F. D. Vegetable Oils in Food Technology: Composition, Properties and Uses. Wiley-Blackwell, 2011).

FIG. 10 shows a compilation of different spectra regarding the Vitride reduction.

Z11 desaturase with *Homo sapiens* codon optimization (pPV199), *H. zea* HS opt YI leader=*H. zea* Z11 desaturase with *Homo sapiens* codon optimization and swapped *Y. lipolytica* OLE1 leader sequence (pPV200), *A. transitella* native=*A. transitella* Z11 desaturase with native codon usage (pPV201). All data average of 3 biological replicates. Error bars represent standard deviation.

Figure 13:
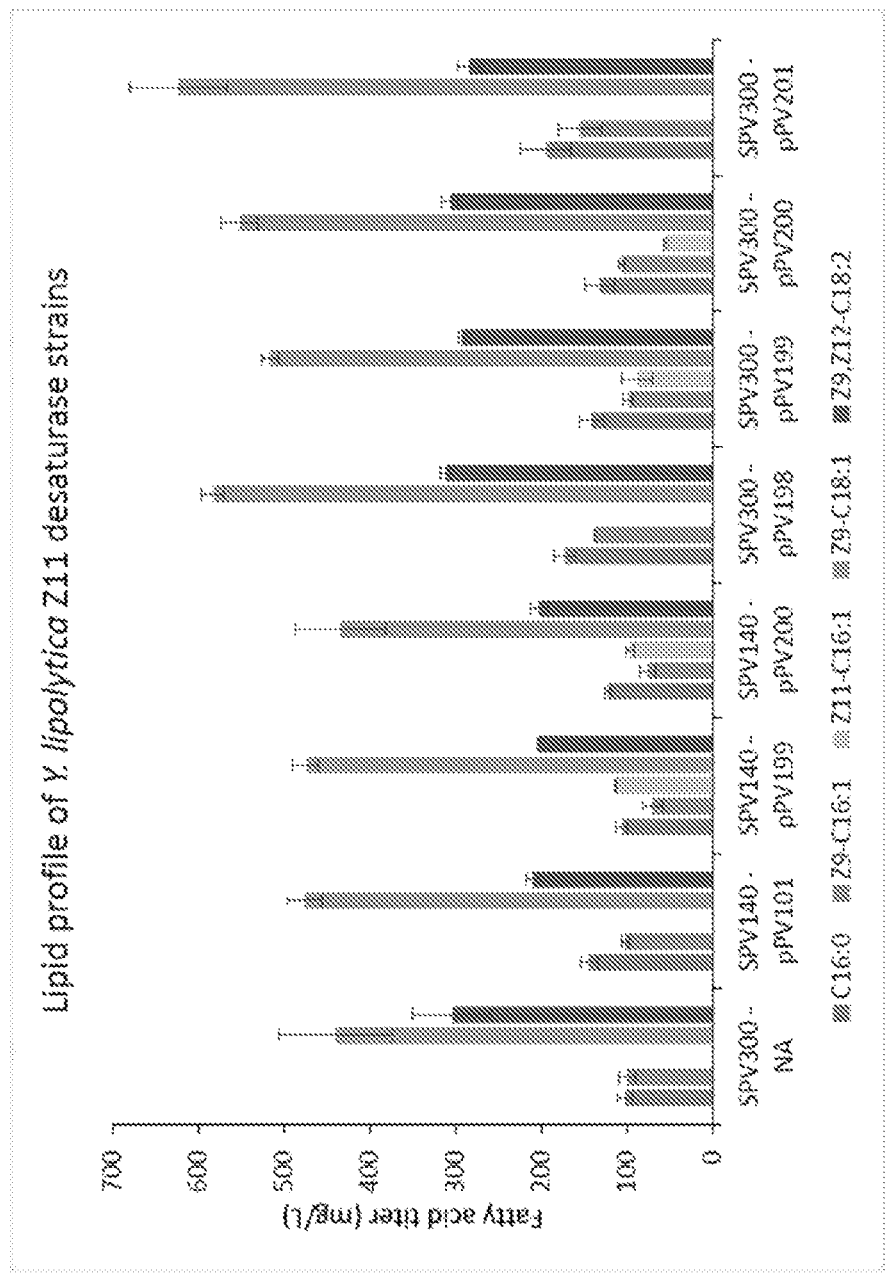

FIG. 13 shows only codon optimized *H. zea* desaturase variants produce detectable Z11-hexadecenoic acid in SPV300 screen. Labels indicate parent strain and plasmid of desaturase expression cassette. pPV101=hrGFP control, pPV198=*H. zea* Z11 desaturase with native codon usage, pPV199=*H. zea* Z11 desaturase with *Homo sapiens* codon optimization, pPV200=*H. zea* Z11 desaturase with *Homo sapiens* codon optimization and swapped *Y. lipolytica* OLE1 leader sequence, pPV201=*A. transitella* Z11 desaturase with native codon usage.

Figure 14:
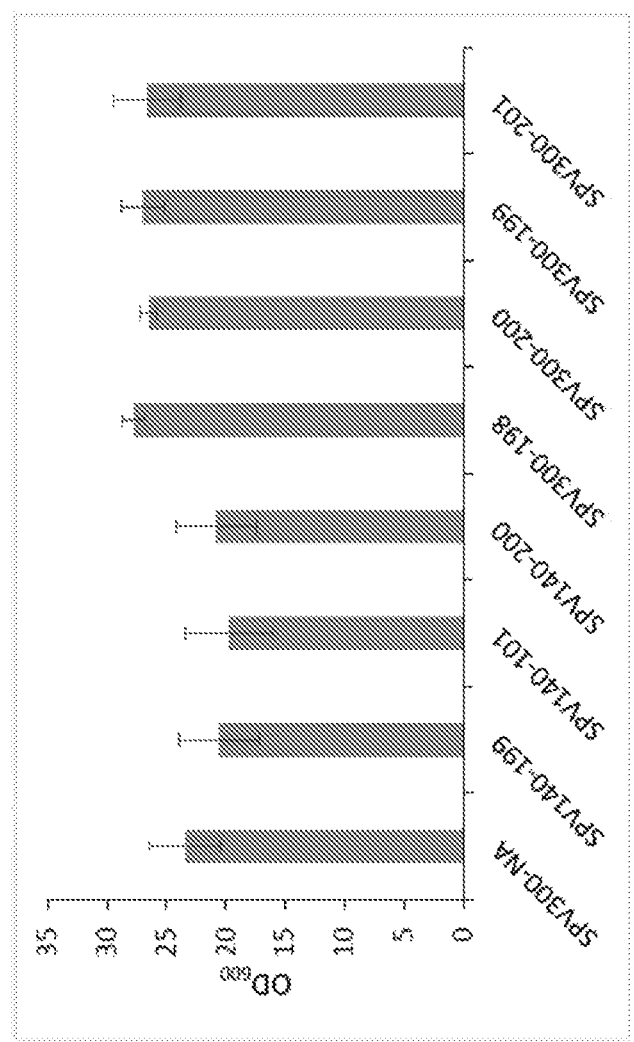

FIG. 14 shows final cell densities for desaturase screen in SPV140 and SPV300 backgrounds. SPV300 strains with integrated desaturase cassettes grew to higher cell densities.

Figure 15:
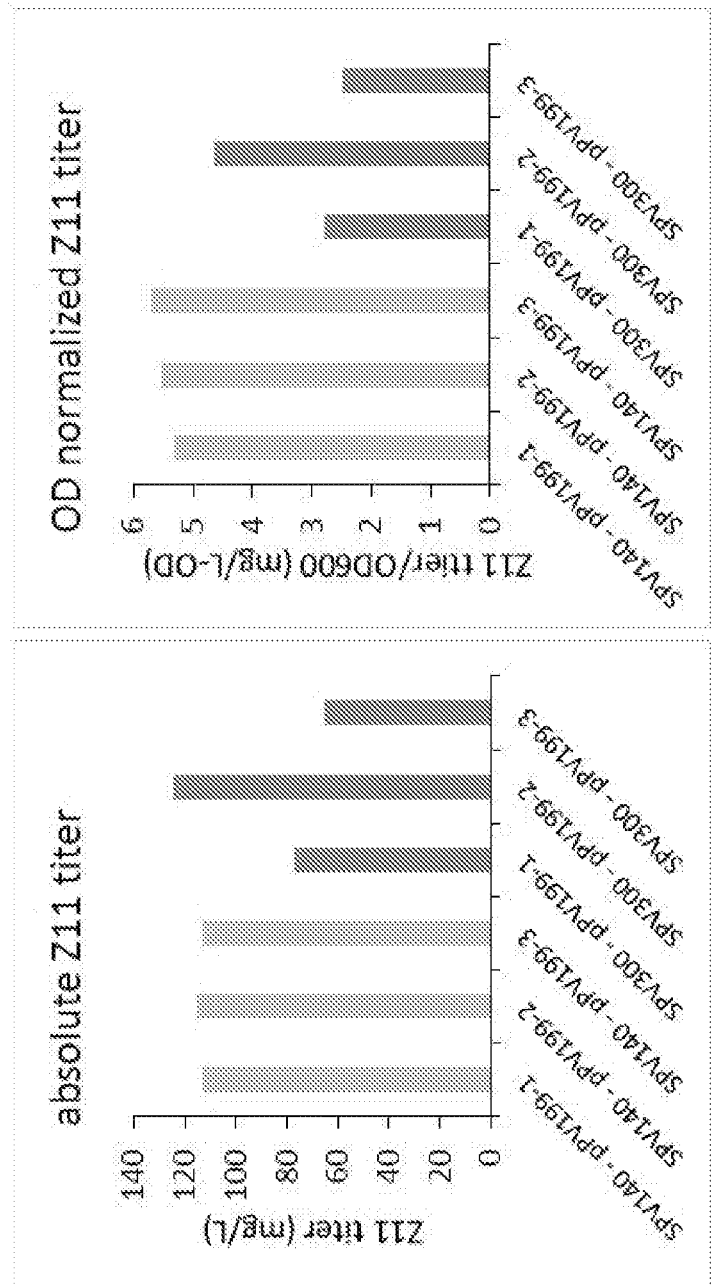

FIG. 15 shows individual isolate Z11-hexadecenoic acid titers for SPV140 and SPV300 strains expressing *H. zea* Z11 desaturase with *H. sapiens* codon optimization.

Figure 16:
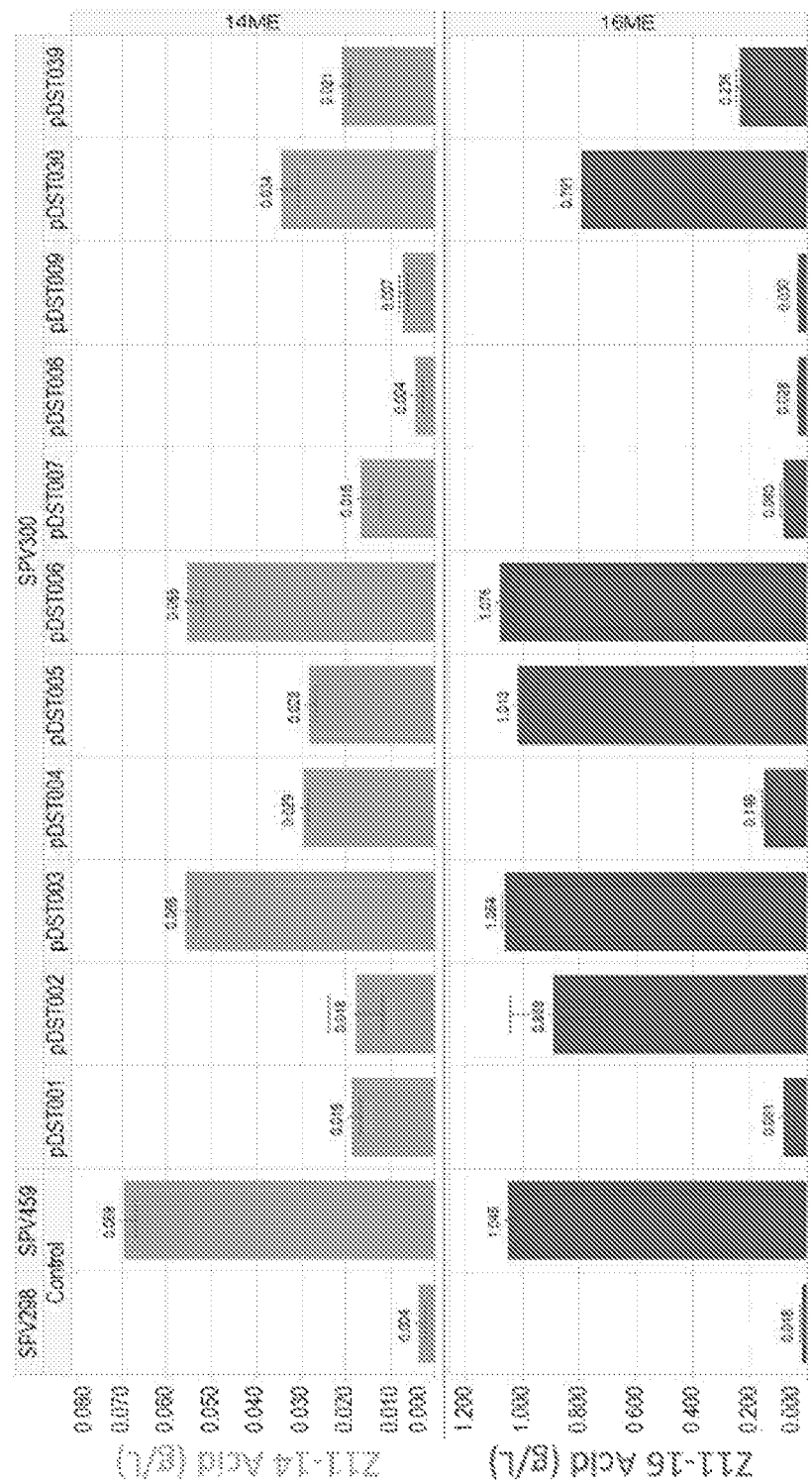

FIG. 16 shows Z11-14Acid (methyl myristate fed-14ME) and Z11-16Acid (methyl palmitate fed-16ME) titers of characterized Δ11 desaturases. SPV300=desaturase library integration parent. SPV298=prototrophic parent of SPV300, negative control. SPV459=SPV300 with current best desaturase (*Helicoverpa zea*, SEQ ID NO: 1), positive control. The desaturase in DST006 is genetically equivalent to the *H. zea* desaturase expressed in SPV459 and served as an internal library control.

Figure 17:
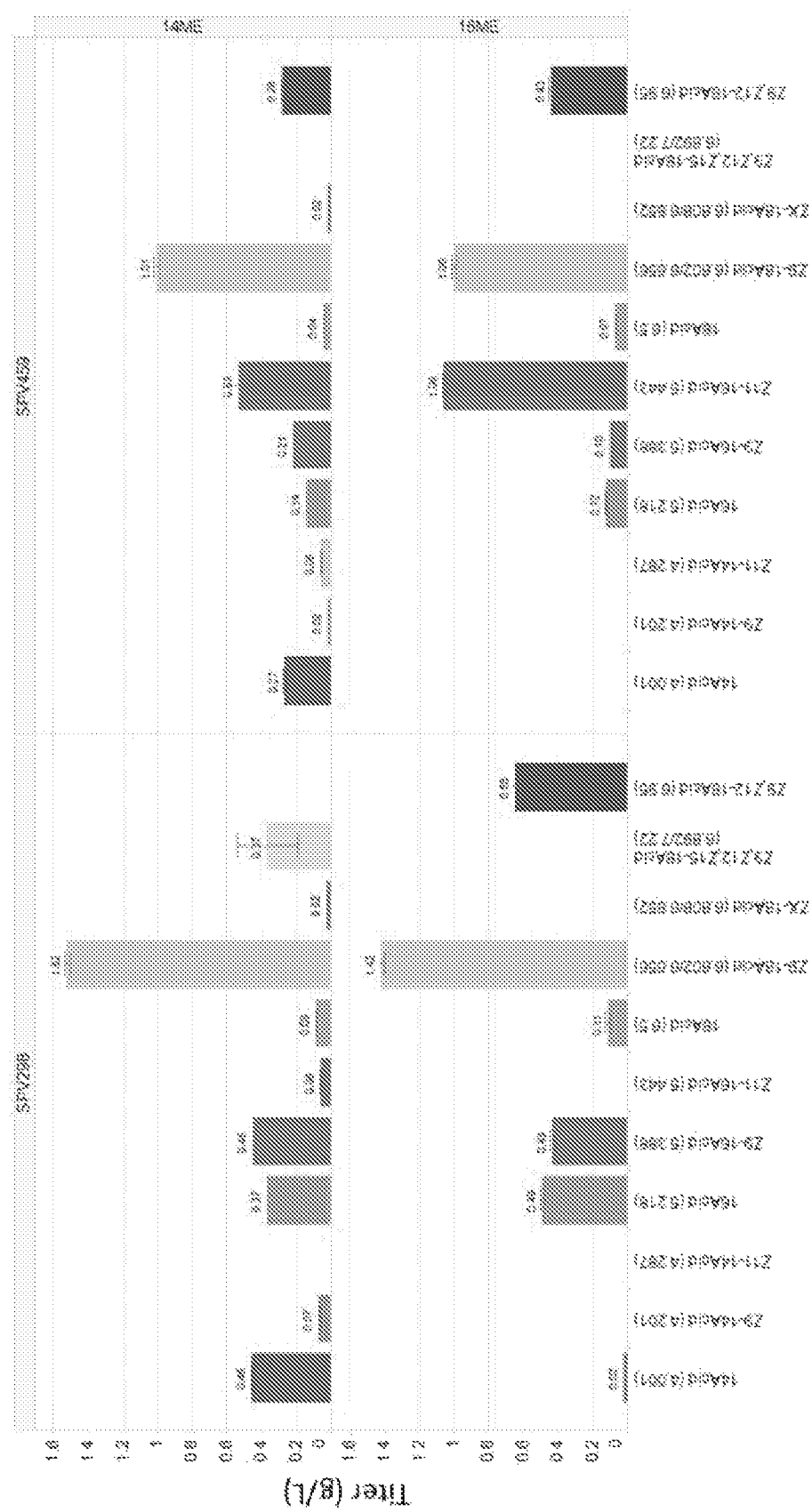

FIG. 17 shows C14 and C18 product profiles of SPV298 (negative control, parent strain) and SPV459 (SPV298 lineage with *H. zea* desaturase, SEQ ID NO: 1) fed on either methyl palmitate (16ME) or methyl myristate (14ME).

Figure 18:
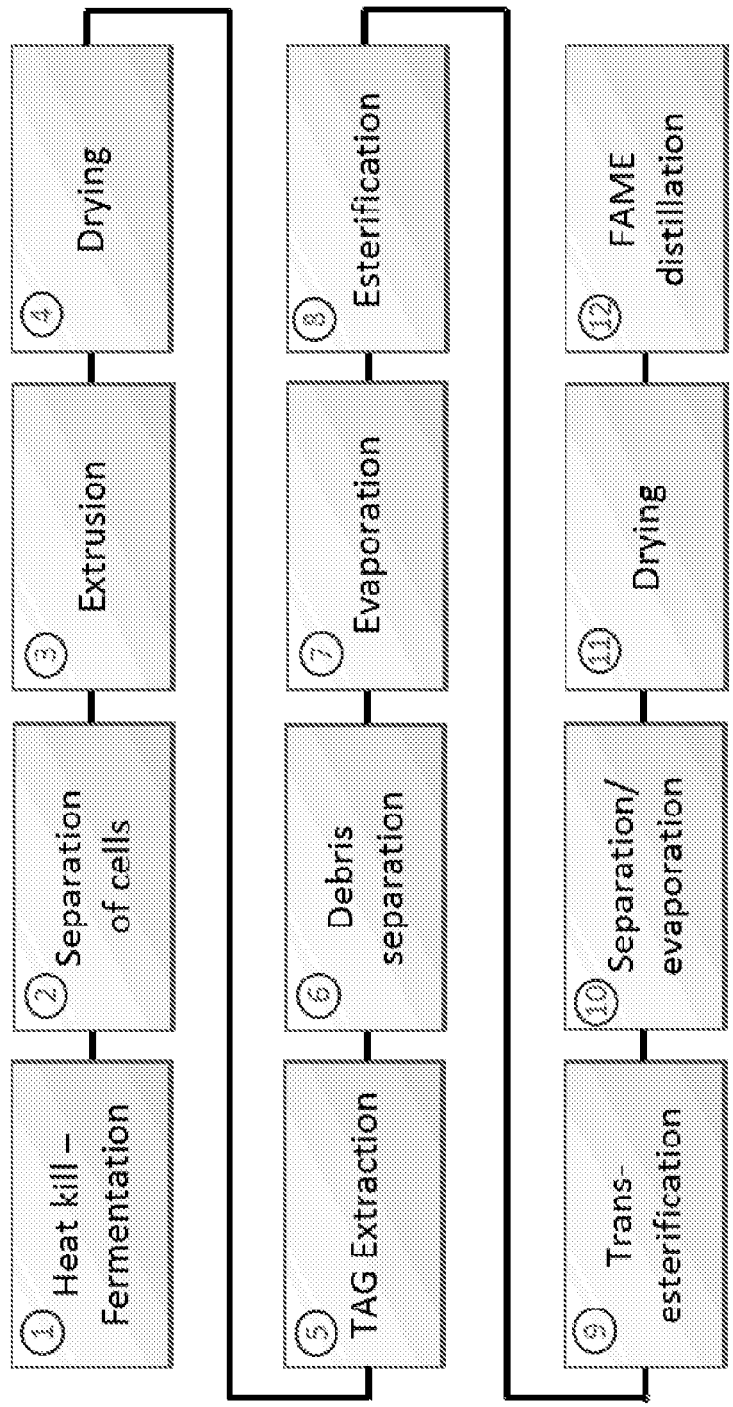

FIG. 18 shows a downstream process (DSP) overview. Individual unit operations of the DSP process are shown.

Figure 19:
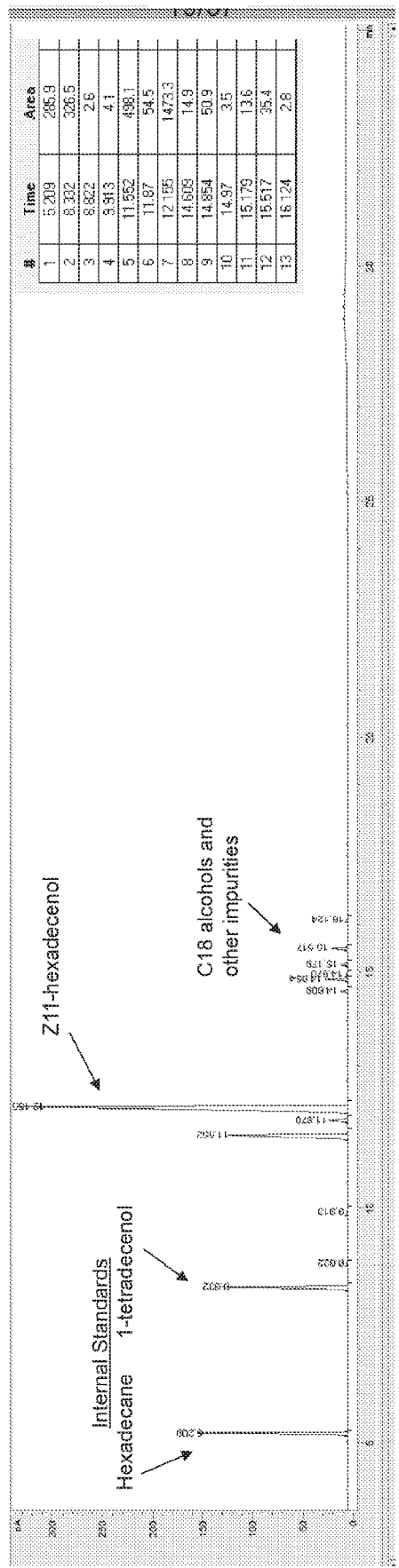

FIG. 19 shows a GC-FID trace of Z11-hexadecenol starting material.

Figure 20:
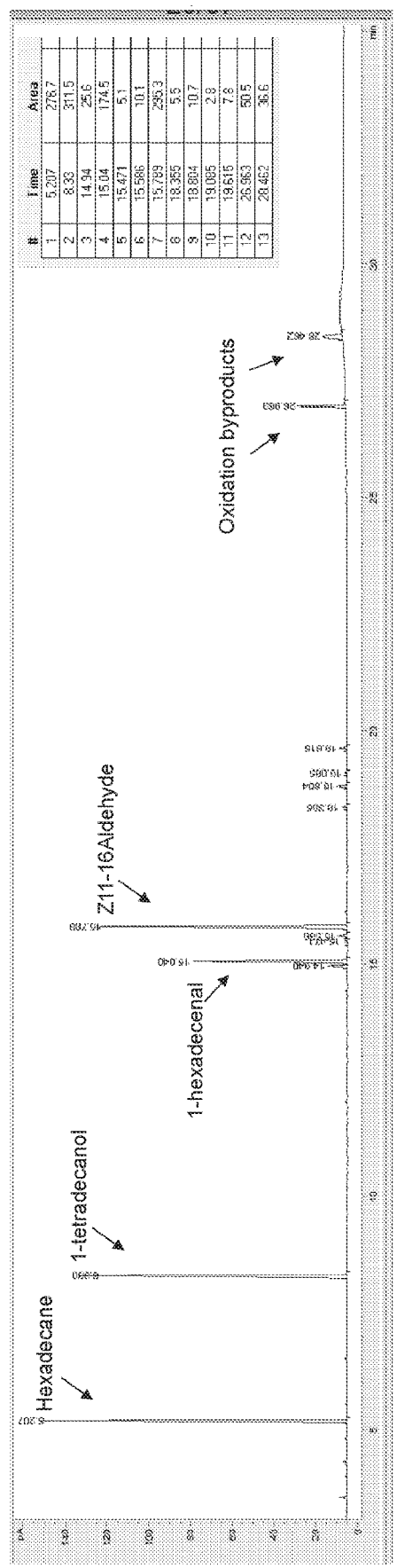

FIG. 20 shows a GC-FID trace of oxidation products from TEMPO-bleach oxidation of Z11-hexadecenol to Z11-hexadecenal.

Figure 21:
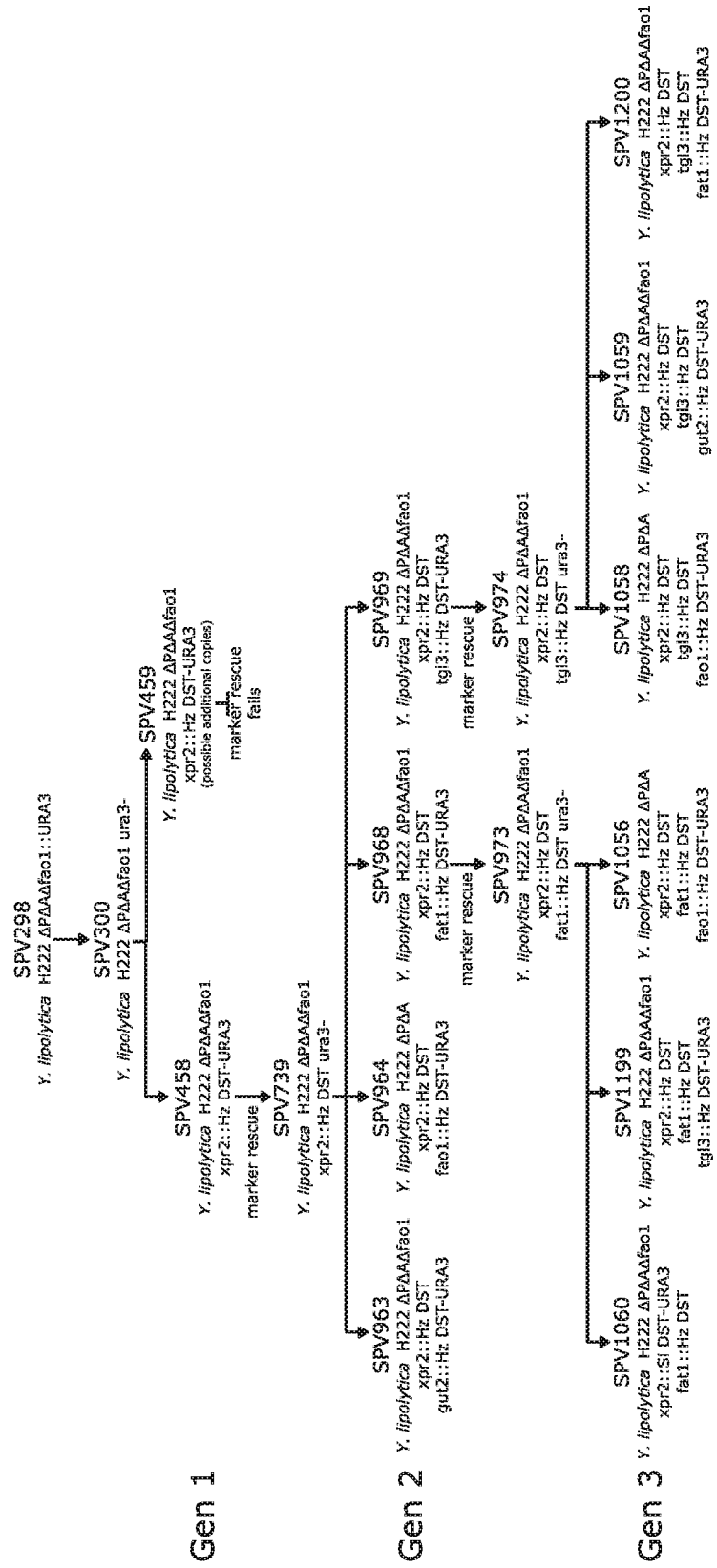

FIG. 21 shows a Z11-16Acid production strain lineage tree. Strain lineages for all strains are described Example 6. The genotypes of SPV1199 and SPV1200 are identical but were derived from different parent strains.

Figures 22A, 22B:
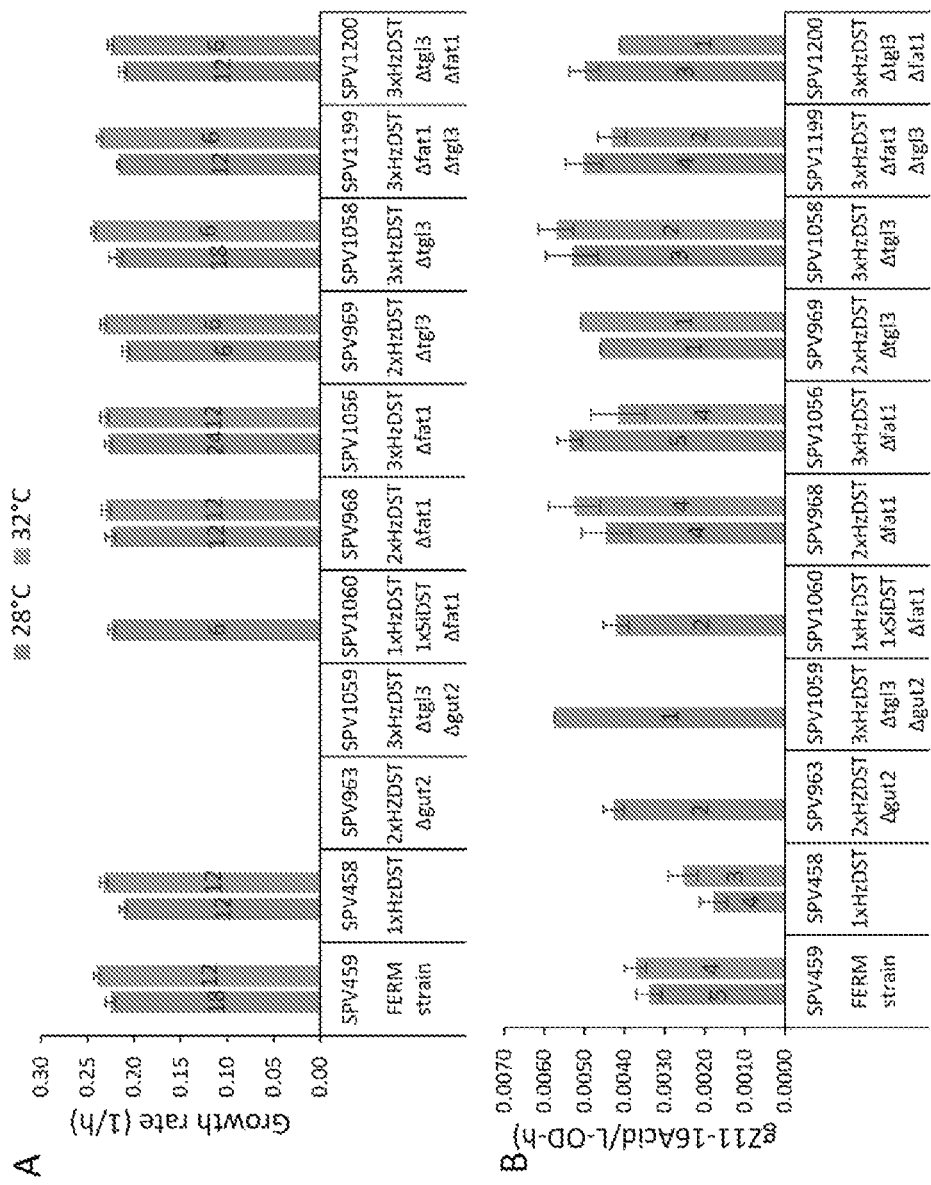
Figure 22C:
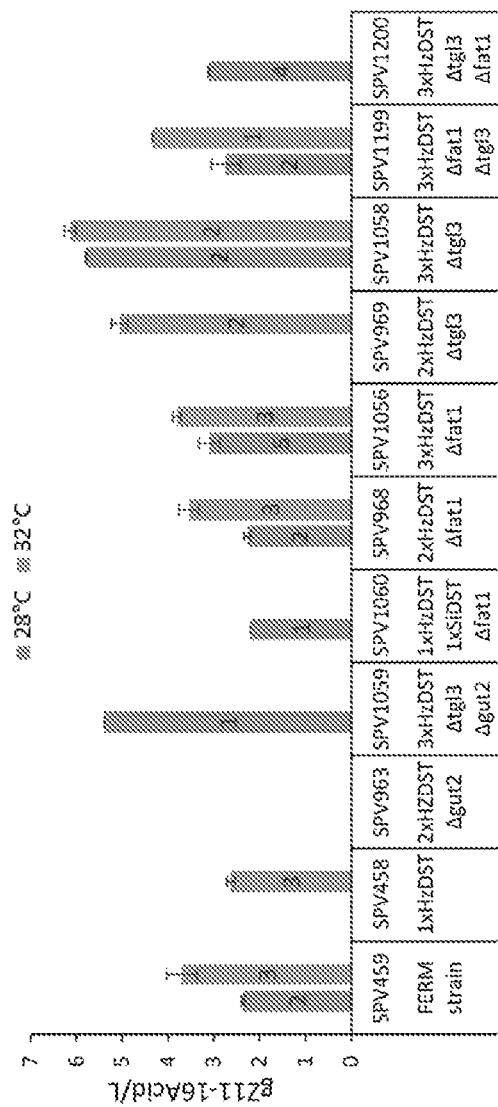

FIG. 22A-FIG. 22C show growth rate and Z11-16Acid production in High Glucose Medium at both 28 and 32° C. FIG. 22A: Initial growth rates during the first 7 hours before the first substrate addition. Calculated from online cell density measurements. FIG. 22B: Maximum specific productivities (from 7-23 hours). Cell densities are taken from independent measurements using a plate reader. FIG. 22C: 48 hour (maximum observed) Z11-16Acid titers. Inset numbers indicate number of independent measurements.

Figure 23:
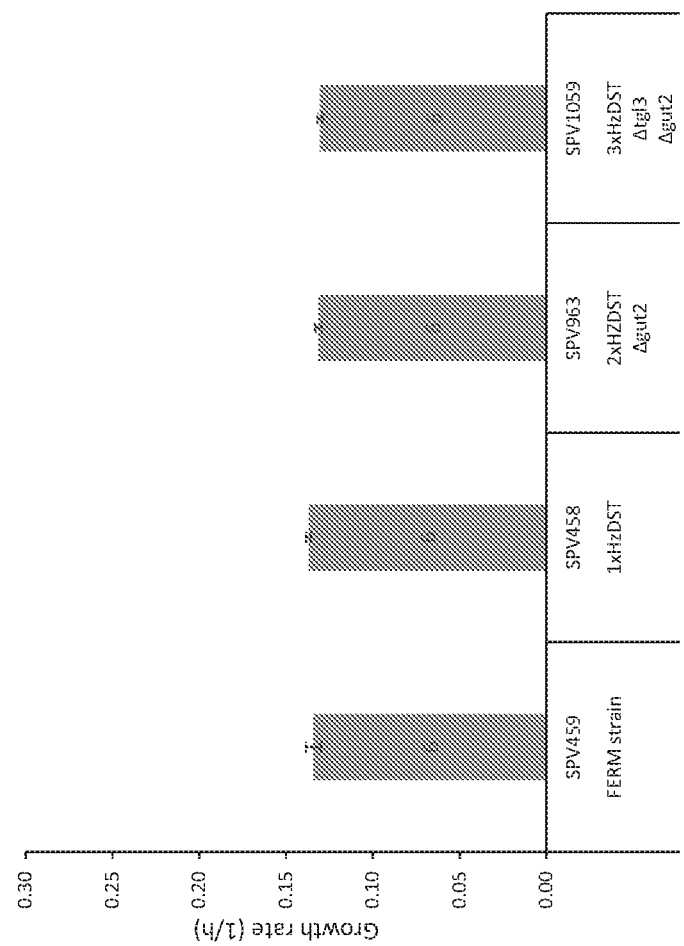

FIG. 23 shows initial growth rates of control and GUT2 deletion strains in High Glucose w/out Glycerol Medium. Initial growth rates were lower across all four strains tested using the media without 5 g/L glycerol.

Figures 24A, 24B:
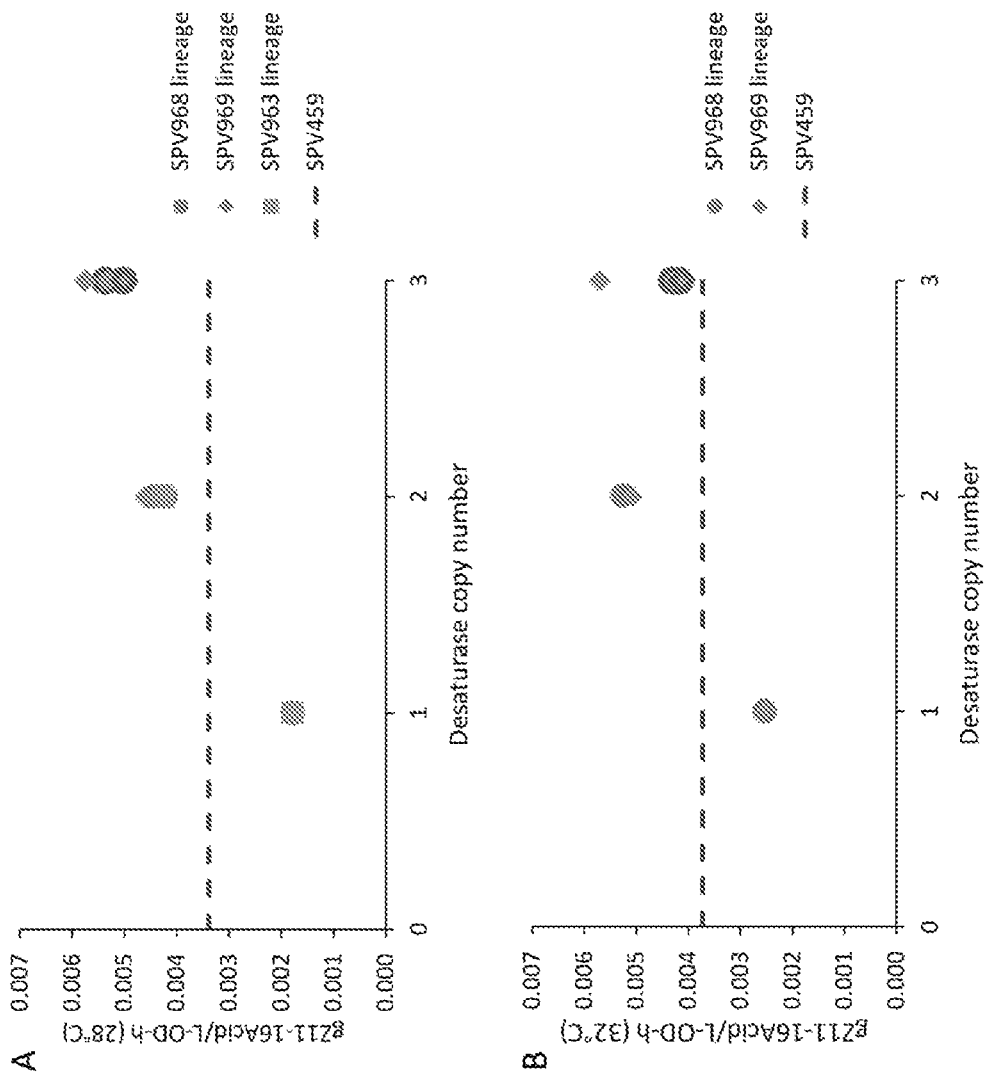

FIG. 24A-FIG. 24B show maximum specific productivities increase with desaturase copy number in High Glucose Medium. Average specific productivities for each strain in SPV963, SPV968, and SPV969 lineages is represented by a point. The single copy point is the average specific productivity for SPV458. Due to the presence of flanking repeat sequences in SPV459 the exact copy number is unknown. The SPV459 average specific productivity is indicated by the dashed line. Strains SPV1056, SPV1199, and SPV1200 which all have three *H. zea* Z11 desaturase copies and include a FAT1 deletion are indicated by a red outline. These strains displayed a drop in specific productivity when cultured at 32° C. FIG. 24A: Average specific productivities at 28° C. as a function of desaturase copy number. FIG. 24B: Average specific productivities at 32° C. as a function of desaturase copy number.

Figures 25A, 25B, 25C, 25D:
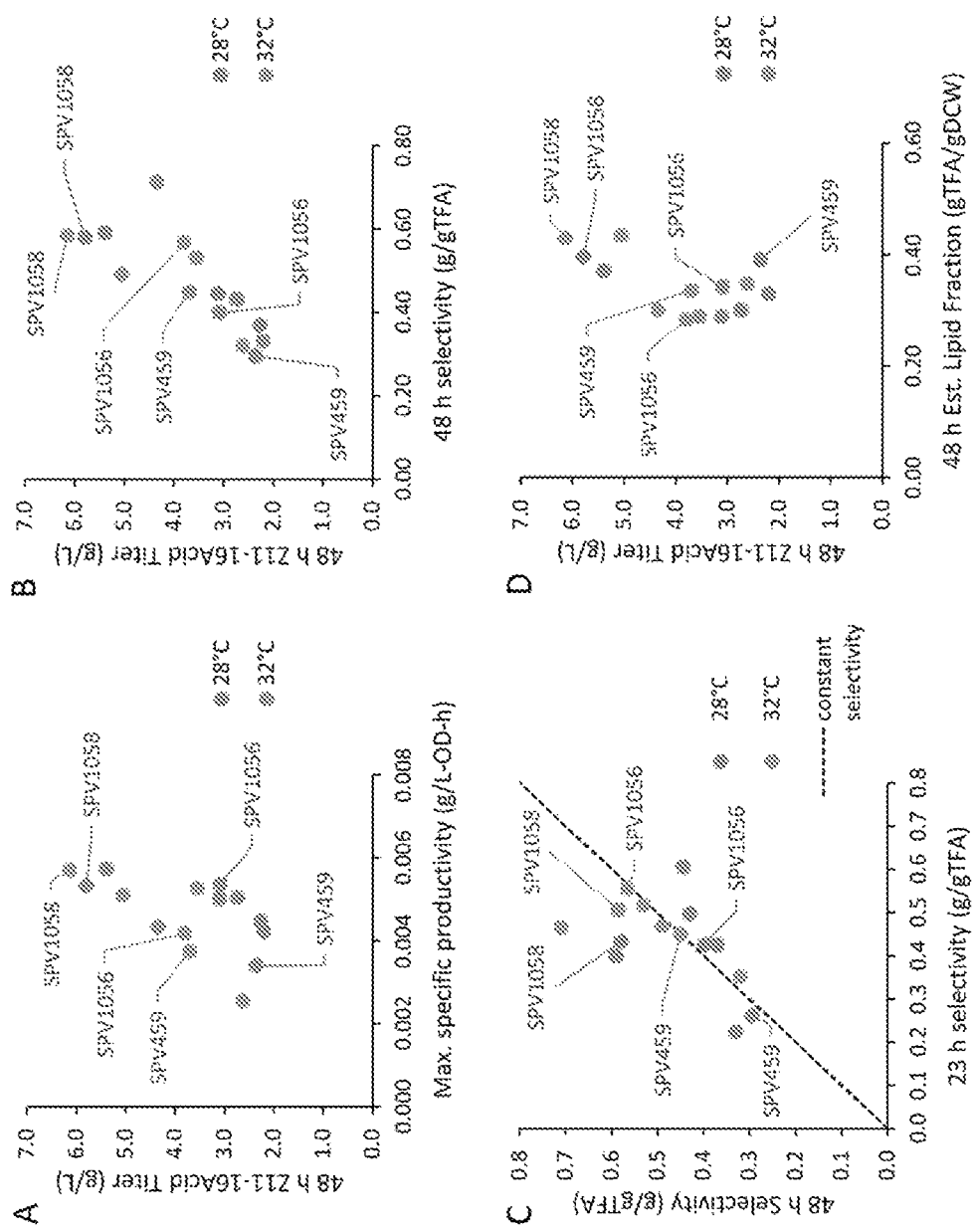
Figures 25E, 25F:
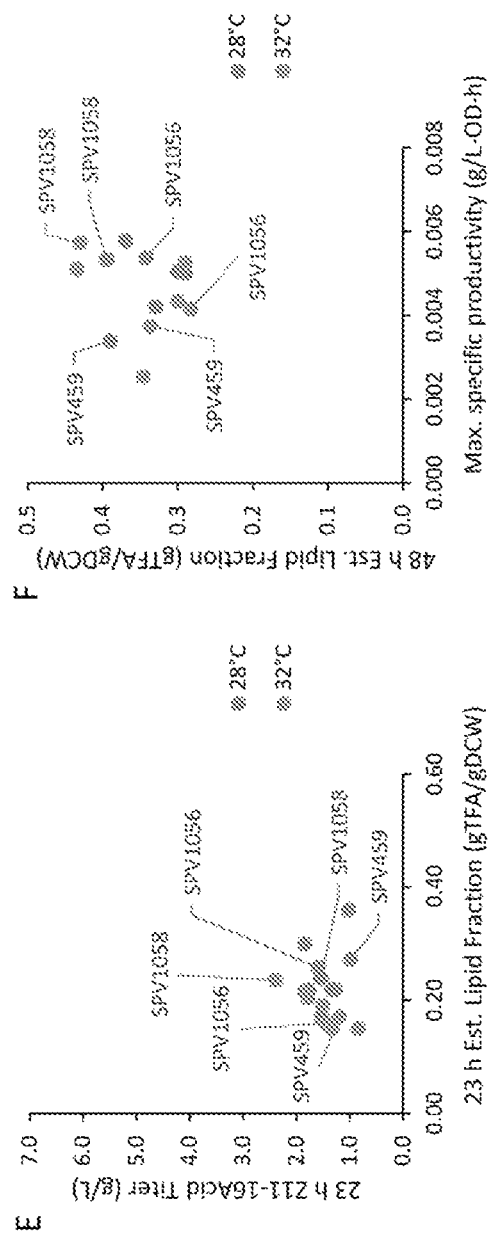

FIG. 25A-FIG. 25F show correlation of Z11-16Acid performance metrics in High Glucose Medium. FIG. 25A: 48 h titers of Z11-16Acid moderately correlate with observed maximum specific productivity. Correlation is improved at 32° C. FIG. 25B: 48 h Z11-16Acid titer and selectivity are also moderately correlated. FIG. 25C: 23 h and 48 h Z11-16Acid selectivity are weakly correlated at 32° C. FIG. 25D: 48 h Z11-16Acid titer and estimated lipid fraction are not well correlated. FIG. 25E: 23 h Z11-16Acid titer and selectivity are tightly clustered. FIG. 25F: Estimates of total lipid fraction do not correlate with observed maximum specific productivities.

Figures 26A, 26B:
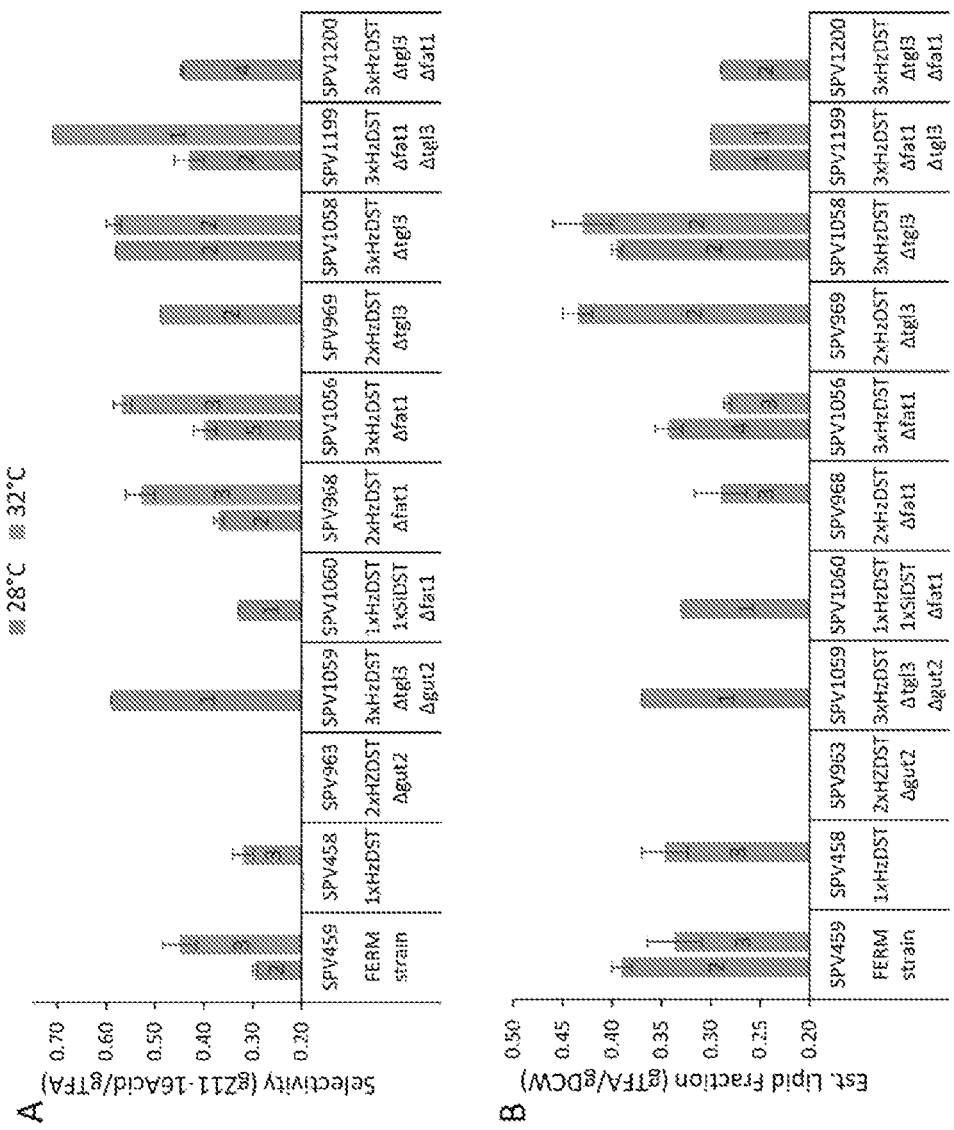

FIG. 26A-FIG. 26B show Z11-16Acid selectivity and estimated lipid fractions in High Glucose Medium at both 28 and 32° C. FIG. 26A: Z11-16Acid selectivity at the 48 hour timepoint. FIG. 26B: Lipid fractions (total fatty acid/dry cell weight) were estimated using measured fatty acid concentrations and by multiplying measured OD600 cell densities by a previously observed coefficient of 0.78 gDCW/L/OD600. Inset numbers indicate number of independent measurements. TFA=total fatty acids, DCW=dry cell weight.

FIG. 27 shows initial growth rates for HSD062 comparing High Glucose and High Glycerol media. Initial growth rates were similar in both media.

Figures 28A, 28B:
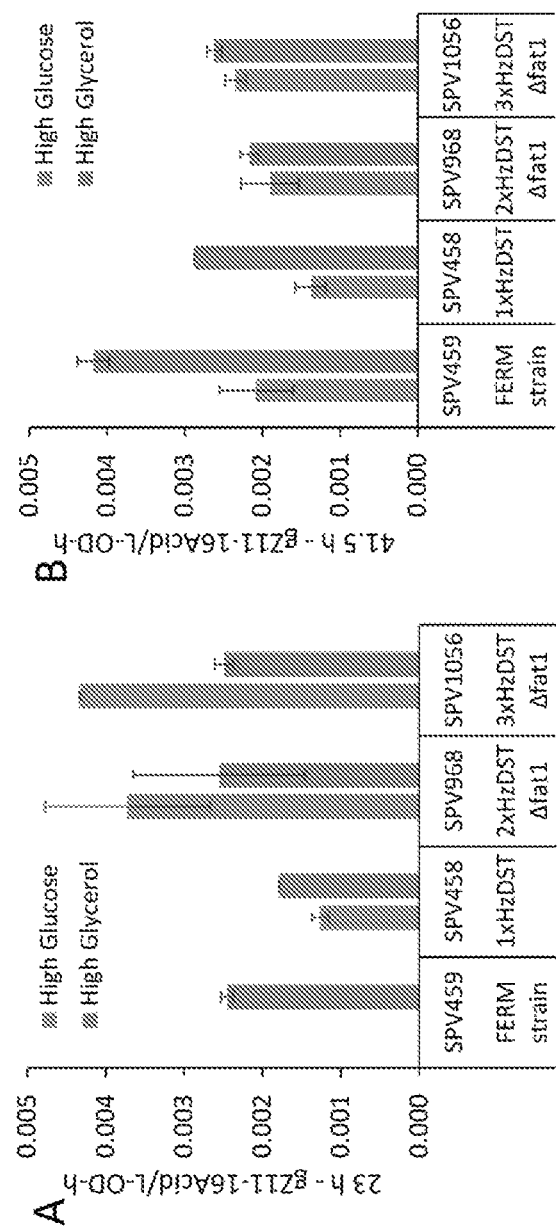

FIG. 28A-FIG. 28E show strain-specific response to a High Glycerol vs. High Glucose medium at 28° C. FIG. 28A: Z11-16Acid specific productivities from 7-23 hours. FIG. 28B: Z11-16Acid specific productivities from 7-41.5 hours. FIG. 28C: Z11-16Acid titer at 41.5 hours. FIG. 28D: Z11-16Acid selectivity at 41.5 hours. FIG. 28E: Estimated lipid fraction (total fatty acids/dry cell weight) at 41.5 hours. Lipid fractions were estimated using measured fatty acid concentrations and by multiplying measured OD600 cell densities by a previously observed coefficient of 0.78 gDCW/L/OD600.

Figure 29:
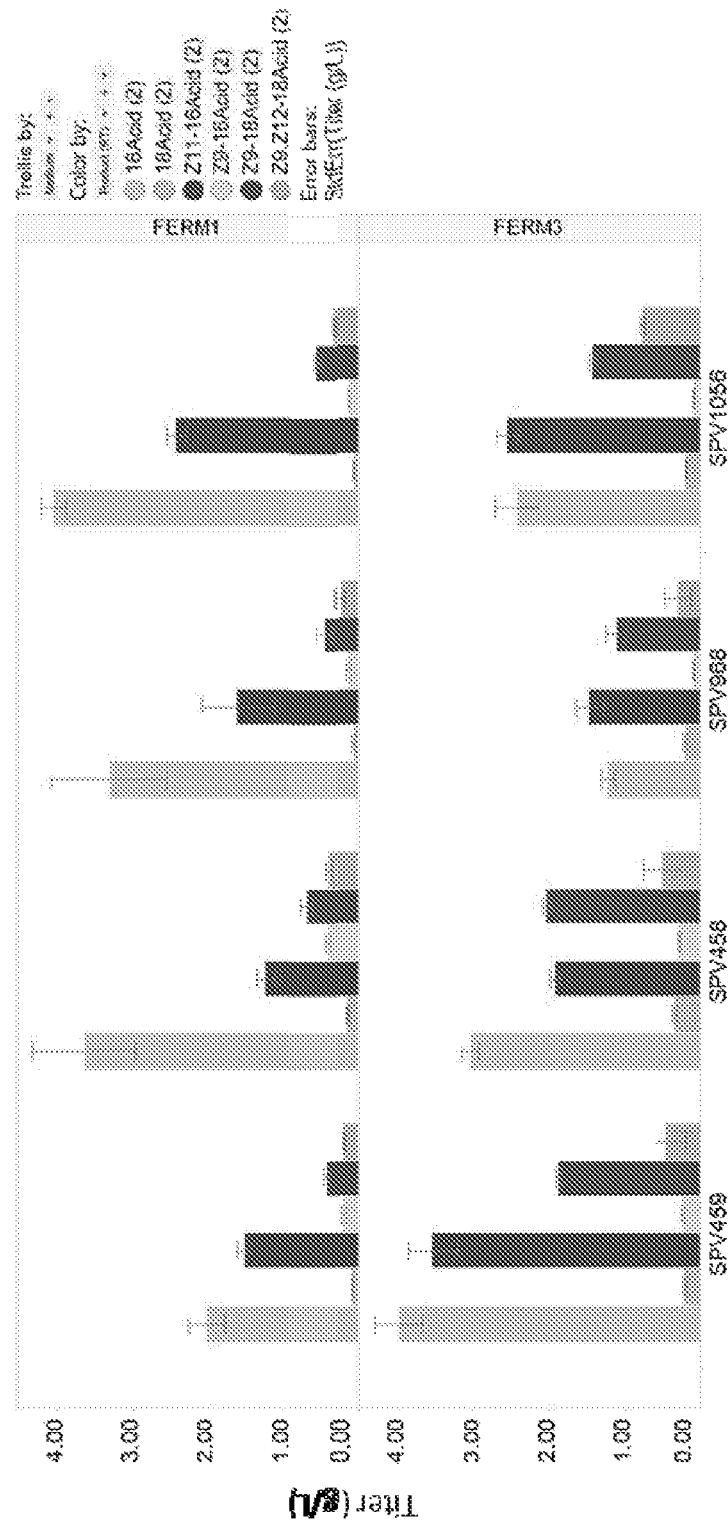

FIG. 29 shows fatty acid titers from HSD062. Top row: Titers in High Glucose Medium (FERM1). Bottom Row: Titers in High Glycerol Medium (FERM3).

Figure 30:
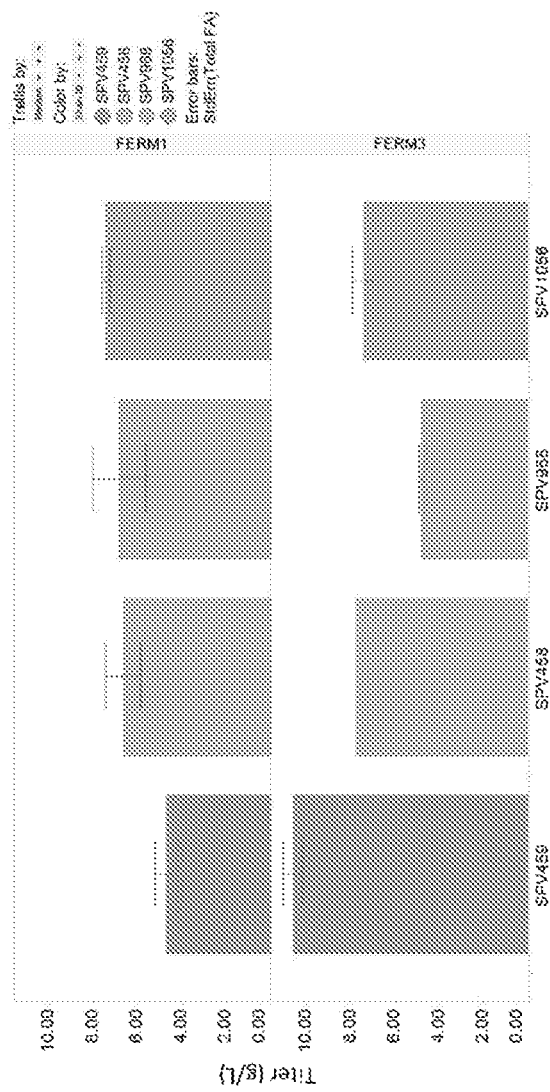

FIG. 30 shows total fatty acid (TFA) titers from HSD062. Top row: TFA Titers in High Glucose Medium (FERM1). Bottom Row: TFA Titers in High Glycerol Medium (FERM3).

Figures 31A, 31B:
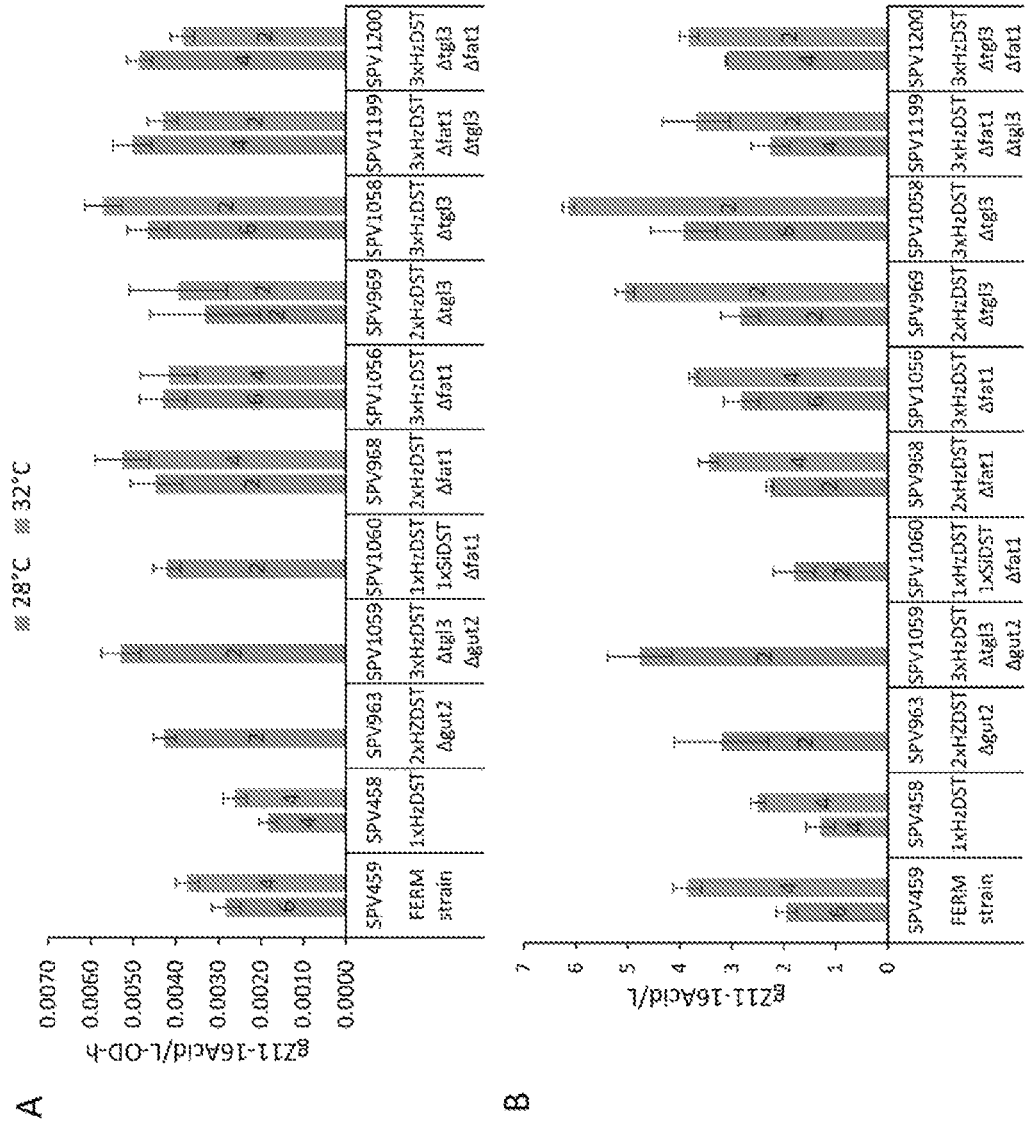
Figure 31E:
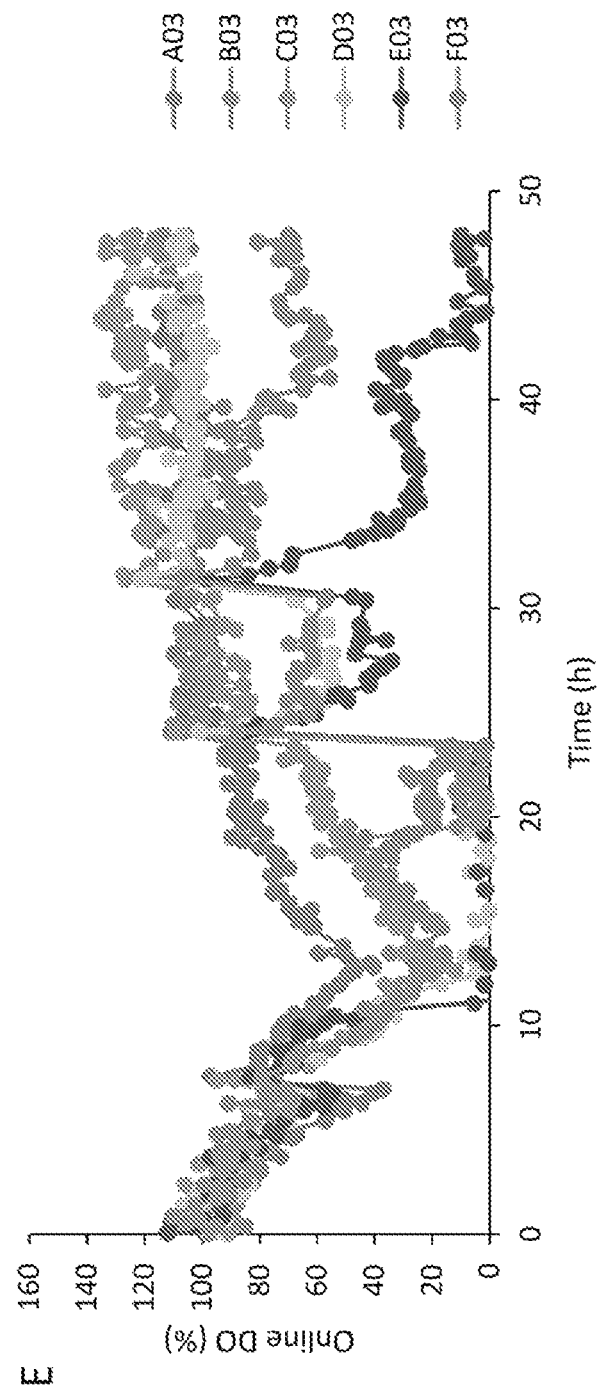

FIG. 31A-FIG. 31E show performance parameters of Z11-16Acid $B_d$ including data from all sampled wells. Some replicate cultures were incubated under hypoxic conditions when a substrate/biofilm formed on the underside of the plate seal in individual wells. Affected wells were identified by tracking the online dissolved oxygen concentration. In addition, cell densities and fatty acid titers were consistently lower in these wells. Here data is presented for all wells across all experiments. Inset numbers indicate number of independent measurements. FIG. 31A: Maximum specific productivities (from 7-23 hours). Cell densities are taken from independent measurements using a plate reader. FIG. 31B: 48 hour (maximum observed) Z11-16Acid titers. FIG. 31C: 48 hour Z11-16Acid selectivity. FIG. 31D: Lipid fractions (total fatty acid/dry cell weight) were estimated using measured fatty acid concentrations and by multiplying measured OD600 cell densities by a previously observed coefficient of 0.78 gDCW/L/OD600. FIG. 31E: Example of online dissolved oxygen measurements indicating hypoxic conditions for Column 3 wells of HSD043. All wells started under the same conditions and were inoculated with the same strain. The seal was replaced at 23 and 31 hours. Wells D03, E03, and F03 were hypoxic for varying durations during the period after substrate addition (7 hours) and first sampling (23 hours).

Figure 32:
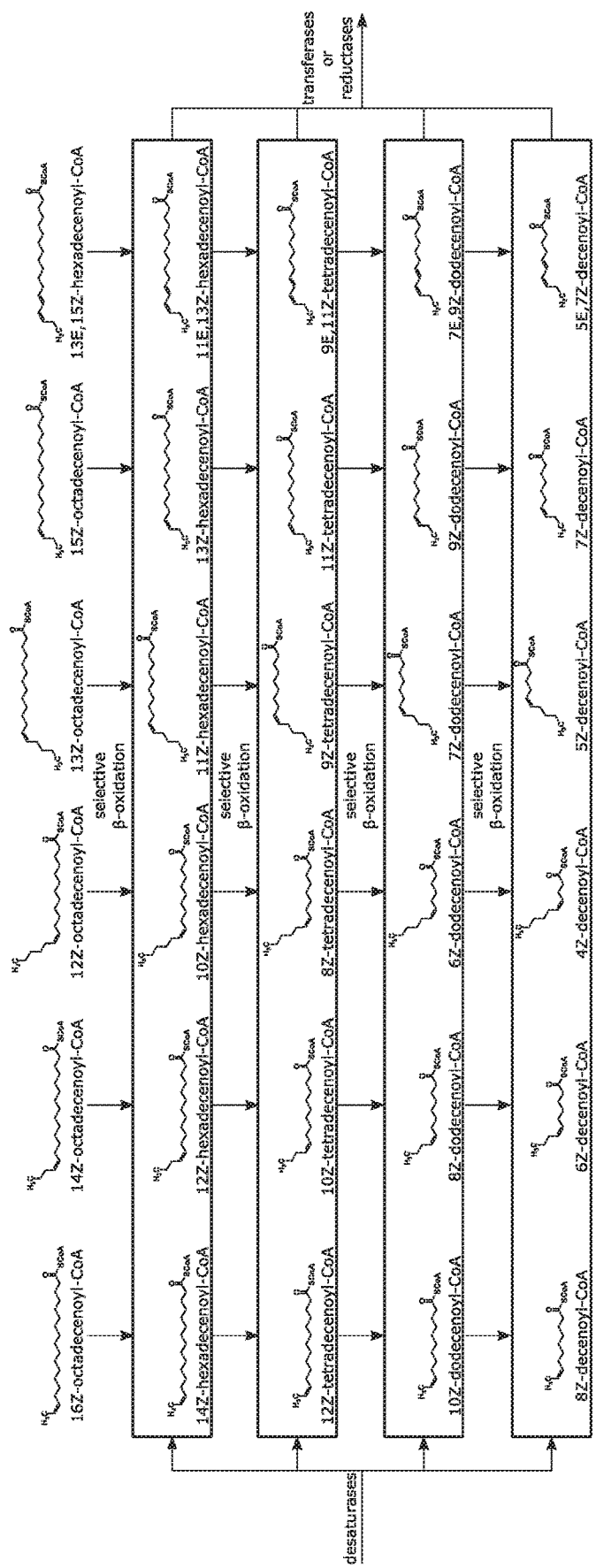

FIG. 32 shows examples of acyl-CoA intermediates generated through selective β-oxidation controlled by acyl-CoA oxidase activity.

SEQUENCES

A sequence listing for SEQ ID NO: 1-SEQ ID NO: 47 is part of this application and is incorporated by reference herein. The sequence listing is provided at the end of this document.

DETAILED DESCRIPTION

Definitions

The following definitions and abbreviations are to be used for the interpretation of the disclosure.

As used herein and in the appended claims, the singular forms "a," "an," and "the" include plural referents unless the context clearly dictates otherwise. Thus, for example, reference to "a pheromone" includes a plurality of such pheromones and reference to "the microorganism" includes reference to one or more microorganisms, and so forth.

As used herein, the terms "comprises," "comprising," "includes," "including," "has," "having, "contains," "containing," or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or."

The terms "about" and "around," as used herein to modify a numerical value, indicate a close range surrounding that explicit value. If "X" were the value, "about X" or "around X" would indicate a value from 0.9X to 1.1X, or, in some embodiments, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

As used herein, the terms "microbial," "microbial organism," and "microorganism" include any organism that exists as a microscopic cell that is included within the domains of archaea, bacteria or eukarya, the latter including yeast and filamentous fungi, protozoa, algae, or higher Protista. Therefore, the term is intended to encompass prokaryotic or eukaryotic cells or organisms having a microscopic size and includes bacteria, archaea, and eubacteria of all species as well as eukaryotic microorganisms such as yeast and fungi. Also included are cell cultures of any species that can be cultured for the production of a chemical.

As described herein, in some embodiments, the recombinant microorganisms are prokaryotic microorganism. In some embodiments, the prokaryotic microorganisms are bacteria. "Bacteria", or "eubacteria", refers to a domain of prokaryotic organisms. Bacteria include at least eleven distinct groups as follows: (1) Gram-positive (gram+) bacteria, of which there are two major subdivisions: (1) high G+C group (Actinomycetes, Mycobacteria, *Micrococcus*, others) (2) low G+C group (*Bacillus, Clostridia, Lactobacillus, Staphylococci, Streptococci, Mycoplasmas*); (2) Proteobacteria, e.g., Purple photosynthetic+non-photosynthetic Gram-negative bacteria (includes most "common" Gram-negative bacteria); (3) Cyanobacteria, e.g., oxygenic phototrophs; (4) Spirochetes and related species; (5) *Planctomyces*; (6) *Bacteroides*, Flavobacteria; (7) *Chlamydia*; (8) Green sulfur bacteria; (9) Green non-sulfur bacteria (also anaerobic phototrophs); (10) Radioresistant micrococci and relatives; (11) *Thermotoga* and *Thermosipho* thermophiles.

"Gram-negative bacteria" include cocci, nonenteric rods, and enteric rods. The genera of Gram-negative bacteria include, for example, *Neisseria, Spirillum, Pasteurella, Brucella, Yersinia, Francisella, Haemophilus, Bordetella, Escherichia, Salmonella, Shigella, Klebsiella, Proteus, Vibrio, Pseudomonas, Bacteroides, Acetobacter, Aerobacter, Agrobacterium, Azotobacter, Spirilla, Serratia, Vibrio, Rhizobium, Chlamydia, Rickettsia, Treponema*, and *Fusobacterium*.

"Gram positive bacteria" include cocci, nonsporulating rods, and sporulating rods. The genera of gram positive bacteria include, for example, *Actinomyces, Bacillus, Clostridium, Corynebacterium, Erysipelothrix, Lactobacillus, Listeria, Mycobacterium, Myxococcus, Nocardia, Staphylococcus, Streptococcus*, and *Streptomyces*.

The term "recombinant microorganism" and "recombinant host cell" are used interchangeably herein and refer to microorganisms that have been genetically modified to express or to overexpress endogenous enzymes, to express heterologous enzymes, such as those included in a vector, in an integration construct, or which have an alteration in expression of an endogenous gene. By "alteration" it is meant that the expression of the gene, or level of a RNA molecule or equivalent RNA molecules encoding one or more polypeptides or polypeptide subunits, or activity of one or more polypeptides or polypeptide subunits is up regulated or down regulated, such that expression, level, or activity is greater than or less than that observed in the absence of the alteration. For example, the term "alter" can mean "inhibit," but the use of the word "alter" is not limited to this definition. It is understood that the terms "recombinant microorganism" and "recombinant host cell" refer not only to the particular recombinant microorganism but to the progeny or potential progeny of such a microorganism. Because certain modifications may occur in succeeding generations due to either mutation or environmental influences, such progeny may not, in fact, be identical to the parent cell, but are still included within the scope of the term as used herein.

The term "expression" with respect to a gene sequence refers to transcription of the gene and, as appropriate, translation of the resulting mRNA transcript to a protein. Thus, as will be clear from the context, expression of a protein results from transcription and translation of the open reading frame sequence. The level of expression of a desired product in a host cell may be determined on the basis of either the amount of corresponding mRNA that is present in the cell, or the amount of the desired product encoded by the selected sequence. For example, mRNA transcribed from a selected sequence can be quantitated by qRT-PCR or by Northern hybridization (see Sambrook et al., Molecular Cloning: A Laboratory Manual, Cold Spring Harbor Laboratory Press (1989)). Protein encoded by a selected sequence can be quantitated by various methods, e.g., by ELISA, by assaying for the biological activity of the protein, or by employing assays that are independent of such activity, such as western blotting or radioimmunoassay, using antibodies that recognize and bind the protein. See Sambrook et al., 1989, supra.

The term "polynucleotide" is used herein interchangeably with the term "nucleic acid" and refers to an organic polymer composed of two or more monomers including nucleotides, nucleosides or analogs thereof, including but not limited to single stranded or double stranded, sense or antisense deoxyribonucleic acid (DNA) of any length and, where appropriate, single stranded or double stranded, sense or antisense ribonucleic acid (RNA) of any length, including siRNA. The term "nucleotide" refers to any of several compounds that consist of a ribose or deoxyribose sugar joined to a purine or a pyrimidine base and to a phosphate group, and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers, respectively, to a nucleotide or nucleoside in which one or more individual atoms have been replaced with a different atom or with a different functional group. Accordingly, the term polynucleotide includes nucleic acids of any length, DNA, RNA, analogs and fragments thereof. A polynucleotide of three or more nucleotides is also called nucleotidic oligomer or oligonucleotide.

It is understood that the polynucleotides described herein include "genes" and that the nucleic acid molecules described herein include "vectors" or "plasmids." Accordingly, the term "gene", also called a "structural gene" refers to a polynucleotide that codes for a particular sequence of amino acids, which comprise all or part of one or more proteins or enzymes, and may include regulatory (non-transcribed) DNA sequences, such as promoter sequences, which determine for example the conditions under which the gene is expressed. The transcribed region of the gene may include untranslated regions, including introns, 5'-untranslated region (UTR), and 3'-UTR, as well as the coding sequence.

The term "enzyme" as used herein refers to any substance that catalyzes or promotes one or more chemical or biochemical reactions, which usually includes enzymes totally or partially composed of a polypeptide or polypeptides, but can include enzymes composed of a different molecule including polynucleotides.

As used herein, the term "non-naturally occurring," when used in reference to a microorganism of the disclosure, is intended to mean that the microorganism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microorganism's genetic material. Such modifications include, for example, coding regions and functional fragments thereof, for heterologous, homologous, or both heterologous and homologous polypeptides for the referenced species. Additional modifications include, for example, non-coding regulatory regions in which the modifications alter expression of a gene or operon. Exemplary non-naturally occurring microorganisms include recombinant microorganisms engineered for the production of unsaturated lipid moieties described herein.

By contrast, the term "naturally occurring," when used in reference to a organism of the disclosure, is intended to mean an organism that has not been manipulated to comprise a genetically engineered biosynthesis pathway for the recombinant production of the one or more unsaturated lipid moieties.

The term "exogenous" as used herein with reference to various molecules, e.g., polynucleotides, polypeptides, enzymes, etc., refers to molecules that are not normally or naturally found in and/or produced by a given yeast, bacterium, organism, microorganism, or cell in nature.

On the other hand, the term "endogenous" or "native" as used herein with reference to various molecules, e.g., polynucleotides, polypeptides, enzymes, etc., refers to molecules that are normally or naturally found in and/or produced by a given yeast, bacterium, organism, microorganism, or cell in nature.

The term "heterologous" as used herein in the context of a modified host cell refers to various molecules, e.g., polynucleotides, polypeptides, enzymes, etc., wherein at least one of the following is true: (a) the molecule(s) is/are foreign ("exogenous") to (i.e., not naturally found in) the host cell; (b) the molecule(s) is/are naturally found in (e.g., is "endogenous to") a given host microorganism or host cell but is either produced in an unnatural location or in an unnatural amount in the cell; and/or (c) the molecule(s) differ(s) in nucleotide or amino acid sequence from the endogenous nucleotide or amino acid sequence(s) such that the molecule differing in nucleotide or amino acid sequence from the endogenous nucleotide or amino acid as found endogenously is produced in an unnatural (e.g., greater than naturally found) amount in the cell or is produced with an unnatural (e.g., greater than naturally found) activity level in the cell.

The term "homolog," as used herein with respect to an original enzyme or gene of a first family or species, refers to distinct enzymes or genes of a second family or species which are determined by functional, structural, or genomic analyses to be an enzyme or gene of the second family or species which corresponds to the original enzyme or gene of the first family or species. Homologs most often have functional, structural, or genomic similarities. Techniques are known by which homologs of an enzyme or gene can readily be cloned using genetic probes and PCR. Identity of cloned sequences as homologs can be confirmed using functional assays and/or by genomic mapping of the genes.

A protein has "homology" or is "homologous" to a second protein if the amino acid sequence encoded by a gene has a similar amino acid sequence to that of the second gene. Alternatively, a protein has homology to a second protein if the two proteins have "similar" amino acid sequences. Thus, the term "homologous proteins" is intended to mean that the two proteins have similar amino acid sequences. In certain instances, the homology between two proteins is indicative of its shared ancestry, related by evolution.

The term "fatty acid" as used herein refers to a compound of structure R—COOH, wherein R is a $C_6$ to $C_{24}$ saturated, unsaturated, linear, branched or cyclic hydrocarbon and the carboxyl group is at position 1. In a particular embodiment, R is a $C_6$ to $C_{24}$ saturated or unsaturated linear hydrocarbon and the carboxyl group is at position 1.

The term "fatty alcohol" as used herein refers to an aliphatic alcohol having the formula R—OH, wherein R is a $C_6$ to $C_{24}$ saturated, unsaturated, linear, branched or cyclic hydrocarbon. In a particular embodiment, R is a $C_6$ to $C_{24}$ saturated or unsaturated linear hydrocarbon.

The term "fatty acyl-CoA" refers to a compound having the structure R—(CO)—S—$R_1$, wherein $R_1$ is Coenzyme A, and the term "fatty acyl-ACP" refers to a compound having the structure R—(CO)—S—$R_1$, wherein $R_1$ is an acyl carrier protein ACP.

The term "fatty acid derivative" as used herein refers to any organic molecular entity derived from a fatty acid. Fatty acid derivatives include, but are not limited to, saturated fatty acids, monounsaturated fatty acids, polyunsaturated fatty acids, branched fatty acids, triacylglycerol (triglyceride) and alkyl esters of fatty acids.

The term "semi-biosynthesis" as used herein refers to synthesis of products by combining biological and non-biological means. In one embodiment, the biological means comprises obtaining one or more compounds or molecules from one or more natural sources, such as a naturally occurring organism. In some embodiments, the one or more naturally occurring organism can be a plant, a bacteria, an algae, a yeast, and/or cell cultures. In another embodiment, the biological means comprises obtaining one or more compounds or molecules from one or more recombinant microorganisms that have been engineered to produce the compounds or molecules. These compounds or molecules can further be modified to final products by non-biological means such as chemical synthesis. Chemical synthesis is the preparation of a compound by performing various chemical reactions using a starting material and changing its molecular structure by reactions with other chemicals. The starting materials for organic synthesis can be simple compounds removed from oil and natural gas or more complex chemicals isolated in large amounts from plant and animal sources. In certain embodiments, the semi-biosynthesis of one or more fatty alcohols and/or fatty aldehydes from one or more unsaturated lipid moieties comprise: obtaining one or more unsaturated lipid moieties from one or more naturally occurring organisms or producing the one or more unsaturated lipid moieties in one or more recombinant microorganisms manipulated to comprise a biosynthesis pathway for the production of the one or more unsaturated lipid moieties, chemically converting the one or more unsaturated lipid moieties to one or more free fatty acid (FFAs) and/or one or more fatty acid methyl esters (FAAEs), and reducing the one or more FFAs and/or one or more FAAEs, wherein the reduction produces one or more fatty alcohols and/or one or more fatty aldehydes.

The term "unsaturated lipid moieties" as used herein refers to lipids or lipid derivatives with one or more double bonds. Lipids are biological molecules that are insoluble in aqueous solution and soluble in organic solvents. Unsaturated lipid moieties can include, but are not limited to, monounsaturated fatty acids, polyunsaturated fatty acids, branched unsaturated fatty acids and unsaturated triacylglycerol (unsaturated triglyceride). Unsaturated lipid moieties can include fats, sterols, waxes, oils, fat soluble vitamins, phospholipids, sphingolipids, plasmalogen, eicosanoids, terpenes, and soaps and detergents.

The term "non-biological conversion" as used herein refers to conversion of one or more substrates to one or more products using chemical means. In one embodiment, one or more unsaturated lipid moieties are chemically converted to one or more FFAs and/or one or more FAAEs. In another embodiment, one or more unsaturated lipid moieties, one or more FFAs and/or one or more FAAEs are reduced to one or more fatty alcohols and/or one or more fatty aldehydes by contacting the one or more unsaturated lipid moieties, the one or more FFAs and/or the one or more FAAEs with one or more stoichiometric reducing agents such as sodium bis(2-methoxyethoxy)aluminumhydrideVitride (Red-Al, Vitride, SMEAH) and/or diisobutylaluminumhydride (DIBAL). Additionally, a bulky cyclic nitrogen Lewis base can be used to modify the reducing agent to allow for selectivity of the reducing step for the production of one or more fatty aldehydes. In another embodiment, the step of reducing the one or more unsaturated lipid moieties, the one or more FFAs and/or the one or more FAAEs to one or more fatty alcohols comprises contacting the one or more unsaturated lipid moieties, the one or more FFAs and/or the one or more FAAEs with one or more transition metal catalysts such as one or more group VIII catalysts. In another embodiment, the fatty alcohols produced are further oxidized to fatty aldehydes by an oxidation step. The oxidation step can be one or more partial oxidation methods such as NaOCl/TEMPO. In other embodiments, the oxidation step comprises a copper-catalyzed aerobic oxidation.

INTRODUCTION

The present disclosure addresses the need for novel technologies for the cost-efficient production of valuable products from low-cost feedstocks. Specifically, the present inventors have addressed this need with the development of methods of producing one or more fatty alcohols and/or one or more fatty aldehydes from one or more unsaturated lipid moieties by combining the obtainment or production of the one or more unsaturated lipid moieties from a biological source with conversion by non-biological means of the one or more unsaturated lipid moieties to one or more fatty alcohols and/or one or more fatty aldehydes. The one or more fatty alcohols and/or one or more fatty aldehydes may be useful as insect pheromones, fragrances, flavors, and polymer intermediates. Thus, aspects of the disclosure are based on the inventors' discovery that unsaturated lipid moieties can be obtained from either naturally occurring organisms or produced by recombinant microorganisms that have been engineered to produce unsaturated lipid moieties from low-cost feedstocks, and that can be combined with conventional synthetic methodologies to produce one or more fatty alcohols and/or one or more fatty aldehydes useful as a variety of valuable products, including but not limited to, insect pheromones, fragrances, flavors and polymer intermediates.

The application further relates to recombinant microorganisms useful in the biosynthesis of unsaturated lipid moieties as well as compositions comprising one or more fatty alcohols and/or one or more fatty aldehydes. Thus, various embodiments of the present disclosure can be used to synthesize a variety of insect pheromones selected from fatty alcohols, aldehydes, and acetates. Additionally, embodiments described herein can also be used for the synthesis of fragrances, flavors, and polymer intermediates.

Pheromones

As described above, embodiments of the disclosure provide for the semi-biosynthesis of one or more fatty alcohols and/or one or more fatty aldehydes from one or more unsaturated lipid moieties. The one or more fatty alcohols and/or one or more fatty aldehydes may be useful as insect pheromones. A pheromone is a volatile chemical compound that is secreted by a particular insect for the function of chemical communication within the species. That is, a pheromone is secreted or excreted chemical factor that triggers a social response in members of the same species. There are, inter alia, alarm pheromones, food trail pheromones, sex pheromones, aggregation pheromones, epideictic pheromones, releaser pheromones, primer pheromones, and territorial pheromones, that affect behavior or physiology.

Non-limiting examples of insect pheromones which can be synthesized using the recombinant microorganisms and methods disclosed herein include linear alcohols, aldehydes, and acetates listed in Table 1.

TABLE 1

$C_6$-$C_{20}$ Linear Pheromones

| Name | Name |
|---|---|
| (E)-2-Decen-1-ol | (E,E)-10,12-Tetradecadien-1-ol |
| (E)-2-Decenyl acetate | (E,E)-10,12-Tetradecadienyl acetate |
| (E)-2-Decenal | (E,E)-10,12-Tetradecadienal |
| (Z)-2-Decen-1-ol | (E,Z)-10,12-Tetradecadienyl acetate |
| (Z)-2-Decenyl acetate | (Z,E)-10,12-Tetradecadienyl acetate |
| (Z)-2-Decenal | (Z,Z)-10,12-Tetradecadien-1-ol |
| (E)-3-Decen-1-ol | (Z,Z)-10,12-Tetradecadienyl acetate |
| (Z)-3-Decenyl acetate | (E,Z,Z)-3,8,11-Tetradecatrienyl acetate |
| (Z)-3-Decen-1-ol | (E)-8-Pentadecen-1-ol |
| (Z)-4-Decen-1-ol | (E)-8-Pentadecenyl acetate |
| (E)-4-Decenyl acetate | (Z)-8-Pentadecen-1-ol |
| (Z)-4-Decenyl acetate | (Z)-8-Pentadecenyl acetate |
| (Z)-4-Decenal | (Z)-9-Pentadecenyl acetate |
| (E)-5-Decen-1-ol | (E)-9-Pentadecenyl acetate |
| (E)-5-Decenyl acetate | (Z)-10-Pentadecenyl acetate |
| (Z)-5-Decen-1-ol | (Z)-10-Pentadecenal |
| (Z)-5-Decenyl acetate | (E)-12-Pentadecenyl acetate |
| (Z)-5-Decenal | (Z)-12-Pentadecenyl acetate |
| (E)-7-Decenyl acetate | (Z,Z)-6,9-Pentadecadien-1-ol |
| (Z)-7-Decenyl acetate | (Z,Z)-6,9-Pentadecadienyl acetate |
| (E)-8-Decen-1-ol | (Z,Z)-6,9-Pentadecadienal |
| (E,E)-2,4-Decadienal | (E,E)-8,10-Pentadecadienyl acetate |
| (E,Z)-2,4-Decadienal | (E,Z)-8,10-Pentadecadien-1-ol |
| (Z,Z)-2,4-Decadienal | (E,Z)-8,10-Pentadecadienyl acetate |
| (E,E)-3,5-Decadienyl acetate | (Z,E)-8,10-Pentadecadienyl acetate |
| (Z,E)-3,5-Decadienyl acetate | (Z,Z)-8,10-Pentadecadienyl acetate |
| (Z,Z)-4,7-Decadien-1-ol | (E,Z)-9,11-Pentadecadienal |
| (Z,Z)-4,7-Decadienyl acetate | (Z,Z)-9,11-Pentadecadienal |
| (E)-2-Undecenyl acetate | (Z)-3-Hexadecenyl acetate |
| (E)-2-Undecenal | (E)-5-Hexadecen-1-ol |
| (Z)-5-Undecenyl acetate | (E)-5-Hexadecenyl acetate |
| (Z)-7-Undecenyl acetate | (Z)-5-Hexadecen-1-ol |
| (Z)-8-Undecenyl acetate | (Z)-5-Hexadecenyl acetate |
| (Z)-9-Undecenyl acetate | (E)-6-Hexadecenyl acetate |
| (E)-2-Dodecenal | (E)-7-Hexadecen-1-ol |
| (Z)-3-Dodecen-1-ol | (E)-7-Hexadecenyl acetate |
| (E)-3-Dodecenyl acetate | (E)-7-Hexadecenal |
| (Z)-3-Dodecenyl acetate | (Z)-7-Hexadecen-1-ol |
| (E)-4-Dodecenyl acetate | (Z)-7-Hexadecenyl acetate |
| (E)-5-Dodecen-1-ol | (Z)-7-Hexadecenal |
| (E)-5-Dodecenyl acetate | (E)-8-Hexadecenyl acetate |
| (Z)-5-Dodecen-1-ol | (E)-9-Hexadecen-1-ol |
| (Z)-5-Dodecenyl acetate | (E)-9-Hexadecenyl acetate |
| (Z)-5-Dodecenal | (E)-9-Hexadecenal |
| (E)-6-Dodecen-1-ol | (Z)-9-Hexadecen-1-ol |
| (Z)-6-Dodecenyl acetate | (Z)-9-Hexadecenyl acetate |
| (E)-6-Dodecenal | (Z)-9-Hexadecenal |
| (E)-7-Dodecen-1-ol | (E)-10-Hexadecen-1-ol |
| (E)-7-Dodecenyl acetate | (E)-10-Hexadecenal |
| (E)-7-Dodecenal | (Z)-10-Hexadecenyl acetate |
| (Z)-7-Dodecen-1-ol | (Z)-10-Hexadecenal |
| (Z)-7-Dodecenyl acetate | (E)-11-Hexadecen-1-ol |
| (Z)-7-Dodecenal | (E)-11-Hexadecenyl acetate |
| (E)-8-Dodecen-1-ol | (E)-11-Hexadecenal |
| (E)-8-Dodecenyl acetate | (Z)-11-Hexadecen-1-ol |
| (E)-8-Dodecenal | (Z)-11-Hexadecenyl acetate |
| (Z)-8-Dodecen-1-ol | (Z)-11-Hexadecenal |
| (Z)-8-Dodecenyl acetate | (Z)-12-Hexadecenyl acetate |
| (E)-9-Dodecen-1-ol | (Z)-12-Hexadecenal |
| (E)-9-Dodecenyl acetate | (E)-14-Hexadecenal |
| (E)-9-Dodecenal | (Z)-14-Hexadecenyl acetate |
| (Z)-9-Dodecen-1-ol | (E,E)-1,3-Hexadecadien-1-ol |
| (Z)-9-Dodecenyl acetate | (E,Z)-4,6-Hexadecadien-1-ol |
| (Z)-9-Dodecenal | (E,Z)-4,6-Hexadecadienyl acetate |
| (E)-10-Dodecen-1-ol | (E,Z)-4,6-Hexadecadienal |

TABLE 1-continued $C_6$-$C_{20}$ Linear Pheromones

| Name | Name |
|---|---|
| (E)-10-Dodecenyl acetate | (E,Z)-6,11-Hexadecadienyl acetate |
| (E)-10-Dodecenal | (E,Z)-6,11-Hexadecadienal |
| (Z)-10-Dodecen-1-ol | (Z,Z)-7,10-Hexadecadien-1-ol |
| (Z)-10-Dodecenyl acetate | (Z,Z)-7,10-Hexadecadienyl acetate |
| (E,Z)-3,5-Dodecadienyl acetate | (Z,E)-7,11-Hexadecadien-1-ol |
| (Z,E)-3,5-Dodecadienyl acetate | (Z,E)-7,11-Hexadecadienyl acetate |
| (Z,Z)-3,6-Dodecadien-1-ol | (Z,E)-7,11-Hexadecadienal |
| (E,E)-4,10-Dodecadienyl acetate | (Z,Z)-7,11-Hexadecadien-1-ol |
| (E,E)-5,7-Dodecadien-1-ol | (Z,Z)-7,11-Hexadecadienyl acetate |
| (E,E)-5,7-Dodecadienyl acetate | (Z,Z)-7,11-Hexadecadienal |
| (E,Z)-5,7-Dodecadien-1-ol | (Z,Z)-8,10-Hexadecadienyl acetate |
| (EZ)-5,7-Dodecadienyl acetate | (E,Z)-8,11-Hexadecadienal |
| (E,Z)-5,7-Dodecadienal | (E,E)-9,11-Hexadecadienal |
| (Z,E)-5,7-Dodecadien-1-ol | (E,Z)-9,11-Hexadecadienyl acetate |
| (Z,E)-5,7-Dodecadienyl acetate | (E,Z)-9,11-Hexadecadienal |
| (Z,E)-5,7-Dodecadienal | (Z,E)-9,11-Hexadecadienal |
| (Z,Z)-5,7-Dodecadienyl acetate | (Z,Z)-9,11-Hexadecadienal |
| (Z,Z)-5,7-Dodecadienal | (E,E)-10,12-Hexadecadien-1-ol |
| (E,E)-7,9-Dodecadienyl acetate | (E,E)-10,12-Hexadecadienyl acetate |
| (E,Z)-7,9-Dodecadien-1-ol | (E,E)-10,12-Hexadecadienal |
| (E,Z)-7,9-Dodecadienyl acetate | (E,Z)-10,12-Hexadecadien-1-ol |
| (E,Z)-7,9-Dodecadienal | (E,Z)-10,12-Hexadecadienyl acetate |
| (Z,E)-7,9-Dodecadien-1-ol | (E,Z)-10,12-Hexadecadienal |
| (Z,E)-7,9-Dodecadienyl acetate | (Z,E)-10,12-Hexadecadienyl acetate |
| (Z,Z)-7,9-Dodecadien-1-ol | (Z,E)-10,12-Hexadecadienal |
| (Z,Z)-7,9-Dodecadienyl acetate | (Z,Z)-10,12-Hexadecadienal |
| (E,E)-8,10-Dodecadien-1-ol | (E,E)-11,13-Hexadecadien-1-ol |
| (E,E)-8,10-Dodecadienyl acetate | (E,E)-11,13-Hexadecadienyl acetate |
| (E,E)-8,10-Dodecadie al | (E,E)-11,13-Hexadecadienal |
| (E,Z)-8,10-Dodecadien-1-ol | (E,Z)-11,13-Hexadecadien-1-ol |
| (E,Z)-8,10-Dodecadienyl acetate | (E,Z)-11,13-Hexadecadienyl acetate |
| (E,Z)-8,10-Dodecadienal | (E,Z)-11,13-Hexadecadienal |
| (Z,E)-8,10-Dodecadien-1-ol | (Z,E)-11,13-Hexadecadien-1-ol |
| (Z,E)-8,10-Dodecadienyl acetate | (Z,E)-11,13-Hexadecadienyl acetate |
| (Z,E)-8,10-Dodecadienal | (Z,E)-11,13-Hexadecadienal |
| (Z,Z)-8,10-Dodecadien-1-ol | (Z,Z)-11,13-Hexadecadien-1-ol |
| (Z,Z)-8,10-Dodecadienyl acetate | (Z Z)-11,13-Hexadecadienyl acetate |
| (Z,E,E)-3,6,8-Dodecatrien-1-ol | (Z,Z)-11,13-Hexadecadienal |
| (Z,Z,E)-3,6,8-Dodecatrien-1-ol | (E,E)-10,14-Hexadecadienal |
| (E)-2-Tridecenyl acetate | (Z,E)-11,14-Hexadecadienyl acetate |
| (Z)-2-Tridecenyl acetate | (E,E,Z)-4,6,10-Hexadecatrien-1-ol |
| (E)-3-Tridecenyl acetate | (E,E,Z)-4,6,10-Hexadecatrienyl acetate |
| (E)-4-Tridecenyl acetate | (E,Z,Z)-4,6,10-Hexadecatrien-1-ol |
| (Z)-4-Tridecenyl acetate | (E,Z,Z)-4,6,10-Hexadecatrienyl acetate |
| (Z)-4-Tridecenal | (E,E,Z)-4,6,11-Hexadecatrienyl acetate |
| (E)-6-Tridecenyl acetate | (E,E,Z)-4,6,11-Hexadecatrienal |
| (Z)-7-Tridecenyl acetate | (Z,Z,E)-7,11,13-Hexadecatrienal |
| (E)-8-Tridecenyl acetate | (E,E,E)-10,12,14-Hexadecatrienyl acetate |
| (Z)-8-Tridecenyl acetate | (E,E,E)-10,12,14-Hexadecatrienal |
| (E)-9-Tridecenyl acetate | (E,E,Z)-10,12,14-Hexadecatrienyl acetate |
| (Z)-9-Tridecenyl acetate | (E,E,Z)-10,12,14-Hexadecatrienal |
| (Z)-10-Tridecenyl acetate | (E,E,Z,Z)-4,6,11,13-Hexadecatetraenal |
| (E)-11-Tridecenyl acetate | (E)-2-Heptadecenal |
| (Z)-11-Tridecenyl acetate | (Z)-2-Heptadecenal |
| (E,Z)-4,7-Tridecadienyl acetate | (E)-8-Heptadecen-1-ol |
| (Z,Z)-4,7-Tridecadien-1-ol | (E)-8-Heptadecenyl acetate |
| (Z,Z)-4,7-Tridecadienyl acetate | (Z)-8-Heptadecen-1-ol |
| (E,Z)-5,9-Tridecadienyl acetate | (Z)-9-Heptadecenal |
| (Z,E)-5,9-Tridecadienyl acetate | (E)-10-Heptadecenyl acetate |
| (Z,Z)-5,9-Tridecadienyl acetate | (Z)-11-Heptadecen-1-ol |
| (Z,Z)-7,11-Tridecadienyl acetate | (Z)-11-Heptadecenyl acetate |
| (E,Z,Z)-4,7,10-Tridecatrienyl acetate | (E,E)-4,8-Heptadecadienyl acetate |
| (E)-3-Tetradecen-1-ol | (Z,Z)-8,10-Heptadecadien-1-ol |
| (E)-3-Tetradecenyl acetate | (Z,Z)-8,11-Heptadecadienyl acetate |
| (Z)-3-Tetradecen-1-ol | (E)-2-Octadecenyl acetate |
| (Z)-3-Tetradecenyl acetate | (E)-2-Octadecenal |
| (E)-5-Tetradecen-1-ol | (Z)-2-Octadecenyl acetate |
| (E)-5-Tetradecenyl acetate | (Z)-2-Octadecenal |
| (E)-5-Tetradecenal | (E)-9-Octadecen-1-ol |
| (Z)-5-Tetradecen-1-ol | (E)-9-Octadecenyl acetate |
| (Z)-5-Tetradecenyl acetate | (E)-9-Octadecenal |
| (Z)-5-Tetradecenal | (Z)-9-Octadecen-1-ol |
| (E)-6-Tetradecenyl acetate | (Z)-9-Octadecenyl acetate |
| (Z)-6-Tetradecenyl acetate | (Z)-9-Octadecenal |

TABLE 1-continued

$C_6$-$C_{20}$ Linear Pheromones

| Name | Name |
|---|---|
| (E)-7-Tetradecen-1-ol | (E)-11-Octadecen-1-ol |
| (E)-7-Tetradecenyl acetate | (E)-11-Octadecenal |
| (Z)-7-Tetradecen-1-ol | (Z)-11-Octadecen-1-ol |
| (Z)-7-Tetradecenyl acetate | (Z)-11-Octadecenyl acetate |
| (Z)-7-Tetradecenal | (Z)-11-Octadecenal |
| (E)-8-Tetradecenyl acetate | (E)-13-Octadecenyl acetate |
| (Z)-8-Tetradecen-1-ol | (E)-13-Octadecenal |
| (Z)-8-Tetradecenyl acetate | (Z)-13-Octadecen-1-ol |
| (Z)-8-Tetradecenal | (Z)-13-Octadecenyl acetate |
| (E)-9-Tetradecen-1-ol | (Z)-13-Octadecenal |
| (E)-9-Tetradecenyl acetate | (E)-14-Octadecenal |
| (Z)-9-Tetradecen-1-ol | (E,Z)-2,13-Octadecadien-1-ol |
| (Z)-9-Tetradecenyl acetate | (E,Z)-2,13-Octadecadienyl acetate |
| (Z)-9-Tetradecenal | (E,Z)-2,13-Octadecadienal |
| (E)-10-Tetradecenyl acetate | (Z,E)-2,13-Octadecadienyl acetate |
| (Z)-10-Tetradecenyl acetate | (Z,Z)-2,13-Octadecadien-1-ol |
| (E)-11-Tetradecen-1-ol | (Z,Z)-2,13-Octadecadienyl acetate |
| (E)-11-Tetradecenyl acetate | (E,E)-3,13-Octadecadienyl acetate |
| (E)-11-Tetradecenal | (E,Z)-3,13-Octadecadienyl acetate |
| (Z)-11-Tetradecen-1-ol | (E,Z)-3,13-Octadecadienal |
| (Z)-11-Tetradecenyl acetate | (Z,E)-3,13-Octadecadienyl acetate |
| (Z)-11-Tetradecenal | (Z,Z)-3,13-Octadecadienyl acetate |
| (E)-12-Tetradecenyl acetate | (Z,Z)-3,13-Octadecadienal |
| (Z)-12-Tetradecenyl acetate | (E,E)-5,9-Octadecadien-1-ol |
| (E,E)-2,4-Tetradecadienal | (E,E)-5,9-Octadecadienyl acetate |
| (E,E)-3,5-Tetradecadienyl acetate | (E,E)-9,12-Octadecadien-1-ol |
| (E,Z)-3,5-Tetradecadienyl acetate | (Z,Z)-9,12-Octadecadienyl acetate |
| (Z,E)-3,5-Tetradecadienyl acetate | (Z,Z)-9,12-Octadecadienal |
| (E,Z)-3,7-Tetradecadienyl acetate | (Z,Z)-11,13-Octadecadienal |
| (E,Z)-3,8-Tetradecadienyl acetate | (E,E)-11,14-Octadecadienal |
| (E,Z)-4,9-Tetradecadienyl acetate | (Z,Z)-13,15-Octadecadienal |
| (E,Z)-4,9-Tetradecadienal | (Z,Z,Z)-3,6,9-Octadecatrienyl acetate |
| (E,Z)-4,10-Tetradecadienyl acetate | (E,E,E)-9,12,15-Octadecatrien-1-ol |
| (E,E)-5,8-Tetradecadienal | (Z,Z,Z)-9,12,15-Octadecatnenyl acetate |
| (Z,Z)-5,8-Tetradecadien-1-ol | (Z,Z,Z)-9,12,15-Octadecatrienal |
| (Z,Z)-5,8-Tetradecadienyl acetate | |
| (Z,Z)-5,8-Tetradecadienal | |

TABLE 1-continued

$C_6$-$C_{20}$ Linear Pheromones

| Name | Name |
|---|---|
| (E,E)-8,10-Tetradecadien-1-ol | |
| (E,E)-8,10-Tetradecadienyl acetate | |
| (E,E)-8,10-Tetradecadienal | |
| (E,Z)-8,10-Tetradecadienyl acetate | |
| (E,Z)-8,10-Tetradecadienal | |
| (Z,E)-8,10-Tetradecadien-1-ol | |
| (Z,E)-8,10-Tetradecadienyl acetate | |
| (Z,Z)-8,10-Tetradecadienal | |
| (E,E)-9,11-Tetradecadienyl acetate | |
| (E,Z)-9,11-Tetradecadienyl acetate | |
| (Z,E)-9,11-Tetradecadien-1-ol | |
| (Z,E)-9,11-Tetradecadienyl acetate | |
| (Z,E)-9,11-Tetradecadienal | |
| (Z,Z)-9,11-Tetradecadien-1-ol | |
| (Z,Z)-9,11-Tetradecadienyl acetate | |
| (Z,Z)-9,11-Tetradecadienal | |
| (E,E)-9,12-Tetradecadienyl acetate | |
| (Z,E)-9,12-Tetradecadien-1-ol | |
| (Z,E)-9,12-Tetradecadienyl acetate | |
| (Z,E)-9,12-Tetradecadienal | |
| (Z,Z)-9,12-Tetradecadien-1-ol | |
| (Z,Z)-9,12-Tetradecadienyl acetate | |

In some aspects, the one or more fatty alcohols and/or one or more fatty aldehydes produced by the methods taught in this disclosure can be useful as insect pheromones. Exemplary pheromones to modulate the behavior of an insect are listed in Table 2. However, the methods and microorganisms described herein are not limited to the synthesis of C6-C20 pheromones listed in Table 1 and Table 2. Rather, the disclosed methods and microorganisms can also be utilized in the synthesis of various fatty alcohols, fatty aldehydes, and fatty acetates, including fragrances, flavors, and polymer intermediates.

TABLE 2

Exemplary pheromones that can be synthesized according to methods described in the present disclosure.

| Name | Structure | Example of Biological importance |
|---|---|---|
| (Z)-3-hexen-1-ol | 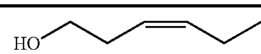 | See, Sugimoto et al. (2014) |
| (Z)-3-nonen-1-ol | 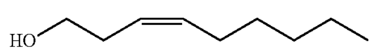 | West Indian Fruity Fly male sex pheromone |
| (Z)-5-decen-1-ol | 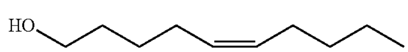 | |
| (Z)-5-decenyl acetate | 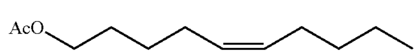 | *Agrotis segetum* sex pheromone component |
| (E)-5-decen-1-ol | 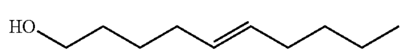 | *Anarsia lineatella* sex pheromone component |
| (E)-5-decenyl acetate | 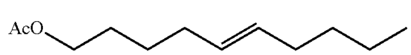 | *Anarsia lineatella* sex pheromone component |
| (Z)-7-dodecen-1-ol | 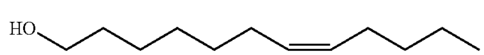 | |
| (Z)-7-dodecenyl acetate | 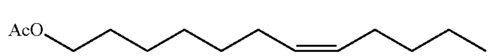 [SMILES: CCCC/C=C\CCCCCCOC(C)=O] | *Pseudoplusia includens* sex pheromone *Agrotis segetum* sex pheromone component |
| (E)-8-dodecen-1-ol | 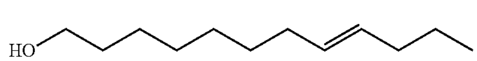 | Citrus Fruit Moth sex pheromone |

TABLE 2-continued

Exemplary pheromones that can be synthesized according to methods described in the present disclosure.

| Name | Structure | Example of Biological importance |
|---|---|---|
| (E)-8-dodecenyl acetate | 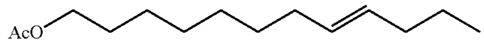 [SMILES: CCC/C=C/CCCCCCCOC(C)=O] | *Grapholitha molesta*, *Ecdytolopha aurantiana* sex pheromone component |
| (Z)-8-dodecen-1-ol | 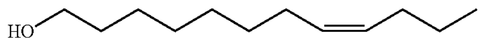 | *Grapholitha molesta*, *Ecdytolopha aurantiana* sex pheromone component |
| (Z)-8-dodecenyl acetate | 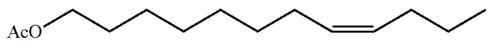 [SMILES: CCC/C=C\CCCCCCCOC(C)=O] | *Grapholitha molesta* sex pheromone component |
| (Z)-9-dodecen-1-ol | 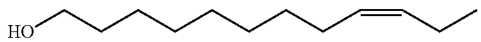 | |
| (Z)-9-dodecenyl acetate | 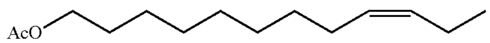 | *Eupoecilia ambiguella* sex pheromone |
| (E,E)-8,10-dodecadien-1-ol | 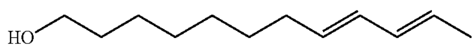 | *Cydia pomonella* |
| (7E,9Z)-dodecadienyl acetate | 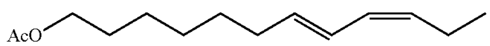 [SMILES: CC/C=C\C=C\CCCCCCOC(C)=O] | *Lobesia botrana* |
| (Z)-9-tetradecen-1-ol | 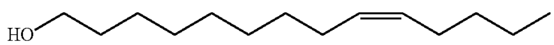 | |
| (Z)-9-tetradecenyl acetate | 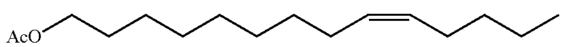 [SMILES: CCCC/C=C\CCCCCCCCOC(C)=O] | *Pandemis pyrusana*, *Naranga aenescens*, *Agrotis segetum* sex pheromone component |
| (Z)-11-tetradecen-1-ol | 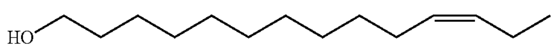 | |
| (Z)-11-tetradecenyl acetate | 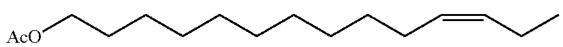 [SMILES: CC/C=C\CCCCCCCCCCOC(C)=O] | *Pandemis pyrusana*, *Choristoneura roseceana* sex pheromone component |
| (E)-11-tetradecen-1-ol | 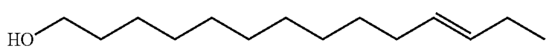 | |
| (E)-11-tetradecenyl acetate | 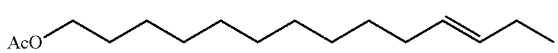 [SMILES: CC/C=C/CCCCCCCCCCOC(C)=O] | *Choristoneura roseceana*, *Crocidolomia pavonana* sex pheromone component |
| Z)-7-hexadecen-1-ol | 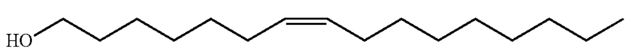 [SMILES: CCCCCCCC/C=C\CCCCCCO] | |
| (Z)-7-hexadecenal | 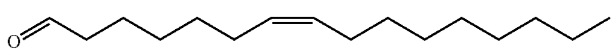 | *Diatraea considerata* sex pheromone component |
| (Z)-9-hexadecen-1-ol | 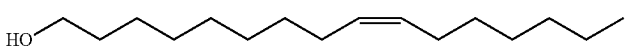 [SMILES: CCCCCC/C=C\CCCCCCCCO] | |
| (Z)-9-hexadecenal | 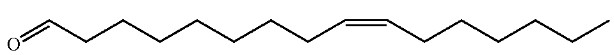 [SMILES: CCCCCC/C=C\CCCCCCCC=O] | *Helicoverpa zea*, *Helicoverpa armigera*, *Heliothis virescens* sex pheromone component |
| (Z)-9-hexadecenyl acetate | 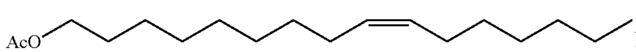 | *Naranga aenescens* sex pheromone component |
| (Z)-11-hexadecen-1-ol | 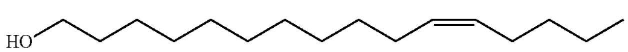 [SMILES: CCCC/C=C\CCCCCCCCCCO] | |
| (Z)-11-hexadecenal | 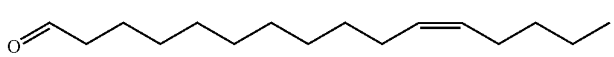 | *Platyptila carduidactyla*, *Heliothis virescens* sex pheromone *Helicoverpa zea*, *Helicoverpa armigera*, *Plutella xylostella*, *Diatraea considerate*, *Diatraea grandiosella*, *Diatraea saccharalis*, *Acrolepiopsis assectella* sex pheromone component |

TABLE 2-continued

Exemplary pheromones that can be synthesized according to methods described in the present disclosure.

| Name | Structure | Example of Biological importance |
|---|---|---|
| (Z)-11-hexadecenyl acetate | AcO~~~~~~~~= | *Discestra trifolii* sex pheromone *Heliothis virescens*, *Plutella xylostella*, *Acrolepiopsis assectella*, *Crocidolomia pavonana*, *Naranga aenescens* sex pheromone component |
| (Z,Z)-11,13-hexadecadienal | O=~~~~~~~=~ | *Amyelosis transitella* |
| (Z,Z)-11,13-hexadecadien-1-ol | HO~~~~~~~=~ | *Amyelosis transitella* |
| (11Z, 13E)-hexadecadien-1-ol | HO~~~~~~~=~ | *Amyelosis transitella* |
| (9Z, 11E)-hexadecadienal | O=~~~~~~=~ | |
| (Z)-13-octadecen-1-ol | HO~~~~~~~~~=~ | |
| (Z)-13-octadecenal | O=~~~~~~~~=~ | *Diatraea considerate*, *Diatraea grandiosella* sex pheromone component |
| (Z,Z,Z,Z,Z)-3,6,9,12,15-tricosapentaene | (macrocyclic structure) | *Amyelosis transitella* |

Most pheromones comprise a hydrocarbon skeleton with the terminal hydrogen substituted by a functional group (Ryan M F (2002). Insect Chemoreception. Fundamental and Applied. Kluwer Academic Publishers). Table 2b shows some common functional groups, along with their formulas, prefixes and suffixes. The presence of one or more double bonds, generated by the loss of hydrogens from adjacent carbons, determines the degree of unsaturation of the molecule and alters the designation of a hydrocarbon from -ane (no multiple bonds) to -ene. The presence of two and three double bonds is indicated by ending the name with -diene and -triene, respectively. The position of each double bond is represented by a numeral corresponding to that of the carbon from which it begins, with each carbon numbered from that attached to the functional group. The carbon to which the functional group is attached is designated -1-. Pheromones may have, but are not limited to, hydrocarbon chain lengths numbering 10 (deca-), 12 (dodeca-), 14 (tetradeca-), 16 (hexadeca-), or 18 (octadeca-) carbons long. The presence of a double bond has another effect. It precludes rotation of the molecule by fixing it in one of two possible configurations, each representing geometric isomers that are different molecules. These are designated either E (from the German word Entgegen, opposite) or Z (Zusammen, together), when the carbon chains are connected on the opposite (trans) or same (cis) side, respectively, of the double bond.

TABLE 2b

Prefixes and suffixes for common functional groups

| Functional group | Formula | Prefix | Suffix |
|---|---|---|---|
| Alcohol | —OH | Hydroxy- | -ol |
| Aldehyde | —CH=O | Formyl- | -al |
| Amine | —NH$_2$ | Amino- | -amine |
| Carboxylic add | —COOH | Carboxy- | -oic acid |
| Ester | —COOR | R-oxycarbonyl- | -R-oate |
| Ketone | >C=O | Oxo- | -one |

From Howse, PE, Stevens, IDR and Jones, OT (1998). Insect pheromones and their use in pest management. London: Chapman and Hall.

Pheromones described herein can be referred to using IUPAC nomenclature or various abbreviations or variations known to one skilled in the art. For example, (11Z)-hexadecen-1-al, can also be written as Z-11-hexadecen-1-al, Z-11-hexadecenal, Z-11-16:Ald, or Z-x-y:Ald, wherein x represents the position of the double bond and y represents the number of carbons in the hydrocarbon skeleton. Abbreviations used herein and known to those skilled in the art to identify functional groups on the hydrocarbon skeleton include "Ald," indicating an aldehyde, "OH," indicating an alcohol, and "Ac," indicating an acetyl. Also, the number of carbons in the chain can be indicated using numerals rather than using the written name. Thus, as used herein, an unsaturated carbon chain comprised of sixteen carbons can be written as hexadecene or 16.

Similar abbreviation and derivations are used herein to describe pheromone precursors. For example, the fatty acyl- CoA precursors of (11Z)-hexadecen-1-al can be identified as (11Z)-hexadecenyl-CoA or Z-11-16:Acyl-CoA. An abbreviation for a carboxylic acid functional group is "COOH." Fatty acids are carboxylic acids with a long hydrocarbon chain. In IUPAC nomenclature, the carboxyl carbon is C-1. Common nomenclature refers to α, ρ3, γ, δ, ε, etc. from C-1, and the carbon farthest from the carboxyl is ω. A shorthand notation exists to describe a fatty acid: total #carbons: #double bonds, Δdouble bond positions, where the position of double bonds is indicated by $\Delta^n$, where n indicates the lower numbered carbon of each pair where the double bond occurs. For example, 18:3Δ8t, Δ10t, Δ12c refers to a fatty acid that is 18 carbons long with 3 double bonds at positions C8, C10 and C12 of the hydrocarbon chain. The double bond at positions C8 and C10 are in the trans (t) configuration, while the double bond at position C12 is in the cis (c) configuration.

In one aspect, a method of producing one or more fatty alcohols and/or one or more fatty aldehydes from one or more unsaturated lipid moieties comprises obtaining the one or more unsaturated lipid moieties from one or more naturally occurring organisms Naturally Occurring Organisms as Sources of Unsaturated Lipid Moieties In one embodiment, the one or more naturally occurring organisms is one or more insects. In another embodiment, the one or more insects comprise the orders of Coleoptera, Diptera, Hymenoptera and Lepidoptera.

In another embodiment, the one or more naturally occurring organisms is not an insect.

In some embodiments, the one or more naturally occurring organisms comprise one or more plants. In some embodiments, the plants comprise soybean, Canola, cotton, sunflower, peanut, palm, coconut, olive, sesame and/or linseed.

In one embodiment, the soybean is a member of the genus *Glycine*. In another embodiment, the soybean is *Glycine max*. The major unsaturated fatty acids in soybean oil triglycerides are the polyunsaturates α-linolenic acid (C18:3, about 7% to about 10%), and linoleic acid (C18:2, about 51%); and the monounsaturate oleic acid (C18:1, about 23%). It also contains the saturated fatty acids stearic acid (C18:0, about 4%) and palmitic acid (C16:0, about 10%). Variation in the fatty acid profile can occur due to genetics and/or climate.

In one embodiment, the Canola is a member of the family Brassicaceae. In another embodiment, the Canola is a member of the genus *Brassica*. In certain embodiments, the Canola is selected from the group consisting of *Brassica napus, Brassica rapa, Brassica oleracea,* and *Brassica juncea*. Canola oil can have about 61% oleic acid, about 21% linoleic acid, about 9% to about 11% α-linolenic acid, about 4% palmitic acid and about 2% stearic acid, with the remaining percentages being other fatty acids. Variation in the fatty acid profile can occur due to genetics and/or climate. Commercial, food-grade canola oil is bred to contain less than 2% erucic acid (C22:1).

In one embodiment, the cotton is a member of the genus *Gossypium*. In another embodiment, the cotton is selected from the group consisting of *Gossypium hirsutum, Gossypium barbadense, Gossypium arboretum* and *Gossypium herbaceum*. Cotton has an oil-bearing kernel surrounded by a hard outer hull. Cottonseed oil can have about 52% linoleic acid, about 17% oleic acid, and about 24% palmitic acid, with the remaining percentages being other fatty acids. Variation in the fatty acid profile can occur due to genetics and/or climate.

In one embodiment, the sunflower is a member of the genus *Helianthus*. In another embodiment, the sunflower is selected from the group consisting of *Helianthus agrestis, Helianthus ambiguous, Helianthus angustifolius, Helianthus annuus, Helianthus anomalus, Helianthus argophyllus, Helianthus arizonensis, Helianthus atrorubens, Helianthus bolanderi, Helianthus x brevifolius, Helianthus californicus, Helianthus carnosus, Helianthus ciliaris, Helianthus cinereus, Helianthus coloradensis, Helianthus cusickii, Helianthus debilis, Helianthus decapetalus, Helianthus deserticola, Helianthus diffuses, Helianthus dissectifolius, Helianthus divaricatus, Helianthus x divariserratus, Helianthus x doronicoides, Helianthus eggertii, Helianthus exilis, Helianthus floridanus, Helianthus giganteus, Helianthus glaucophyllus, Helianthus x glaucus, Helianthus gracilentus, Helianthus grosseserratus, Helianthus heterophyllus, Helianthus hirsutus, Helianthus x intermedius, Helianthus laciniatus, Helianthus x laetiflorus, Helianthus laevigatus, Helianthus lenticularis, Helianthus longifolius, Helianthus x luxurians, Helianthus maximiliani, Helianthus membranifolius, Helianthus mollis, Helianthus multiflorus, Helianthus navarri, Helianthus neglectus, Helianthus niveus, Helianthus nuttallii, Helianthus occidentalis, Helianthus x orgyaloides, Helianthus paradoxus, Helianthus pauciflorus, Helianthus petiolaris, Helianthus porteri, Helianthus praecox, Helianthus praetermissus, Helianthus pumilus, Helianthus radula, Helianthus resinosus, Helianthus salicifolius, Helianthus sarmentosus, Helianthus scaberrimus, Helianthus schweinitzii, Helianthus silphioides, Helianthus simulans, Helianthus smithii, Helianthus speciosus, Helianthus strumosus, Helianthus subcanescens, Helianthus subtuberosus, Helianthus tuberosus,* and *Helianthus x verticillatus*. Sunflower oil can have about 5% palmitic acid, about 6% stearic acid, about 30% oleic acid and about 59% linoleic acid. However, several types of sunflower oils are produced, such as high linoleic, high oleic and mid oleic. Mid-oleic sunflower oil typically has at least 69% oleic acid. High oleic sunflower oil has at least 82% oleic acid. Variation in unsaturated fatty acids profile is strongly influenced by both genetics and climate.

Peanut is also known as groundnut. In one embodiment, the peanut is a member of the genus *Arachis*. In another embodiment, the peanut is *Arachis hypogaea*. Peanut oil can have about 46% to about 47% oleic acid, about 33% linoleic acid and about 10% palmitic acid. The oil can also have stearic acid, arachidic acid (eicosanoic acid, C20:0), behenic acid (docosanoic acid, C22:0), lignoceric acid (tetracosanoic acid, C24:0) and other fatty acids. Variation in the fatty acid profile can occur due to genetics and/or climate.

In one embodiment, the palm is a member of the family Arecaceae. In another embodiment, the palm is a member of the genus *Elaeis*. In certain embodiments, the palm is selected from the group consisting of *Elaeis guineensis* (African oil palm) and *Elaeis oleifera* (American oil palm). Palm oil is derived from the mesocarp, or reddish pulp, of the fruit. Palm oil can have about 43.5% palmitic acid, about 36.6% oleic acid, about 9.1% linoleic acid, about 4.3% stearic acid, about 1% myristic acid (C14:0) and about 5.5% other fatty acids. The seed, or palm kernel, is also rich in oil. Palm kernel oil is more saturated than palm oil, and can have about 48% lauric acid (C12:0), about 16% myristic acid, about 15% oleic acid, about 8% palmitic acid, about 3% capric acid (C10:0), about 3% caprylic acid (C8:0), about 2% to about 3% stearic acid and about 2% linoleic acid. The remaining percentages comprise other fatty acids. Variation in the fatty acid profile can occur due to genetics and/or climate.

In one embodiment, the coconut is a member of the family Arecaceae. In another embodiment, the coconut is a member of the genus *Cocos*. In certain embodiments, the coconut is *Cocos nucifera*. Coconut oil can have about 51% lauric acid, about 19% myristic acid, about 8% to about 9% palmitic acid, about 6% caprylic acid, about 6% capric acid and about 6% oleic acid. The remaining percentages comprise other fatty acids. Variation in the fatty acid profile can occur due to genetics and/or climate.

In one embodiment, the olive is a member of the family Oleaceae. In another embodiment, the olive is a member of the genus *Olea*. In certain embodiments, the olive is *Olea europaea*. Olive oil can be composed mainly of the mixed triglyceride esters of oleic acid (about 55% to about 83%) and palmitic acid (about 7.5% to about 20%) and of other fatty acids (linoleic acid: about 3.5% to about 21%; stearic acid: about 0.5% to about 5%); α-linolenic acid (about 0% to about 1.5%), along with traces of squalene (up to about 0.7%) and sterols (about 0.2% phytosterol and tocosterols). The composition varies by cultivar, region, altitude, time of harvest, and extraction process.

In one embodiment, the sesame is a member of the genus *Sesamum*. In another embodiment, the sesame is *Sesamum indicum*. Sesame oil can have about 41% linoleic acid, about 39% oleic acid, about 8% palmitic acid, about 5% stearic acid, with the remaining percentage comprised of other fatty acids. Variation in the fatty acid profile can occur due to genetics and/or climate.

Linseed is also known as flax or common flax. In one embodiment, the linseed is a member of the family Linaceae. In another embodiment, the linseed is a member of the genus *Linum*. In certain embodiments, the linseed is *Linum usitatissimum*. Linseed oil, also known as flaxseed oil, is a colorless to yellowish oil obtained from the dried, ripened seeds of the flax plant. Linseed oil is distinctive for its unusually large amount of α-linolenic acid (an omega-3 fatty acid), about 51.9% to about 55.2%. It also can have the saturated acids palmitic acid (about 7%) and stearic acid (about 3.4% to about 4.6%); the monounsaturated oleic acid (about 18.5% to about 22.6%); the doubly unsaturated linoleic acid (about 14.2% to about 17%). Variation in the fatty acid profile can occur due to genetics and/or climate.

In some embodiments, the plants are from families selected from the group consisting of Proteaceae and Rhamnaceae. The Proteaceae are a family of flowering plants predominantly distributed in the Southern Hemisphere. The family comprises about 80 genera with about 1,600 species. Together with the Platanaceae and Nelumbonaceae, they make up the order Proteales. Well-known genera include *Protea, Banksia, Embothrium, Grevillea, Hakea, Dryandra* and *Macadamia*. Species such as the New South Wales waratah (*Telopea speciosissima*), king protea (*Protea cynaroides*), and various species of *Banksia, Grevillea*, and *Leucadendron* are popular cut flowers, while the nuts of *Macadamia integrifolia* are widely grown commercially and consumed. Australia and South Africa have the greatest concentrations of diversity. Rhamnaceae is a large family of flowering plants, mostly trees, shrubs, and some vines, commonly called the buckthorn family. The family contains 50-60 genera and approximately 870-900 species. Rhamnaceae have a worldwide distribution, but are more common in the subtropical and tropical regions.

In certain embodiments, the plants comprise species from the genus *Gevuina, Calendula, Limnanthes*, Lunaria, *Carum, Daucus, Coriandrum, Macadamia, Myristica, Licania, Aleurites, Ricinus, Corylus, Kermadecia, Asclepias, Cardwellia, Grevillea, Orites, Ziziphus, Hicksbeachia, Hippophae, Ephedra, Placospermum, Xylomelum* and/or *Simmondsia*.

*Calendula* is a genus of about 15-20 species of annual and perennial herbaceous plants in the daisy family Asteraceae that are often known as marigolds. They are native to southwestern Asia, western Europe, Macaronesia, and the Mediterranean. The oil of *C. officinalis* is used as an anti-inflammatory, an antitumor agent, and a remedy for healing wounds. Species of *Calendula* include *Calendula arvensis, Calendula denticulate, Calendula eckerleinii, Calendula incana, Calendula lanzae, Calendula maritima, Calendula maroccana, Calendula meuselii, Calendula officinalis, Calendula palaestina, Calendula stellate, Calendula suffruticosa*, and *Calendula tripterocarpa*.

*Limnanthes*, the type genus of the family Limnanthaceae, consists of annual herbaceous plants commonly known as the meadowfoams. The seven species are all native to coastal and adjoining regions (inland valleys, foothills and mountains) of western North America, where they typically grow in marshy habitats, such as the margins of vernal pools. Some are endemic to California. The genus is divided into two sections, *Limnanthes*, in which the sepals curve back during fruit maturation, and Inflexae, in which the sepals curve over the maturing fruit. Section *Limnanthes* include *Limnanthes bakeri, Limnanthes douglasii, Limnanthes macounii*, and *Limnanthes vinculans*. Section Inflexae include *Limnanthes alba, Limnanthes floccose* and *Limnanthes montana*.

*Lunaria* is a genus of flowering plants in the family Brassicaceae, native to central and southern Europe. It includes four species, the annual or biennial *Lunaria annua* (*L. biennis*), *Lunaria elongata*, the perennial *Lunaria rediviva* and the rare Balkan species *Lunaria telekiana*.

*Carum* is a genus of about 20 species of flowering plants in the family Apiaceae, native to temperate regions of the Old World. The most important species is caraway (*C. carvi*), the seeds of which are widely used as a culinary spice. In the Mongolian Flora are two species (*C. carve* L., *C. buriaticum* Turcz.) that belong to the genus *Carum* L.

*Daucus* is a worldwide genus of herbaceous plants of the family Apiaceae of which the best-known species is the cultivated carrot. The *Daucus* genus of Umbelliferae Apiaceae has about 25 species. The species include *Daucus aureus, Daucus azoricus, Daucus broteri, Daucus bicolor, Daucus carota, Daucus durieui, Daucus foliosus, Daucus glochidiatus, Daucus gadeceaui, Daucus guttatus, Daucus involucratus, Daucus littoralis, Daucus montanus, Daucus muricatus, Daucus pulcherrima, Daucus pusillus*, and *Daucus visnaga*.

*Coriandrum* is a genus of herbs in the Apiaceae family containing the cultivated species *Coriandrum sativum* (coriander) and the wild species *Coriandrum tordylium*. The leaves and seeds of *Coriandrum sativum* are used in cooking. The leaves are often referred to as cilantro in North America.

*Macadamia* is a genus of four species of trees indigenous to Australia and constituting part of the plant family Proteaceae. They are native to northeastern New South Wales and central and southeastern Queensland. The tree is commercially important for its fruit, the macadamia nut. Other names include Queensland nut, bush nut, maroochi nut, bauple nut, and Hawaii nut. *Macadamia* species include *Macadamia integrifolia, Macadamia jansenii, Macadamia ternifolia* and *Macadamia tetraphylla*. The nut has a high amount of monounsaturated fats (59% of total content). *Macadamia* oil is prized for containing approximately 22% of the omega-7 palmitoleic acid, which makes it a botanical alternative to mink oil. This relatively high content of palmitoleic acid plus macadamia's high oxidative stability make it a desirable ingredient in cosmetics.

*Myristica* is a genus of trees in the family Myristicaceae. There are about 150 species distributed in Asia and the western Pacific. The most important commercial species is *Myristica fragrans*, the main source of the spices nutmeg and mace. Species of *Myristica* can include *M. acsmithii, M. agusanensis, M. alba, M. albertisii, M. amboinensis, M. ampliata, M. amplifolia, M. amygdalina, M. anceps, M. andamanica, M. apiculate, M. archboldiana, M. arfakensis, M. argentea, M. aruensis, M. atrescens, M. atrocorticata, M. attenuate, M. avis-paradisiacae, M. baeuerlenii, M. bancana, M. basilanica, M. batjanica, M. beccarii, M. beddomei, M. bivalvis, M. bombycina, M. brachiate, M. brachypoda, M. brassii, M. brevistipes, M. buchneriana, M. byssacea, M. cagayanensis, M. canariformis, M. cantleyi, M. carrii, M. castaneifolia, M. celebica, M. cerifera, M. ceylanica, M. chartacea, M. chrysophylla, M. cimicifera, M. cinerea, M. cinnamomea, M. clemensii, M. coacta, M. colinridsdalei, M. collettiana, M. commersonii, M. concinna, M. conspersa, M. contorta, M. contracta, M. cookie, M. coriacea, M. cornutiflora, M. corticata, M. corticosa, M. costata, M. costulata, M. crassa, M. crassifolia, M. crassinervis, M. crassipes, M. cucullata, M. cumingii, M. curtisii, M. cylindrocarpa, M. dactyloides, M. dardaini, M. dasycarpa, M. depressa, M. devogelii, M. diversifolia, M. duplopunctata, M. duthiei, M. elegans, M. elliptica, M. ensifolia, M. eugeniifolia, M. euryocarpa, M. extensa, M. fallax, M. faroensis, M. farquhariana, M. fasciculate, M. fatua, M. filipes, M. finlaysoniana, M. firmipes, M. fissiflora, M. fissurata, M. flavovirens, M. flocculosa, M. flosculosa, M. forbesii, M. fragrans, M. frugifera, M. fugax, M. furfurascerts, M. fusca, M. fusiformis, M. gamblei, M. garciniifolia, M. geminate, M. gibbosa, M. gigantean, M. gillespieana, M. globose, M. gracilipes, M. grandifolia, M. grandis, M. griffithii, M. guadalcanalensis, M. guatteriifolia, M. guillauminiana, M. hackenbergii, M. hellwigii, M. heritierifolia, M. hollrungii, M. hooglandii, M. horsfieldia, M. hypargyraea, M. hyposticta, M. impressa, M. impressinervia, M. inaequalis, M. incredibilis, M. iners, M. ingens, M. ingrate, M. inopinata, M. insipida, M. intermedia, M. inundata, M. inutilis, M. irya, M. iteophylla, M. johnsii, M. kajewskii, M. kalkmanii, M. kjellbergii, M. koordersii, M. korthalsii, M. kunstleri, M. kurzii, M. laevifolia, M. laevigata, M. laevis, M. lakilaki, M. lasiocarpa, M. laurella, M. laurina, M. laxiflora, M. lemanniana, M. lenta, M. lepidota, M. leptophylla, M. leucoxyla, M. litoralis, M. longipes, M. longipetiolata, M. lowiana, M. macgregori, M. macrantha, M. macrocarpa, M. macrocarya, M. macrocoma, M. macrothyrsa, M. magnifica, M. maingayi, M. majuscule, M. malabarica, M. malayana, M. mandaharan, M. markgraviana, M. mascula, M. maxima, M. mediovibex, M. mediterranea, M. micrantha, M. microcarpa, M. millepunctata, M. mindanaensis, M. mindorensis, M. miohu, M. mouchio, M. multinervia, M. murtoni, M. myrmecophila, M. nana, M. neglecta, M. negrosensis, M. nesophila, M. niobue, M. niohne, M. nitida, M. nivea, M. oblongifolia, M. olivacea, M. orinocensis, M. ornate, M. ovicarpa, M. pachycarpidia, M. pachyphylla, M. pachythyrsa, M. palawanensis, M. paludicola, M. papillatifolia, M. papuana, M. papyracea, M. parviflora, M. pectinate, M. pedicellata, M. peltata, M. pendulina, M. perlaevis, M. petiolate, M. philippensis, M. pilosella, M. pilosigemma, M. pinnaeformis, M. platysperma, M. plumeriifolia, M. polyantha, M. polyspherula, M. pseudoargentea, M. psilocarpa, M. pubicarpa, M. pulchra, M. pumila, M. pygmaea, M. quercicarpa, M. racemose, M. radja, M. resinosa, M. retusa, M. ridleyana, M. ridleyi, M. riedelii, M. robusta, M. rosselensis, M. rubiginosa, M. rubrinervis, M. rumphii, M. sagotiana, M. salomonensis, M. sangowoensis, M. sapida, M. sarcantha, M. schlechteri, M. schleinitzii, M. schumanniana, M. scortechinii, M. scripta, M. sericea, M. sesquipedalis, M. simiarum, M. simulans, M. sinclairii, M. smythiesii, M. sogeriensis, M. spanogheana, M. sphaerosperma, M. sphaerula, M. spicata, M. sprucei, M. stenophylla, M. suavis, M. subalulata, M. subglobosa, M. subtilis, M. succedanea, M. succosa, M. sulcata, M. suluensis, M. sumbavana, M. superba, M. tamrauensis, M. teijsmannii, M. tenuivenia, M. teysmanni, M. tingens, M. tomentella, M. tomentosa, M. trianthera, M. tristis, M. tuberculate, M. tubiflora, M. ultrabasica, M. umbellate, M. umbrosa, M. uncinata, M. undulatifolia, M. urdanetensis, M. uviformis, M. valida, M. velutina, M. verruculosa, M. villosa, M. vinkeana, M. vordermanni, M. wallaceana, M. wallichii, M. warburgii, M. wenzelii, M. womersleyi, M. wrayi, M. wyatt-smithii, M. yunnanensis* and *M. zeylanica*.

*Licania* is a plant genus in the family Chrysobalanaceae. Several species are used as ornamental plants. *Licania* fruit are important food for many animals and can also be eaten by humans. Species in *Licania* include *Licania arborea, Licania caldasiana, Licania chiriquiensis, Licania conferruminata, Licania fasciculate, Licania grandibracteata, Licania hedbergii, Licania humilis, Licania kunthiana, Licania longicuspidata, Licania longipetala, Licania megalophylla, Licania michauxii, Licania morii, Licania pyrifolia, Licania rigida, Licania salicifolia, Licania splendens, Licania tomentosa, Licania vasquezii* and *Licania velutina*.

*Aleurites* is a small genus of arborescent flowering plants in the Euphorbiaceae. It is native to China, the Indian Subcontinent, Southeast Asia, Papuasia, and Queensland. It is also reportedly naturalized on various islands (Pacific and Indian Oceans, plus the Caribbean) as well as scattered locations in Africa, South America, and Florida. These monoecious, evergreen trees are perennials or semi-perennials. The fruits are rather large drupes with a fleshy exocarp and a thin, woody endocarp. They vary in shape, according to the numbers of developed locules. They contain oleiferous, poisonous seeds. The oil has been used as a paraffin, lubricant and as a constituent of varnish, paint and soap. Once poisonous substances are removed, it can be used as a cooking oil. Species of *Aleurites* include *A. cordatus, A. erraticus, A. fordii, A. japonicas, A. laccifer, A. montanus, A. peltatus, A. saponarius, A. trispermus, A. vernicifluus* and *A. vernicius*.

*Ricinus communis*, the castor bean or castor-oil-plant, is a species of flowering plant in the spurge family, Euphorbiaceae. It is the sole species in the monotypic genus, *Ricinus*, and subtribe, Ricininae. Its seed is the castor bean, which, despite its name, is not a true bean. Castor is indigenous to the southeastern Mediterranean Basin, Eastern Africa, and India, but is widespread throughout tropical regions (and widely grown elsewhere as an ornamental plant). Castor seed is the source of castor oil, which has a wide variety of uses. The seeds contain between 40% and 60% oil that is rich in triglycerides, mainly ricinolein. The seed also contains ricin, a water-soluble toxin, which is also present in lower concentrations throughout the plant.

*Corylus* (hazel) is a genus of deciduous trees and large shrubs native to the temperate Northern Hemisphere. The genus is usually placed in the birch family Betulaceae, though some botanists split the hazels into a separate family Corylaceae. The fruit of the hazel is the hazelnut. The fruits are nuts 1-2.5 cm long and 1-2 cm diameter, surrounded by a husk which partly to fully encloses the nut. Species of *Corylus* include *Corylus Americana, Corylus avellana, Corylus heterophylla, Corylus yunnanensis, Corylus colchica, Corylus cornuta, Corylus maxima, Corylus sieboldiana* (*C. mandshurica*), *Corylus chinensis, Corylus colurna, Corylus fargesii, Corylus jacquemontii, Corylus wangii* and *Corylus ferox*.

*Kermadecia* is a genus of flowering plants in the family Proteaceae. The genus comprises four species (*K. elliptica, K. pronyensis, K. rotundifolia* and *K. sinuata*), all endemic to New Caledonia. *Kermadecia sinuata* is an up to 30 m high tree, and the trunk reaches up to 1 m in diameter. It is found in the central range of the Mainland of New Caledonia, rarer in the north. It grows in dense rainforest above average sea level on the ground more or less on deep sedimentary substrate. *K. sinuata* has pale golden brown or yellow flowers with a thick robust inflorescence of 10-45 cm. The tree has Drupes (40-50×25-30 mm) (www.endemia.nc).

*Asclepias*, the milkweeds, is an American genus of herbaceous perennial, dicotyledonous plants that contains over 140 known species. It is classified in the subfamily Asclepiadoideae of the dogbane family Apocynaceae. Milkweed is named for its milky sap, which consists of a latex containing alkaloids and several other complex compounds including cardenolides. Species of *Asclepias* include *Asclepias albicans, Asclepias amplexicaulis, Asclepias asperula, Asclepias californica, Asclepias cordifolia, Asclepias cryptoceras, Asclepias curassavica, Asclepias curtissii, Asclepias eriocarpa, Asclepias erosa, Asclepias exaltata, Asclepias fascicularis, Asclepias humistrata, Asclepias incarnata, Asclepias lanceolata, Asclepias linaria, Asclepias linearis, Asclepias longifolia, Asclepias meadii, Asclepias nyctaginifolia, Asciepias obovate, Asclepias purpurascens, Asclepias quadrifolia, Asclepias rubra, Asclepias solanoana, Asclepias speciose, Asclepias subulata, Asclepias subverticillata, Asclepias sullivantii, Asclepias syriaca, Asclepias tuberosa, Asclepias uncialis, Asclepias variegate, Asclepias verticillata, Asclepias vestita, Asclepias viridiflora, Asclepias viridis* and *Asclepias welshii*.

*Cardwellia* is a genus of a sole described species of large trees, constituting a part of the plant family Proteaceae. The species *Cardwellia sublimis* (northern silky oak) is endemic to the rainforests of the wet tropics region of north eastern Queensland, Australia. Other common names include bull oak, golden spanglewood, lacewood, oak and oongaary. The compound leaves have up to 17 leaflets. It produces white inflorescences followed by woody fruits which are prominently displayed outside the canopy.

*Grevillea* is a massive genus of close to 340 species of trees and shrubs in the family Proteaceae that are native to only Australia—less often, New Caledonia (Bombarda I et al. (2010) *J. Am. Oil Chem. Soc.* 87: 981-986; Kato M and Kawakita A. (2004) *Am. J. Bot.* 91:1814-1827; Bailey L H and Miller W (1900) *Cyclopedia of American Horticulture: Comprising Suggestions for Cultivation of Horticultural Plants, Descriptions of the Species of Fruits, Vegetables, Flowers, and Ornamental Plants Sold in the United States and Canada*; Randy Stewart Landscape Design blog-rs-landscapedesign.blogspot.com). Most species do not like organic compost or phosphorous rich soil. Fertilizer containing phosphorus or potassium can kill. Pruning after flowering improves vigor. They are deer resistant and most species can tolerate severe drought, many preferring dry summers. The flowers attract hummingbirds. They are also used as food plants by the larvae of some Lepidoptera species, including the dryandra moth and the *Pieris rapae* (small white). Phytophora rot is a severe problem on Mediterranean species that are overwatered during summer. It not only occurs in Australia but has been also found in places outside its native range such as Italy where it is cultivated.

*Grevillea exul* is a small tree (other sources refer to the plant also as shrub), reaching a maximum size of 30 feet, that is one of the few Grevilleas native exclusively to New Caledonia. It is a close relative to *Grevillea robusta*. The smooth-edged, non-lobed leaves, up to 9 inches in length, are rusty or silky haired beneath. The white flowers are borne on long, toothbrush-like clusters from winter into summer. It thrives in hardy zones 9 to 12 in full sun on well-drained soil. Information on the subspecies *Grevillea exul* var. *rubiginosa* is very scarce. *G. exul* var. *rubiginosa* growth in the present of Ni-salts has been investigated. The seeds have been classified as nondormant (ND)—fully developed embryo, water-permeable seed (or fruit) coat in less than 30 days. The estimated pollinators of the plant are either honey bees or birds. The foliage of subsp. *rubiginosa* is wider and rusty-red beneath. The flowers are borne on larger clusters.

*G. exul* is closely related to *G. robusta*, for which more information is available. *Grevillea robusta* is a fast growing, deep rooted, semi-evergreen large tree, reaching 70 feet or more, that is native to the southeastern part of Queensland, Australia. It is grown as a shade tree in mild climates around the world including Santiago, Chile, California and Florida. It is also valued for its timber and is grown commercially in South Africa. The valuable timber is often used for building cabinets. The wood is rot resistant. It thrives in hardy zones 8b to 12 (would correspond to CA, TX, LA, FL in the US) in full sun preferring a fertile, clay based but well drained soil and requires a warm dry summer. Young plants are much less hardy than mature plants (anpsa.org.au).

*Grevillea decora* is a medium sized, upright shrub, 2-5 m high. Leaves are narrowly egg-shaped or oval, leathery, dull greyish-green, 7-18 cm×2.5-7 cm with bronze-red and densely hairy new growth. This is a colorful plant which does well in dry tropical areas as long as it has well drained soil. It is not suited to cold, temperate climates. The species is best propagated from scarified seed. Cuttings have been successful but can be difficult to strike. The species has been successfully grafted onto *G. robusta* root stock—grafted plants grow successfully in cooler areas. Some botanists regard this plant as a subspecies of *G. goodii*.

*Orites* is a genus of nine known species in the family Proteaceae. Seven species are endemic to Australia, two in South America, one in the Chilean Andes and one in Bolivia. The species include *Orites acicularis, Orites diversifolius, Orites excelsus, Orites fiebrigii, Orites lancifolius, Orites megacarpus, Orites milliganii, Orites myrtoidea* and *Orites revolutus*.

*Orites diversifolius* is a common species (slow growing shrub to 2 m, frost and snow hardy) that ranges from the lowland rainforest in western Tasmania to the lower parts of the alpine zone (sub-alpine woodland). The leaves are very variable, but are usually more than twice as wide as long. Rainforest plants often have leaves approximately 10 cm long, whereas plants from exposed subalpine areas are more likely to be about 3-5 cm long. Attractive white flowers in axillary spikes appear in early summer, although the flowering season can be irregular. They may be entire, but more often have sharp, shallow lobes. The undersides of the leaves are glaucous. The species needs well composted soil, ample moisture and cool location. The species can form a small tree in good conditions. It grows in partial to full shade (www.utas.edu.au; www.desertnorthwest.com; www.apstas.com; www.australianplants.com).

*Orites revolutus*, also known as Narrow-Leaf *Orites*, is a Tasmanian endemic plant species. Scottish botanist Robert Brown formally described the species in Transactions of the Linnean Society of London in 1810 from a specimen collected at Lake St Clair. Abundant in alpine and subalpine heath, *Orites revolutus* grows as a spreading bush or an erect, woody shrub, usually 0.5-1.5 m (1 ft 8 in-4 ft 11 in) in height. Branching is dense and the leaves are alternate up the stem. Leaf shape is narrow and fairly blunt at the apex, 7-20 mm long, 1-1.5 mm wide, with tightly revolute margins and a hairy surface on the underside. Flowering occurs in early to mid-summer with the sour-scented flowers arising on terminal spikes to twice the length of the leaves. White in colour, they are 5 mm long, actinomorphic and bisexual with 4 adnate stamens and a superior ovary. The corolla is valvate, tubular in bud and split at maturity. Fruit is a hairy follicle to 15 mm containing winged seeds. Being proteaceous, *O. revolutus* is likely to provide a substantial food source for nectivorous animal species within its range. The mean annual temperature within the plant's range hovers around 8° C. and rainfall tends to be as high as 1700 or even 2000 mm annually.

Ziziphus is a genus of about 40 species of spiny shrubs and small trees in the buckthorn family, Rhamnaceae, distributed in the warm-temperate and subtropical regions throughout the world. Some species are deciduous, while others are evergreen. The fruit is an edible drupe, yellow-brown, red, or black, globose or oblong, 1-5 cm (0.39-1.97 in) long, often very sweet and sugary, reminiscent of a date in texture and flavour. Species of *Ziziphus* include *Ziziphus abyssinica, Ziziphus angolito, Ziziphus apetala, Ziziphus attopensis, Ziziphus budhensis, Ziziphus celata, Ziziphus cotinifolia, Ziziphus fungii, Ziziphus funiculosa, Ziziphus guaranitica, Ziziphus havanensis, Ziziphus horrida, Ziziphus hutchinsonii, Ziziphus incurve, Ziziphus joazeiro, Ziziphus jujube, Ziziphus laui, Ziziphus lotus, Ziziphus mairei, Ziziphus mauritiana, Ziziphus melastomoides, Ziziphus Mexicana, Ziziphus mistol, Ziziphus montana, Ziziphus mucronata, Ziziphus nummularia, Ziziphus obtusifolia, Ziziphus oenoplia, Ziziphus oxyphylla, Ziziphus parryi, Ziziphus platyphylla, Ziziphus quadrilocularis, Ziziphus robertsoniana, Ziziphus rugose, Ziziphus saeri, Ziziphus spina-christi, Ziziphus talanai, Ziziphus trinervia, Ziziphus undulata, Ziziphus xiangchengensis* and *Ziziphus xylopyrus*.

*Ziziphus jujuba* is commonly called jujube (sometimes *jujuba*), red date, Chinese date, Korean date, or Indian date. It is used primarily as a shade tree that also bears fruit. It is a small deciduous tree or shrub reaching a height of 5-12 m, usually with thorny branches. The leaves are shiny-green, ovate-acute, 2-7 cm wide and 1-3 cm broad, with three conspicuous veins at the base, and a finely toothed margin. The flowers are small, 5 mm wide, with five inconspicuous yellowish-green petals. The fruit is an edible oval drupe 1.5-3 cm deep; when immature it is smooth-green, with the consistency and taste of an apple, maturing brown to purplish-black and eventually wrinkled, looking like a small date. There is a single hard stone similar to an olive stone. Fruit yield is 100-150 g/tree. The spacing is approximately 10 m. The lipid content in fruits is about 0.06% to 0.10% and in dried fruits about 1.1%. Compared to *jojoba* the jujube fruit has a smaller kernel and also less lipid content. In contrast to *jojoba*, jujube is therefore also not considered biodiesel feedstock. Dried fruits and oily extracts are commercially available.

*Hicksbeachia* is a genus of two species of trees in the family Proteaceae. They are native to rainforests of northern New South Wales and southeastern Queensland. They are commonly known as red bopple nut or beef nut due to the bright red color of their fruits. The two species are *Hicksbeachia pilosa* and *Hicksbeachia pinnatifolia*.

*Hicksbeachia pinnatifolia* is a rare species native to subtropical rainforest in New South Wales and Queensland in Australia. Common names include red bopple nut, monkey nut, red nut, beef nut, rose nut and ivory silky oak. The tree produces fleshy, red fruits during spring and summer. These contain edible seeds. *H. pinnatifolia* leaves are either compound or pinnate and from 40-100 cm long. The plant flowers generally in winter time. The Red Bopple Nut produces fleshy, red fruits during spring and summertime. Fruits are edible, drupe-like, ovoid, 2-4 cm long, indehiscent, fleshy, red, furrowed on one side, containing a large almond sized kernel (nut). Red Bopple Nut has a flavor akin to that of Macadamias and may be used for similar purposes. The tree bears relatively high quantitites of high quality nuts. Tree propagation is by seeds, but the seeds are only briefly viable. *H. pinnatifolia* is hard to establish as seedlings are prone to various disorders. In reality, poor seedling establishment and poor development limit the potentiality of this species (www.fruitandnuttrees.com). It is considered similar but inferior to the macadamia.

*Hippophae*, the sea buckthorns, are deciduous shrubs in the family Elaeagnaceae. It is also referred to as sandthorn, sallowthorn or seaberry. *Hippophae rhamnoides*, the common sea buckthorn, is by far the most widespread of the species in the genus, with the ranges of its eight subspecies extending from the Atlantic coasts of Europe across to northwestern Mongolia and northwestern China. More than 90% or about 1,500,000 ha of the world's natural sea buckthorn habitat is found in China, Mongolia, Russia, northern Europe and Canada, where the plant is used for soil, water and wildlife conservation, anti-desertification purposes and for consumer products. As species belonging to this genus accumulate lipids in the mesocarp, oil can be extracted from either the seeds or the pulp of the fruit. Oil content in seeds of sea buckthorn is on average 7-11% while oil content of pulp is around 1.5-3% (per fresh weight). Seed oil is characterized by high content of polyunsaturated fatty acids while pulp oil contains monounsaturated fatty acids and carotenoids. While linoleic acid and α-linolenic acid are the major fatty acids in seed oil, sea buckthorn pulp oil contains approximately 65% combined of the monounsaturated fatty acid, palmitoleic acid, and the saturated fatty acid, palmitic acid. Both oils also contain dense amounts of tocopherols, tocotrienols and plant sterols. The species of *Hippophae* include *Hippophae goniocarpa, Hippophae gyantsensis, Hippophae litangensis, Hippophae neurocarpa, Hippophae rhamnoides, Hippophae salicifolia* and *Hippophae tibetana*.

*Ephedra* is a genus of gymnosperm shrubs, the only genus in its family, Ephedraceae, and order, Ephedrales. The various species of *Ephedra* are widespread in many lands, native to southwestern North America, southern Europe, northern Africa, and southwest and central Asia, northern China, and western South America. Common names in English include joint-pine, jointfir, Mormon-tea or Brigham tea. Plants of the genus *Ephedra*, including *E. sinica* and others, have traditionally been used by indigenous people for a variety of medicinal purposes, including treatment of asthma, hay fever, and the common cold. The alkaloids ephedrine and pseudoephedrine are active constituents of *E. sinica* and other members of the genus. These compounds are sympathomimetics with stimulant and decongestant qualities and are chemically substituted amphetamines. Species of *Ephedra* include *Ephedra alata, Ephedra altissima, Ephedra Americana, Ephedra antisyphilitica, Ephedra aphylla, Ephedra x arenicola, Ephedra aspera, Ephedra aurantiaca, Ephedra boelckei, Ephedra botschantzevii, Ephedra Breana, Ephedra brevifoliata, Ephedra californica, Ephedra chilensis, Ephedra compacta, Ephedra coryi, Ephedra cutleri, Ephedra dahurica, Ephedra dawuensis, Ephedra distachya, Ephedra x eleutherolepis, Ephedra equisetina, Ephedra fasciculata, Ephedra fedtschenkoae, Ephedra foeminea, Ephedra foliata, Ephedra fragilis, Ephedra frustillata, Ephedra funereal, Ephedra gerardiana, Ephedra glauca, Ephedra holoptera, Ephedra intermedia, Ephedra x intermixta, Ephedra kardangensis, Ephedra khurikensis, Ephedra laristanica, Ephedra likiangensis, Ephedra lomatolepis, Ephedra major, Ephedra milleri, Ephedra minuta, Ephedra monosperma, Ephedra multiflora, Ephedra nevadensis, Ephedra ochreata, Ephedra oxyphylla, Ephedra pachyclada, Ephedra pedunculata, Ephedra pentandra, Ephedra przewalskii, Ephedra pseudodistachya, Ephedra regeliana, Ephedra rhytidosperma, Ephedra rituensis, Ephedra rupestris, Ephedra sarcocarpa, Ephedra sinica, Ephedra somalensis, Ephedra strobilacea, Ephedra sumlingensis, Ephedra tilhoana, Ephedra torreyana, Ephedra transitoria, Ephedra triandra, Ephedra trifurca, Ephedra tweedieana, Ephedra viridis* and *Ephedra vvedenskyi*.

*Placospermum* is a genus of a single species of large trees, constituting part of the plant family Proteaceae. The species *Placospermum coriaceum* is endemic to the rainforests of the wet tropics region of north eastern Queensland, Australia. Common names include rose silky oak and plate-seeded oak.

*Xylomelum* is a genus of six species in the plant family Proteaceae. They are native to Australia, growing in the form of tall shrubs and trees. The genus includes at least two species with the common name woody pear, *Xylomelum pyriforme* in the eastern states of Australia, and *Xylomelum occidentale* in Western Australia. Species of *Xylomelum* include *Xylomelum angustifolium, Xylomelum benthamii, Xylomelum cunninghamianum, Xylomelum occidentale, Xylomelum pyriforme* and *Xylomelum scottianum*.

*Jojoba*, with the botanical name *Simmondsia chinensis*, is also known as goat nut, deer nut, pignut, wild hazel, quinine nut, coffeeberry, and gray box bush. It is native to Southwestern North America. *Simmondsia chinensis* is the sole species of the family Simmondsiaceae, placed in the order Caryophyllales. *Jojoba* is grown commercially to produce jojoba oil, a liquid wax ester extracted from its seed. This oil is rare in that it is an extremely long (C36-C46) straight-chain wax ester and not a triglyceride, making *jojoba* and its derivative *jojoba* esters more similar to human sebum and whale oil than to traditional vegetable oils. *Jojoba* oil is interesting for the industry because it is odorless and it has a viscosity which is temperature-independent. Applications vary from engine lubricating oil to cooking oil. *Jojoba* wax is used predominantly for pharmaceutical compounds, especially for skin products. Its use as biodiesel fuel is becoming more and more important. *Jojoba* oil consists of long straight monoesters of 22 to 44 carbon atoms (as opposed to most vegetable oils which consist of triglycerides), which makes it comparable to diesel in terms of energy density.

*Gevuina avellana*, also called Hardy *Macadamia*, Chile Nut, and in Spanish Avellano, is native to south Chile and Argentina and little cultivated or known in the northern hemisphere (San B and Yildirim A N (2010) *J. Food Compos. Anal.* 23: 706-710). It is a broadleaf evergreen in the family Proteaceae that varies from a shrub to a tree 60 feet tall. It grows from sea level to nearly 2,300 feet (700 meters) in elevation. Its range extends from 35 to 44° south latitude. The plant may be adversely affected by heat, while the cold freezes of interior North America can kill it. It is able to thrive in locations such as Ireland, Scotland, milder parts of England, and New Zealand. Even an isolated tree can set fertile nuts. Nuts can be produced every year. The nuts are easily shelled. An analysis showed the nuts contain about 12.5% protein, about 49.5% oil, and about 24.1% carbohydrate. The highly monosaturated oil is also extracted for varied uses in Chile. Germinated seeds are susceptible to being eaten by rodents. The tree is adaptable to highly varied soils and sun levels. This species is averse to fertilization with phosphorus (www.arthurleej.com). In some classifications, *Gevuina* is recognised with three species endemic to each of Australia (*Gevuina bleasdalei*), New Guinea (*Gevuina papuana*), and one species in Chile and Argentina (*Gevuina avellana*). Other taxonomic reports place the Australian and New Guinea species in the genus *Bleasdalea* or in the Fijian endemic genus *Turrillia*, and leave *Gevuina* with only *Gevuina avellana*. The Flora of Australia retains these 2 species in *Gevuina*, but the most recent classification places the Australian and New Guinea species as *Bleasdalea bleasdalei* and *B. papuana*.

In some embodiments, the plants are selected from the group consisting of *Gevuina avellana, Corylus avellana, Kermadecia sinuata, Asclepias syriaca, Cardwellia sublimis, Grevillea exul* var. *rubiginosa, Orites diversifolius, Orites revoluta, Ziziphus jujube, Hicksbeachia pinnatifolia,* and *Grevillea decora*.

In some embodiments, the one or more naturally occurring organisms comprise one or more algae. In various embodiments described herein, the one or more algae may be selected from green algae, yellow-green algae, and red algae.

In some embodiments, the one or more algae comprise one or more green algae. In certain embodiments, the one or more green algae comprise species from the genus *Pediastrum*. In some embodiments, the one or more green algae comprise *Pediastrum simplex*. In certain embodiments, the one or more green algae comprise species from the genus *Chlorococcum*. In some embodiments, the one or more green algae comprise *Chlorococcum isabeliense*. In certain embodiments, the one or more green algae comprise species from the genus *Parachlorella*. In some embodiments, the one or more green algae comprise *Parachlorella kessleri*. In certain embodiments, the one or more green algae comprise species from the genus *Oocystis*. In some embodiments, the one or more green algae comprise *Oocystis heteromucosa*. In certain embodiments, the one or more green algae comprise species from the genus *Phacotus*. In some embodiments, the one or more green algae comprise *Phacotus lenticularis*. In certain embodiments, the one or more green algae comprise species from the genus *Dactylococcus*. In certain embodiments, the one or more green algae comprise species from the genus *Eremosphaera*. In some embodiments, the one or more green algae comprise *Eremosphaera viridis*. In certain embodiments, the one or more green algae comprise species from the genus *Chlamydomonas*. In some embodiments, the one or more green algae comprise *Chlamydomonas monticola*. In certain embodiments, the one or more green algae comprise species from the genus *Dicranochaete*. In some embodiments, the one or more green algae comprise *Dicranochaete reniformis*.

In some embodiments, the one or more algae comprise one or more yellow-green algae. In certain embodiments, the one or more yellow-green algae comprise species from the genus *Heterococcus*. In some embodiments, the one or more yellow-green algae comprise *Heterococcus crassulus*. In some embodiments, the one or more yellow-green algae comprise *Heterococcus pleurococcoides*. In certain embodiments, the one or more yellow-green algae comprise species from the genus *Chlorobotrys*. In some embodiments, the one or more yellow-green algae comprise *Chlorobotrys regularis*.

In some embodiments, the one or more algae comprise one or more red algae. In certain embodiments, the one or more red algae comprise species from the genus *Compsopogon*. In some embodiments, the one or more red algae comprise *Compsopogon coeruleus*.

In some embodiments, the one or more naturally occurring organisms comprise one or more flagellates. In some embodiments, the one or more flagellates comprise species from the genus *Distigma*. In some embodiments, the one or more flagellates comprise *Distigma curvata*. In some embodiments, the one or more flagellates comprise species from the genus *Gyropaigne*. In some embodiments, the one or more flagellates comprise *Gyropaigne lefevrei*.

In some embodiments, the one or more naturally occurring organisms comprise one or more diatoms. In some embodiments, the one or more diatoms comprise species from the genus *Skeletonema*. In some embodiments, the one or more diatoms comprise *Skeletonema subsalsum*.

In some embodiments, the one or more naturally occurring organisms comprise one or more bacteria. In some embodiments, the bacteria comprise gram-negative bacteria. In some embodiments, the gram-negative bacteria comprise species from the genus *Myxococcus*. In certain embodiments, the gram-negative bacteria comprise *Myxococcus xanthus*.

In some embodiments, the bacteria comprise cyanobacteria. In some embodiments, the cyanobacteria comprise species from the genus *Synechococcus*. In certain embodiments, the cyanobacteria comprise *Synechococcus elongatus*. In some embodiments, the cyanobacteria comprise species from the genus *Chlorogloeopsis*. In certain embodiments, the cyanobacteria comprise *Chlorogloeopsis fritschii*. In some embodiments, the cyanobacteria comprise species from the genus *Aphanothece*. In certain embodiments, the cyanobacteria comprise *Aphanothece hegewaldii*. In some embodiments, the cyanobacteria comprise species from the genus *Chroococcus*. In certain embodiments, the cyanobacteria comprise *Aphanothece hegewaldii*.

Enzymes and/or Proteins to Introduce into One or More Recombinant Microorganisms The present disclosure relates to methods of producing one or more fatty alcohols and/or one or more fatty aldehydes from one or more unsaturated lipid moieties comprising producing the one or more unsaturated lipid moieties in one or more recombinant microorganisms manipulated to comprise a biosynthesis pathway for the production of one or more unsaturated lipid moieties. In one embodiment, the one or more recombinant microorganisms manipulated to comprise a biosynthesis pathway for the production of one or more unsaturated lipid moieties comprises one or more exogenous biosynthetic enzymes.

Desaturase

The present disclosure describes enzymes that desaturate fatty acyl substrates to corresponding unsaturated fatty acyl substrates.

In some embodiments, a desaturase is used to catalyze the conversion of a fatty acyl-CoA or acyl-ACP to a corresponding unsaturated fatty acyl-CoA or acyl-ACP. A desaturase is an enzyme that catalyzes the formation of a carbon-carbon double bond in a saturated fatty acid or fatty acid derivative, e.g., fatty acyl-CoA or fatty acyl-ACP (collectively referred to herein as "fatty acyl"), by removing at least two hydrogen atoms to produce a corresponding unsaturated fatty acid/acyl. Desaturases are classified with respect to the ability of the enzyme to selectively catalyze double bond formation at a subterminal carbon relative to the methyl end of the fatty acid/acyl or a subterminal carbon relative to the carbonyl end of the fatty acid/acyl. Omega ($\omega$) desaturases catalyze the formation of a carbon-carbon double bond at a fixed subterminal carbon relative to the methyl end of a fatty acid/acyl. For example, an $\omega^3$ desaturase catalyzes the formation of a double bond between the third and fourth carbon relative the methyl end of a fatty acid/acyl. Delta ($\Delta$) desaturases catalyze the formation of a carbon-carbon double bond at a specific position relative to the carboxyl group of a fatty acid or the carbonyl group of a fatty acyl CoA. For example, a $\Delta^9$ desaturase catalyzes the formation of a double bond between the $C_9$ and $C_{10}$ carbons with respect to the carboxyl end of the fatty acid or the carbonyl group of a fatty acyl CoA.

As used herein, a desaturase can be described with reference to the location in which the desaturase catalyzes the formation of a double bond and the resultant geometric configuration (i.e., E/Z) of the unsaturated hydrocarbon. Accordingly, as used herein, a Z9 desaturase refers to a $\Delta$ desaturase that catalyzes the formation of a double bond between the $C_9$ and $C_{10}$ carbons with respect to the carbonyl end of a fatty acid/acyl, thereby orienting two hydrocarbons on opposing sides of the carbon-carbon double bonds in the cis or Z configuration. Similarly, as used herein, a Z11 desaturase refers to a $\Delta$ desaturase that catalyzes the formation of a double bond between the $C_{11}$ and $C_{12}$ carbons with respect to the carbonyl end of a fatty acid/acyl.

Desaturases have a conserved structural motif. This sequence motif of transmembrane desaturases is characterized by [HX3-4HX7-41(3 non-His)HX2-3(1 nonHis)HHX61-189(40 non-His)HX2-3(1 non-His)HH]. The sequence motif of soluble desaturases is characterized by two occurrences of [D/EEXXH].

In some embodiments, the desaturase is a fatty acyl-CoA desaturase that catalyzes the formation of a double bond in a fatty acyl-CoA. In some such embodiments, the fatty acyl-CoA desaturase described herein is capable of utilizing a fatty acyl-CoA as a substrate that has a chain length of 6, 7, 8, 9, 10, 11, 12, 13, 14, 15, 16, 17, 18, 19, 20, 21, 22, 23, or 24 carbon atoms. Thus, the desaturase used in the recombinant microorganism can be selected based on the chain length of the substrate.

In some embodiments, the fatty acyl desaturase described herein is capable of catalyzing the formation of a double bond at a desired carbon relative to the terminal CoA on the unsaturated fatty acyl-CoA. Thus, in some embodiments, a desaturase can be selected for use in the recombinant microorganism which catalyzes double bond insertion at the 3, 4, 5, 6, 7, 8, 9, 10, 11, 12, or 13 position with respect to the carbonyl group on a fatty acyl-CoA.

In some embodiments, the fatty acyl desaturase described herein is capable of catalyzing the formation of a double bond in a saturated fatty acyl-CoA such that the resultant unsaturated fatty acyl-CoA has a cis or trans (i.e., Z or E) geometric configuration.

In some embodiments, the desaturase is a fatty acyl-ACP desaturase that catalyzes the formation of a double bond in a fatty acyl-ACP. In some embodiments, the fatty acyl-ACP desaturase described herein is capable of utilizing a fatty acyl-CoA as a substrate that has a chain length of 6, 7, 8, 9, 10, 11, 12, 13, 14, 15, 16, 17, 18, 19, 20, 21, 22, 23, or 24 carbon atoms. Thus, the desaturase used in the recombinant microorganism can be selected based on the chain length of the substrate.

In some embodiments, the fatty acyl-ACP desaturase described herein is capable of catalyzing the formation of a double bond at a desired carbon relative to the terminal carbonyl on the unsaturated fatty acyl-ACP. Thus, in some embodiments, a desaturase can be selected for use in the recombinant microorganism which catalyzes double bond insertion at the 3, 4, 5, 6, 7, 8, 9, 10, 11, 12, or 13 position with respect to the carbonyl group on a fatty acyl-ACP.

In some embodiments, the fatty acyl desaturase described herein is capable of catalyzing the formation of a double bond in a saturated fatty acyl-CoA such that the resultant unsaturated fatty acyl-ACP has a cis or trans (i.e., Z or E) geometric configuration.

In some embodiments, the fatty acyl desaturase is a stearyl-CoA Δ9 desaturase. In certain embodiments, the stearyl-CoA Δ9 desaturase is OLE1. In some embodiments, the stearyl-CoA Δ9 desaturase is YGL055W from *Saccharomyces cerevisiae*. In some embodiments, the stearyl-CoA Δ9 desaturase is YALI0C05951g from *Yarrowia lipolytica*. In some embodiments, the stearyl-CoA Δ9 desaturase is CaO19.12583 from *Candida albicans*. In some embodiments, the stearyl-CoA Δ9 desaturase is CaO19.5117 from *Candida albicans*. In some embodiments, the stearyl-CoA Δ9 desaturase is CTRG_05479 from *Candida tropicalis*.

In some embodiments, the fatty acyl desaturase is an oleoyl-CoA Δ12 desaturase. In certain embodiments, the oleoyl-CoA Δ12 desaturase is FAD2. In some embodiments, the oleoyl-CoA Δ12 desaturase is YALI0B10153g from *Yarrowia lipolytica*. In some embodiments, the oleoyl-CoA Δ12 desaturase is CaO19.118 from *Candida albicans*. In some embodiments, the oleoyl-CoA Δ12 desaturase is CaO19.7765 from *Candida albicans*. In some embodiments, the oleoyl-CoA Δ12 desaturase is CTRG_02975 from *Candida tropicalis*.

In some embodiments, the fatty acyl desaturase is a linoleoyl-CoA Δ15 desaturase. In certain embodiments, the linoleoyl-CoA Δ15 desaturase is FAD3. In some embodiments, the linoleoyl-CoA Δ15 desaturase is CaO19.4933 from *Candida albicans*. In some embodiments, the linoleoyl-CoA M15 desaturase is CaO19.12399 from *Candida albicans*. In some embodiments, the stearyl-CoA Δ9 desaturase is CTRG_03583 from *Candida tropicalis*.

In one exemplary embodiment, the fatty-acyl desaturase is a Z11 desaturase. In various embodiments described herein, the Z11 desaturase, or the nucleic acid sequence that encodes it, can be isolated from organisms of the species *Agrotis segetum, Amyelois transitella, Argyrotaenia velutiana, Choristoneura rosaceana, Lampronia capitella, Trichoplusia ni, Helicoverpa zea*, or *Thalassiosira pseudonana*. Further Z11-desaturases, or the nucleic acid sequences encoding them, can be isolated from *Bombyx mori, Manduca sexta, Diatraea grandiosella, Earias insulana, Earias vittella, Plutella xylostella, Bombyx mori* or *Diaphania nitidalis*. In exemplary embodiments, the Z11 desaturase comprises a sequence selected from GenBank Accession Nos. JX679209, JX964774, AF416738, AF545481, EU152335, AAD03775, AAF81787, and AY493438. In some embodiments, a nucleic acid sequence encoding a Z11 desaturase from organisms of the species *Agrotis segetum, Amyelois transitella, Argyrotaenia velutiana, Choristoneura rosaceana, Lampronia capitella, Trichoplusia ni, Helicoverpa zea*, or *Thalassiosira pseudonana* is codon optimized. In some embodiments, the Z11 desaturase comprises a nucleotide sequence selected from SEQ ID NOs: 3, 11, 17 and 19 from *Trichoplusia ni*. In some embodiments, the Z11 desaturase comprises an amino acid sequence set forth in SEQ ID NO: 25 from *Trichoplusia ni*. In other embodiments, the Z11 desaturase comprises a nucleotide sequence selected from SEQ ID NOs: 4 and 9 from *Agrotis segetum*. In some embodiments, the Z11 desaturase comprises an amino acid sequence set forth in SEQ ID NO: 29 from *Agrotis segetum*. In some embodiments, the Z11 desaturase comprises a nucleotide sequence selected from SEQ ID NOs: 5 and 16 from *Thalassiosira pseudonana*. In some embodiments, the Z11 desaturase comprises an amino acid sequence selected from SEQ ID NOs: 26 and 27 from *Thalassiosira pseudonana*. In certain embodiments, the Z11 desaturase comprises a nucleotide sequence selected from SEQ ID NOs: 6, 10 and 23 from *Amyelois transitella*. In some embodiments, the Z11 desaturase comprises an amino acid sequence set forth in SEQ ID NO: 28 from *Amyelois transitella*. In further embodiments, the Z11 desaturase comprises a nucleotide sequence selected from SEQ ID NOs: 7, 12, 18, 20 and 24 from *Helicoverpa zea*. In some embodiments, the Z11 desaturase comprises an amino acid sequence set forth in SEQ ID NO: 1 from *Helicoverpa zea*. In some embodiments, the Z11 desaturase comprises an amino acid sequence set forth in SEQ ID NO: 2 from *S. inferens*. In some embodiments, the Z11 desaturase comprises an amino acid sequence set forth in GenBank Accession nos. AF416738, AGH12217.1, AII21943.1, CAJ43430.2, AF441221, AAF81787.1, AF545481, AJ271414, AY362879, ABX71630.1 and NP001299594.1, Q9N9Z8, ABX71630.1 and AIM40221.1. In some embodiments, the Z11 desaturase comprises a chimeric polypeptide. In some embodiments, a complete or partial Z11 desaturase is fused to another polypeptide. In certain embodiments, the N-terminal native leader sequence of a Z11 desaturase is replaced by an oleosin leader sequence from another species. In certain embodiments, the Z11 desaturase comprises a nucleotide sequence selected from SEQ ID NOs: 8, 21 and 22. In some embodiments, the Z11 desaturase comprises an amino acid sequence selected from SEQ ID NOs: 33, 34, 35, 36, 37 and 38.

In another exemplary embodiment, the fatty-acyl desaturase is a Z9 desaturase. In various embodiments described herein, the Z9 desaturase, or the nucleic acid sequence that encodes it, can be isolated from organisms of the species *Ostrinia furnacalis, Ostrinia nobilalis, Choristoneura rosaceana, Lampronia capitella, Helicoverpa assulta,* or *Helicoverpa zea*. In exemplary embodiments, the Z9 desaturase comprises a sequence selected from GenBank Accession Nos. AY057862, AF243047, AF518017, EU152332, AF482906, and AAF81788. In some embodiments, a nucleic acid sequence encoding a Z9 desaturase is codon optimized. In some embodiments, the Z9 desaturase comprises a nucleotide sequence set forth in SEQ ID NO: 13 from *Ostrinia furnacalis*. In some embodiments, the Z9 desaturase comprises an amino acid sequence set forth in SEQ ID NO: 30 from *Ostrinia furnacalis*. In other embodiments, the Z9 desaturase comprises a nucleotide sequence set forth in SEQ ID NO: 14 from *Lampronia capitella*. In some embodiments, the Z9 desaturase comprises an amino acid sequence set forth in SEQ ID NO: 31 from *Lampronia capitella*. In some embodiments, the Z9 desaturase comprises a nucleotide sequence set forth in SEQ ID NO: 15 from *Helicoverpa zea*. In some embodiments, the Z9 desaturase comprises an amino acid sequence set forth in SEQ ID NO: 32 from *Helicoverpa zea*.

Flavoprotein Pyridine Nucleotide Cytochrome Reductases

The present disclosure describes enzymes that catalyze the interchange of reducing equivalents between one-electron carriers and the two-electron-carrying nicotinamide dinucleotides. The enzymes can include ferredoxin: NADP+ reductases (FNR), plant and fungal NAD(P)H: nitrate reductases, NADH: cytochrome b5 reductases, NADPH: P450 reductases, NADPH: sulphite reductases, nitric oxide synthases, phthalate dioxygenase reductase, and various other flavoproteins.

In one embodiment, the flavoprotein pyridine nucleotide cytochrome reductase is NADH: cytochrome B5 reductase that catalyzes the reaction: 2 a ferricytochrome b5+NADH→2 a ferrocytochrome b5+NAD++H+

NADH: cytochrome B5 reductase (CBR) is a flaviprotein oxidoreductase that serves as electron donor for cytochrome B5, a ubiquitous electron carrier. Cytochrome B5 reductase participates in a variety of metabolic pathways including, but not limited to, steroid biosynthesis, desaturation and elongation of fatty acids, P450-dependent reactions and methaemoglobin reduction.

Cytochrome B5 reductase occurs both as a soluble enzyme and a membrane-bound enzyme due to alternative splicing of a single mRNA. The soluble form is present mainly in erythrocytes and is involved in the reduction of methemoglobin. The membrane-bound form of the enzyme is found primarily in the endoplasmic reticulum and outer mitochondrial membrane, where it participates in the desaturation of fatty acids, cholesterol biosynthesis and drug metabolism. In the membrane-bound form, the N-terminal residue is myristoylated. A deficiency in the enzyme can result in methemoglobinemia.

Cytochrome B5 reductase is also known as methemoglobin reductase, NADH cytochrome B5 reductase, NADH methemoglobin reductase and NADH-ferrihemoglobin reductase.

In one embodiment, the flavoprotein pyridine nucleotide cytochrome reductase is a cytochrome B5 reductase. In some embodiments, the cytochrome B5 reductase is *Saccharomyces cerevisiae* YIL043C. In other embodiments, the cytochrome B5 reductase is *Yarrowia lipolytica* YALI0D04983g. In some embodiments, the cytochrome B5 reductase is *Candida albicans* CaO19.1801. In some embodiments, the cytochrome B5 reductase is *Candida albicans* CaO19.9367. In some embodiments, the cytochrome B5 reductase is *Candida tropicalis* CTRG_03865. In some embodiments, the cytochrome B5 reductase is *Spodoptera exigua* HQ852050. In some embodiments, the cytochrome B5 reductase is *Spodoptera exigua* JX569756. In some embodiments, the cytochrome B5 reductase is *Helicoverpa armigera* HQ638220. In some embodiments, the cytochrome B5 reductase is *Helicoverpa armigera* HQ190046. In another embodiment, the flavoprotein pyridine nucleotide cytochrome reductase is an NADPH-dependent cytochrome P450 reductase (CPR1 or NCP1). In some embodiments, the NADPH-dependent cytochrome P450 reductase is *Saccharomyces cerevisiae* YHR042W. In other embodiments, the NADPH-dependent cytochrome P450 reductase is *Yarrowia lipolytica* YALI0D04422g. In some embodiments, the NADPH-dependent cytochrome P450 reductase is *Candida albicans* CaO19.10187. In some embodiments, the NADPH-dependent cytochrome P450 reductase is *Candida albicans* CaO19.2672. In some embodiments, the NADPH-dependent cytochrome P450 reductase is *Candida tropicalis* CTRG_00485. In some embodiments, the NADPH-dependent cytochrome P450 reductase is *Spodoptera littoralis* JX310073. In some embodiments, the NADPH-dependent cytochrome P450 reductase is *Spodoptera exigua* HQ852049. In some embodiments, the NADPH-dependent cytochrome P450 reductase is *Helicoverpa armigera* HM347785.

In some embodiments, the Cytochrome reductases described herein is used to catalyze the conversion of a fatty acyl-CoA or acyl-ACP to a corresponding unsaturated fatty acyl-CoA or acyl-ACP.

Elongases

The present disclosure describes enzymes that extend the chain length of fatty acids.

Two different types of fatty acid elongation takes place in different organisms. These elongation pathways use Coenzyme-A as acyl carrier rather than acyl carrier protein (ACP) of fatty acid synthesis systems FAS I and FAS II. The first type, mitochondrial fatty acid elongation, is the reversal of fatty acid oxidation. This utilises acetyl-CoA as a substrate and extends the chain length of fatty acids with two carbons. This process acts mainly on acyl-CoA shorter than $C_{16}$.

The second process is the elongation pathway of endoplasmic reticulum, which is present in plants, mammals, yeast and other lower eukaryotes. This is a four-step reaction each catalysed by individual enzymes. These enzymes are beta-ketoacyl-CoA synthase, beta-ketoacyl-CoA reductase, beta-hydroxyacyl-CoA dehydratase and trans-2-enoyl-CoA reductase. This pathway mainly acts with acyl-CoA of chain length $C_{16}$ or larger and important in the generation of very long chain fatty acids. This process utilises malonyl-CoA rather than acetyl-CoA for chain elongation. The first enzyme which leads to condensation of malonyl-CoA with acyl-CoA (beta-ketoacyl-CoA synthase) is also called elongase.

Several variants of elongase exist, depending upon the host organism. In *S. cerevisiae*, three different genes encode elongases (ELO1, ELO2 (FEN1) and ELO3 (FEN12)), and they have different substrate specificities. ELO1 prefers shorter saturated fatty acids (C14-C16), ELO2 prefers longer saturated and monounsaturated fatty acids and ELO3 prefers monounsaturated and polyunsaturated fatty acids. In contrast, *Trypanosoma brucei* have two elongase genes which has specificity for shorter fatty acids (ELO1-C4 to C10 elongation and ELO2-C10 to C14 elongation). The orthologs of the three yeast elongase genes were identified in both *Plasmodium falciparum* and *Toxoplasma gondii* and they might have similar substrate specificity to that of yeast.

In some embodiments, the elongase is ELO1 from *S. cerevisiae* (YJL196C). In another embodiment, the elongase is ELO2 (FEN1) from *S. cerevisiae* (YCR034W). In certain embodiments, the elongase is CaO19.6343 from *Candida albicans*. In certain embodiments, the elongase is CaO19.13699 from *Candida albicans*. In certain embodiments, the elongase is CTRG_03563 from *Candida tropicalis*. In another embodiment, the elongase is ELO3 (FEN12) from *S. cerevisiae* (YLR372W). In certain embodiments, the elongase is YALI0B20196g from *Yarrowia lipolytica*. In certain embodiments, the elongase is CaO19.8526 from *Candida albicans*. In certain embodiments, the elongase is Ca019.908 from *Candida albicans*. In certain embodiments, the elongase is CTRG_01179 from *Candida tropicalis*.

In addition to fatty acid elongation, fatty acid salvage has also been included to this pathway. The fatty acids salvaged from host with the action of acyl-CoA binding proteins (ACBP) can be converted to triacylglycerides and cholesterol ester with the action of ER-localised enzymes diacylglycerol O-acyltransferase (DGAT) and sterol O-acyltransferase respectively and can be stored in lipid bodies. There is strong biochemical evidence in *P. falciparum* and *T. gondii* to support the acquisition of fatty acids from host.

Thioesterases

The present disclosure describes enzymes that release free fatty acids from acyl-ACP or acyl-CoA.

Acyl-ACP thioesterase releases free fatty acids from Acyl-ACPs, synthesized from de novo fatty acid biosynthesis. The reaction terminates fatty acid biosynthesis. In plants, fatty acid biosynthesis occurs in the plastid and thus requires plastid-localized acyl-ACP thioesterases. The main products of acyl-ACP thioesterase are oleate (C18:0) and to a lesser extent palmitate (C16:0) in the vegetative tissues of all plants. The released free fatty acids are re-esterified to coenzyme A in the plastid envelope and exported out of plastid.

There are two isoforms of acyl-ACP thioesterase, FatA and FatB. Substrate specificity of these isoforms determines the chain length and level of saturated fatty acids in plants. The highest activity of FatA is with C18:1-ACP. FatA has very low activities towards other acyl-ACPs when compared with C18:1-ACP. FatB has highest activity with C16:0-ACP. It also has significant high activity with C18:1-ACP, followed by C18:0-ACP and C16:1-ACP. Kinetics studies of FatA and FatB indicate that their substrate specificities with different acyl-ACPs come from the Kcat values, rather than from Km. Km values of the two isoforms with different substrates are similar, in the micromolar order. Domain swapping of FatA and FatB indicates the N-terminus of the isoforms determines their substrate specificities. For those plants which predominantly accumulate medium-chain length saturated fatty acids in seeds, they evolved with specialized FatB and/or FatA thioesterases (Voelker T, Kinney A J (2001) Variations in the biosynthesis of seed-storage lipids. Annu Rev Plant Physiol Plant Mol Biol 52: 335-361). For example, laurate (12:0) is the predominant seed oil in coconut. Correspondingly, the medium-chain specific acyl-ACP thioesterase activity was detected in coconut seeds.

Fatty acids are often found in the cell in the activated form of an acyl-coA. Acyl-CoAs are used in the biosynthesis of many cellular products and components. In plants they are involved in the biosynthesis of membrane lipids, seed storage lipids, wax, cutins and suberin.

Acyl-CoA thioesterase hydrolyzes fatty acyl-CoAs to free fatty acids. In eukaryotes, the enzyme activity has been detected in the cytosol, ER, mitochondrion and peroxisome. In prokaryotes, the enzymes activity is localized in the periplasm and cytosol. In prokaryotes acyl-CoA thioesterases are involved in catabolism, supporting growth on fatty acids or conjugated fatty acid as the sole source of carbon (Nie L et al. (2008) A novel paradigm of fatty acid beta-oxidation exemplified by the thioesterase-dependent partial degradation of conjugated linoleic acid that fully supports growth of *Escherichia coli*. Biochemistry 47(36): 9618-26). The physiological roles of acyl-CoA thioesterase in eukaryotic organisms remain unclear. Works in animal and yeast shed some preliminary clue about the involvement of the enzyme in fatty acid oxidation. ACH2 is the first cloned plant acyl-CoA thioesterase (Tilton G B et al. (2004) Biochemical and molecular characterization of ACH2, an acyl-CoA thioesterase from *Arabidopsis thaliana*. J Biol Chem 279(9): 7487-94). The gene is highly expressed in mature tissues rather than in germinating seedlings where fatty acid beta-oxidation predominantly occurs. It indicates the role of ACH2 is not linked to fatty acid oxidation.

In some embodiments, the acyl-ACP thioesterase is FatB from *Arabidopsis thaliana* (Gene ID AT1G08510). In some embodiments, the acyl-ACP thioesterase is FatA from *Arabidopsis thaliana* (Gene ID AT3G25110).

In some embodiments, the acyl-CoA thioesterase is tesA from *Escherichia coli* (Gene ID EG11542). In some embodiments, the acyl-CoA thioesterase is ACH2 from *Arabidopsis thaliana* (Gene ID AT1G01710).

Glycerol-3-Phosphate Acyltransferase

The present disclosure describes enzymes that catalyze the acylation reaction at the sn-1 position of glycerol 3-phosphate shown as follows:

a long-chain acyl-CoA+sn-glycerol 3-phosphate→a 1-acyl-sn-glycerol 3-phosphate+coenzyme A.

Glycerol-3-phosphate acyltransferase (GPAT) catalyzes the acylation reaction at the sn-1 position of glycerol 3-phosphate. The plant cell contains three types of GPAT, which are located in the chloroplasts, mitochondria and cytoplasm. The enzyme in chloroplasts is soluble and uses acyl-(acyl-carrier protein) as the acyl donor, whereas the enzymes in the mitochondria and the cytoplasm are bound to membranes and use acyl-CoA as the acyl donor (Nishida I et al. (1993) The gene and the RNA for the precursor to the plastid-located glycerol-3-phosphate acyltransferase of *Arabidopsis thaliana*. Plant Mol Biol. 21(2): 267-77; Murata N and Tasaka Y (1997) Glycerol-3-phosphate acyltransferase in plants. Biochim Biophys Acta. 1348(1-2):10-16).

Eight GPAT genes have been identified in *Arabidopsis* (Zheng Z et al. (2003) *Arabidopsis* AtGPAT1, a member of the membrane-bound glycerol-3-phosphate acyltransferase gene family, is essential for tapetum differentiation and male fertility. Plant Cell 15(8):1872-87). GPAT1 was shown to encode a mitochondrial enzyme (Zheng et al. 2003). GPAT4, GPAT5 and GPAT8 were shown to be essential for cutin biosynthesis (Beisson F et al. (2007) The acyltransferase GPAT5 is required for the synthesis of suberin in seed coat and root of *Arabidopsis*. Plant Cell 19(1): 351-368; Li, Y et al. (2007) Identification of acyltransferases required for cutin biosynthesis and production of cutin with suberin-like monomers. Proc Natl Acad Sci USA 104(46): 18339-18344). GPAT2, GPAT3, GPAT6 and GPAT7 have not been characterized yet.

The cytoplasmic GPAT is responsible for the synthesis of triacylglycerol and non-chloroplast membrane phospholipids. It is expected to have a substrate preference for palmitate (C16:0) and oleate (C18:1) since these two fatty acids are the most common ones found at the sn-1 position of plant triacylglycerols. The cytoplasmic GPAT was partially purified from avocado (Eccleston V S and Harwood J L (1995) Solubilisation, partial purification and properties of acyl-CoA: glycerol-3-phosphate acyltransferase from avocado (*Persea americana*) fruit mesocarp. Biochim Biophys Acta 1257(1):1-10).

Membrane-bound glycerol-3-phosphate acyltransferase (PlsB) from *E. coli* catalyzes the first committed step in phospholipid biosynthesis and is thought to function in close proximity to the succeeding enzyme 1-acylglycerol-3-phosphate O-acyltransferase (PlsC) (Kessels J M et al. (1983) Facilitated utilization of endogenously synthesized lysophosphatidic acid by 1-acylglycerophosphate acyltransferase from *Escherichia coli*. Biochim Biophys Acta 753(2): 227-235). It is specific for acylation at position 1 of sn-glycerol 3-phosphate and can utilize either fatty acyl-acyl carrier protein (acyl-ACP) or fatty acyl-coenzyme A (acyl- CoA) thioesters as acyl donors to form a 1-acyl-sn-glycerol 3-phosphate. Fatty acids that are endogenously synthesized are attached to ACP and exogenously added fatty acids are attached to CoA. In *E. coli* phospholipids, the sn 1 position is occupied mainly by either palmitate, or cis-vaccenate, whereas the sn 2 position is predominantly palmitoleate, or cis-vaccenate. This is thought to result from the substrate preferences of the PlsB and PlsC enzymes.

The plsB gene has been shown to be regulated by stress response regulators such as RNA polymerase, sigma 24 (sigma E) factor and ppGpp (Wahl A et al. (2011) Antagonistic regulation of dgkA and plsB genes of phospholipid synthesis by multiple stress responses in *Escherichia coli*. Mol Microbiol 80(5): 1260-75. PlsB is part of a protein network for phospholipid synthesis and interacts with a holo-[acyl-carrier protein] (ACP), esterase/thioesterase (YbgC) and phosphatidylserine synthase (PssA) to form a complex at the cytoplasmic side of the inner membrane.

plsB is essential for growth (Baba T et al. (2006) Construction of *Escherichia coli* K-12 in-frame, single-gene knockout mutants: the Keio collection. Mol Syst Biol. 2:2006-2008; Yoshimura M et al. (2007) Involvement of the YneS/YgiH and PlsX proteins in phospholipid biosynthesis in both *Bacillus subtilis* and *Escherichia coli*. BMC Microbiol 7: 69).

Site-directed mutagenesis and chemical modification studies have demonstrated catalytically important amino acid residues in PlsB, including an invariant histidine residue that is essential for catalysis (Lewin™ et al. (1999) Analysis of amino acid motifs diagnostic for the sn-glycerol-3-phosphate acyltransferase reaction. Biochemistry 38(18): 5764-5771). Genetic studies have identified the plsB locus as involved in the formation of multidrug tolerant persister cells.

The properties of the *E. coli* B enzyme were studied in earlier work (Kito M et al. (1972) Inhibition of L-glycerol 3-phosphate acyltransferase from *Escherichia coli* by cis-9, 10-methylenehexadecanoic acid. J Biochem 71(1): 99-105; Okuyama H and Wakil S J (1973) Positional specificities of acyl coenzyme A: glycerophosphate and acyl coenzyme A: monoacylglycerophosphate acyltransferases in *Escherichia coli*. J Biol Chem 248(14): 5197-5205; Kito M et al. (1978) Function of phospholipids on the regulatory properties of solubilized and membrane-bound sn-glycerol-3-phosphate acyltransferase of *Escherichia coli*. Biochim Biophys Acta 529(2): 237-249).

A glycerol-3-phosphate/dihydroxyacetone phosphate dual substrate-specific sn-1 acyltransferase is located in lipid particles and the ER and is involved in the stepwise acylation of glycerol-3-phosphate and dihydroxyacetone in lipid biosynthesis. The most conserved motifs and functionally relevant residues are oriented towards the ER lumen.

A gene (SCT1) encoding a dual glycerol-3-phosphate O-acyltransferase (GAT)/dihydroxyacetone phosphate acyltransferase (DHAT) was identified, cloned and biochemically characterized from *Saccharomyces cerevisiae*. In the yeast Δgpt1 mutant which exhibits very low GAT/DHAT activity, the overexpression of SCT1 through a plasmid vector showed increased GAT/DHAT activity underlining the proposed molecular function as glycerol-3-phosphate O-acyltransferase/dihydroxyacetone phosphate acyltransferase. The GAT/DHAT activity towards acyl-donors was highest with palmitoleoyl-CoA followed by palmitoyl-CoA, oleoyl-CoA and stearoyl-CoA. The SCT1p was localized to membranes in the cytosol, most probably to the endoplasmic reticulum. In vivo studies of Δsct1 mutants did reveal an impact on all four phospholipids but the observed decrease of 16:0 fatty acids in the phosphatidylethanolamine class was balanced out by an increase in other fatty acids, particularly 18:0 molecular species. The null mutants of SCT1 and GPT2 were synthetically lethal in yeast (Zheng Z and Zou J (2001) The initial step of the glycerolipid pathway: identification of glycerol 3-phosphate/dihydroxyacetone phosphate dual substrate acyltransferases in *Saccharomyces cerevisiae*. J Biol Chem 276(45): 417104-41716).

The gene (GPT2) encoding a dual glycerol-3-phosphate O-acyltransferase (GAT)/dihydroxyacetone phosphate acyltransferase (DHAT) from *Saccharomyces cerevisiae* was identified, cloned and biochemically characterized. GPT2 was recombinantly expressed in *E. coli* in the ΔplsB background devoid of GAT/DHAT activity and showed an increased GAT activity but could not rescue the mutant probably because of the incorrect embedding of GPT2 in the membrane. In the yeast Δgpt1 mutant which exhibits very low GAT/DHAT activity, the overexpression of GPT2 from a plasmid vector showed increased GAT/DHAT activity, underlining the proposed molecular function as glycerol-3-phosphate O-acyltransferase/dihydroxyacetone phosphate acyltransferase. The GAT/DHAT activity towards acyl-donors was highest with oleoyl-CoA followed by palmitoleoyl-CoA, palmitoyl-CoA and stearoyl-CoA.

The GPT2p was localized to membranes in the cytosol. In vivo studies of Δgpt2 mutants did not reveal any significant impact on the total fatty acid profile but a decrease of 16:1 fatty acids in the phosphatidylethanolamine class was observed which was compensated by an increase in 16:0 and 18:1 molecular species. Analysis of a known yeast mutant TTA1 deficient in GAT activity showed that the TTA1 GPT2 gene had a missense mutation with one nucleotide change in the conserved motif Ill for acyltransferases. The null mutants of SCT1 and GPT2 were synthetically lethal in yeast (Zheng and Zou 2001).

In some embodiments, the glycerol-3-phosphate acyltransferase is a GPAT from *Arabidopsis thaliana* (At1g02390). In some embodiments, the glycerol-3-phosphate acyltransferase is PlsB from *E. coli* (Gene ID EG10740). In some embodiments, the glycerol-3-phosphate acyltransferase is the dual glycerol-3-phosphate O-acyltransferase (GAT)/dihydroxyacetone phosphate acyltransferase (DHAT) SCT1 from *S. cerevisiae* (YBL011w). In some embodiments, the glycerol-3-phosphate acyltransferase is YALI0C00209g from *Yarrowia lipolytica*. In some embodiments, the glycerol-3-phosphate acyltransferase is 1503_02577 from *Candida albicans*. In some embodiments, the glycerol-3-phosphate acyltransferase is CTRG_02630 from *Candida tropicalis*. In some embodiments, the glycerol-3-phosphate acyltransferase is the dual glycerol-3-phosphate O-acyltransferase (GAT)/dihydroxyacetone phosphate acyltransferase (DHAT) GPT2 from *S. cerevisiae* (YKR067w). In some embodiments, the glycerol-3-phosphate acyltransferase is CaO19.5815 from *Candida albicans*. In some embodiments, the glycerol-3-phosphate acyltransferase is CaO19.13237 from *Candida albicans*. In some embodiments, the glycerol-3-phosphate acyltransferase is CTRG_02630 from *Candida tropicalis*.

Lysophosphatidic Acid Acyltransferase

The present disclosure describes enzymes that catalyze acylation of the sn-2 position of triacylglycerol.

Membrane-bound 1-acylglycerol-3-phosphate O-acyltransferase encoded by gene plsC catalyzes the second step in phospholipid biosynthesis and is thought to function in close proximity to the preceding enzyme glycerol-3-phosphate acyltransferase encoded by gene plsB (Kessels J M et al. 1983). It is specific for acylation at the sn-2 position of a 1-acyl-sn-glycerol 3-phosphate and can utilize either acyl-acyl carrier protein (acyl-ACP), or acyl-coenzyme A (acyl-CoA) as the fatty acyl donor to form a 1,2-diacyl-sn-glycerol 3-phosphate (a phosphatidate, a phosphatidic acid). Fatty acids that are endogenously synthesized are attached to ACP and exogenously added fatty acids are attached to CoA (Greenway D L and Silbert D F (1983) Altered acyltransferase activity in Escherichia coli associated with mutations in acyl coenzyme A synthetase. J Biol Chem 258(21): 13034-13042). In E. coli phospholipids at the sn 1 position is occupied mainly by either palmitate, or cis-vaccenate, whereas the sn 2 position is predominantly palmitoleate, or cis-vaccenate. This is thought to result from the substrate preferences of the PlsB and PlsC enzymes (Rock Colo. et al. (1981) Phospholipid synthesis in Escherichia coli. Characteristics of fatty acid transfer from acyl-acyl carrier protein to sn-glycerol 3-phosphate. J Biol Chem 256(2): 736-742; Goelz S E and Cronan J E (1980) The positional distribution of fatty acids in Escherichia coli phospholipids is not regulated by sn-glycerol 3-phosphate levels. J Bacteriol 144(1): 462-464).

Site directed mutagenesis studies showed that changing threonine-122 to alanine or leucine resulted in changes in acyl-CoA substrate specificity (Morand L Z et al. (1998) Alteration of the fatty acid substrate specificity of lysophosphatidate acyltransferase by site-directed mutagenesis. Biochem Biophys Res Commun 244(1): 79-84).

In an engineered strain of E. coli, overexpression of PlsC and GalU resulted in increased production of glycoglycerolipids (Mora-Buye N et al. (2012). An engineered E. coli strain for the production of glycoglycerolipids. Metab Eng 14(5): 551-559).

The plsC gene of Streptococcus pneumoniae encodes a 1-acylglycerol-3-phosphate acyltransferase homologous to the E. coli enzyme. The gene was cloned and expressed in E. coli, and membranes expressing it were shown to catalyze the predicted function (Lu Y J et al. (2006) Acyl-phosphates initiate membrane phospholipid synthesis in Gram-positive pathogens. Mol Cell 23(5): 765-772).

Plant lysophosphatidate acyltransferase (LPAAT) catalyzes acylation of the sn-2 position of triacylglycerol. The substrate specificity of LPAAT in a given plant species generally determines what fatty acid species are incorporated at the sn-2 position. LPAAT has been cloned from maize and meadow foam. There are two LPAAT genes in meadow foam, whereas only one in maize. The enzyme activity of both LAT1 and LAT2 in meadow foam was confirmed by in vitro assay. In addition, LAT2 was shown to functional complement the E. coli LPAAT deficient strain (Brown A P et al. (2002) Limnanthes douglasii lysophosphatidic acid acyltransferases: immunological quantification, acyl selectivity and functional replacement of the Escherichia coli plsC gene. Biochem J 364(Pt 3):795-805).

LAT1 is a highly selective acyltransferase that only uses 18:1-CoA as a substrate. LAT2 is less selective. The highest activity was shown towards 22:1-CoA, followed by 16:0- and 18:1-CoA. The substrate specificities of LAT1 and LAT2 are consistent with their proposed roles, for LAT1 in membrane lipid biosynthesis and LAT2 in storage lipid biosynthesis. Plant cell membranes predominantly contain C16 and C18 unsaturated fatty acids, whereas storage lipids contain a wide range of fatty acids including saturated fatty acids and very long-chain unsaturated fatty acids. The protein level of LAT1 and LAT2 in different plant tissues was detected by antibodies. LAT1 is present in both leaves and developing seeds, whereas LAT2 is only detected in developing seeds. This again is consistent with their proposed roles. The role of LAT2 in triacylglycerol biosynthesis was further shown by transformation of LAT2 in oil seed rape which does not normally contain 22:1-CoA at the sn-2 position. The transformation of the meadow foam LAT2 inserted 22:1-CoA at the sn-2 position (Lassner M W et al. (1995) Lysophosphatidic acid acyltransferase from meadowfoam mediates insertion of erucic acid at the sn-2 position of triacylglycerol in transgenic rapeseed oil. Plant Physiol 109(4): 1389-1394).

Utilizing viable mutant Saccharomyces cerevisiae strains lacking sphingolipid biosynthesis, the gene SLC1 was isolated and demonstrated to encode a acyl-CoA: lysophosphatidate acyltransferase. Sequence homology with the PLSC protein of E. coli which is classified as 1-acyl-sn-glycerol-3-phosphate acyltransferase indicated a similar function. This presumed molecular function of SLC1p was corroborated by the ability to rescue the ΔplsC mutant of E. coli. It could be shown that a single nucleotide alteration changing an L-glutamine to an L-leucine at position 131 transformed the substrate preference from C16 and C18 fatty acids to C26 fatty acids which was reflected in vivo in the corresponding fatty acid composition of wild type (SLC1) versus mutant (SLC1-1) (Nagiec M M et al. (1993) A suppressor gene that enables Saccharomyces cerevisiae to grow without making sphingolipids encodes a protein that resembles an Escherichia coli fatty acyltransferase. J Biol Chem 268(29): 22156-22163).

In vitro assays with the recombinantly expressed and purified SLC1p in E. coli revealed a substrate preference towards lyso-phosphatidate and oleoyl-CoA but also accepted 1-palmitoylglycerol 3-phosphate and 1-stearoyl-sn-glycerol 3-phosphate. In vivo studies of mutants such as Δslc1, Δslc4 (another potential acyl-CoA:phosphatidyl acyltransferase) and double mutants of Δslc1Δslc4 bearing a plasmid with either the SLC1 or SLC4 gene referred to as 2.ΔSLC1 (or 2.ΔSLC4) showed that SLC1 promoted the biosyntheses of phosphatidate and also phosphatidylinositol and diacylglycerol. It was suggested that SLC1 is involved in phospholipid remodeling by exchanging fatty acids on glycerophospholipids in vivo (Benghezal M et al. (2007) SLC1 and SLC4 encode partially redundant acyl-coenzyme A 1-acylglycerol-3-phosphate O-acyltransferases of budding yeast. J Biol Chem 282(42): 30845-30855).

Screening the yeast genome with candidate open reading frames (ORFs) of known acyltransferase enzymes and testing the associated deletion strains, the gene encoding an acyl-CoA dependent lyso-phospholipid acyltransferase (ALE1) was identified. In the Δale1 strain a dramatic decrease of lyso-phosphatidylethanolamine acyltransferase (LPEAT) activity was observed but it could also be demonstrated that ALE1p may provide redundant lyso-phosphatidate acyltransferase (LPAAT) activity when the main LPAAT in Saccharomyces cerevisiae, i.e. SLC1p, is absent or rendered inactive. ALE1p preferably attaches unsaturated acyl chains of varying length to the sn-2 position of lyso-phospholipids. The enzyme was localized to both microsomal and mitochondrial membranes utilizing high purity cell fractionation. It has been proposed that ALE1 may be the major LPEAT in the exogenous lysolipid metabolism (ELM) pathway in yeast but it is also required for efficient functioning of the endogenous Kennedy pathway (Riekhof W R et al. (2007) Identification and characterization of the major lysophosphatidylethanolamine acyltransferase in Saccharomyces cerevisiae. J Biol Chem 282 (39): 28344-28352).

In a simultaneous study, LPT1 (synonymous to ALE1) was identified by applying a synthetic genetic array analysis and shown to have lyso-phospholipid acyltransferase activity. In this study the best substrate for LPT1 (=ALE1) was lyso-phosphatidylcholine, hence acting as a lyso-phosphatidylcholine acyltransferase (LPCAT) and the residual activity as LPAAT reported earlier was also demonstrated utilizing single Δlpt1 and double Δscl1Δlpt1 mutants, the latter being inviable. The ratio of incorporating oleate into phosphatidylcholine was determined as 70% towards the de novo synthesis and 30% towards remodeling (Jain S et al. (2007) Identification of a novel lysophospholipid acyltransferase in *Saccharomyces cerevisiae*. J Biol Chem 282(42): 30562-30569).

The molecular function of ALE1 (also referred to as LCA1 or SLC4) as a lyso-phosphatidylcholine acyltransferase (LPCAT) was corroborated in another simultaneous study monitoring the incorporation of radioactive labeled lyso-phosphatidylcholine and/or palmitoyl-CoA into phosphatidylcholine (PC). The study confirmed that ALE1p (=LCA1p in this study) was accepting a variety of acyl-donors but showed highest activity as LPCAT regardless of the acyl-chain of lyso-phosphatidylcholine species (16:0 or 18:1). In addition, a high sensitivity towards Zn2+ was observed which was inhibitory at concentrations above 0.1 mM and activating at lower concentrations (10 to 25 μM). The high PC turnover-rate measured for ALE1p (=LCA1p) emphasized the enzyme as a key catalyst involved in the re-acylation of PC (Chen Q et al. (2007) The yeast acylglycerol acyltransferase LCA1 is a key component of Lands cycle for phosphatidylcholine turnover." FEBS Lett 581 (28): 5511-5516).

The search for genes causing aberrations in the formation of lipid droplets (LD) in *Saccharomyces cerevisiae* identified the gene LOA1 (formerly VPS66) encoding for an acyl-CoA dependent lysophosphatidate acyltransferase. The in vivo molecular function of LOA1p was determined using the comparison of the lipidome of wild type and Δloa1 yeast strains. The analysis showed that in the LOA1 deficient mutant (Δloa1) the percentage of oleate containing phosphatidate molecular species was considerably reduced and the content of triacylglycerols (TGA) was lowered by 20 percent. The protein was recombinantly expressed in *E. coli* and partially purified by obtaining the highly enriched lipid droplet fraction and by affinity chromatography with LOA1p still attached to the matrix beads. The purified LOA1p was characterized in in vitro assays demonstrating that LOA1p was specific for lysophosphatidate and oleoyl-CoA, thus acting as a oleoyl-CoA: lysophosphatidate acyltransferase in yeast. Based upon the results, LOA1p was proposed to be significantly involved in channeling excess oleate—containing phosphatidate species into TAG biosynthesis and the proper development of lipid droplets (LD's). Utilizing a genomic-tagging construct, subcellular fractionation, immunohistochemistry and fluorescence microscopy LOA1 could be localized to both endoplasmic reticulum (ER) and lipid droplets (LD's) (Ayciriex S et al. (2012) YPR139c/LOA1 encodes a novel lysophosphatidic acid acyltransferase associated with lipid droplets and involved in TAG homeostasis. Mol Biol Cell 23(2): 233-246).

In some embodiments, the lysophosphatidic acid acyltransferase is plsC from *E. coli* (MetaCyc Accession ID EG11377). In other embodiments, the lysophosphatidic acid acyltransferase is plsC from *S. pneumoniae* (MetaCyc Accession ID G-10763). In some embodiments, the lysophosphatidic acid acyltransferase is LAT1 from *Limnanthes douglasii*. In some embodiments, the lysophosphatidic acid acyltransferase is LAT2 from *Limnanthes douglasii* (MetaCyc Accession ID G-9398). In some embodiments, the lysophosphatidic acid acyltransferase is SLC1 from *Saccharomyces cerevisiae* (YDL052c). In some embodiments, the lysophosphatidic acid acyltransferase is YALI0E18964g from *Yarrowia lipolytica*. In some embodiments, the lysophosphatidic acid acyltransferase is CaO19.250 from *Candida albicans*. In some embodiments, the lysophosphatidic acid acyltransferase is CaO19.7881 from *Candida albicans*. In some embodiments, the lysophosphatidic acid acyltransferase is CTRG_02437 from *Candida tropicalis*. In some embodiments, the lysophosphatidic acid acyltransferase is ALE1 from *Saccharomyces cerevisiae* (YOR175C). In some embodiments, the lysophosphatidic acid acyltransferase is YALI0F19514g from *Yarrowia lipolytica*. In some embodiments, the lysophosphatidic acid acyltransferase is CaO19.1881 from *Candida albicans*. In some embodiments, the lysophosphatidic acid acyltransferase is CaO19.9437 from *Candida albicans*. In some embodiments, the lysophosphatidic acid acyltransferase is CTRG_01687 from *Candida tropicalis*. In some embodiments, the lysophosphatidic acid acyltransferase is LOA1 from *Saccharomyces cerevisiae* (YPR139C). In some embodiments, the lysophosphatidic acid acyltransferase is YALI0C14014g from *Yarrowia lipolytica*. In some embodiments, the lysophosphatidic acid acyltransferase is CaO19.1043 from *Candida albicans*. In some embodiments, the lysophosphatidic acid acyltransferase is CaO19.8645 from *Candida albicans*. In some embodiments, the lysophosphatidic acid acyltransferase is CTRG_04750 from *Candida tropicalis*.

Diacylglycerol Acyltransferase

The present disclosure describes enzymes that add an acyl group to the sn-3 position of diacylglycerol (DAG) to form triacylglycerol (TAG).

Diacylglycerol acyltransferase (DGAT) catalyzes the only unique reaction in triacylglycerol biosynthesis. It adds an acyl group to the sn-3 position of diacylglycerol (DAG) and forms triacylglycerol (TAG), shown as follows:

an acyl-CoA+a 1,2-diacyl-sn-glycerol→a triacyl-sn-glycerol+coenzyme A.

DGAT accepts a broad range of acyl-CoA as acyl donor including C18:1, C18:2, and C20:1 acyl-CoA as demonstrated for the *Arabidopsis* DGAT (Jako C et al. (2001) Seed-specific over-expression of an *Arabidopsis* cDNA encoding a diacylglycerol acyltransferase enhances seed oil content and seed weight. Plant Physiol 126(2): 861-874). Expressing the *Arabidopsis* cDNA of DGAT in an insect cell culture and in yeast, as well as over-expressing the cDNA in wild type *Arabidopsis*, demonstrated the DGAT activity in transferring an acyl group to the sn-3 position of DAG (Hobbs D H et al. (1999) Cloning of a cDNA encoding diacylglycerol acyltransferase from *Arabidopsis thaliana* and its functional expression. FEBS Lett 452(3): 145-149; Zou J et al. (1999) The *Arabidopsis thaliana* TAG1 mutant has a mutation in a diacylglycerol acyltransferase gene. Plant J 19(6): 645-653). Over-expression of the *Arabidopsis* cDNA in wild type *Arabidopsis* increased oil deposition in seeds and this increase is correlated to the increased mRNA expression level of DGAT. This indicates that DGAT is a regulatory point of the triacylglycerol biosynthesis pathway.

The gene encoding the bifunctional acyl-CoA:acylglycerol acyltransferase (DGAT) has been identified in *Saccharomyces cerevisiae* as a major contributor to triacylglycerol biosynthesis (Sandager L et al. (2002) Storage lipid synthesis is non-essential in yeast. J Biol Chem 277(8): 6478-6482). The gene (DGA1) belongs in the DGAT2 family which members are characterized as acyl-CoA dependent acyltransferases (Lardizabal K D et al. (2001) DGAT2 is a new diacylglycerol acyltransferase gene family: purification, cloning, and expression in insect cells of two polypeptides from *Mortierella ramanniana* with diacylglycerol acyltransferase activity." J Biol Chem 276(42): 38862-38869). It has been demonstrated that DGA1p is the only acyl-CoA dependent acyltransferase catalyzing the esterification of diacylglycerol (DAG) to triacylglycerol (TAG) in the yeast genome. This has been shown in deletion mutants of DGA1 (Δdga1) and in combination with the deletion of the other diacylglycerol acyltransferase of importance in yeast, i.e. LRO1 which esterifies DAG utilizing a phospholipid acyl donor (Δlro1). In the Δdga1lro1 double mutant almost all of the diacylglycerol acyltransferase has been lost and TAG synthesis was abolished. A plasmid carrying the DGA1 gene could rescue the TAG synthetic deficiency in the mutant indicating that in vivo DGA1 was prominently involved in the TAG biosynthetic route (Sorger D, Daum G (2002). Synthesis of triacylglycerols by the acyl-coenzyme A:diacyl-glycerol acyltransferase Dga1p in lipid particles of the yeast *Saccharomyces cerevisiae*. J Bacteriol 184(2): 519-524; Oelkers P et al. (2002) The DGA1 gene determines a second triglyceride synthetic pathway in yeast. J Biol Chem 277(11): 8877-8881). In vitro a preference of DGA1p towards oleoyl-CoA and palmitoyl-CoA was observed which is inverted for the phospholipid dependent acyltransferase LRO1p (Oelkers et al. 2002).

In addition, the function of DGA1p as an acyl-CoA dependent monoacylglycerol acyltransferase (MGAT) was demonstrated in vivo utilizing Δdga1 mutants which had lost more than 60% of the MGAT activity. The in vitro MGAT activity of DGA1 was shown by the oleoyl-CoA dependent esterification of 2-oleoylglycerol yielding 1,2-dioleoylglycerol in the process (Heier C et al. (2010) Identification of Yju3p as functional orthologue of mammalian monoglyceride lipase in the yeast *Saccharomyces cerevisiae*. Biochim Biophys Acta 1801(9): 1063-1071).

More insights into the functional importance and topological orientation of sequence motifs in the primary sequence of DGA1p has been gained by in silico analyses, site-directed mutagenesis of signature motifs and deletion mutations of the C- and N-termini. It could be demonstrated that besides the signature motifs found in other DGAT2 family members *Saccharomyces* possesses a unique hydrophilic stretch which was shown to significantly modulate enzyme activity. Also, the histidine residue 195 in the second of the four determined transmembrane domains was proven to be essential for enzyme activity. The topology of DGA1 revealed that both C- and N-termini face the cytoplasm and that the C-terminus was more important for DGA1 activity than the N-terminus (Liu Q et al. (2011) Functional and topological analysis of yeast acyl-CoA: diacylglycerol acyltransferase 2, an endoplasmic reticulum enzyme essential for triacylglycerol biosynthesis. J Biol Chem 286(15): 13115-13126).

Using highly purified cell fragments and immunoblotting, Sorger et al. (2002) and Liu et al. (2011) demonstrated that DGA1 was localized to lipid droplets and microsomal membranes, most probably the endoplasmic reticulum.

*Acinetobacter* sp. ADP1 expresses a bifunctional enzyme that exhibits both wax ester synthase (WS) and acyl-coA: diacylglycerol acyltransferase (DGAT) activities (Kalscheuer R and Steinbuchel A (2003) A novel bifunctional wax ester synthase/acyl-CoA:diacylglycerol acyltransferase mediates wax ester and triacylglycerol biosynthesis in *Acinetobacter calcoaceticus* ADP1. J Biol Chem 278(10): 8075-8082). This homodimer catalyzes the final steps in TAG and WE biosynthesis (Stoveken T et al. (2005) The wax ester synthase/acyl coenzyme A:diacylglycerol acyltransferase from *Acinetobacter* sp. strain ADP1: characterization of a novel type of acyltransferase. J Bacteriol 187(4): 1369-1376). It mediates both oxo ester and thio ester bond formation and has a broad substrate range, accepting medium chain fatty alcohols and acyl-CoA esters as well as monoacylglycerols (MAGs) (Uthoff S et al. (2005) Thio wax ester biosynthesis utilizing the unspecific bifunctional wax ester synthase/acyl coenzyme A:diacylglycerol acyltransferase of *Acinetobacter* sp. strain ADP1. Appl Environ Microbiol 71(2): 790-796).

In some embodiments, the diacylglycerol acyltransferase is TAG1 from *Arabidopsis thaliana* (Gene ID AT2G19450). In some embodiments, the diacylglycerol acyltransferase is DGA1 from *S. cerevisiae* (YOR245c). In some embodiments, the diacylglycerol acyltransferase is atfA from *Acinetobacter* sp. ADP1 (MetaCyc Accession ID ACIAD0832). In some embodiments, the diacylglycerol acyltransferase is YALI0E32769g from *Yarrowia lipolytica*. In some embodiments, the diacylglycerol acyltransferase is CaO19.6941 from *Candida albicans*. In some embodiments, the diacylglycerol acyltransferase is CaO19.14203 from *Candida albicans*. In some embodiments, the diacylglycerol acyltransferase is CTRG_06209 from *Candida tropicalis*.

Phospholipid: diacylglycerol acyltransferase (PDAT) catalyzes the following reaction: a phosphatidylcholine+a 1,2-diacyl-sn-glycerol→a triacyl-sn-glycerol+a 1-acyl-sn-glycero-3-phosphocholine.

The *Arabidopsis* PDAT can use different phospholipids as acyl donor, with acyl groups of 10-22 carbon chain length at either sn-positions (Stahl U et al. (2004) Cloning and functional characterization of a phospholipid:diacylglycerol acyltransferase from *Arabidopsis*. Plant Physiol 135(3): 1324-1335). Acyl group at the sn-2 position of phosphatidylcholine is however used three times greater than at the sn-1 position. The highest activity is with acyl groups having multiple double bonds, epoxy or hydroxy groups. Among the tested, the enzyme activity was highest with ricinoleoyl. 18:0- and 22:1-acyl groups gave the lowest enzyme activity. Among different phospholipid species, higher activity is with phosphatidylethanolamine than with phosphatidate or phosphatidylcholine.

A PDAT activity was detected in castor bean seed microsome fraction. Radio-labeled ricinoleoyl and vernoloyl groups are effectively transferred from phosphatidylcholine to DAG forming triacylglycerol (Dahlqvist A et al. (2000) Phospholipid: diacylglycerol acyltransferase: an enzyme that catalyzes the acyl-CoA-independent formation of triacylglycerol in yeast and plants. Proc Natl Acad Sci USA 97(12): 6487-6492).

In other embodiments, the diacylglycerol acyltransferase is a phospholipid: diacylglycerol acyltransferase (PDAT). In some embodiments, the PDAT is from *Arabidopsis thaliana* (Gene ID AT5G13640). In some embodiments, the PDAT is from *Ricinus communis*. In some embodiments, the PDAT is LRO1 from *Saccharomyces cerevisiae* (YNR008w). In some embodiments, the PDAT is YALI0E16797g from *Yarrowia lipolytica*. In some embodiments, the PDAT is CaO19.13439 from *Candida albicans*. In some embodiments, the PDAT is CTRG_04390 from *Candida tropicalis*.

In some embodiments, one or more genes of the recombinant microorganism encoding glycerol-3-phosphate acyl transferases (GPATs), lysophosphatidic acid acyltransferases (LPAATs), glycerolphospholipid acyltransferase (GPLATs) and/or diacylglycerol acyltransferases (DGATs) are deleted or downregulated, and replaced with one or more heterologous GPAT, LPAAT, GPLAT, or DGAT variants. In some embodiments, the one or more acyltransferase variant is derived from one or more heterologous acyltransferase selected from Table 3c. In some embodiments, the recombinant microorganism comprises a deletion, disruption, mutation, and/or reduction in the activity of one or more endogenous acyltransferase enzyme selected from the group consisting of *Y. lipolytica* YALI0CO00209g, *Y. lipolytica* YALI0E18964g, *Y. lipolytica* YALI0F19514g, *Y. lipolytica* YALI0C14014g, *Y. lipolytica* YALI0E16797g, *Y. lipolytica* YALI0E32769g, and *Y. lipolytica* YALI0D07986g, *S. cerevisiae* YBL011w, *S. cerevisiae* YDL052c, *S. cerevisiae* YOR175C, *S. cerevisiae* YPR139C, *S. cerevisiae* YNR008w, and *S. cerevisiae* YOR245c, and *Candida* 1503_02577, *Candida* CTRG_02630, *Candida* CaO19.250, *Candida* CaO19.7881, *Candida* CTRG_02437, *Candida* CaO19.1881, *Candida* CaO19.9437, *Candida* CTRG_01687, *Candida* CaO19.1043, *Candida* CaO19.8645, *Candida* CTRG_04750, *Candida* CaO19.13439, *Candida* CTRG_04390, *Candida* CaO19.6941, *Candida* CaO19.14203, and *Candida* CTRG_06209.

TABLE 3c

Exemplary acyltransferases from which variants can be derived for expression in recombinant microorganisms of the present disclosure

| Accession No. | Source Organism |
|---|---|
| AAL49962.1 | *Bos taurus* |
| BAC43739.1 | *Rattus norvegicus* |
| AAH89846.1 | *Rattus norvegicus* |
| F6TMU0 | *Equus caballus* |
| F6PXX7 | *Equus caballus* |
| F7B020 | *Equus caballus* |
| ALT83519.1 | *Macadamia tetraphylla* |
| ANN46862.1 | *Cuphea avigera* |
| ANN46863.1 | *Cuphea avigera* |
| ANN46864.1 | *Cuphea avigera* |
| ANN46865.1 | *Cuphea avigera* |
| AAC49119.1 | *Cocos nucifera* |
| JAT48335.1 | *Anthurium amnicola* |
| XP_008793203.1 | *Phoenix dactylifera* |
| XP_008806896.1 | *Phoenix dactylifera* |
| XP_008806740.1 | *Phoenix dactylifera* |
| XP_010908895.1 | *Elaeis guineensis* |
| XP_010908896.1 | *Elaeis guineensis* |
| Q96UY2 | *Umbelopsis ramanniana* |
| A0A077WEU5 | *Lichtheimia ramosa* |
| A0A068SDP4 | *Lichtheimia corymbifera* JMRC |
| A0A068RXA2 | *Lichtheimia corymbifera* JMRC |
| A0A197JCE2 | *Mortierella elongata* AG-77 |
| A0A1C7N060 | *Choanephora cucurbitarum* |
| I1BLC3 | *Rhizopus delemar* |
| A0A1C7NC56 | *Choanephora cucurbitarum* |
| A0A077X3B5 | *Lichtheimia ramosa* |
| Q96UY1 | *Umbelopsis ramanniana* |
| A0A077WVD4 | *Lichtheimia ramosa* |
| A0A163K8G3 | *Absidia glauca* |
| S2J8P3 | *Mucor circinelloides* |
| A0A168J818 | *Mucor circinelloides* |
| A0A0C9MR10 | *Mucor ambiguus* |
| A0A162PN39 | *Phycomyces blakesleeanus* |
| A0A167QXD0 | *Phycomyces blakesleeanus* |
| A0A0C9M4C3 | *Mucor ambiguus* |
| A0A0B7NDT1 | *Parasitella parasitica* |
| A0A015LM78 | *Rhizophagus irregularis* |
| A0A0B7NHQ3 | *Parasitella parasitica* |
| A0A0A1NVK5 | *Rhizopus microsporus* |
| A0A0A1P436 | *Rhizopus microsporus* |
| A0A0D7BI48 | *Cylindrobasidium torrendii* |
| A0A1B9HZT8 | *Kwoniella pini* |
| A0A1D1XN50 | *Anthurium amnicola* |
| A0A1B9ILF0 | *Kwoniella mangroviensis* |
| S2JU94 | *Mucor circinelloides* |
| A0A1B9GCB0 | *Kwoniella bestiolae* CBS 10118 |
| A0A068RKT0 | *Lichtheimia corymbifera* |
| Q5KFU4 | *Cryptococcus neoformans* |

TABLE 3c-continued

Exemplary acyltransferases from which variants can be derived for expression in recombinant microorganisms of the present disclosure

| Accession No. | Source Organism |
|---|---|
| Q55QC2 | *Cryptococcus neoformans* |
| U5GY58 | *Microbotryum lychnidis* |
| A0A197KA94 | *Mortierella elongata* AG-77 |
| A0A088FR92 | *Rhodotorula diobovata* |
| A0A194SBY3 | *Rhodotorula graminis* |
| E6R8N8 | *Cryptococcus gattii* |
| M7WKS9 | *Rhodosporidium toruloides* |
| A0A191UMW0 | *Rhodosporidium toruloides* |
| C6KZS6 | *Rhodosporidium toruloides* |
| J9VS50 | *Cryptococcus neoformans* |
| A0A109FM23 | *Rhodotorula sp.* JG-1b |
| I4YE91 | *Wallemia mellicola* |
| A0A066WAJ3 | *Tilletiaria anomala* UBC 951 |
| A0A151VHJ4 | *Hypsizygus marmoreus* |
| A0A168LDJ3 | *Absidia glauca* |
| A0A0A1ULK8 | *Rhizoctonia solani* AG-3 Rhs1AP |
| A0A074RWU7 | *Rhizoctonia solani* 123E |
| A0A0K6FWT6 | *Rhizoctonia solani* |
| R9AL76 | *Wallemia ichthyophaga* |
| E6ZMU5 | *Sporisorium reilianum* |
| A0A0K3CJX4 | *Rhodosporidium toruloides* |
| A0A162Y103 | *Phycomyces blakesleeanus* |
| A0A0B7FYU9 | *Thanatephorus cucumeris* |
| A0A1A5ZUI2 | *Kwoniella dejecticola* |
| A0A1B9GXE9 | *Kwoniella heveanensis* BCC8398 |
| V5EIP7 | *Kalmanozyma brasiliensis* |
| A0A127ZHG0 | *Sporisorium scitamineum* |
| M5FTN9 | *Dacryopinax primogenitus* |
| A0A166HX72 | *Sistotremastrum suecicum* |
| A0A067QH80 | *Jaapia argillacea* MUCL 33604 |
| A0A165PFB6 | *Neolentinus lepideus* |
| G7DXE4 | *Mixia osmundae* |
| A0A165KJK5 | *Exidia glandulosa* HHB12029 |
| A0A0F7TLQ7 | *Penicillium brasilianum* |
| S8FI87 | *Fomitopsis pinicola* |
| S7ZL04 | *Penicillium oxalicum* |
| I2FMX3 | *Ustilago hordei* |
| F8P370 | *Serpula lacrymans* |
| V2WTH2 | *Moniliophthora roreri* |
| S7Q9H4 | *Gloeophyllum trabeum* |
| W3VTZ4 | *Pseudozyma aphidis* |
| B8M0V7 | *Talaromyces stipitatus* |
| A0A0D7B6H5 | *Cylindrobasidium torrendii* |
| R7SCW4 | *Tremella mesenterica* |
| A0A093UWD0 | *Talaromyces marneffei* PM1 |
| B6Q8Q9 | *Talaromyces marneffei* |
| A0A093VC12 | *Talaromyces marneffei* PM1 |
| A0A167SF58 | *Calocera viscosa* TUFC12733 |
| A0A180GQ68 | *Puccinia triticina* |
| E3KWZ5 | *Puccinia graminis* f. sp. |
| F4S978 | *Melampsora larici-populina* |
| A0A0U5GN87 | *Aspergillus calidoustus* |
| W9WBT1 | *Cladophialophora yegresii* |
| A0A0D2A9G0 | *Verruconis gallopava* |
| S3DKQ1 | *Glarea lozoyensis* |
| A0A167S691 | *Penicillium chrysogenum* |
| A0A0C3G1P8 | *Piloderma croceum* F 1598 |
| A0A117NM34 | *Penicillium freii* |
| A0A0M8NPT1 | *Penicillium nordicum* |
| M2R3J5 | *Ceriporiopsis subvermispora* |
| A0A1E3JS60 | *Cryptococcus depauperates* |
| V9DJY4 | *Cladophialophora carrionii* |
| A0A1C1D128 | *Cladophialophora carrionii* |
| A0A194XRZ1 | *Phialocephala scopiformis* |
| A0A135LQY4 | *Penicillium patulum* |
| F2S034 | *Trichophyton tonsurans* |
| A0A059J710 | *Trichophyton interdigitale* |
| R7YTC1 | *Coniosporium apollinis* |
| A0A0G4PR11 | *Penicillium camemberti* FM 013 |
| F2SHG6 | *Trichophyton rubrum* |
| A0A022VWY8 | *Trichophyton rubrum* CBS 288.86 |
| A0A178F1Q9 | *Trichophyton rubrum* |
| A0A022XM67 | *Trichophyton soudanense* |
| F2PHM1 | *Trichophyton equinum* |
| A0A178FDV0 | *Trichophyton violaceum* |

TABLE 3c-continued

Exemplary acyltransferases from which variants can be derived for expression in recombinant microorganisms of the present disclosure

| Accession No. | Source Organism |
|---|---|
| A0A0F8UUV5 | Aspergillus ochraceoroseus |
| A0A0F8XD12 | Aspergillus rambellii |
| D8Q1Z6 | Schizophyllum commune |
| A0A0L0VQ99 | Puccinia striiformis |
| W6QE33 | Penicillium roqueforti |
| A0A0J0XU39 | Cutaneotrichosporon |
| K2RIY7 | Macrophomina phaseolina |
| A0A1B9HIE8 | Kwoniella heveanensis CBS 569 |
| A0A0A2KLE4 | Penicillium italicum |
| A0A177FP94 | Fonsecaea monophora |
| Q0CU51 | Aspergillus terreus |
| A0A0D2C195 | Exophiala spinifera |
| K9GS70 | Penicillium digitatum |
| K9H4T7 | Penicillium digitatum |
| A0A0A2IRX2 | Penicillium expansum |
| A0A165XA55 | Fibulorhizoctonia sp. |
| A0A1E3HS30 | Cryptococcus depauperatus |
| R0JHT6 | Setosphaeria turcica |
| W6XT38 | Bipolaris zeicola 26-R-13 |
| K1WNS8 | Marssonina brunnea f. sp. |
| A0A077R6Q5 | Melanopsichium pennsylvanicum |
| A0A0G2F2K4 | Phaeomoniella chlamydospora |
| M2UB23 | Cochliobolus heterostrophus |
| N4WZB4 | Cochliobolus heterostrophus |
| A0A0D2ECJ4 | Capronia semi-immersa |
| K5ULK6 | Phanerochaete carnosa |
| A0A081CNS6 | Pseudozyma antarctica |
| W7E3D1 | Bipolaris victoriae FI3 |
| A0A0D1YAT0 | Exophiala sideris |
| V5FVB4 | Byssochlamys spectabilis |
| A0A150V2J4 | Acidomyces richmondensis BFW |
| A0A0D2P224 | Hypholoma sublateritium |
| C5FY83 | Arthroderma otae |
| A0A0E9NND3 | Saitoella complicata |
| A0A163JYI7 | Absidia glauca |
| M2SYN8 | Cochliobolus sativus |
| A0A0D2A9Y8 | Exophiala oligosperma |
| B2WFQ5 | Pyrenophora tritici |
| A0A178Z686 | Fonsecaea erecta |
| R1GYF1 | Botryosphaeria parva |
| A0A0D2AM77 | Cladophialophora immunda |
| A0A067TPJ7 | Galerina marginata CBS 339.88 |
| A0A0G2DT71 | Diplodia seriata |
| A0A0S6XG57 | fungal sp. No. 11243 |
| A1CD57 | Aspergillus clavatus strain |
| W6ZE59 | Bipolaris oryzae ATCC 44560 |
| W9X299 | Cladophialophora psammophila |
| A0A0L1HS74 | Stemphylium lycopersici |
| E3RYE6 | Pyrenophora teres |
| A0A178C491 | Fonsecaea multimorphosa |
| A0A0D2JW30 | Fonsecaea multimorphosa |
| A0A100ISZ7 | Aspergillus niger |
| G7XRR4 | Aspergillus kawachii |
| E4ZGH1 | Leptosphaeria maculans |
| A0A0C3AU69 | Serendipita vermifera |
| A0A0U1M481 | Talaromyces islandicus |
| A0A179UDB8 | Ajellomyces dermatitidis |
| A0A177DML0 | Alternaria alternata |
| A0A074XTA2 | Aureobasidium namibiae |
| R8BK00 | Togninia minima |
| A0A178E1M9 | Pyrenochaeta sp. DS3sAY3a |
| A0A074XCF2 | Aureobasidium pullulans |
| A0A178CVL7 | Fonsecaea nubica |
| J4H349 | Fibroporia radiculosa |
| F2T2H3 | Ajellomyces dermatitidis |
| T5C9R0 | Blastomyces dermatitidis |
| C5GGF5 | Ajellomyces dermatitidis |
| F8Q4F5 | Serpula lacrymans |
| A0A074YHW3 | Aureobasidium subglaciale |
| A0A0D2E953 | Exophiala xenobiotica |
| A0A0D2ETM7 | Exophiala xenobiotica |
| A0A163ADJ9 | Didymella rabiei |
| U7PLY5 | Sporothrix schenckii |
| A0A0F2MF45 | Sporothrix schenckii 1099-18 |
| A0A0C2J820 | Sporothrix brasiliensis 5110 |
| A0A1E3B843 | Aspergillus cristatus |
| A0A0L6WTD3 | Termitomyces sp. J132 |
| G2YTS7 | Botryotinia fuckeliana |
| W9XGA9 | Capronia epimyces CBS 606.96 |
| A0A0F4YS69 | Rasamsonia emersonii |
| M9LWR9 | Pseudozyma antarctica |
| A0A074WDM7 | Aureobasidium melanogenum |
| M3CBZ0 | Sphaerulina musiva |
| A0A0C7C2J7 | Rhizopus microsporus |
| W9YU83 | Capronia coronate CBS 617.96 |
| I8IUH8 | Aspergillus oryzae |
| A0A139HZI0 | Pseudocercospora musae |
| E9DGY4 | Coccidioides posadasii |
| A0A0J6F9P8 | Coccidioides posadasii |
| H6BM52 | Exophiala dermatitidis |
| Q2UDX3 | Aspergillus oryzae |
| M3ASJ4 | Pseudocercospora fijiensis |
| A0A177BZU0 | Paraphaeosphaeria sporulosa |
| A0A017S910 | Aspergillus ruber CBS 135680 |
| A0A175VVF2 | Madurella mycetomatis |
| A0A0J8UWI6 | Coccidioides immitis |
| A0A0J6YFS7 | Coccidioides immitis RMSCC |
| J3K3F7 | Coccidioides immitis |
| A0A0D2FX82 | Rhinocladiella mackenziei |
| A0A072PSS5 | Exophiala aquamarina |
| A0A0A1MWE2 | Rhizopus microsporus |
| W2RSU8 | Cyphellophora europaea |
| C0S1D5 | Paracoccidioides brasiliensiensis |
| C1G9R2 | Paracoccidioides brasiliensiensis |
| A0A1D2JGH6 | Paracoccidioides brasiliensis |
| A0A166PXN0 | Cordyceps brongniartii |
| Q54GC1 | Dictyostelium discoideum |
| A0A0H1B9A9 | Emmonsia parva UAMH 139 |
| R4XEF3 | Taphrina deformans |
| D3B2U8 | Polysphondylium pallidum |
| U1HHT8 | Endocarpon pusillum |
| A0A1E3JYY5 | Tsuchiyaea wingfieldii |
| A0A0C3JN41 | Pisolithus tinctorius Marx 270 |
| B6HF05 | Penicillium rubens |
| A0A060S368 | Pycnoporus cinnabarinus |
| K5W449 | Agaricus bisporus |
| B0CTA0 | Laccaria bicolor |
| F0XD96 | Grosmannia clavigera |
| A0A165EP91 | Calocera cornea HHB12733 |

Lipid Binding Proteins

The present disclosure describes proteins that can transfer steroids, phospholipids and gangliosides between cellular membranes.

Sterol carrier proteins are also known as nonspecific lipid transfer proteins. These proteins are different from plant nonspecific lipid transfer proteins but structurally similar to small proteins of unknown function from *Thermus thermophilus*. The human sterol carrier protein 2 (SCP2) is a basic protein that is believed to participate in the intracellular transport of cholesterol and various other lipids.

SCP-2 belongs to the SCP-2 gene family including SCP-X, SCP-2, 17β-hydroxysteroid dehydrogenase IV, stomatin, UNC-24, and Metallo-β-lactomase and is identified in many species including vertebrates, insects, plants, yeast, bacteria and fungi.

Sterol carrier proteins have been mainly implicated in a wide array of cholesterol/lipid related functions in vertebrates and insects. Recent studies have demonstrated that SCP-2 has cholesterol/lipid binding activities. SCP-2 can bind to cholesterol, palmitic acid, fatty acyl-CoA, acidic phospholipids and bile salts. The binding affinity of SCP-2 to cholesterol is the strongest among the lipids.

SCP2 is thought to be a soluble sterol carrier because of its ability to bind to sterols and its localization to multiple organelles, such as the peroxisomes, mitochondria, endoplasmic reticulum, and cytosol.

The multiple actions of sterol carrier protein-2 (SCP-2) in intracellular lipid circulation and metabolism originate from its gene and protein structure. The SCP-x/pro-SCP-2 gene is a fusion gene with separate initiation sites coding for 15-kDa pro-SCP-2 (no enzyme activity) and 58-kDa SCP-x (a 3-ketoacyl CoA thiolase). Both proteins share identical cDNA and amino acid sequences for 13-kDa SCP-2 at their C-termini. Cellular 13-kDa SCP-2 derives from complete, posttranslational cleavage of the 15-kDa pro-SCP-2 and from partial posttranslational cleavage of 58-kDa SCP-x. Putative physiological functions of SCP-2 have been proposed on the basis of enhancement of intermembrane lipid transfer (e.g., cholesterol, phospholipid) and activation of enzymes involved in fatty acyl CoA transacylation (cholesterol esters, phosphatidic acid) in vitro, in transfected cells, and in genetically manipulated animals. At least four important SCP-2 structural domains have been identified and related to specific functions. First, the 46-kDa N-terminal presequence present in 58-kDa SCP-x is a 3-ketoacyl-CoA thiolase specific for branched-chain acyl CoAs. Second, the N-terminal 20 amino acid presequence in 15-kDa pro-SCP-2 dramatically modulates the secondary and tertiary structure of SCP-2 as well as potentiating its intracellular targeting coded by the C-terminal peroxisomal targeting sequence. Third, the N-terminal 32 amino acids form an amphipathic α-helical region, one face of which represents a membrane-binding domain. Positively charged amino acid residues in one face of the amphipathic helices allow SCP-2 to bind to membrane surfaces containing anionic phospholipids. Fourth, the hydrophobic faces of the N-terminal amphipathic α helices along with p strands 4, 5, and helix D form a ligand-binding cavity able to accommodate multiple types of lipids (e. g., fatty acids, fatty acyl CoAs, cholesterol, phospholipids, isoprenoids) (Stolowich N J et al. (2002) Sterol carrier protein-2: structure reveals function. Cell Mol Life Sci 59(2): 193-212).

In one embodiment, the lipid binding protein is sterol carrier protein. In another embodiment, the sterol carrier protein is sterol carrier protein-2 (SCP-2) from *Homo sapiens* (NP_002970). In another embodiment, the sterol carrier protein is sterol carrier protein-2 (SCP-2) from *Yarrowia lipolytica* (YALI0E01298-CAG78989.1-SCP2). In another embodiment, the sterol carrier protein is from *Candida tropicalis* (CTRG_02171-EER33353.1).

Fatty Acid Synthase Complex

The present disclosure describes enzymes that catalyze the elongation of a carbon chain in fatty acid.

In some embodiments, a fatty acid synthase complex is used to catalyze initiation and elongation of a carbon chain in a fatty acid. A "fatty acid synthase complex" refers to a group of enzymes that catalyzes the initiation and elongation of a carbon chain on a fatty acid. The ACP along with the enzymes in the fatty acid synthase (FAS) pathway control the length, degree of saturation, and branching of the fatty acids produced. The steps in this pathway are catalyzed by enzymes of the fatty acid biosynthesis (fab) and acetyl-CoA carboxylase (acc) gene families. Depending upon the desired product, one or more of these genes can be attenuated, expressed or over-expressed. In exemplary embodiments, one or more of these genes is attenuated, deleted, disrupted and/or mutated.

There are two principal classes of fatty acid synthases. Type I (FAS I) systems utilize a single large, multifunctional polypeptide and are common to both mammals and fungi (although the structural arrangement of fungal and mammalian synthases differs). The Type I FAS system is also found in the CMN group of bacteria (corynebacteria, mycobacteria, and *nocardia*). The Type II FAS (FAS II) is characterized by the use of discrete, monofunctional enzymes for fatty acid synthesis, and is found in archaea and bacteria.

The mechanism of FAS I and FAS II elongation and reduction is the substantially similar, as the domains of the FAS I multienzyme polypeptides and FAS II enzymes are largely conserved.

Fatty acids are synthesized by a series of decarboxylative Claisen condensation reactions from acetyl-CoA and malonyl-CoA. The steps in this pathway are catalyzed by enzymes of the fatty acid biosynthesis (fab) and acetyl-CoA carboxylase (acc) gene families. For a description of this pathway, see, e.g., Heath et al., *Prog. Lipid Res.* 40:467, 2001, which is herein incorporated by reference in its entirety. Without being limited by theory, in bacteria, acetyl-CoA is carboxylated by acetyl-CoA carboxylase (Acc, a multi-subunit enzyme encoded by four separate genes, accABCD), to form malonyl-CoA. In yeast, acetyl-CoA is carboxylated by the yeast equivalents of the acetyl-CoA carboxylase, encoded by ACC1 and ACC2. In bacteria, the malonate group is transferred to ACP by malonyl-CoA:ACP transacylase (FabD) to form malonyl-ACP. In yeast, a malonyl-palmityl transferase domain adds malonyl from malonyl-CoA to the ACP domain of the FAS complex. A condensation reaction then occurs, where malonyl-ACP merges with acyl-CoA, resulting in β-ketoacyl-ACP. In this manner, the hydrocarbon substrate is elongated by 2 carbons.

Following elongation, the β-keto group is reduced to the fully saturated carbon chain by the sequential action of a keto-reductase (KR), dehydratase (DH), and enol reductase (ER). The elongated fatty acid chain is carried between these active sites while attached covalently to the phosphopantetheine prosthetic group of ACP. First, the β-ketoacyl-ACP is reduced by NADPH to form β-hydroxyacyl-ACP. In bacteria, this step is catalyzed by β-ketoacyl-ACP reductase (FabG). The equivalent yeast reaction is catalyzed by the ketoreductase (KR) domain of FAS. β-hydroxyacyl-ACP is then dehydrated to form trans-2-enoyl-ACP, which is catalyzed by either β-hydroxyacyl-ACP dehydratase/isomerase (FabA) or β-hydroxyacyl-ACP dehydratase (FabZ) in bacteria or the dehydratase (DH) domain of FAS in yeast. NADPH-dependent trans-2-enoyl-ACP reductase I, II, or III (FabI, FabK, and FabL, respectively) in bacteria and the enol reductase (ER) domain of FAS in yeast reduces trans-2-enoyl-ACP to form acyl-ACP. Subsequent cycles are started by the condensation of malonyl-ACP with acyl-ACP by β-ketoacyl-ACP synthase I or β-ketoacyl-ACP synthase II (FabB and FabF, respectively, in bacteria or the beta-ketoacyl synthase (KS) domain in yeast).

In some embodiments, a fatty acid synthase complex can be used to catalyze elongation of a fatty acyl-ACP to a corresponding fatty acyl-ACP with a two carbon elongation relative to the substrate.

In some embodiments, the acetyl-CoA carboxylase is ACC1. In certain embodiments, the acetyl-CoA carboxylase is YNR016C from *Saccharomyces cerevisiae*. In certain embodiments, the acetyl-CoA carboxylase is YALI0C11407g from *Yarrowia lipolytica*. In certain embodiments, the acetyl-CoA carboxylase is CaO19.7466 from *Candida albicans*. In certain embodiments, the acetyl-CoA carboxylase is CTRG_01007 from *Candida tropicalis*. In some embodiments, the fatty acid synthase, β subunit is FAS1. In certain embodiments, the fatty acid synthase, β subunit is YKL182W from *Saccharomyces cerevisiae*. In certain embodiments, the fatty acid synthase,β subunit is YALI0B15059g from *Yarrowia lipolytica*. In certain embodiments, the fatty acid synthase, β subunit is CaO19.979 from *Candida albicans*. In certain embodiments, the fatty acid synthase, β subunit is CaO19.8594 from *Candida albicans*. In certain embodiments, the fatty acid synthase, β subunit is CTRG_05241 from *Candida tropicalis*. In some embodiments, the fatty acid synthase, a subunit is FAS2. In certain embodiments, the fatty acid synthase, a subunit is S000006152 from *Saccharomyces cerevisiae*. In certain embodiments, the fatty acid synthase, a subunit is YALI0B19382g from *Yarrowia lipolytica*. In certain embodiments, the fatty acid synthase, a subunit is CaO19.13370-72 from *Candida albicans*. In certain embodiments, the fatty acid synthase, a subunit is CaO19.5949-51 from *Candida albicans*. In certain embodiments, the fatty acid synthase, a subunit is CTRG_02501 from *Candida tropicalis*.

Pentose Phosphate Pathway

The pentose phosphate pathway (PPP) is a central and widely conserved metabolic pathway of carbohydrate metabolism located in the cytoplasm in eukaryotic cells. This pathway serves two major functions: production of precursors for biosynthesis of macromolecules and production of reducing equivalents in the form of NADPH. Accordingly, these two roles are reflected in the two major phases of the PPP: in the "oxidative phase," glucose 6-phosphate (G6P) is converted into ribulose 5-phosphate (Ru5P) through the sequential action of: glucose-6-phosphate dehydrogenase (ZWF1) which converts G6P to 6-phospho D-glucono-1,5-lactone with generation of NADPH; 6-phosphogluconolactonase (SOL3, SOL4) which converts 6-phospho D-glucono-1,5-lactone to D-gluconate 6-phosphate; 6-phosphogluconate dehydrogenase (GND1, GND2) which converts D-gluconate 6-phosphate to Ru5P with generation of NADPH. The "non-oxidative phase" carries out the isomerization of Ru5P to ribose 5-phosphate (R5P), the epimerization of Ru5P to xylulose 5-phosphate (X5P) and, through the actions of transketolase (TKL1, TKL2) and transaldolase (TAL1, NQM1), a series of carbon skeleton transfers that can interconvert pentose phosphate into fructose 6-phosphate (F6P) and glyceraldehyde 3-phosphate (GAP)—both glycolytic intermediates—and erythrose 4-phosphate (E4P). The net effect of the non-oxidative phase is to produce an equilibrium between the pentoses needed for biosynthesis of macromolecules and the hexoses needed for energy management, allowing the two pools of sugars easily to interconvert.

The oxidative branch is considered to be largely irreversible under normal cellular conditions, whilst the non-oxidative branch is reversible. The PPP is not a simple linear pathway since several carbon atoms are recycled back into glycolysis. Furthermore, the enzyme transketolase catalyses two different reactions in the pathway, resulting in the substrates of these reactions being competitive inhibitors of one another. The PPP has three main products: reduced equivalents in the form of NADPH, produced in the oxidative phase, needed in biosynthetic pathways and for maintenance of the oxidative level of cells; R5P, for the biosynthesis of all nucleic acids; and E4P, for biosynthesis of the three aromatic amino acids. Different physiological states require operation of this biochemical network in different modes: in actively growing cells, such as during culture growth in reactors, the pathway must produce a sufficient amount of all three products, since all are required in the construction of new cells. Under stress conditions growth slows and the only product in considerable demand is NADPH.

Enzymes to Express to Increase Levels of One or More Coenzymes

Nicotinamide adenine dinucleotide (NAD, including NAD+ and NADH) and nicotinamide adenine dinucleotide phosphate (NADP, including NADP+ and NADPH) belong to the fundamental common mediators of various biological processes, including energy metabolism, mitochondrial functions, calcium homeostasis, antioxidation/generation of oxidative stress, gene expression, immunological functions, aging, and cell death: NAD mediates energy metabolism and mitochondrial functions; NADPH is a key component in cellular antioxidation systems; NADH-dependent reactive oxygen species (ROS) generation from mitochondria and NADPH oxidase-dependent ROS generation are two critical mechanisms of ROS generation; cyclic ADP-ribose and several other molecules that are generated from NAD and NADP could mediate calcium homeostasis; NAD and NADP modulate multiple key factors in cell death, such as mitochondrial permeability transition, energy state, poly (ADP-ribose) polymerase-1, and apoptosis-inducing factor; and NAD and NADP profoundly affect aging-influencing factors such as oxidative stress and mitochondrial activities, and NAD-dependent sirtuins also mediate the aging process. Additionally, the in situ regeneration of reduced nicotinamide cofactors (NAD(P)H) is necessary for practical synthesis of many important chemicals in recombinant microorganisms.

The present disclosure describes enzymes that catalyze the oxidation of a given substrate and the concomitant production of reduced nicotinamide adenine dinucleotide or reduced nicotinamide adenine dinucleotide phosphate (NAD (P)H). There are several enzymatic components involved in the maintenance of the pool of NADP and NADPH. NAD kinases (NADKs) catalyze the direct phosphorylation of NAD to NADP and therefore contribute to the generation of the cellular NADP pool (Pollak N et al. (2007) The power to reduce: pyridine nucleotides-small molecules with a multitude of functions. Biochem. J. 402: 205-218; Agledal L et al. (2010) The phosphate makes a difference: cellular functions of NADP. Redox Rep. 15: 2-10). On the other hand, ferrodoxin-NADP reductase (FNR) in photosynthetic cells during the light phase is recognized as a principal source of NADPH. However, in non-photosynthetic cells during the dark phase of photosynthesis, the main enzymes capable of generating power reduction in the form of NADPH are the following: glucose-6-phosphate dehydrogenase (G6PDH, EC1.1.1.49) and 6-phosphogluconate dehydrogenase (6PGDH, EC1.1.1.44) (both belonging to the pentose phosphate pathway), NADP-isocitrate dehydrogenase (NADP-ICDH, EC1.1.1.42) and NAD- or NADP-malic enzyme (NADP-ME, EC1.1.1.40), also known as NAD- or NADP-malate dehydrogenase.

In *Saccharomyces cerevisiae* the interconvertibility of the various NAD/NADP species is of utmost importance for maintaining the redox balance of the cells which, in turn determines growth efficiency and metabolite excretion (Marres C A et al. (1991) Isolation and inactivation of the nuclear gene encoding the rotenone-insensitive internal NADH: ubiquinone oxidoreductase of mitochondria from *Saccharomyces cerevisiae*. Eur J Biochem 195(3): 857-62). The various pyridine nucleotides, in particular NADH, cannot permeate the inner membrane of mitochondrion. For that reason direct transversal exchanges of NAD+ and reduced and/or phosphorylated derivatives from the cytosol to the mitochondria and vice versa are not possible. Moreover, yeast does not possess transhydrogenases. Hence, they cannot directly convert NAD+ and NADPH into NADP+ and NADH (Bruinenberg P M (1986) The NADP(H) redox couple in yeast metabolism. Antonie Van Leeuwenhoek 52(5): 411-29). Consequently, to ensure the availability of the required NAD+ metabolites in each organelle, yeast has developed independent sets of interconversion reactions that provide the supply of all NAD+ types through various enzymatic reactions.

In the cytoplasm two NAD kinases have been characterized that can phosphorylate NAD+. The main cytosolic NAD kinase is encoded by UTR1 (Kawai S et al. (2001) Molecular cloning and identification of UTR1 of a yeast *Saccharomyces cerevisiae* as a gene encoding an NAD kinase. FEMS Microbiol Lett 200(2): 181-184; Shi F et al. (2005) Identification of ATP-NADH kinase isozymes and their contribution to supply of NADP(H) in *Saccharomyces cerevisiae*. FEBS J 272(13): 3337-3349). A second, less important NAD kinase for phosphorylation of NAD+, i.e. YEF1, has also been described and shown to compensate for the loss of UTR1 (Shi et al. 2005). The deletion of both the mitochondrial POS5 and cytosolic UTR1 is lethal in yeast and YEF1 can only compensate when POS5 still operates. These findings support the notion that the main NADH kinases of yeast, i.e. POS5 and UTR1 can partially compensate for the loss of each one's respective activity (Bieganowski P et al. (2006) Synthetic lethal and biochemical analyses of NAD and NADH kinases in *Saccharomyces cerevisiae* establish separation of cellular functions. J Biol Chem 281(32): 22439-22445). Both UTR1 and YEF1 have been shown to exhibit NADH kinase activity as well providing the cytosolic set of enzymes with the catalytic ability to phosphorylate NADH.

Various enzymatic reactions have been shown to account for the provision of the cytosol with NADPH required for biosynthetic pathways and anti-oxidant functions. The cytosolic acetaldehyde dehydrogenase encoded by ALD6 (Meaden P G et al. (1997) The ALD6 gene of *Saccharomyces cerevisiae* encodes a cytosolic, Mg(2+)-activated acetaldehyde dehydrogenase. Yeast 13(14): 1319-1327; Wang X et al. (1998) Molecular cloning, characterization, and potential roles of cytosolic and mitochondrial aldehyde dehydrogenases in ethanol metabolism in *Saccharomyces cerevisiae*. J Bacteriol 180(4): 822-830) and the glucose-6-phosphate dehydrogenase (ZWF1) catalyzing the first step in the pentose phosphate pathway to convert β-D-glucose 6-phosphate to 6-phospho D-glucono-1,5-lactone (Nogae I and Johnston M (1990) Isolation and characterization of the ZWF1 gene of *Saccharomyces cerevisiae*, encoding glucose-6-phosphate dehydrogenase. Gene 96(2): 161-169; Grabowska D and Chelstowska A (2003) The ALD6 gene product is indispensable for providing NADPH in yeast cells lacking glucose-6-phosphate dehydrogenase activity. J Biol Chem 278(16): 13984-13988; Minard K I and McAlister-Henn L (2001) Antioxidant function of cytosolic sources of NADPH in yeast. Free Radic Biol Med 31(6): 832-843) are considered the main suppliers of NADPH. A third enzyme producing NADPH in the cytoplasm is the cytosolic NADP-dependent isocitrate dehydrogenase (IDP2) (Loftus T M et al. (1994) Isolation, characterization, and disruption of the yeast gene encoding cytosolic NADP-specific isocitrate dehydrogenase. Biochemistry 33(32): 9661-9667; Contreras-Shannon V et al. (2005) Kinetic properties and metabolic contributions of yeast mitochondrial and cytosolic NADP+-specific isocitrate dehydrogenases. J Biol Chem 280(6): 4469-4475). It has been demonstrated that ZWF1 has overlapping functions with the isocitrate dehydrogenase (IDP2) and the acetaldehyde oxidoreductase (ALD6), indicating the compensation for the deficiency of NADPH should one of the involved reactions fail to operate (Minard K I and McAlister-Henn L (2005) Sources of NADPH in yeast vary with carbon source. J Biol Chem 280(48): 39890-39896).

Currently available enzymatic systems for NAD(P)H regeneration include formate/formate dehydrogenase for NADH, isopropanol/alcohol dehydrogenase (*Pseudomonas* sp.) for NADH, isopropanol/alcohol dehydrogenase (*T. brocki*) for NADPH, H2/hydrogenase (*M. thermoautotrophicum*) for both NADH and NADPH, glucose-6-phosphate/glucose-6-phosphate dehydrogenase (*L. mesenteroides*) for NADPH and glucose/glucose dehydrogenase for both NADH and NADPH (Hummel W (1999) Large-scale applications of NAD(P)-dependent oxidoreductases: Recent developments. Trends Biotechnol. 17:487-492; Wichmann R and Vasic-Racki D (2005) Cofactor regeneration at the lab scale. Adv Biochem Eng Biotechnol 92: 225-260). The engineering of a highly stable and active mutant phosphite dehydrogenase from *Pseudomonas stutzeri* and evaluation of its potential as an effective NADPH regeneration system has also been described (Johannes T W et al. (2007) Efficient regeneration of NADPH using an engineered phosphite dehydrogenase. Biotechnology and Bioengineering 96(1): 18-26).

In one embodiment, one or more recombinant microorganisms are manipulated to increase intracellular levels of a coenzyme. In another embodiment, the coenzyme is NADH and/or NADPH. In some embodiments, one or more recombinant microorganisms express a dehydrogenase.

In certain embodiments, the one or more recombinant microorganisms express a glucose-6-phosphate dehydrogenase. In some embodiments, the glucose-6-phosphate dehydrogenase is ZWF1 from yeast. In another embodiment, the glucose-6-phosphate dehydrogenase is ZWF1 (YNL241C) from *Saccharomyces cerevisiae*. In another embodiment, the glucose-6-phosphate-1-dehydrogenase is zwf from bacteria. In certain embodiments, the glucose-6-phosphate-1-dehydrogenase is zwf (NP_416366) from *E. coli*.

In certain embodiments, the one or more recombinant microorganisms express a 6-phosphogluconate dehydrogenase. In some embodiments, the 6-phosphogluconate dehydrogenase is GND1 from yeast. In certain embodiments, the 6-phosphogluconate dehydrogenase is GND1 (YHR183W) from *Saccharomyces cerevisiae*. In some embodiments, the 6-phosphogluconate dehydrogenase is GND2 from yeast. In certain embodiments, the 6-phosphogluconate dehydrogenase is GND2 (YGR256W) from *Saccharomyces cerevisiae*. In some embodiments, the 6-phosphogluconate dehydrogenase is gnd from bacteria. In certain embodiments, the 6-phosphogluconate dehydrogenase is gnd (NP_416533) from *E. coli*.

In certain embodiments, the one or more recombinant microorganisms express an $NADP^+$-dependent isocitrate dehydrogenase. In some embodiments, the $NADP^+$-dependent isocitrate dehydrogenase is IDP2 from yeast. In some embodiments, the $NADP^+$-dependent isocitrate dehydrogenase is YALI0_F04095g from *Yarrowia lipolytica*. In other embodiments, the $NADP^+$-dependent isocitrate dehydrogenase is CaO19.3733 from *Candida albicans*. In certain embodiments, the $NADP^+$-dependent isocitrate dehydrogenase is CTRG_00909 from *Candida tropicalis*. In some embodiments, the $NADP^+$-dependent isocitrate dehydrogenase is YLR174W from *Saccharomyces cerevisiae*.

In certain embodiments, the one or more recombinant microorganisms express an NAD+ or NADP+ dependent malate dehydrogenase (malic enzyme). In one embodiment, the malate dehydrogenase is NAD+ dependent. In another embodiment, the malate dehydrogenase is NADP+ dependent. In one embodiment, the malic enzyme is an NAD+ dependent malate dehydrogenase from bacteria. In some embodiments, the NAD+ dependent malate dehydrogenase is maeA (NP_415996) from E. co/i. In some embodiments, the NAD+ dependent malate dehydrogenase is maeE (CAQ68119) from *Lactobacillus casei*. In another embodiment, the malate dehydrogenase is a mitochondrial NAD+ dependent malate dehydrogenase from yeast. In some embodiments, the NAD+ dependent malate dehydrogenase is MAE1 (YKL029C) from *S. cerevisiae*. In another embodiment, the malate dehydrogenase is a mitochondrial NAD+ dependent malate dehydrogenase from a parasitic nematode. In some embodiments, the NAD+ dependent malate dehydrogenase is M81055 from *Ascaris suum*. In one embodiment, the malate dehydrogenase is an NADP+ dependent malate dehydrogenase from bacteria. In some embodiments, the NADP+ dependent malate dehydrogenase is maeB (NP_416958) from *E. coli*. In one embodiment, the malate dehydrogenase is an NADP+ dependent malate dehydrogenase from corn. In some embodiments, the NADP+ dependent malate dehydrogenase is me1 from *Zea mays*.

In certain embodiments, the one or more recombinant microorganisms express an aldehyde dehydrogenase. In one embodiment, the aldehyde dehydrogenase is NAD+ dependent. In another embodiment, the aldehyde dehydrogenase is NADP+ dependent. In one embodiment, the aldehyde dehydrogenase is an NAD+ dependent aldehyde dehydrogenase from bacteria. In some embodiments, the NAD+ dependent aldehyde dehydrogenase is aldA (NP_415933) from *E. coli*. In another embodiment, the aldehyde dehydrogenase is a cytosolic NADP+ dependent aldehyde dehydrogenase from yeast. In some embodiments, the NADP+ dependent aldehyde dehydrogenase is ALD6 (YPL061VW) from *S. cerevisiae*. In another embodiment, the aldehyde dehydrogenase is a cytosolic NADP+ dependent aldehyde dehydrogenase from bacteria. In some embodiments, the NADP+ dependent aldehyde dehydrogenase is aldB (NP_418045) from *E. coli*.

In certain embodiments, the one or more recombinant microorganisms express a transhydrogenase. In one embodiment, the expression of a transhydrogenase is increased to interconvert NADH and NADPH. In some embodiments, the transhydrogenase is a pyridine nucleotide transhydrogenase. In some embodiments, the pyridine nucleotide transhydrogenase is from bacteria. In certain embodiments, the pyridine nucleotide transhydrogenase is pntAB (beta subunit: NP_416119; alpha subunit: NP_416120) from *E. coli*. In some embodiments, the pyridine nucleotide transhydrogenase is from human. In certain embodiments, the pyridine nucleotide transhydrogenase is NNT (NP_036475) from *Homo sapiens*. In certain embodiments, the pyridine nucleotide transhydrogenase is from *Solanum tuberosum*. In certain embodiments, the pyridine nucleotide transhydrogenase is from *Spinacea oleracea*.

In some embodiments, the one or more recombinant microorganisms express a glucose-1-dehydrogenase. In some embodiments, the glucose-1-dehydrogenase is from bacteria. In certain embodiments, the glucose-1-dehydrogenase is GOX2015 from *Gluconobacter oxydans* (*Gluconobacter suboxydans*) (Q5FPE5). In certain embodiments, the glucose-1-dehydrogenase is gdh from *Sulfolobus solfataricus* (093715). In certain embodiments, the glucose-1-dehydrogenase is gdh from *Bacillus subtilis* (P12310).

In some embodiments, the one or more recombinant microorganisms express a glycerol dehydrogenase. In certain embodiments, the glycerol dehydrogenase is NADP+ dependent glycerol 2-dehydrogenase gld2 from *Hypocrea jecorina* (*Trichoderma reesei*) (Q0GYU4). In certain embodiments, the glycerol dehydrogenase is NADP+ dependent glycerol dehydrogenase gldB from *Emericella nidulans* (*Aspergilius nidulans*) (Q7Z8L1).

In some embodiments, the one or more recombinant microorganisms express an alcohol dehydrogenase. In certain embodiments, the alcohol dehydrogenase is NADPH-dependent alcohol dehydrogenase YMR318C from *Saccharomyces cerevisiae*. In certain embodiments, the alcohol dehydrogenase is alcohol dehydrogenase CAETHG_0553 from *Clostridium autoethanogenum*.

In some embodiments, an alcohol dehydrogenase from Table 3 is used for the regeneration of NAD(P)H.

In some embodiments, the one or more recombinant microorganisms express a combination of the above enzymes to increase intracellular levels of a coenzyme. In one embodiment, the overexpression of an enzyme coupled with supplementation of a co-substrate of that enzyme increase intracellular levels of a coenzyme.

TABLE 3

Exemplary alcohol dehydrogenase enzymes.

| Organism | Gene Name | Accession No. |
|---|---|---|
| *Bactrocera oleae* (Olive fruit fly) (*Dacus oleae*) | ADH | Q9NAR7 |
| *Cupriavidus necator* (*Alcaligenes eutrophus*) (*Ralstonia eutropha*) | adh | P14940 |
| *Drosophila adiastola* (Fruit fly) (*Idiomyia adiastola*) | Adh | Q00669 |
| *Drosophila affinidisjuncta* (Fruit fly) (*Idiomyia affinidisjuncta*) | Adh | P21518 |
| *Drosophila ambigua* (Fruit fly) | Adh | P25139 |
| *Drosophila borealis* (Fruit fly) | Adh | P48584 |
| *Drosophila differens* (Fruit fly) | Adh | P22245 |
| *Drosophila equinoxialis* (Fruit fly) | Adh | Q9NG42 |
| *Drosophila flavomontana* (Fruit fly) | Adh | P48585 |
| *Drosophila guanche* (Fruit fly) | Adh | Q09009 |
| *Drosophila hawaiiensis* (Fruit fly) | Adh | P51549 |
| *Drosophila heteroneura* (Fruit fly) | Adh | P21898 |
| *Drosophila immigrans* (Fruit fly) | Adh | Q07588 |
| *Drosophila insularis* (Fruit fly) | Adh | Q9NG40 |
| *Drosophila lebanonensis* (Fruit fly) (*Scaptodrosophila lebanonensis*) | Adh | P10807 |

TABLE 3-continued

Exemplary alcohol dehydrogenase enzymes.

| Organism | Gene Name | Accession No. |
|---|---|---|
| *Drosophila mauritiana* (Fruit fly) | Adh | P07162 |
| *Drosophila madeirensis* (Fruit fly) | Adh | Q09010 |
| *Drosophila mimica* (Fruit fly) (*Idiomyia mimica*) | Adh | Q00671 |
| *Drosophila nigra* (Fruit fly) (*Idiomyia nigra*) | Adh | Q00672 |
| *Drosophila orena* (Fruit fly) | Adh | P07159 |
| *Drosophila pseudoobscura bogotana* (Fruit fly) | Adh | P84328 |
| *Drosophila picticornis* (Fruit fly) (*Idiomyia picticornis*) | Adh | P23361 |
| *Drosophila planitibia* (Fruit fly) | Adh | P23277 |
| *Drosophila paulistorum* (Fruit fly) | Adh | Q9U8S9 |
| *Drosophila silvestris* (Fruit fly) | Adh | P23278 |
| *Drosophila subobscura* (Fruit fly) | Adh | Q03384 |
| *Drosophila teissieri* (Fruit fly) | Adh | P28484 |
| *Drosophila tsacasi* (Fruit fly) | Adh | P51550 |
| *Fragaria ananassa* (Strawberry) | ADH | P17648 |
| *Malus domestica* (Apple) (*Pyrus malus*) | ADH | P48977 |
| *Scaptomyza albovittata* (Fruit fly) | Adh | P25988 |
| *Scaptomyza crassifemur* (Fruit fly) (*Drosophila crassifemur*) | Adh | Q00670 |
| *Sulfolobus* sp. (strain RC3) | adh | P50381 |
| *Zaprionus tuberculatus* (Vinegar fly) | Adh | P51552 |
| *Geobacillus stearothermophilus* (*Bacillus stearothermophilus*) | adh | P42327 |
| *Drosophila mayaguana* (Fruit fly) | Adh, Adh2 | P25721 |
| *Drosophila melanogaster* (Fruit fly) | Adh, CG3481 | P00334 |
| *Drosophila pseudoobscura pseudoobscura* (Fruit fly) | Adh, GA17214 | Q6LCE4 |
| *Drosophila simulans* (Fruit fly) | Adh, GD23968 | Q24641 |
| *Drosophila yakuba* (Fruit fly) | Adh, GE19037 | P26719 |
| *Drosophila ananassae* (Fruit fly) | Adh, GF14888 | Q50L96 |
| *Drosophila erecta* (Fruit fly) | Adh, GG25120 | P28483 |
| *Drosophila grimshawi* (Fruit fly) (*Idiomyia grimshawi*) | Adh, GH13025 | P51551 |
| *Drosophila willistoni* (Fruit fly) | Adh, GK18290 | Q05114 |
| *Drosophila persimilis* (Fruit fly) | Adh, GL25993 | P37473 |
| *Drosophila sechellia* (Fruit fly) | Adh, GM15656 | Q9GN94 |
| *Cupriavidus necator* (strain ATCC 17699/H16/DSM 428/Stanier 337) (*Ralstonia eutropha*) | adh, H16_A0757 | Q0KDL6 |
| *Mycobacterium tuberculosis* (strain CDC 1551/Oshkosh) | adh, MT1581 | P9WQC2 |
| *Staphylococcus aureus* (strain MW2) | adh, MW0568 | Q8NXU1 |
| *Mycobacterium tuberculosis* (strain ATCC 25618/H37Rv) | adh, Rv1530 | P9WQC3 |
| *Staphylococcus aureus* (strain N315) | adh, SA0562 | Q7A742 |
| *Staphylococcus aureus* (strain bovine RF122/ET3-1) | adh, SAB0557 | Q2YSX0 |
| *Sulfolobus acidocaldarius* (strain ATCC 33909/DSM 639/JCM 8929/NBRC 15157/NCIMB 11770) | adh, Saci_2057 | Q4J781 |
| *Staphylococcus aureus* (strain COL) | adh, SACOL0660 | Q5HI63 |
| *Staphylococcus aureus* (strain NCTC 8325) | adh, SAOUHSC_00608 | Q2G0G1 |
| *Staphylococcus aureus* (strain MRSA252) | adh, SAR0613 | Q6GJ63 |
| *Staphylococcus aureus* (strain MSSA476) | adh, SAS0573 | Q6GBM4 |
| *Staphylococcus aureus* (strain USA300) | adh, SAUSA300_0594 | Q2FJ31 |
| *Staphylococcus aureus* (strain Mu50/ATCC 700699) | adh, SAV0605 | Q99W07 |
| *Staphylococcus epidermidis* (strain ATCC 12228) | adh, SE_0375 | Q8CQ56 |
| *Staphylococcus epidermidis* (strain ATCC 35984/RP62A) | adh, SERP0257 | Q5HRD6 |
| *Sulfolobus solfataricus* (strain ATCC 35092/DSM 1617/JCM 11322/P2) | adh, SSO2536 | P39462 |
| *Sulfolobus tokodaii* (strain DSM 16993/JCM 10545/NBRC 100140/7) | adh, STK_25770 | Q96XE0 |
| *Anas platyrhynchos* (Domestic duck) (*Anas boschas*) | ADH1 | P30350 |
| *Apteryx australis* (Brown kiwi) | ADH1 | P49645 |
| *Ceratitis capitata* (Mediterranean fruit fly) (*Tephritis capitata*) | ADH1 | P48814 |

TABLE 3-continued

Exemplary alcohol dehydrogenase enzymes.

| Organism | Gene Name | Accession No. |
|---|---|---|
| *Ceratitis cosyra* (Mango fruit fly) (*Trypeta cosyra*) | ADH1 | Q70UN9 |
| *Gallus gallus* (Chicken) | ADH1 | P23991 |
| *Columba livia* (Domestic pigeon) | ADH1 | P86883 |
| *Coturnix coturnix japonica* (Japanese quail) (*Coturnix japonica*) | ADH1 | P19631 |
| *Drosophila hydei* (Fruit fly) | Adh1 | P23236 |
| *Drosophila montana* (Fruit fly) | Adh1 | P48586 |
| *Drosophila mettleri* (Fruit fly) | Adh1 | P22246 |
| *Drosophila mulleri* (Fruit fly) | Adh1 | P07161 |
| *Drosophila navojoa* (Fruit fly) | Adh1 | P12854 |
| *Geomys attwateri* (Attwater's pocket gopher) (*Geomys bursarius attwateri*) | ADH1 | Q9Z2M2 |
| *Geomys bursarius* (Plains pocket gopher) | ADH1 | Q64413 |
| *Geomys knoxjonesi* (Knox Jones's pocket gopher) | ADH1 | Q64415 |
| *Hordeum vulgare* (Barley) | ADH1 | P05336 |
| *Kluyveromyces marxianus* (Yeast) (*Candida kefyr*) | ADH1 | Q07288 |
| *Zea mays* (Maize) | ADH1 | P00333 |
| *Mesocricetus auratus* (Golden hamster) | ADH1 | P86885 |
| *Pennisetum americanum* (Pearl millet) (*Pennisetum glaucum*) | ADH1 | P14219 |
| *Petunia hybrida* (Petunia) | ADH1 | P25141 |
| *Oryctolagus cuniculus* (Rabbit) | ADH1 | Q03505 |
| *Solanum tuberosum* (Potato) | ADH1 | P14673 |
| *Struthio camelus* (Ostrich) | ADH1 | P80338 |
| *Trifolium repens* (Creeping white clover) | ADH1 | P13603 |
| *Zea luxurians* (Guatemalan teosinte) (*Euchlaena luxurians*) | ADH1 | Q07264 |
| *Saccharomyces cerevisiae* (strain ATCC 204508/S288c) (Baker's yeast) | ADH1, ADC1, YOL086C, O0947 | P00330 |
| *Arabidopsis thaliana* (Mouse-ear cress) | ADH1, ADH, At1g77120, F22K20.19 | P06525 |
| *Schizosaccharomyces pombe* (strain 972/ATCC 24843) (Fission yeast) | adh1, adh, SPCC13B11.01 | P00332 |
| *Drosophila lacicola* (Fruit fly) | Adh1, Adh-1 | Q27404 |
| *Mus musculus* (Mouse) | Adh1, Adh-1 | P00329 |
| *Peromyscus maniculatus* (North American deer mouse) | ADH1, ADH-1 | P41680 |
| *Rattus norvegicus* (Rat) | Adh1, Adh-1 | P06757 |
| *Drosophila virilis* (Fruit fly) | Adh1, Adh-1, GJ18208 | B4M8Y0 |
| *Scheffersomyces stipitis* (strain ATCC 58785/CBS 6054/NBRC 10063/NRRL Y-11545) (Yeast) (*Pichia stipitis*) | ADH1, ADH2, PICST_68558 | O00097 |
| *Aspergillus flavus* (strain ATCC 200026/FGSC A1120/NRRL 3357/JCM 12722/SRRC 167) | adh1, AFLA_048690 | P41747 |
| *Neurospora crassa* (strain ATCC 24698/74-OR23-1A/CBS 708.71/DSM 1257/FGSC 987) | adh-1, B17C10.210, NCU01754 | Q9P6C8 |
| *Candida albicans* (Yeast) | ADH1, CAD | P43067 |
| *Oryza sativa* subsp. *japonica* (Rice) | ADH1, DUPR11.3, Os11g0210300, LOC_Os11g10480, OsJ_032001 | Q2R8Z5 |
| *Drosophila mojavensis* (Fruit fly) | Adh1, GI17644 | P09370 |
| *Kluyveromyces lactis* (strain ATCC 8585/CBS 2359/DSM 70799/NBRC 1267/NRRL Y-1140/WM37) (Yeast) (*Candida sphaerica*) | ADH1, KLLA0F21010g | P20369 |
| *Oryza sativa* subsp. *indica* (Rice) | ADH1, OsI_034290 | Q75ZX4 |
| *Pongo abelii* (Sumatran orangutan) (*Pongo pygmaeus abelii*) | ADH1A | Q5RBP7 |
| *Homo sapiens* (Human) | ADH1A, ADH1 | P07327 |
| *Macaca mulatta* (Rhesus macaque) | ADH1A, ADH1 | P28469 |
| *Pan troglodytes* (Chimpanzee) | ADH1B | Q5R1W2 |
| *Papio hamadryas* (Hamadryas baboon) | ADH1B | P14139 |
| *Homo sapiens* (Human) | ADH1B, ADH2 | P00325 |
| *Homo sapiens* (Human) | ADH1C, ADH3 | P00326 |

TABLE 3-continued

Exemplary alcohol dehydrogenase enzymes.

| Organism | Gene Name | Accession No. |
| --- | --- | --- |
| *Papio hamadryas* (Hamadryas baboon) | ADH1C, ADH3 | O97959 |
| *Ceratitis capitata* (Mediterranean fruit fly) (*Tephritis capitata*) | ADH2 | P48815 |
| *Ceratitis cosyra* (Mango fruit fly) (*Trypeta cosyra*) | ADH2 | Q70UP5 |
| *Ceratitis rosa* (Natal fruit fly) (*Pterandrus rosa*) | ADH2 | Q70UP6 |
| *Drosophila arizonae* (Fruit fly) | Adh2 | P27581 |
| *Drosophila buzzatii* (Fruit fly) | Adh2 | P25720 |
| *Drosophila hydei* (Fruit fly) | Adh2 | P23237 |
| *Drosophila montana* (Fruit fly) | Adh2 | P48587 |
| *Drosophila mulleri* (Fruit fly) | Adh2 | P07160 |
| *Drosophila wheeleri* (Fruit fly) | Adh2 | P24267 |
| *Entamoeba histolytica* | ADH2 | Q24803 |
| *Hordeum vulgare* (Barley) | ADH2 | P10847 |
| *Kluyveromyces marxianus* (Yeast) (*Candida kefyr*) | ADH2 | Q9P4C2 |
| *Zea mays* (Maize) | ADH2 | P04707 |
| *Oryza sativa* subsp. *indica* (Rice) | ADH2 | Q4R1E8 |
| *Solanum lycopersicum* (Tomato) (*Lycopersicon esculentum*) | ADH2 | P28032 |
| *Solanum tuberosum* (Potato) | ADH2 | P14674 |
| *Scheffersomyces stipitis* (strain ATCC 58785/CBS 6054/NBRC 10063/NRRL Y-11545) (Yeast) (*Pichia stipitis*) | ADH2, ADH1, PICST_27980 | O13309 |
| *Arabidopsis thaliana* (Mouse-ear cress) | ADH2, ADHIII, FDH1, At5g43940, MRH10.4 | Q96533 |
| *Saccharomyces cerevisiae* (strain ATCC 204508/S288c) (Baker's yeast) | ADH2, ADR2, YMR303C, YM9952.05C | P00331 |
| *Candida albicans* (strain SC5314/ATCC MYA-2876) (Yeast) | ADH2, Ca41C10.04, CaO19.12579, CaO19.5113 | O94038 |
| *Oryza sativa* subsp. *japonica* (Rice) | ADH2, DUPR11.1, Os11g0210500, LOC_Os11g10510 | Q0ITW7 |
| *Drosophila mojavensis* (Fruit fly) | Adh2, GI17643 | P09369 |
| *Kluyveromyces lactis* (strain ATCC 8585/CBS 2359/DSM 70799/NBRC 1267/NRRL Y-1140/WM37) (Yeast) (*Candida sphaerica*) | ADH2, KLLA0F18260g | P49383 |
| *Oryctolagus cuniculus* (Rabbit) | ADH2-1 | O46649 |
| *Oryctolagus cuniculus* (Rabbit) | ADH2-2 | O46650 |
| *Hordeum vulgare* (Barley) | ADH3 | P10848 |
| *Solanum tuberosum* (Potato) | ADH3 | P14675 |
| *Kluyveromyces lactis* (strain ATCC 8585/CBS 2359/DSM 70799/NBRC 1267/NRRL Y-1140/WM37) (Yeast) (*Candida sphaerica*) | ADH3, KLLA0B09064g | P49384 |
| *Saccharomyces cerevisiae* (strain ATCC 204508/S288c) (Baker's yeast) | ADH3, YMR083W, YM9582.08 | P07246 |
| *Homo sapiens* (Human) | ADH4 | P08319 |
| *Mus musculus* (Mouse) | Adh4 | Q9QYY9 |
| *Rattus norvegicus* (Rat) | Adh4 | Q64563 |
| *Struthio camelus* (Ostrich) | ADH4 | P80468 |
| *Kluyveromyces lactis* (strain ATCC 8585/CBS 2359/DSM 70799/NBRC 1267/NRRL Y-1140/WM37) (Yeast) (*Candida sphaerica*) | ADH4, KLLA0F13530g | P49385 |
| *Schizosaccharomyces pombe* (strain 972/ATCC 24843) (Fission yeast) | adh4, SPAC5H10.06c | Q09669 |
| *Saccharomyces cerevisiae* (strain YJM789) (Baker's yeast) | ADH4, ZRG5, SCY_1818 | A6ZTT5 |
| *Saccharomyces cerevisiae* (strain ATCC 204508/S288c) (Baker's yeast) | ADH4, ZRG5, YGL256W, NRC465 | P10127 |
| *Saccharomyces pastorianus* (Lager yeast) (*Saccharomyces cerevisiae* × *Saccharomyces eubayanus*) | ADH5 | Q6XQ67 |
| *Bos taurus* (Bovine) | ADH5 | Q3ZC42 |
| *Equus caballus* (Horse) | ADH5 | P19854 |
| *Mus musculus* (Mouse) | Adh5, Adh-2, Adh2 | P28474 |
| *Rattus norvegicus* (Rat) | Adh5, Adh-2, Adh2 | P12711 |

TABLE 3-continued

Exemplary alcohol dehydrogenase enzymes.

| Organism | Gene Name | Accession No. |
|---|---|---|
| *Oryctolagus cuniculus* (Rabbit) | ADH5, ADH3 | O19053 |
| *Homo sapiens* (Human) | ADH5, ADHX, FDH | P11766 |
| *Dictyostelium discoideum* (Slime mold) | adh5, DDB_G0281865 | Q54TC2 |
| *Saccharomyces cerevisiae* (strain ATCC 204508/S288c) (Baker's yeast) | ADH5, YBR145W, YBR1122 | P38113 |
| *Homo sapiens* (Human) | ADH6 | P28332 |
| *Peromyscus maniculatus* (North American deer mouse) | ADH6 | P41681 |
| *Pongo abelii* (Sumatran orangutan) (*Pongo pygmaeus abelii*) | ADH6 | Q5R7Z8 |
| *Rattus norvegicus* (Rat) | Adh6 | Q5XI95 |
| *Homo sapiens* (Human) | ADH7 | P40394 |
| *Rattus norvegicus* (Rat) | Adh7 | P41682 |
| *Mus musculus* (Mouse) | Adh7, Adh-3, Adh3 | Q64437 |
| *Mycobacterium tuberculosis* (strain CDC 1551/Oshkosh) | adhA, MT1911 | P9WQC0 |
| *Rhizobium meliloti* (strain 1021) (*Ensifer meliloti*) (*Sinorhizobium meliloti*) | adhA, RA0704, SMa1296 | O31186 |
| *Mycobacterium tuberculosis* (strain ATCC 25618/H37Rv) | adhA, Rv1862 | P9WQC1 |
| *Zymomonas mobilis* subsp. *mobilis* (strain ATCC 31821/ZM4/CP4) | adhA, ZMO1236 | P20368 |
| *Mycobacterium bovis* (strain ATCC BAA-935/AF2122/97) | adhB, Mb0784c | Q7U1B9 |
| *Mycobacterium tuberculosis* (strain CDC 1551/Oshkosh) | adhB, MT0786 | P9WQC6 |
| *Mycobacterium tuberculosis* (strain ATCC 25618/H37Rv) | adhB, Rv0761c, MTCY369.06c | P9WQC7 |
| *Zymomonas mobilis* subsp. *mobilis* (strain ATCC 31821/ZM4/CP4) | adhB, ZMO1596 | P0DJA2 |
| *Zymomonas mobilis* subsp. *mobilis* (strain ATCC 10988/DSM 424/LMG 404/NCIMB 8938/NRRL B-806/ZM1) | adhB, Zmob_1541 | F8DVL8 |
| *Mycobacterium tuberculosis* (strain CDC 1551/Oshkosh) | adhD, MT3171 | P9WQB8 |
| *Mycobacterium tuberculosis* (strain ATCC 25618/H37Rv) | adhD, Rv3086 | P9WQB9 |
| *Clostridium acetobutylicum* (strain ATCC 824/DSM 792/JCM 1419/LMG 5710/VKM B-1787) | adhE, aad, CA_P0162 | P33744 |
| *Escherichia coli* (strain K12) | adhE, ana, b1241, JW1228 | P0A9Q7 |
| *Escherichia coli* O157:H7 | adhE, Z2016, ECs1741 | P0A9Q8 |
| *Rhodobacter sphaeroides* (strain ATCC 17023/2.4.1/NCIB 8253/DSM 158) | adhI, RHOS4_11650, RSP_2576 | P72324 |
| *Oryza sativa* subsp. *indica* (Rice) | ADHIII, OsI_009236 | A2XAZ3 |
| *Escherichia coli* (strain K12) | adhP, yddN, b1478, JW1474 | P39451 |
| *Geobacillus stearothermophilus* (*Bacillus stearothermophilus*) | adhT | P12311 |
| *Emericella nidulans* (strain FGSC A4/ATCC 38163/CBS 112.46/NRRL 194/M139) (*Aspergillus nidulans*) | alcA, AN8979 | P08843 |
| *Emericella nidulans* (strain FGSC A4/ATCC 38163/CBS 112.46/NRRL 194/M139) (*Aspergillus nidulans*) | alc, AN3741 | P54202 |
| *Emericella nidulans* (strain FGSC A4/ATCC 38163/CBS 112.46/NRRL 194/M139) (*Aspergillus nidulans*) | alcC, adh3, AN2286 | P07754 |
| *Arabidopsis thaliana* (Mouse-ear cress) | At1g22430, F12K8.22 | Q9SK86 |
| *Arabidopsis thaliana* (Mouse-ear cress) | At1g22440, F12K8.21 | Q9SK87 |
| *Arabidopsis thaliana* (Mouse-ear cress) | At1g32780, F6N18.16 | A1L4Y2 |
| *Arabidopsis thaliana* (Mouse-ear cress) | At1g64710, F13O11.3 | Q8VZ49 |
| *Arabidopsis thaliana* (Mouse-ear cress) | At4g22110, F1N20.210 | Q0V7W6 |
| *Arabidopsis thaliana* (Mouse-ear cress) | At5g24760, T4C12_30 | Q8LEB2 |

TABLE 3-continued

Exemplary alcohol dehydrogenase enzymes.

| Organism | Gene Name | Accession No. |
|---|---|---|
| *Arabidopsis thaliana* (Mouse-ear cress) | At5g42250, K5J14.5 | Q9FH04 |
| *Zea mays* (Maize) | FDH | P93629 |
| *Drosophila melanogaster* (Fruit fly) | Fdh, gfd, ODH, CG6598 | P46415 |
| *Bacillus subtilis* (strain 168) | gbsB, BSU31050 | P71017 |
| *Caenorhabditis elegans* | H24K24.3 | Q17335 |
| *Oryza sativa* subsp. *japonica* (Rice) | Os02g0815500, LOC_Os02g57040, OsJ_008550, P0643F09.4 | Q0DWH1 |
| *Mycobacterium tuberculosis* (strain ATCC 25618/H37Rv) | Rv1895 | O07737 |
| *Caenorhabditis elegans* | sodh-1, K12G11.3 | Q17334 |
| *Caenorhabditis elegans* | sodh-2, K12G11.4 | O45687 |
| *Pseudomonas* sp. | terPD | P33010 |
| *Escherichia coli* (strain K12) | yiaY, b3589, JW5648 | P37686 |
| *Moraxella* sp. (strain TAE123) | | P81786 |
| *Alligator mississippiensis* (American alligator) | | P80222 |
| *Catharanthus roseus* (Madagascar periwinkle) (*Vinca rosea*) | | P85440 |
| *Gadus morhua* subsp. *callarias* (Baltic cod) (*Gadus callarias*) | | P26325 |
| *Naja naja* (Indian cobra) | | P80512 |
| *Pisum sativum* (Garden pea) | | P12886 |
| *Pelophylax perezi* (Perez's frog) (*Rana perezi*) | | P22797 |
| *Saara hardwickii* (Indian spiny-tailed lizard) (*Uromastyx hardwickii*) | | P25405 |
| *Saara hardwickii* (Indian spiny-tailed lizard) (*Uromastyx hardwickii*) | | P25406 |
| *Equus caballus* (Horse) | | P00327 |
| *Equus caballus* (Horse) | | P00328 |
| *Geobacillus stearothermophilus* (*Bacillus stearothermophilus*) | | P42328 |
| *Gadus morhua* (Atlantic cod) | | P81600 |
| *Gadus morhua* (Atlantic cod) | | P81601 |
| *Myxine glutinosa* (Atlantic hagfish) | | P80360 |
| *Octopus vulgaris* (Common octopus) | | P81431 |
| *Pisum sativum* (Garden pea) | | P80572 |
| *Saara hardwickii* (Indian spiny-tailed lizard) (*Uromastyx hardwickii*) | | P80467 |
| *Scyliorhinus canicula* (Small-spotted catshark) (*Squalus canicula*) | | P86884 |
| *Sparus aurata* (Gilthead sea bream) | | P79896 |

Acyl-CoA Oxidase

Acyl-CoA oxidase (ACO) acts on CoA derivatives of fatty acids with chain lengths from 8 to 18. They are flavoenzymes containing one noncovalently bound FAD per subunit and belong to the same superfamily as mitochondrial acyl-CoA dehydrogenases. Like mitochondrial fatty acyl-CoA dehydrogenases, peroxisomal acyl-CoA oxidases catalyze the initial and rate-determining step of the peroxisomal fatty acid β-oxidation pathway, i.e. α,β-dehydrogenation of acyl-CoA, yielding trans-2-enoyl-CoA in the reductive half-reaction. In the oxidative half-reaction of peroxisomal acyl-CoA oxidase, the reduced FAD is reoxidized by molecular oxygen, producing hydrogen peroxide.

Acyl-CoA oxidase is a homodimer and the polypeptide chain of the subunit is folded into the N-terminal alpha-domain, beta-domain, and C-terminal alpha-domain. Functional differences between the peroxisomal acyl-CoA oxidases and the mitochondrial acyl-CoA dehydrogenases are attributed to structural differences in the FAD environments.

In some embodiments, recombinant microorganisms and methods are provided for the production of one or more unsaturated lipid moieties. In certain embodiments, the one or more unsaturated lipid moieties have carbon chain length shorter than or equal to C18. In some embodiments, the short chain unsaturated lipid moieties are produced from long chain unsaturated lipid moieties. Examples of suitable chain shortening enzymes include FAD-dependent acyl-CoA oxidase. In the case of fatty acid molecules with an even number of carbons, chain shortening enzymes produce a molecule of acetyl-CoA, and a fatty acyl-CoA shortened by two carbons. Fatty acid molecules with an odd number of carbons are oxidized in a similar fashion producing acetyl-CoA molecules during every round of oxidation until the chain-length is reduced to 5 carbons. In the final cycle of oxidation, this 5-carbon acyl-CoA is oxidized to produce acetyl-CoA and propionyl-CoA.

It is known that acyl-CoA oxidases exhibit varying specificity towards substrates with different chain-length (FIG. 32). Therefore, controlling the degree of fatty acyl-CoA truncation relies on engineering or selecting the appropriate enzyme variant. Examples of acyl-CoA oxidases that are suitable for this purpose are listed in Table 3a.

In some preferred embodiments of recombinant microorganisms and methods for the production of one or more unsaturated lipid moieties, one or more genes of the microbial host encoding acyl-CoA oxidases are deleted or down-regulated to eliminate or reduce the truncation of desired fatty acyl-CoAs beyond a desired chain-length. Such deletion or down-regulation targets include but are not limited to *Y. lipolytica* POX1(YALI0E32835g), *Y. lipolytica* POX2 (YALI0F10857g), *Y. lipolytica* POX3(YALI0D24750g), *Y. lipolytica* POX4(YALI0E27654g), *Y. lipolytica* POX5 (YALI0C23859g), *Y. lipolytica* POX6(YALI0E06567g); *S. cerevisiae* POX1(YGL205W); *Candida* POX2 (CaO19.1655, CaO19.9224, CTRG_02374, M18259), *Candida* POX4 (CaO19.1652, CaO19.9221, CTRG_02377, M12160), and *Candida* POX5 (CaO19.5723, CaO19.13146, CTRG_02721, M12161). In other embodiments, the one or more endogenous acyl-CoA oxidase enzymes that are deleted, disrupted, mutated, or downregulated control chain length of the one or more unsaturated lipid moieties.

TABLE 3a

Exemplary acyl-CoA oxidases

| Accession No. | Source Organism |
|---|---|
| P07872 | *Rattus norvegicus* |
| A0A178WDE4 | *Arabidopsis thaliana* |
| P0CZ23 | *Arabidopsis thaliana* |
| D7KG20 | *Arabidopsis lyrata* |
| R0I9Z2 | *Capsella rubella* |
| V4KEW0 | *Eutrema salsugineum* |
| M4DG68 | *Brassica rapa* |
| A0A078IZG1 | *Brassica napus* |
| A0A087HLF0 | *Arabis alpina* |
| A0A0D3C825 | *Brassica oleracea* |
| A0A078FAW4 | *Brassica napus* |
| A0A178W833 | *Arabidopsis thaliana* |
| Q9LMI7 | *Arabidopsis thaliana* |
| D7KG21 | *Arabidopsis lyrata* |
| A0A0D3C827 | *Brassica oleracea* |
| M4DG69 | *Brassica rapa* |
| A0A078J4V6 | *Brassica napus* |
| A0A078FAY6 | *Brassica napus* |
| V4KY71 | *Eutrema salsugineum* |
| A0A061E5C2 | *Theobroma cacao* |
| A0A061E4K0 | *Theobroma cacao* |
| M1APJ5 | *Solanum tuberosum* |
| J7KBI6 | *Prunus persica* |
| K4CXY8 | *Solanum lycopersicum* |
| V4W234 | *Citrus clementina* |
| G8XNW7 | *Malus domestica* |
| F6H4X3 | *Vitis vinifera* |
| A0A068V5Q3 | *Coffea canephora* |
| M1APJ6 | *Solanum tuberosum* |
| A0A067KHP0 | *Jatropha curcas* |
| A0A0D2PZG8 | *Gossypium raimondii* |
| B9IQS0 | *Populus trichocarpa* |
| W9RG01 | *Morus notabilis* |
| A0A0S3SB10 | *Vigna angularis* var. *angularis* |
| A0A0L9V573 | *Phaseolus angularis* |
| A0A0B0PPT6 | *Gossypium arboreum* |
| A0A0D2T164 | *Gossypium raimondii* |
| I1KEV4 | *Glycine max* |
| I1LS94 | *Glycine max* |
| G7JUZ2 | *Medicago truncatula* |
| U5FVP5 | *Populus trichocarpa* |
| V7AGL5 | *Phaseolus vulgaris* |
| A0A059A0G8 | *Eucalyptus grandis* |
| A0A059A0N3 | *Eucalyptus grandis* |
| A0A166AUM6 | *Daucus carota* subsp. *sativus* |
| A0A061EB81 | *Theobroma cacao* |
| A0A0A0LQY1 | *Cucumis sativus* |
| A0A022QRB0 | *Erythranthe guttata* |
| A0A0S3SB01 | *Vigna angularis* var. *angularis* |
| A0A0D2Q6S9 | *Gossypium raimondii* |
| B9SGN6 | *Ricinus communis* |

TABLE 3a-continued

Exemplary acyl-CoA oxidases

| Accession No. | Source Organism |
|---|---|
| A0A0B2PER8 | *Glycine soja* |
| A0A0B0NGI2 | *Gossypium arboreum* |
| A0A0D2SKF2 | *Gossypium raimondii* |
| A0A0B0NRR7 | *Gossypium arboreum* |
| A0A0J8EFZ4 | *Beta vulgaris* subsp. *vulgaris* |
| A0A0J8BLD2 | *Beta vulgaris* subsp. *vulgaris* |
| M4DG71 | *Brassica rapa* |
| W1Q1I1 | *Amborella trichopoda* |
| M0S864 | *Musa acuminata* |
| A0A166ABS1 | *Daucus carota* subsp. *sativus* |
| A0A1D6CA75 | *Triticum aestivum* |
| A0A0A9CN11 | *Arundo donax* |
| A0A1D6CKJ3 | *Triticum aestivum* |
| A0A164W703 | *Daucus carota* subsp. *sativus* |
| A0A1D1YDC5 | *Anthurium amnicola* |
| I1Q2B7 | *Oryza glaberrima* |
| A0A0D9WQH3 | *Leersia perrieri* |
| Q69XR7 | *Oryza sativa* subsp. *japonica* |
| A0A1D6CA73 | *Triticum aestivum* |
| A0A0E0A9E1 | *Oryza glumipatula* |
| A0A199W504 | *Ananas comosus* |
| A0A0E0HQR9 | *Oryza nivara* |
| M0T4I4 | *Musa acuminata* subsp. *malacc.* |
| C0PTG5 | *Picea sitchensis* |
| I1I3F1 | *Brachypodium distachyon* |
| K3XV57 | *Setaria italica* |
| A0A0D3GGF4 | *Oryza barthii* |
| A2YCR4 | *Oryza sativa* subsp. *indica* |
| A0A0K9RYF5 | *Spinacia oleracea* |
| A0A0D3GGF3 | *Oryza barthii* |
| A0A0D3GGF2 | *Oryza barthii* |
| A0A0E0HQR8 | *Oryza nivara* |
| A0A1D6CA72 | *Triticum aestivum* |
| A3BBK8 | *Oryza sativa* subsp. *japonica* |
| A0A199V6E4 | *Ananas comosus* |
| C5XPR4 | *Sorghum bicolor* |
| A0A0E0PXN1 | *Oryza rufipogon* |
| B6U7U8 | *Zea mays* |
| A0A1D6N7A4 | *Zea mays* |
| A0A0E0E1N7 | *Oryza meridionalis* |
| A0A0K9NPK9 | *Zostera marina* |
| A0A059Q1I9 | *Saccharum hybrid cultivar* R570 |
| J3MDZ2 | *Oryza brachyantha* |
| A0A0K9RYH2 | *Spinacia oleracea* |
| A0A103YIT3 | *Cynara cardunculus* |
| A0A0E0PXN2 | *Oryza rufipogon* |
| A9RZ70 | *Physcomitrella patens* |
| D8TES8 | *Selaginella moellendorffii* |
| D8SQF1 | *Selaginella moellendorffii* |
| M5X7E6 | *Prunus persica* |
| A9T150 | *Physcomitrella patens* |
| A0A176WTU5 | *Marchantia polymorpha* |
| A0A0D2QZ34 | *Gossypium raimondii* |
| A0A1D6N7A2 | *Zea mays* |
| A0A1D1Z3C0 | *Anthurium amnicola* |
| A0A067DSI1 | *Citrus sinensis* |
| A0A1D6CA74 | *Triticum aestivum* |
| M8CMI0 | *Aegilops tauschii* |
| A0A0S3SB72 | *Vigna angularis* var. *angularis* |
| M0UX36 | *Hordeum vulgare* subsp. *vulgare* |
| A0A1D6CA76 | *Triticum aestivum* |
| A0A151SDZ7 | *Cajanus cajan* |
| Q9LNB8 | *Arabidopsis thaliana* |
| A0A1D6CKJ4 | *Triticum aestivum* |
| F2EGJ0 | *Hordeum vulgare* subsp. *vulgare* |
| A0A0D2U3V1 | *Gossypium raimondii* |
| M0UX35 | *Hordeum vulgare* subsp. *vulgare* |
| M2Y3U7 | *Galdieria sulphuraria* |
| S8CGJ3 | *Genlisea aurea* |
| A0A0E0HQS2 | *Oryza nivara* |
| A0A199VU62 | *Ananas comosus* |
| M2WTY9 | *Galdieria sulphuraria* |
| A0A1D6N7A3 | *Zea mays* |
| A0A0E0HQS0 | *Oryza nivara* |
| A0A1E5VL23 | *Dichanthelium oligosanthes* |
| R7Q7I1 | *Chondrus crispus* |

TABLE 3a-continued

Exemplary acyl-CoA oxidases

| Accession No. | Source Organism |
|---|---|
| S0F2R6 | *Chondrus crispus* |
| S0F2T2 | *Chondrus crispus* |
| A0A0E0HQS1 | *Oryza nivara* |
| D3BSZ9 | *Polysphondylium pallidum* |
| A0A0D2WJ11 | *Capsaspora owczarzaki* strai. |
| R7QDC3 | *Chondrus crispus* |
| M1VCW4 | *Cyanidioschyzon merolae* str. |
| F1A2F0 | *Dictyostelium purpureum* |
| F4PI57 | *Dictyostelium fasciculatum.* |
| Q54II1 | *Dictyostelium discoideum* |
| A0A0E0LBG6 | *Oryza punctata* |
| A0A151ZKZ0 | *Dictyostelium lacteum* |
| M1BZ65 | *Solanum tuberosum* |
| H8MFT9 | *Corallococcus coralloides* s. |
| F8CEB4 | *Myxococcus fulvus* |
| A0A0H4WJP1 | *Myxococcus hansupus* |
| Q1CYG7 | *Myxococcus xanthus* |
| F1A3A8 | *Dictyostelium purpureum* |
| L7UK64 | *Myxococcus stipitatus* |
| A0A0F7BPX0 | *Myxococcus fulvus* 124B02 |
| A0A0G4J3N5 | *Plasmodiophora brassicae* |
| D5H9X3 | *Salinibacter ruber* strain M8 |
| Q2S1W1 | *Salinibacter ruber* strain D. |
| A0A085WN59 | *Hyalangium minutum* |
| A0A0G2ZRH9 | *Archangium gephyra* |
| A0A0S8HAC5 | *Gemmatimonas* sp. SM23_52 |
| A0A177Q5I1 | Verrucomicrobia bacterium SC |
| D8TVM2 | *Volvox carteri* f. *nagariensis* |
| A0A084SWJ9 | *Cystobacter violaceus* Cb vi76 |
| Q096A6 | *Stigmatella aurantiaca* stra. |
| R7QMZ0 | *Chondrus crispus* |
| A0A0G4J5Q9 | *Plasmodiophora brassicae* |
| A0A0Q9RNC6 | *Nocardioides* sp. Soil797 |
| A0A010YG34 | *Cryptosporangium arvum* DSM 4 |
| A0A098BJC6 | Putative *Rhodococcus ruber* |
| A0A059ML28 | *Rhodococcus aetherivorans* |
| N1M744 | *Rhodococcus* sp. EsD8 |
| W3ZXB8 | *Rhodococcus rhodochrous* ATCC 2 |
| A0A0A9CKJ6 | *Arundo donax* |
| F4PQH3 | *Dictyostelium fasciculatum* |
| I0Z1P9 | *Coccomyxa subellipsoidea* st. |
| A0A076ESS0 | *Rhodococcus opacus* |
| D3BKV2 | *Polysphondylium pallidum* |
| X0Q4M3 | Putative *Rhodococcus wratislaviensis* |
| A0A1D6BHN7 | *Triticum aestivum* |
| C1AZ37 | Putative *Rhodococcus opacus* strain B4 |
| M7ZG40 | *Triticum urartu* |
| W8HEJ3 | *Rhodococcus opacus* PD630 |
| A0A135GJ74 | *Rhodococcus* sp. SC4 |
| A0A149ZW75 | *Rhodococcus* sp. LB1 |
| Q0SF32 | *Rhodococcus jostii* strain R. |
| J2JJ09 | *Rhodococcus* sp. JVH1 |
| K8XW36 | *Rhodococcus opacus* M213 |
| A0A152A546 | *Dictyostelium lacteum* |
| A0A0Q8ZY28 | *Flavobacterium* sp. Root901 |
| L2TJT8 | *Rhodococcus wratislaviensis* |
| I0WB64 | *Rhodococcus imtechensis* |
| A0A1B1KC92 | *Rhodococcus opacus* |
| I3C521 | *Joostella marina* DSM 19592 |
| A0A0F6W8X8 | *Sandaracinus amylolyticus* |
| I3Z8X9 | *Belliella baltica* strain DS |
| A0A0J6W3K0 | *Mycobacterium obuense* |
| A0A0Q7GA13 | *Flavobacterium* sp. Root420 |
| D3BUR8 | *Polysphondylium pallidum* |
| A0A098SD35 | *Phaeodactylibacter xiamenensis* |
| A0A0D1LF86 | *Mycobacterium llatzerense* |
| A0A0Q5QHB8 | *Williamsia* sp. Leaf354 |
| A0A139VJG5 | *Mycobacterium phlei* DSM 4323 |
| F4PMW9 | *Dictyostelium fasciculatum* |
| A0A180ERQ3 | *Lewinella* sp. 4G2 |
| Q8MMS1 | *Dictyostelium discoideum* |
| A0A101CR99 | Flavobacteriaceae bacterium |
| A0A0Q9TDE2 | *Nocardioides* sp. Soil805 |
| A0A0Q9DX23 | *Flavobacterium* sp. Root935 |
| A0A0C1XE41 | *Hassallia byssoidea* VB512170 |
| A0A0J6W7K0 | *Mycobacterium chubuense* |
| A0A0H4PGA5 | *Cyclobacterium amurskyense* |
| A0A1B1WLB8 | *Mycobacterium* sp. djl-10 |
| A0A0Q8NET9 | *Flavobacterium* sp. Root186 |
| A0A0J6ZGS8 | *Mycobacterium chlorophenolicum* |
| A0A085ZIW1 | *Flavobacterium reichenbachii* |
| J3BZ97 | *Flavobacterium* sp. strain C. |
| A0A066WRY7 | *Flavobacterium seoulense* |
| K2PYQ1 | *Galbibacter marinus* |
| A0A0G4IN41 | *Plasmodiophora brassicae* |
| A0A1B5ZW29 | *Arenibacter* sp. C-21 |
| A0A1B9DW83 | *Flavobacterium piscis* |
| A0A099CMP1 | *Mycobacterium rufum* |
| A0A1B2U6C7 | *Flavobacterium johnsoniae* |
| A0A0M8YPK7 | *Saccharothrix* sp. NRRL B-16348 |
| A0A0T1WAX5 | *Mycobacterium* sp. Root135 |
| K0VAQ4 | *Mycobacterium vaccae* |
| A0A0Q9JG60 | *Mycobacterium* sp. Soil538 |
| A0A0M0TLE5 | *Flavobacterium* sp. VMW |
| A0A151ZK81 | *Dictyostelium lacteum* |
| K6WMK4 | Putative *Gordonia rhizosphera* NBRC 16 |
| L8GZJ4 | *Acanthamoeba castellanii* |
| I4BLB8 | *Mycobacterium chubuense* |
| H0RLL0 | Putative *Gordonia polyisoprenivorans* |
| A0A0C1LEQ5 | *Prauserella* sp. Am3 |
| A0A1E4NXS4 | *Pseudonocardia* sp. SCN 73-27 |
| A0A1A1YGK6 | *Mycobacterium* sp. ACS4331 |
| A0A0G3ILT8 | *Mycobacterium* sp. EPa45 |
| G7GR35 | Putative *Gordonia amarae* NBRC 15530 |
| A0A1A2LUF7 | *Mycobacterium* sp. E136 |
| A0A1A3GTN2 | *Mycobacterium mucogenicum* |
| A0A1A0RZ49 | *Mycobacterium* sp. 852002-519.. |
| A0A101AHK0 | *Mycobacterium* sp. IS-1496 |
| A0A126YBZ9 | *Streptomyces albus* |
| A0A0X3WJ69 | *Streptomyces griseus* subsp. |
| A0A1C4KUQ6 | *Streptomyces* sp. BvitLS-983 |
| A0A1C4T5K2 | *Streptomyces* sp. OspMP-M43 |
| A0A1A3C0V1 | *Mycobacterium* sp. E740 |
| A0A0G4IKE4 | *Plasmodiophora brassicae* |
| K1VUE5 | *Streptomyces* sp. SM8 |
| D6B5U8 | *Streptomyces albus* J1074 |
| A0A1C4NBH5 | *Streptomyces* sp. ScaeMP-6W |
| A0A1C4Q3W7 | *Streptomyces* sp. IgraMP-1 |
| R7WSQ4 | *Rhodococcus rhodnii* LMG 5362 |
| A0A0K2YP95 | *Rhodococcus* sp. RD6.2 |
| XP_011566937 | *Plutella xylostella* peroxisomal acyl-coenzyme A oxidase 1-like |
| XP_011568279 | *Plutella xylostella* probable peroxisomal acyl-coenzyme A oxidase 1 |
| XP_011568389.1 | *Plutella xylostella* probable peroxisomal acyl-coenzyme A oxidase 1 |
| XP_011554180.1 | *Plutella xylostella* probable peroxisomal acyl-coenzyme A oxidase 1 |
| XP_011549583.1 | *Plutella xylostella* probable peroxisomal acyl-coenzyme A oxidase 3 |
| XP_011548846.1 | *Plutella xylostella* probable peroxisomal acyl-coenzyme A oxidase 3 |
| AAP37772 | *A. thaliana* Acyl-CoA oxidase - 3 (ACX3) |
| XP_011548846.1 | plutella_xylostella_dbmfjv1x1_core_32_8 5_1_protein_XP_011548846.1 predicted peroxisomal acyl-coenzyme A oxidase 3 |

Acylglycerol Lipases and Sterol Esterases

In some embodiments, recombinant microorganisms and methods are provided for the production of one or more short chain unsaturated lipid moieties. In certain embodiments, the one or more short chain unsaturated lipid moieties have carbon chain length shorter than or equal to C18. In some preferred embodiments of methods to produce short chain pheromones, select enzymes which prefer to hydrolyze ester bonds of long-chain acylglycerols are co-expressed with one or more fatty acyl desaturases. Such suitable enzymes are exemplified by heterologous or engineered acylglycerol lipases. Examples of acylglycerol lipases that are suitable for this purpose are listed in Table 3b.

Carboxylic ester hydrolases (EC 3.1.1.-) are a large class of enzymes catalyzing the hydrolysis or synthesis of ester bonds. They have been described in all life domains, prokaryotic and eukaryotic. Most of them belong to the α/β-hydrolase superfamily and have a conserved "catalytic triad" formed by His, an acidic amino acid and a Ser residue that is located in a highly conserved GXSXG sequence. During hydrolysis, the catalytic Ser will start the nucleophilic attack of the substrate helped by the other two residues from the triad, which are in close spatial vicinity. These are presumed to facilitate the hydrolysis of esters by a mechanism similar to that of chymotrypsin-like serine proteases. Another characteristic feature is the presence of an amino acidic region whose sequence is not as conserved as that of the catalytic triad, the oxyanion hole, which serves to stabilize a transition state generated during catalysis. In addition, these enzymes generally do not require cofactors. Acylglycerol lipases and sterol esterases belong to the carboxylic ester hydrolase family.

An acylglycerol lipase enzyme catalyzes a chemical reaction that uses water molecules to break the glycerol monoesters of long-chain fatty acids. The systematic name of this enzyme class is glycerol-ester acylhydrolase. Other names in common use include monoacylglycerol lipase, monoacylglycerolipase, monoglyceride lipase, monoglyceride hydrolase, fatty acyl monoester lipase, monoacylglycerol hydrolase, monoglyceridyllipase, and monoglyceridase. This enzyme participates in glycerolipid metabolism.

A sterol esterase enzyme catalyzes the chemical reaction:

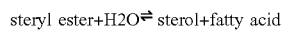
steryl ester+H2O⇌ sterol+fatty acid

Thus, the two substrates of this enzyme are steryl ester and H2O, whereas its two products are sterol and fatty acid.

The systematic name of this enzyme class is steryl-ester acylhydrolase. Other names in common use include cholesterol esterase, cholesteryl ester synthase, triterpenol esterase, cholesteryl esterase, cholesteryl ester hydrolase, sterol ester hydrolase, cholesterol ester hydrolase, cholesterase, and acylcholesterol lipase. This enzyme participates in bile acid biosynthesis. Sterol esterases are widespread in nature and have been identified from mammals' tissues such as the pancreas, intestinal mucosa, liver, placenta, aorta, and brain, to filamentous fungi, yeast, and bacteria.

In terms of substrate specificity, many sterol esterases are able to catalyze the hydrolysis or synthesis of a rather broad range of other substrates containing ester linkages, such as acylglycerols, aryl esters, and in some cases alcohol esters, cinnamyl esters, xhantophyl esters, or synthetic polymers.

TABLE 3b

Exemplary acylglycerol lipases

| Accession No. | Source Organism |
|---|---|
| EAY76846.1 | Oryza sativa |
| OEL29276.1 | Dichanthelium oligosanthes |
| ONM35522.1 | Zea mays |
| AFW56472.1 | Zea mays |
| AFW60230.1 | Zea mays |
| ACG33769.1 | Zea mays |

TABLE 3b-continued

Exemplary acylglycerol lipases

| Accession No. | Source Organism |
|---|---|
| ACG30143.1 | Zea mays |
| ACG39100.1 | Zea mays |
| ACG48810.1 | Zea mays |
| KQK11040.1 | Brachypodium distachyon |
| CAA64004.1 | Saccharomyces cerevisiae |
| CAA81640.1 | Saccharomyces cerevisiae |
| CAG78037.1 | Yarrowia lipolytica |
| EEF47288.1 | Ricinus communis |
| EEF45491.1 | Ricinus communis |
| EEF52390.1 | Ricinus communis |
| EEF38788.1 | Ricinus communis |
| EEF38789.1 | Ricinus communis |
| EEF28563.1 | Ricinus communis |
| EEF46013.1 | Ricinus communis |
| AFQ93681.1 | Ricinus communis |
| EEF45592.1 | Ricinus communis |
| EEF43592.1 | Ricinus communis |
| EEF50924.1 | Ricinus communis |
| EEF33440.1 | Ricinus communis |

In some embodiments, one or more acylglycerol lipases or sterol ester esterases are deleted, disrupted, mutated and/or reduced in activity in the recombinant microorganism. In some embodiments, the triacylglycerol lipase to be deleted, disrupted, mutated and/or reduced in activity is YALI0D17534g (TGL3).

Recombinant Microorganism

The present application relates to recombinant microorganisms having a biosynthesis pathway for the production of one or more unsaturated lipid moieties, which are converted by non-biological means to one or more fatty alcohols and/or one or more fatty aldehydes.

In one embodiment, the one or more recombinant microorganisms use one or more carbon sources for production of the one or more unsaturated lipid moieties. In another embodiment, the one or more carbon sources comprise sugars, glycerol, ethanol, organic acids, alkanes, and/or fatty acids. In certain embodiments, the one or more carbon sources is selected from the group consisting of alkanes and fatty acids. In some embodiments, the one or more recombinant microorganisms have high tolerance to alkanes and/or fatty acids. In some embodiments, the one or more recombinant microorganisms accumulate lipid.

The disclosure provides microorganisms that can be engineered to express various exogenous enzymes. In one embodiment, the one or more recombinant microorganisms are manipulated to comprise a biosynthesis pathway for the production of one or more unsaturated lipid moieties.

In some embodiments, the recombinant microorganism comprises one or more exogenous biosynthetic enzymes selected from one or more desaturases, one or more acyl-CoA oxidases, one or more acylglycerol lipases, one or more flavoprotein pyridine nucleotide cytochrome reductases, one or more elongases, one or more thioesterases, and/or one or more lipid binding proteins. In another embodiment, the one or more desaturases is selected from the group consisting of a fatty acyl-CoA desaturase and a fatty acyl-ACP desaturase. In some embodiments, the one or more flavoprotein pyridine nucleotide cytochrome reductases is selected from the group consisting of a cytochrome-b5 reductase and a NADPH-dependent cytochrome P450 reductase. In some embodiments, the one or more elongases is selected from the group consisting of ELO1, ELO2, ELO3, or any combination thereof. In some embodiments, the one or more thioesterases is selected from the group consisting of an acyl-ACP thioesterase and an acyl-CoA thioesterase. In some embodiments, the one or more lipid binding proteins is sterol carrier protein 2 (SCP2). In some embodiments, the one or more exogenous biosynthetic enzymes are from a genus selected from the group consisting of *Saccharomyces, Yarrowia, Candida, Helicoverpa, Agrotis, Trichoplusia, Spodoptera, Ostrinia, Amyelois, Lobesia, Cydia, Grapholita, Lampronia, Sesamia, Plodia, Bombyx, Phoenix, Rattus, Arabidopsis, Plutella* and *Bicyclus*. In some embodiments, the one or more exogenous biosynthetic enzymes are from a species selected from the group consisting of *Saccharomyces cerevisiae, Yarrowia lipolytica, Candida albicans, Candida tropicalis, Candida viswanathii, Helicoverpa armigera, Helicoverpa zea, Agrotis segetum, Trichoplusia ni, Spodoptera littoralis, Spodoptera exigua, Amyelois transitella, Lobesia botrana, Cydia pomonella, Lampronia capitella, Grapholita molesta, Ostrinia scapulalis, Ostrinia furnacalis, Ostrinia nubilalis, Ostrinia latipennis, Ostrinia ovalipennis, Plodia interpunctella, Sesamia inferens, Bombyx mori, Phoenix dactylifera, Rattus norvegicus, Arabidopsis thaliana, Plutella xylostella* and *Bicyclus anynana*.

In some embodiments, the fatty-acyl desaturase is a desaturase capable of utilizing a fatty acyl-CoA as a substrate that has a chain length of 6, 7, 8, 9, 10, 11, 12, 13, 14, 15, 16, 17, 18, 19, 20, 21, 22, 23, or 24 carbon atoms.

In some embodiments, the fatty-acyl desaturase is capable of generating a double bond at position C5, C6, C7, C8, C9, C10, C11, C12, or C13 in the fatty acid or its derivatives, such as, for example, fatty acid CoA esters.

In one exemplary embodiment, the fatty-acyl desaturase is a Z11 desaturase. In various embodiments described herein, the Z11 desaturase, or the nucleic acid sequence that encodes it, can be isolated from organisms of the species *Agrotis segetum, Amyelois transitella, Argyrotaenia velutiana, Choristoneura rosaceana, Lampronia capitella, Trichoplusia ni, Helicoverpa zea,* or *Thalassiosira pseudonana*. Further Z11-desaturases, or the nucleic acid sequences encoding them, can be isolated from *Bombyx mori, Manduca sexta, Diatraea grandiosella, Earias insulana, Earias vittella, Plutella xylostella, Bombyx mori* or *Diaphania nitidalis*. In exemplary embodiments, the Z11 desaturase comprises a sequence selected from GenBank Accession Nos. JX679209, JX964774, AF416738, AF545481, EU152335, AAD03775, AAF81787, and AY493438. In some embodiments, a nucleic acid sequence encoding a Z11 desaturase from organisms of the species *Agrotis segetum, Amyelois transitella, Argyrotaenia velutiana, Choristoneura rosaceana, Lampronia capitella, Trichoplusia ni, Helicoverpa zea,* or *Thalassiosira pseudonana* is codon optimized. In some embodiments, the Z11 desaturase comprises a nucleotide sequence selected from SEQ ID NOs: 3, 11, 17 and 19 from *Trichoplusia ni*. In some embodiments, the Z11 desaturase comprises an amino acid sequence set forth in SEQ ID NO: 25 from *Trichoplusia ni*. In other embodiments, the Z11 desaturase comprises a nucleotide sequence selected from SEQ ID NOs: 4 and 9 from *Agrotis segetum*. In some embodiments, the Z11 desaturase comprises an amino acid sequence set forth in SEQ ID NO: 29 from *Agrotis segetum*. In some embodiments, the Z11 desaturase comprises a nucleotide sequence selected from SEQ ID NOs: 5 and 16 from *Thalassiosira pseudonana*. In some embodiments, the Z11 desaturase comprises an amino acid sequence selected from SEQ ID NOs: 26 and 27 from *Thalassiosira pseudonana*. In certain embodiments, the Z11 desaturase comprises a nucleotide sequence selected from SEQ ID NOs: 6, 10 and 23 from *Amyelois transitella*. In some embodiments, the Z11 desaturase comprises an amino acid sequence set forth in SEQ ID NO: 28 from *Amyelois transitella*. In further embodiments, the Z11 desaturase comprises a nucleotide sequence selected from SEQ ID NOs: 7, 12, 18, 20 and 24 from *Helicoverpa zea*. In some embodiments, the Z11 desaturase comprises an amino acid sequence set forth in SEQ ID NO: 1 from *Helicoverpa zea*. In some embodiments, the Z11 desaturase comprises an amino acid sequence set forth in SEQ ID NO: 2 from *S. inferens*. In some embodiments, the Z11 desaturase comprises an amino acid sequence set forth in GenBank Accession nos. AF416738, AGH12217.1, AII21943.1, CAJ43430.2, AF441221, AAF81787.1, AF545481, AJ271414, AY362879, ABX71630.1 and NP001299594.1, Q9N9Z8, ABX71630.1 and AIM40221.1. In some embodiments, the Z11 desaturase comprises a chimeric polypeptide. In some embodiments, a complete or partial Z11 desaturase is fused to another polypeptide. In certain embodiments, the N-terminal native leader sequence of a Z11 desaturase is replaced by an oleosin leader sequence from another species. In certain embodiments, the Z11 desaturase comprises a nucleotide sequence selected from SEQ ID NOs: 8, 21 and 22. In some embodiments, the Z11 desaturase comprises an amino acid sequence selected from SEQ ID NOs: 33, 34, 35, 36, 37 and 38.

In certain embodiments, the Z11 desaturase catalyzes the conversion of a fatty acyl-CoA into a mono- or poly-unsaturated product selected from Z11-13:Acyl-CoA, E11-13:Acyl-CoA, (Z,Z)-7,11-13:Acyl-CoA, Z11-14:Acyl-CoA, E11-14:Acyl-CoA, (E,E)-9,11-14:Acyl-CoA, (E,Z)-9,11-14:Acyl-CoA, (Z,E)-9,11-14:Acyl-CoA, (Z,Z)-9,11-14:Acyl-CoA, (E,Z)-9,11-15:Acyl-CoA, (Z,Z)-9,11-15:Acyl-CoA, Z11-16:Acyl-CoA, E11-16:Acyl-CoA, (E,Z)-6,11-16:Acyl-CoA, (E,Z)-7,11-16:Acyl-CoA, (E,Z)-8,11-16:Acyl-CoA, (E,E)-9,11-16:Acyl-CoA, (E,Z)-9,11-16:Acyl-CoA, (Z,E)-9,11-16:Acyl-CoA, (Z,Z)-9,11-16:Acyl-CoA, (E,E)-11,13-16:Acyl-CoA, (E,Z)-11,13-16:Acyl-CoA, (Z,E)-11,13-16:Acyl-CoA, (Z,Z)-11,13-16:Acyl-CoA, (Z,E)-11,14-16:Acyl-CoA, (E,E,Z)-4,6,11-16:Acyl-CoA, (Z,Z,E)-7,11,13-16:Acyl-CoA, (E,E,Z,Z)-4,6,11,13-16:Acyl-CoA, Z11-17:Acyl-CoA, (Z,Z)-8,11-17:Acyl-CoA, Z11-18:Acyl-CoA, E11-18:Acyl-CoA, (Z,Z)-11,13-18:Acyl-CoA, (E,E)-11,14-18:Acyl-CoA, or combinations thereof.

In another exemplary embodiment, the fatty-acyl desaturase is a Z9 desaturase. In various embodiments described herein, the Z9 desaturase, or the nucleic acid sequence that encodes it, can be isolated from organisms of the species *Ostrinia furnacalis, Ostrinia nobilalis, Choristoneura rosaceana, Lampronia capitella, Helicoverpa assulta,* or *Helicoverpa zea*. In exemplary embodiments, the Z9 desaturase comprises a sequence selected from GenBank Accession Nos. AY057862, AF243047, AF518017, EU152332, AF482906, and AAF81788. In some embodiments, a nucleic acid sequence encoding a Z9 desaturase is codon optimized. In some embodiments, the Z9 desaturase comprises a nucleotide sequence set forth in SEQ ID NO: 13 from *Ostrinia furnacalis*. In some embodiments, the Z9 desaturase comprises an amino acid sequence set forth in SEQ ID NO: 30 from *Ostrinia furnacalis*. In other embodiments, the Z9 desaturase comprises a nucleotide sequence set forth in SEQ ID NO: 14 from *Lampronia capitella*. In some embodiments, the Z9 desaturase comprises an amino acid sequence set forth in SEQ ID NO: 31 from *Lampronia capitella*. In some embodiments, the Z9 desaturase comprises a nucleotide sequence set forth in SEQ ID NO: 15 from *Helicoverpa zea*. In some embodiments, the Z9 desaturase comprises an amino acid sequence set forth in SEQ ID NO: 32 from *Helicoverpa zea*.

In certain embodiments, the Z9 desaturase catalyzes the conversion of a fatty acyl-CoA into a monounsaturated or polyunsaturated product selected from Z9-11:Acyl-CoA, Z9-12:Acyl-CoA, E9-12:Acyl-CoA, (E,E)-7,9-12:Acyl-CoA, (E,Z)-7,9-12:Acyl-CoA, (Z,E)-7,9-12:Acyl-CoA, (Z,Z)-7,9-12:Acyl-CoA, Z9-13:Acyl-CoA, E9-13:Acyl-CoA, (E,Z)-5,9-13:Acyl-CoA, (Z,E)-5,9-13:Acyl-CoA, (Z,Z)-5,9-13:Acyl-CoA, Z9-14:Acyl-CoA, E9-14:Acyl-CoA, (E,Z)-4,9-14:Acyl-CoA, (E,E)-9,11-14:Acyl-CoA, (E,Z)-9,11-14:Acyl-CoA, (Z,E)-9,11-14:Acyl-CoA, (Z,Z)-9,11-14:Acyl-CoA, (E,E)-9,12-14:Acyl-CoA, (Z,E)-9,12-14:Acyl-CoA, (Z,Z)-9,12-14:Acyl-CoA, Z9-15:Acyl-CoA, E9-15:Acyl-CoA, (Z,Z)-6,9-15:Acyl-CoA, Z9-16:Acyl-CoA, E9-16:Acyl-CoA, (E,E)-9,11-16:Acyl-CoA, (E,Z)-9,11-16:Acyl-CoA, (Z,E)-9,11-16:Acyl-CoA, (Z,Z)-9,11-16:Acyl-CoA, Z9-17:Acyl-CoA, E9-18:Acyl-CoA, Z9-18:Acyl-CoA, (E,E)-5,9-18:Acyl-CoA, (E,E)-9,12-18:Acyl-CoA, (Z,Z)-9,12-18:Acyl-CoA, (Z,Z,Z)-3,6,9-18:Acyl-CoA, (E,E,E)-9,12,15-18:Acyl-CoA, (Z,Z,Z)-9,12,15-18:Acyl-CoA, or combinations thereof.

In some embodiments, the fatty acyl desaturase catalyzes the conversion of a fatty acyl-CoA into a mono- or polyunsaturated intermediate selected from E5-10:Acyl-CoA, E7-12:Acyl-CoA, E9-14:Acyl-CoA, E11-16:Acyl-CoA, E13-18:Acyl-CoA, Z7-12:Acyl-CoA, Z9-14:Acyl-CoA, Z11-16:Acyl-CoA, Z13-18:Acyl-CoA, Z8-12:Acyl-CoA, Z10-14:Acyl-CoA, Z12-16:Acyl-CoA, Z14-18:Acyl-CoA, Z7-10:Acyl-coA, Z9-12:Acyl-CoA, Z11-14:Acyl-CoA, Z13-16:Acyl-CoA, Z15-18:Acyl-CoA, E7-10:Acyl-CoA, E9-12:Acyl-CoA, E11-14:Acyl-CoA, E13-16:Acyl-CoA, E15-18:Acyl-CoA, E5Z7-12:Acyl-CoA, E7Z9-12:Acyl-CoA, E9Z11-14:Acyl-CoA, E11Z13-16:Acyl-CoA, E13Z15-18:Acyl-CoA, E6E8-10:Acyl-CoA, E8E10-12:Acyl-CoA, E10E12-14:Acyl-CoA, E12E14-16:Acyl-CoA, Z5E8-10:Acyl-CoA, Z7E10-12:Acyl-CoA, Z9E12-14:Acyl-CoA, Z11E14-16:Acyl-CoA, Z13E16-18:Acyl-CoA, Z3-10:Acyl-CoA, Z5-12:Acyl-CoA, Z7-14:Acyl-CoA, Z9-16:Acyl-CoA, Z11-18:Acyl-CoA, Z3Z5-10:Acyl-CoA, Z5Z7-12:Acyl-CoA, Z7Z9-14:Acyl-CoA, Z9Z11-16:Acyl-CoA, Z11Z13-16:Acyl-CoA, and Z13Z15-18:Acyl-CoA.

In some embodiments, the recombinant microorganism may express a bifunctional desaturase capable of catalyzing the subsequent desaturation of two double bonds.

In some embodiments, the recombinant microorganism may express more than one exogenous nucleic acid molecule encoding a fatty-acyl desaturase that catalyzes the conversion of a saturated $C_6$-$C_{24}$ fatty acyl-CoA to a corresponding mono- or poly-unsaturated $C_6$-$C_{24}$ fatty acyl-CoA. For instance, the recombinant microorganism may express an exogenous nucleic acid molecule encoding a Z11 desaturase and another exogenous nucleic acid molecule encoding a Z9 desaturase.

In some embodiments, the one or more recombinant microorganisms manipulated to comprise a biosynthesis pathway for the production of one or more unsaturated lipid moieties comprise at least one exogenous nucleic acid molecule encoding an acyl-CoA oxidase that catalyzes the conversion of a mono- or poly-unsaturated $C_6$-$C_{24}$ fatty acyl-CoA into a truncated mono- or poly-unsaturated fatty acyl-CoA after one or more successive cycle of acyl-CoA oxidase activity, with a given cycle producing a mono- or poly-unsaturated $C_4$-$C_{22}$ fatty acyl-CoA intermediate with a two carbon truncation relative to a starting mono- or poly-unsaturated $C_6$-$C_{24}$ fatty acyl-CoA substrate in that cycle. In some embodiments, the acyl-CoA oxidase is selected from Table 3a.

In some embodiments, the recombinant microorganism further comprises at least one endogenous or exogenous nucleic acid molecule encoding an acylglycerol lipase and/or sterol ester esterase enzyme that preferably hydrolyzes ester bonds of >C16, of >C14, of >C12 or of >C10 acylglycerol substrates. In some embodiments, the acylglycerol lipase and/or sterol ester esterase enzyme being expressed are selected from Table 3b.

In one embodiment, the one or more recombinant microorganisms manipulated to comprise a biosynthesis pathway for the production of one or more unsaturated lipid moieties are further manipulated to delete, disrupt, mutate, and/or reduce the activity of one or more endogenous proteins in a pathway that competes with the biosynthesis pathway for the production of one or more unsaturated lipid moieties.

In some embodiments, the recombinant microorganism is manipulated to delete, disrupt, mutate, and/or reduce the activity of one or more endogenous proteins involved in one or more undesired fatty acid elongation pathways. In certain embodiments, the one or more endogenous proteins involved in one or more undesired fatty acid elongation pathways is selected from the group consisting of a β-ketoacyl-CoA reductase, a β-hydroxyacyl-CoA dehydratase, an enoyl-CoA reductase, or any combination thereof.

In other embodiments, the recombinant microorganism is manipulated to delete, disrupt, mutate, and/or reduce the activity of one or more endogenous proteins involved in one or more lipid body storage and/or recycling pathways. In certain embodiments, the one or more endogenous proteins involved in one or more lipid body storage and/or recycling pathways is selected from the group consisting of a triacylglycerol lipase, a lysophosphatidic acid acyltransferase, a steryl ester hydrolase, an acyl-CoA synthetase, or any combination thereof. In some embodiments, the triacylglycerol lipase to be deleted, disrupted, mutated and/or reduced in activity is YALI0D17534g (TGL3). In some embodiments, the fatty acyl-CoA synthetase (fatty acid transporter) to be deleted, disrupted, mutated and/or reduced in activity is YALI0E16016g (FAT1).

In some embodiments, the recombinant microorganism is manipulated to delete, disrupt, mutate, and/or reduce the activity of one or more endogenous proteins involved in one or more fatty acid degradation pathways. In certain embodiments, the fatty acid degradation pathway is a beta-oxidation pathway. In certain embodiments, the one or more endogenous proteins is selected from the group consisting of an acyl-CoA oxidase, a multifunctional enoyl-CoA hydratase-β-hydroxyacyl-CoA dehydrogenase, a β-ketoacyl-CoA thiolase, or any combination thereof. In some preferred embodiments, one or more genes of the microbial host encoding acyl-CoA oxidases are deleted or down-regulated to eliminate or reduce the truncation of desired fatty acyl-CoAs beyond a desired chain-length. In some embodiments, the recombinant microorganism comprises a deletion, disruption, mutation, and/or reduction in the activity of one or more endogenous acyl-CoA oxidase enzyme selected from the group consisting of *Y. lipolytica* POX1 (YALI0E32835g), *Y. lipolytica* POX2 (YALI0F10857g), *Y. lipolytica* POX3 (YALI0D24750g), *Y. lipolytica* POX4 (YALI0E27654g), *Y. lipolytica* POX5 (YALI0C23859g), *Y. lipolytica* POX6 (YALI0E06567g); *S. cerevisiae* POX1 (YGL205W); *Candida* POX2 (CaO19.1655, CaO19.9224, CTRG_02374, M18259), *Candida* POX4 (CaO19.1652, CaO19.9221, CTRG_02377, M12160), and *Candida* POX5 (CaO19.5723, CaO19.13146, CTRG_02721, M12161).

In some embodiments, one or more genes of the recombinant microorganism encoding glycerol-3-phosphate acyl transferases (GPATs), lysophosphatidic acid acyltransferases (LPAATs), glycerolphospholipid acyltransferase (GPLATs) and/or diacylglycerol acyltransferases (DGATs) are deleted or downregulated, and replaced with one or more heterologous GPAT, LPAAT, GPLAT, or DGAT variants. In some embodiments, the one or more acyltransferase variant is derived from one or more heterologous acyltransferase selected from Table 3c. In some embodiments, the recombinant microorganism comprises a deletion, disruption, mutation, and/or reduction in the activity of one or more endogenous acyltransferase enzyme selected from the group consisting of *Y. lipolytica* YALI0C00209g, *Y. lipolytica* YALI0E18964g, *Y. lipolytica* YALI0F19514g, *Y. lipolytica* YALI0C14014g, *Y. lipolytica* YALI0E16797g, *Y. lipolytica* YALI0E32769g, and *Y. lipolytica* YALI0D07986g, *S. cerevisiae* YBL011w, *S. cerevisiae* YDL052c, *S. cerevisiae* YOR175C, *S. cerevisiae* YPR139C, *S. cerevisiae* YNR008w, and *S. cerevisiae* YOR245c, and *Candida* 1503_02577, *Candida* CTRG_02630, *Candida* CaO19.250, *Candida* CaO19.7881, *Candida* CTRG_02437, *Candida* CaO19.1881, *Candida* CaO19.9437, *Candida* CTRG_01687, *Candida* CaO19.1043, *Candida* CaO19.8645, *Candida* CTRG_04750, *Candida* CaO19.13439, *Candida* CTRG_04390, *Candida* CaO19.6941, *Candida* CaO19.14203, and *Candida* CTRG_06209.

In certain embodiments, the fatty acid degradation pathway is an omega-oxidation pathway. In certain embodiments, the one or more endogenous proteins is selected from the group consisting of a monooxygenase (CYP52), a fatty alcohol oxidase, a fatty alcohol dehydrogenase, an alcohol dehydrogenase, a fatty aldehyde dehydrogenase, or any combination thereof. In some preferred embodiments, the recombinant microorganism comprises a deletion, disruption, mutation, and/or reduction in the activity of one or more endogenous cytochrome P450 monooxygenases selected from the group consisting of *Y. lipolytica* YALI0E25982g (ALK1), *Y. lipolytica* YALI0F01320g (ALK2), *Y. lipolytica* YALI0E23474g (ALK3), *Y. lipolytica* YALI0B13816g (ALK4), *Y. lipolytica* YALI0B13838g (ALK5), *Y. lipolytica* YALI0B01848g (ALK6), *Y. lipolytica* YALI0A15488g (ALK7), *Y. lipolytica* YALI0C12122g (ALK8), *Y. lipolytica* YALI0B06248g (ALK9), *Y. lipolytica* YALI0B20702g (ALK10), *Y. lipolytica* YALI0C10054g (ALK11) and *Y. lipolytica* YALI0A20130g (ALK12).

In other embodiments, the recombinant microorganism is manipulated to delete, disrupt, mutate, and/or reduce the activity of one or more endogenous proteins involved in peroxisome biogenesis. In certain embodiments, the one or more endogenous proteins involved in peroxisome biogenesis is selected from the group consisting of PEX1, PEX2, PEX3, PEX4, PEX5, PEX6, PEX7, PEX8, PEX10, PEX11, PEX12, PEX13, PEX14, PEX15, PEX17, PEX18, PEX19, PEX21, PEX22, PEX25, PEX27, PEX28, PEX29, PEX30, PEX31, PEX32 and PEX34, or any combination thereof.

In another embodiment, the one or more recombinant microorganisms are further manipulated to increase intracellular levels of a coenzyme. In certain embodiments, the coenzyme is NADH and/or NADPH. In some embodiments, the one or more recombinant microorganisms are further manipulated to express one or more endogenous or exogenous proteins selected from the group consisting of a glucose-6-phosphate dehydrogenase, a 6-phosphogluconolactonase, a 6-phosphogluconate dehydrogenase, a transaldolase, a transketolase, a ribose-5-phosphate ketol-isomerase, a D-ribulose-5-phosphate 3-epimerase, an NADP+-dependent isocitrate dehydrogenase, an NAD+ or NADP+ dependent malate dehydrogenase, an alcohol dehydrogenase, an aldehyde dehydrogenase, a transhydrogenase, or any combination thereof. In another embodiment, the expression of one or more endogenous or exogenous proteins is coupled with supplementation of a co-substrate. In some embodiments, the one or more recombinant microorganisms are further manipulated to delete, disrupt, mutate, and/or reduce the activity of one or more endogenous proteins selected from the group consisting of a glucose-6-phosphate dehydrogenase, a 6-phosphogluconolactonase, a 6-phosphogluconate dehydrogenase, a transaldolase, a transketolase, a ribose-5-phosphate ketol-isomerase, a D-ribulose-5-phosphate 3-epimerase, or any combination thereof.

In some embodiments, the recombinant microorganism expresses one or more acyl-CoA oxidase enzymes and is manipulated to delete, disrupt, mutate, and/or reduce the activity of one or more endogenous acyl-CoA oxidase enzymes. In some embodiments, the one or more acyl-CoA oxidase enzymes being expressed are different from the one or more endogenous acyl-CoA oxidase enzymes being deleted or downregulated. In other embodiments, the one or more acyl-CoA oxidase enzymes that are expressed regulate chain length of the one or more unsaturated lipid moieties. In other embodiments, the one or more acyl-CoA oxidase enzymes being expressed are selected from Table 3a.

In various embodiments described herein, the recombinant microorganism is a eukaryotic microorganism. In some embodiments, the eukaryotic microorganism is a yeast. In exemplary embodiments, the yeast is a member of a genus selected from the group consisting of *Yarrowia*, *Candida*, *Saccharomyces*, *Pichia*, *Hansenula*, *Kluyveromyces*, *Issatchenkia*, *Zygosaccharomyces*, *Debaryomyces*, *Schizosaccharomyces*, *Pachysolen*, *Cryptococcus*, *Trichosporon*, *Rhodotorula*, and *Myxozyma*.

In some embodiments, the one or more recombinant microorganisms accumulate lipid. In an exemplary embodiment, the recombinant microorganism of the invention is an oleaginous yeast. In further embodiments, the oleaginous yeast is a member of a genus selected from the group consisting of *Yarrowia*, *Candida*, *Rhodotorula*, *Rhodosporidium*, *Cryptococcus*, *Trichosporon*, and *Lipomyces*. In even further embodiments, the oleaginous yeast is a member of a species selected from *Yarrowia lipolytica*, *Candida viswanathii*, *Rhodosporidium toruloides*, *Lipomyces starkey*, *L. lipoferus*, *C. revkaufi*, *C. pulcherrima*, *C. utilis*, *C. tropicalis*, *Rhodotorula minuta*, *Trichosporon pullans*, *T. cutaneum*, *Cryptococcus curvatus*, *R. glutinis*, and *R. graminis*.

In some embodiments, the recombinant microorganism is a prokaryotic microorganism. In exemplary embodiments, the prokaryotic microorganism is a member of a genus selected from the group consisting of *Escherichia*, *Clostridium*, *Zymomonas*, *Salmonella*, *Rhodococcus*, *Pseudomonas*, *Bacillus*, *Lactobacillus*, *Enterococcus*, *Alcaligenes*, *Klebsiella*, *Paenibacillus*, *Arthrobacter*, *Corynebacterium*, and *Brevibacterium*.

In some embodiments, the recombinant microorganism is used to produce one or more unsaturated lipid moieties.

Accordingly, in another aspect, the present inventions provide a method of producing one or more unsaturated lipid moieties using a recombinant microorganism described herein. In one embodiment, the method comprises cultivating the recombinant microorganism in a culture medium containing a feedstock providing a carbon source until the one or more unsaturated lipid moieties is produced. In a further embodiment, the one or more unsaturated lipid moieties is recovered. Recovery can be by methods known in the art, such as distillation, membrane-based separation gas stripping, solvent extraction, and expanded bed adsorption.

In some embodiments, the feedstock comprises a carbon source. In various embodiments described herein, the carbon source may be selected from sugars, glycerol, alcohols, organic acids, alkanes, fatty acids, lignocellulose, proteins, carbon dioxide, and carbon monoxide. In a further embodiment, the sugar is selected from the group consisting of glucose, fructose, and sucrose.

In some embodiments, the one or more recombinant microorganisms have high tolerance to alkanes and/or fatty acids.

In another aspect, a recombinant microorganism used in any of the methods of producing one or more fatty alcohols and/or one or more fatty aldehydes from one or more unsaturated lipid moieties is disclosed herein.

Methods of Producing Fatty Alcohols and/or Aldehydes

As described above, in one aspect, a method of producing one or more fatty alcohols and/or one or more fatty aldehydes from one or more unsaturated lipid moieties comprise the steps of: obtaining the one or more unsaturated lipid moieties from one or more naturally occurring organisms; and reducing the one or more unsaturated lipid moieties directly, wherein the reduction produces one or more fatty alcohols and/or one or more fatty aldehydes.

In another aspect, a method of producing one or more fatty alcohols and/or one or more fatty aldehydes from one or more unsaturated lipid moieties comprises the steps of: obtaining the one or more unsaturated lipid moieties from one or more naturally occurring organisms; chemically converting the one or more unsaturated lipid moieties to one or more free fatty acids (FFAs); esterifying the one or more FFAs to one or more fatty acid alkyl esters (FAAEs); and reducing the one or more FFAs and/or the one or more FAAEs, wherein the reduction produces one or more fatty alcohols and/or one or more fatty aldehydes. In one embodiment, the FAAEs comprise fatty acid methyl esters (FAMEs).

In another aspect, a method of producing one or more fatty alcohols and/or one or more fatty aldehydes from one or more unsaturated lipid moieties comprises the steps of: obtaining the one or more unsaturated lipid moieties from one or more naturally occurring organisms; chemically converting the one or more unsaturated lipid moieties to one or more FAAEs; and reducing the one or more FAAEs, wherein the reduction produces one or more fatty alcohols and/or one or more fatty aldehydes. In one embodiment, the FAAEs comprise fatty acid methyl esters (FAMEs).

In one embodiment, the one or more naturally occurring organisms is an insect. In another embodiment, the one or more naturally occurring organisms is not an insect. In some embodiments, the one or more naturally occurring organisms is selected from the group consisting of plants, algae and bacteria. In some embodiments, the plants are from families selected from the group consisting of Proteaceae and Rhamnaceae. In certain embodiments, the plants comprise species from the genus *Gevuina, Calendula, Limnanthes, Lunaria, Carum, Daucus, Coriandrum, Macadamia, Myristica, Licania, Aleurites, Ricinus, Corylus, Kermadecia, Asclepias, Cardwellia, Grevillea, Orites, Ziziphus, Hicksbeachia, Hippophae, Ephedra, Placospermum, Xylomelum* and/or *Simmondsia*. In some embodiments, the plants are selected from the group consisting of *Gevuina avellana, Corylus avellana, Kermadecia sinuata, Asclepias syriaca, Cardwellia sublimis, Grevillea exul* var. *rubiginosa, Orites diversifolius, Orites revoluta, Ziziphus jujube, Hicksbeachia pinnatifolia,* and *Grevillea decora*. In some embodiments, the algae comprise green algae. In certain embodiments, the green algae comprise species from the genus *Pediastrum*. In some embodiments, the green algae comprise *Pediastrum simplex*. In some embodiments, the bacteria comprise gram-negative bacteria. In some embodiments, the gram-negative bacteria comprise species from the genus *Myxococcus*. In certain embodiments, the gram-negative bacteria comprise *Myxococcus xanthus*. In some embodiments, the bacteria comprise cyanobacteria. In some embodiments, the cyanobacteria comprise species from the genus *Synechococcus*. In certain embodiments, the cyanobacteria comprise *Synechococcus elongatus*.

In another aspect, a method of producing one or more fatty alcohols and/or one or more fatty aldehydes from one or more unsaturated lipid moieties comprises the steps of: producing the one or more unsaturated lipid moieties in one or more recombinant microorganisms manipulated to comprise a biosynthesis pathway for the production of one or more unsaturated lipid moieties; chemically converting the one or more unsaturated lipid moieties to one or more free fatty acid (FFAs) and/or one or more fatty acid methyl esters (FAAEs); and reducing the one or more FFAs and/or the one or more FAAEs, wherein the reduction produces one or more fatty alcohols and/or one or more fatty aldehydes. In one embodiment, the FAAEs comprise fatty acid methyl esters (FAMEs).

In one embodiment of any of the methods of producing one or more fatty alcohols and/or one or more fatty aldehydes from one or more unsaturated lipid moieties disclosed herein comprising a chemical conversion step, the step of chemically converting the one or more unsaturated lipid moieties to one or more FFAs and/or one or more FAAEs further comprises the steps of: isolating the one or more unsaturated lipid moieties; optionally enriching for one or more unsaturated lipid moieties having specific chain lengths; and processing the one or more unsaturated lipid moieties to produce fatty acid derivatives. In some embodiments, the step of processing the one or more unsaturated lipid moieties comprises saponification of the one or more unsaturated lipid moieties to one or more FFAs. In some embodiments, the step of processing the one or more unsaturated lipid moieties comprises esterification of the one or more unsaturated lipid moieties to one or more FAAEs. In one embodiment, the optional step of enriching for one or more unsaturated lipid moieties having specific chain lengths comprises a separation method. In another embodiment, the separation method comprises distillation and/or chromatography. In one embodiment, the FAAEs comprise fatty acid methyl esters (FAMEs).

In one embodiment of any of the methods of producing one or more fatty alcohols and/or one or more fatty aldehydes from one or more unsaturated lipid moieties disclosed herein, the step of reducing the one or more unsaturated lipid moieties, the one or more FFAs and/or the one or more FAAEs to one or more fatty alcohols and/or one or more fatty aldehydes comprises contacting the one or more unsaturated lipid moieties, the one or more FFAs and/or the one or more FAAEs with one or more stoichiometric reducing agents. In some embodiments, the one or more stoichiometric reducing agents comprise sodium bis(2-methoxyethoxy)aluminum hydride Vitride (Red-Al, Vitride, SMEAH) and/or diisobutylaluminum hydride (DIBAL). In certain embodiments, the step of reducing the one or more unsaturated lipid moieties, the one or more FFAs and/or the one or more FAAEs comprises a bulky cyclic nitrogen Lewis base to modify the reducing agent. In one embodiment, the bulky cyclic nitrogen Lewis base allows selectivity of the reducing step for the production of one or more fatty aldehydes. In one embodiment, the FAAEs comprise fatty acid methyl esters (FAMEs).

In one embodiment of any of the methods of producing one or more fatty alcohols and/or one or more fatty aldehydes from one or more unsaturated lipid moieties disclosed herein, the step of reducing the one or more unsaturated lipid moieties, the one or more FFAs and/or the one or more FAAEs to one or more fatty alcohols comprises contacting the one or more unsaturated lipid moieties, the one or more FFAs and/or the one or more FAAEs with one or more transition metal catalysts. In certain embodiments, the one or more transition metal catalysts comprise one or more group VIII catalysts. In one embodiment, the FAAEs comprise fatty acid methyl esters (FAMEs).

In one embodiment of any of the methods of producing one or more fatty alcohols and/or one or more fatty aldehydes from one or more unsaturated lipid moieties disclosed herein, the fatty alcohols produced are further oxidized to fatty aldehydes by an oxidation step. In some embodiments, the oxidation step comprises one or more partial oxidation methods. In certain embodiments, the one or more partial oxidation methods comprise NaOCl/TEMPO. In other embodiments, the oxidation step comprises a copper-catalyzed aerobic oxidation.

In one embodiment of any of the methods of producing one or more fatty alcohols and/or one or more fatty aldehydes from one or more unsaturated lipid moieties disclosed herein, the one or more fatty alcohols produced are further chemically converted to one or more corresponding fatty acetate esters. In certain embodiments, the step of chemically converting the one or more fatty alcohols to one or more corresponding fatty acetate esters comprises contacting the one or more fatty alcohols with acetic anhydride.

In one embodiment of any of the methods of producing one or more fatty alcohols, one or more fatty aldehydes and/or one or more fatty acetates from one or more unsaturated lipid moieties disclosed herein, the one or more fatty alcohols, one or more fatty aldehydes and/or one or more fatty acetates are further enriched by a separation procedure.

In another aspect, a method of producing a recombinant microorganism capable of producing one or more unsaturated lipid moieties used in any of the methods of producing one or more fatty alcohols and/or one or more fatty aldehydes is disclosed herein.

Enzyme Engineering

The enzymes in the recombinant microorganism can be engineered to improve one or more aspects of the substrate to product conversion. Non-limiting examples of enzymes that can be further engineered for use in methods of the disclosure include a desaturase (e.g., a fatty acyl-CoA desaturase or fatty acyl-ACP desaturase), a cytochrome-b5 reductase, an elongase, a thioesterase, a glycerol-3-phosphate acyltransferase, a lysophosphatidic acid acyltransferase, a diacylglycerol acyltransferase, a lipid binding protein, a glucose-6-phosphate dehydrogenase, and/or a 6-phosphogluconate dehydrogenase, and combinations thereof. These enzymes can be engineered for improved catalytic activity, improved selectivity, improved stability, improved tolerance to various fermentations conditions (temperature, pH, etc.), or improved tolerance to various metabolic substrates, products, by-products, intermediates, etc.

Desaturase enzymes can be engineered for improved catalytic activity in the desaturation of an unsaturated substrate, for improved hydrocarbon selectivity, for improved selectivity of a Z product over an E product, or an E product over a Z product. For example, the Z9 fatty-acyl desaturase can be engineered to improve the yield in the substrate to product conversion of a saturated fatty acyl-CoA to the corresponding unsaturated fatty acyl-CoA, and, in addition or in the alternative, to improve selectivity of the desaturation at the 9 position to produce a corresponding Z-9 fatty acyl-CoA. In further non-limiting examples, the cytochrome-b5 reductase can be engineered for improved catalytic activity in the interchange of reducing equivalents between one-electron carriers and the two-electron-carrying nicotinamide dinucleotides; an elongase enzyme can be engineered for improved catalytic activity of elongation of a fatty acid substrate; a thioesterase can be engineered for improved catalytic activity in the conversion of acyl-ACP or acyl-CoA to free fatty acids; a glycerol-3-phosphate acyltransferase can be engineered for improved catalytic activity in the acylation at the sn-1 position of glycerol 3-phosphate; a lysophosphatidic acid acyltransferase can be engineered for improved catalytic activity in the acylation of the sn-2 position of triacylglycerol; an diacylglycerol acyltransferase can be engineered for improved catalytic activity in the addition of an acyl group to the sn-3 position of diacylglycerol to form triacylglycerol; a lipid binding protein can be engineered for improved sterol binding; a glucose-6-phosphate dehydrogenase can be engineered for improved catalytic activity in the oxidation of glucose-6-phosphate to 6-phospho D-glucono-1,5-lactone, and, in addition or in the alternative, to alter or improve the selectivity of the enzyme for a coenzyme; and a 6-phosphogluconate dehydrogenase can be engineered for improved catalytic activity in the oxidation of D-gluconate 6-phosphate to ribulose 5-phosphate, and, in addition or in the alternative, to alter or improve the selectivity of the enzyme for a coenzyme.

The term "improved catalytic activity" as used herein with respect to a particular enzymatic activity refers to a higher level of enzymatic activity than that measured relative to a comparable non-engineered enzyme, such as a non-engineered desaturase (e.g. fatty acyl-CoA desaturase or fatty acyl-ACP desaturase), cytochrome-b5 reductase, elongase, thioesterase, glycerol-3-phosphate acyltransferase, lysophosphatidic acid acyltransferase, diacylglycerol acyltransferase, lipid binding protein, glucose-6-phosphate dehydrogenase, or 6-phosphogluconate dehydrogenase. For example, overexpression of a specific enzyme can lead to an increased level of activity in the cells for that enzyme. Mutations can be introduced into a desaturase (e.g. fatty acyl-CoA desaturase or fatty acyl-ACP desaturase), a cytochrome-b5 reductase, an elongase, a thioesterase, a glycerol-3-phosphate acyltransferase, a lysophosphatidic acid acyltransferase, a diacylglycerol acyltransferase, a lipid binding protein, a glucose-6-phosphate dehydrogenase, or a 6-phosphogluconate dehydrogenase, resulting in engineered enzymes with improved catalytic activity. Methods to increase enzymatic activity are known to those skilled in the art. Such techniques can include increasing the expression of the enzyme by increasing plasmid copy number and/or use of a stronger promoter and/or use of activating riboswitches, introduction of mutations to relieve negative regulation of the enzyme, introduction of specific mutations to increase specific activity and/or decrease the KM for the substrate, or by directed evolution. See, e.g., *Methods in Molecular Biology* (vol. 231), ed. Arnold and Georgiou, Humana Press (2003).

Metabolic Engineering—Enzyme Overexpression, and Gene Deletion/Downregulation for Increased Pathway Flux In various embodiments described herein, the exogenous and endogenous enzymes in the recombinant microorganism participating in the biosynthesis pathways described herein may be overexpressed.

The terms "overexpressed" or "overexpression" refers to an elevated level (e.g., aberrant level) of mRNAs encoding for a protein(s), and/or to elevated levels of protein(s) in cells as compared to similar corresponding unmodified cells expressing basal levels of mRNAs or having basal levels of proteins. In particular embodiments, mRNA(s) or protein(s) may be overexpressed by at least 2-fold, 3-fold, 4-fold, 5-fold, 6-fold, 8-fold, 10-fold, 12-fold, 15-fold or more in microorganisms engineered to exhibit increased gene mRNA, protein, and/or activity.

In some embodiments, a recombinant microorganism of the disclosure is generated from a host that contains the enzymatic capability to synthesize a substrate fatty acid. In this specific embodiment it can be useful to increase the synthesis or accumulation of a fatty acid to, for example, increase the amount of fatty acid available for chemical conversion to FFAs and/or FAAEs and subsequent reduction to one or more fatty alcohols and/or one or more fatty aldehydes.

In some embodiments, it may be useful to increase the expression of endogenous or exogenous enzymes to increase intracellular levels of a coenzyme. In one embodiment, the coenzyme is NADH. In another embodiment, the coenzyme is NADPH. In one embodiment, the expression of proteins in the pentose phosphate pathway is increased to increase the intracellular levels of NADPH. The pentose phosphate pathway is an important catabolic pathway for supplying reduction equivalents and an important anabolic pathway for biosynthesis reactions. In one embodiment, a glucose-6-phosphate dehydrogenase that converts glucose-6-phosphate to 6-phospho D-glucono-1,5-lactone is overexpressed. In some embodiments, the glucose-6-phosphate dehydrogenase is ZWF1 from yeast. In another embodiment, the glucose-6-phosphate dehydrogenase is ZWF1 (YNL241C) from *Saccharomyces cerevisiae*. In one embodiment, a glucose-6-phosphate-1-dehydrogenase that converts D-glucopyranose-6-phosphate to 6-phospho D-glucono-1,5-lactone is overexpressed. In another embodiment, the glucose-6-phosphate-1-dehydrogenase is zwf from bacteria. In certain embodiments, the glucose-6-phosphate-1-dehydrogenase is zwf (NP_416366) from *E. coli*. In one embodiment, a 6-phosphogluconolactonase that converts 6-phospho D-glucono-1,5-lactone to D-gluconate 6-phosphate is overexpressed. In some embodiments, the 6-phosphogluconolactonase is SOL3 of yeast. In certain embodiments, the 6-phosphogluconolactonase is SOL3 (NP_012033) of *Saccharomyces cerevisiae*. In some embodiments, the 6-phosphogluconolactonase is SOL4 of yeast. In certain embodiments, the 6-phosphogluconolactonase is SOL4 (NP_011764) of *Saccharomyces cerevisiae*. In some embodiments, the 6-phosphogluconolactonase is pgl of bacteria. In certain embodiments, the 6-phosphogluconolactonase is pgl (NP_415288) of *E. coli*. In one embodiment, a 6-phosphogluconate dehydrogenase that converts D-gluconate 6-phosphate to D-ribulose 5-phosphate is overexpressed. In some embodiments, the 6-phosphogluconate dehydrogenase is GND1 from yeast. In certain embodiments, the 6-phosphogluconate dehydrogenase is GND1 (YHR183W) from *Saccharomyces cerevisiae*. In some embodiments, the 6-phosphogluconate dehydrogenase is GND2 from yeast. In certain embodiments, the 6-phosphogluconate dehydrogenase is GND2 (YGR256W) from *Saccharomyces cerevisiae*. In some embodiments, the 6-phosphogluconate dehydrogenase is gnd from bacteria. In certain embodiments, the 6-phosphogluconate dehydrogenase is gnd (NP_416533) from *E. coli*. In one embodiment, a transaldolase that interconverts D-glyceraldehyde 3-phosphate and D-sedoheptulose 7-phosphate to β-D-fructofuranose 6-phosphate and D-erythrose 4-phosphate is overexpressed. In some embodiments, the transaldolase is TAL1 of yeast. In certain embodiments, the transaldolase is TAL1 (NP_013458) of *Saccharomyces cerevisiae*. In some embodiments, the transaldolase is NQM1 of yeast. In certain embodiments, the transaldolase is NQM1 (NP_011557) of *Saccharomyces cerevisiae*. In some embodiments, the transaldolase is tal of bacteria. In certain embodiments, the transaldolase is talB (NP_414549) of *E. coli*. In certain embodiments, the transaldolase is talA (NP_416959) of *E. coli*. In one embodiment, a transketolase that interconverts D-erythrose 4-phosphate and D-xylulose 5-phosphate to β-D-fructofuranose 6-phosphate and D-glyceraldehyde 3-phosphate and/or interconverts D-sedoheptulose 7-phosphate and D-glyceraldehyde 3-phosphate to D-ribose 5-phosphate and D-xylulose 5-phosphate is overexpressed. In some embodiments, the transketolase is TKL1 of yeast. In certain embodiments, the transketolase is TKL1 (NP_015399) of *Saccharomyces cerevisiae*. In some embodiments, the transketolase is TKL2 of yeast. In certain embodiments, the transketolase is TKL2 (NP_009675) of *Saccharomyces cerevisiae*. In some embodiments, the transketolase is tkt of bacteria. In certain embodiments, the transketolase is tktA (YP_026188) of *E. coli*. In certain embodiments, the transketolase is tktB (NP_416960) of *E. coli*. In one embodiment, a ribose-5-phosphate ketol-isomerase that interconverts D-ribose 5-phosphate and D-ribulose 5-phosphate is overexpressed. In some embodiments, the ribose-5-phosphate ketol-isomerase is RKI1 of yeast. In certain embodiments, the ribose-5-phosphate ketol-isomerase is RKI1 (NP_014738) of *Saccharomyces cerevisiae*. In some embodiments, the ribose-5-phosphate isomerase is rpi of bacteria. In certain embodiments, the ribose-5-phosphate isomerase is rpiA (NP_417389) of *E. coli*. In certain embodiments, the ribose-5-phosphate isomerase is rpiB (NP_418514) of *E. coli*. In one embodiment, a D-ribulose-5-phosphate 3-epimerase that interconverts D-ribulose 5-phosphate and D-xylulose 5-phosphate is overexpressed. In some embodiments, the D-ribulose-5-phosphate 3-epimerase is RPE1 of yeast. In certain embodiments, the D-ribulose-5-phosphate 3-epimerase is RPE1 (NP_012414) of *Saccharomyces cerevisiae*. In some embodiments, the D-ribulose-5-phosphate 3-epimerase is rpe of bacteria. In certain embodiments, the D-ribulose-5-phosphate 3-epimerase is rpe (NP_417845) of *E. coli*.

In one embodiment, the expression of an NADP+-dependent isocitrate dehydrogenase is increased to increase intracellular levels of a coenzyme. In one embodiment, an NADP+ dependent isocitrate dehydrogenase oxidizes D-threo-isocitrate to 2-oxoglutarate with concomitant generation of NADPH. In another embodiment, an NADP+ dependent isocitrate dehydrogenase oxidizes D-threo-isocitrate to 2-oxalosuccinate with concomitant generation of NADPH. In some embodiments, the NADP+-dependent isocitrate dehydrogenase is IDP from yeast. In certain embodiments, the NADP+-dependent isocitrate dehydrogenase is IDP2 (YLR174W) from *Saccharomyces cerevisiae*. In some embodiments, the NADP+-dependent isocitrate dehydrogenase is icd from bacteria. In certain embodiments, the NADP+-dependent isocitrate dehydrogenase is icd (NP_415654) from *E. coli*.

In some embodiments, the expression of a malic enzyme that decarboxylates malate to pyruvate with concomitant generation of NADH or NADPH is increased to increase intracellular levels of a coenzyme. In one embodiment, the malic enzyme is NAD+ dependent. In another embodiment, the malic enzyme is NADP+ dependent. In one embodiment, the malic enzyme is an NAD+ dependent malate dehydrogenase from bacteria. In some embodiments, the NAD+ dependent malate dehydrogenase is maeA (NP_415996) from *E. coli*. In some embodiments, the NAD+ dependent malate dehydrogenase is maeE (CAQ68119) from *Lactobacillus casei*. In another embodiment, the malic enzyme is a mitochondrial NAD+ dependent malate dehydrogenase from yeast. In some embodiments, the NAD+ dependent malate dehydrogenase is MAE1 (YKL029C) from *S. cerevisiae*. In another embodiment, the malic enzyme is a mitochondrial NAD+ dependent malate dehydrogenase from a parasitic nematode. In some embodiments, the NAD+ dependent malate dehydrogenase is M81055 from *Ascaris suum*. In one embodiment, the malic enzyme is an NADP+ dependent malate dehydrogenase from bacteria. In some embodiments, the NADP+ dependent malate dehydrogenase is maeB (NP_416958) from *E. coli*. In one embodiment, the malic enzyme is an NADP+ dependent malate dehydrogenase from corn. In some embodiments, the NADP+ dependent malate dehydrogenase is me1 from *Zea mays*.

In some embodiments, the expression of an aldehyde dehydrogenase that oxidizes an aldehyde to a carboxylic acid with concomitant generation of NADH or NADPH is increased to increase intracellular levels of a coenzyme. In one embodiment, the aldehyde dehydrogenase is NAD+ dependent. In another embodiment, the aldehyde dehydrogenase is NADP+ dependent. In one embodiment, the aldehyde dehydrogenase is an NAD+ dependent aldehyde dehydrogenase from bacteria. In some embodiments, the NAD+ dependent aldehyde dehydrogenase is aldA (NP_415933) from *E. coli*. In another embodiment, the aldehyde dehydrogenase is a cytosolic NADP+ dependent aldehyde dehydrogenase from yeast. In some embodiments, the NADP+ dependent aldehyde dehydrogenase is ALD6 (YPL061W) from *S. cerevisiae*. In another embodiment, the aldehyde dehydrogenase is a cytosolic NADP+ dependent aldehyde dehydrogenase from bacteria. In some embodiments, the NADP+ dependent aldehyde dehydrogenase is aldB (NP_418045) from *E. coli*.

In one embodiment, overexpression of an enzyme to increase intracellular levels of a coenzyme comprises coupling supplementation of a co-substrate and overexpression of the enzyme. In one embodiment, the overexpression of an enzyme coupled with supplementation of a co-substrate of that enzyme increase flux through a biochemical pathway. In one embodiment, an $NAD^+$ or $NADP^+$ dependent alcohol dehydrogenase is expressed with a co-substrate. In certain embodiments, an alcohol dehydrogenase is expressed with an isopropanol co-substrate. In one embodiment, an $NAD^+$ or $NADP^+$ dependent glucose dehydrogenase is expressed with a co-substrate. In certain embodiments, a glucose dehydrogenase is expressed with a glucose co-substrate.

In one embodiment, the expression of a transhydrogenase is increased to interconvert NADH and NADPH. In some embodiments, the transhydrogenase is a pyridine nucleotide transhydrogenase. In some embodiments, the pyridine nucleotide transhydrogenase is from bacteria. In certain embodiments, the pyridine nucleotide transhydrogenase is pntAB (beta subunit: NP_416119; alpha subunit: NP_416120) from *E. coli*. In some embodiments, the pyridine nucleotide transhydrogenase is from human. In certain embodiments, the pyridine nucleotide transhydrogenase is NNT (NP_036475) from *Homo sapiens*. In certain embodiments, the pyridine nucleotide transhydrogenase is from *Solanum tuberosum*. In certain embodiments, the pyridine nucleotide transhydrogenase is from *Spinacea oleracea*.

Increased synthesis or accumulation can be accomplished by, for example, overexpression of nucleic acids encoding one or more of the above-described enzymes for production of one or more unsaturated lipid moieties. Overexpression of an enzyme or enzymes useful for production of one or more unsaturated lipid moieties can occur, for example, through increased expression of an endogenous gene or genes, or through the expression, or increased expression, of an exogenous gene or genes. Therefore, naturally occurring organisms can be readily modified to generate non-natural microorganisms producing one or more unsaturated lipid moieties through overexpression of one or more nucleic acid molecules encoding one or more enzymes useful for production of one or more unsaturated lipid moieties. In addition, a non-naturally occurring organism can be generated by mutagenesis of an endogenous gene that results in an increase in activity of an enzyme in a pathway for production of one or more unsaturated lipid moieties.

Equipped with the present disclosure, the skilled artisan will be able to readily construct the recombinant microorganisms described herein, as the recombinant microorganisms of the disclosure can be constructed using methods well known in the art as exemplified above to exogenously express at least one nucleic acid encoding an enzyme in a pathway for production of one or more unsaturated lipid moieties in sufficient amounts to produce one or more unsaturated lipid moieties.

Methods for constructing and testing the expression levels of a non-naturally occurring host producing one or more unsaturated lipid moieties can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); Ausubo et al., *Current Protocols in Molecular Biology*, John Wiley and Sons, Baltimore, Md. (1999).

A variety of mechanisms known in the art can be used to express, or overexpress, exogenous or endogenous genes. For example, an expression vector or vectors can be constructed to harbor one or more nucleic acids encoding enzymes useful in a biosynthetic pathway for production of one or more unsaturated lipid moieties as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art.

Expression control sequences are known in the art and include, for example, promoters, enhancers, polyadenylation signals, transcription terminators, internal ribosome entry sites (IRES), and the like, that provide for the expression of the polynucleotide sequence in a host cell. Expression control sequences interact specifically with cellular proteins involved in transcription (Maniatis et al., *Science*, 236: 1237-1245 (1987)). Exemplary expression control sequences are described in, for example, Goeddel, *Gene Expression Technology: Methods in Enzymology*, Vol. 185, Academic Press, San Diego, Calif. (1990).

In various embodiments, an expression control sequence may be operably linked to a polynucleotide sequence. By "operably linked" is meant that a polynucleotide sequence and an expression control sequence(s) are connected in such a way as to permit gene expression when the appropriate molecules (e.g., transcriptional activator proteins) are bound to the expression control sequence(s). Operably linked promoters are located upstream of the selected polynucleotide sequence in terms of the direction of transcription and translation. Operably linked enhancers can be located upstream, within, or downstream of the selected polynucleotide.

In some embodiments, the recombinant microorganism is manipulated to delete, disrupt, mutate, and/or reduce the activity of one or more endogenous proteins in a pathway that competes with the biosynthesis pathway for the production of one or more unsaturated lipid moieties.

In some embodiments, the recombinant microorganism is manipulated to delete, disrupt, mutate, and/or reduce the activity of one or more endogenous enzymes that catalyzes the conversion of a fatty acid into a ω-hydroxyfatty acid. In some such embodiments, the enzymes that catalyze the conversion of a fatty acid into a ω-hydroxyfatty acid are selected from the group consisting of XP_504406, XP_504857, XP_504311, XP_500855, XP_500856, XP_500402, XP_500097, XP_501748, XP_500560, XP_501148, XP_501667, XP_500273, BAA02041, CAA39366, CAA39367, BAA02210, BAA02211, BAA02212, BAA02213, BAA02214, AAO73952, AAO73953, AAO73954, AAO73955, AAO73956, AAO73958, AAO73959, AAO73960, AAO73961, AAO73957, XP_002546278, BAM49649, AAB80867, AAB17462, ADL27534, AAU24352, AAA87602, CAA34612, ABM17701, AAA25760, CAB51047, AAC82967, WP_011027348, or homologs thereof.

In some embodiments, the enzymes that catalyze the conversion of a fatty acid into a ω-hydroxyfatty acid are monooxygenases (CYP52). In some embodiments, the monooxygenases are selected from the group consisting of ALK1, ALK2, ALK3, ALK4, ALK5, ALK6, ALK7, ALK8, ALK9, ALK10, ALK11 and ALK12. In certain embodiments, the monooxygenases are *Yarrowia lipolytica* monooxygenases selected from the group consisting of YALI0B13838g, YALI0A15488g, YALI0B01848g, YALI0B13816g, YALI0E23474g, YALI0A20130g, YALI0C12122g, YALI0E25982g, YALI0B06248g, YALI0F01320g, YALI1B20702g and YALI0C10054g. In certain embodiments, the monooxygenases are *Candida albicans* monooxygenases selected from the group consisting of CaO19.10, CaO19.7683, CaO19.7512, CaO19.13150, CaO19.13927 and CaO19.6574. In certain embodiments, the monooxygenases are *Candida tropicalis* monooxygenases selected from the group consisting of CTRG_03115, CTRG_03120, CTRG_01061, CTRG_01060, CTRG_02725, CTRG_03114 and CTRG_04959.

In some embodiments, the enzymes that catalyze the conversion of a fatty acid into a ω-hydroxyfatty acid are fatty alcohol oxidases. In some embodiments, the fatty alcohol oxidases are selected from the group consisting of FAO1 and FAO2. In certain embodiments, the fatty alcohol oxidase is *Yarrowia lipolytica* YALI0B14014g. In certain embodiments, the fatty alcohol oxidases are *Candida albicans* fatty alcohol oxidases selected from the group consisting of CaO19.6143 and CaO19.13562. In certain embodiments, the fatty alcohol oxidases are *Candida tropicalis* fatty alcohol oxidases selected from the group consisting of CTRG_03062 and CTRG_03063.

In some embodiments, the enzymes that catalyze the conversion of a fatty acid into a ω-hydroxyfatty acid are fatty alcohol dehydrogenases. In some embodiments, the fatty alcohol dehydrogenase is FADH. In certain embodiments, the fatty alcohol dehydrogenase is *Yarrowia lipolytica* YALI0F09603g. In certain embodiments, the fatty alcohol dehydrogenases are *Candida albicans* fatty alcohol dehydrogenases selected from the group consisting of 1503_06411 and CaO19.7600. In certain embodiments, the fatty alcohol dehydrogenase is *Candida tropicalis* fatty alcohol dehydrogenase CTRG_05836.

In some embodiments, the enzymes that catalyze the conversion of a fatty acid into a ω-hydroxyfatty acid are alcohol dehydrogenases. In some embodiments, the alcohol dehydrogenases are selected from the group consisting of ADH1, ADH2, ADH3, ADH4, ADH5, ADH6, ADH7 and ADH8. In certain embodiments, the alcohol dehydrogenases are *Yarrowia lipolytica* alcohol dehydrogenases selected from the group consisting of YALI0E07766g, YALI0D25630g, YALI0E17787g, YALI0A16379g, YALI0A15147g, YALI0E15818g, YALI0D02167g and YALI0C12595g. In certain embodiments, the alcohol dehydrogenases are *Candida albicans* alcohol dehydrogenases selected from the group consisting of CaO19.11480, CaO19.12579, CaO19.5113, CaO19.4287, CaO19.11763, CaO19.10139, CaO19.2608, CaO19.11981, CaO19.4504, CaO19.11980, CaO19.12963 and CaO19.5517. In certain embodiments, the alcohol dehydrogenases are *Candida tropicalis* alcohol dehydrogenases selected from the group consisting of CTRG_06113, CTRG_05482, CTRG_05127 and CTRG_05197.

In some embodiments, the enzymes that catalyze the conversion of a fatty acid into a ω-hydroxyfatty acid are fatty aldehyde dehydrogenases. In some embodiments, the fatty aldehyde dehydrogenases are selected from the group consisting of FALDH1, FALDH2, FALDH3 and FALDH4. In certain embodiments, the fatty aldehyde dehydrogenases are *Yarrowia lipolytica* fatty aldehyde dehydrogenases selected from the group consisting of YALI0A17875g, YALI0E15400g, YALI0B01298g and YALI0F23793g. In certain embodiments, the fatty aldehyde dehydrogenases are *Candida albicans* fatty aldehyde dehydrogenases selected from the group consisting of CaO19.13871, CaO19.6518, CaO19.13487 and CaO19.6066. In certain embodiments, the fatty aldehyde dehydrogenases are *Candida tropicalis* fatty aldehyde dehydrogenases selected from the group consisting of CTRG_05010, CTRG_04471 and CTRG_04473.

In other embodiments, the recombinant microorganism is manipulated to delete, disrupt, mutate, and/or reduce the activity of one or more endogenous enzymes that catalyzes the conversion of a fatty acyl-CoA into α,β-enoyl-CoA. In some such embodiments, the enzymes that catalyze the conversion of a fatty acyl-CoA into α,β-enoyl-CoA are selected from the group consisting of CAA04659, CAA04660, CAA04661, CAA04662, CAA04663, CAG79214, AAA34322, AAA34361, AAA34363, CAA29901, BAA04761, AAA34891, AAB08643, CAB15271, BAN55749, CAC44516, ADK16968, AE137634, WP_000973047, WP_025433422, WP_035184107, WP_026484842, CEL80920, WP_026818657, WP_005293707, WP_005883960, or homologs thereof.

In some embodiments, the enzymes that catalyze the conversion of a fatty acyl-CoA into α,β-enoyl-CoA are acyl-CoA oxidases. In some embodiments, the acyl-CoA oxidases are selected from the group consisting of POX1, POX2, POX3, POX4, POX5, POX6 and PXP2. In certain embodiments, the acyl-CoA oxidase is *Saccharomyces cerevisiae* YGL205W. In certain embodiments, the acyl-CoA oxidases are *Yarrowia lipolytica* acyl-CoA oxidases selected from the group consisting of YALI0E32835g, YALI0F10857g, YALI0D24750g, YALI0E27654g, YALI0C23859g and YALI0E06567g. In certain embodiments, the acyl-CoA oxidases are *Candida albicans* acyl-CoA oxidases selected from the group consisting of CaO19.1655, CaO19.9224, CaO19.1652, CaO19.9221, CaO19.5723 and CaO19.13146. In certain embodiments, the acyl-CoA oxidases are *Candida tropicalis* acyl-CoA oxidases selected from the group consisting of CTRG_02374, CTRG_02377 and CTRG_02721. In certain embodiments, the acyl-CoA oxidases are *Candida viswanathii* acyl-CoA oxidases selected from the group consisting of M18259, M12160 and M12161.

In some embodiments, the enzymes that catalyze the conversion of a fatty acyl-CoA into α,β-enoyl-CoA are multifunctional enoyl-CoA hydratase-β-hydroxyacyl-CoA dehydrogenases. In some embodiments, the multifunctional enoyl-CoA hydratase-β-hydroxyacyl-CoA dehydrogenase is FOX2 (MFE1). In certain embodiments, the multifunctional enoyl-CoA hydratase-β-hydroxyacyl-CoA dehydrogenase is *Saccharomyces cerevisiae* YKR009C. In certain embodiments, the multifunctional enoyl-CoA hydratase-β-hydroxyacyl-CoA dehydrogenase is *Yarrowia lipolytica* YALI0E15378g. In certain embodiments, the multifunctional enoyl-CoA hydratase-β-hydroxyacyl-CoA dehydrogenase is *Candida albicans* CaO19.1809. In certain embodiments, the multifunctional enoyl-CoA hydratase-β-hydroxyacyl-CoA dehydrogenase is *Candida tropicalis* CTRG_05506.

In some embodiments, the enzymes that catalyze the conversion of a fatty acyl-CoA into α,β-enoyl-CoA are β-ketoacyl-CoA thiolases. In some embodiments, the β-ketoacyl-CoA thiolases are selected from the group consisting of POT1 and FOX3. In certain embodiments, the β-ketoacyl-CoA thiolase is *Saccharomyces cerevisiae* YIL160C. In certain embodiments, the β-ketoacyl-CoA thiolase is *Yarrowia lipolytica* YALI0E18568g. In certain embodiments, the β-ketoacyl-CoA thiolases are *Candida albicans* β-ketoacyl-CoA thiolases selected from the group consisting of CaO19.7520, CaO19.1704 and CaO19.9271. In certain embodiments, the β-ketoacyl-CoA thiolases are *Candida tropicalis* β-ketoacyl-CoA thiolases selected from the group consisting of CTRG_01068 and CTRG_02168.

In some embodiments, the recombinant microorganism is manipulated to delete, disrupt, mutate, and/or reduce the activity of one or more proteins involved in peroxisome biogenesis. In such embodiments, the one or more proteins involved in peroxisome biogenesis are selected from the group consisting of XP_505754, XP_501986, XP_501311, XP_504845, XP_503326, XP_504029, XP_002549868, XP_002547156, XP_002545227, XP_002547350, XP_002546990, EIW11539, EIW08094, EIW11472, EIW09743, EIW0828, or homologs thereof.

In some embodiments, the one or more proteins involved in peroxisome biogenesis are selected from the group consisting of PEX1, PEX2, PEX3, PEX4, PEX5, PEX6, PEX7, PEX8, PEX10, PEX11, PEX12, PEX13, PEX14, PEX15, PEX17, PEX18, PEX19, PEX21, PEX22, PEX25, PEX27, PEX28, PEX29, PEX30, PEX31, PEX32 and PEX34. In certain embodiments, the one or more proteins involved in peroxisome biogenesis is PEX2. In some embodiments, the PEX2 is YJL210W from *Saccharomyces cerevisiae*. In some embodiments, the PEX2 is YALI0_F01012g from *Yarrowia lipolytica*. In some embodiments, the PEX2 is CaO19.11030 from *Candida albicans*. In some embodiments, the PEX2 is CaO19.3546 from *Candida albicans*. In some embodiments, the PEX2 is CTRG_01657 from *Candida tropicalis*. In certain embodiments, the one or more proteins involved in peroxisome biogenesis is PEX12. In some embodiments, the PEX12 is YMR026C from *Saccharomyces cerevisiae*. In some embodiments, the PEX12 is YALI0_D26642g from *Yarrowia lipolytica*. In some embodiments, the PEX12 is CaO19.2009 from *Candida albicans*. In some embodiments, the PEX12 is CaO19.9560 from *Candida albicans*. In some embodiments, the PEX12 is CTRG_01296 from *Candida tropicalis*. In certain embodiments, the one or more proteins involved in peroxisome biogenesis is PEX10. In some embodiments, the PEX10 is YDR265W from *Saccharomyces cerevisiae*. In some embodiments, the PEX10 is YALI0_C01023g from *Yarrowia lipolytica*. In some embodiments, the PEX10 is CaO19.13105 from *Candida albicans*. In some embodiments, the PEX10 is CaO19.5660 from *Candida albicans*. In some embodiments, the PEX10 is CTRG_00008 from *Candida tropicalis*. In certain embodiments, the one or more proteins involved in peroxisome biogenesis is PEX1. In some embodiments, the PEX1 is YKL197C from *Saccharomyces cerevisiae*. In some embodiments, the PEX1 is YALI0_C15356g from *Yarrowia lipolytica*. In some embodiments, the PEX1 is CaO19.13818 from *Candida albicans*. In some embodiments, the PEX1 is CaO19.6460 from *Candida albicans*. In some embodiments, the PEX1 is CTRG_04869 from *Candida tropicalis*. In certain embodiments, the one or more proteins involved in peroxisome biogenesis is PEX22. In some embodiments, the PEX22 is YAL055W from *Saccharomyces cerevisiae*. In some embodiments, the PEX22 is YALI0_F06226g from *Yarrowia lipolytica*. In certain embodiments, the one or more proteins involved in peroxisome biogenesis is PEX16. In some embodiments, the PEX16 is YALI0_E16599g from *Yarrowia lipolytica*. In certain embodiments, the one or more proteins involved in peroxisome biogenesis is PEX14. In some embodiments, the PEX14 is YGL153W from *Saccharomyces cerevisiae*. In some embodiments, the PEX14 is YALI0_E09405g from *Yarrowia lipolytica*. In some embodiments, the PEX14 is CaO19.1805 from *Candida albicans*. In some embodiments, the PEX14 is CaO19.9371 from *Candida albicans*. In some embodiments, the PEX14 is CTRG_00541 from *Candida tropicalis*.

In some embodiments, the recombinant microorganism is manipulated to delete, disrupt, mutate, and/or reduce the activity of one or more endogenous proteins involved in one or more lipid body storage and/or recycling pathways. In certain embodiments, the one or more endogenous proteins is a triacylglycerol lipase. In one embodiment, the triacylglycerol lipase is *S. cerevisiae* TGL3 (YMR313c). In some embodiments, the triacylglycerol lipase is YALI0D17534g from *Yarrowia lipolytica*. In some embodiments, the triacylglycerol lipase is W5Q_03398 from *Candida albicans*. In some embodiments, the triacylglycerol lipase is CTRG_00057 from *Candida tropicalis*. In another embodiment, the lipase is *S. cerevisiae* TGL4 (YKR089c). In some embodiments, the triacylglycerol lipase is YALI0F10010g from *Yarrowia lipolytica*. In some embodiments, the triacylglycerol lipase is CaO19.5426 from *Candida albicans*. In some embodiments, the triacylglycerol lipase is CaO19.12881 from *Candida albicans*. In some embodiments, the triacylglycerol lipase is CTRG_06185 from *Candida tropicalis*. In certain embodiments, the one or more endogenous proteins is a lysophosphatidic acid acyltransferase that mediates fatty acyl transfer from triacylglycerides containing fatty acids. In one embodiment, the lysophosphatidic acid acyltransferase is *S. cerevisiae* TGL5 (YOR081c). In certain embodiments, the one or more endogenous proteins is a steryl ester hydrolase that mediates hydrolysis of sterol esters containing fatty acids. In one embodiment, the steryl ester hydrolase is *S. cerevisiae* TGL1 (YKL140w). In some embodiments, the steryl ester hydrolase is YALI0E32035g from *Yarrowia lipolytica*. In some embodiments, the steryl ester hydrolase is CaO19.2050 from *Candida albicans*. In some embodiments, the steryl ester hydrolase is CaO19.9598 from *Candida albicans*. In some embodiments, the steryl ester hydrolase is CTRG_01138 from *Candida tropicalis*. In one embodiment, the steryl ester hydrolase is *S. cerevisiae* YEH1 (YLL012W). In some embodiments, the steryl ester hydrolase is YALI0E00528g from *Yarrowia lipolytica*. In some embodiments, the steryl ester hydrolase is Ca019.1887 from *Candida albicans*. In some embodiments, the steryl ester hydrolase is CaO19.9443 from *Candida albicans*. In some embodiments, the steryl ester hydrolase is CTRG_01683 from *Candida tropicalis*. In one embodiment, the steryl ester hydrolase is *S. cerevisiae* YEH2 (YLR020C). In some embodiments, the steryl ester hydrolase is CTRG_04630 from *Candida tropicalis*. In certain embodiments, the one or more endogenous proteins is an acyl-CoA synthetase which reactivates fatty acyl moieties to fatty acyl-CoA thioesters. In one embodiment, the acyl-CoA synthetase is FAT1 (AAC17118).

In some embodiments, the recombinant microorganism is manipulated to delete, disrupt, mutate, and/or reduce the activity of one or more endogenous enzymes that catalyzes a reaction in a pathway that competes with the biosynthesis pathway for one or more unsaturated fatty acyl-CoA intermediates. In one embodiment, the one or more endogenous enzymes comprise one or more diacylglycerol acyltransferases. In the context of a recombinant yeast microorganism, the recombinant yeast microorganism is engineered to delete, disrupt, mutate, and/or reduce the activity of one or more diacylglycerol acyltransferases selected from the group consisting of YALI0E32769g, YALI0D07986g and CTRG_06209, or homolog thereof. In another embodiment, the one or more endogenous enzymes comprise one or more glycerolphospholipid acyltransferases. In the context of a recombinant yeast microorganism, the recombinant yeast microorganism is engineered to delete, disrupt, mutate, and/or reduce the activity of one or more glycerolphospholipid acyltransferases selected from the group consisting of YALI0E16797g and CTG_04390, or homolog thereof. In another embodiment, the one or more endogenous enzymes comprise one or more acyl-CoA/sterol acyltransferases. In the context of a recombinant yeast microorganism, the recombinant yeast microorganism is engineered to delete, disrupt, mutate, and/or reduce the activity of one or more acyl-CoA/sterol acyltransferases selected from the group consisting of YALI0F06578g, CTRG_01764 and CTRG_01765, or homolog thereof.

In some embodiments, the recombinant microorganism is manipulated to delete, disrupt, mutate, and/or reduce the activity of one or more endogenous proteins involved in one or more fatty acid elongation pathways. In certain embodiments, the one or more endogenous proteins is a β-ketoacyl-CoA synthase which catalyzes the condensation of malonyl-ACP with acyl-CoA, resulting in β-ketoacyl-ACP. In one embodiment, the β-ketoacyl-CoA synthase is a β-ketoacyl-CoA synthase domain of yeast FAS. In certain embodiments, the one or more endogenous proteins is a β-ketoacyl-ACP synthase I which condenses malonyl-ACP with acyl-ACP to form β-ketoacyl-ACP. In one embodiment, the β-ketoacyl-ACP synthase I is FabB from bacteria. In certain embodiments, the one or more endogenous proteins is a β-ketoacyl-ACP synthase II which condenses malonyl-ACP with acyl-ACP to form β-ketoacyl-ACP. In one embodiment, the β-ketoacyl-ACP synthase II is FabF from bacteria. In certain embodiments, the one or more endogenous proteins is a β-ketoacyl-ACP reductase that reduces the β-keto group of β-ketoacyl-ACP with NADPH to form β-hydroxyacyl-ACP. In one embodiment, the β-ketoacyl-ACP reductase is FabG from bacteria. In another embodiment, the β-ketoacyl-ACP reductase is the ketoreductase (KR) domain of yeast FAS. In certain embodiments, the one or more endogenous proteins is a β-ketoacyl-CoA reductase. In some embodiments, the β-ketoacyl-CoA reductase is IFA38 from *Saccharomyces cerevisiae* (YBR159W). In some embodiments, the β-ketoacyl-CoA reductase is YALI0A06787g from *Yarrowia lipolytica*. In some embodiments, the β-ketoacyl-CoA reductase is CaO19.11340 from *Candida albicans*. In some embodiments, the β-ketoacyl-CoA reductase is CaO19.3859 from *Candida albicans*. In some embodiments, the β-ketoacyl-CoA reductase is CTRG_00620 from *Candida tropicalis*. In certain embodiments, the one or more endogenous proteins is a p-hydroxyacyl-ACP dehydratase that dehydrates β-hydroxyacyl-ACP to form trans-2-enoyl-ACP. In one embodiment, the dehydratase is β-hydroxyacyl-ACP dehydratase/isomerase. In another embodiment, the β-hydroxyacyl-ACP dehydratase/isomerase is FabA from bacteria. In one embodiment, the dehydratase is β-hydroxyacyl-ACP dehydratase. In another embodiment, the p-hydroxyacyl-ACP dehydratase is FabZ from bacteria. In another embodiment, the dehydratase is the dehydratase (DH) domain of yeast FAS. In certain embodiments, the one or more endogenous proteins is a β-hydroxyacyl-CoA dehydratase. In some embodiments, the β-hydroxyacyl-CoA dehydratase is PHS1 (TPL1) from *Saccharomyces cerevisiae* (YJL097W). In some embodiments, the β-hydroxyacyl-CoA dehydratase is YALI0F11935g from *Yarrowia lipolytica*. In some embodiments, the β-hydroxyacyl-CoA dehydratase is CaO19.5156 from *Candida albicans*. In some embodiments, the β-hydroxyacyl-CoA dehydratase is CaO19.12623 from *Candida albicans*. In some embodiments, the β-hydroxyacyl-CoA dehydratase is CTRG_05224 from *Candida tropicalis*. In certain embodiments, the one or more endogenous proteins is an enoyl-ACP reductase which reduces trans-2-enoyl-ACP to form acyl-ACP. In one embodiment, the reductase is an NADPH-dependent trans-2-enoyl-ACP reductase I. In another embodiment, the NADPH-dependent trans-2-enoyl-ACP reductase I is FabI from bacteria. In one embodiment, the reductase is an NADPH-dependent trans-2-enoyl-ACP reductase II. In another embodiment, the NADPH-dependent trans-2-enoyl-ACP reductase II is FabK from bacteria. In one embodiment, the reductase is an NADPH-dependent trans-2-enoyl-ACP reductase III. In another embodiment, the NADPH-dependent trans-2-enoyl-ACP reductase Ill is FabL from bacteria. In another embodiment, the reductase is the enol reductase (ER) domain of FAS in yeast. In certain embodiments, the one or more endogenous proteins is an enoyl-CoA reductase. In some embodiments, the enoyl-CoA reductase is TSC13 from *Saccharomyces cerevisiae* (YDL015C). In some embodiments, the enoyl-CoA reductase is YALI0A04983g from *Yarrowia lipolytica*. In some embodiments, the enoyl-CoA reductase is CaO19.10803 from *Candida albicans*. In some embodiments, the enoyl-CoA reductase is CaO19.3293 from *Candida albicans*. In some embodiments, the enoyl-CoA reductase is CTRG_04406 from *Candida tropicalis*.

In another embodiment, the recombinant microorganism is manipulated to delete, disrupt, mutate, and/or reduce the activity of one or more endogenous proteins involved in the pentose phosphate pathway. In some embodiments, expression of proteins in the pentose phosphate pathway is decreased to increase the intracellular level of NADH. In one embodiment, the one or more endogenous proteins is a glucose-6-phosphate dehydrogenase that converts glucose-6-phosphate to 6-phospho D-glucono-1,5-lactone. In some embodiments, the glucose-6-phosphate dehydrogenase is ZWF1 from yeast. In another embodiment, the glucose-6-phosphate dehydrogenase is ZWF1 (YNL241C) from *Saccharomyces cerevisiae*. In one embodiment, the one or more endogenous proteins is a glucose-6-phosphate-1-dehydrogenase that converts D-glucopyranose-6-phosphate to 6-phospho D-glucono-1,5-lactone. In another embodiment, the glucose-6-phosphate-1-dehydrogenase is zwf from bacteria. In certain embodiments, the glucose-6-phosphate-1-dehydrogenase is zwf (NP_416366) from *E. coli*. In one embodiment, the one or more endogenous proteins is a 6-phosphogluconolactonase that converts 6-phospho D-glucono-1,5-lactone to D-gluconate 6-phosphate. In some embodiments, the 6-phosphogluconolactonase is SOL3 of yeast. In certain embodiments, the 6-phosphogluconolactonase is SOL3 (NP_012033) of *Saccharomyces cerevisiae*. In some embodiments, the 6-phosphogluconolactonase is SOL4 of yeast. In certain embodiments, the 6-phosphogluconolactonase is SOL4 (NP_011764) of *Saccharomyces cerevisiae*. In some embodiments, the 6-phosphogluconolactonase is pgl of bacteria. In certain embodiments, the 6-phosphogluconolactonase is pgl (NP_415288) of *E. coli*. In one embodiment, the one or more endogenous proteins is a 6-phosphogluconate dehydrogenase that converts D-gluconate 6-phosphate to D-ribulose 5-phosphate In some embodiments, the 6-phosphogluconate dehydrogenase is GND1 from yeast. In certain embodiments, the 6-phosphogluconate dehydrogenase is GND1 (YHR183W) from *Saccharomyces cerevisiae*. In some embodiments, the 6-phosphogluconate dehydrogenase is GND2 from yeast. In certain embodiments, the 6-phosphogluconate dehydrogenase is GND2 (YGR256W) from *Saccharomyces cerevisiae*. In some embodiments, the 6-phosphogluconate dehydrogenase is gnd from bacteria. In certain embodiments, the 6-phosphogluconate dehydrogenase is gnd (NP_416533) from *E. coli*. In one embodiment, the one or more endogenous proteins is a transaldolase that interconverts D-glyceraldehyde 3-phosphate and D-sedoheptulose 7-phosphate to β-D-fructofuranose 6-phosphate and D-erythrose 4-phosphate. In some embodiments, the transaldolase is TAL1 of yeast. In certain embodiments, the transaldolase is TAL1 (NP_013458) of *Saccharomyces cerevisiae*. In some embodiments, the transaldolase is NQM1 of yeast. In certain embodiments, the transaldolase is NQM1 (NP_011557) of *Saccharomyces cerevisiae*. In some embodiments, the transaldolase is tal of bacteria. In certain embodiments, the transaldolase is talB (NP_414549) of *E. coli*. In certain embodiments, the transaldolase is talA (NP_416959) of *E. coli*. In one embodiment, the one or more endogenous proteins is a transketolase that interconverts D-erythrose 4-phosphate and D-xylulose 5-phosphate to β-D-fructofuranose 6-phosphate and D-glyceraldehyde 3-phosphate and/or interconverts D-sedoheptulose 7-phosphate and D-glyceraldehyde 3-phosphate to D-ribose 5-phosphate and D-xylulose 5-phosphate. In some embodiments, the transketolase is TKL1 of yeast. In certain embodiments, the transketolase is TKL1 (NP_015399) of *Saccharomyces cerevisiae*. In some embodiments, the transketolase is TKL2 of yeast. In some embodiments, the transketolase is TKL2 (NP_009675) of *Saccharomyces cerevisiae*. In some embodiments, the transketolase is tkt of bacteria. In certain embodiments, the transketolase is tktA (YP_026188) of *E. coli*. In certain embodiments, the transketolase is tktB (NP_416960) of *E. coli*. In one embodiment, the one or more endogenous proteins is a ribose-5-phosphate ketol-isomerase that interconverts D-ribose 5-phosphate and D-ribulose 5-phosphate. In some embodiments, the ribose-5-phosphate ketol-isomerase is RKI1 of yeast. In certain embodiments, the ribose-5-phosphate ketol-isomerase is RKI1 (NP_014738) of *Saccharomyces cerevisiae*. In some embodiments, the ribose-5-phosphate isomerase is rpi of bacteria. In certain embodiments, the ribose-5-phosphate isomerase is rpiA (NP_417389) of *E. coli*. In certain embodiments, the ribose-5-phosphate isomerase is rpiB (NP_418514) of *E. coli*. In one embodiment, the one or more endogenous proteins is a D-ribulose-5-phosphate 3-epimerase that interconverts D-ribulose 5-phosphate and D-xylulose 5-phosphate. In some embodiments, the D-ribulose-5-phosphate 3-epimerase is RPE1 of yeast. In certain embodiments, the D-ribulose-5-phosphate 3-epimerase is RPE1 (NP_012414) of *Saccharomyces cerevisiae*. In some embodiments, the D-ribulose-5-phosphate 3-epimerase is rpe of bacteria. In certain embodiments, the D-ribulose-5-phosphate 3-epimerase is rpe (NP_417845) of *E. coli*.

In some embodiments, the *Y. lipolytica* microorganism into which biosynthesis pathways for the production of one or more unsaturated lipid moieties are introduced is H222 ΔP ΔA ΔF ΔURA3. ΔP denotes deletion of the acyl-CoA oxidase genes (POX 1-6) in *Y. lipolytica*. ΔA denotes deletion of the (fatty) alcohol dehydrogenase genes (FADH, ADH 1-7) in *Y. lipolytica*. ΔF denotes deletion of the (fatty) alcohol oxidase gene (FAO1) in *Y. lipolytica*. ΔURA3 denotes deletion of the URA3 gene in *Y. lipolytica*, rendering the yeast a uracil auxotroph. In some embodiments, the *Y. lipolytica* microorganism into which biosynthesis pathways for the production of one or more unsaturated lipid moieties are introduced is H222 ΔP ΔA ΔF. In some embodiments, the *Y. lipolytica* microorganism into which biosynthesis pathways for the production of one or more unsaturated lipid moieties are introduced is MATA ura3-302::SUC2 Δpox1 Δpox2 Δpox3 Δpox4 Δpox5 Δpox6 Δfadh Δadh1 Δadh2 Δadh3 Δadh4 Δadh5 Δadh6 Δadh7 Δfao1.

A wild type isolate of the yeast *Y. lipolytica*, preferably of the strain H222, can be used as the starting strain for the construction of strains according to the disclosure. The strain H222 was deposited on 29 Apr. 2013 at the DSMZ (Deutsche Sammlung fur Mikroorganismen and Zellkulturen GmbH, D-38142 Braunschweig) under the number DSM 27185 according to the Budapest Treaty on the International Recognition of the Deposit of Microorganisms for the Purposes of Patent Procedure. A selection marker is required for the use of a strain for further genetic processing. This selection marker can be introduced into the strain in a manner known per se, e.g. in the form of the uracil auxotroph. Alternatively, already known uracil auxotrophic strains can be used, preferably the strain H222-S4 (Mauersberger S, Wang H J, Gaillard in C, Barth G & Nicaud J M (2001) J Bacterial 183: 5102-5109). The respective deletion cassette (e.g. POX I-6, FADH, ADH 1-7, FAO1) is obtained by PCR or restriction and transformed into *Y. lipolytica* H222-S4, which can be produced from *Y. lipolytica* H222 (Mauers-berger et al. (2001)), according to Barth and Gaillardin (Barth G & Gaillardin C (1996) *Yarrowia lipolytica*. Springer-Verlag, Berlin, Heidelberg, N.Y.). The creation of H222 ΔP ΔA ΔF ΔURA3 is described in WO 2015/086684, which is herein incorporated by reference in its entirety. *Y. lipolytica* strain H222 ΔP ΔA ΔF is used as the starting microorganism for introduction of desaturases in the present disclosure (see, for example, Examples 3, 4 and 6).

Chemical Conversion of Product from Naturally Occurring Organisms or from Microorganism Synthesis The present disclosure describes chemical conversions that can be used to convert a product obtained from one or more naturally occurring organisms or synthesized by one or more recombinant microorganisms into one or more downstream products.

In some embodiments, one or more unsaturated lipid moieties obtained from one or more naturally occurring organisms or produced by one or more recombinant microorganisms can undergo subsequent chemical conversion to produce one or more fatty alcohols and/or one or more fatty aldehydes. The one or more fatty alcohols and/or one or more fatty aldehydes are useful as a pheromone, fragrance, flavor, polymer, or polymer intermediate. Non-limiting examples of chemical transformations include saponification, esterification, reduction, oxidation, metathesis, and polymerization.

Unsaturated fatty carboxylic acids can be esterified by methods known in the art. For example, Fischer esterification can be used to covert a fatty carboxylic acid to a corresponding fatty ester. See, e.g., Komura, K. et al., *Synthesis* 2008. 3407-3410.

An ester can undergo saponification to form a carboxylate ion and an alcohol by reaction with water and a base. Saponification methods include hot saponification, cold saponification, microwave saponification and ultrasound-assisted saponification.

Elongation of the carbon chain can be performed by known methods to covert an unsaturated fatty alcohol into an elongated derivative thereof. Olefin metastasis catalysts can be performed to increase the number of carbons on the fatty carbon chain and impart Z or E stereochemistry on the corresponding unsaturated product.

In general, any metathesis catalyst stable under the reaction conditions and nonreactive with functional groups on the fatty substrate (e.g., alcohol, ester, carboxylic acid, aldehyde, or acetate) can be used with the present disclosure. Such catalysts are, for example, those described by Grubbs (Grubbs, R. H., "Synthesis of large and small molecules using olefin metathesis catalysts." *PMSE Prepr.*, 2012), herein incorporated by reference in its entirety. Depending on the desired isomer of the olefin, as cis-selective metathesis catalyst may be used, for example one of those described by Shahane et al. (Shahane, S., et al. *ChemCatChem*, 2013. 5(12): p. 3436-3459), herein incorporated by reference in its entirety. Specific catalysts 1-5 exhibiting cis-selectivity are shown below (Scheme 1) and have been described previously (Khan, R. K., et al. *J. Am. Chem. Soc.*, 2013. 135(28): p. 10258-61; Hartung, J. et al. *J. Am. Chem. Soc.*, 2013. 135(28): p. 10183-5.; Rosebrugh, L. E., et al. *J. Am. Chem. Soc.*, 2013. 135(4): p. 1276-9.; Marx, V. M., et al. *J. Am. Chem. Soc.*, 2013. 135(1): p. 94-7.; Herbert, M. B., et al. *Angew. Chem. Int. Ed. Engl.*, 2013. 52(1): p. 310-4; Keitz, B. K., et al. *J. Am. Chem. Soc.*, 2012. 134(4): p. 2040-3.; Keitz, B. K., et al. *J. Am. Chem. Soc.*, 2012. 134(1): p. 693-9.; Endo, K. et al. *J. Am. Chem. Soc.*, 2011. 133(22): p. 8525-7).

Scheme 1

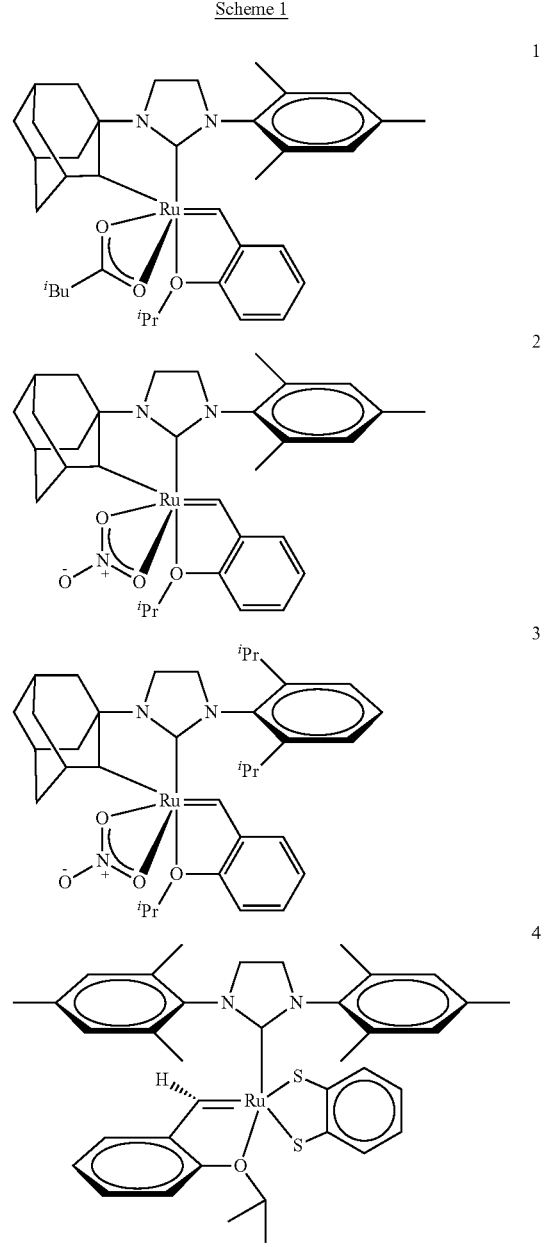

-continued

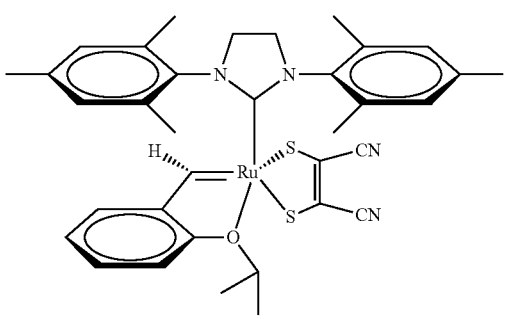

Additional Z-selective catalysts are described in (Cannon and Grubbs 2013; Bronner et al. 2014; Hartung et al. 2014; Pribisko et al. 2014; Quigley and Grubbs 2014) and are herein incorporated by reference in their entirety. Due to their excellent stability and functional group tolerance, in some embodiments metathesis catalysts include, but are not limited to, neutral ruthenium or osmium metal carbene complexes that possess metal centers that are formally in the +2 oxidation state, have an electron count of 16, are penta-coordinated, and are of the general formula LL'AA'M=CRbRc or LL'AA'M=(C=)nCRbRc (Pederson and Grubbs 2002); wherein M is ruthenium or osmium;

L and L' are each independently any neutral electron donor ligand and selected from phosphine, sulfonated phosphine, phosphite, phosphinite, phosphonite, arsine, stibnite, ether, amine, amide, imine, sulfoxide, carboxyl, nitrosyl, pyridine, thioether, or heterocyclic carbenes; and A and A' are anionic ligands independently selected from halogen, hydrogen, $C_1$-$C_{20}$ alkyl, aryl, $C_1$-$C_{20}$ alkoxide, aryloxide, $C_2$-$C_{20}$ alkoxycarbonyl, arylcarboxylate, $C_1$-$C_{20}$ carboxylate, arylsulfonyl, $C_1$-$C_{20}$ alkylsulfonyl, $C_1$-$C_{20}$ alkylsulfinyl; each ligand optionally being substituted with $C_1$-$C_5$ alkyl, halogen, $C_1$-$C_5$ alkoxy; or with a phenyl group that is optionally substituted with halogen, $C_1$-$C_5$ alkyl, or $C_1$-$C_5$ alkoxy; and A and A' together may optionally comprise a bidentate ligand; and $R_b$ and $R_c$ are independently selected from hydrogen, $C_1$-$C_{20}$ alkyl, aryl, $C_1$-$C_{20}$ carboxylate, $C_1$-$C_{20}$ alkoxy, aryloxy, $C_1$-$C_{20}$ alkoxycarbonyl, $C_1$-$C_{20}$ alkylthio, $C_1$-$C_{20}$ alkylsulfonyl and $C_1$-$C_{20}$ alkylsulfinyl, each of $R_b$ and $R_c$ optionally substituted with $C_1$-$C_5$ alkyl, halogen, $C_1$-$C_5$ alkoxy or with a phenyl group that is optionally substituted with halogen, $C_1$-$C_5$ alkyl, or $C_1$-$C_5$ alkoxy.

Other metathesis catalysts such as "well defined catalysts" can also be used. Such catalysts include, but are not limited to, Schrock's molybdenum metathesis catalyst, 2,6-diisopropylphenylimido neophylidenemolybdenum (VI) bis(hexafluoro-t-butoxide), described by Grubbs et al. (*Tetrahedron* 1998, 54: 4413-4450) and Basset's tungsten metathesis catalyst described by Couturier, J. L. et al. (*Angew. Chem. Int. Ed. Engl.* 1992, 31: 628).

Catalysts useful in the methods of the disclosure also include those described by Peryshkov, et al. *J. Am. Chem. Soc.* 2011, 133: 20754-20757; Wang, et al. *Angewandte Chemie,* 2013, 52: 1939-1943; Yu, et al. *J. Am. Chem. Soc.,* 2012, 134: 2788-2799; Halford. *Chem. Eng. News,* 2011, 89 (45): 11; Yu, et al. *Nature,* 2011, 479: 88-93; Lee. *Nature,* 2011, 471: 452-453; Meek, et al. *Nature,* 2011: 471, 461-466; Flook, et al. *J. Am. Chem. Soc.* 2011, 133: 1784-1786; Zhao, et al. *Org Lett.,* 2011, 13(4): 784-787; Ondi, et al. "High activity, stabilized formulations, efficient synthesis and industrial use of Mo- and W-based metathesis catalysts" *XiMo Technology Updates,* 2015: http://www.ximo-inc.com/files/ximo/uploads/download/Summary_3.11.15.pdf; Schrock, et al. *Macromolecules,* 2010: 43, 7515-7522; Peryshkov, et al. *Organometallics* 2013: 32, 5256-5259; Gerber, et al. *Organometallics* 2013: 32, 5573-5580; Marinescu, et al. *Organometallics* 2012: 31, 6336-6343; Wang, et al. *Angew. Chem. Int. Ed.* 2013: 52, 1939-1943; Wang, et al. *Chem. Eur. J.* 2013: 19, 2726-2740; and Townsend et al. *J. Am. Chem. Soc.* 2012: 134, 11334-11337.

Catalysts useful in the methods of the disclosure also include those described in International Pub. No. WO 2014/155185; International Pub. No. WO 2014/172534; U.S. Pat. Appl. Pub. No. 2014/0330018; International Pub. No. WO 2015/003815; and International Pub. No. WO 2015/003814.

Catalysts useful in the methods of the disclosure also include those described in U.S. Pat. Nos. 4,231,947; 4,245,131; 4,427,595; 4,681,956; 4,727,215; International Pub. No. WO 1991/009825; U.S. Pat. Nos. 5,087,710; 5,142,073; 5,146,033; International Pub. No. WO 1992/019631; U.S. Pat. Nos. 6,121,473; 6,346,652; 8,987,531; U.S. Pat. Appl. Pub. No. 2008/0119678; International Pub. No. WO 2008/066754; International Pub. No. WO 2009/094201; U.S. Pat. Appl. Pub. No. 2011/0015430; U.S. Pat. Appl. Pub. No. 2011/0065915; U.S. Pat. Appl. Pub. No. 2011/0077421; International Pub. No. WO 2011/040963; International Pub. No. WO 2011/097642; U.S. Pat. Appl. Pub. No. 2011/0237815; U.S. Pat. Appl. Pub. No. 2012/0302710; International Pub. No. WO 2012/167171; U.S. Pat. Appl. Pub. No. 2012/0323000; U.S. Pat. Appl. Pub. No. 2013/0116434; International Pub. No. WO 2013/070725; U.S. Pat. Appl. Pub. No. 2013/0274482; U.S. Pat. Appl. Pub. No. 2013/0281706; International Pub. No. WO 2014/139679; International Pub. No. WO 2014/169014; U.S. Pat. Appl. Pub. No. 2014/0330018; and U.S. Pat. Appl. Pub. No. 2014/0378637.

Catalysts useful in the methods of the disclosure also include those described in International Pub. No. WO 2007/075427; U.S. Pat. Appl. Pub. No. 2007/0282148; International Pub. No. WO 2009/126831; International Pub. No. WO 2011/069134; U.S. Pat. Appl. Pub. No. 2012/0123133; U.S. Pat. Appl. Pub. No. 2013/0261312; U.S. Pat. Appl. Pub. No. 2013/0296511; International Pub. No. WO 2014/134333; and U.S. Pat. Appl. Pub. No. 2015/0018557.

Catalysts useful in the methods of the disclosure also include those set forth in the following table:

| Structure | Name |
|---|---|
| 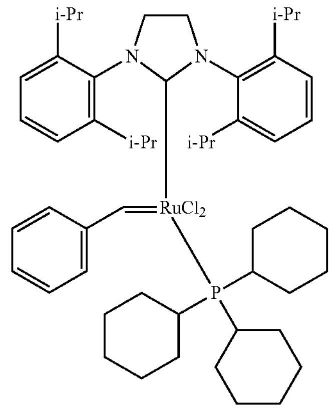 | dichloro[1,3-bis(2,6-isopropylphenyl)-2-imidazolidinylidene](benzylidene)(tricyclohexylphosphine)ruthenium(II) |
| 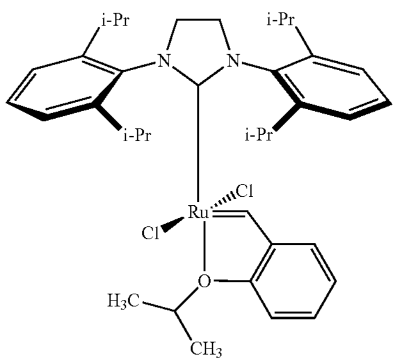 | dichloro[1,3-bis(2,6-isopropylphenyl)-2-imidazolidinylidene](2-isopropoxyphenylmethylene)ruthenium(II) |
| 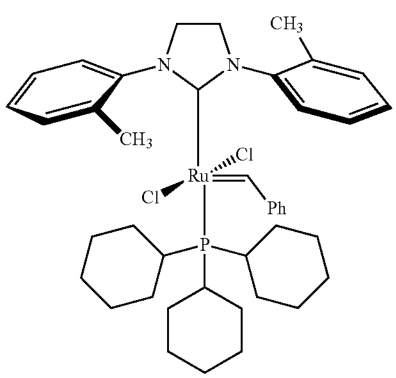 | dichloro[1,3-Bis(2-methylphenyl)-2-imidazolidinylidene](benzylidene)(tricyclohexylphosphine)ruthenium(II) |
| 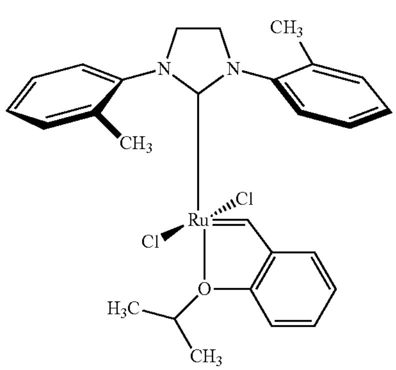 | dichloro[1,3-bis(2-methylphenyl)-2-imidazolidinylidene](2-isopropoxyphenylmethylene)ruthenium(II) |

-continued

| Structure | Name |
|---|---|
| 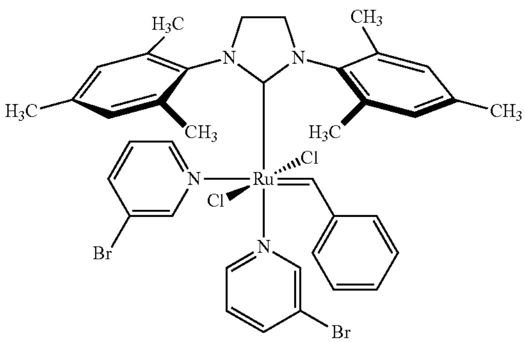 | dichloro[1,3-bis(2,4,6-trimethylphenyl)-2-imidazolidinylidene](benzylidene)bis(3-bromopyridine)ruthenium(II) |
| 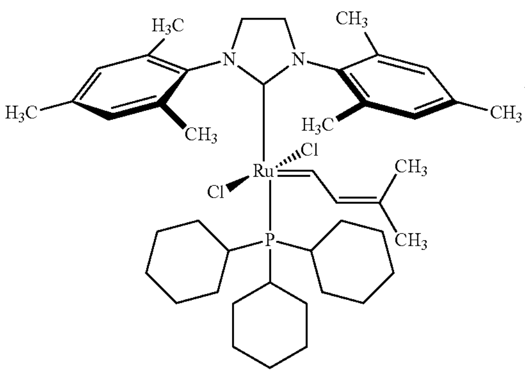 | dichloro[1,3-bis(2,4,6-trimethylphenyl)-2-imidazolidinylidene](3-methyl-2-butenylidene) (tricyclohexylphosphine) ruthenium(II) |
| 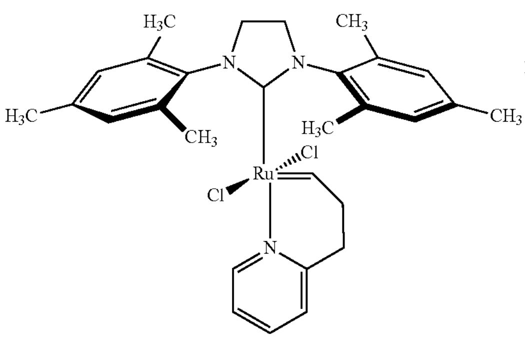 | dichloro[1,3-bis(2,4,6-trimethylphenyl)-2-imidazolidinylidene][3-(2-pyridinyl) propylidene]ruthenium(II) |
| 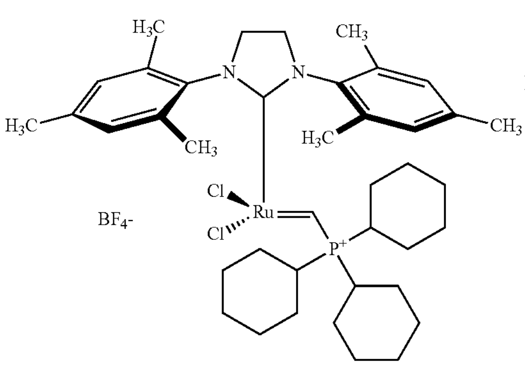 | dichloro[1,3-bis(2,4,6-trimethylphenyl)-2-imidazolidinylidene][(tricyclohexylphosphoranyl)methylidene]ruthenium(II) tetrafluoroborate |

| Structure | Name |
|---|---|
| 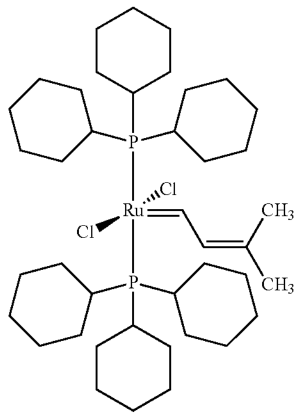 | dichloro(3-methyl-2-butenylidene)bis(tricyclohexylphosphine)ruthenium(II) |
| 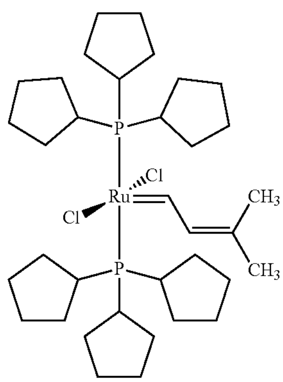 | dichloro(3-methyl-2-butenylidene)bis(tricyclopentylphosphine)ruthenium(II) |
| 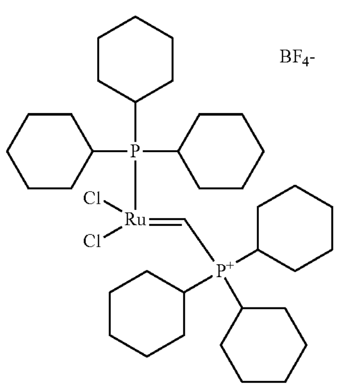 | dichloro(tricyclohexylphosphine)[(tricyclohexylphosphoranyl)methylidene]ruthenium(II) tetrefluoroborate |
| 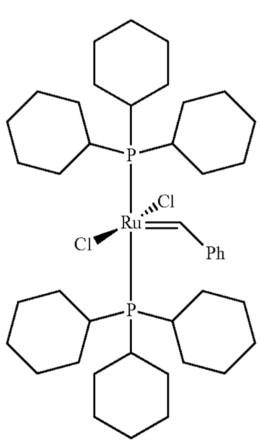 | bis(tricyclohexylphosphine) benzylidine ruthenium(IV) dichloride |

-continued

| Structure | Name |
|---|---|
| 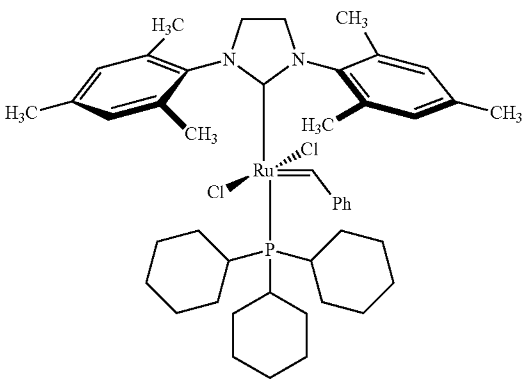 | [1,3-bis-(2,4,6-trimethylphenyl)-2-imidazolidinylidene]dichloro(phenylmethylene)(tricyclohexylphosphine)ruthenium |
| 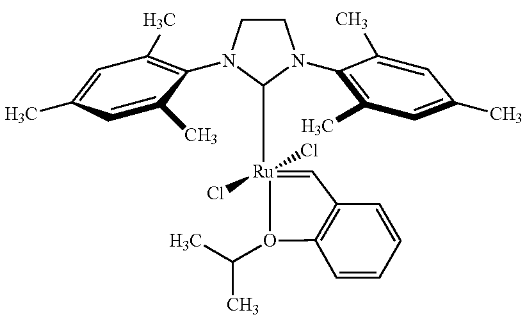 | (1,3-bis-(2,4,6-trimethylphenyl)-2-imidazolidinylidene)dichloro(o-isopropoxyphenylmethylene)ruthenium |
| 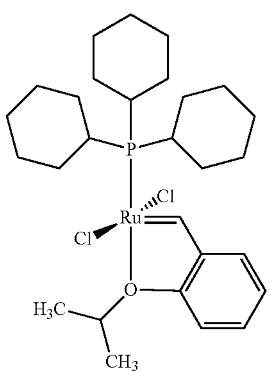 | dichloro(o-isopropoxyphenylmethylene)(tricyclohexylphosphine)ruthenium(II) |
| 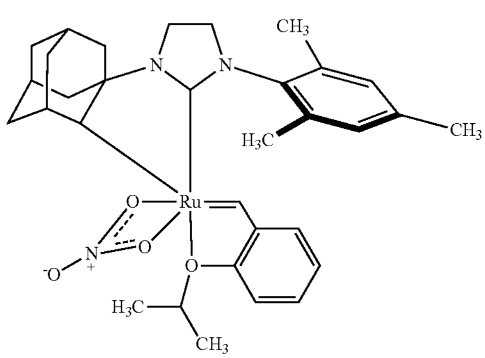 | [2-(1-methylethoxy-O)phenylmethyl-C](nitrato-O,O){rel-(2R,5R,7R)-adamantane-2,1-diyl[3-(2,4,6-trimethylphenyl)-1-imidazolidinyl-2-ylidene]}ruthenium |

Catalysts useful in the methods of the disclosure also include those described in U.S. Pat. Appl. Pub. No. 2008/0009598; U.S. Pat. Appl. Pub. No. 2008/0207911; U.S. Pat. Appl. Pub. No. 2008/0275247; U.S. Pat. Appl. Pub. No. 2011/0040099; U.S. Pat. Appl. Pub. No. 2011/0282068; and U.S. Pat. Appl. Pub. No. 2015/0038723.

Catalysts useful in the methods of the disclosure include those described in International Pub. No. WO 2007/140954; U.S. Pat. Appl. Pub. No. 2008/0221345; International Pub. No. WO 2010/037550; U.S. Pat. Appl. Pub. No. 2010/0087644; U.S. Pat. Appl. Pub. No. 2010/0113795; U.S. Pat. Appl. Pub. No. 2010/0174068; International Pub. No. WO 2011/091980; International Pub. No. WO 2012/168183; U.S. Pat. Appl. Pub. No. 2013/0079515; U.S. Pat. Appl. Pub. No. 2013/0144060; U.S. Pat. Appl. Pub. No. 2013/0211096; International Pub. No. WO 2013/135776; International Pub. No. WO 2014/001291; International Pub. No. WO 2014/067767; U.S. Pat. Appl. Pub. No. 2014/0171607; and U.S. Pat. Appl. Pub. No. 2015/0045558.

The catalyst is typically provided in the reaction mixture in a sub-stoichiometric amount (e.g., catalytic amount). In certain embodiments, that amount is in the range of about 0.001 to about 50 mol % with respect to the limiting reagent of the chemical reaction, depending upon which reagent is in stoichiometric excess. In some embodiments, the catalyst is present in less than or equal to about 40 mol % relative to the limiting reagent. In some embodiments, the catalyst is present in less than or equal to about 30 mol % relative to the limiting reagent. In some embodiments, the catalyst is present in less than about 20 mol %, less than about 10 mol %, less than about 5 mol %, less than about 2.5 mol %, less than about 1 mol %, less than about 0.5 mol %, less than about 0.1 mol %, less than about 0.015 mol %, less than about 0.01 mol %, less than about 0.0015 mol %, or less, relative to the limiting reagent. In some embodiments, the catalyst is present in the range of about 2.5 mol % to about 5 mol %, relative to the limiting reagent. In some embodiments, the reaction mixture contains about 0.5 mol % catalyst. In the case where the molecular formula of the catalyst complex includes more than one metal, the amount of the catalyst complex used in the reaction may be adjusted accordingly.

In some cases, the methods described herein can be performed in the absence of solvent (e.g., neat). In some cases, the methods can include the use of one or more solvents. Examples of solvents that may be suitable for use in the disclosure include, but are not limited to, benzene, p-cresol, toluene, xylene, diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, and the like, as well as mixtures thereof. In some embodiments, the solvent is selected from benzene, toluene, pentane, methylene chloride, and THF. In certain embodiments, the solvent is benzene.

In some embodiments, the method is performed under reduced pressure. This may be advantageous in cases where a volatile byproduct, such as ethylene, may be produced during the course of the metathesis reaction. For example, removal of the ethylene byproduct from the reaction vessel may advantageously shift the equilibrium of the metathesis reaction towards formation of the desired product. In some embodiments, the method is performed at a pressure of about less than 760 torr. In some embodiments, the method is performed at a pressure of about less than 700 torr. In some embodiments, the method is performed at a pressure of about less than 650 torr. In some embodiments, the method is performed at a pressure of about less than 600 torr. In some embodiments, the method is performed at a pressure of about less than 550 torr. In some embodiments, the method is performed at a pressure of about less than 500 torr. In some embodiments, the method is performed at a pressure of about less than 450 torr. In some embodiments, the method is performed at a pressure of about less than 400 torr. In some embodiments, the method is performed at a pressure of about less than 350 torr. In some embodiments, the method is performed at a pressure of about less than 300 torr. In some embodiments, the method is performed at a pressure of about less than 250 torr. In some embodiments, the method is performed at a pressure of about less than 200 torr. In some embodiments, the method is performed at a pressure of about less than 150 torr. In some embodiments, the method is performed at a pressure of about less than 100 torr. In some embodiments, the method is performed at a pressure of about less than 90 torr. In some embodiments, the method is performed at a pressure of about less than 80 torr. In some embodiments, the method is performed at a pressure of about less than 70 torr. In some embodiments, the method is performed at a pressure of about less than 60 torr. In some embodiments, the method is performed at a pressure of about less than 50 torr. In some embodiments, the method is performed at a pressure of about less than 40 torr. In some embodiments, the method is performed at a pressure of about less than 30 torr. In some embodiments, the method is performed at a pressure of about less than 20 torr. In some embodiments, the method is performed at a pressure of about 20 torr.

In some embodiments, the method is performed at a pressure of about 19 torr. In some embodiments, the method is performed at a pressure of about 18 torr. In some embodiments, the method is performed at a pressure of about 17 torr. In some embodiments, the method is performed at a pressure of about 16 torr. In some embodiments, the method is performed at a pressure of about 15 torr. In some embodiments, the method is performed at a pressure of about 14 torr. In some embodiments, the method is performed at a pressure of about 13 torr. In some embodiments, the method is performed at a pressure of about 12 torr. In some embodiments, the method is performed at a pressure of about 11 torr. In some embodiments, the method is performed at a pressure of about 10 torr. In some embodiments, the method is performed at a pressure of about 10 torr. In some embodiments, the method is performed at a pressure of about 9 torr. In some embodiments, the method is performed at a pressure of about 8 torr. In some embodiments, the method is performed at a pressure of about 7 torr. In some embodiments, the method is performed at a pressure of about 6 torr. In some embodiments, the method is performed at a pressure of about 5 torr. In some embodiments, the method is performed at a pressure of about 4 torr. In some embodiments, the method is performed at a pressure of about 3 torr. In some embodiments, the method is performed at a pressure of about 2 torr. In some embodiments, the method is performed at a pressure of about 1 torr. In some embodiments, the method is performed at a pressure of less than about 1 torr.

In some embodiments, the two metathesis reactants are present in equimolar amounts. In some embodiments, the two metathesis reactants are not present in equimolar amounts. In certain embodiments, the two reactants are present in a molar ratio of about 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20. In certain embodiments, the two reactants are present in a molar ratio of about 10:1. In certain embodiments, the two reactants are present in a molar ratio of about 7:1. In certain embodiments, the two reactants are present in a molar ratio of about 5:1. In certain embodiments, the two reactants are present in a molar ratio of about 2:1. In certain embodiments, the two reactants are present in a molar ratio of about 1:10. In certain embodiments, the two reactants are present in a molar ratio of about 1:7. In certain embodiments, the two reactants are present in a molar ratio of about 1:5. In certain embodiments, the two reactants are present in a molar ratio of about 1:2.

In general, the reactions with many of the metathesis catalysts disclosed herein provide yields better than 15%, better than 50%, better than 75%, or better than 90%. In addition, the reactants and products are chosen to provide at least a 5° C. difference, a greater than 20° C. difference, or a greater than 40° C. difference in boiling points. Additionally, the use of metathesis catalysts allows for much faster product formation than byproduct, it is desirable to run these reactions as quickly as practical. In particular, the reactions are performed in less than about 24 hours, less than 12 hours, less than 8 hours, or less than 4 hours.

One of skill in the art will appreciate that the time, temperature and solvent can depend on each other, and that changing one can require changing the others to prepare the pyrethroid products and intermediates in the methods of the disclosure. The metathesis steps can proceed at a variety of temperatures and times. In general, reactions in the methods of the disclosure are conducted using reaction times of several minutes to several days. For example, reaction times of from about 12 hours to about 7 days can be used. In some embodiments, reaction times of 1-5 days can be used. In some embodiments, reaction times of from about 10 minutes to about 10 hours can be used. In general, reactions in the methods of the disclosure are conducted at a temperature of from about 0° C. to about 200° C. For example, reactions can be conducted at 15-100° C. In some embodiments, reaction can be conducted at 20-80° C. In some embodiments, reactions can be conducted at 100-150° C.

Unsaturated fatty esters can be reduced using a suitable reducing agent which selectively reduces the ester to the corresponding aldehyde or alcohol but does not reduce the double bond. An unsaturated fatty ester can be reduced to the corresponding unsaturated fatty aldehyde using di-isobutyl aluminum halide (DIBAL) or Vitride®. The unsaturated fatty aldehyde can be reduced to the corresponding fatty alcohol with, e.g., DIBAL or Vitride®. In some embodiments, the unsaturated fatty ester can be reduced to the corresponding fatty alcohol using $AlH_3$ or 9-Borabicyclo (3.3.1)nonane (9-BBN). (See Galatis, P. *Encyclopedia of Reagents for Organic Synthesis*. 2001. New York: John Wiley & Sons; and Carey & Sunderburg. *Organic Chemistry, Part B: Reactions and Synthesis*, 5th edition. 2007. New York. Springer Sciences.).

In some embodiments, the partial reduction of esters to aldehydes without over-reduction to alcohols is useful for the synthesis of aldehydes. Partial reducing agents include lithium diisobutyl-t-butoxyaluminum hydride (LDBBA) (Kim M S et al. (2007) Tetrahedron Lett. 48: 5061) and sodium diisobutyl-t-butoxyaluminum hydride (SDBBA) (Song J I and An DK (2007) Chem. Lett. 36: 886). Red-Al (sodium bis[2-methoxyethoxy]aluminum hydride) derivatives of secondary amines (e.g., morpholine, N-methylpiperazine, or pyrrolidine) can be used for the partial reduction of esters or diesters. In certain embodiments, the reducing agent comprises a bulky cyclic nitrogen Lewis base to allow for the selective reduction of unsaturated fatty esters to fatty aldehydes. In some embodiments, a modified Red-Al is prepared by reacting commercially available Red-Al with cis-2,6-dimethyl morpholine (Shin W K et al. (2014) *Bull. Korean Chem. Soc.* 35: 2169).

Reduction of an ester to the corresponding alcohol can also be accomplished through hydrogenolysis using transition metal catalysts. Examples of homogeneous hydrogenolysis catalysts include, but are not limited to, the group VIII catalysts described by Goussev et al. (US 20160023200 A1), which is herein incorporated in its entirety.

A catalyst or a pre-catalyst as disclosed by Goussev et al. can be in the form of a transition metal complex of Formulae IV or V

$$M(PWNN)X_kY \qquad (IV)$$

$$M(PWNWP)X_kY \qquad (V)$$

wherein M is a transition metal;
each X represents simultaneously or independently a hydrogen or a halogen atom, a $C_1$-$C_5$ alkyl radical, a hydroxyl group, or a $C_1$-$C_7$ alkoxy radical;
Y is CO, NO, carbene, isonitrile, nitrile, phosphite, phosphinite, or a phosphine, such as $PMe_3$, $PPh_3$, $PCy_3$, $P(iPr)_3$;
k is an integer 1 or 2; and
PWNN and PWNWP are ligands represented by Formula A

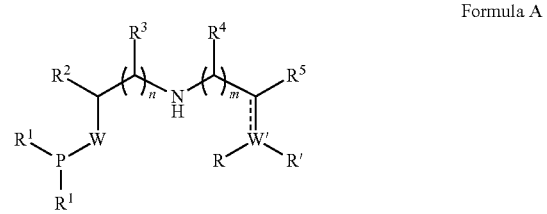

Formula A wherein
each $R^1$, $R^2$, $R^3$, and $R^4$ are each independently H, a substituted or unsubstituted linear or branched $C_1$-$C_{12}$ alkyl (such as $C_1$-$C_8$ alkyl or $C_8$-$C_{12}$ alkyl), a substituted or unsubstituted cyclic $C_3$-$C_{12}$ alkyl (such as cyclic $C_3$-$C_8$ alkyl or cyclic $C_8$-$C_{12}$ alkyl), a substituted or unsubstituted $C_3$-$C_{12}$ alkenyl (such as $C_3$-$C_8$ alkenyl or $C_8$-$C_{12}$ alkenyl), or a substituted or unsubstituted aryl or heteroaryl group, or when taken together with the atoms to which they are attached, any two of the $R^2$, $R^3$, $R^4$ groups form an optionally substituted saturated or partially saturated cycloalkyl, or an optionally substituted aryl or heteroaryl;
W is an oxygen atom or an NH group;
W' is an oxygen or a nitrogen atom;
the dashed line is either present and denotes the presence of one bond of a double bond or is absent;
R is absent, H, a substituted or unsubstituted linear or branched $C_1$-$C_{12}$ alkyl (such as $C_1$-$C_8$ alkyl or $C_8$-$C_{12}$ alkyl), a substituted or unsubstituted cyclic $C_3$-$C_{12}$ alkyl (such as cyclic $C_3$-$C_8$ alkyl or cyclic $C_8$-$C_{12}$ alkyl), a substituted or unsubstituted $C_3$-$C_{12}$ alkenyl (such as $C_3$-$C_8$ alkenyl or $C_8$-$C_{12}$ alkenyl), or a substituted or unsubstituted aryl or heteroaryl group;
R' is H, a substituted or unsubstituted linear or branched $C_1$-$C_{12}$ alkyl (such as $C_1$-$C_8$ alkyl or $C_8$-$C_{12}$ alkyl), a substituted or unsubstituted cyclic $C_3$-$C_{12}$ alkyl (such as cyclic $C_3$-$C_8$ alkyl or cyclic $C_8$-$C_{12}$ alkyl), a substituted or unsubstituted $C_3$-$C_{12}$ alkenyl (such as $C_3$-$C_8$ alkenyl or $C_8$-$C_{12}$ alkenyl), or a substituted or unsubstituted aryl or heteroaryl group, $PR_2$ or, when taken together with $R^5$ and the atoms to which they are attached forms a substituted or unsubstituted heteroaryl (non-limiting examples of which are pyridyl, furanyl, imidazolyl, pyrazolyl or oxazolyl); and n and m are each independently an integer 1 or 2 wherein in the PWNN ligand W is a nitrogen atom and in the PWNWP ligand W is an oxygen or a nitrogen atom and R' is $PR_2$, and wherein the metal complex of Formulae IV or V is either neutral or cationic.

Other embodiments of catalysts disclosed by Goussev et al. (US 20160023200 A1) are also encompassed by the present application.

Other exemplary embodiments of homogeneous hydrogenolysis catalysts for reduction of an ester to the corresponding alcohol are disclosed in Saudan et al. (U.S. Pat. No. 8,124,816), which is herein incorporated in its entirety.

A catalyst or pre-catalyst of a ruthenium complex as disclosed by Saudan et al. can be in the form of an ionic or neutral species. According to an embodiment of the invention, the ruthenium complex can be of the general formula

$$[Ru(L4)Y_2] \quad (1)$$

$$[Ru(L4)(X)_n(Y)_{2-n}](Z)_n \quad (2)$$

wherein L4 represents a tetradentate ligand wherein the coordinating groups consist of at least one amino or imino group and at least one phosphino group; and each Y represents, simultaneously or independently, CO, a hydrogen or halogen atom, a hydroxyl group, or a $C_1$-$C_6$ alkoxy or carboxylic radical, or also a $BH_4$ or $AlH_4$ group;

X represents a $C_3$-$C_{30}$ mono-phosphine or a solvent;

Z represents a non-coordinated anion; and n is 0, 1 or 2.

In particular L4 is a tetradentate ligand, such as a $C_8$-$C_{45}$ compound, wherein the coordinating groups consist of two amino or imino group and two phosphino group, and in particular the amino groups are a primary (i.e. $NH_2$) or a secondary (i.e. NH) amino groups.

In a particular embodiment of the invention, in formula (1) or (2), each Y represents, simultaneously or independently, a hydrogen or chlorine atom, a hydroxy radical, a $C_1$-$C_6$ alkoxy radical, such as a methoxy, ethoxy or isopropoxy radical, or a $C_1$-$C_6$ acyloxy radical such as a $CH_3COO$ or $CH_3CH2COO$ radical. More preferably, each Y represents, simultaneously or independently, a hydrogen or chlorine atom, a methoxy, ethoxy or isopropoxy radical, or a $CH_3COO$ or $CH_3CH_2COO$ radical.

In a particular embodiment of the invention, in formula (2), X represents a mono-phosphine of formula $PR^d_3$, wherein $R^d$ is a $C_1$-$C_{12}$ group, such as linear, branched or cyclic alkyl, alkoxy or aryloxy group optionally substituted, substituted or unsubstituted phenyl, diphenyl or naphthyl or di-naphthyl group. More particularly $R^d$ may represent a substituted or unsubstituted phenyl, diphenyl or naphthyl or di-naphthyl group.

X may also be a solvent, the term "solvent" has to be understood according to the usual meaning in the art and includes compounds used as diluent in the preparation of the complex or during the invention's process, non-limiting examples are dimethylsulfoxide, acetonitrile, dimethylformamide, an alcohol (e.g. an $C_1$-$C_4$ alcohol), or also THF, acetone, pyridine or a $C_3$-$C_8$ ester or the substrate of the invention's process.

In a particular embodiment of the invention, in formula (2), Z represents a halogen atom, a hydroxyl group, or a $C_1$-$C_6$ alkoxy, phenoxy or carboxylic radical.

The complex of formula (1) represents, in general for practical reasons, a preferred embodiment of the invention.

Embodiments of L4 tetradentate ligands are as disclosed in Saudan et al. Other embodiments of catalysts disclosed by Saudan et al. (U.S. Pat. No. 8,124,816) are encompassed by the present application.

Fatty alcohols can be oxidized to fatty aldehydes by an oxidation step. In some embodiments, the oxidation step comprises one or more partial oxidation methods. In certain embodiments, the one or more partial oxidation methods comprise NaOCl/TEMPO (2,2,6,6-tetramethylpiperidine 1-oxyl). The oxidation can be stopped at the aldehyde stage by running it for a short time. Alternatively, it can be brought to the carboxylic acid stage by adding a phase-transfer catalyst that causes a great acceleration of the oxidation. U.S. Pat. No. 6,127,573, which is herein incorporated in its entirety, describes a method to oxidize primary alcohols to carboxylic acids with a TEMPO catalyst using $CaClO_3$ and NaClO. Zhao et al., Organic Synthesis, Vol. 81, p. 195 (2005), describes the oxidation of primary alcohols to carboxylic acids with sodium chlorite catalyzed by TEMPO and bleach.

In TEMPO oxidation, a secondary oxidant transforms TEMPO, or a related stable radical, in an oxoammonium salt that operates as the primary oxidant, transforming the alcohol into the corresponding aldehyde. This results in the formation of a hydroxylamine that is oxidized to a TEMPO radical, thus completing the catalytic cycle.

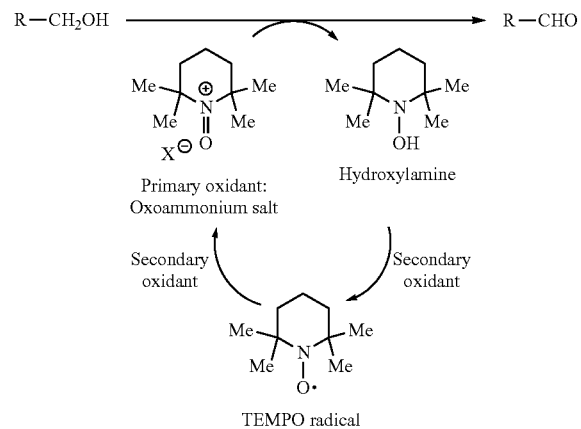

From Tojo G. and Fernandez, MI. Oxidation of Primary Alcohols to Carboxylic Acids: A Guide to Current Common Practice. 2007, XVI, 116p. ISBN: 978-0-387-35431-6, Chapter 6-TEMPO-mediated Oxidations The most common stoichiometric oxidants in TEMPO-mediated transformations of primary alcohols into aldehydes and carboxylic acids are: sodium hypochlorite (NaOCl) (Anelli's oxidation, Anelli P L. et al. (1987) *J. Org. Chem.* 52: 2559); sodium chlorite (NaClO2) (Zhao's modification of Anelli's oxidation, Zhao M et al. (1999) *J. Org. Chem.* 64: 2564); and PhI(OAc)$_2$ (oxidation of Epp and Widlanski, Epp J B and Widlanski T S (1999) *J. Org. Chem.* 64: 293). Other stoichiometric oxidants less commonly used include: MCPBA (Cella J A et al. (1975) *J. Org. Chem.* 40: 1860); Ca(ClO)$_2$ (swimming pool bleach, Ying L and Gervay-Hague J (2003) *Carbohydr. Res.* 338: 835); t-BuOCl (Li K and Helm R F (1995) *Carbohydr. Res.* 273: 249; Rye C S and Withers S G (2002) *J. Am. Chem. Soc.* 124: 9756);

CuCl—O$_2$ (Semmelhack M F et al. (1984) *J. Am. Chem. Soc.* 106: 3374); NaBrO$_2$ (Inokuchi T et al. (1990) *J. Org. Chem.* 55: 462); Cl$_2$ (Merbouh N et al. (2002) *J. Carbohydr. Res.* 21: 65); Br$_2$, (Merbouh N et al. 2002); and trichloroisocyanuric acid (De Luca L et al. (2003) *J. Org. Chem.* 68: 4999). It is possible to perform the oxidation under electrochemical conditions in the presence of catalytic TEMPO (Schnatbaum K and Schafer H J (1999) *Synthesis* 5: 864).

In some embodiments, other di-tert-alkyl nitroxyls, such as 4,4-dimethyloxazolidine-N-oxyl (DOXYL), 2,2,5,5-tetramethylpyrrolidine-N-oxyl (PROXYL) and 4-hydroxy-TEMPO and derivatives thereof and those described in WO 95/07303 can be substituted for TEMPO.

In other embodiments, the oxidation step comprises a copper-catalyzed aerobic oxidation as described by McCann and Stahl 2015 (McCann S D and Stahl S S (2015) *Acc. Chem. Res.* 48: 1756-1766), which is herein incorporated in its entirety.

Pheromone Compositions and Uses Thereof

In one aspect, one or more compositions produced by any of the methods of producing one or more fatty alcohols and/or one or more fatty aldehydes from one or more unsaturated lipid moieties disclosed herein are provided.

Exemplary insect pheromones in the form of fatty alcohols, fatty aldehydes, or fatty acetates capable of being generated using the recombinant microorganisms and methods described herein include, but are not limited to, (Z)-11-hexadecenal, (Z)-11hexadecenyl acetate, (Z)-9-tetradecenyl acetate, (Z,Z)-11,13-hexadecadienal, (9Z,11E)-hexadecadienal, (E,E)-8,10-dodecadien-1-ol, (7E,9Z)-dodecadienyl acetate, (Z)-3-nonen-1-ol, (Z)-5-decen-1-ol, (Z)-5-decenyl acetate, (E)-5-decen-1-ol, (E)-5-decenyl acetate, (Z)-7-dodecen-1-ol, (Z)-7-dodecenyl acetate, (E)-8-dodecen-1-ol, (E)-8-dodecenyl acetate, (Z)-8-dodecen-1-ol, (Z)-8-dodecenyl acetate, (Z)-9-dodecen-1-ol, (Z)-9-dodecenyl acetate, (Z)-9-tetradecen-1-ol, (Z)-11-tetraceden-1-ol, (Z)-11-tetracedenyl acetate, (E)-11-tetradecen-1-ol, (E)-11-tetradecenyl acetate, (Z)-7-hexadecen-1-ol, (Z)-7-hexadecenal, (Z)-9-hexadecen-1-ol, (Z)-9-hexadecenal, (Z)-9-hexadecenyl acetate, (Z)-11-hexadecen-1-ol, (Z)-13-octadecen-1-ol, and (Z)-13-octadecenal.

As described above, products made via the methods described herein are pheromones. Pheromones prepared according to the methods of the invention can be formulated for use as insect control compositions. The pheromone compositions can include a carrier, and/or be contained in a dispenser. The carrier can be, but is not limited to, an inert liquid or solid.

Examples of solid carriers include but are not limited to fillers such as kaolin, bentonite, dolomite, calcium carbonate, talc, powdered magnesia, Fuller's earth, wax, gypsum, diatomaceous earth, rubber, plastic, China clay, mineral earths such as silicas, silica gels, silicates, attaclay, limestone, chalk, loess, clay, dolomite, calcium sulfate, magnesium sulfate, magnesium oxide, ground synthetic materials, fertilizers such as ammonium sulfate, ammonium phosphate, ammonium nitrate, thiourea and urea, products of vegetable origin such as cereal meals, tree bark meal, wood meal and nutshell meal, cellulose powders, attapulgites, montmorillonites, mica, vermiculites, synthetic silicas and synthetic calcium silicates, or compositions of these.

Examples of liquid carriers include, but are not limited to, water; alcohols, such as ethanol, butanol or glycol, as well as their ethers or esters, such as methylglycol acetate; ketones, such as acetone, cyclohexanone, methylethyl ketone, methylisobutylketone, or isophorone; alkanes such as hexane, pentane, or heptanes; aromatic hydrocarbons, such as xylenes or alkyl naphthalenes; mineral or vegetable oils; aliphatic chlorinated hydrocarbons, such as trichloroethane or methylene chloride; aromatic chlorinated hydrocarbons, such as chlorobenzenes; water-soluble or strongly polar solvents such as dimethylformamide, dimethyl sulfoxide, or N-methylpyrrolidone; liquefied gases; waxes, such as beeswax, lanolin, shellac wax, carnauba wax, fruit wax (such as bayberry or sugar cane wax) candelilla wax, other waxes such as microcrystalline, ozocerite, ceresin, or montan; salts such as monoethanolamine salt, sodium sulfate, potassium sulfate, sodium chloride, potassium chloride, sodium acetate, ammonium hydrogen sulfate, ammonium chloride, ammonium acetate, ammonium formate, ammonium oxalate, ammonium carbonate, ammonium hydrogen carbonate, ammonium thiosulfate, ammonium hydrogen diphosphate, ammonium dihydrogen monophosphate, ammonium sodium hydrogen phosphate, ammonium thiocyanate, ammonium sulfamate or ammonium carbamate and mixtures thereof. Baits or feeding stimulants can also be added to the carrier.

Synergist

In some embodiments, the pheromone composition is combined with an active chemical agent such that a synergistic effect results. The synergistic effect obtained by the taught methods can be quantified according to Colby's formula (i.e. (E)=X+Y−(X*Y/100). See Colby, R. S., "Calculating Synergistic and Antagonistic Responses of Herbicide Combinations", 1967 Weeds, vol. 15, pp. 20-22, incorporated herein by reference in its entirety. Thus, by "synergistic" is intended a component which, by virtue of its presence, increases the desired effect by more than an additive amount. The pheromone compositions and adjuvants of the present methods can synergistically increase the effectiveness of agricultural active compounds and also agricultural auxiliary compounds.

Thus, in some embodiments, a pheromone composition can be formulated with a synergist. The term, "synergist," as used herein, refers to a substance that can be used with a pheromone for reducing the amount of the pheromone dose or enhancing the effectiveness of the pheromone for attracting at least one species of insect. The synergist may or may not be an independent attractant of an insect in the absence of a pheromone.

In some embodiments, the synergist is a volatile phytochemical that attracts at least one species of Lepidoptera. The term, "phytochemical," as used herein, means a compound occurring naturally in a plant species. In a particular embodiment, the synergist is selected from the group comprising β-caryophyllene, iso-caryophyllene, α-humulene, inalool, Z3-hexenol/yl acetate, β-farnesene, benzaldehyde, phenylacetaldehyde, and combinations thereof.

The pheromone composition can contain the pheromone and the synergist in a mixed or otherwise combined form, or it may contain the pheromone and the synergist independently in a non-mixed form.

Insecticide

The pheromone composition can include one or more insecticides. In one embodiment, the insecticides are chemical insecticides known to one skilled in the art. Examples of the chemical insecticides include one or more of pyrethoroid or organophosphorus insecticides, including but are not limited to, cyfluthrin, permethrin, cypermethrin, bifinthrin, fenvalerate, flucythrinate, azinphosmethyl, methyl parathion, buprofezin, pyriproxyfen, flonicamid, acetamiprid, dinotefuran, clothianidin, acephate, malathion, quinolphos, chloropyriphos, profenophos, bendiocarb, bifenthrin, chlorpyrifos, cyfluthrin, diazinon, pyrethrum, fenpropathrin, kinoprene, insecticidal soap or oil, neonicotinoids, diamides, avermectin and derivatives, spinosad and derivatives, azadirachtin, pyridalyl, and mixtures thereof.

In another embodiment, the insecticides are one or more biological insecticides known to one skilled in the art. Examples of the biological insecticides include, but are not limited to, azadirachtin (neem oil), toxins from natural pyrethrins, *Bacillus thuringiencis* and *Beauveria bassiana*, viruses (e.g., CYD-X™, CYD-X HP™, Germstar™, Madex HP™ and Spod-X™), peptides (Spear-T™, Spear-P™, and Spear-C™)

In another embodiment, the insecticides are insecticides that target the nerve and muscle. Examples include acetylcholinesterase (AChE) inhibitors, such as carbamates (e.g., methomyl and thiodicarb) and organophosphates (e.g., chlorpyrifos) GABA-gated chloride channel antagonists, such as cyclodiene organochlorines (e.g., endosulfan) and phenylpyrazoles (e.g., fipronil), sodium channel modulators, such as pyrethrins and pyrethroids (e.g., cypermethrin and A-cyhalothrin), nicotinic acetylcholine receptor (nAChR) agonists, such as neonicotinoids (e.g., acetamiprid, tiacloprid, thiamethoxam), nicotinic acetylcholine receptor (nAChR) allosteric modulators, such as spinosyns (e.g., spinose and spinetoram), chloride channel activators, such as avermectins and milbemycins (e.g., abamectin, emamectin benzoate), Nicotinic acetylcholine receptor (nAChR) blockers, such as bensultap and cartap, voltage dependent sodium channel blockers, such as indoxacarb and metaflumizone, ryanodine receptor modulator, such as diamides (e.g. dhlorantraniliprole and flubendiamide). In another embodiment, the insecticides are insecticides that target respiration. Examples include chemicals that uncouple oxidative phosphorylation via disruption of the proton gradient, such as chlorfenapyr, and mitochondrial complex I electron transport inhibitors.

In another embodiment, the insecticides are insecticides that target midgut. Examples include microbial disruptors of insect midgut membranes, such as *Bacillus thuringiensis* and *Bacillus sphaericus*.

In another embodiment, the insecticides are insecticides that target growth and development. Examples include juvenile hormone mimics, such as juvenile hormone analogues (e.g. fenoxycarb), inhibitors of chitin biosynthesis, Type 0, such as benzoylureas (e.g., flufenoxuron, lufenuron, and novaluron), and ecdysone receptor agonists, such as diacylhydrazines (e.g., methoxyfenozide and tebufenozide)

Stabilizer

According to another embodiment of the disclosure, the pheromone composition may include one or more additives that enhance the stability of the composition. Examples of additives include, but are not limited to, fatty acids and vegetable oils, such as for example olive oil, soybean oil, corn oil, safflower oil, canola oil, and combinations thereof.

Filler

According to another embodiment of the disclosure, the pheromone composition may include one or more fillers. Examples of fillers include, but are not limited to, one or more mineral clays (e.g., attapulgite). In some embodiments, the attractant-composition may include one or more organic thickeners. Examples of such thickeners include, but are not limited to, methyl cellulose, ethyl cellulose, and any combinations thereof.

Solvent

According to another embodiment, the pheromone compositions of the present disclosure can include one or more solvents. Compositions containing solvents are desirable when a user is to employ liquid compositions which may be applied by brushing, dipping, rolling, spraying, or otherwise applying the liquid compositions to substrates on which the user wishes to provide a pheromone coating (e.g., a lure). In some embodiments, the solvent(s) to be used is/are selected so as to solubilize, or substantially solubilize, the one or more ingredients of the pheromone composition. Examples of solvents include, but are not limited to, water, aqueous solvent (e.g., mixture of water and ethanol), ethanol, methanol, chlorinated hydrocarbons, petroleum solvents, turpentine, xylene, and any combinations thereof.

In some embodiments, the pheromone compositions of the present disclosure comprise organic solvents. Organic solvents are used mainly in the formulation of emulsifiable concentrates, ULV formulations, and to a lesser extent granular formulations. Sometimes mixtures of solvents are used. In some embodiments, the present disclosure teaches the use of solvents including aliphatic paraffinic oils such as kerosene or refined paraffins. In other embodiments, the present disclosure teaches the use of aromatic solvents such as xylene and higher molecular weight fractions of C9 and C10 aromatic solvents. In some embodiments, chlorinated hydrocarbons are useful as co-solvents to prevent crystallization when the formulation is emulsified into water. Alcohols are sometimes used as co-solvents to increase solvent power.

Solubilizing Agent

In some embodiments, the pheromone compositions of the present disclosure comprise solubilizing agents. A solubilizing agent is a surfactant, which will form micelles in water at concentrations above the critical micelle concentration. The micelles are then able to dissolve or solubilize water-insoluble materials inside the hydrophobic part of the micelle. The types of surfactants usually used for solubilization are non-ionics: sorbitan monooleates; sorbitan monooleate ethoxylates; and methyl oleate esters.

Binder

According to another embodiment of the disclosure, the pheromone composition may include one or more binders. Binders can be used to promote association of the pheromone composition with the surface of the material on which said composition is coated. In some embodiments, the binder can be used to promote association of another additive (e.g., insecticide, insect growth regulators, and the like) to the pheromone composition and/or the surface of a material. For example, a binder can include a synthetic or natural resin typically used in paints and coatings. These may be modified to cause the coated surface to be friable enough to allow insects to bite off and ingest the components of the composition (e.g., insecticide, insect growth regulators, and the like), while still maintaining the structural integrity of the coating.

Non-limiting examples of binders include polyvinylpyrrolidone, polyvinyl alcohol, partially hydrolyzed polyvinyl acetate, carboxymethylcellulose, starch, vinylpyrrolidone/vinyl acetate copolymers and polyvinyl acetate, or compositions of these; lubricants such as magnesium stearate, sodium stearate, talc or polyethylene glycol, or compositions of these; antifoams such as silicone emulsions, long-chain alcohols, phosphoric esters, acetylene diols, fatty acids or organofluorine compounds, and complexing agents such as: salts of ethylenediaminetetraacetic acid (EDTA), salts of trinitrilotriacetic acid or salts of polyphosphoric acids, or compositions of these.

In some embodiments, the binder also acts a filler and/or a thickener. Examples of such binders include, but are not limited to, one or more of shellac, acrylics, epoxies, alkyds, polyurethanes, linseed oil, tung oil, and any combinations thereof.

Surface-Active Agents

In some embodiments, the pheromone compositions comprise surface-active agents. In some embodiments, the surface-active agents are added to liquid agricultural compositions. In other embodiments, the surface-active agents are added to solid formulations, especially those designed to be diluted with a carrier before application. Thus, in some embodiments, the pheromone compositions comprise surfactants. Surfactants are sometimes used, either alone or with other additives, such as mineral or vegetable oils as adjuvants to spray-tank mixes to improve the biological performance of the pheromone on the target. The surface-active agents can be anionic, cationic, or nonionic in character, and can be employed as emulsifying agents, wetting agents, suspending agents, or for other purposes. In some embodiments, the surfactants are non-ionics such as: alky ethoxylates, linear aliphatic alcohol ethoxylates, and aliphatic amine ethoxylates. Surfactants conventionally used in the art of formulation and which may also be used in the present formulations are described, in *McCutcheon's Detergents and Emulsifiers Annual*, MC Publishing Corp., Ridgewood, N.J., 1998, and in *Encyclopedia of Surfactants*, Vol. I-III, Chemical Publishing Co., New York, 1980-81. In some embodiments, the present disclosure teaches the use of surfactants including alkali metal, alkaline earth metal or ammonium salts of aromatic sulfonic acids, for example, ligno-, phenol-, naphthalene- and dibutylnaphthalenesulfonic acid, and of fatty acids of arylsulfonates, of alkyl ethers, of lauryl ethers, of fatty alcohol sulfates and of fatty alcohol glycol ether sulfates, condensates of sulfonated naphthalene and its derivatives with formaldehyde, condensates of naphthalene or of the naphthalenesulfonic acids with phenol and formaldehyde, condensates of phenol or phenolsulfonic acid with formaldehyde, condensates of phenol with formaldehyde and sodium sulfite, polyoxyethylene octylphenyl ether, ethoxylated isooctyl-, octyl- or nonylphenol, tributylphenyl polyglycol ether, alkylaryl polyether alcohols, isotridecyl alcohol, ethoxylated castor oil, ethoxylated triarylphenols, salts of phosphated triarylphenolethoxylates, lauryl alcohol polyglycol ether acetate, sorbitol esters, lignin-sulfite waste liquors or methylcellulose, or compositions of these.

In some embodiments, the present disclosure teaches other suitable surface-active agents, including salts of alkyl sulfates, such as diethanolammonium lauryl sulfate; alkylarylsulfonate salts, such as calcium dodecylbenzenesulfonate; alkylphenol-alkylene oxide addition products, such as nonylphenol-C18 ethoxylate; alcohol-alkylene oxide addition products, such as tridecyl alcohol-C16 ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, particularly methyl esters.

Wetting Agents

In some embodiments, the pheromone compositions comprise wetting agents. A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank or other vessel to reduce the wetting time of wettable powders and to improve the penetration of water into water-dispersible granules. In some embodiments, examples of wetting agents used in the pheromone compositions of the present disclosure, including wettable powders, suspension concentrates, and water-dispersible granule formulations are: sodium lauryl sulphate; sodium dioctyl sulphosuccinate; alkyl phenol ethoxylates; and aliphatic alcohol ethoxylates.

Dispersing Agent

In some embodiments, the pheromone compositions of the present disclosure comprise dispersing agents. A dispersing agent is a substance which adsorbs onto the surface of particles and helps to preserve the state of dispersion of the particles and prevents them from reaggregating. In some embodiments, dispersing agents are added to pheromone compositions of the present disclosure to facilitate dispersion and suspension during manufacture, and to ensure the particles redisperse into water in a spray tank. In some embodiments, dispersing agents are used in wettable powders, suspension concentrates, and water-dispersible granules. Surfactants that are used as dispersing agents have the ability to adsorb strongly onto a particle surface and provide a charged or steric barrier to re-aggregation of particles. In some embodiments, the most commonly used surfactants are anionic, non-ionic, or mixtures of the two types.

In some embodiments, for wettable powder formulations, the most common dispersing agents are sodium lignosulphonates. In some embodiments, suspension concentrates provide very good adsorption and stabilization using polyelectrolytes, such as sodium naphthalene sulphonate formaldehyde condensates. In some embodiments, tristyrylphenol ethoxylated phosphate esters are also used. In some embodiments, such as alkylarylethylene oxide condensates and EO-PO block copolymers are sometimes combined with anionics as dispersing agents for suspension concentrates.

Polymeric Surfactant

In some embodiments, the pheromone compositions of the present disclosure comprise polymeric surfactants. In some embodiments, the polymeric surfactants have very long hydrophobic 'backbones' and a large number of ethylene oxide chains forming the 'teeth' of a 'comb' surfactant. In some embodiments, these high molecular weight polymers can give very good long-term stability to suspension concentrates, because the hydrophobic backbones have many anchoring points onto the particle surfaces. In some embodiments, examples of dispersing agents used in pheromone compositions of the present disclosure are: sodium lignosulphonates; sodium naphthalene sulphonate formaldehyde condensates; tristyrylphenol ethoxylate phosphate esters; aliphatic alcohol ethoxylates; alky ethoxylates; EO-PO block copolymers; and graft copolymers.

Emulsifying Agent

In some embodiments, the pheromone compositions of the present disclosure comprise emulsifying agents. An emulsifying agent is a substance, which stabilizes a suspension of droplets of one liquid phase in another liquid phase. Without the emulsifying agent the two liquids would separate into two immiscible liquid phases. In some embodiments, the most commonly used emulsifier blends include alkylphenol or aliphatic alcohol with 12 or more ethylene oxide units and the oil-soluble calcium salt of dodecylbenzene sulphonic acid. A range of hydrophile-lipophile balance ("HLB") values from 8 to 18 will normally provide good stable emulsions. In some embodiments, emulsion stability can sometimes be improved by the addition of a small amount of an EO-PO block copolymer surfactant.

Gelling Agent

In some embodiments, the pheromone compositions comprise gelling agents. Thickeners or gelling agents are used mainly in the formulation of suspension concentrates, emulsions, and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. In some embodiments, the pheromone compositions comprise one or more thickeners including, but not limited to: montmorillonite, e.g. bentonite; magnesium aluminum silicate; and attapulgite. In some embodiments, the present disclosure teaches the use of polysaccharides as thickening agents. The types of polysaccharides most commonly used are natural extracts of seeds and seaweeds or synthetic derivatives of cellulose. Some embodiments utilize xanthan and some embodiments utilize cellulose. In some embodiments, the present disclosure teaches the use of thickening agents including, but are not limited to: guar gum; locust bean gum; carrageenam; alginates; methyl cellulose; sodium carboxymethyl cellulose (SCMC); hydroxyethyl cellulose (HEC). In some embodiments, the present disclosure teaches the use of other types of anti-settling agents such as modified starches, polyacrylates, polyvinyl alcohol, and polyethylene oxide. Another good anti-settling agent is xanthan gum.

Anti-Foam Agent

In some embodiments, the presence of surfactants, which lower interfacial tension, can cause water-based formulations to foam during mixing operations in production and in application through a spray tank. Thus, in some embodiments, in order to reduce the tendency to foam, anti-foam agents are often added either during the production stage or before filling into bottles/spray tanks. Generally, there are two types of anti-foam agents, namely silicones and non-silicones. Silicones are usually aqueous emulsions of dimethyl polysiloxane, while the nonsilicone anti-foam agents are water-insoluble oils, such as octanol and nonanol, or silica. In both cases, the function of the anti-foam agent is to displace the surfactant from the air-water interface.

Preservative

In some embodiments, the pheromone compositions comprise a preservative.

Additional Active Agent

According to another embodiment of the disclosure, the pheromone composition may include one or more insect feeding stimulants. Examples of insect feeding stimulants include, but are not limited to, crude cottonseed oil, fatty acid esters of phytol, fatty acid esters of geranyl geraniol, fatty acid esters of other plant alcohols, plant extracts, and combinations thereof.

According to another embodiment of the disclosure, the pheromone composition may include one or more insect growth regulators ("IGRs"). IGRs may be used to alter the growth of the insect and produce deformed insects. Examples of insect growth regulators include, for example, dimilin.

According to another embodiment of the disclosure, the attractant-composition may include one or more insect sterilants that sterilize the trapped insects or otherwise block their reproductive capacity, thereby reducing the population in the following generation. In some situations allowing the sterilized insects to survive and compete with non-trapped insects for mates is more effective than killing them outright.

Sprayable Compositions

In some embodiments, the pheromone compositions disclosed herein can be formulated as a sprayable composition (i.e., a sprayable pheromone composition). An aqueous solvent can be used in the sprayable composition, e.g., water or a mixture of water and an alcohol, glycol, ketone, or other water-miscible solvent. In some embodiments, the water content of such mixture is at least about 10%, at least about 20%, at least about 30%, at least about 40%, 50%, at least about 60%, at least about 70%, at least about 80%, or at least about 90%. In some embodiments, the sprayable composition is concentrate, i.e. a concentrated suspension of the pheromone, and other additives (e.g., a waxy substance, a stabilizer, and the like) in the aqueous solvent, and can be diluted to the final use concentration by addition of solvent (e.g., water).

In some embodiments, a waxy substance can be used as a carrier for the pheromone and its positional isomer in the sprayable composition. The waxy substance can be, e.g., a biodegradable wax, such as bees wax, carnauba wax and the like, candelilla wax (hydrocarbon wax), montan wax, shellac and similar waxes, saturated or unsaturated fatty acids, such as lauric, palmitic, oleic or stearic acid, fatty acid amides and esters, hydroxylic fatty acid esters, such as hydroxyethyl or hydroxypropyl fatty acid esters, fatty alcohols, and low molecular weight polyesters such as polyalkylene succinates.

In some embodiments, a stabilizer can be used with the sprayable pheromone compositions. The stabilizer can be used to regulate the particle size of concentrate and/or to allow the preparation of a stable suspension of the pheromone composition. In some embodiments, the stabilizer is selected from hydroxylic and/or ethoxylated polymers. Examples include ethylene oxide and propylene oxide copolymer, polyalcohols, including starch, maltodextrin and other soluble carbohydrates or their ethers or esters, cellulose ethers, gelatin, polyacrylic acid and salts and partial esters thereof and the like. In other embodiments, the stabilizer can include polyvinyl alcohols and copolymers thereof, such as partly hydrolyzed polyvinyl acetate. The stabilizer may be used at a level sufficient to regulate particle size and/or to prepare a stable suspension, e.g., between 0.1% and 15% of the aqueous solution.

In some embodiments, a binder can be used with the sprayable pheromone compositions. In some embodiments, the binder can act to further stabilize the dispersion and/or improve the adhesion of the sprayed dispersion to the target locus (e.g., trap, lure, plant, and the like). The binder can be polysaccharide, such as an alginate, cellulose derivative (acetate, alkyl, carboxymethyl, hydroxyalkyl), starch or starch derivative, dextrin, gum (arabic, guar, locust bean, tragacanth, carrageenan, and the like), sucrose, and the like. The binder can also be a non-carbohydrate, water-soluble polymer such as polyvinyl pyrrolidone, or an acidic polymer such as polyacrylic acid or polymethacrylic acid, in acid and/or salt form, or mixtures of such polymers.

Microencapsulated Pheromones

In some embodiments, the pheromone compositions disclosed herein can be formulated as a microencapsulated pheromone, such as disclosed in Ill'Ichev, A L et al., *J. Econ. Entomol.* 2006; 99(6):2048-54; and Stelinki, L L et al., *J. Econ. Entomol.* 2007; 100(4):1360-9. Microencapsulated pheromones (MECs) are small droplets of pheromone enclosed within polymer capsules. The capsules control the release rate of the pheromone into the surrounding environment, and are small enough to be applied in the same method as used to spray insecticides. The effective field longevity of the microencapsulated pheromone formulations can range from a few days to slightly more than a week, depending on inter alia climatic conditions, capsule size and chemical properties.

Slow-Release Formulation

Pheromone compositions can be formulated so as to provide slow release into the atmosphere, and/or so as to be protected from degradation following release. For example, the pheromone compositions can be included in carriers such as microcapsules, biodegradable flakes and paraffin wax-based matrices. Alternatively, the pheromone composition can be formulated as a slow release sprayable.

In certain embodiments, the pheromone composition may include one or more polymeric agents known to one skilled in the art. The polymeric agents may control the rate of release of the composition to the environment. In some embodiments, the polymeric attractant-composition is impervious to environmental conditions. The polymeric agent may also be a sustained-release agent that enables the composition to be released to the environment in a sustained manner.

Examples of polymeric agents include, but are not limited to, celluloses, proteins such as casein, fluorocarbon-based polymers, hydrogenated rosins, lignins, melamine, polyurethanes, vinyl polymers such as polyvinyl acetate (PVAC), polycarbonates, polyvinylidene dinitrile, polyamides, polyvinyl alcohol (PVA), polyamide-aldehyde, polyvinyl aldehyde, polyesters, polyvinyl chloride (PVC), polyethylenes, polystyrenes, polyvinylidene, silicones, and combinations thereof. Examples of celluloses include, but are not limited to, methylcellulose, ethyl cellulose, cellulose acetate, cellulose acetate-butyrate, cellulose acetate-propionate, cellulose propionate, and combinations thereof.

Other agents which can be used in slow-release or sustained-release formulations include fatty acid esters (such as a sebacate, laurate, palmitate, stearate or arachidate ester) or fatty alcohols (such as undecanol, dodecanol, tridecanol, tridecenol, tetradecanol, tetradecenol, tetradecadienol, pentadecanol, pentadecenol, hexadecanol, hexadecenol, hexadecadienol, octadecenol and octadecadienol).

Pheromones prepared according to the methods of the invention, as well as compositions containing the pheromones, can be used to control the behavior and/or growth of insects in various environments. The pheromones can be used, for example, to attract or repel male or female insects to or from a particular target area. The pheromones can be used to attract insects away from vulnerable crop areas. The pheromones can also be used example to attract insects as part of a strategy for insect monitoring, mass trapping, lure/attract-and-kill or mating disruption.

Lures

The pheromone compositions of the present disclosure may be coated on or sprayed on a lure, or the lure may be otherwise impregnated with a pheromone composition.

Traps

The pheromone compositions of the disclosure may be used in traps, such as those commonly used to attract any insect species, e.g., insects of the order Lepidoptera. Such traps are well known to one skilled in the art, and are commonly used in many states and countries in insect eradication programs. In one embodiment, the trap includes one or more septa, containers, or storage receptacles for holding the pheromone composition. Thus, in some embodiments, the present disclosure provides a trap loaded with at least one pheromone composition. Thus, the pheromone compositions of the present disclosure can be used in traps for example to attract insects as part of a strategy for insect monitoring, mass trapping, mating disruption, or lure/attract and kill for example by incorporating a toxic substance into the trap to kill insects caught.

Mass trapping involves placing a high density of traps in a crop to be protected so that a high proportion of the insects are removed before the crop is damaged. Lure/attract-and-kill techniques are similar except once the insect is attracted to a lure, it is subjected to a killing agent. Where the killing agent is an insecticide, a dispenser can also contain a bait or feeding stimulant that will entice the insects to ingest an effective amount of an insecticide. The insecticide may be an insecticide known to one skilled in the art. The insecticide may be mixed with the attractant-composition or may be separately present in a trap. Mixtures may perform the dual function of attracting and killing the insect.

Such traps may take any suitable form, and killing traps need not necessarily incorporate toxic substances, the insects being optionally killed by other means, such as drowning or electrocution. Alternatively, the traps can contaminate the insect with a fungus or virus that kills the insect later. Even where the insects are not killed, the trap can serve to remove the male insects from the locale of the female insects, to prevent breeding.

It will be appreciated by a person skilled in the art that a variety of different traps are possible. Suitable examples of such traps include water traps, sticky traps, and one-way traps. Sticky traps come in many varieties. One example of a sticky trap is of cardboard construction, triangular or wedge-shaped in cross-section, where the interior surfaces are coated with a non-drying sticky substance. The insects contact the sticky surface and are caught. Water traps include pans of water and detergent that are used to trap insects. The detergent destroys the surface tension of the water, causing insects that are attracted to the pan, to drown in the water. One-way traps allow an insect to enter the trap but prevent it from exiting. The traps of the disclosure can be colored brightly, to provide additional attraction for the insects.

In some embodiments, the pheromone traps containing the composition may be combined with other kinds of trapping mechanisms. For example, in addition to the pheromone composition, the trap may include one or more florescent lights, one or more sticky substrates and/or one or more colored surfaces for attracting moths. In other embodiments, the pheromone trap containing the composition may not have other kinds of trapping mechanisms.

The trap may be set at any time of the year in a field. Those of skill in the art can readily determine an appropriate amount of the compositions to use in a particular trap, and can also determine an appropriate density of traps/acre of crop field to be protected.

The trap can be positioned in an area infested (or potentially infested) with insects. Generally, the trap is placed on or close to a tree or plant. The aroma of the pheromone attracts the insects to the trap. The insects can then be caught, immobilized and/or killed within the trap, for example, by the killing agent present in the trap.

Traps may also be placed within an orchard to overwhelm the pheromones emitted by the females, so that the males simply cannot locate the females. In this respect, a trap need be nothing more than a simple apparatus, for example, a protected wickable to dispense pheromone.

The traps of the present disclosure may be provided in made-up form, where the compound of the disclosure has already been applied. In such an instance, depending on the half-life of the compound, the compound may be exposed, or may be sealed in conventional manner, such as is standard with other aromatic dispensers, the seal only being removed once the trap is in place.

Alternatively, the traps may be sold separately, and the compound of the disclosure provided in dispensable format so that an amount may be applied to trap, once the trap is in place. Thus, the present disclosure may provide the compound in a sachet or other dispenser.

Dispenser

Pheromone compositions can be used in conjunction with a dispenser for release of the composition in a particular environment. Any suitable dispenser known in the art can be used. Examples of such dispensers include but are not limited to, aerosol emitters, hand-applied dispensers, bubble caps comprising a reservoir with a permeable barrier through which pheromones are slowly released, pads, beads, tubes rods, spirals or balls composed of rubber, plastic, leather, cotton, cotton wool, wood or wood products that are impregnated with the pheromone composition. For example, polyvinyl chloride laminates, pellets, granules, ropes or spirals from which the pheromone composition evaporates, or rubber septa. One of skill in the art will be able to select suitable carriers and/or dispensers for the desired mode of application, storage, transport or handling.

In another embodiment, a device may be used that contaminates the male insects with a powder containing the pheromone substance itself. The contaminated males then fly off and provide a source of mating disruption by permeating the atmosphere with the pheromone substance, or by attracting other males to the contaminated males, rather than to real females.

Behavior Modification

Pheromone compositions prepared according to the methods disclosed herein can be used to control or modulate the behavior of insects. In some embodiments, the behavior of the target insect can be modulated in a tunable manner inter alia by varying the ratio of the pheromone to the positional isomer in the composition such that the insect is attracted to a particular locus but does not contact said locus or such the insect in fact contacts said locus. Thus, in some embodiments, the pheromones can be used to attract insects away from vulnerable crop areas. Accordingly, the disclosure also provides a method for attracting insects to a locus. The method includes administering to a locus an effective amount of the pheromone composition.

The method of mating disruption may include periodically monitoring the total number or quantity of the trapped insects. The monitoring may be performed by counting the number of insects trapped for a predetermined period of time such as, for example, daily, Weekly, bi-Weekly, monthly, once-in-three months, or any other time periods selected by the monitor. Such monitoring of the trapped insects may help estimate the population of insects for that particular period, and thereby help determine a particular type and/or dosage of pest control in an integrated pest management system. For example, a discovery of a high insect population can necessitate the use of methods for removal of the insect. Early warning of an infestation in a new habitat can allow action to be taken before the population becomes unmanageable. Conversely, a discovery of a low insect population can lead to a decision that it is sufficient to continue monitoring the population. Insect populations can be monitored regularly so that the insects are only controlled when they reach a certain threshold. This provides cost-effective control of the insects and reduces the environmental impact of the use of insecticides.

Mating Disruption

Pheromones prepared according to the methods of the disclosure can also be used to disrupt mating. Mating disruption is a pest management technique designed to control insect pests by introducing artificial stimuli (e.g., a pheromone composition as disclosed herein) that confuses the insects and disrupts mating localization and/or courtship, thereby preventing mating and blocking the reproductive cycle.

In many insect species of interest to agriculture, such as those in the order Lepidoptera, females emit an airborne trail of a specific chemical blend constituting that species' sex pheromone. This aerial trail is referred to as a pheromone plume. Males of that species use the information contained in the pheromone plume to locate the emitting female (known as a "calling" female). Mating disruption exploits the male insects' natural response to follow the plume by introducing a synthetic pheromone into the insects' habitat, which is designed to mimic the sex pheromone produced by the female insect. Thus, in some embodiments, the synthetic pheromone utilized in mating disruption is a synthetically derived pheromone composition comprising a pheromone having a chemical structure of a sex pheromone and a positional isomer thereof which is not produced by the target insect.

The general effect of mating disruption is to confuse the male insects by masking the natural pheromone plumes, causing the males to follow "false pheromone trails" at the expense of finding mates, and affecting the males' ability to respond to "calling" females. Consequently, the male population experiences a reduced probability of successfully locating and mating with females, which leads to the eventual cessation of breeding and collapse of the insect infestation Strategies of mating disruption include confusion, trail-masking and false-trail following. Constant exposure of insects to a high concentration of a pheromone can prevent male insects from responding to normal levels of the pheromone released by female insects. Trail-masking uses a pheromone to destroy the trail of pheromones released by females. False-trail following is carried out by laying numerous spots of a pheromone in high concentration to present the male with many false trails to follow. When released in sufficiently high quantities, the male insects are unable to find the natural source of the sex pheromones (the female insects) so that mating cannot occur.

In some embodiments, a wick or trap may be adapted to emit a pheromone for a period at least equivalent to the breeding season(s) of the midge, thus causing mating disruption. If the midge has an extended breeding season, or repeated breeding season, the present disclosure provides a wick or trap capable of emitting pheromone for a period of time, especially about two weeks, and generally between about 1 and 4 weeks and up to 6 weeks, which may be rotated or replaced by subsequent similar traps. A plurality of traps containing the pheromone composition may be placed in a locus, e.g., adjacent to a crop field. The locations of the traps, and the height of the traps from ground may be selected in accordance with methods known to one skilled in the art.

Alternatively, the pheromone composition may be dispensed from formulations such as microcapsules or twist-ties, such as are commonly used for disruption of the mating of insect pests.

Attract and Kill

The attract and kill method utilizes an attractant, such as a sex pheromone, to lure insects of the target species to an insecticidal chemical, surface, device, etc., for mass-killing and ultimate population suppression, and can have the same effect as mass-trapping. For instance, when a synthetic female sex pheromone is used to lure male pests, e.g., moths, in an attract-and-kill strategy, a large number of male moths must be killed over extended periods of time to reduce matings and reproduction, and ultimately suppress the pest population. The attract-and-kill approach may be a favorable alternative to mass-trapping because no trap-servicing or other frequent maintenance is required. In various embodiments described herein, a recombinant microorganism can co-express (i) a pathway for production of an insect pheromone and (ii) a protein, peptide, oligonucleotide, or small molecule which is toxic to the insect. In this way, the recombinant microorganism can co-produce substances suitable for use in an attract-and-kill approach.

As will be apparent to one of skill in the art, the amount of a pheromone or pheromone composition used for a particular application can vary depending on several factors such as the type and level of infestation; the type of composition used; the concentration of the active components; how the composition is provided, for example, the type of dispenser used; the type of location to be treated; the length of time the method is to be used for; and environmental factors such as temperature, wind speed and direction, rainfall and humidity. Those of skill in the art will be able to determine an effective amount of a pheromone or pheromone composition for use in a given application.

As used herein, an "effective amount" means that amount of the disclosed pheromone composition that is sufficient to affect desired results. An effective amount can be administered in one or more administrations. For example, an effective amount of the composition may refer to an amount of the pheromone composition that is sufficient to attract a given insect to a given locus. Further, an effective amount of the composition may refer to an amount of the pheromone composition that is sufficient to disrupt mating of a particular insect population of interest in a given locality.

EXAMPLES

Example 1. Sourcing Fatty Acid Precursors from Natural Sources

Figure 3:
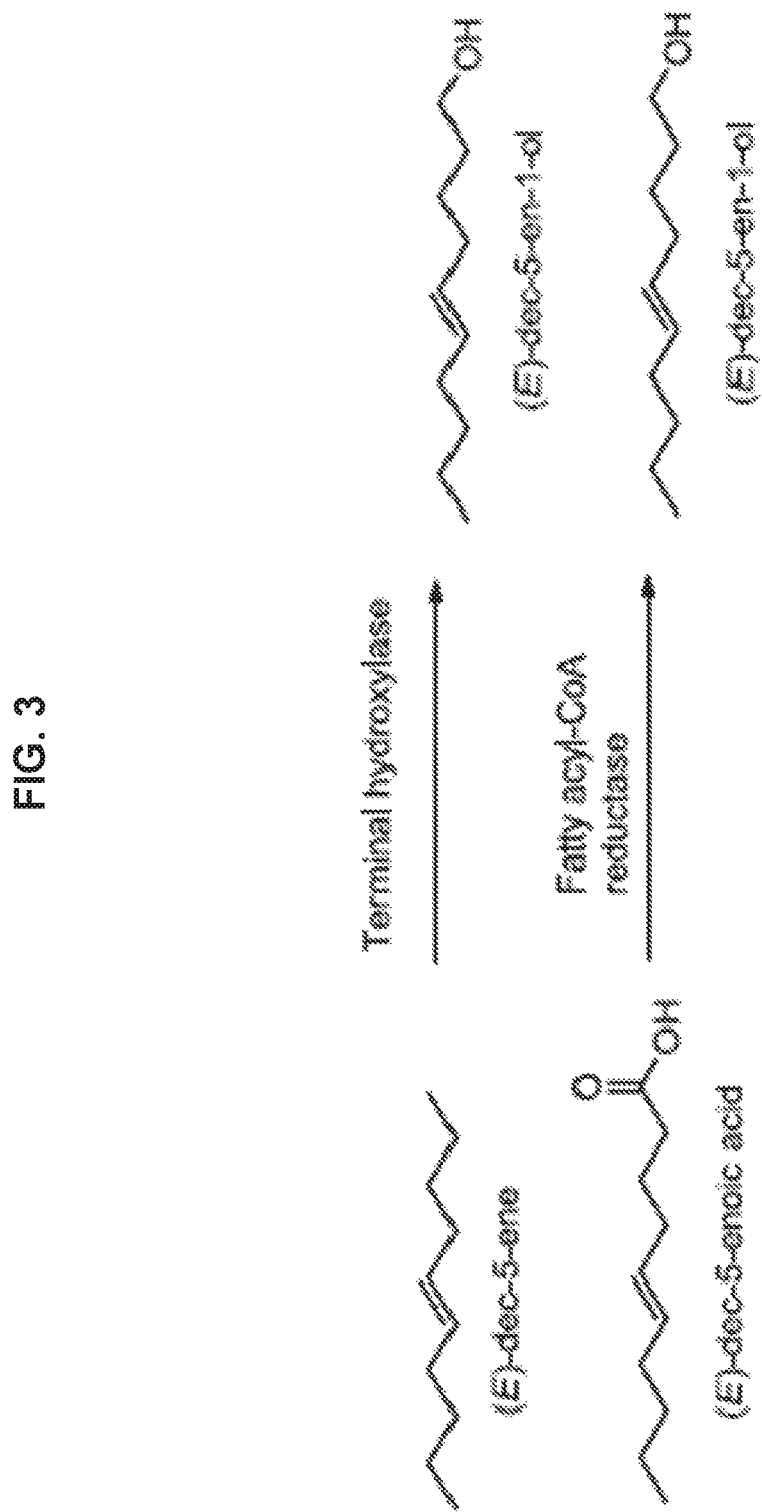
FIG. 3 illustrates proposed biohydroxylation and fatty acyl-CoA reduction routes to (E)-5-decene.

The reduction of fatty acids, by cells expressing a fatty acyl-CoA reductase (FAR) is an alternative synthesis route to the proposed biohydroxylation based synthesis of insect pheromone, see FIG. 3. The reduction of the fatty acid to the alcohol is expected to be much easier than terminal hydroxylation because: (i) far more FAR sequences are known and it is the native reaction of these enzymes; and (ii) hydrogenation of the acid to the alcohol with heterogenous catalysts is well established. The ability to source the target fatty acids with the appropriate unsaturations is the major challenge of this approach.

To understand the potential to source the fatty acid precursors of target insect pheromone from natural sources, the Seed Oil Fatty Acid database (sofa.mri.bund.de), the reported fatty acid profiles of microalgal strains from the culture collection of Gottingen University (SAG) (Lang I K et al. (2011) Fatty acid profiles and their distribution patterns in microalgae: a comprehensive analysis of more than 2000 strains from the SAG culture collection. BMC Plant Biol. 11: 124) and the general literature were investigated.

Fourteen fatty acids that could serve as precursors for insect pheromones were searched (see Table 4). Of these 14 fatty acids, only three, Z-11-octadecenoic, Z-13-octadecenoic and Z-11-hexadecenoic were reported to have been found in seed oils. The plants that produced the highest purity for each of these fatty acids are: *Asclepias Syriaca*: Z-11-octadecenoic (44.9%) (Kuemmel D F and Chapman L R (1968) 9-hexadecenoic and 11-octadecenoic acid content of natural fats and oils. Lipids 3: 313-316); *Cardwellia sublimis*: Z-13 octadecenoic (22%) (Vickery J R (1971) The fatty acid composition of the seed oils of proteaceae: A chemotaxonomic study. Phytochemistry 10: 123-130). Plants containing Z-11-hexadecenoic are *Kermadecia sinuata* (40.3%) (Vickery 1971); *Gevuina avellana* (25.4%) (B. San, A. N. Yildirim, J. Food Compos. Anal. 2010, 23, 706-710); *Ziziphus jujube* var. *inermis* (33.3%) (B. San, A. N. Yildirim, J. Food Compos. Anal. 2010, 23, 706-710); *Orites revoluta* (35.6%) (G. Hill, R S and Jordan, Pap. Proc. R. Soc. Tasmania 1996, 130, 9-15); *Grevillea exul* var. *rubiginosa* (45.6%) (I. Bombarda, C. Zongo, C. R. McGill, P. Doumenq, B. Fogliani, B. J. Am. Oil Chem. Soc. 2010, 87, 981-986, and M. Kato, A. Kawakita, Am. J. Bot. 2004, 91, 1814-1827). Similarly, for microalgae, only two of the 14 fatty acids were identified in the database: Z-11-octadecenoic made by *Pediastrum simplex* (68%) and Z-11-hexadecenoic made by *Synechococcus elongatus* (35%). In the search of general literature, 2E,4Z,7Z-decatrienoic has been identified from the juice of Noni fruit (Basar S and Westendor J (2011) Identification of (2E,4Z,7Z)-decatrienoic acid in Noni fruit and its use in quality screening of commercial Noni products. Food Anal. Meth. 4: 57-65) and isolated from *Streptomyces viridochromogenes* Tu 6105 (7.7 mg/L) (Maier A et al. (1999) (2E,4Z)-decadienoic acid and (2E,4Z,7Z)-decatrienoic acid, two herbicidal metabolites from *Streptomyces viridochromogenes* Tu 6105. Pestic. Sci. 55: 733-739).

TABLE 4

SOFA and SAG search results for target fatty acids.

| Fatty acid | Δ notation | SOFA | SAG |
|---|---|---|---|
| E-5-decenoic | 10:1Δ5t | — | — |
| Z-5-decenoic | 10:1Δ5c | — | — |
| Z-11-octadecenoic | 18:1Δ11c | 1508 entries *Asclepias Syriaca* (44.9%) *Hippophae goniocarpa* sp. (9.9%) *Ephedra virdis* (9.7%) | *Pediastrum simplex* (68%) *Parachlorella kessleri* (59%) *Oocystis heteromucosa* (52%) |
| Z-13-octadecenoic | 18:1Δ13c | 34 entries *Cardwellia sublimis* (22%) *Placospermum coriaceum* (20.4%) *Xylomelum pyriforme* (14.7%) | — |
| E-11-hexadecenoic | 16:1Δ11t | — | — |

TABLE 4-continued

SOFA and SAG search results for target fatty acids.

| Fatty acid | Δ notation | SOFA | SAG |
|---|---|---|---|
| Z-11-hexadecenoic | 16:1Δ11c | 76 entries Kermadecia sinuata (40.3%) Orites diversifolia (35.6%) Hicksbeachia pinnatifolia (28.5%) | Synechococous elongates (35%) Chlorococcum isabeliense (18%) Heterococcus crassulus (17%) |
| Z-8-dodecanoic | 10:1Δ8c | — | — |
| (Z,Z)-11,13-hexadecadienoic | 16:2Δ11c, 13c | — | — |
| 2E,4Z,7Z-decatrienoic | 10:3Δ2t, 4c, 7c | — | — |
| E8,E10-dodecanoic | 10:2Δ8t, 10t | — | — |
| (E,Z)-3,13-Octadecadienoic | 18:2Δ3t, 13c | — | — |
| (E,Z)-2,13-Octadecadienoic | 18:2Δ2t, 13c | — | — |
| E/Z-11-tetradecenoic | 14:1Δ11c/t | — | — |

To determine the fatty acids that can be sourced from seed oils produced as commodities, the literature was searched to identify the commodity seed oils and their compositions. FIG. 4 lists the major seed oils produced from 1976 to 2000 and projections for 2006 to 2020. The major seed oils are soybean, cottonseed, groundnut (peanut), sunflower, Canola, sesame, corn, olive, palm, palm kernel, coconut, linseed, castor and tallow. The fatty acid compositions of these oils are listed in Table 5. The major components of commodity seed oils are: lauric (12:0): coconut (47.8%) and palm kernel (48.4%); palmitic (16:0): palm (44%) and cotton (24.7%); oleic (18:1Δ9c): Canola (64.1%), peanut (46.5%), palm (39.2%), olive (76.9%) and sesame (40.6%); linoleic (18:2Δ9c, Δ12c): soybean (53.2%), cotton (53.3%), sunflower (68.2%), peanut (31.4%), and sesame (42.6%); and linolenic (18:3 Δ9c, Δ12c, Δ15c): linseed (47.4%). In addition to the base crops, modified crops have been engineered to increase the contents of a particular fatty acid. Examples of modified soybean and Canola crops are listed in Table 6. Of these crops, the production of highly pure oleic acid, >75%, could be the most promising feedstock if a pheromone from oleic acid could be identified.

In addition to the fatty acids found in the major commodity seed oils, minor crops with interesting fatty acid compositions are listed in Table 7. These minor crops produce unique monoenes: 20:Δ5c, 22:Δ9c, 18:1Δ6c, 16:1Δ9c; trienes: 18:3Δ8t, Δ10t, Δ12c, 18:3Δ9c, Δ11t, Δ13t; and oxygenated trienes: 18:3Δ9,Δ11,Δ13, 4-oxo, 18:1Δ9c, Δ12-hydroxy.

TABLE 5

Fatty acids compositions of major commodity seed oils[†]

| Fatty acid | Δ notation | Soybean | Canola | Cottonseed | Sunflower | Peanut | Palm | Coconut | Palmkernel oil | Olive | Sesame | Linseed |
|---|---|---|---|---|---|---|---|---|---|---|---|---|
| Hexanoic | 6:0 | — | — | — | — | — | — | 0.4 | 0.3 | — | — | — |
| Octanoic (Caprylic) | 8:0 | — | — | — | — | — | — | 7.3 | 4.4 | — | — | — |
| Decanoid acid (Capric) | 10:0 | — | — | — | — | — | — | 6.6 | 3.7 | — | — | — |
| Lauric | 12:0 | — | — | — | 0.5 | — | 0.2 | 47.8 | 48.4 | — | — | — |
| Myristic | 14:0 | 0.1 | — | 0.9 | 0.2 | 0.1 | 1.1 | 18.1 | 15.6 | 0.02 | 0.1 | — |
| Palmitic | 16:0 | 11 | 3.9 | 24.7 | 6.8 | 11.6 | 44 | 8.9 | 7.7 | 10.5 | 9.2 | 6 |
| Palmitoleic | 16:1Δ9c | 0.1 | 0.2 | 0.7 | 0.1 | 0.2 | 0.1 | — | — | 0.6 | 0.1 | 1 |
| Stearic | 18:0 | 4 | 1.9 | 2.3 | 4.7 | 3.1 | 45 | 2.7 | 1.9 | 2.6 | 5.8 | 2.5 |
| Oleic | 18:1Δ9c | 23.4 | 64.1 | 17.6 | 18.6 | 46.5 | 39.2 | 6.4 | 15 | 76.9 | 40.6 | 19 |
| Linoleic | 18:2Δ9c, Δ12c | 53.2 | 18.7 | 53.3 | 68.2 | 31.4 | 10.1 | 1.6 | 2.7 | 7.5 | 42.6 | 24.1 |
| Linolenic | 18:3Δ9c, Δ12c, Δ15c | 7.8 | 9.2 | 0.3 | 0.5 | — | 0.4 | — | — | 0.6 | 0.3 | 47.4 |
| Arachidic | 20:0 | 0.3 | 0.6 | 0.1 | 0.4 | 1.5 | 0.4 | 0.1 | — | 0.4 | 0.7 | 0.5 |
| Gadoleic | 20:Δ9c | — | 1 | — | — | 1.4 | — | — | — | 0.3 | 0.2 | — |
| Eicosadienoic | 20:2Δ11c, D14c | — | — | — | — | 0.1 | — | — | — | — | — | — |
| Behenic | 22:0 | 0.1 | 0.2 | — | — | 3 | — | — | — | 0.2 | 0.2 | — |
| Lignoceric | 24:0 | — | 0.2 | — | — | 1 | — | — | — | 0.1 | — | — |

[†]Gunstone, F.D. Structured and Modified Lipids. (CRC, 2001)

TABLE 6

Fatty acids compositions of modified Soybean and Canola seed oils[†]

| Fatty acid | Δ notation | Soybean | high-unsat | high-palmitic | high-stearic | high-oleic | Canola | high-oleic | high-lauric |
|---|---|---|---|---|---|---|---|---|---|
| Hexanoic | 6:0 | — | — | — | — | — | — | — | — |
| Octanoic (Caprylic) | 8:0 | — | — | — | — | — | — | — | — |
| Decanoid acid (Capric) | 10:0 | — | — | — | — | — | — | — | — |
| Lauric | 12:0 | — | — | — | — | — | — | — | 38.8 |
| Myristic | 14:0 | 0.1 | — | — | — | — | — | 0.1 | 4.1 |
| Palmitic | 16:0 | 11 | 4 | 25 | 9 | 6 | 3.9 | 3.4 | 2.7 |
| Palmitoleic | 16:1Δ9c | 0.1 | — | — | — | — | 0.2 | 0.2 | 0.2 |
| Stearic | 18:0 | 4 | 3 | 4 | 26 | 3 | 1.9 | 2.5 | 1.6 |
| Oleic | 18:1Δ9c | 23.4 | 28 | 16 | 18 | 86 | 64.1 | 77.8 | 32.8 |
| Linoleic | 18:2Δ9c, Δ12c | 53.2 | 61 | 44 | 39 | 2 | 18.7 | 9.8 | 11.3 |

TABLE 6-continued

Fatty acids compositions of modified Soybean and Canola seed oils[†]

| Fatty acid | Δ notation | Soybean | high-unsat | high-palmitic | high-stearic | high-oleic | Canola | high-oleic | high-lauric |
|---|---|---|---|---|---|---|---|---|---|
| Linolenic | 18:3Δ9c, Δ12c, Δ15c | 7.8 | 3 | 10 | 8 | 2 | 9.2 | 2.6 | 6.3 |
| Arachidic | 20:0 | 0.3 | — | — | — | — | 0.6 | 0.9 | 0.4 |
| Gadoleic | 20:Δ9c | — | — | — | — | — | 1 | 1.6 | 0.8 |
| Eicosadienoic | 20:2Δ11c, D14c | — | — | — | — | — | — | — | — |
| Behenic | 22:0 | 0.1 | — | — | — | — | 0.2 | 0.5 | 0.2 |
| Lignoceric | 24:0 | — | — | — | — | — | 0.2 | — | 0.2 |

[†]Gunstone, F.D. Structured and Modified Lipids. (CRC, 2001)

TABLE 7

Fatty acids compositions of minor crop seed oils[†]
Other interesting plant oils

| Common name | species name | major/ unique FA | % of FA | notes |
|---|---|---|---|---|
| Calendula oil | Calendula officinalis | 18:3Δ8t, Δ10t, Δ12c | 58% | |
| Meadowfoam oil | Limnanthes alba | 20:Δ5c | 63-67% | |
| Honest Seed oil | Lunaria annua | 22:Δ9c | 46% | high monoene |
| Caraway | Carum carvii | 18:1Δ6c | 35-43% | |
| Carrot | Daucus carta | 18:1Δ6c | 66-73% | |
| Coriander | Coriandrum sativum | 18:1Δ6c | 31-75% | |
| Macadamia | Macadamia integrifolia | 16:1Δ9c | 16-23% | high monoene |
| Nutmeg | Myristica malabarica | 14:0 | 60-72% | |
| Oiticica | Licania rigida | 18:3Δ9, Δ11, Δ13, 4-oxo | 78% | |
| Tung oil | Aleurites fordii | 18:3Δ9c, Δ11t, Δ13t | 69% | |
| Castor | Ricinus communis | 18:1Δ9c, 12-hydroxy | 95% | |
| Jojoba | | 20:1Δ11 c | | |

[†]Gunstone, F. D. Structured and Modified Lipids. (CRC, 2001)

The following fatty acids are produced by plants and microalgae: Z-11-octadecenoic: *Asclepias Syriaca* (44.9%), *Pediastrum simplex* (68%); Z-13 octadecenoic: *Cardwellia sublimis* (22%); and Z-11-hexadecenoic: *Kermadecia sinuata* (40.3%), *Synechococcus elongatus* (35%). The major components of commodity seed oils are: Lauric (12:0): Coconut (47.8%) and Palm kernel (48.4%); Palmitic (16:0): Palm (44%) and Cotton (24.7%); Oleic (18:1Δ9c): Canola (64.1%), Peanut (46.5%), Palm (39.2%), Olive (76.9%) and Sesame (40.6%); Linoleic (18:2Δ9c,Δ12c): Soybean (53.2%), Cotton (53.3%), Sunflower (68.2%), Peanut (31.4%), and Sesame (42.6%); and Linolenic (18:3 Δ9c, Δ12c, Δ15c): Linseed (47.4%). Commodity seed oils are composed of mostly saturated fatty acids and monoenes.

Minor crops (*Calendula*, Meadowfoam, Honesty, Caraway, Carrot, Coriander, *Macadamia*, Nutmeg, Oiticica, Tung, and Castor) produce unique monoenes: 20:Δ5c, 22:Δ9c, 18:1Δ6c, 16:1Δ9c, trienes: 18:3Δ8t,Δ10t,Δ12c, 18:3Δ9c,Δ11t,Δ13t and oxygenated trienes: 18:3Δ9,Δ11, Δ13, 4-oxo, 18:1Δ9c, Δ12-hydroxy.

Example 2: Production of (Z)-Hexadec-11-Enal by Semi-Reduction of Naturally Occurring Oils Background and Rationale The target pheromones are very akin to naturally occurring fatty acids, but the use of naturally occurring fatty acids as substrates for production of target pheromones has not been elucidated. To determine whether plant oils with reasonable amounts of (Z)-hexadec-11-enoic acid could be used for this purpose, more information about the specific plants on the substrate side was necessary.

The only commercially available plant oil containing a significant amount of (Z)-hexadec-11-enoic acid, Chilean hazelnut oil, was used as a feedstock for the production of (Z)-hexadec-11-enal.

Figure 1:
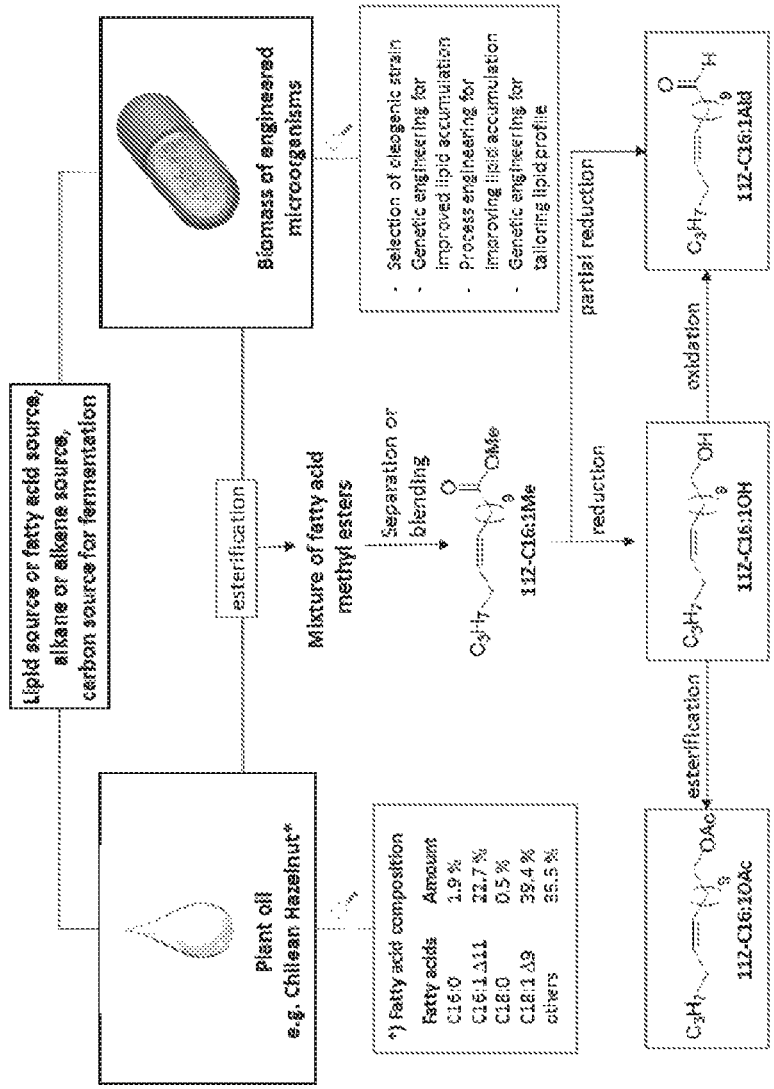
FIG. 1 illustrates the concept for semi-biosynthetic production of fatty alcohols and fatty aldehydes.
Figure 2:
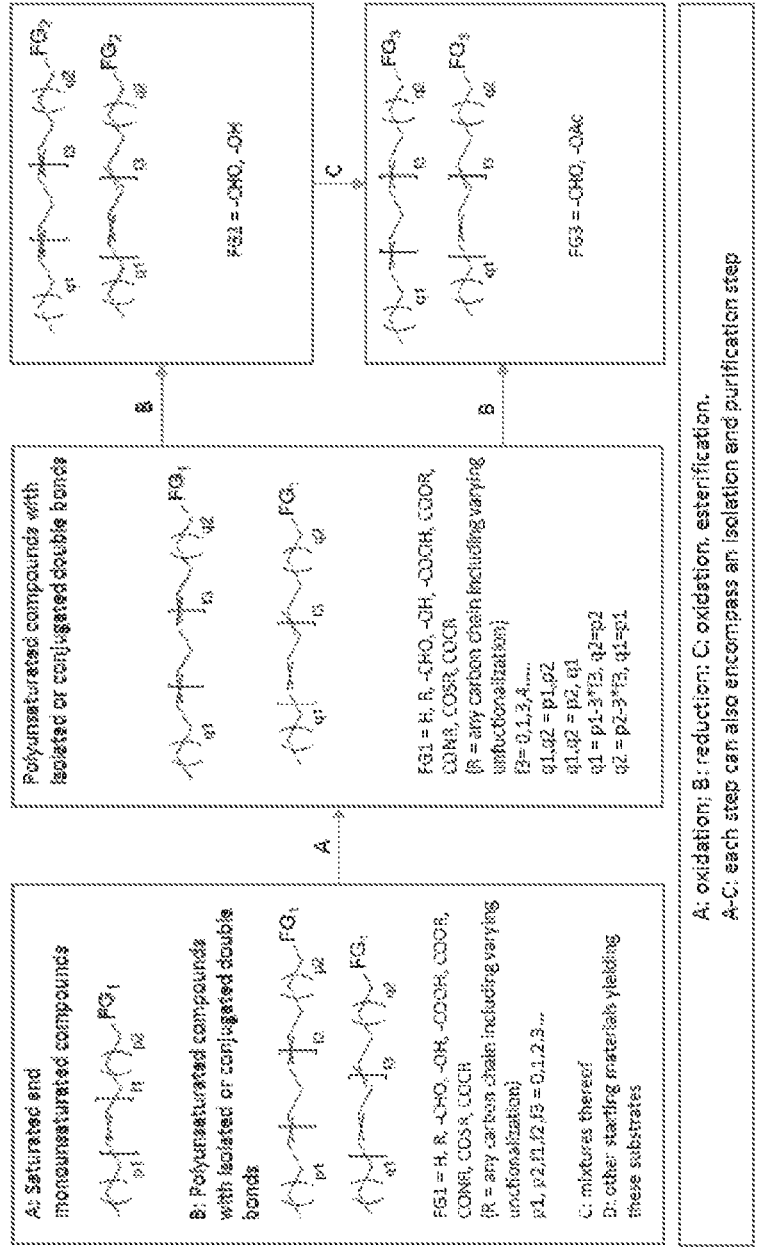
FIG. 2 illustrates the transformation of saturated and unsaturated molecules into alcohols and aldehydes.

A synopsis illustrating the overall reaction scheme is depicted in FIG. 1. After isolation of the lipids from natural sources, they are subjected to transesterification. The preparation of methyl esters is a standard procedure for the production of biodiesel. The reaction can be either acid or base catalyzed. As the double bond is prone to isomerization under acidic conditions, alkaline conditions were preferred for this approach (Li H-Y et al. (2005) *Chem. Phys. Lett.* 404: 384-388).

Depending on the raw material, the resulting mixture contains only a fraction of the target material. In order to minimize the amount of reducing equivalents needed for the subsequent reduction reaction, purification or at least enrichment of the precursor acid seems to be favorable. Amongst the viable options are, for example, distillation and simulated moving bed (SMB) chromatography. As the topic of preliminary purification is a separate topic, a small scale distillation was performed to probe the stability of compounds of interest under elevated temperatures. In a next step the purified methyl (Z)-hexadec-11-enoate is then subject to reduction to the corresponding aldehyde. A possible reagent for this purpose could be Vitride (sodium bis(2-methoxyethoxy)aluminumhydride) (Abe, T et al. (2001) *Tetrahedron* 57: 2701-2710). Vitride is an aluminum based hydride reducing agent which has a comparable reaction profile to DIBAL (diisobutylaluminium hydride). Unlike DIBAL, Vitride is not pyrophoric upon contact with air and the reaction with water is less vigorous, making it safer and easier to handle. Comparing Vitride to other known partial reducing agents in the literature, the reagent can be used at 0° C., whereas others require −78° C. and shows a high selectivity to similar substrates as well as only little over-reduction byproducts (Shin W K et al. (2014) *Bull. Korean Chem. Soc.* 35: 2169-2171).

Summary of Approach

Different reported plants with a high content of (Z)-hexadec-11-enoic acid (>20%) were compared. Relevant parameters were oil content, cultivation conditions, overall yield and market availability.

A representative plant oil sample (*Gevuina avellana*—Chilean hazel) was purchased and analyzed.

Base catalyzed transesterification was performed to produce methyl esters of the plant oil fatty acids (biodiesel production).

Small scale purification/substrate enrichment of methyl (Z)-hexadec-11-enoate was accomplished by distillation.

Semi-reduction of the methyl esters was accomplished with a modified variant of Vitride (2,6-dimethylmorpholine modified sodium bis[2-methoxyethoxy]aluminium hydride) to produce (Z)-hexadec-11-enal.

Results

The study focused on the general practicability of sourcing natural oils and reducing them to pheromones. As a major target is (Z)-hexadec-11-enal, this compound was the center of investigation. The SOFA (Seed Oil Fatty Acids) and SAG (Culture Collection of Algae at Goettingen University) databases were reviewed (see Example 1).

Part I of the report focused on the identification of plants having high content of unusual fatty acids suitable as precursors for pheromone production. Part II demonstrated proof of principle for utilization of oils to produce pheromones. Part I confirmed the previous survey of candidate plants. Investigation of the overall technology seemed to be reasonable as other lipid sources, such as microbial lipids, would be processed by the very same procedure. FIG. 1 illustrates a route for the development of an intermediate production platform.

1.1 Sourcing Plant Oils in Detail

Plants with a high content of (Z)-hexadec-11-enoic acid are referenced in many studies investigating unusual fatty acid profiles of plant oils (Aitzetmuller K, *J. Am. Oil Chem. Soc.* 81: 721-723). Interestingly, except for *Ziziphus jujube* which belongs to the family of Rhamnaceae, all other plants with an (Z)-hexadec-11-enoic acid fraction of over 20% belong to the Proteaceae family.

Information regarding oil yields and and cultivation conditions is very scarce. However, other parameters can be used to assess the potential of the plants. The study focused on two plants. First, *Grevillea exul* var. *rubiginosa* has the highest amount of (Z)-hexadec-11-enoic acid of all reported plants so far with 45.6% in the seed oil. Depending on the report, *G. exul* is a shrub or a small tree up to 30 feet in height and it is native exclusively to New Caledonia. More information is only available for other closely related species like *G. robusta* and the genus *Grevillea* in general. The hardy zones in general are 9 to 12, matching, for example, southern California. They are drought and deer resistant, fast growing but sensitive to fertilizers. No information was available regarding productivity or oil yield. Many *Grevillea* species are used as food plants by Lepidoptera species, including the dryandra moth.

The second plant of interest is the Chilean hazel because the plant oil naturally contains around 25% of (Z)-hexadec-11-enoic acid and is commercially available. The plant is not widely cultivated.

1.2 Comparison of Several Plant Oils by GC-FID

Figure 5:
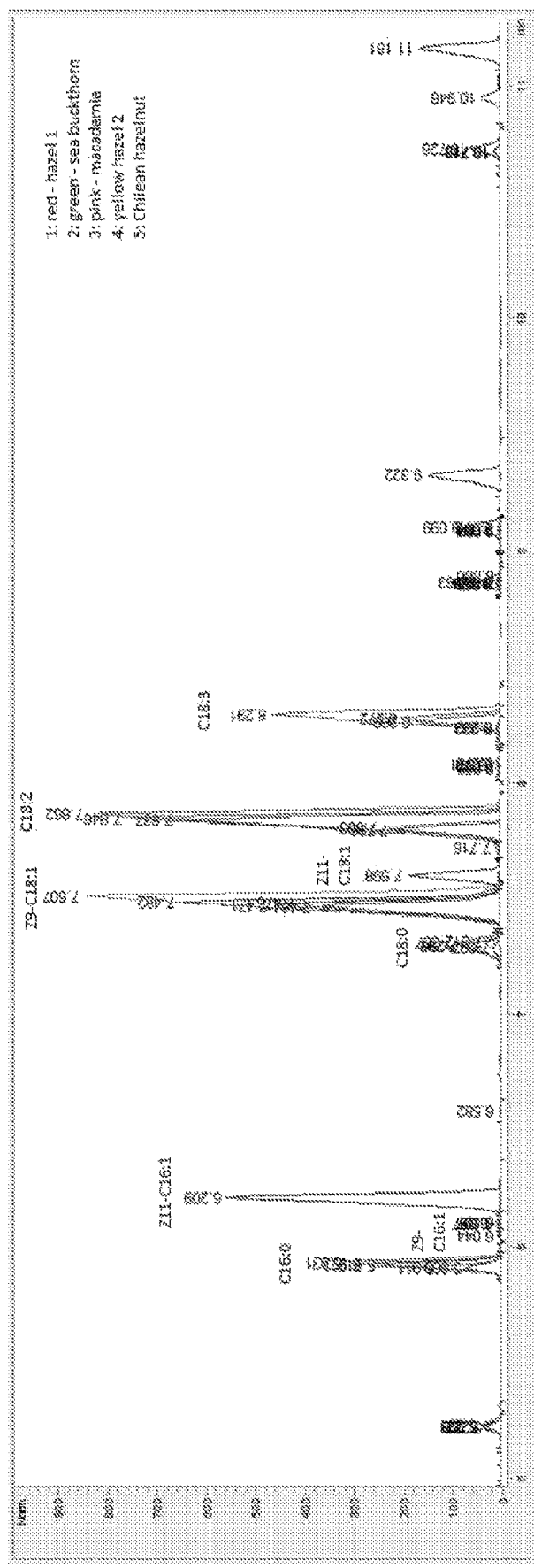
FIG. 5 shows an overlay of the chromatograms of different plant oils. Only no. 5 (blue), the Chilean hazelnut oil, shows a peak at the retention time 6.2 min corresponding to methyl (Z)-hexadec-11-enoate.

The Chilean hazelnut oil is used in many lotions for its sun protective properties. In many cases the different regioisomers of the fatty acids are not distinguished by retailers. Chilean and European hazelnut oil were compared. The results are summarized in Table 8, and an overlay of the different GC-FID is shown in FIG. 5. The only oil containing (Z)-hexadec-11-enoic acid is the Chilean hazelnut oil. The fraction of 22.5% is close to the reported values in literature with about 22.7% and about 23.83% (Bertoli C et al. *J. Am. Oil Chem. Soc.* 75: 1037-1040; Medel F and Carillo T in Acta Hortic., International Society For Horticultural Science (ISHS), Leuven, Belgium, 2005, pp. 631-638). Although other sources were not exhaustively studied, it is very unlikely that other commercial oils contain a similar high amount of (Z)-hexadec-11-enoic acid. The fact that the European hazelnut (*Corylus avellana*) is totally different is not surprising, as it is not related to the Chilean hazel (*Gevuina avellana*). Surprisingly, the macadamia nut oil showed only 0.59% of palmitoleic acid—normally a higher content 16-34% is observed. The content of oleic acid on the other hand was a little bit higher, which is normally found between 41-59%. Around 3% Z11-C18:1 is normally also present (Kaijser A et al. (2000) *Food Chem.* 71: 67-70). None of these parameters are in accordance with reported data, leading to the conclusion that this oil is not pure macadamia nut oil.

TABLE 8

Comparison of the fatty acid composition of various plant oils.
Reported values are representing percent values [%] of the total lipid content.

| RT | compound | 1 | 2 | 3 | 4 | 5 |
|---|---|---|---|---|---|---|
| 5.92 | C16:0 | 10.56 | 8.13 | 5.03 | 10.44 | 2.29 |
| 6.10 | Z9-C16:1 | 0.00 | 0.22 | 0.59 | 0.12 | 0.11 |
| 6.21 | Z11-C16:1 | 0.00 | 0.00 | 0.00 | 0.00 | 22.50 |
| 7.29 | C18:0 | 4.36 | 3.73 | 2.16 | 4.34 | 0.65 |
| 7.46 | Z9-C18:1 | 22.36 | 24.25 | 76.67 | 22.33 | 35.37 |
| 7.60 | Z11-C18:1 | 0.00 | 0.00 | 0.00 | 0.00 | 6.58 |
| 7.84 | C18:2 | 52.39 | 36.92 | 12.05 | 52.27 | 8.09 |
| 8.26 | C18:3 | 7.56 | 23.33 | 0.49 | 7.57 | 0.22 |
| — | others | 2.77 | 3.43 | 3.00 | 2.93 | 24.20 |

1: Hazelnut Oil.
2: Sibu Beauty Sea Buckthorn Seed Oil.
3: Macadamia Nut Oil.
4: La Tourangelle Hazelnut Oil.
5: Chilean Hazelnut Oil.

2. Transesterification and Purification of (Z)-Hexadec-11-Enoic Acid

The production route investigated in the study is the direct production of the aldehyde by semi-reduction of the corresponding fatty acid derivative. In contrast to the full reduction, which can also be performed starting from the free fatty acid, the semi-reduction requires the methyl ester. Methyl esters have in general about 20 K lower boiling point, enabling easier purification via distillation. The route, which was pursued in this approach, therefore utilized transesterification instead of saponification and distillation instead of chromatography.

2.1 Preparation of Methyl (Z)-Hexade-11-Enoate/Chilean Hazelnut Biodiesel

Figure 6:
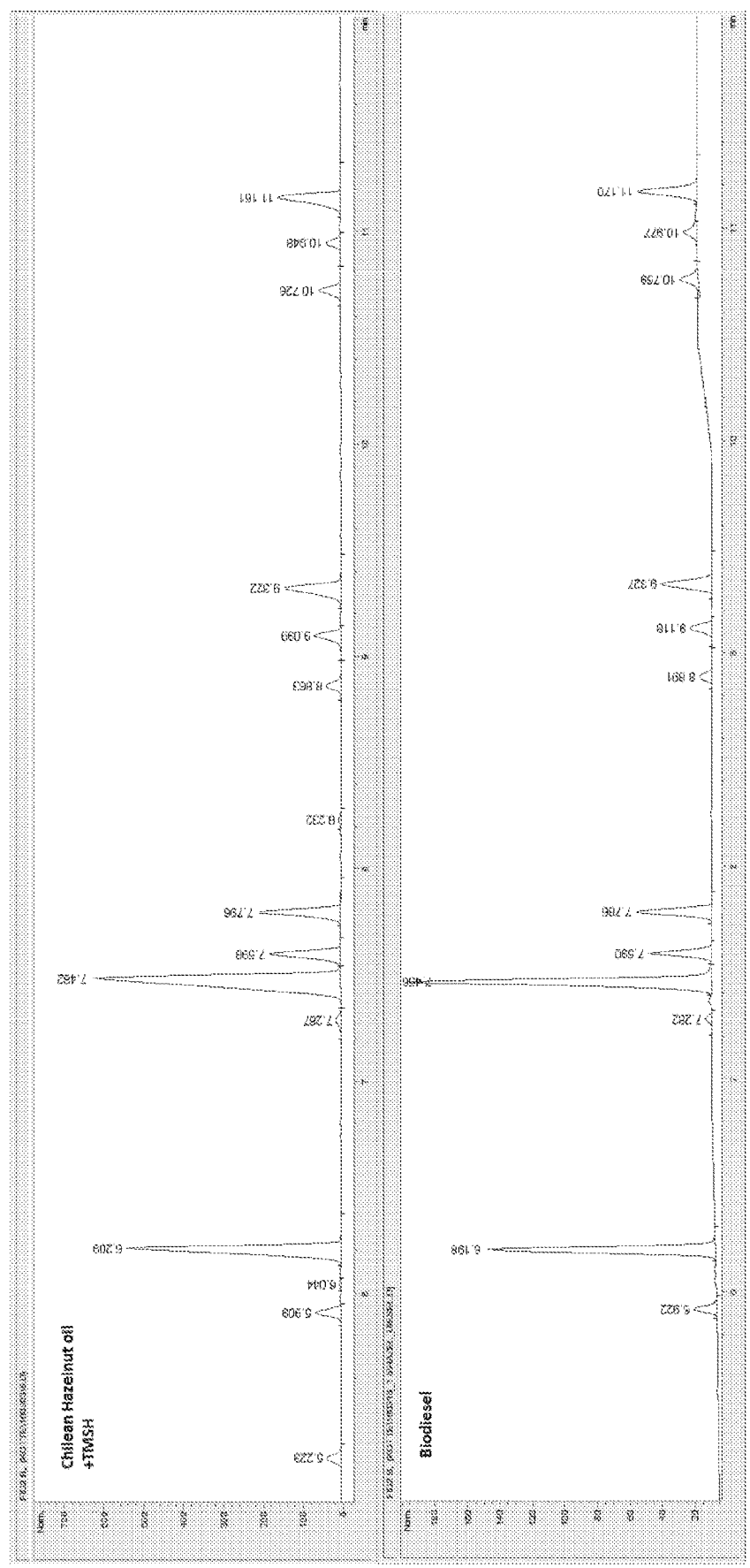
FIG. 6 shows a comparison of the Chilean hazelnut oil transesterified with TMSH (top) and the produced biodiesel (bottom), which was produced by alkaline methanolysis. Although the chromatograms look comparable, slight differences can be seen in the apparent peak areas.

Chilean hazelnut oil was transesterified using the optimized protocol from Ullah et al. (2013) for biodiesel production from linseed oil (Ullah F et al. (2013) *Polish J. Chem. Technol.* 15: 74). The actual composition of the reagents used is summarized in Table 9 and FIG. 6. A detailed protocol is described in the Materials & Methods section.

TABLE 9

Reagent composition of the transesterification reaction.

| compound | FW [g/mol] | n [mmol] | m [g] | ρ [g/ml] | V [ml] | comment |
|---|---|---|---|---|---|---|
| C. hazel oil | 942.90 | 10.84 | 10.22 | — | — | — |
| NaOH | 40.00 | 1.28 | 0.05 | — | — | ~0.5 mass % |
| methanol | 32.04 | 74.25 | 2.38 | 0.79 | 3.00 | ~6x mol |

The reaction was stirred for 180 min at 65° C. and gave 8.97 g of a light yellowish liquid with a yield of 88%. The biodiesel composition is shown in Table 10 and compared with the direct methylation using TMSH with the original Chilean hazelnut oil.

The composition of the biodiesel compared to the direct methylated hazelnut oil is slightly changed (Table 10). For methyl Z11-hexadecenoate there was an apparent decrease of 2.85%. The relative amount of other compounds, especially higher chain length compounds, increased by 10.63%. Overall the method proved suitable to transfer the Z11-C16:1 acid bound in triacylglycerides to its methyl derivative.

TABLE 10

Comparison of direct methylation of Chilean hazelnut oil with TMSH and the product of the biodiesel reaction. All values are listed in percent [%].

| Oil Compound | C16:0 | Z9-C16:1 | Z11-C16:1 | C18:0 | Z9-C16:1 | Z11-C16:1 | C18:2 | C18:3 | others |
|---|---|---|---|---|---|---|---|---|---|
| C. hazel oil | 2.29 | 0.11 | 22.50 | 0.65 | 35.37 | 6.58 | 8.09 | 0.22 | 24.20 |
| Biodiesel | 1.89 | 0.00 | 19.65 | 0.56 | 30.65 | 5.58 | 6.84 | 0.00 | 34.83 |

2.2 Distillation of Methyl (Z)-Hexade-11-Enoate

To enrich the amount of methyl (Z)-hexadec-11-enoate and also to assess the stability of the compounds under these required conditions, the mixture was subject to distillation. The distillation was performed in a fractional manner using a 5 inch Vigreux column. The oil was heated to 210° C. The pressure was kept constant ranging from 0.95-1.22 mbar. Over the course of two hours, two fractions were collected, cut I (2.21 g head temperature 55-82° C.) and cut II (2.25 g head temperature 120-146° C.). Table 11 shows the composition of the different fractions also in comparison to the crude mixture.

Before collecting the second fraction the Vigreux column was removed as the required high head temperatures could not be reached with the initially used setup.

Figure 7:
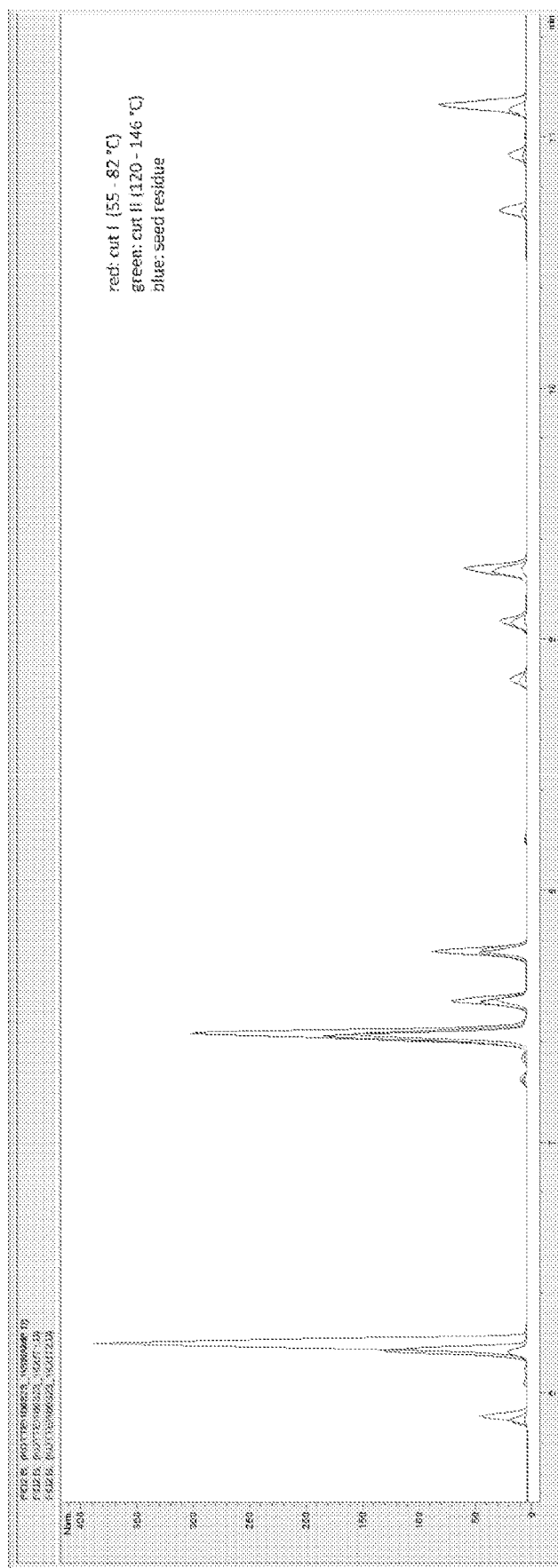
FIG. 7 shows an overlay of the GC-FID chromatograms of the different fractions collected by a simple distillation. The first fraction (red) was collected between 55-82° C. and contains the highest fraction of C16 compounds (around 6 min). The second fraction (green) was collected between 120-146° C. Most of the material are different C18 acids but still a notable amount of C16 can be found in this fraction. Fraction 3 (blue) comprises the seed leftovers. Nearly no C16 can be found but most of the higher chain homologues (around 9 to 11 min) are seen.

Starting from an initial methyl (Z)-hexade-11-enoate content of 23.4%, the concentration could be enriched to 60% by a relatively simple distillation. It would have been possible to collect even smaller fractions as the temperature frame of 55-82° C. consisted of 5 different head temperatures (55-60° C., 63° C., 68° C., 790C and 820C). A detailed overview over the fractions is shown in Table 11 and FIG. 7.

TABLE 11

Comparison of the different fractions with the biodiesel starting material. All values are listed in percent [%].

| Compound/fraction | Diesel/seed (8.62 g) | cut I (2.21 g) [55-82° C.] | cut II (2.25 g) [120-146° C.] | Residue (3.54 g) |
|---|---|---|---|---|
| C16:0 | 2.2 | 5.4 | 1.9 | 0.0 |
| Z11-C16:1 | 23.4 | 60.0 | 16.8 | 3.3 |
| Z9-C18:1 | 36.2 | 23.1 | 49.2 | 35.0 |
| Z9, Z11-C18:1 | 8.1 | 5.6 | 11.1 | 7.4 |
| others | 30.1 | 6.0 | 20.9 | 54.4 |

3. Vitride Reduction of Methyl (Z)-Hexade-11-Enoate

Figure 8:
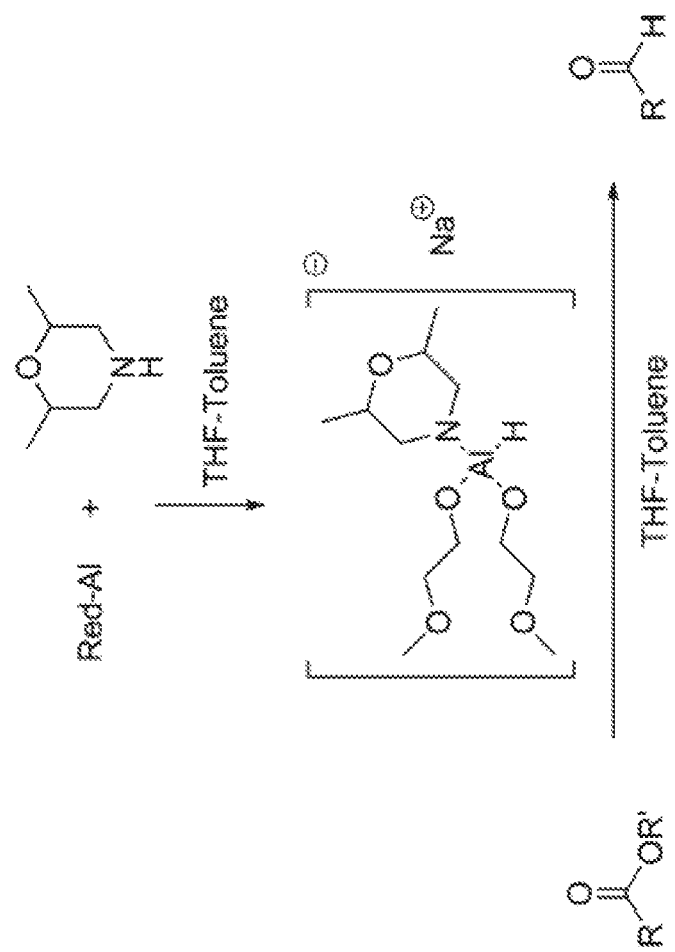
FIG. 8 shows reduction of ester to aldehyde using modified Red-Al as well as the preparation thereof (Shin W K et al. (2014) *Bull. Korean Chem. Soc.* 35: 2169-2171).

The fraction containing the highest amount of methyl (Z)-hexadec-11-enoate was then used to perform the partial reduction using a modified version of Vitride. For this purpose, a modified variant of the reagent was used. As shown in FIG. 8 the reaction comprises two steps. In a first step the modified reducing agent has to be prepared using a nitrogen base, in this case 2,6-dimethyl morpholine. In a second step the reagent is used to reduce the actual substrate.

Figure 9:
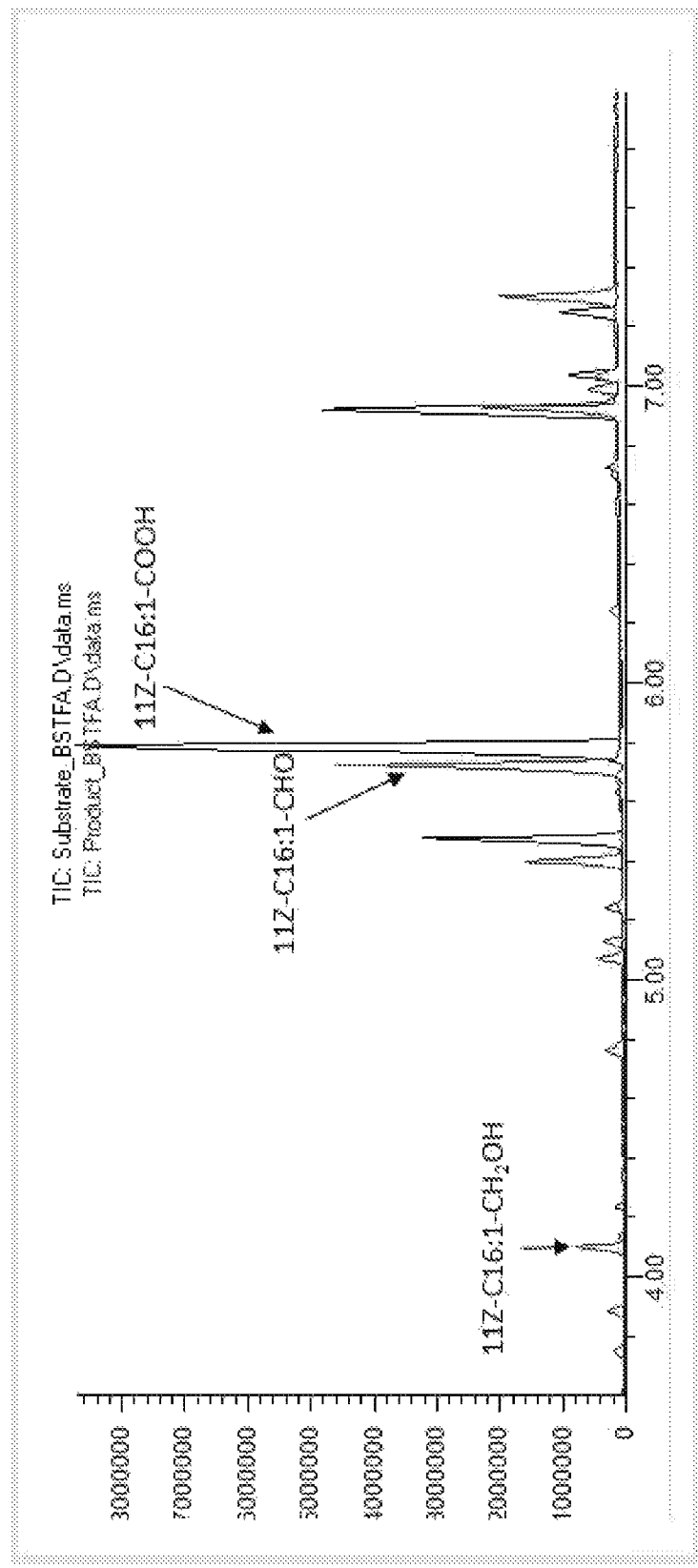
FIG. 9 shows a part of the overlay of the substrate and product mixture. The substrate (methyl (Z)-hexadec-11-enoate, 11Z-C16:1-COOH) spectrum is shown in black, and the product ((Z)-hexadec-11-enal, 11Z-C16:-CHO; 12% (Z)-hexadec-11-enol, 11Z-C16:1-CH2OH) spectrum is shown in purple.
Figures 10A, 10B, 10C, 10D, 10E, 10F:
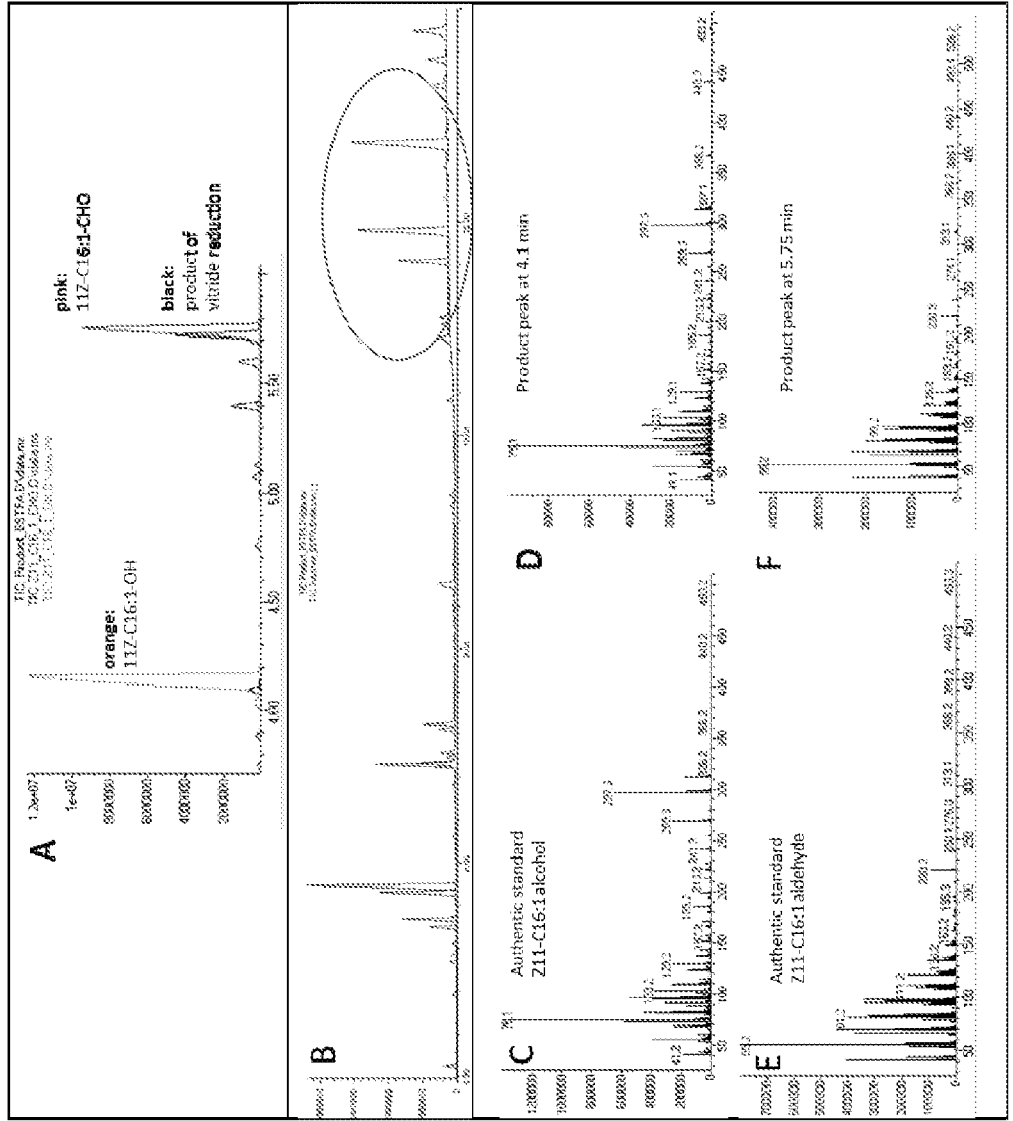
FIG. 10A: Overlay of authentic standards [(Z)-hexadec-11-enal and (Z)-hexadec-11-enol) with the product mixture obtained in the Vitride reduction reaction.
FIG. 10B: Observation that there are additional peaks in the spectrum. This was not observed in a one-month older spectrum, where no derivatization agent was used instead of BSTFA.
FIG. 10C: Fragmentation pattern of the authentic standard (Z)-hexadec-11-enol.
FIG. 10D: Fragmentation pattern of the product peak at 4.1 min.
FIG. 10E: Fragmentation pattern of the authentic standard (Z)-hexadec-11-enal.
FIG. 10F: Fragmentation pattern of the product peak at 5.75 min.

Although not as sensitive as diisobutylaluminium hydride, the reagent is susceptible to moisture, and the usage of inert gas as well as dry solvents is crucial. Therefore, argon was used as inert atmosphere and only dry solvents were used. The reaction was performed as described in the Materials & Methods section. As a crude mixture was employed it is not possible to calculate a yield for this first reaction. FIG. 9 shows a part of the overlay of the substrate and product mixture. The substrate was quantitatively converted. The only methyl (Z)-hexadec-11-enoate related product are 88% (Z)-hexadec-11-enal and 12% (Z)-hexadec-11-enol.

The products were identified by comparison with authentic standards with respect to retention time and fragmentation pattern (FIG. 10A-FIG. 10F).

Figure 11:
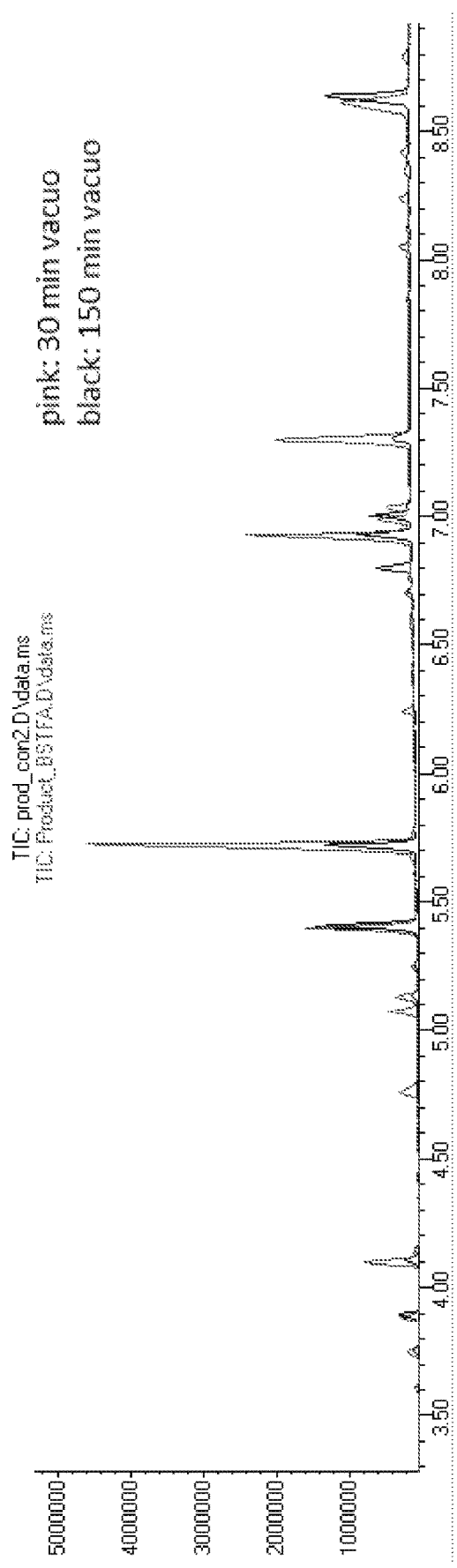
FIG. 11 shows an overlay of the product mixture obtained by the Vitride reduction. The main product (Z)-hexadec-11-enal (5.7 min) is lost over time while concentrating the mixture in vacuo at 40° C. Whereas a relatively high amount can be found after 30 min, after 150 min there is only around 25%. This also indicates that some of the product was lost during the initial 30 min in vacuo. This step can be further investigated for purification purposes.

Moreover, it was observed that 11Z-C16:1 aldehyde is volatile enough to evaporate under full vacuum at 40° C., albeit at a very slow rate. FIG. 11 shows the comparison at different time points during the solvent removal using the rotovap. The same amounts of substances were used but only about 24% of the products were left after additional 2 h in vacuo. A full-pull down should be avoided when the reaction is performed. The peak 5.4 min corresponds to the hexadecanal. This observation can be utilized to develop a relatively easy and mild purification method.

As a result, it can be stated, that Z11-hexadecenal can be produced by this route with good selectivity.

4. Plants with High Content of 'Palmitvaccenic Acid'

Despite the already performed SOFA and SAG database search, the search was extended to SciFinder and Google Scholar using the various trivial names, which emerged over time. Beside the systematic name 11Z-hexadecenoic acid, the following trivial names were also used: Lycopodiumoleic acid (Arch. Pharm. 227, 241, 289, 625 (1889), which was then later disproved as a mixture but was reintroduced later by Riebsomer and Johnson (Riebsomer J L and Johnson J R (1933) *J. Am. Chem. Soc.* 55: 3352-3357). Sometimes the trivial names tanacetumoleic acid and palmitvaccenic acid were also used, but palmitvaccenic acid was the most prominent trivial name.

Additional information was collected form several blogs of plant enthusiasts, plant associations, seed shops and Wikipedia, if available.

*Grevillea exul* var. *rubiginosa* in the family Proteaceae has 45.6% 11Z-hexadecenoic acid in seed oil.

*Kermadecia sinuata* in the family Proteaceae has 40.3% 11Z-hexadecenoic acid in seed oil.

*Orites diversifolius* in the family Proteaceae has 35.6% 11Z-hexadecenoic acid in seed oil.

*Orites revoluta* in the family Proteaceae has 35.6% 11Z-hexadecenoic acid in seed oil.

*Ziziphus jujube* var. *inermis* in the family Rhamnaceae has 33.3% 11Z-hexadecenoic acid in seed oil.

*Hicksbeachia pinnatifolia* in the family Proteaceae has 28.5% 11Z-hexadecenoic acid in seed oil.

*Gevuina avellana* in the family Proteaceae has 25.4% 11Z-hexadecenoic acid in seed oil.

*Grevillea decora* in the family Proteaceae has 21.4% 11Z-hexadecenoic acid in seed oil.

Conclusions

Nearly all of the plants containing an amount of (Z)-hexadec-11-enoic acid belong to the Proteaceae family. Depending on the species and the location the specimens grow either as shrubs or small to relatively large trees.

Chilean hazel is a readily available oil source with a high amount of (Z)-hexadec-11-enoic acid (22.5%).

Transesterification/biodiesel production is an established chemical process which can be easily performed. On the 10 g scale the reaction can be performed with 88% yield.

Distillation on small scale is difficult due to low number of theoretical plates. However, methyl (Z)-hexadec-11-enoate could be enriched up to 60% from the original 23.4%. The data shows that the double bond configuration is stable for prolonged times at elevated temperatures (30 min at 200° C.) and that a substantial enrichment can be relatively easily achieved.

Using two molar equivalents of Vitride/2,6-dimethylmorpholine, the semi-reduction could be performed quantitatively. An actual yield cannot be calculated at this stage as a complex mixture was used. The results demonstrate that (Z)-hexadec-11-enal can be produced via this route. The product distribution of compounds (relative selectivities) derived from methyl (Z)-hexadec-11-enoate is 88% (Z)-hexadec-11-enal and 12% (Z)-hexadec-11-enol.

In addition to plant sources, lipids from genetically engineered microorganisms (like *Candida tropicalis* and *Yarrowia lipolytica*) rich in (Z)-hexadec-11-enoate are also suitable substrates for insect fatty alcohol/aldehyde synthesis using this method. Production of oils from microbial biomass can be more advantageous than sourcing oils from plants since microbial cultivation is an easily scalable process. Unlike plant cultivation, microbial cultivation does not rely on aeral land availability, climate, irrigation, and fertilizer.

Materials & Methods

TABLE 12

Commercially available plant oil used

| no. | compound | S/N | Vendor |
|---|---|---|---|
| 1 | Hazelnut Oil | B00JKTYBQC | Amazon |
| 2 | Sibu Beauty Sea Buckthorn Seed Oil | B003IU9HI0 | Amazon |
| 3 | La Tourangelle Hazelnut Oil | B0087G8TL6 | Amazon |
| 4 | Macadamia Nut Oil | B00DV65QO0 | Amazon |
| 5 | Chilean Hazelnut Oil | N/A | From Nature with Love |

Analytics

10 µL of plant oil were dissolved in 450 µl methyl tert-butyl ether in a 1.8 mL screw-cap GC-glass vial. Prior to capping an GC-FID analysis 50 µl 0.2 M Trimethylsulfonium hydroxide solution in methanol was added. This procedure is derived from Macherey-Nagel (application no. 213060) based on a protocol from Butte et al. 1983 (Butte W (1983) J. Chromatogr. A 261: 142-145). The GC program used was KO-DESATUR01.M with the following parameters (Table 13).

TABLE 13

Instrument parameters

| | |
|---|---|
| System | Agilent 6890 GC, ChemStation Rev. B.03.02 (341) |
| Column | J&W DB-23 30 m × 25 mm × 25 µm |
| | Pressure = 16 psi; Flow = 0.9 mL/min; Run Time = 14.4 min |
| Inlet | Heater = 240° C.; Pressure = 16 psi; Total Flow {He} = 31.4 mL/min |
| Carrier | $H_2$ @ 1 mL/min, 9 psi, 35 cm/sec |
| Signal | Data rate = 2 Hz/0.1 min |
| Oven | 150° C. for 1 min |
| | Ramp 12° C./min to 220° C., hold 3 min |
| | Ramp 35° C./min to 240° C., hold 6 min |
| | Equilibration Time: 2 min |
| Injection | Split, 240° C. |
| | Split ratio - 30:1; 29.1 mL/min |

TABLE 13-continued

Instrument parameters

| | |
|---|---|
| Detector | FID, 240° C. |
| | $H_2$ @ 35.0 mL/min, Air @ 350 mL/min; Electrometer {Lit Offset} @ 2.0 pA |
| Sample | Injection volume = 1 µL |

Biodiesel was analyzed by dissolving 10 µL biodiesel in 1 mL chloroform using the same GC-FID method. The Vitride reaction was analyzed by dissolving 10 µL of the substrate or the product mixture in 1 mL chloroform. After the addition of 100 µL N,O-bis(trimethylsilyl)trifluoroacetamide containing 1% trimethylsilyl chloride, the sample was analyzed by GC-FID. For GC-MS analysis the same temperature program was used and the MS was configured in SCAN mode.

Transesterification of Chilean Hazelnut Oil

Based on the optimized protocol from Ullah et al. (2013), the transesterification was performed with the 6:1 molar ratio of methanol to TAG (triacylglyceride). 10.22 g Chilean hazelnut oil (10.84 mmol) were placed in a 25 mL round bottom flask equipped with a magnetic stirring bar. 1 mL of 5% NaOH in methanol was mixed with 2 mL methanol and added to the round bottom flask. The mixture was stirred vigorously at 65° C. for 180 min. Prior to the extraction with two times 20 mL methyl tert-butyl ether, the mixture was diluted with 20 mL water. The organic phases were combined, dried with anhydrous sodium sulfate and concentrated in vacuo. The reaction yielded 8.97 g of a slightly yellow liquid (88% yield), which was analyzed by GC-FID.

Distillation of Chilean Hazelnut Biodiesel 8.62 g of biodiesel were placed in 25 mL round bottom flask equipped with a magnetic stirring bar. The flask was fitted with a 5 inch Vigreux column connected to a 5.5 inch short path distillation head with water cooling. The condenser was connected to a three-way glass receiver attached to three 10 mL glass round bottom flasks. The Vigreux column was insulated using aluminum foil. The head temperature was monitored using a PTFE-coated T-type thermocouple connected to a JKEM Model 210 temperature controller. The pressure was monitored using thermocouple pressure transducer (Mastercool Model 98061). The round bottom flask containing the seed oil methyl esters was placed in an oil bath and was carefully heated to 210° C. with stirring via a magnetic hotplate stirrer. Over the time course of 2 h two different fraction were collected. The first fraction (cut I—2.21 g) was collected over the temperature range of 55-80° C. and the second fraction (cut II—2.25 g) was collected between 120-146° C. As the high head temperatures for cut II could not be reached using the Vigreux column it was removed before collecting the second fraction. After the distillation procedure 3.54 g were left in the 25 mL round bottom flask. The different fractions were analyzed by GC-FID.

Vitride Reduction of the 1st Cut—Crude Fraction with Highest Content of Methyl (Z)-Hexadec-11-Enoate Preparation of Reducing Agent (Cis-2,6-Dimethyl Morpholine-Modified Red-Al).

A dry three-neck flask was equipped with a dry dropping funnel, a magnetic stirring bar and septa. After four pump-purge cycles with argon the flask was placed in an ice bath. The flask was charged with 14 mL anhydrous tetrahydrofuran and 1.17 mL (9.54 mmol). After allowing the mixture to cool to 0° C., a solution of 3.5 M solution of sodium bis(2-methoxyethoxy)aluminumhydride in toluene (2.48 mL, 8.67 mmol) was added dropwise and stirred for 1 h to give a clear colorless homogeneous solution.

Partial Reduction of Cut I from the Chilean Hazelnut Biodiesel

A dry three-neck flask was equipped with a dropping funnel, a magnetic stirring bar and septa. After four pump-purge cycles with argon the flask was placed in an ice bath. The flask was charged with 20 mL anhydrous tetrahydrofuran and 0.97 g of cut I from the Chilean hazelnut biodiesel (3.81 mmol: assuming only 11Z-C16:1-COOMe). The dropping funnel was equipped with the previously prepared cis-2,6-dimethyl morpholine modified Red-Al by cannula transfer. After cooling the mixture to 0° C., the modified Red-Al was added dropwise (the reagent was not cooled at this stage). The mixture was stirred for 30 min allowing it to warm to room temperature. The reaction was quenched by 80 mL 2 N hydrochloric acid and the product was extracted two times with 50 mL methyl tert-butyl ether. The organic phases were combined and dried over anhydrous sodium sulfate and concentrated in vacuo. The reduced mixture was analyzed by GC-MS and the products deriving form methyl (Z)-hexadec-11-enoate were identified by comparison with authentic standards on retention time and fragmentation pattern.

Example 3: Expression of Transmembrane Desaturases in Yarrowia lipolytica

Background and Rationale

Engineering microbial production of unsaturated lipid moieties requires the functional expression of a synthetic pathway. One such pathway comprises a transmembrane desaturase to mediate the conversion of fatty acyl-CoA into regio- and stereospecific unsaturated fatty acyl-CoA. A number of genes encoding these enzymes are found in some insects as well as some microalgae. Regio- and stereospecific desaturases can be used to produce a microbial oil rich in fatty acid precursors. The microbial oil can then be derivatized and reduced to active ingredients. A number of gene variants were screened to identify enzyme activities that allow the creation of pathways capable of high level synthesis of a single or a blend of unsaturated lipid moieties. Additionally, these enzymes were screened across multiple hosts (Saccharomyces cerevisiae, Candida viswanathii (tropicalis), and Yarrowia lipolytica) to optimize the search toward finding a suitable host for optimum expression of these transmembrane proteins.

Initial screening of desaturases in S. cerevisiae and C. viswanathii (tropicalis) identified three active Z11-C16:1 desaturase variants from Amyelois transitella, Helicoverpa zea, and Trichoplusia ni. The S. cerevisiae screening used coding sequences with an N-terminal leader sequence of the S. cerevisiae Ole1p Z9 desaturase fused to the full length insect Z11 desaturase sequence. This strategy has been used previously in the scientific literature to express eukaryotic desaturases in S. cerevisiae. All three of the above desaturases displayed Z11 desaturase activity with the Ole1p leader fusion when expressed in a OLE1 deletion background. An analogous design with a C. albicans Ole1p leader sequence was used with the Z11 desaturase from H. zea. While active, this Ole1p-H. zea desaturase fusion did not significantly increase Z11-hexadecenoic acid titer. Additionally, a conservatively optimized A. transitella Z11 desaturase was active in both S. cerevisiae and C. viswanathii. The following study focused on testing the functional expression of the H. zea, T. ni, and A. transitella Z11 desaturases in two different Y. lipolytica strains, SPV140 and SPV300. Both native and Homo sapiens codon optimized sequences were used for the H. zea and T. ni desaturases while only the native sequence was used for A. transitella. Finally, the N-terminus of the Y. lipolytica Ole1p Z9 stearoly-CoA desaturase aligns more closely with insect desaturases than the N-terminus of Ole1p from either S. cerevisiae or C. albicans. Based on this alignment two additional desaturase versions were created. A putative leader sequence was swapped from the Y. lipolytica Ole1p onto the T. ni and H. zea desaturases.

Summary of Approach

A focused library of Z11 desaturases (insect origin: Amyelois transitella, Helicoverpa zea, Trichoplusia ni), which had observed activity in either S. cerevisiae or C. viswanathii were cloned into a double crossover cassette targeting the XPR2 locus with a URA3 selection marker. Protein coding sequences use either the native insect sequence (SEQ ID NOs: 17, 18), Homo sapiens optimized coding sequence (SEQ ID NOs: 19, 20), or the Homo sapiens optimized sequence with the N-terminal 84 bases (H. zea, SEQ ID NO: 22) or 81 bases (T. ni, SEQ ID NO: 21) swapped for the N-terminal 96 bases of the Y. lipolytica OLE1 (YALI0C05951) gene. Unlike in the S. cerevisiae and C. viswanathii screens, the leader sequence chimeras test a direct swap of leader sequences instead of concatenating a host leader sequence to the N-terminus of the full length desaturase coding sequence. Only the native coding sequence was used for the A. transitella desaturase (SEQ ID NO: 23).

Each of the 7 desaturase constructs was transformed into SPV140 (PO1f) and SPV300 (H222 ΔP ΔA ΔF ΔURA3) and site-specific integrants were confirmed.

Desaturase activity was tested via an in vivo bioconversion of hexadecanoic acid (palmitic acid) into (Z)-11-hexadecenoic acid (palmitvaccenic acid) in YPD medium.

GC-FID analyses were used to identify and quantify metabolites.

Results

Strain Construction

Desaturase variants were cloned into the pPV101 vector which contains a Y. lipolytica expression cassette targeting integration into the XPR2 locus.

The T. ni and H. zea desaturases were each synthesized with the native insect sequence (SEQ ID NOs: 17, 18), full length insect sequence codon optimized for Homo sapiens (SEQ ID NOs: 19, 20), or with the putative leader sequence replaced by the leader sequence from Y. lipolytica OLE1 desaturase (SEQ ID NOs: 21, 22). The A. transitella desaturase was also synthesized using the native insect coding sequence (SEQ ID NO: 23). All seven desaturase variants were transformed into SPV140. Based on previous activity results, only the H. zea and A. transitella desaturase variants were transformed into SPV300.

Functional Expression Assay

Functional activity was assessed by a modification of the protocol used for transmembrane desaturase expression in C. viswanathii SPV053. Briefly, Y. lipolytica SPV140 and SPV300 derived stains expressing insect desaturases were cultured in rich (YPD) to generate biomass. Using the YPD generated biomass, small scale (2 ml) cultures were cultivated with palmitic acid for a total of 48 hours in 24 deep well plates (See Materials & Methods for detail).

Figure 12:
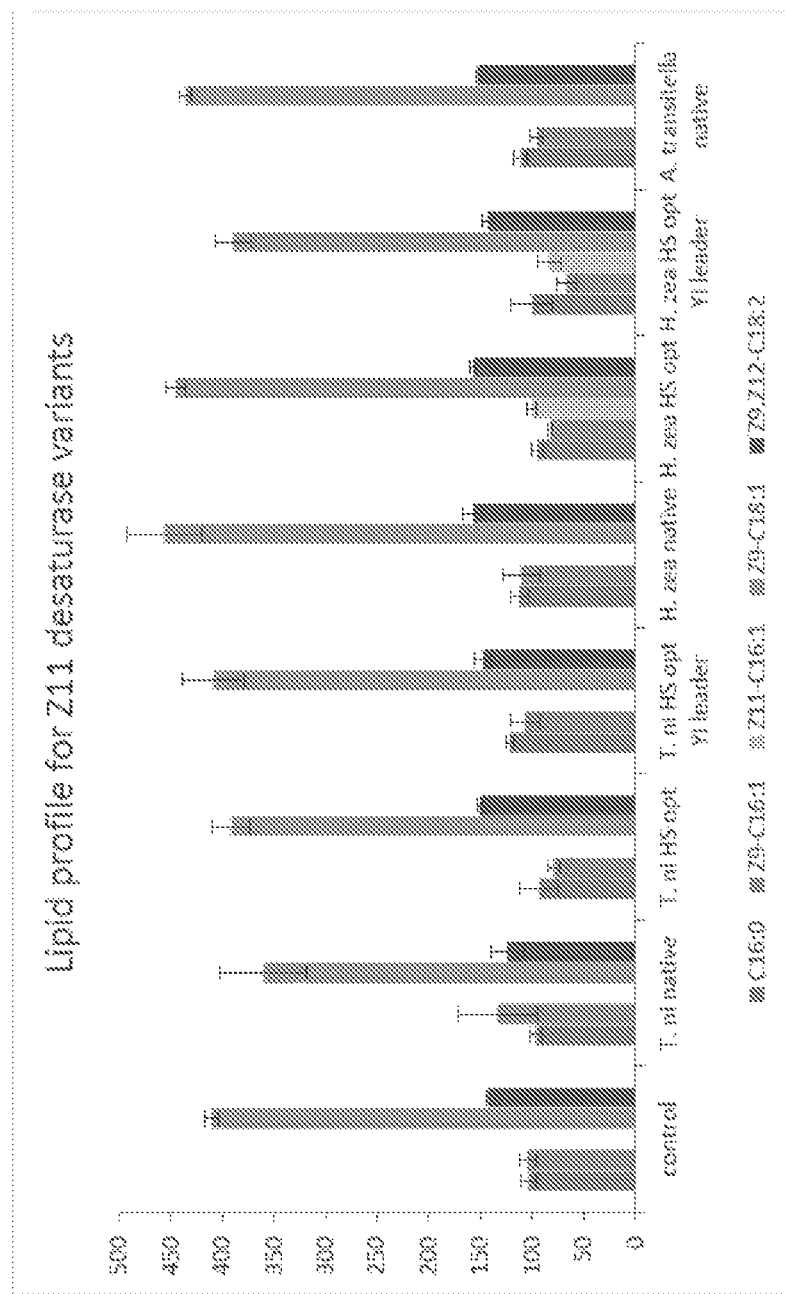
FIG. 12 shows only codon optimized *H. zea* desaturase variants produce detectable Z11-hexadecenoic acid in SPV140 screen. control=pPV101 integrants of SPV140, *T. ni* native=*T. ni* Z11 desaturase with native codon usage (pPV195), *T. ni* HS opt=*T. ni* Z11 desaturase with *Homo sapiens* codon optimization (pPV196), *T. ni* HS opt YI leader=*T. ni* Z11 desaturase with *Homo sapiens* codon optimization and swapped *Y. lipolytica* OLE1 leader sequence (pPV197), *H. zea* native=*H. zea* Z11 desaturase with native codon usage (pPV198), *H. zea* HS opt=*H. zea*

In the initial screen of T. ni, H. zea, and A. transitella variants, only H. zea desaturase variants that were codon optimized for Homo sapiens produced detectable Z11-hexadecenoic acid (FIG. 12). Expression of native H. zea desaturase conferred production of 100±5 mg/L Z11-hexadecenoic acid and the version with a *Y. lipolytica* OLE1 leader sequence produced 83±11 mg/L. As seen in FIG. 12, the distribution of the other major fatty acid species was relatively unaffected by functional desaturase expression. In the active strains, Z11-hexadecenoic acid made up ~10% (g/g) of the fatty acid species (including palmitic acid substrate which may be adsorbed to the outer cell surface).

A follow up experiment was conducted comparing active variants in the SPV140 background to SPV300 derived desaturase strains. The parent SPV300 and SPV140 expressing hrGFP were used as negative controls. The same bioconversion assay protocol was used. As in SPV140, only *H. sapiens* optimized variants produced detectable activity (FIG. 13). SPV300 strains grew to higher final cell densities (SPV300 OD600=26-28, SPV140 OD600=19-22) (FIG. 14). The highest titers were observed for strains expressing the native *H. zea* Z11-desaturase with *H. sapiens* codon optimization (pPV199). The retested SPV140 strains produced 113±1 mg/L (5.5±0.2 mg/L/OD) Z11-hexadecenoic acid which is 13% higher than titers observed in the first experiment (FIG. 15). SPV300 strains expressing the same desaturase generated a wider range of productivity. On average they produced 89±18 mg/L (3.3±1.2 mg/L/OD) Z11-hexadecenoic acid, but one clone produced 124 mg/L (4.6 mg/L/OD) Z11-hexadecenoic acid (FIG. 15).

In summary, only the *H. zea* Z11 desaturase variants with *Homo sapiens* codon optimization produced detectable Z11-hexadecenoic acid. Under the current assay condition, marginally higher titers were observed in the SPV140 background over SPV300. Table 14 summarizes the Z11-hexadecenoic acid titers.

TABLE 14

Z11-hexadecenoic acid titers obtained from expression of exemplary desaturases in *Yarrowia lipolytica*

| Desaturase | Codon optimization | Parent Strain | Z11-hexadecenoic acid titer (mg/L) |
|---|---|---|---|
| Z11 *T. ni* | Native | SPV140 | ND |
| Z11 *T. ni* | Homo sapiens | SPV140 | ND |
| Yl OLE1-Z11 *T. ni* | Homo sapiens | SPV140 | ND |
| Z11 *H. zea* | Native | SPV140 | ND |
|  |  | SPV300 | ND |
| Z11 *H. zea* | Homo sapiens | SPV140 | 100 ± 5 |
|  |  | SPV300 | 87 ± 18 |
| Yl OLE1-Z11 *H. zea* | Homo sapiens | SPV140 | 83 ± 11 |
|  |  | SPV300 | 55 ± 1 |
| Z11 *A. transitella* | Native | SPV140 | ND |
|  |  | SPV300 | ND |

In SPV300, one non-site-specific integrant of pPV200 (*Y. lipolytica* OLE1-*H. zea* Z11 desaturase with *Homo sapiens* codon optimization) was tested. This integrant did not produce detectable Z11-hexadecenoic acid, while the two site-specific integrants produced 55±1 mg/L.

No major hydroxy or diacid peaks were observed from pellets of SPV140 or SPV300 derived strains, and deletion of β-oxidation/ω-oxidation genes in SPV300 did not increase Z11-hexadecenoic acid accumulation under the current assay condition (relatively low substrate concentration, rich medium).

Conclusions

The *H. zea* Z11 desaturase is active and confers production of ~100 mg/L Z11-hexadecenoic acid, from ~500 mg/L palmitic acid substrate. The functional expression was demonstrated across three positive integrants and replicate experiments in a 24 well plate assay.

*H. zea* desaturase required codon optimization (*Homo sapiens* or potentially *Y. lipolytica*) for activity in *Y. lipolytica*.

The *T. ni* Z11 desaturase, while active in *S. cerevisiae*, does not produce detectable Z11-hexadecenoic acid in *Y. lipolytica*.

The reproducibility of the assay for *Y. lipolytica* strains can be confirmed starting from glycerol stock.

*A. transitella* desaturase can be codon optimized for expression in *Y. lipolytica*.

Since *Y. lipolytica* is a candidate production host, additional copies of active desaturases can be integrated in *Y. lipolytica*, culture conditions to improve bioconversion can be identified, and substrate conversion can be quantified.

Materials & Methods

Strain Construction

All desaturase genes were synthesized (Genscript). Either native sequences or *Homo sapiens* codon optimization was used. Synthesized genes were subcloned into pPV101. Plasmids were transformed and prepped from *E. coli* EP1400 using the Zyppy Plasmid Miniprep Kit (Zymo Research, Irvine, Calif.). Approximately ~1-2 µg of linearized DNA was transformed using Frozen-EZ Yeast Transformation II Kit (Zymo Research, Irvine, Calif.). The entire transformation mixture was plated on CM glucose -ura agar plates. Positive integrants were found to be site-specific and genotyping was conducted by check PCR.

Functional Expression Assay

Palmitic Acid Supplementation in YPD

Positive isolates were re-patched onto YPD, grown overnight, and then stored at 4° C. Strains were inoculated from patch plates into 2 ml of YPD in 24 deep well plates (square well, pyramid bottom). Three positive clones were inoculated for each desaturase variant. Three isolates of pPV101 in SPV140 and the parent SPV300 were used as negative controls. Deep well plates were incubated at 28° C. and 250 rpm in the Infors Multitron refrigerated flask shaker for 24 hrs. After 24 hrs of incubation, a 1 ml volume of each culture was pelleted by centrifugation at 500×g. Each pellet was resuspended in 2 ml of YPD. 500 mg/L palmitic acid was added to cultures from a 90 g/L stock solution in ethanol. The result was the addition of 0.5% ethanol with the palmitic acid substrate. All cultures were incubated for 48 hours before endpoint sampling. Final cell densities were measured with the Tecan Infinite 200pro plate reader. 0.75 or 0.8 ml of each culture was harvested in 1.7 ml microcentrifuge tubes and pelleted. Supernatant was removed and pellets were processed as described below.

Metabolite Extraction and GC-FID Analysis

Total lipid composition as well as the (Z)-11-hexadecenoic acid quantification was based on modified procedures by Moss et al. (1982) (Moss, C. W., Shinoda, T. & Samuels, J. W. Determination of cellular fatty acid compositions of various yeasts by gas-liquid chromatography. *J. Clin. Microbiol.* 16: 1073-1079 (1982)) and Yousuf et al (2010) (Yousuf, A., Sannino, F., Addorisio, V. & Pirozzi, D. Microbial Conversion of Olive Oil Mill Wastewaters into Lipids Suitable for Biodiesel Production. *J. Agric. Food Chem.* 58: 8630-8635 (2010)). The pelleted cells (in 1.5 mL plastic tubes), usually about 10 mg to 80 mg, were resuspended in methanol containing 5% (w/w) of sodium hydroxide. The alkaline cell suspension was transferred into a 1.8 mL crimp vial. The mixture was heated for 1 h in the heat block at 90° C. Prior to acidification with 400 2.5 N HCl the vial was allowed to cool to room temperature. 500 µL chloroform containing 1 mM methyl heptadecanoate were added and the mixture was shaken vigorously, then both aqueous and organic phase were transferred into a 1.5 mL plastic tube. The mixture was centrifuged at 13,000 rpm, afterwards 450 µL of the organic phase were transferred into a GC vial. For the analysis of lipids and the quantification of fatty acids 50 µL of 0.2 M TMSH (trimethylsulfonium hydroxide in methanol) was added and the sample analyzed by GC-FID.

Example 4: Production of Z11-14Acid in *Yarrowia lipolytica*

Background and Rationale

*Yarrowia lipolytica* was engineered to produce Z11-14Acid, the precursor to target Lepidoptera pheromone Z11-14Ac.

A library of 73 desaturases was chosen to target potential pheromones including Z11-14Ac, Z7-12Ac, Z9E12-14Ac, E8E10-C12OH and Z9E11-14Ac. All desaturases were tested in the H222 ΔPΔAΔF (SPV300) background.

Eleven desaturases were identified from literature to have Δ11 activity (DST001-DST009, DST030, and DST039, Table 15). All desaturases were screened by feeding either methyl palmitate (C16), methyl myristate (C14), or methyl laurate (C12) as substrate, and full product profiles were determined by GC analysis.

The resulting activity of the purported Δ11 desaturase library, and other desaturases shown to produce Δ11 compounds, specifically Z11-14Acid, is discussed.

TABLE 15

Desaturases discussed in Example 4

| Enzyme Code | Organism of origin | GenBank Accession |
|---|---|---|
| DST001 | *Argyrotaenia velutinana* | AF416738 |
| DST002 | *Spodoptera litura* | AGH12217.1 |
| DST003 | *Sesamia inferens* | AII21943.1 |
| DST004 | *Manduca sexta* | CAJ43430.2 |
| DST005 | *Ostrinia nubilalis* | AF441221 |
| DST006 | *Helicoverpa zea* | AAF81787.1 |
| DST007 | *Choristoneura rosaceana* | AF545481 |
| DST008 | *Drosophila melanogaster* | AJ271414 |
| DST009 | *Spodoptera littoralis* | AY362879 |
| DST030 | *Lampronia capitella* | ABX71630.1 |
| DST039 | *Amyelois transitella* | NP001299594.1 |

Results

Up to 69 mg/L Z11-14Acid production was observed when feeding 2 g/L methyl myristate to the desaturase library (FIG. 16). The current best desaturase, *Helicoverpa zea* (Hz) DST (SPV459, encoded by amino acid sequence set forth in SEQ ID NO: 1, nucleotide sequence set forth in SEQ ID NO: 20), in addition to desaturases DST001 through DST007, DST030 and DST039, produce some amount of Z11-14Acid ranging from 16 mg/L to 69 mg/L. DST001 (*A. velutinana*), DST004 (*M. sexta*), and DST039 (*A. transitella*) are more specific for Z11-14Acid production than Z11-16Acid production, although these desaturases produce ~20 mg/L Z11-14Acid. Strains producing higher Z11-14Acid titer also produced Z9-14Acid from the methyl myristate substrate at 20-30 mg/L, which was reduced compared to the negative control SPV298. The C14-C18 product profile of Hz DST (SPV459) compared to SPV298 is shown in FIG. 17.

Proof-of-concept of Z11-14Acid synthesis is shown. Attempts were made to identify enzymes that had improved Z11-16Acid titer or product specificity over *Helicoverpa zea* DST (1.05 g/L Z11-16Acid; 69 mg/L Z11-14Acid). While there were no desaturases that had higher production than Hz DST (SPV459), DST003 (SEQ ID NO: 2) had similar production phenotypes to the HzDesat strain, and DST002 and DST005 had similar Z11-16Acid production with reduced Z11-14Acid. The desaturase in DST006 is genetically equivalent to the *H. zea* desaturase expressed in SPV459 and served as a library control. DST006 produced equivalent levels of Z11-16Acid when fed methyl palmitate; however this strain produced a lower titer of Z11-14Acid on methyl myristate. Genetic variation in strain background may account for the observed difference.

DST039 (*A. transitella*) was previously screened under different conditions. In rich media, Z11-16Acid production with the native *A. transitella* coding sequence was not observed. The *H. sapiens* optimized sequence was tested and still no activity was observed with the rich medium condition. In this screen, DST039 was tested in nitrogen limited condition with Hs optimized sequence and resulted in 235 mg/L production of Z11-16Acid and 21 mg/L Z11-14Acid on the relevant substrates.

Δ11 products from DST008 (*Drosophila melanogaster*) or DST009 (*Spodoptera littoralis*) in the SPV300 background were not observed.

SUMMARY

Z11-14Acid production was observed in ten desaturases with titers ranging from 16 mg/L to 69 mg/L (2 g/L methyl myristate fed).

*H. zea* DST (encoded by amino acid sequence set forth in SEQ ID NO: 1, nucleotide sequence set forth in SEQ ID NO: 20) remained the best Z11-16Acid producer (>1 g/L when fed with methyl palmitate).

DST003 (*S. inferens*, SEQ ID NO: 2) has the most similar phenotype to *H. zea* DST.

DST002 (*S. litura*) and DST005 (*O. nubialis*) are more specific than *H. zea* DST for Z11-16Acid production (reduced Z11-14Acid production).

DST001 (*A. velutinana*), DST004 (*M. sexta*), and DST039 (*A. transitella*) are more specific than *H. zea* DST for Z11-14Acid production.

Conclusions

Z11-14Acid can be produced with the heterologous expression of specific desaturases in *Yarrowia lipolytica* when feeding methyl myristate.

Multiple copies of desaturase (identical or combination of sequences) are integrated in improved strain backgrounds for increased Z11-14Acid titer, product specificity, and genetic stability.

Materials & Methods

Library Generation

Desaturase sequences were provided to Genscript for codon optimization (*Homo sapiens* expression organism) cloning into pPV266 (XPR2 locus integration vector with TEF promoter and terminator) using PacI/SapI restriction digestion. Lyophilized DNA was provided as well as EP400 agar stabs. Desaturase constructs are listed in Table 16.

Constructs were linearized using PmeI restriction enzyme and directly transformed into host strain SPV300. Transformants were verified by check PCR using primers outside of the XPR2 integration junction and within the pTEF promoter.

TABLE 16

Desaturase constructs

| Enzyme Code | Species | GenBank Accession | E. coli SPV | Plasmid pPV |
|---|---|---|---|---|
| DST001 | Argyrotaenia velutinana | AF416738 | SPV0609 | pPV0300 |
| DST002 | Spodoptera litura | AGH12217.1 | SPV0610 | pPV0301 |
| DST003 | Sesamia inferens | AII21943.1 | SPV0611 | pPV0302 |
| DST004 | Manduca sexta | CAJ43430.2 | SPV0612 | pPV0303 |
| DST005 | Ostrinia nubilalis | AF441221 | SPV0613 | pPV0304 |
| DST006 | Helicoverpa zea | AAF81787.1 | SPV0614 | pPV0305 |
| DST007 | Choristoneura rosaceana | AF545481 | SPV0615 | pPV0306 |
| DST008 | Drosophila melanogaster | AJ271414 | SPV0616 | pPV0307 |
| DST009 | Spodoptera littoralis | AY362879 | SPV0617 | pPV0308 |
| DST030 | Lampronia capitella | ABX71630.1 | SPV0638 | pPV0329 |
| DST039 | Amyelois transitella | NP_001299594.1 | SPV0647 | pPV0338 |

Plasmid Digest

~10 μg of lyophilized DNA was ordered from Genscript. DNA was resuspsended in 50 μL water for a final concentration of ~200 ng/μL. 10 μL of DNA was mixed with 1.25 μL 10× CutSmart Buffer and 1.25 μL PmeI restriction enzyme (12.5 μL reaction volume). The reaction was incubated in the PCR machine for 1.5 hours at 37° C. and heat inactivated at 65° C. for 30 minutes.

Transformation

SPV300 competent cells were grown by inoculating a YPD culture at 0.001 OD in a baffled flask and growing until 0.5-1.0 OD. Cells were harvested at 800×g and washed with 0.25× volume of Solution 1 from the Zymo Frozen-EZ Transformation II Kit for Yeast. Cells were resuspended in Solution 2 at 1000× concentration of the original culture volume and slowly frozen at −80° C. while insulated in a styrofoam container (frozen cells may have better transformation efficiency over fresh). 50 μL of cells were first mixed with the 12.5 μL digestion reaction (no cleanup necessary), and then with 500 μL Solution 3. Transformations were incubated for 3 hours at 28° C. without shaking, after which the full transformation mixture was plated to appropriate selective agar media. Petri dishes were incubated for 3-4 days before the appearance of colonies.

Check PCR

Transformation colonies were picked to 7 μL water in a PCR plate. 5 μL of cells were patched by multichannel to selective omni trays and grown overnight. The remaining 2 μL of cells were microwaved for 2 minutes before adding 15 μL of PCR master mix.

| PCR Master Mix | 1X reaction |
|---|---|
| 2× Phusion Master Mix (HF Buffer) | 7.5 μL |
| 100 μM OPV204 (XPR2 locus F) | 0.1 μL |
| 100 μM OPV195 (pTEF R) | 0.1 μL |
| Water | 7.3 μL |

PCR Cycle:

| Temp. | Time | Cycles |
|---|---|---|
| 98° C. | 2 min | 1× |
| 98° C. | 15 sec | 30× |
| 64° C. | 30 sec | |
| 72° C. | 60 sec | |
| 72° C. | 5 min | 1× |
| 4° C. | ∞ | 1× |

Colony Patching

Positive clones were re-patched to YPD omni trays in 24-well format including assay controls. Omni trays were grown overnight at 28° C. and used to inoculate bioassay cultures.

Bioassay

Positive transformants (N=4 clones per construct) were inoculated into 1 mL YPD in a 24-well culture plate and incubated for 24 hours in the Infors HT Mulitron Pro at 28° C. with 1000 rpm shaking. Cells were pelleted at 800×g and resuspended in S2 media with 5 μL substrate (~2 g/L concentration). 250 μL of culture was sampled into glass crimp top vials after 48 hours of bioconversion.

S2 Media 2 g/L Yeast Extract, 1 g/L Peptone, 0.1M Phosphate buffer, 1.7 g/L YNB w/o aa, NH4, 60 g/L Glucose, 5 g/L Glycerol GC Sample Processing Front Inlet/Detector:

| System | 6890 GC, ChemStation Rev. B.03.02 (341) |
|---|---|
| Column | J&W DB-23 30 m × 25 mm × 25 um |
| | Run Time = 14.4 min |
| Inlet | Heater = 240° C.; Pressure = 9.0 psi; Total Flow {H2} = 36.2 mL/min |
| Carrier | H2 @ 1.0 mL/min, 9.0 psi, 35 cm/sec |
| Signal | Data rate = 2 Hz/0.1 min |
| Oven | 150° C. for 1 min |
| | Ramp 12° C./min to 220° C., hold 3 min |
| | Ramp 35° C./min to 240° C., hold 4 min |
| | Equilibration Time: 2 min |
| Injection | Split, 240° C. |
| | Split ratio - 30:1; 29.1 mL/min |
| Detector | FID, 240° C. |
| | H2 @ 35.0 mL/min, Air @ 350 mL/min |
| | Electrometer {Lit Offset} @ 2.0 pA |
| Sample | Injection volume = 1 μL |

Back Inlet/Detector:

| System | 6890 GC, ChemStation Rev. B.03.02 (341) |
|---|---|
| Column | J&W DB-23 30 m × 25 mm × 25 um |
| | Run Time = 14.4 min |
| Inlet | Heater = 240° C.; Pressure = 9.0 psi; Total Flow {H2} = 40.1 mL/min |
| Carrier | H2 @ 1.1 mL/min, 9.8 psi, 38 cm/sec |
| Signal | Data rate = 2 Hz/0.1 min |
| Oven | 150° C. for 1 min |
| | Ramp 12° C./min to 220° C., hold 3 min |
| | Ramp 35° C./min to 240° C., hold 4 min |
| | Equilibration Time: 2 min |
| Injection | Split, 240° C. |
| | Split ratio - 30:1; 32.3 mL/min |
| Detector | FID, 240° C. |
| | H2 @ 35.0 mL/min, Air @ 350 mL/min |
| | Electrometer {Lit Offset} @ 2.0 pA |
| Sample | Injection volume = 1 μL |

TMSH: Trimethylsulfonium Hydroxide (0.2 mol/L in Methanol)—VWR TCT1576-025ML

Example 5: Transformation of Fatty Acid Methyl Ester (Z11-16FAME) Precursor to Z11-16Ald Background and Rationale Z11-16Ald is one active ingredient (AI) of interest in the present disclosure. Research and development around synthesis of this AI centers on four major areas, namely: 1. Biocatalyst engineering 2. Fermentation process development 3. Downstream process (DSP) development (transformation of microbially produced Z11-16 precursors into purified Z11-16FAME). 4. The final chemical transformation of the FAME precursor to the target AI (either to acetate or aldehyde).

DSP involves transforming Z11-16Acid-containing microbial lipids into Z11-16FAME, and its subsequent enrichment via distillation, and chemical conversions into Z11-16Ald. An illustration of the designed process to yield crude Z11-16FAME is depicted in FIG. 18. Initially, multiple options of DSP at each stage were scouted. The most efficient method and its compatibility with industrial instruments for each stage was determined. The selection of a method was also evaluated based on its estimated cost contribution in the overall pheromone Cost of Manufacturing.

This Example focuses on proof-of-concept of the final chemical transformation of Z11-16FAME precursor to Z11-16Ald.

Results

Generation of Z11-16FAME

1. Heat Kill Fermentation, and 2. Separation of Cells

The fermentation culture of SPV459 was heated to 70° C. and held there for 3 h to heat kill the cells and inactive lipases. Before filtration, filter aid was added. The Seitz filter casing was equipped with filter cloth. Immediately after filling up the Seitz filter and applying a pressure of 0.5 bar, approximately 250 mL of the first filtrate were collected and the filtration was stopped. The turbid filtrate was refilled into the Seitz filter and the filtration was continued at 1 bar N2.

3. Extrusion

The cake was pressed into the vane and for the formation of pellets, the nascent yeast pellets were scraped off with a spatula.

4. Drying

Drying was performed in a ventilated oven. The pellets were uniformly distributed in a monolayer on a metal tray and dried in the ventilated oven for 20 h at 36° C.

5. TAG Extraction, 6. Debri Separation, 7. Evaporation

A 500 mL three-neck flask was equipped with 65 g cell pellets, a mechanical stirrer, thermometer, and reflux condenser. After the addition of 330 mL n-heptane the mixture was heated to 70° C. and stirred at 40 rpm. The mixture was kept at 70° C. for 3 h. The still hot mixture was filtered directly through the Seitz pressure filter using the same 20-micron filter cloth, which was used initially for cell filtration. After the first filtering the empty three neck flask was washed out with. 50 mL n-heptane. The wash heptane was used to flush through the filter and was collected into the same flask as the first filtrate. After filtering the pellets were placed back into the same flask as before and the filtrate was evaporated under reduced pressure at 50° C. The weight of the extract was determined and a sample of the extract was taken for GC and acid value analysis.

For the 2nd extraction step 250 mL n-heptane were added and the mixture was stirred for 1.5 h. Workup and sampling was identical to the 1st extraction step. The 3rd extraction was performed nearly identical to the 2nd extraction, except that the extraction time was prolonged to 2 h.

8. Esterification, 9. Transesterification, 10. Separation/Evaporation, 11. Drying A 500 mL three-neck flask was equipped with 17.36 g TAG extract, 100 ml methanol, a mechanical stirrer, thermometer, and reflux condenser. After addition of 0.506 g p-toluene sulfonic acid monohydrate (2.66 mmol) the mixture was heated to 60° C. (set temp 60° C.; actual temp 53.8° C.) and stirred at 180 rpm. After the final temperature was reached, the stirring was increased to 240 rpm and 3 mL of trimethyl orthoacetate (23.57 mmol) were added. The reaction was monitored with TLC. After 60 min, the TLC indicated that all palmitic acid leftovers were converted. Before the addition of 1 mL sodium methoxide solution (25% in methanol, 4.36 mmol) another portion of 2 mL trimethyl orthoacetate (15.71 mmol) were added. The mixture was stirred for another 80 min and monitored via TLC. After all TAG was converted the reaction was quenched with 0.4 mL acetic acid. The mixture was extracted with 100 ml n-heptane. The organic layer was separated and the aqueous layer extracted with another 20 mL n-heptane. The organic phases were combined and washed with 30 mL dH2O. The organic phase was concentrated in vacuo.

12. Distillation

A 100 mL round bottom flask was filled with 30g of crude FAME. A magnetic stir bar was added to the pot contents. The flask was equipped with a Vigreux column connected to a micro-distilling variable-reflux distillation head for fractional collection of distillate. The distillation head was fitted with a thermometer, cold finger, collection flask, and vacuum line. The setup was insulated. The distillation was performed under reduced pressure at around 500 mtorr, with a temperature up to 250° C. Different fractions were collected and analyzed via GC.

Reduction

Briefly based on the protocols of (Bažant, V., et al. "Properties of sodium-bis-(2-methoxyethoxy) aluminiumhydride. I. Reduction of some organic functional groups." Tetrahedron Letters 9.29 (1968): 3303-3306) and (Anonymous 2014), a dry three-neck flask was equipped with a dropping funnel, a magnetic stirring bar, and septa. After pruging the flask with argon, the flask was placed in an ice bath. The flask was charged with 10 mL anhydrous tetrahydrofuran and 2.36 g of Z11-16FAME (about 70% purity). The dropping funnel was equipped with 20 mL anhydrous tetrahydrofuran and 3.13 mL (21.98 mmol) 60% SMEAH reagent in toluene. After cooling the mixture to 0° C., the SMEAH solution was added dropwise over a time period of 30 min. After SMEAH addition the ice bath was replaced and the mixture was stirred for 4 h. The reaction was quenched with 5 mL 10% sulfuric acid and the product was extracted two times with 20 mL methyl tert-butyl ether. The organic phases were combined and dried over anhydrous sodium sulfate and concentrated in vacuo.

TEMPO-Bleach Oxidation of Z11-Hexadecenol to Z11-Hexadecenal

Into a 250 mL glass beaker containing 50 mL of Buffer solution (Dissolve 10.08 g $NaHCO_3$, 15.3 g $Na_2HPO_4$, and 1.44 g $NaH_2PO_4$ in 500 mL $H_2O$, pH=7.8), tetrabutylammonium hydrogensulfate (TBAH) (407 mg), 30 mL of toluene containing 2.89 g of Z11-hexadecenol (54.3% purity), and 1 mL of HO-TEMPO solution (207 mg/mL in toluene) was added. The mixture was stirred via a Silverson Mixer at 4000 RPM for 30 seconds, after which 25 mL of the 4.4% Bleach solution (pH 8.58) was added via a syringe pump over 90 seconds. With stirring, temperature and pH of the reaction were monitored over the course of 8 minutes. After 8 min of stirring, the reaction was neutralized with addition of 550 µL of concentrated HCl to a measured pH of 7.06. The reaction mixture was transferred into a separatory funnel and extracted with toluene. The organic layer was collected and concentrated in vacuo.

A GC-FID trace of the Z11-hexadecenol starting material is shown in FIG. 19.

pH and temperature over the course of the oxidation reaction is shown below:

| Time (min) | pH | Temp (° C.) |
|---|---|---|
| 0 | 7.65 | 18 |
| 1.5 | 8.23 | 22.5 |
| 2 | 8.38 | 24.3 |
| 3 | 8.44 | 24 |
| 4 | 8.5 | 24 |
| 5 | 8.53 | 24 |
| 6 | 8.57 | 24 |
| 7 | 8.59 | 23.8 |
| 8 | 8.61 | 24 |

A GC-FID trace of oxidation products is shown in FIG. 20.

Reaction Results are shown below:

| Z11-16OH (mg) | | Product Quantity (mg) | Conversion | Selectivity (%) | | | Yield |
|---|---|---|---|---|---|---|---|
| Input | Consumed | Z11-16OH | Z11-16Ald | (%) | Z11-16OH | Z11-16Ald* | Other | (%) |
| 1570 | 1570 | 0 | 895 | 100 | 0 | 58 | 42 | 57.5 |

Product Concentration Calculation $$Z11-16Ald\ [mg/ml] = \frac{\frac{Z11-16Ald\ \text{Peak Area}}{(1-\text{tetradecanol Peak Area})} - (\text{Calibration curve intercept})}{(mg\ of\ 1-\text{tetradecanol})} * (\text{Calibration Curve slope})$$

Calibration Curve Based on 1-Tetradecanol Internal Standard:

| Front Detector Calibration Curves Derivatization with BSTFA | | | |
|---|---|---|---|
| Analytes | Equation | Slope | y-intercept |
| OH | Y = 1.0283X + 0.029 | 1.0283 | 0.029 |
| Ald | Y = 0.7214X + 0.0232 | 0.7214 | 0.0232 |

Analytics

All samples were analyzed on an Agilent 6890 GC, equipped with a J&W DB-23 column. For the analysis of bleach oxidation samples the following temperature program was used: 100° C. for 1 min, ramp 5° C./min to 200° C., hold 3 min, ramp 35° C./min to 240° C., hold 10 min. All other samples were derivatized with KOH/H$_2$SO$_4$ and analyzed with the following program: 150° C. for 1 min, ramp 12° C./min to 220° C., hold 3 min, ramp 35° C./min to 240° C., hold 4 min.

Example 6: Improved Z11-16Acid Producing Strains

Background and Rationale

Screening of a small library of Z11 specific insect desaturases identified the variant from *Helicoverpa zea* as the most active in a *Y. lipolytica* H222 ΔP ΔA ΔF background on a 16Acid substrate (See Example 3). Three integrants of the *H. zea* desaturase were screened and stored in the strain database as SPV458, SPV459, and SPV460. SPV459 produced a higher titer than sister strains SPV458 and SPV460 in the initial screening and was selected for further process development. SPV459 was also initially selected for further strain engineering, but the selection marker could not be stably removed from the strain. SPV458 was selected to replace SPV459 for strain engineering purposes and the marker was successfully rescued from SPV458. A total of 22 plasmid constructs were integrated into SPV739, the marker rescued descendant of SPV458. Strains harboring additional copies of the *H. zea* desaturase produced increased Z11-16Acid titer. Four of those strains were evaluated for improved performance in both a Biolector small-scale assay and in DASGIP 1 L fermentors. Strains harboring additional desaturase copies performed better than their SPV458 parent, but did not outperform SPV459. Two strains, SPV968 and SPV969, were selected for further engineering based on these results. These two strains were marker rescued and additional DNA cassettes were integrated to create a small library of strains with 2 or 3 copies of Z11 desaturase and deletions of key lipid metabolism genes (FIG. 21).

Additionally, several changes were made to improve the Biolector assay. While generally predictive of strain performance at the 1 L scale, lower cell densities and maximum titers were observed in the Biolector assay. To increase cell density, enhance titers, and improve correlation with fermentation performance, a semi-defined medium used in Fermentation Batch Process v1.1 (SOP026.2) was selected. The current fermentation process also uses an incubation temperature of 32° C. Temperatures of 28° C. and 32° C. were compared using the new medium. Finally, the current fermentation fed-batch process utilizes an initial batch phase with higher glycerol and lower glucose concentrations. An alternative Biolector batch medium was tested with 60 g/L glycerol and 40 g/L glucose.

Improved Z11-16Acid B$_d$ (biodesaturation) strains were identified through gene deletions of lipid mobilization genes and integration of additional copies of Z11-16Acid desaturases.

Response of the improved Z11-16Acid B$_d$ strains to differences in co-substrate composition (glycerol and glucose concentration) were investigated.

Approach

Linear DNA cassettes expressing either the *Helicoverpa zea* desaturase (amino acid sequence set forth in SEQ ID NO: 1; codon optimized nucleotide sequence set forth in SEQ ID NO: 20) or *Sesamia inferens* Z11 desaturase (amino acid sequence set forth in SEQ ID NO: 2; codon optimized nucleotide sequence set forth in SEQ ID NO: 39) were integrated in *Y. lipolytica* H222 ΔPΔAΔF (SPV298) derived strains at multiple loci.

Resulting strains were assayed in 700 µl bioconversions using 48-well flower plates in the M2P Labs Biolector.

Two incubation temperatures were tested, 28 and 32° C.

Two media compositions were tested for a subset of strains. Media were identical except for the glucose and glycerol content. Both media contained: 1.7 g/L yeast nitrogen base without ammonium sulfate or amino acids, 1 g/L yeast extract, 3.3 g/L ammonium sulfate, 100 mM potassium phosphate buffer, and 8.5 mg/L iron sulfate. A total of 20 g/L 16ME (methyl palmitate) was added as two 10 g/L boluses. The co-substrate concentrations were as follows:

High glucose primary medium: 120 g/L glucose and 5 g/L glycerol

High glycerol medium: 40 g/L glucose and 60 g/L glycerol

Growth rate, Z11-16Acid specific productivity, maximum Z11-16Acid titer, and Z11-16Acid selectivity were compared across strains.

Selectivity is defined as:

$$S = \frac{gZ11-16Acid}{g16Acid_s + g16Acid_i + gZ9-16Acid + gZ11-16Acid + g18Acid + gZ9-18Acid + gZ9Z12-18Acid},$$

Here the g16Acid$_s$ is unconverted substrate and g16Acid$_i$ is 16Acid which has been internalized and stored as triacylglyceride or another intracellular lipid.

Results

Nine second- and third-generation strains were tested in addition to the first-generation controls SPV458 and SPV459. All constructs contained copies of the H. zea Z11 desaturase except for SPV1060 which contained one copy of the H. zea Z11 desaturase and one copy of the S. inferens Z11 desaturase identified in the first-generation desaturase library (DSTg1) (See Example 4). Some strains also contained deletions of key genes in lipid metabolism: FAT1 (fatty acyl-CoA synthetase/fatty acid transporter), TGL3 (intracellular triacyl glycerol lipase), and GUT2 (glycerol-3-phosphate dehydrogenase). The Gut2p dehydrogenase catalyzes the second reaction in the glycerol utilization pathway converting glycerol-3-phosphate to DHAP. A GUT2 knockout grown in the presence of high concentrations of glycerol would likely build up high concentrations of glycerol-3-phosphate which may cause dysregulation of catabolism. This was observed in screening of second-generation strains. To avoid this growth inhibition, GUT2 deletion strains were grown in a medium without glycerol (See Materials and Methods).

High Glucose Medium with Comparison of 28 and 32° C. Incubation Temperature (HSD036, HSD043, HSD055, HSD056, and HSD061)

Growth Rate

Five independent experiments were run testing bioconversions in the High Glucose Medium at both 28 and 32° C. All 11 strains were tested under at least one temperature condition. Initial growth rates were similar regardless of genotype (FIG. 22A). At 28° C. growth rates were between 0.21 and 0.23 h$^{-1}$. Growth rates were slightly higher for some strains at 32° C. with an overall range of 0.23-0.24 h$^{-1}$. Strains incubated in the High Glucose without Glycerol medium used in HSD043 grew at a slower rate (0.13-0.14 h$^{-1}$) indicating that even 5 g/L of glycerol can have a significant positive impact on growth rate (FIG. 23).

Specific Productivity

In the High Glucose Medium, maximum specific productivities (gZ11-16Acid/L-OD-h) were observed at the first sampling at 23 hours (with substrate addition occurring at 7 hours). In some cases, especially at 32° C., specific productivities were sustained through later timepoints. At 28° C. both second- and third-generation strains derived from SPV458 displayed higher specific productivities than SPV459 (FIG. 22B). A nearly linear dependence of specific productivity on desaturase copy number (~2 mg/L-OD-h-copy #) was observed for the first two desaturase copies (FIG. 24A). Addition of the third desaturase copy leads to a smaller increase in specific productivity.

At 32° C. higher specific productivities are observed across all strains save three: SPV1056, SPV1199, and SPV1200 (FIG. 22B, FIG. 24B). These three were all strains harboring three copies of the H. zea desaturase and all contain a FAT1 deletion. SPV1199 and SPV1200 have identical genotypes with TGL3 deletions, but were derived from separate lineages, SPV968 and SPV969 respectively (FIG. 21). The observed drop is not solely dependent on the presence of a FAT1 deletion because SPV968, the parent of SPV1056 and SPV1199, contains a FAT1 deletion and displayed a higher average specific productivity at 32° C. (FIG. 22B, FIG. 24B). The same linear dependence of specific productivity on desaturase copy number was observed at 32° C. (FIG. 24B). The slope increased to ~2.5 (mg/L-OD-h-copy #).

Z11-16Acid Titer

Maximum Z11-16Acid titers were consistently observed at the final 48-hour sampling. Maximum specific productivities correlate moderately well with 48-hour titer (FIG. 25A). Variation in how well productivities are sustained leads to a spread in the data.

Three strains in the SPV969 lineage containing the TGL3 deletion sustained productivity longer, leading to higher titers (FIG. 22C). SPV969 produced 5.06±0.17 g/L at 32° C. Strain SPV1058 with three H. zea desaturase copies consistently sustained productivity leading to the largest observed titers, 5.79±0.01 g/L at 28° C. and 6.1±0.08 g/L at 32° C. A second descendent of SPV969, SPV1059, contained both TGL3 and GUT2 deletions. When cultured in High Glucose without Glycerol Medium, a single replicate of SPV1059 survived without becoming hypoxic due to seal clogging and reached a titer of 5.39 g/L (See Materials and Methods for description of seal clogging).

While strains SPV968 and SPV1056 displayed similar maximum specific productivities to strains in the SPV969 lineage at 28° C., productivity tapered more rapidly leading to 48-hour titers of 2.27±0.07 g/L and 3.09±0.23 g/L, respectively. At 32° C. productivity was sustained longer leading to higher final titers. SPV968 produced 3.55±0.22 g/L Z11-16Acid. SPV1056 reached a final 48-hour titer of 3.80±0.09 g/L at 32° C. The control SPV459 produced 2.36±0.03 g/L at 28° C. and 3.70±0.33 g/L at 32° C. (FIG. 22C).

Selectivity and Lipid Content

Selectivity at 48 hours was also used to gauge strain performance. As defined above, selectivity indicates both how selectively the biocatalyst produces Z11-16Acid over other fatty acid products and how well the 16Acid substrate is converted to product. For most strains, selectivity was higher at 32° C. (FIG. 26A). This primarily results from sustained conversion of 16Acid to Z11-16Acid as native fatty acid titers are consistent and relatively low at both temperatures. As a result, selectivity correlates moderately-well with Z11-16Acid titer (FIG. 25B). For most strains selectivity was relatively constant between 23 and 48 hours (FIG. 25C). At 28° C., second- and third-generation strains with multiple desaturase copies displayed significantly higher selectivities than SPV459. The highest selectivities were observed for SPV1058 and SPV1059 at nearly 59% (FIG. 26A). The difference in selectivity was reduced at 32° C., with SPV459 at 45% Z11-16Acid and SPV1058 again at 59% (FIG. 26A).

While cell density was measured by OD600 absorbance, estimates of the lipid fraction of biomass were made by converting absorbance to dry cell weight (DCW) using a coefficient of 0.78 gDCW/L-OD for moderately obese Y. lipolytica cells. Lipid fractions were calculated by dividing the sum of fatty acid titers by this estimate of dry cell weight concentration. Generally, these estimated lipid fractions fell between 30% and 40% of total cell weight at 48 hours. SPV969 and SPV1058 had the highest lipid fractions of 44% and 43%, respectively, at 32° C. (FIG. 26B). Both SPV459 and SPV1056 had lower lipid fractions at 32° C. (FIG. 26B). Conversely, SPV1058 produced a slightly higher fraction at 32° C. (FIG. 26B).

Lipid fraction appears to be controlled independently of other measured parameters indicating independent regulation of total lipid storage. This hypothesis agrees with the observation that SPV459 imports 16Acid and initially stores a combination of 16Acid and Z11-16Acid before further converting the 16Acid fraction to Z11-16Acid in DASGIP fermentor experiments. In the Biolector assay, there is no observed correlation between Z11-16Acid productivity and final lipid fraction indicating that increased flux to Z11-16Acid does not influence lipid storage (FIG. 25F). The lipid fraction also does not correlate well with Z11-16Acid titer for the strains tested (FIG. 25D and FIG. 25E). As mentioned above, lipid fractions were similar for all strains and the difference in Z11-16Acid titer is primarily a function of the degree of conversion of 16Acid to Z11-16Acid. Further increases in Z11-16Acid titer may be achieved by increasing the lipid content of cells.

Comparison of High Glucose Medium and High Glycerol Medium Performance at 28° C. (HSD062)

In experiment HSD062, the primary High Glucose Medium was compared to a High Glycerol Medium used in the batch phase of the current fed-batch fermentation process using SPV459 (See Material and Methods for media compositions). The only difference between the High Glucose and High Glycerol media were the concentrations of the glucose and glycerol co-substrates. While the High Glucose Medium contains 120 g/L glucose and 5 g/L glycerol, the High Glycerol Medium contains 40 g/L glucose and 60 g/L glycerol. Initial growth rates for experiment HSD062 were similar in High Glucose and High Glycerol media (FIG. 27).

Specific Productivity

Specific productivities varied as a function of strain, medium, and timepoint. Wells dedicated to 23-hour samples of SPV459 in High Glucose Medium were lost to seal clogging preventing accurate measurement of specific productivity. Specific productivities at 23 hours from the High Glycerol condition were lower (2.4±0.1 mg/L-OD-h) than previously observed at High Glucose values (FIG. 28A). Despite lower early specific productivity, SPV459 increased Z11-16Acid production later in the High Glycerol medium. Specific productivities calculated from the 41.5 hour timepoint were 4.2±0.2 mg/L-OD-h for the High Glycerol Medium and 2.1±0.5 mg/L-OD-h for the High Glucose Medium (FIG. 28B).

As previously observed in the High Glucose Medium, SPV968 and SPV1056 had higher specific productivity early in the bioconversion (FIG. 28A). Compared to the High Glucose Medium, both strains had lower early specific productivity in the High Glycerol Medium, but sustained that lower productivity through the 41.5 hour timepoint (FIG. 28A and FIG. 28B).

Z11-16Acid Titer

Z11-16Acid titers varied by strain and medium because of the specific productivity patterns described above. SPV458 and SPV459 produced more Z11-16Acid in the High Glycerol Medium, while SPV968 and SPV1056 titers are similar in both media (FIG. 28C).

Selectivity and Lipid Content

The dependence of selectivity and lipid content on medium also varied by strain. SPV459 selectivity was equivalent in the two media, despite the significant difference in Z11-16Acid titer (FIG. 28D). SPV458 selectivity was 35% higher in High Glycerol Medium while the Z11-16Acid titer was 56% higher (FIG. 28D and FIG. 28C). Smaller increases in Z11-16Acid selectivity were observed from SPV968 (17%) and SPV1056 (6%) (FIG. 28D).

The correlation between Z11-16Acid selectivity and titer observed for the High Glucose Medium did not carry over to the High Glycerol Medium because SPV459 accumulated higher titers of 16Acid, Z9-18Acid, and Z9Z12-18Acid in the High Glycerol Medium. Strains SPV968 and SPV1056 maintained similar selectivity by reducing 16Acid accumulation while increasing Z9-18Acid and Z9Z12-18Acid titers in the High Glycerol Medium (FIG. 29).

Trends in estimated lipid content were consistent with observations about Z11-16Acid titer and selectivity. The estimated lipid content of SPV459 and SPV458 in High Glycerol Medium was 95% and 56% higher, respectively (FIG. 28E, FIG. 30). SPV968 and SPV1056 accumulated similar lipid content in both media.

SUMMARY

When combined, these results support the hypothesis that higher 16Acid uptake rates in SPV459 and SPV458 leads to higher intracellular concentrations of substrate for the desaturase and a resulting higher Z11-16Acid titer. SPV968 and SPV1056 do not accumulate increased 16Acid in High Glycerol Medium consistent with the uptake rate being insensitive to glycerol and glucose concentrations in these strains. Both SPV968 and SPV1056 harbor a FAT1 deletion which may explain the insensitivity to the change in medium. FAT1 has been identified as a lipid body/peroxisome fatty acid transporter involved in lipid mobilization (Dulermo, R., Gamboa-Melendez, H., Ledesma-Amaro, R., Thévenieau, F., & Nicaud, J. M. (2015) Unraveling fatty acid transport and activation mechanisms in *Yarrowia lipolytica. Biochimica et Biophysica Acta (BBA)-Molecular and Cell Biology of Lipids*, 1851(9): 1202-1217). Without being bound by any one theory, it is possible that Fat1p may be differentially targeted to different membranes in a medium dependent manner and contribute to fatty acid uptake under some conditions. Alternatively, it may contribute to intracellular fatty acid activation. The increase in native C18 fatty acids for all strains supports either higher rates of de novo fatty acid synthesis or CoA-elongation in the High Glycerol Medium.

Productivities, max titers, and selectivities for key strains grown under the primary High Glucose medium are given in Table 17 below. Several key observations can be made from the data:

Specific productivities increase with the desaturase copy number at 28° C. The increase is non-linear; a smaller increase is observed with the addition of the third desaturase copy.

Specific productivities increase for most strains when the incubation temperature is increased from 28 to 32° C. The exceptions are SPV1056, SPV1199, and SPV1200. These strains all have three copies of the *H. zea* desaturase and a FAT1 deletion.

Z11-16Acid titer generally increases with desaturase copy number. TGL3 deletion strains SPV969 and SPV1058 produced the highest titers (5-6 g/L) at 48 hours.

Z11-16Acid titers are higher at 32° C. across all strains.

Selectivities correlate with Z11-16Acid titer. The highest repeatable selectivities were observed for SPV1056 (0.57±0.02) and SPV1058 (0.59±0.01).

TABLE 17

Strain performance metrics of key Z11-16Acid production strains.

| Strain ID | Genotype | Temp. (° C.) | Est. max. specific productivity (mg/gDCW-h) | 48 h titer (g/L) | 48 h selectivity (gZ11-16Acid/gTFA) |
|---|---|---|---|---|---|
| SPV459 | xpr2::HzDST, ? | 28 | 4.3 ± 0.2 | 2.36 ± 0.03 | 0.30 ± 0.01 |
|  |  | 32 | 4.8 ± 0.2 | 3.70 ± 0.33 | 0.45 ± 0.04 |
| SPV458 | xpr2::HzDST | 28 | 2.3 ± 0.3 | ± | ± |
|  |  | 32 | 3.3 ± 0.3 | 2.63 ± 0.09 | 0.32 ± 0.02 |
| SPV968 | xpr2::HzDST, fat1::HzDST, | 28 | 5.7 ± 0.3 | 2.27 ± 0.07 | 0.37 ± 0.01 |
|  |  | 32 | 6.7 ± 0.3 | 3.55 ± 0.22 | 0.53 ± 0.03 |
| SPV1056 | xpr2::HzDST, fat1::HzDST fao1::HzDST | 28 | 6.9 ± 0.2 | 3.09 ± 0.23 | 0.40 ± 0.02 |
|  |  | 32 | 5.3 ± 0.3 | 3.80 ± 0.09 | 0.57 ± 0.02 |
| SPV969 | xpr2::HzDST, tgl3::HzDST, | 28 | 5.9 ± — | ± | ± |
|  |  | 32 | 6.5 ± — | 5.06 ± 0.17 | 0.49 ± 0.00 |
| SPV1058 | xpr2::HzDST, tgl3::HzDST, fao1::HzDST | 28 | 6.8 ± 0.3 | 5.79 ± 0.01 | 0.58 ± 0.00 |
|  |  | 32 | 7.3 ± 0.2 | 6.14 ± 0.08 | 0.59 ± 0.01 |
| SPV1199 | xpr2::HzDST, fat1::HzDST tgl3::HzDST | 28 | 6.4 ± 0.2 | 2.74 ± 0.32 | 0.43 ± 0.03 |
|  |  | 32 | 5.5 ± 0.2 | 4.34 ± — | 0.71 ± — |
| SPV1200 | xpr2::HzDST, tgl3::HzDST, fat1::HzDST | 28 | 6.4 ± 0.2 | 3.11 ± 0.01 | 0.45 ± 0.00 |
|  |  | 32 | 5.3 ± — | ± | ± |

Experiment HSD062 compared the performance of SPV459, SPV458, SPV968, and SPV1056 under the High Glucose and High Glycerol media conditions at 28° C. (Table 18).

When cultured in the High Glycerol medium, SPV458 and SPV459 displayed higher total fatty acid titer (7.8 and 10.6 gTFA/L respectively), Z11-16Acid titer (2.1 and 3.8 gZ11-16Acid/L), and lipid fraction (0.47 and 0.52 gZ11-16Acid/gTFA).

SPV968 and SPV1056 displayed higher specific productivities in the first 23 hours in the High Glucose medium. Overall performance was similar in both media for SPV1056 and better in the High Glucose medium for SPV968.

TABLE 18

Strain performance in High Glycerol medium relative to High Glucose medium (HSD062). Values show the percent increase or decrease for each strain in the High Glycerol medium relative to performance of that strain in the High Glucose medium at 28° C.

| Strain ID | Avg. specific productivity at 41.5 h (% increase) | Z11-16Acid titer at 41.5 h (% increase) | Total fatty acid titer at 41.5 h (% increase) | Est. lipid fraction of biomass at 41.5 h (% increase) |
|---|---|---|---|---|
| SPV459 | 100% | 154% | 144% | 95% |
| SPV458 | 110% | 56% | 17% | 57% |
| SPV968 | 14% | −16% | −30% | −5% |
| SPV1056 | 12% | 5% | 0% | 6% |

Observed specific productivities, estimated specific productivities, max titers, and selectivities for all strains grown under the primary High Glucose medium are given in Table 19 below.

TABLE 19

Strain performance metrics of all strains tested.

| Strain ID | Genotype | Temp. (° C.) | Observed specific productivity (mg/L-OD-h) | Est. specific productivity (mg/gDCW-h) | 48 h titer (g/L) | 48 h selectivity (gZ11-16Acid/gTFA) |
|---|---|---|---|---|---|---|
| SPV459 | xpr2::HzDST, ? | 28 | 3.4 ± 0.3 | 4.3 ± 0.2 | 2.36 ± 0.03 | 0.30 ± 0.01 |
|  |  | 32 | 3.7 ± 0.3 | 4.8 ± 0.2 | 3.70 ± 0.33 | 0.45 ± 0.04 |
| SPV458 | xpr2::HzDST | 28 | 1.8 ± 0.3 | 2.3 ± 0.3 | ± | ± |
|  |  | 32 | 2.5 ± 0.4 | 3.3 ± 0.3 | 2.63 ± 0.09 | 0.32 ± 0.02 |

TABLE 19-continued

Strain performance metrics of all strains tested.

| Strain ID | Genotype | Temp. (° C.) | Observed specific productivity (mg/L-OD-h) | Est. specific productivity (mg/gDCW-h) | 48 h titer (g/L) | 48 h selectivity (gZ11-16Acid/gTFA) |
|---|---|---|---|---|---|---|
| SPV963 | xpr2::HzDST, gut2::HzDST | 28<br>32 | 4.3 ± 0.3<br>± | 5.5 ± 0.2<br>± | ±<br>± | ±<br>± |
| SPV1059 | xpr2::HzDST, tgl3::HzDST, gut2::HzDST | 28<br>32 | 5.7 ±<br>± | 7.4 ±<br>± | 5.39 ±<br>± | 0.59 ±<br>± |
| SPV1060 | xpr2::SiDST, fat1::HzDST | 28<br>32 | 4.2 ± 0.3<br>± | 5.4 ± 0.2<br>± | 2.20 ±<br>± | 0.33 ±<br>± |
| SPV968 | xpr2::HzDST, fat1::HzDST | 28<br>32 | 4.5 ± 0.6<br>5.3 ± 0.6 | 5.7 ± 0.3<br>6.7 ± 0.3 | 2.27 ± 0.07<br>3.55 ± 0.22 | 0.37 ± 0.01<br>0.53 ± 0.03 |
| SPV1056 | xpr2::HzDST, fat1::HzDST faol::HzDST | 28<br>32 | 5.4 ± 0.3<br>4.2 ± 0.7 | 6.9 ± 0.2<br>5.3 ± 0.3 | 3.09 ± 0.23<br>3.80 ± 0.09 | 0.40 ± 0.02<br>0.57 ± 0.02 |
| SPV969 | xpr2::HzDST, tgl3::HzDST, | 28<br>32 | 4.6 ±<br>5.1 ± | 5.9 ±<br>6.5 ± | <br>5.06 ± 0.17 | <br>0.49 ± 0.00 |
| SPV1058 | xpr2::HzDST, tgl3::HzDST, faol::HzDST | 28<br>32 | 5.3 ± 0.6<br>5.7 ± 0.3 | 6.8 ± 0.3<br>7.3 ± 0.2 | 5.79 ± 0.01<br>6.14 ± 0.08 | 0.58 ± 0.00<br>0.59 ± 0.01 |
| SPV1199 | xpr2::HzDST, fat1::HzDST tgl3::HzDST | 28<br>32 | 5.0 ± 0.5<br>4.3 ± 0.4 | 6.4 ± 0.2<br>5.5 ± 0.2 | 2.74 ± 0.32<br>4.34 ± | 0.43 ± 0.03<br>0.71 ± |
| SPV1200 | xpr2::HzDST, tgl3::HzDST, fat1::HzDST | 28<br>32 | 5.0 ± 0.4<br>4.1 ± | 6.4 ± 0.2<br>5.3 ± | 3.11 ± 0.01<br>± | 0.45 ± 0.00<br>± |

Conclusions

In the High Glucose Medium:

Additional Copies of Z11 Desaturase Increased Z11-16Acid Specific Productivity

Lipid Metabolism Deletions LED to Increased Z11-16Acid Titers

A combination of additional desaturase copies and deletion of the intracellular lipase TGL3 in SPV1058 led to a ~65% increase in Z11-16Acid titer (6.1 g/L) and ~55% increase in specific productivity (5.7 mg/L-OD-h) when compared to SPV459 (3.7 g/L, 3.7 mg/L-OD-h).

A change to the High Glycerol medium affects strains differently. SPV459 and SPV458 produce significantly higher Z11-16Acid titer in the High Glycerol medium compared to the High Glucose medium at 700 µl scale. SPV1056 performs similarly in both media.

SPV1056 and/or SPV1058 may serve as second generation strains for process development.

Development of a second-generation process takes into account co-substrate composition.

Recombinant acyl transferase expression is tested to increase fatty acid storage content (gTFA/gDCW). Current strains show 40-50% fatty acid in Biolector 700 µl assay.

Materials & Methods

Biolector Strain Screening Bioconversion

Y. lipolytica strains were inoculated from YPD agar patches and grown in 2 ml YPD seed cultures for 16 hours at 28° C. and 1000 rpm (Infors plate incubator) to an OD600=10. Seed cultures were pelleted and concentrated to OD600=80 in fresh YPD. A 1.5-2.5% inoculum was used to seed fresh media in the M2Plabs 48-well flower plate. Generally, 700 µl volumes were used except for experiment HSD061 which tested both 600 and 700 µl volumes at 32° C. Generally, the High Glucose medium was used except for experiment HSD043 in which GUT2 deletions and control strains used the High Glucose without Glycerol medium and experiment HSD062 in which strains were cultured in the High Glycerol medium (Table 20 below). After growing for 7 hours at 28 or 32° C. and 1500 rpm in the Biolector, the plate was removed and 8.4 µl of 37° C. methyl palmitate was added to each well as a liquid and the plate was resealed and returned to the Biolector. At 23 hours post-inoculation, a 250 µl sample was taken from rows A and B and transferred to glass crimp-top GC vials. Sample vials were frozen and stored at −80° C. After sampling, an additional 8.4 µl of 37° C. methyl palmitate was added to each well. The flower plate seal was replaced and incubated an additional 8 hours (31 hour timepoint). Rows C and D were then sampled as described for rows A and B. The plate was then incubated for 17 hours (48 hour timepoint) and samples were taken from rows E and F. Cell density was measured with a Tecan M200 Pro plate reader at each sampling. HSD062 was conducted as described above except that samples were not taken at 31 hours and four replicate samples from rows C-F were taken at 41.5 hours after inoculation.

In all experiments dissolved oxygen (DO) was monitored using oxygen sensitive optodes on the Biolector plate. Some experimental replicates were lost due to hypoxic conditions developing from a biofilm clogging the plate seal (See FIG. 31A-FIG. 31E for an example). Based on the DO data, clogging could occur for varying leading to varying degrees of perturbations in growth rate and Z11-16Acid production. Only data from replicates with sustained oxygen transfer were used in the analysis. Plots of all data are presented in FIG. 31A-FIG. 31E.

TABLE 20

Media composition

| Media Components | High Glucose | High Glucose w/out Glycerol | High Glycerol | units |
|---|---|---|---|---|
| Yeast Extract | 1 | 1 | 1 | g/L |
| Phosphate buffer | 0.1 | 0.1 | 0.1 | M |

TABLE 20-continued

| | Media composition | | | |
|---|---|---|---|---|
| Media Components | High Glucose | High Glucose w/out Glycerol | High Glycerol | units |
| YNB w/o aa, NH4 | 1.7 | 1.7 | 1.7 | g/L |
| Ammonium sulfate | 3.3 | 3.3 | 3.3 | g/L |
| Glucose | 120 | 120 | 40 | g/L |
| Glycerol | 5 | 0 | 60 | g/l |
| Iron Sulfate | 8.54 | 8.54 | 8.54 | mg/L |

GC Sample Processing-Lyophilized Samples

250 μL of culture were lyophilized in open glass crimp top vials for at least 3 hours. 500 μL of TMSH were added to the vials and sealed with a crimp cap. These vials were arrayed in racks, which were placed in a 28° C. plate shaker for 2 hours at 250 rpm. After mixing these dried cells with the derivatizing agent, the vials were incubated in a heat block for 1 hour at 85° C. to lyse the cell membranes. Finally, the liquid portion of the methylated sample was transferred to a clean GC vial with glass insert to prevent solid debris from clogging the column during GC analysis. Samples were run on GC-FID using the PROVIVI_002_DUAL_EXTRAWASH_1.M method, whose parameters can be found below.

Front Inlet/Detector:

| | |
|---|---|
| System | 6890 GC, ChemStation Rev. B.03.02 (341) |
| Column | J&W DB-23 30 m × 25 mm × 25 μm |
| | Run Time = 14.4 min |
| Inlet | Heater = 240° C.; Pressure = 9.0 psi; Total Flow {H2} = 36.2 mL/min |
| Carrier | H$_2$ @ 1.0 mL/min, 9.0 psi, 35 cm/sec |
| Signal | Data rate = 2 Hz/0.1 min |
| Oven | 150° C. for 1 min |
| | Ramp 12° C./min to 220° C., hold 3 min |
| | Ramp 35° C./min to 240° C., hold 4 min |
| | Equilibration Time: 2 min |
| Injection | Split, 240° C. |
| | Split ratio - 30:1; 29.1 mL/min |
| Detector | FID, 240° C. |
| | H$_2$ @ 35.0 mL/min, Air @ 350 mL/min |
| | Electrometer {Lit Offset} @ 2.0 pA |
| Sample | Injection volume = 1 μL |

Back Inlet/Detector:

| | |
|---|---|
| System | 6890 GC, ChemStation Rev. B.03.02 (341) |
| Column | J&W DB-23 30 m × 25 mm × 25 μm |
| | Run Time = 14.4 min |
| Inlet | Heater = 240° C.; Pressure = 9.8 psi; Total Flow {H2} 40.1 mL/min |
| Carrier | H$_2$ @ 1.1 mL/min, 9.8 psi, 38 cm/sec |
| Signal | Data rate = 2 Hz/0.1 min |
| Oven | 150° C. for 1 min |
| | Ramp 12° C./min to 220° C., hold 3 min |
| | Ramp 35° C./min to 240° C., hold 4 min |
| | Equilibration Time: 2 min |
| Injection | Split, 240° C. |
| | Split ratio - 30:1; 32.3 mL/min |
| Detector | FID, 240° C. |
| | H$_2$ @ 35.0 mL/min, Air @ 350 mL/min |
| | Electrometer {Lit Offset} @ 2.0 pA |
| Sample | Injection volume = 1 μL |

TMSH: Trimethylsulfonium Hydroxide (0.2 mol/L in Methanol)—VWR TCT1576-025ML

SEQUENCE LISTING

SEQ ID NO: 1   *Helicoverpa zea* desaturase
```
MAQSYQSTTV LSEEKELTLQ HLVPQASPRK YQIVYPNLIT FGYWHIAGLY
GLYLCFTSAK WATILFSYIL FVLAEIGITA GAHRLWAHKT YKAKLPLEIL
LMVFNSIAFQ NSAIDWVRDH RLHHKYSDTD ADPHNASRGF FYSHVGWLLV
RKHPEVKKRG KELNMSDIYN NPVLRFQKKY AIPFIGAVCF ALPTMIPVYF
WGETWSNAWH ITMLRYIMNL NVTFLVNSAA HIWGNKPYDA KILPAQNVAV
SVATGGEGFH NYHHVFPWDY RAAELGNNSL NLTTKFIDLF AAIGWAYDLK
TVSEDMIKQR IKRTGDGTDL WGHEQNCDEV WDVKDKSS
```

SEQ ID NO: 2   pDST003_*Sesamia inferens* desaturase
```
MLSQEEPTDTSLVPRAAPRKYQIVYPNLITFGYWHLAGLYGLYLCFTSAKWTTILFSFILC
VIAEIGVTAGAHRLWAHKTYKANLPLQILLMVMNSIAFQNSAIDWVRDHRLHHKYSDTDAD
PHNASRGFFYSHVGWLLVKKHPEVKKRGKELDMSDIYSNPVLRFQKQYAIPFIGAVCFILP
TVIPVYCWGETWTNAWHITMLRYITNLNVTFLVNSAAHIWGYKPYDENILPAQNIAVSIAT
CGEGFHNYHHVFPWDYRAAELGNNNLNLTTKFIDFFAWLGWAYDLKTVSSDMIKLRAKRTG
DGTNLWGSHNDELKEGKED
```

SEQ ID NO: 3   *T. ni* desaturase
```
ATGGCTGTGATGGCTCAAACAGTACAAGAAACGGCTACAGTGTTGGAAGAGGAAGCTCGCA
CAGTGACTCTTGTGGCTCCAAAGACAACGCCAAGGAAATATAAATATATATACACCAACTT
TCTTACATTTTCATATGCGCATTTAGCTGCATTATACGGACTTTATTTGTGCTTCACCTCT
GCGAATGGGAAACATTGCTATTCTCTTTCGTACTCTTCCACATGTCAAATATAGGCATCA
CCGCAGGGGCTCACCGACTCTGGACTCACAAGACTTTCAAAGCCAAATTGCCTTTGGAAAT
TGTCCTCATGATATTCAACTCTTTAGCCTTTCAAAACACGGCTATTACATGGGCTAGAGAA
CATCGGCTACATCACAAATACAGCGATACTGATGCTGATCCCCACAATGCGTCAAGAGGGT
TCTTCTACTCGCATGTTGGCTGGCTATTAGTAAAAAAACATCCCGATGTCCTGAAATATGG
AAAAACTATAGACATGTCGGATGTATACAATAATCCTGTGTTAAAATTTCAGAAAAAGTAC
GCAGTACCCTTAATTGGAACAGTTTGTTTTGCTCTGCCAACTTTGATTCCAGTCTACTGTT
GGGGCGAATCGTGGAACAACGCTTGGCACATAGCCTTATTTCGATACATATTCAATCTTAA
CGTGACTTTCCTAGTCAACAGTGCTGCGCATATCTGGGGGAATAAGCCTTATGATAAAGC
ATCTTGCCCGCTCAAAACCTGCTGGTTTCCTTCCTAGCAAGTGGAGAAGGCTTCCATAATT
ACCATCACGTCTTTCCATGGGATTACCGCACAGGAGAATTAGGGAATAACTTCCTGAATTT
GACGACGCTGTTCATTGATTTTGTGCCTGGTTTGGATGGGCTTATGACTTGAAGTCTGTA
TCAGAGGATATTATAAAACAGAGAGCTAAACGAACAGGTGACGGTTCTTCAGGGGTCATTT
GGGGATGGGACGACAAAGACATGGACCGCGATATAAAATCTAAAGCTAACATTTTTTATGC
TAAAAAGGAATGA
```

SEQUENCE LISTING

| | |
|---|---|
| SEQ ID NO: 4 | *A. segetum* desaturase<br>ATGGCTCAAGGTGTCCAAACAACTACGATATTGAGGGAGGAGGAGCCGTCATTGACTTTCG<br>TGGTACCTCAAGAACCGAGAAAGTATCAAATCGTGTACCCAAACCTTATCACATTTGGGTA<br>CTGGCATATAGCTGGTTTATACGGGCTATATTTGTGCTTTACTTCGGCAAAATGGCAAACA<br>ATTTTATTCAGTTTCATGCTCGTTGTGTTAGCAGAGTTGGGAATAACAGCCGGCGCTCACA<br>GGTTATGGGCCCACAAAACATATAAAGCGAAGCTTCCCTTACAAATTATCCTGATGATACT<br>GAACTCCATTGCCTTCCAAAATTCCGCCATTGATTGGGTGAGGG<br>ACCACCGTCTCCATCATAAGTACAGTGACACTGATGCAGACCCTCACAATGCTACTCGTGG<br>TTTCTTCTATTCTCATGTTGGATGGTTGCTCGTAAGAAAACATCCAGAAGTCAAGAGACGT<br>GGAAAGGAACTTGACATGTCTGATATTTACAACAATCCAGTGCTGAGATTTCAAAAGAAGT<br>ATGCTATACCCTTCATCGGGGCAATGTGCTTCGGATTACCAACTTTTATCCCTGTTTACTT<br>CTGGGGAGAAACCTGGAGTAATGCTTGGCATATCACCATGCTTCGGTACATCCTCAACCTA<br>AACATTACTTTCCTGGTCAACAGTGCTGCTCATATCTGGGGATACAAACCTTATGACATCA<br>AAATATTGCCTGCCCAAAATATAGCAGTTTCCATAGTAACCGGCGGCGAAGTTTCCATAAC<br>TACCACCACGTTTTTTCCTTGGGATTATCGTGCAGCAGAATTGGGGAACAATTATCTTAAT<br>TTGACGACTAAGTTCATAGATTTCTTCGCTTGGATCGGATGGGCTTACGATCTTAAGACGG<br>TGTCCAGTGATGTTATAAAAAGTAAGGCGGAAAGAACTGGTGATGGGACGAATCTTTGGGG<br>TTTAGAAGACAAAGGTGAAGAAGATTTTTTGAAAATCTGGAAAGACAATTAA |
| SEQ ID NO: 5 | *T. pseudonana* desaturase<br>ACTAGTATGGACTTTCTCTCCGGCGATCCTTTCCGGACAC<br>TCGTCCTTGCAGCACTTGTTGTCATCGGATTTGCTGCGGCGTGGC<br>AATGCTTCTACCCGCCGAGCATCGTCGGCAAGCCTCGTACATTAA<br>GCAATGGTAAACTCAATACCAGAATCCATGGCAAATTGTACGACC<br>TCTCATCGTTTCAGCATCCAGGAGGCCCCGTGGCTCTTTCTCTTG<br>TTCAAGGTCGCGACGGAACAGCTCTATTTGAGTCACACCATCCCT<br>TCATACCTCGAAAGAATCTACTTCAGATCCTCTCCAAGTACGAGG<br>TTCCGTCGACTGAAGACTCTGTTTCCTTCATCGCCACCCTAGACG<br>AACTCAATGGTGAATCTCCGTACGATTGGAAGGACATTGAAAATG<br>ATGATTTCGTATCTGACCTACGAGCTCTCGTAATTGAGCACTTTT<br>CTCCTCTCGCCAAGGAAAGGGGAGTTTCACTCGTTGAGTCGTCGA<br>AGGCAACACCTCAGCGGTGGATGGTGGTTCTACTGCTCCTTGCGT<br>CGTTCTTCCTCAGCATCCCATTATATTTGAGTGGTTCGTGGACTT<br>TCGTTGTCGTCACTCCCATCCTCGCTTGGCTGGCGGTTGTCAATT<br>ACTGGCACGATGCTACTCACTTTGCATTGAGCAGCAACTGGATTT<br>TGAATGCTGCGCTCCCATATCTCCTCCCTCTCCTATCGAGTCCGT<br>CAATGTGGTATCATCATCACGTCATTGGACATCACGCATACACCA<br>ACATTTCCAAAAGAGATCCAGATCTTGCTCACGCTCCACAACTCA<br>TGAGAGAACACAAGAGTATCAAATGGAGACCATCTCACTTAAATC<br>AAACACAGCTTCCGCGGATTCTCTTCATCTGGTCGATTGCAGTCG<br>GTATTGGGTTGAACTTACTGAACGACGTGAGAGCACTAACCAAGC<br>TTTCATACAACAACGTTGTTCGGGTGGAGAAGATGTCATCGTCGC<br>GAACATTACTCCATTTCCTTGGACGTATGTTGCACATCTTTGTGA<br>CTACACTTTGGCCCTTTTTGGCGTTTCCGGTGTGGAAGGCCATCG<br>TTTGGGCGACTGTACCGAATGCCATACTGAGTTTGTGCTTCATGC<br>TGAATACGCAAATCAATCACCTCATCAACACGTGTGCACATGCTT<br>CCGATAACAACTTTTACAAGCATCAAGTTGTAACTGCTCAGAACT<br>TTGGCCCGATCAAGTGCCTTTTGCTTCATCTTCTCGGGAGGTCTCA<br>ACTACCAAATTGAACATCATTTGTTGCCGACGGTGAACCATTGCC<br>ATTTGCCAGCTTTGGCCCCGGGTGTAGAGCGTTTGTGTAAGAAAC<br>ACGGGGTGACATACAACTCTGTTGAAGGATACAGAGAGGCCATCA<br>TTGCACACTTTGCACATACCAAAGATATGTCGACGAAGCCTACTG<br>ATTGA |
| SEQ ID NO: 6 | *A. transitella* desaturase<br>ATGGTCCCTAACAAGGGTTCCAGTGACGTTTTGTCTGAACATTCTGAGCCCCAGTTCACTA<br>AACTCATAGCTCCACAAGCAGGGCCGAGGAAATACAAGATAGTGTATCGAAATTTGCTCAC<br>ATTCGGCTATTGGCACTTATCAGCTGTTTATGGGCTCTACTTGTGCTTTACTTGTGCGAAA<br>TGGGCTACCATCTTATTTGCATTTTTCTTATACGTGATCGCGGAAATCGGTATAACAGGTG<br>GCGCTCATAGGCTATGGGCACATCGGACTTATAAAGCCAAGTTGCCTTTAGAGATTTTGTT<br>ACTCATAATG<br>AACTCTATTGCCTTCCAAGACACTGCTTTCACCTGGGCTCGTGATCACCGCCTTCATCACA<br>AATATTCGGATACTGACGCTGATCCCCACAATGCTACCAGAGGGTTTTTCTATTCACATGT<br>AGGCTGGCTTTTGGTGAAGAAACACCCTGAAGTCAAAGCAAGAGGAAAATACTTGTCGTTA<br>GATGATCTTAAGAATAATCCATTGCTTAAATTCCAAAAGAAATACGCTATTCTAGTTATAG<br>GCACGTTATGCTTCCTTATGCCAACATTTGTGCCCGTATACTTCTGGGGCGAGGGCATCAG<br>CACGGCCTGGAACATCAATCTATTGCGATACGTCATGAATCTTAACATGACTTTCTTAGTT<br>AACAGTGCAGCGCATATCTTTGGCAACAAACCATACGATAAGAGCATAGCCTCAGTCCAAA<br>ATATTTCAGTTAGCTTAGCTACTTTTGGCGAAGGATTCCATAATTACCATCACACTTACCC<br>CTGGGATTATCGTGCGGCAGAATTAGGAAATAATAGGCTAAATATGACTACTGCTTTCATA<br>GATTTCTTCGCTTGGATCGGCTGGGCTTATGACTTGAAGTCTGTGCCACAAGAGGCCATTG<br>CAAAAGGTGTGCGAAAACTGGCGATGGAACGGATATGTGGGGTCGAAAAGATAA |

| SEQUENCE LISTING | |
|---|---|
| SEQ ID NO: 7 | *H. zea* desaturase<br>ATGGCCCAAAGCTATCAATCAACTACGGTTTTGAGTGAGGAGAAAGAACTAACACTGCAAC<br>ATTTGGTGCCCCAAGCATCGCCCAGGAAGTATCAAATAGTGTATCCGAACCTCATTACGTT<br>TGGTTACTGGCACATAGCCGGACTTTATGGCCTTTACTTGTGCTTCACTTCTGCTAAATGG<br>GCTACGATTTTATTCAGCTACATCCTCTTCGTGTTAGCAGAAATAGGAATCACGGCTGGCG<br>CTCACAGACTCTGGGCCCACAAAACTTACAAAGCGAAACTACCATTAGAAATACTCTTAAT<br>GGTATTCAACTCCATCGCTTTTCAAAACTCAGCCATTGACTGGGTGAGGGACCACCGACTC<br>CACCATAAGTATAGCGATACAGATGCTGATCCCCACAATGCCAGCCGAGGGTTCTTTTATT<br>CCCATGTAGGATGGCTACTTGTGAGAAAACATCCTGAAGTCAAAAAGCGAGGGAAAGAACT<br>CAATATG<br>TCCGATATTTACAACAATCCTGTCCTGCGGTTTCAGAAAAAATACGCCATACCCTTCATTG<br>GGGCTGTTTGTTTCGCCTTACCTACAATGATACCTGTTTACTTCTGGGGAGAAACCTGGTC<br>CAATGCTTGGCATATCACCATGCTTCGCTACATCATGAACCTCAATGTCACCTTTTTGGTA<br>AACAGCGCTGCTCATATATGGGGAAACAAGCCTTATGACGCAAAAATATTACCTGCACAAA<br>ATGTAGCTGTGTCGGTCGCCACTGGTGGAGAAGGTTTCCATAATTACCACCATGTCTTCCC<br>CTGGGATTATCGAGCAGCGGAACTCGGTAACAATAGCCTCAATCTGACGACTAAATTCATA<br>GATTTATTCGCAGCAATCGGATGGGCATATGATCTGAAGACGGTTTCGGAGGATATGATAA<br>AACAAAGGATTAAACGCACTGGAGATGGAACGGATCTTTGGGGACACGAACAAAACTGTGA<br>TGAAGTGTGGGATGTAAAAGATAAATCAAGTTAA |
| SEQ ID NO: 8 | CaOLE1-*A. segetum* Z11 desaturase<br>ATGACTACAGTTGAACAACTTGAAACTGTTGATATCACTAAATTGAATGCCATTGCTGCTG<br>GTACTAATAAGAAGGTGCCAATGGCTCAAGGTGTCCAAACAACTACGATATTGAGGGAGGA<br>AGAGCCGTCATTGACTTTCGTGGTACCTCAAGAACCGAGAAAGTATCAAATCGTGTACCCA<br>AACCTTATCACATTTGGGTACTGGCATATAGCTGGTTTATACGGGCTATATTTGTGCTTTA<br>CTTCGGCAAAATGGCAAACAATTTTATTCAGTTTCATGCTCGTTGTGTTAGCAGAGTTGGG<br>AATAACAGCCGGCGCTCACAGGTTATGGGCCCACAAAACATATAAAGCGAAGCTTCCCTTA<br>CAAATTATCTTAATGATATTAAACTCCATTGCCTTCCAAAATTCCGCCATTGATTGGGTGA<br>GGGACCACCGTCTCCATCATAAGTACAGTGACACTGATGCAGACCCTCACAATGCTACTCG<br>TGGTTTCTTCTATTCTCATGTTGGATGGTTGCTCGTAAGAAAACATCCAGAAGTCAAGAGA<br>CGTGGAAAGGAACTTGACATGTCTGATATTTACAACAATCCAGTGTTAAGATTTCAAAAGA<br>AGTATGCTATACCCTTCATCGGGGCAATGTGCTTCGGATTACCAACTTTTATCCCTGTTTA<br>CTTCTGGGGAGAAACCTGGAGTAATGCTTGGCATATCACCATGCTTCGGTACATCCTCAAC<br>CTAAACATTACTTTCTTAGTCAACAGTGCTGCTCATATCTGGGGATACAAACCTTATGACA<br>TCAAAATATTGCCTGCCCAAAATATAGCAGTTTCCATAGTAACCGGCGGCGAAGTTTCCAT<br>AACTACCACCACGTTTTTTCCTTGGGATTATCGTGCAGCAGAATTGGGGAACAATTATCTT<br>AATTTGACGACTAAGTTCATAGATTTCTTCGCTTGGATCGGATGGGCTTACGATCTTAAGA<br>CGGTGTCCAGTGATGTTATAAAAAGTAAGGCGGAAAGAACTGGTGATGGGACGAATCTTTG<br>GGGTTTAGAAGACAAAGGTGAAGAAGATTTTTTGAAATCTGGAAAGACAATTAA |
| SEQ ID NO: 9 | *A. segetum* Z11 desaturase<br>ATGGCTCAAGGTGTCCAAACAACTACGATATTGAGGGAGGAAGAGCCGTCATTGACTTTCG<br>TGGTACCTCAAGAACCGAGAAAGTATCAAATCGTGTACCCAAACCTTATCACATTTGGGTA<br>CTGGCATATAGCTGGTTTATACGGGCTATATTTGTGCTTTACTTCGGCAAAATGGCAAACA<br>ATTTTATTCAGTTTCATGCTCGTTGTGTTAGCAGAGTTGGGAATAACAGCCGGCGCTCACA<br>GGTTATGGGCCCACAAAACATATAAAGCGAAGCTTCCCTTACAAATTATCTTAATGATATT<br>AAACTCCATTGCCTTCCAAAATTCCGCCATTGATTGGGTGAGGGACCACCGTCTCCATCAT<br>AAGTACAGTGACACT<br>GATGCAGACCCTCACAATGCTACTCGTGGTTTCTTCTATTCTCATGTTGGATGGTTGCTCG<br>TAAGAAAACATCCAGAAGTCAAGAGACGTGGAAAGGAACTTGACATGTCTGATATTTACAA<br>CAATCCAGTGTTAAGATTTCAAAAGAAGTATGCTATACCCTTCATCGGGGCAATGTGCTTC<br>GGATTACCAACTTTTATCCCTGTTTACTTCTGGGGAGAAACCTGGAGTAATGCTTGGCATA<br>TCACCATGCTTCGGTACATCCTCAACCTAAACATTACTTTCTTAGTCAACAGTGCTGCTCA<br>TATCTGGGGATACAAACCTTATGACATCAAAATATTGCCTGCCCAAAATATAGCAGTTTCC<br>ATAGTAACCGGCGGCGAAGTTTCCATAACTACCACCACGTTTTTTCCTTGGGATTATCGTG<br>CAGCAGAATTGGGGAACAATTATCTTAATTTGACGACTAAGTTCATAGATTTCTTCGCTTG<br>GATCGGATGGGCTTACGATCTTAAGACGGTGTCCAGTGATGTTATAAAAAGTAAGGCGGAA<br>AGAACTGGTGATGGGACGAATCTTTGGGGTTTAGAAGACAAAGGTGAAGAAGATTTTTTGA<br>AAATCTGGAAAGACAATTAA |
| SEQ ID NO: 10 | *A. transitella* Z11 desaturase<br>ATGGTCCCTAACAAGGGTTCCAGTGACGTTTTGTCTGAACATTCTGAGCCCCAGTTCACTA<br>AACTCATAGCTCCACAAGCAGGGCCGAGGAAATACAAGATAGTGTATCGAAATTTGCTCAC<br>ATTCGGCTATTGGCACTTATCAGCTGTTTATGGGCTCTACTTGTGCTTTACTTGTGCGAAA<br>TGGGCTACCATCTTATTTGCATTTTTCTTATACGTGATCGCGGAAATCGGTATAACAGGTG<br>GCGCTCATAGGCTATGGGCACATCGGACTTATAAAGCCAAGTTGCCTTTAGAGATTTTGTT<br>ACTCATAATGAATTCTATTGCCTTCCAAGCACACTGCTTTCACCTGGGCTCGAGATCACCGC<br>CTTCATCACAAATATTCGGATACTGACGCTGATCCCCACAATGCTACCAGAGGGTTTTTCT<br>ATTCACATGTAGGCTGGCTTTTGGTGAAGAAACACCCTGAAGTCAAAGCAAGAGGAAAATA<br>CTTGTCGTTAGATGATCTTAAGAATAATCCATTGCTTAAATTCCAAAAGAAATACGCTATT<br>CTAGTTATAGGCACGTTATGCTTCCTTATGCCAACATTTGTGCCCGTATACTTCTGGGGCG<br>AGGGCATCAGCACGGCCTGGAACATCAATCTATTGCGATACGTCATGAATCTTAACATGAC<br>TTTCTTAGTTAACAGTGCAGCGCATATCTTTGGCAACAAACCATACGATAAGAGCATAGCC<br>TCAGTCCAAAATATTTCAGTTAGCTTAGCTACTTTTGGCGAAGGATTCCATAATTACCATC<br>ACACTTACCCCTGGGATTATCGTGCGGCAGAATTAGGAAATAATAGGCTAAATATGACTAC |

| SEQUENCE LISTING | |
|---|---|
| | TGCTTTCATAGATTTCTTCGCTTGGATCGGCTGGGCTTATGACTTGAAGTCTGTGCCACAA<br>GAGGCCATTGCAAAAAGGTGTGCGAAAACTGGCGATGGAACGGATATGTGGGGTCGAAAAA<br>GATAA |
| SEQ ID NO: 11 | *T. ni* Z11 desaturase<br>ATGGCTGTGATGGCTCAAACAGTACAAGAAACGGCTACAGTGTTGGAAGAGGAAGCTCGCA<br>CAGTGACTCTTGTGGCTCCAAAGACAACGCCAAGGAAATATAAATATATATACACCAACTT<br>TCTTACATTTTCATATGCGCATTTAGCTGCATTATACGGACTTTATTTGTGCTTCACCTCT<br>GCGAAATGGGAAACATTGCTATTCTCTTTCGTACTCTTCCACATGTCAAATATAGGCATCA<br>CCGCAGGGGCTCACCGACTCTGGACTCACAAGACTTTCAAAGCCAAATTGCCTTTGGAAAT<br>TGTCCTCATGATATTCAACTCTTTTAGCCTTTCAAAACACGGCTATTACATGGGCTAGAGAA<br>CATCGGCTACATCACAAATACAGCGATACTGATGCTGATCCCCACAATGCGTCAAGAGGGT<br>TCTTCTACTCGCATGTTGGCTGGCTATTAGTAAAAAAACATCCCGATGTCTTAAAATATGG<br>AAAAACTATAGACATGTCGGATGTATACAATAATCCTGTGTTAAAATTTCAGAAAAAGTAC<br>GCAGTACCCTTAATTGGAACAGTTTGTTTTGCTCTTCCAACTTTGATTCCAGTCTACTGTT<br>GGGGCGAATCGTGGAACAACGCTTGGCACATAGCCTTATTTCGATACATATTCAATCTTAA<br>CGTGACTTTCCTAGTCAACAGTGCTGCGCATATCTGGGGGAATAAGCCTTATGATAAAAGC<br>ATCTTGCCCGCTCAAAACTTATTAGTTTCCTTCCTAGCAAGTGGAGAAGGCTTCCATAATT<br>ACCATCACGTCTTTCCATGGGATTACCGCACAGCAGAATTAGGGAATAACTTCTTAAATTT<br>GACGACGTTATTCATTGATTTTTGTGCCTGGTTTGGATGGGCTTATGACTTGAAGTCTGTA<br>TCAGAGGATATTATAAAACAGAGAGCTAAACGAACAGGTGACGGTTCTTCAGGGGTCATTT<br>GGGGATGGGACGACAAAGACATGGACCGCGATATAAAATCTAAAGCTAACATTTTTTATGC<br>TAAAAAGGAATGA |
| SEQ ID NO: 12 | *H. zea* Z11 desaturase<br>ATGGCCCAAAGCTATCAATCAACTACGGTTTTGAGTGAGGAGAAAGAACTAACATTACAAC<br>ATTTGGTGCCCCAAGCATCGCCCAGGAAGTATCAAATAGTGTATCCGAACCTCATTACGTT<br>TGGTTACTGGCACATAGCCGGACTTTATGGCCTTTACTTGTGCTTCACTTCTGCTAAATGG<br>GCTACGATTTTATTCAGCTACATCCTCTTCGTGTTAGCAGAAATAGGAATCACGGCTGGCG<br>CTCACAGACTCTGGGCCCACAAAACTTACAAAGCGAAACTACCATTAGAAATACTCTTAAT<br>GGTATTCAACTCCATCGCTTTTCAAAACTCAGCCATTGACTGGGTGAGGGACCACCGACTC<br>CACCATAAGTATAGCGATACAGATGCTGATCCCCACAATGCCAGCCGAGGGTTCTTTTATT<br>CCCATGTAGGATGGCTACTTGTGAGAAAACATCCTGAAGTCAAAAAGCGAGGGAAAGAACT<br>CAATATGTCCGATATTTACAACAATCCTGTCTTACGGTTTCAGAAAAAATACGCCATACCC<br>TTCATTGGGGCTGTTTGTTTCGCCTTACCTACAATGATACCTGTTTACTTCTGGGGAGAAA<br>CCTGGTCCAATGCTTGGCATATCACCATGCTTCGCTACATCATGAACCTCAATGTCACCTT<br>TTTGGTAAACAGCGCTGCTCATATATGGGGAAACAAGCCTTATGACGCAAAAATATTACCT<br>GCACAAAATGTAGCTGTGTCGGTCGCCACTGGTGGAGAAGGTTTCCATAATTACCACCATG<br>TCTTCCCCTCGGATTATCGAGCAGCGGAACTCGGTAACAATAGCCTCAATTTAACGACTAA<br>ATTCATAGATTTATTCGCAGCAATCGGATGGGCATATGATTTAAAGACGGTTTCGGAGGAT<br>ATGATAAAACAAAGGATTAAACGCACTGGAGATGGAACGGATCTTTGGGGACACGAACAAA<br>ACTGTGATGAAGTGTGGGATGTAAAAGATAAATCAAGTTAA |
| SEQ ID NO: 13 | *O. furnacalis* Z9 desaturase<br>ATGGCTCCTAATATTAAGGACGGAGCTGATTTGAACGGAGTTTTATTTGAAGATGACGCTA<br>GCACCCCGATTATGCCCTTGCCACGGCCCCAGTCCAGAAAGCAGACAACTATCCCAGAAA<br>ACTAGTGTGGAGAAACATCATCTCTTTGCATACCTTCACCTTGCCGCTGTGTATGGAGCA<br>TACCTATTCTTATTTTCAGCGAAATGGCAGACAGATATTTTTGCCTACATTCTTTACGTGA<br>TCTCAGGACTCGGCATCACAGCGGGAGCCCACCGCCTTTGGGCGCACAAGTCATACAAGGC<br>TAAGTGGCCACTTAGACTCATTCTTATTATCTTCAACACTGTATCATTCCAGGACTCTGCT<br>CTCGACTGGTCACGTGACCACCGCATGCACCACAAATACTCGGAGACCGACGCCGACCCGC<br>ACAACGCGACTCGAGGGTTCTTCTTCTCTCATATCGGCTGGTTATTAGTCCGCAAGCACCC<br>GGAATTAAAGAGAAAGGGCAAGGGATTAGACTTAAGCGACTTGTATGCTGATCCCATCCTC<br>CGTTTCCAGAAGAAGTACTATTTACTATTAATGCCTCTTGGCTGCTTCATCATGCCGACGG<br>TGGTCCCGGTGTACTTCTGGGGTGAGACTTGGACTAACGCTTTCTTCGTCGCCGCGCTCTT<br>CCGATACACCTTCATCCTCAATGTCACCTGGTTGGTCAACTCCGCCGCGCACAAGTGGGGC<br>CACAAGCCCTATGACAGCAGCATCAAGCTTCCGAGAACCTCTCAGTCTCCTTATTCGCGT<br>TGGGCGAAGGATTCCACAACTACCACCACACATTCCCCTGGGACTACAAAACTGCCGAGCT<br>CGGCAACAACAGACTCAATTTCACAACAAACTTCATCAACTTCTTCGCTAAAATCGGATGG<br>GCTTACGACTTGAAAACGGTCTCCGACGAGATTATTCAGAATAGAGTCAAGCGCACAGGAG<br>ATGGCTCCCACCACTTATGGGGTTGGGCGACAAGGATCAACCTAAAGAGGAGGTAAACGC<br>AGCCATTAGAATTAATCCTAAAGACGAGTAA |
| SEQ ID NO: 14 | *L. capitella* Z9 desaturase<br>ATGCCGCCGAACGTGACAGAGGCGAACGGAGTGTTATTTGAGAATGACGTGCAGACTCCTG<br>ACATGGGGCTAGAAGTGGCCCCTGTGCAGAAGGCTGACGAGCGTAAGATCCAGCTCGTTTG<br>GAGGAACATCATCGCTTTTGCATGTCTTCATTTAGCAGCTGTGTATGGAGCTTATTTATTC<br>TTCACCTCGGCTATATGGCAGACAGACATATTTGCATACATCCTTTACGTTATGTCTGGAT<br>TAGGAATCACGGCGGGAGCGCACAGATTATGGGCTCATAAGTCATACAAGGCGAAGTGGCC<br>GTTAAGATTAATCCTCGTCGCATTCAACACTTTGGCATTCCAGGATTCGGCAATCGACTGG<br>GCGCGCGACCACCGCATGCACCACAAGTACTCGGAGACGGATGCGGACCCACATAACGCCA<br>CTCGCGGCTTCTTCTTTTCGCACATTGGTTGGTTACTCTGCCGAAAACACCCGGAGCTAAA<br>GCGCAAGGGCCAGGGCCTCGACTTAAGTGACCTCTACGCAGATCCTATTATTCGCTTCCAA<br>AAGAAGTACTACTTATTGTTAATGCCGTTAGCCTGCTTTGTTCTTCCCACCATAATTCCGG<br>TCTACCTCTGGGGCGAGTCCTGGAAAACGCGTTCTTCGTAGCTGCAATGTTCCGTTACAC<br>GTTCATCCTCAACGTAACATGGCTCGTCAACTCCGCCGCCCACAAATGGGGAGGCAAGCCC<br>TATGATAAGAACATCCAGCCCGCTCAGAACATCTCTGTAGCTATCTTCGCATTAGGCGAGG |

| | SEQUENCE LISTING |
|---|---|
| | GCTTCCACAACTACCACCACACGTTCCCCTGGGACTACAAGACCGCTGAATTAGGAAACAA<br>CAGGTTAAATTTCACAACTTCGTTTATCAATTTCTTCGCAAGCTTCGGATGGGCCTACGAC<br>TTAAAGACCGTGTCGGACGAGATTATACAACAGCGCGTTAAGAGGACGGGAGATGGGAGCC<br>ATCACTTACGGGGCTGGGGCGACCAGGACATACCGGCCGAAGAAGCTCAAGCTGCTTTACG<br>CATTAACCGTAAAGATGATTAG |
| SEQ ID NO: 15 | *H. zea* Z9 desaturase<br>ATGGCTCCAAATATATCGGAGGATGTGAACGGGGTGCTCTTCGAGAGTGATGCAGCGACGC<br>CGGACTTAGCGTTATCCACGCCGCCTGTGCAGAAGGCTGACAACAGGCCCAAGCAATTAGT<br>GTGGAGGAACATACTATTATTCGCGTATCTTCACTTAGCGGCTCTTTACGGAGGTTATTTA<br>TTCCTCTTCTCAGCTAAATGGCAGACAGACATATTTGCCTACATCTTATATGTGATCTCCG<br>GGCTTGGTATCACGGCTGGAGCACATCGCTTATGGGCCCACAAGTCCTACAAAGCTAAATG<br>GCCTCTCCGAGTTATCTTAGTCATCTTTAACACAGTGGCATTCCAGGATGCCGCTATGGAC<br>TGGGCGCGCGACCACCGCATGCATCACAAGTACTCGGAAACCGATGCTGATCCTCATAATG<br>CGACCCGAGGATTCTTCTTCTCTCACATTGGCTGGTTACTTGTCAGGAAACATCCCGACCT<br>TAAGGAGAAGGGCAAGGGACTCGACATGAGCGACTTACTTGCTGACCCCATTCTCAGGTTC<br>CAGAAAAAATACTACTTAATCTTAATGCCCTTGGCTTGCTTCGTGATGCCTACCGTGATTC<br>CTGTGTACTTCTGGGGTGAAACCTGGACCAACGCATTCTTTGTGGCGGCCATGTTCCGCTA<br>CGCGTTCATCCTAAATGTGACGTGGCTCGTCAACTCTGCCGCTCACAAGTGGGGAGACAAG<br>CCCTACGACAAAAGCATTAAGCCTTCCGAAAACTTGTCGGTCGCCATGTTCGCTCTCGGAG<br>AAGGATTCCACAACTACCACCACACTTTCCCTTGGGACTACAAAACTGCTGAGTTAGGCAA<br>CAACAAACTCAACTTCACTACCACCTTTATTAACTTCTTCGCTAAAATTGGCTGGGCTTAC<br>GACTTAAAGACAGTGTCTGATGATATCGTCAAGAACAGGGTGAAGCGCACTGGTGACGGCT<br>CCCACCACTTATGGGCTGGGGAGACGAAAATCAATCCAAAGAAGAAATTGATGCCGCTAT<br>CAGAATCAATCCTAAGGACGATTAA |
| SEQ ID NO: 16 | *T. pseudonana* Z11 desaturase<br>ATGGACTTTCTCTCCGGCGATCCTTTCCGGACACTCGTCCTTGCAGCACTTGTTGTCATCG<br>GATTTGCTGCGGCGTGGCAATGCTTCTACCCGCCGAGCATCGTCGGCAAGCCTCGTACATT<br>AAGCAATGGTAAACTCAATACCAGAATCCATGGCAAATTGTACGACCTCTCATCGTTTCAG<br>CATCCAGGAGGCCCCGTGGCTCTTTCTCTTGTTCAAGGTCGCGACGGAACAGCTCTATTTG<br>AGTCACACCATCCCTTCATACCTCGAAAGAATCTACTTCAGATCCTCTCCAAGTACGAGGT<br>TCCGTCGACTGAAGACTCTGTTTCCTTCATCGCCACCCTAGACGAACTCAATGGTGAATCT<br>CCGTACGATTGGAAGGACATTGAAAATGATGATTTCGTATCTGACCTACGAGCTCTCGTAA<br>TTGAGCACTTTTCTCCTCTCGCCAAGGAAAGGGGAGTTTCACTCGTTGAGTCGTCGAAGGC<br>AACACCTCAGCGGTGGATGGTGGTTCTATTACTCCTTGCGTCGTTCTTCCTCAGCATCCCA<br>TTATATTTGAGTGGTTCGTGGACTTTCGTTGTCGTCACTCCCATCCTCGCTTGGTTAGCGG<br>TTGTCAATTACTGGCACGATGCTACTCACTTTGCATTGAGCAGCAACTGGATTTTGAATGC<br>TGCGCTCCCATATCTCCTCCCTCTCCTATCGAGTCCGTCAATGTGGTATCATCATCACGTC<br>ATTGGACATCACGCATACACCAACATTTCCAAAAGAGATCCAGATCTTGCTCACGCTCCAC<br>AACTCATGAGAGAACACAAGAGTATCAAATGGAGACCATCTCACTTAAATCAAACACAGCT<br>TCCGCGGATTCTCTTCATCTGGTCGATTGCAGTCGGTATTGGGTTGAACTTATTAAACGAC<br>GTGAGAGCACTAACCAAGCTTTCATACAACAACGTTGTTCGGGTGGAGAAGATGTCATCGT<br>CGCGAACATTACTCCATTTCCTTGGACGTATGTTCACATCTTTGTGACTACACTTTGGCC<br>CTTTTTGGCGTTTCCGGTGTGGAAGGCCATCGTATTTGGGCGACTGTACCGAATGCCATATA<br>AGTTTGTGCTTCATGTTAAATACGCAAATCAATCACCTCATCAACACGTGTGCACATGCTT<br>CCGATAACAACTTTTACAAGCATCAAGTTGTAACTGCTCAGAACTTTGGCCGATCAAGTGC<br>CTTTTGCTTCATCTTCTCGGGAGGTCTCAACTACCAAATTGAACATCATTTGTTGCCGACG<br>GTGAACCATTGCCATTTGCCAGCTTTGGCCCCGGGTGTAGAGCGTTTGTGTAAGAAACACG<br>GGGTGACATACAACTCTGTTGAAGGATACAGAGAGGCCATCATTGCACACTTTGCACATAC<br>CAAAGATATGTCGACGAAGCCTACTGATTGA |
| SEQ ID NO: 17 | Native *T. ni* Z11 desaturase<br>ATGGCTGTGATGGCTCAAACAGTACAAGAAACGGCTACAGTGTTGGAAGAGGAAGCTCGCA<br>CAGTGACTCTTGTGGCrCCAAAGACAACGCCAAGGAAATATAAATATATACACCAACTT<br>TCTTACATTTTCATATGCGCATTTAGCTGCATTATACGGACTTTATTTGTGCTTCACCTCT<br>GCGAAATGGGAAACATTGCTATTCTCTTTCGTACTCTTCCACATGTCAAATATAGGCATCA<br>CCGCAGGGGCTCACCGACTCTGGACTCACAAGACTTTCAAAGCCAAATTGCCTTTGGAAAT<br>TGTCCTCATGATATTCAACTCTTTAGCCTTTCAAAACACGGCTATTACATGGGCTAGAGAA<br>CATCGGCTACATCACAAATACAGCGATACTGATGCTGATCCCCACAATGCGTCAAGAGGGT<br>TCTTCTACTCGCATGTTGGCTGGCTATTAGTAAAAAACATCCCGATGTCCTGAAATATGG<br>AAAAACTATAGACATGTCGGATGTATACAATAATCCTGTGTTAAAATTTCAGAAAAAGTAC<br>GCAGTACCCTTAATTGGAACAGTTTGTTTTGCTCTGCCAACTTTGATTCCAGTCTACTGTT<br>GGGGCGAATCGTGGAACAACGCTTGGCACATAGCCTTATTTCGATACATATTCAATCTTAA<br>CGTGACTTTCCTAGTCAACAGTGCTGCGCATATCTGGGGGAATAAGCCTTATGATAAAAGC<br>ATCTTGCCCGCTCAAAACCTGCTGGTTTCCTTCCTAGCAAGTGGAGAAGGCTTCCATAATT<br>ACCATCACGTCTTTCCATGGGATTACCGCACAGCAGAATTAGGGAATAACTTCCTGAATTT<br>GACGACGCTGTTCATTGATTTTGTGCCTGGTTTGATGGGCTTATGACTTGAAGTCTGTA<br>TCAGAGGATATTATAAAACAGAGAGCTAAACGAACAGGTGACGGTTCTTCAGGGGTCATTT<br>GGGGATGGGACGACAAAGACATGGACCGCGATATAAAATCTAAAGCTAACATTTTTTATGC<br>TAAAAAGGAATGA |
| SEQ ID NO: 18 | *H. zea* Z11 desaturase<br>ATGGCCCAAAGCTATCAATCAACTACGGTTTTGAGTGAGGAGAAAGAACTAACACTGCAAC<br>ATTTGGTGCCCCAAGCATCGCCCAGGAAGTATCAAATAGTGTATCCGAACCTCATTACGTT<br>TGGTTACTGGCACATAGCCGGACTTTATGGCCTTTACTTGTGCTTCACTTCTGCTAAATGG<br>GCTACGATTTTATTCAGCTACATCCTCTTCGTGTTAGCAGAAATAGGAATCACGGCTGGCG |

| | SEQUENCE LISTING |
|---|---|
| | CTCACAGACTCTGGGCCCACAAAACTTACAAAGCGAAACTACCATTAGAAATACTCTTAAT<br>GGTATTCAACTCCATCGCTTTTCAAAACTCAGCCATTGACTGGGTGAGGGACCACCGACTC<br>CACCATAAGTATAGCGATACAGATGCTGATCCCCACAATGCCAGCCGAGGGTTCTTTTATT<br>CCCATGTAGGATGGCTACTTGTGAGAAAACATCCTGAAGTCAAAAAGCGAGGGAAAGAACT<br>CAATATGTCCGATATTTACAACAATCCTGTCCTGCGGTTTCAGAAAAAATACGCCATACCC<br>TTCATTGGGGCTGTTTGTTTCGCCTTACCTACAATGATACCTGTTTACTTCTGGGGAGAAA<br>CCTGGTCCAATGCTTGGCATATCACCATGCTTCGCTACATCATGAACCTCAATGTCACCTT<br>TTTGGTAAACAGCGCTGCTCATATATGGGGAAACAAGCCTTATGACGCAAAAATATTACCT<br>GCACAAAATGTAGCTGTGTCGGTCGCCACTGGTGGAGAAGGTTTCCATAATTACCACCATG<br>TCTTCCCCTGGGATTATCGAGCAGCGGAACTCGGTAACAATAGCCTCAATCTGACGACTAA<br>ATTCATAGATTTATTCGCAGCAATCGGATGGGCATATGATCTGAAGACGGTTTCGGAGGAT<br>ATGATAAAACAAAGGATTAAACGCACTGGAGATGGAACGGATCTTTGGGGACACGAACAAA<br>ACTGTGATGAAGTGTGGGATGTAAAAGATAAATCAAGTTAA |
| SEQ ID NO: 19 | *T. ni* Z11 aesaturase *Homo sapiens* optimized<br>ATGGCCGTGATGGCCCAGACCGTGCAGGAGACCGCAACAGTGCTGGAGGAGGAGGCAAGGA<br>CCGTGACACTGGTGGCACCCAAGACCACACCTAGAAAGTACAAGTATATCTACACCAACTT<br>CCTGACCTTCAGCTACGCACACCTGGCCGCCCTGTATGGACTGTACCTGTGCTTTACCTCC<br>GCCAAGTGGGAGACACTGCTGTTCTCTTTTGTGCTGTTCCACATGAGCAATATCGGAATCA<br>CCGCAGGAGCACACAGGCTGTGGACCCACAAGACATTCAAGGCCAAGCTGCCTCTGGAGAT<br>CGTGCTGATGATCTTCAACTCTCTGGCCTTTCAGAATACCGCCATCACATGGGCCCGGGAG<br>CACAGACTGCACCACAAGTATAGCGACACCGATGCAGACCCACACAACGCAAGCAGGGGCT<br>TCTTTTACTCCCACGTGGGCTGGCTGCTGGTGAAGAAGCACCCCGACGTGCTGAAGTATGG<br>CAAGACAATCGACATGTCCGACGTGTACAACAATCCCGTGCTGAAGTTTCAGAAGAAGTAT<br>GCCGTGCCTCTGATCGGCACCGTGTGCTTCGCCCTGCCAACACTGATCCCCGTGTATTGTT<br>GGGGCGAGTCTTGGAACAATGCCTGGCACATCGCCCTGTTCCGGTACATCTTTAACCTGAA<br>TGTGACCTTTCTGGTGAACTCCGCCGCCCACATCTGGGGCAATAAGCCTTACGACAAGTCT<br>ATCCTGCCAGCCCAGAACCTGCTGGTGTCCTTCCTGGCCTCTGGCGAGGGCTTTCACAATT<br>ATCACCACGTGTTCCCATGGGACTACAGGACCGCAGAGCTGGGCAACAATTTTCTGAACCT<br>GACCCACTGTTCATCGATTTTTGTGCCTGGTTCGGCTGGGCCTATGACCTGAAGTCTGTG<br>AGCGAGGATATCATCAAGCAGAGGGCAAAGAGGACAGGCGATGGCAGCTCCGGCGTGATCT<br>GGGGATGGGACGATAAGGATATGGACAGAGATATCAAGAGCAAGGCCAATATCTTCTACGC<br>CAAGAAGGAGTGA |
| SEQ ID NO: 20 | *H. zea* Z11 desaturase *Homo sapiens* optimized<br>ATGGCACAGTCATATCAGAGCACTACCGTCCTGAGCGAAGAGAAGGAACTGACACTGCAGC<br>ACCTGGTCCCACAGGCATCACCTAGAAAGTACCAGATCGTGTATCCAAACCTGATCACCTT<br>CGGCTACTGGCACATCGCCGGCCTGTACGCCTGTATCTGTGCTTTACCTCCGCCAAGTGG<br>GCCACAATCCTGTTCTCTTACATCCTGTTTGTGCTGGCAGAGATCGGAATCACCGCAGGAG<br>CACACAGACTGTGGCACACAAGACATATAAGGCCAAGCTGCCCCTGGAGATCCTGCTGAT<br>GGTGTTCAACAGCATCGCCTTTCAGAATTCCGCCATCGATTGGGTGCGGGACCACAGACTG<br>CACCCACAAGTACTCCGACACCGATGCCGACCCCCACAACGCCTCTAGGGGCTTCTTTTATA<br>GCCACGTGGGATGGCTGCTGGTGCGGAAGCACCCTGAGGTGAAGAAGAGGCAAGGAGCT<br>GAATATGTCTGATATCTACAACAATCCTGTGCTGCGCTTCCAGAAGAAGTATGCCATCCCA<br>TTCATCGGCGCCGTGTGCTTTGCCCTGCCCACCATGATCCCCGTGTACTTTTGGGGCGAGA<br>CATGGAGCAACGCCTGGCACATCACAATGCTGCGGTATATCATGAACCTGAATGTGACATT<br>CCTGGTGAACTCCGCCGCCCACATCTGGGGCAATAAGCCATACGACGCCAAGATCCTGCCC<br>GCCCAGAACGTGGCCGTGAGCGTGGCAACCGGAGGAGAGGGCTTCCACAATTACCACCACG<br>TGTTTCCTTGGGATTATCGGGCGCCGAGCTGGGCAACAATTCTCTGAATCTGACCACAAA<br>GTTCATCGACCTGTTTGCCGCCATCGGCTGGGCCTATGATCTGAAGACAGTGAGCGAGGAC<br>ATGATCAAGCAGAGGATCAAGCGCACCGGCGATGGCACAGACCTGTGGGGGCACGAGCAGA<br>ACTGTGATGAAGTGTGGGATGTGAAAGACAAGTCCTCCTAA |
| SEQ ID NO: 21 | *Y. lipolytica* OLE1 leader-*T. ni* Z11 desaturase *Homo sapiens* optimized<br>ATGGTGAAGAACGTGGACCAGGTGGATCTGTCTCAGGTGGACACCATCGCAAGCGGAAGGG<br>ATGTGAATTATAAGGTGAAGTACACATCTGGCGTGAAGACCACACCAAGAAAGTACAAGTA<br>TATCTACACCAACTTCCTGACATTTTCTTACGCCCACCTGGCCGCCCTGTATGGCCTGTAC<br>CTGTGCTTTACCAGCGCCAAGTGGGAGACACTGCTGTTCTCCTTTGTGCTGTTCCACATGT<br>CTAATATCGGAATCACCGCAGGAGCACACAGGCTGTGGACCCACAAGACATTCAAGGCCAA<br>GCTGCCCCTGGAGATCGTGCTGATGATCTTCAACTCCCTGGCCTTTCAGAATACCGCCATC<br>ACATGGGCCCGGGAGCACAGACTGCACCACAAGTATTCTGACACCGATGCAGACCCACACA<br>ACGCAAGCAGGGGCTTCTTTTACTCCCACGTGGGCTGCTGCTGGTGAAGAAGCACCCTGA<br>CGTGCTGAAGTATGGCAAGACAATCGACATGAGCGACGTGTACAACAATCCTGTGCTGAAG<br>TTTCAGAAGAAGTATGCCGTGCCACTGATCGGCACCGTGTGCTTCGCCCTGCCCACACTGA<br>TCCCCGTGTACTGTTGGGGCGAGTCCTGGAACAATGCCTGGCACATCGCCCTGTTCCGGTA<br>CATCTTTAACCTGAATGTGACCTTTCTGGTGAACAGCGCCGCCCACATCTGGGGCAATAAG<br>CCATACGACAAGTCCATCCTGCCCGCCCAGAACCTGCTGGTGTCCTTCCTGGCCTCTGGCG<br>AGGGCTTTCACAATTATCACCACGTGTTCCCTTGGGACTACAGGACCGCAGAGCTGGGCAA<br>CAATTTTCTGAACCTGACCCACACTGTTCATCGATTTTTGTGCCTGGTTCGGCTGGGCCTAT<br>GACCTGAAGTCTGTGAGCGAGGATATCATCAAGCAGAGGGCAAAGAGGACAGGCGATGGCA<br>GCTCCGGCGTGATCTGGGGATGGGACGATAAGGATATGGACAGAGATATCAAGTCCAAGGC<br>CAATATCTTCTACGCCAAGAAGGAGTGA |

SEQUENCE LISTING

SEQ ID NO: 22    *Y. lipolytica* OLE1 leader-H. zea Z11 desaturase *Homo sapiens* optimized

```
ATGGTGAAAAACGTGGACCAAGTGGATCTCTCGCAGGTCGACACCATTGCCTCCGGCCGAG
ATGTCAACTACAAGGTCAAGTACACCTCCGGCGTTCGCAAGTATCAGATCGTGTATCCTAA
CCTGATCACCTTCGGCTACTGGCATATCGCTGGACTGTACGGACTGTATCTGTGCTTCACT
TCCGCCAAGTGGGCCACCATCCTGTTCTCTTACATCCTGTTTGTGCTGGCAGAGATCGGAA
TCACCGCAGGAGCACACAGACTGTGGCACAAGACATATAAGGCCAAGCTGCCACTGGA
GATCCTGCTGATGGTGTTCAACAGCATCGCCTTTCAGAATTCCGCCATCGATTGGGTGCGG
GACCACAGACTGCACCACAAGTACTCCGACACAGATGCCGACCCCCACAACGCCTCTAGGG
GCTTCTTTTATAGCCACGTGGGATGGCTGCTGGTGCGGAAGCACCCTGAGGTGAAGAAGAG
AGGCAAGGAGCTGAATATGTCTGATATCTACAACAATCCTGTGCTGCGCTTCCAGAAGAAG
TATGCCATCCCATTCATCGGCGCCGTGTGCTTTGCCCTGCCCACCATGATCCCCGTGTACT
TTTGGGGCGAGACATGGAGCAACGCCTGGCACATCACAATGCTGCGGTATATCATGAACCT
GAATGTGACATTCCTGGTGAACTCCGCCGCCCACATCGGGGCAATAAGCCATACGACGCC
AAGATCCTGCCCGCCCAGAACGTGGCCGTGAGCGTGGCAACCGGAGGAGAGGGCTTCCACA
ATTACCACCACGTGTTTCCATGGGATTATAGGGCAGCAGAGCTGGGAAACAATTCTCTGAA
TCTGACCACAAAGTTCATCGACCTGTTTGCCGCCATCGGCTGGGCCTATGATCTGAAGACA
GTGAGCGAGGACATGATCAAGCAGAGGATCAAGCGCACCGGCGATGGCACAGACCTGTGGG
GGCACGAGCAGAATTGTGATGAAGTGTGGGATGTGAAGGATAAAAGCAGTTGA
```

SEQ ID NO: 23    Native *A. transitella* Z11 desaturase

```
ATGGTCCCTAACAAGGGTTCCAGTGACGTTTTGTCTGAACATTCTGAGCCCCAGTTCACTA
AACTCATAGCTCCACAAGCAGGGCCGAGGAAATACAAGATAGTGTATCGAAATTTGCTCAC
ATTCGGCTATTGGCACTTATCAGCTGTTTATGGGCTCTACTTGTGCTTTACTTGTGCGAAA
TGGGCTACCATCTTATTTGCATTTTTCTTATACGTGATCGCGGAAATCGGTATAACAGGTG
GCGCTCATAGGCTATGGGCACATCGGACTTATAAAGCCAAGTTGCCTTTAGAGATTTTGTT
ACTCATAATGAATTCTATTGCCTTCCAAGCACACTGCTTTCACCTGGGCTCGAGATCACCGC
CTTCATCACAAATATTCGGATACTGACGCTGATCCCCACAATGCTACCAGAGGGTTTTCT
ATTCACATGTAGGCTGGCTTTTGGTGAAGAAACACCCTGAAGTCAAAGCAAGAGGAAAATA
CTTGTCGTTAGATGATCTTAAGAATAATCCATTGCTTAAATTCCAAAAGAAATACGCTATT
CTAGTTATAGGCACGTTATGCTTCCTTATGCCAACATTTGTGCCCGTATACTTCTGGGGCG
AGGGCATCAGCACGGCCTGGAACATCAATCTATTGCGATACGTCATGAATCTTAACATGAC
TTTCTTAGTTAACAGTGCAGCGCATATCTTTGGCAACAAACCATACGATAAGAGCATAGCC
TCAGTCCAAAATATTTCAGTTAGCTTAGCTACTTTTGGCGAAGGATTCCATAATTACCATC
ACACTTACCCCTGGGATTATCGTGCGGCAGAATTAGGAAATAATAGGCTAAATATGACTAC
TGCTTTCATAGATTTCTTCGCTTGGATCGGCTGGGCTTATGACTTGAAGTCTGTGCCACAA
GAGGCCATTGCAAAAGGTGTGCGAAAACTGGCGATGAACGGATATGTGGGGTCGAAAAA
GATAA
```

SEQ ID NO: 24    pPV0228_-_Z11_*Helicoverpa* zea_desaturase

```
ATGGCCCAAAGCTATCAATCAACTACGGTTTTGAGTGAGGAGAAAGAACTAACATTACAAC
ATTTGGTGCCCCAAGCATCGCCCAGGAAGTATCAAATAGTGTATCCGAACCTCATTACGTT
TGGTTACTGGCACATAGCCGGACTTTATGGCCTTTACTTGTGCTTCACTTCTGCTAAATGG
GCTACGATTTTATTCAGCTACATCCTCTTCGTGTTAGCAGAAATAGGAATCACGGCTGGCG
CTCACAGACTCTGGGCCCACAAAACTTACAAAGCGAAACTACCATTAGAAATACTCTTAAT
GGTATTCAACTCCATCGCTTTTCAAAACTCAGCCATTGACTGGGTGAGGGACCACCGACTC
CACCATAAGTATAGCGATACAGATGCTGATCCCCACAATGCCAGCCGAGGGTTCTTTTATT
CCCATGTAGGATGGCTACTTGTGAGAAAACATCCTGAAGTCAAAAAGCGAGGGAAAGAACT
CAATATGTCCGATATTTACAACAATCCTGTCTTACGGTTTCAGAAAAAATACGCCATACCC
TTCATTGGGCTGTTTGTTTCGCCTTACCTACAATGATACCTGTTTACTTCTGGGGAGAAA
CCTGGTCCAATGCTTGGCATATCACCATGCTTCGCTACATCATGAACCTCAATGTCACCTT
TTTGGTAAACAGCGCTGCTCATATATGGGGAAACAAGCCTTATGACGCAAAAATATTACCT
GCACAAAATGTAGCTGTGTCGGTCGCCACTGGTGGAGAAGGTTTCCATAATTACCACCATG
TCTTCCCCTGGGATTATCGAGCAGCGGAACTCGGTAACAATAGCCTCAATTTAACGACTAA
ATTCATAGATTTATTCGCAGCAATCGGATGGGCATATGATTTAAAGACGGTTTCGGAGGAT
ATGATAAAACAAAGGATTAAACGCACTGGAGATGGAACGGATCTTTGGGGACACGAACAAA
ACTGTGATGAAGTGTGGGATGTAAAAGATAAATCAAGTTAA
```

SEQ ID NO: 25    *Trichoplusia ni* desaturase

```
MAVMAQTVQE TATVLEEEAR TVTLVAPKTT PRKYKYIYTN FLTFSYAHLA
ALYGLYLCFT SAKWETLLFS FVLFHMSNIG ITAGAHRLWT HKTFKAKLPL
EIVLMIFNSL AFQNTAITWA REHRLHHKYS DTDADPHNAS RGFFYSHVGW
LLVKKHPDVL KYGKTIDMSD VYNNPVLKFQ KKYAVPLIGT VCFALPTLIP
VYCWGESWNN AWHIALFRYI FNLNVTFLVN SAAHIWGNKP YDKSILPAQN
LLVSFLASGE GFHNYHHVFP WDYRTAELGN NFLNLTTLFI DFCAWFGWAY
DLKSVSEDII KQRAKRTGDG SSGVIWGWDD KDMDRDIKSK ANIFYAKKE
```

SEQ ID NO: 26    *T. pseudonana* desaturase encoded by SEQ ID NO: 5

```
TSMDFLSGDP FRTLVLAALV VIGFAAAWQC FYPPSIVGKP RTLSNGKLNT
RIHGKLYDLS SFQHPGGPVA LSLVQGRDGT ALFESHHPFI PRKNLLQILS
KYEVPSTEDS VSFIATLDEL NGESPYDWKD IENDDFVSDL RALVIEHFSP
LAKERGVSLV ESSKATPQRW MVVLLLLASF FLSIPLYLSG SWTFVVVTPI
LAWLAVVNYW HDATHFALSS NWILNAALPY LLPLLSSPSM WYHHHVIGHH
AYTNISKRDP DLAHAPQLMR EHKSIKWRPS HLNQTQLPRI LFIWSIAVGI
GLNLLNDVRA LTKLSYNNVV RVEKMSSSRT LLHFLGRMLH IFVTTLWPFL
```

| | SEQUENCE LISTING |
|---|---|
| | AFPVWKAIVW ATVPNAILSL CFMLNTQINH LINTCAHASD NNFYKHQVVT<br>AQNFGRSSAF CFIFSGGLNY QIEHHLLPTV NHCHLPALAP GVERLCKKHG<br>VTYNSVEGYR EAIIAHFAHT KDMSTKPTD |
| SEQ ID NO: 27 | *T. pseudonana* Z11 desaturase encoded by SEQ ID NO: 16<br>MDFLSGDPFR TLVLAALVVI GFAAAWQCFY PPSIVGKPRT LSNGKLNTRI<br>HGKLYDLSSF QHPGGPVALS LVQGRDGTAL FESHHPFIPR KNLLQILSKY<br>EVPSTEDSVS FIATLDELNG ESPYDWKDIE NDDFVSDLRA LVIEHFSPLA<br>KERGVSLVES SKATPQRWMV VLLLLASFFL SIPLYLSGSW TFVVVTPILA<br>WLAVVNYWHD ATHFALSSNW ILNAALPYLL PLLSSPSMWY HHHVIGHHAY<br>TNISKRDPDL AHAPQLMREH KSIKWRPSHL NQTQLPRILF IWSIAVGIGL<br>NLLNDVRALT KLSYNNVVRV EKMSSSRTLL HFLGRMLHIF VTTLWPFLAF<br>PVWKAIVWAT VPNAILSLCF MLNTQINHLI NTCAHASDNN FYKHQVVTAQ<br>NFGRSSAFCF IFSGGLNYQI EHHLLPTVNH CHLPALAPGV ERLCKKHGVT<br>YNSVEGYREA IIAHFAHTKD MSTKPTD |
| SEQ ID NO: 28 | *Amyelois transitella* desaturase<br>MVPNKGSSDV LSEHSEPQFT KLIAPQAGPR KYKIVYRNLL TFGYWHLSAV<br>YGLYLCFTCA KWATILFAFF LYVIAEIGIT GGAHRLWAHR TYKAKLPLEI<br>LLLIMNSIAF QDTAFTWARD HRLHHKYSDT DADPHNATRG FFYSHVGWLL<br>VKKHPEVKAR GKYLSLDDLK NNPLLKFQKK YAILVIGTLC FLMPTFVPVY<br>FWGEGISTAW NINLLRYVMN LNMTFLVNSA AHIFGNKPYD KSIASVQNIS<br>VSLATFGSGF HNYHHTYPWD YRAAELGNNR LNMTTAFIDF FAWIGWAYDL<br>KSVPQEAIAK RCAKTGDGTD MWGRKR |
| SEQ ID NO: 29 | *Agrotis segetum* desaturase<br>MAQGVQTTTI LREEEPSLTF VVPQEPRKYQ IVYPNLITFG YWHIAGLYGL<br>YLCFTSAKWQ TILFSFMLVV LAELGITAGA HRLWAKKTYK AKLPLQIILM<br>ILNSIAFQNS AIDWVRDHRL HHKYSDTDAD PHNATRGFFY SHVGWLLVRK<br>HPEVKRRGKE LDMSDIYNNP VLRFQKKYAI PFIGAMCFGL PTFIPVYFWG<br>ETWSNAWHIT MLRYILNLNI TFLVNSAAHI WGYKPYDIKI LPAQNIAVSI<br>VTGGEVSITT TTFFPWDYRA AELGNNYLNL TTKFIDFFAW IGWAYDLKTV<br>SSDVIKSKAE RTGDGTNLWG LEDKGEEDFL KIWKDN |
| SEQ ID NO: 30 | *Ostrinia furnacalis* Z9 desaturase encoded by SEQ ID NO: 13<br>MAPNIKDGADLNGVLFEDDASTPDYALATAPVQKADNYPRKLVWRNLIFAYLHLAAVYG<br>AYLFLFSAKWQTDIFAYILYVISGLGITAGAHRLWAHKSYKAKWPLRLILIIFNTVSFQD<br>SALDWSRDHRMHHKYSETDADPHNATRGFFFSHIGWLLVRKKPELKRKGKGLDLSDLYAD<br>PILRFQKKYYLLLMPLGCFIMPTVVPVYFWGETWTNAFFVAALFRYTFILNVTWLVNSAA<br>HKWGKKPYDSSIKPSENLSVSLFALGEGFHNYHHTFPWDYKTAELGNNRLNFTTNFINFF<br>AKIGWAYDLKTVSDEIIQNRVKRTGDGSHHLWGWGDKDQPKEEVNAAIRINPKDE |
| SEQ ID NO: 31 | *Lanpronia capitella* Z9 desaturase encoded by SEQ ID NO: 14<br>MPPNVTEANGVLFENDVQTPDMGLEVAPVQKADERKIQLVWRNIIAFACLHLAAVYGAYL<br>FFTSAIWQTDIFAYILYVMSGLGITAGAHRLWAHKSYKAKWPLRLILVAFNTLAFQDSAI<br>DWARDHRMHHKYSETDADPHNATRGFFFSHIGWLLCRKHPELKRKGQGLDLSDLYADPII<br>RFQKKYYLLLMPLACFVLPTIIPVYLWGESWKNAFFVAAMFRYTFILNVTWLVNSAAHKW<br>GGKPYDKNIQPAQNISVAIFALGEGFHNYHHTFPWDYKTAELGNNRLNFTTSFINFFASF<br>GWAYDLKTVSDEIIQQRVKRTGDGSHHLRGWGDQDIPAEEAQAALRINRKDD |
| SEQ ID NO: 32 | *Helicoverpa zea* Z9 desaturase encoded by SEQ ID NO: 15<br>MAPNISEDVNGVLFESDAATPDLALSTPPVQKADNRPKQLVWRNILLFAYLHLAALYGGY<br>LFLFSAKWQTDIFAYILYVISGLGITAGAHRLWAHKSYKAKWPLRVILVIFNTVAFQDAA<br>MDWARDHRMHHKYSETDADPHNATRGFFFSHIGWLLTOKHPDLKEKGKGLDMSDLLADPI<br>LRFQKKYYLILMPLACFVMPTVIPVYFWGETWTNAFFVAAMFRYAFILNVTWLVNSAAHK<br>WGDKPYDKSIKPSENLSVAMFALGEGFHNYHHTFPWDYKTAELGNNKLNFTTTFINFFAK<br>IGWAYDLKTVSDDIVKNRVKRTGDGSHHLWGWGDENQSKEEIDAAIRINPKDD |
| SEQ ID NO: 33 | *Trichoplusia ni* desaturase with *Yarrowia lipolytica* OLE1<br>leader sequence encoded by SEQ ID NO: 21<br>MVKNVDQVDLSQVDTIASGRDVNYKVKYTSGVKTTPRKYKYIYTNFLTFSYAHLAALYGL<br>YLCFTSAKWETLLFSFVLPHMSNIGITAGAHRLWTHKTFPKAKLPLEIVLMIFNSLAFQNT<br>AITWAREHRLHHKYSDTDADPHNASRGFFYSHVGWLLVKKHPDVLKYGKTIDMSDVYNNP<br>VLKFQKKYAVPLIGTVCFALPTLIPVYCWGESWNNAWHIALFRYIFNLNVTFLVNSAAHI<br>WGNKPYDKSILPAQNLLVSFLASGEGFHNYHHVFPWDYRTAELGNNFLNLTTLFIDFCAW<br>FGWAYDLKSVSEDIIKQRAKRTGDGSSGVIWGWDDKDMDRDIKSKANIFYAKKE |
| SEQ ID NO: 34 | *Helicoverpa zea* desaturase with *Yarrowia lipolytica* OLE1<br>leader sequence encoded by SEQ ID NO: 22<br>MVKNVDQVDLSQVDTIASGRDVNYKVKYTSGVRKYQIVYPNLITFGYWHIAGLYGLYLCF<br>TSAKWATILFSYILFVLAEIGITAGAHRLWAHKTYKAKLPLEILLMVFNSIAFQNSAIDW<br>VRDHRLHHKYSDTDADPHNASRGFFYSKVGWLLVRKHPEVKKRGKELNMSDIYNNPVLRF<br>QKKYAIPFIGAVCFALPTMIPVYFWGETWSNAWHITMLRYIMNLNVTFLVNSAAHIWGNK<br>PYDAKILPAQNVAVSVATGGEGFHNYHHVFPWDYRAAELGNNSLNLTTKFIDLFAAIGWA<br>YDLKTVSEDMIKQRIKRTGDGTDLWGHEQNCDEVWDVKDKSS |

-continued

| | SEQUENCE LISTING |
|---|---|
| SEQ ID NO: 35 | *Agrotis segetum* desaturase with *Candida albicans* OLE1 leader sequence encoded by SEQ ID NO: 8<br>MTTVEQLHTVDITKLNAIAAGTNKKVPMAQGVQTTTILREEEPSLTFVVPQEPRKYQIVY<br>PNLITFGYWHIAGLYGLYLCFTSAKWQTILFSFMLVVLAELGITAGAHRLKAHKTYKAKL<br>PLQIILMILNSIAFQNSAIDWVRDHRLHHKYSDTDADPHNATRGFFYSHVGWLLVRKHPE<br>VKRRGKELDMSDIYNNPVLRFQKKYAIPFIGAMCFGLPTFIPVYFWGETWSNAWHITMLR<br>YILNLNITFLVNSAAKIWGYKPYDIKILPAQNIAVSIVTGGEVSITTTTFFPWDYRAAEL<br>GNNYLNLTTKFIDFFAWIGWAYDLKTVSSDVIKSKAERTGDGTNLWGLEDKGEEDFLKIW<br>KDN |
| SEQ ID NO: 36 | *Drosophila melanogaster* fatty acid desaturase (Q9N9Z8)<br>mapysriyhq dkssretgvl feddaqtvds dlttdrfqlk raekrrlplv<br>wrniilfalv hlaalyglhs iftraklatt lfaaglyiig mlgvtagahr<br>lwahrtykak wplrlllvif ntiafqdavy hwardhrvhh kysetdadph<br>natrgfffsh vgwllckkhp dikekgrgld lsdlradpil mfqrkhyyil<br>mplacfvlpt vipmvywnet lasswfvatm frwcfqlnmt wlvnsaahkf<br>gnrpydktmn ptqnafvsaf tfgegwhnyh hafpwdykta ewgcyslnit<br>tafidlfaki gwaydlktva pdviqrrvlr tgdgshelwg wgdkdltaed<br>arnvllvdks r |
| SEQ ID NO: 37 | *Lanpronia capitella* acyl-CoA-delta 11-desaturase(ABX71630.1)<br>mppypeevdt nhifeedish eeskpalkpl vapqadnrkp eivplnlitf<br>gyghlaaiyg iylcftsakw ativfafvly icaelgitag ahrlwshrsy<br>kaklplrlil llfntlafqn taidwvrdhr mhhkysdtda dphnatrgff<br>fshvgwlltr khpevkrrgk didmmdiynd sllkfqkkya ipfvglvcfv<br>iptlmpmyfw netlnnswhi atmlryivnl nmtflvnsaa hiwgykpydk<br>sikpvqnitv sililgegfh nyhhvfpwdy rtselgndfl nfttlfinlf<br>akigwaydlk tasdkvvaar rkrtgdgtnl wgwedkslne eerqaatvly<br>pnkylnlkd |
| SEQ ID NO: 38 | *Cydia pomonella* desaturase (AIM40221.1)<br>mapnvtdvng vlfesdaatp dlalanapvq qaddspriyv wrniilfayl<br>hiaalyggyl flvsakwqtd ifayflyvas glgitagahr lwahksykak<br>wplrlilvif ntiafqdsai dwardhrmhh kysetdadph natrgfffsh<br>igwllvrkhp elkrkgkgld lsdlyadpil rfqkkyylil mplacfvlpt<br>vipvylwnet wtnaffvaal fryafilnvt wlvnsaahkw gdkpydksik<br>psenisvslf afgegfhnyh htfpwdykta elssnrlnft tkfinffaki<br>gwaydmktvs deiiqkrvnr tgdgshhlwg wgdkdhskee vnaavrinpk<br>dd |
| SEQ ID NO: 39 | *Sesamia inferens* Z11 desaturase codon optimized nucleotide sequence<br>ATGCTGTCTCAGGAGGAGCCAACCGATACAAGCCTGGTGCCAAGGGCAGCACCTA<br>GAAAGTACCAGATCGTGTATCCCAATCTGATCACCTTCGGCTACTGGCACCTGGC<br>AGGGCTGTACGGCCTGTATCTGTGCTTTACATCCGCCAAGTGGACCACAATCCTG<br>TTCAGCTTCATCCTGTGCGTGATCGCCGAGATCGGAGTGACCGCAGGAGCACACA<br>GGCTGTGGGCCCACAAGACATATAAGGCCAACCTGCCCCTGCAGATCCTGCTGAT<br>GGTCATGAATTCCATCGCCTTCCAGAACTCTGCCATCGATTGGGTGCGGGACCAC<br>AGACTGCACCACAAGTACTCTGACACCGATGCCGACCCTCACAATGCCAGCAGAG<br>GCTTCTTTTATTCCCACGTGGGCTGGCTGCTGGTGAAGAAGCACCCAGAGGTGAA<br>GAAGAGGGGCAAGGAGCTGGATATGTCTGACATCTACAGCAACCCCGTGCTGCGC<br>TTCCAGAAGCAGTATGCCATCCCTTTCATCGGCGCCGTGTGCTTTATCCTGCCAA<br>CCGTGATCCCCGTGTACTGTTGGGGCGAGACATGGACAAATGCCTGGCACATCAC<br>AATGCTGAGGTATATCACCAATCTGAACGTGACATTTCTGGTGAACAGCGCCGCC<br>CACATCTGGGGCTACAAGCCTTATGATGAGAATATCCTGCCAGCCCAGAACATCG<br>CCGTGTCCATCGCAACCTGCGGAGAGGGCTTCCACAATTACCACCACGTGTTTCC<br>TTGGGATTATCGGGCCGCCGAGCTGGGCAACAATAACCTGAACCTGACCACAAAG<br>TTTATCGACTTCTTTGCCTGGCTGGGCTCGGCCTACGATCTGAAGACAGTGAGCT<br>CCGACATGATCAAGCTGAGGGCAAAGAGGACCGGCGACGGAACAAATCTGTGGGG<br>CGAGCACAACGATGAGCTGAAGGAGGGCAAGGAGGACTGA |
| SEQ ID NO: 40 | *Amyelois transitella* desaturase from DTU WO 2016/207339_SEQ ID NO: 2<br>MVPNKGSSDVLSEHSEPQFTKLIAPQAGPRKYKIVYRNLLTFGYWHLSAVYGLYLCFTCA<br>KWATILFAFFLYVIAEIGITGGAHRLWAHRTYKAKLPLEILLLIMNSIAFQDTAFTWARD<br>HRLHHKYSDTDADPHNATRGFFYSHVGWLLVKKHPEVKARGKYLSLDDLKNNPLLKFQKK<br>YAILVIGTLCFLMPTFVPVYFWGEGISTAWNINLLRYVMNLNMTFLVNSAAHIFGNKPYD<br>KSIASVQNISVSLATFGBGFHNYHHTYPWDYRAAELGNNRLNMTTAFIDFFAWIGWAYDL<br>KSVPQEAIAKRCAKTGDGTDMWGRKR |
| SEQ ID NO: 41 | *Spodoptera littoralis* desaturase from DTU WO 2016/207339_SEQ ID NO: 41<br>MAQCVQTTTI LEQKEEKTVT LLVPQAGKRK FEIVYFNIIT FAYWHIAGLY<br>GLYLCFTSTK WATVLFSFFL FVVAEVGVTA GSHRLWSHKT YKAKLPLQIL<br>LMVMNSLAFQ NTVIDWVRDH RLHHKYSDTD ADPHNASRGF FYSHVGWLLV<br>RKHPDVKKRG KEIDISDIYN NPVLRFQKKY AIPFIGAVCF VLPTLIPVYG |

SEQUENCE LISTING

| | |
|---|---|
| SEQ ID NO: 42 | WGETWTNAWK VAMLRYTMNL NVTFLVNSAA HIYGKRPYDK KILPSQNIAV SIATFGEGFH NYHHVFPWDY RAAELGNNSL NFPTKFIDFF AWIGWAYDLK TVSKEMIKQR SKRTGDGTNL WGLEDVDTPE DLKNTKGE |
| SEQ ID NO: 42 | *Agrotis segetum* desaturase from DTU WO 2016/207339_SEQ ID NO: 43<br>MAQGVQTTTILREEEPSLTFVVPQEPRKYQIVYPNLITFGYWHIAGLYGLYLCFTSAKWQ TILFSFMLVVLAELGITAGAHRLWAHKTYKAKLPLQIILMILNSIAFQNSAIDWVRDHRL HHKYSDTDADPHNATRGFFYSHVGWLLVRKHPEVKRRGKELDMSDIYNNPVLRFQKKYAI PFIGAMCFGLPTFIPVYFWGETWSNAWHITMLRYILNLNITFLVNSAAHIWGYKPYDIKI LPAQNIAVSIVTGGEVSITTTTFFPWDYRAAELGNNYLNLTTKFIDFFAWIGWAYDLKTV SSDVIKSKAERTGDGTNLWGLEDKGEEDFLKIWKDN |
| SEQ ID NO: 43 | *Trichoplusia ni* desaturase from DTU WO 2016/207339_SEQ ID NO: 45<br>MAVMAQTVQETATVLEEEARTVTLVAPKTTPRKYKYIYTNFLTFSYAHLAALYGLYLCFT SAKWETLLFSFVLFHMSNIGITAGAHRLWTHKTFKAKLPLEIVLMIFNSLAFQNTAITWA REHRLHHKYSDTDADPHNASRGFFYSHVGWLLVKKHPDVLKYGKTIDMSDVYNNPVLKFQ KKYAVPLIGTVCFALPTLIPVYCWGESWNNAWHIALFRYIFNLNVTFLVNSAAHIWGNKP YDKSILPAQNLLVSFLASGEGFHNYHHVFPWDYRTAELGNNFLNLTTLFIDFCAWFGWAY DLKSVSEDIIKQRAKRTGDGSSGVIWGWDDKDMDRDIKSKANIFYAKKE |
| SEQ ID NO: 44 | *Amyelois transitella* desaturase from DTU WO 2016/2C7339_SEQ ID NO: 1<br>atg gtt cca aac aag ggt tcc tct gat gtt ttg tct gaa cat tct<br>gaa cca caa ttc acc aag ttg att gct cca caa gct ggt cca aga<br>aag tac aaa atc gtt tac aga aac ttg ttg acc ttc ggt tac tgg<br>cat ttg tct gct gtt tat ggt ttg tac ttg tgt ttc act tgt gct<br>aag tgg gct act att ttg ttc gct ttc ttc ttg tac gtt atc gcc<br>gaa att ggt att act ggt ggt gct cat aga tta tgg gct cat aga<br>act tac aaa gcc aag ttg cca ttg gaa atc ttg ttg ttg atc atg<br>aac tcc att gcc ttc caa gat act gct ttt act tgg gct aga gat<br>cat aga ttg cat cac aag tac tct gat act gat gct gat cca cat<br>aat gct act aga ggt ttc ttc tac tct cat gtt ggt tgg ttg ttg<br>gtt aag aaa cac cca gaa gtt aag gct aga ggt aag tac ttg tct<br>ttg gat gac ttg aag aac aac cct ttg ttg aag ttc caa aag aag<br>tac gcc att ttg gtc att ggt act ttg tgc ttt ttg atg cca act<br>ttc gtt cca gtt tac ttt tgg ggt gaa ggt att tct act gcc tgg<br>aac att aac ttg tta aga tac gtc atg aac ttg aac atg acc ttt<br>ttg gtt aac tcc gct gct cat att ttt ggt aac aag cca tac gat<br>aag tct atc gcc tct gtt caa aac atc tct gtt tct ttg gct act<br>ttc ggt gaa ggt ttc cat aac tac cat cat act tat cca tgg gat<br>tac aga gct gct gaa ttg gtt aac aat aga ttg aat atg acc acc<br>gcc ttc att gat ttc ttt gct tgg att ggt tgg gcc tac gat ttg<br>aaa tct gtt cca caa gaa gct att gct aag aga tgt gct aaa act<br>ggt gat ggt act gat atg tgg ggt aga aag aga tga |
| SEQ ID NO: 45 | *Spodoptera littoralis* desaturase from DTU WO 2016/207339_SEQ ID NO: 40<br>ggacactgac atggactgaa ggagtagaga atcggcccgt ggagttggcc<br>ttcatttttca gccttatctc tcggtgttat ggtagtcact tatatcggta<br>ttaaaataag tgaataaggc ttgtaaaaat ggcgcaatgt gtacaaacaa<br>caacgatttt ggaacaaaaa gaagagaaaa cagtaactt gctggtacct<br>caagcgggaa agaggaagtt tgaaattgtg tattttaata tcatcacctt<br>cgcttactgg catatagctg gactatatgg cctttatttg tgcttcactt<br>caacaaaatg ggcgacagtt ttattctcat tctttctatt cgtcgtagca<br>gaagtagggg tcacggctgg ctcccacaga ctttggtcgc ataaaactta<br>caaagcaaaa ctacctttac aaattctgct aatggtgatg aattcccttg<br>catttcaaaa cacagtcatt gattgggtga gagaccatcg actccatcat<br>aagtatagcg acactgatgc cgatccccat aatgcctccc gaggattttt<br>ctattcgcac gtcggttggc tgcttgtgag aaaacaccct gatgtcaaga<br>aacgaggaaa ggaaattgat atatctgata tttacaacaa tccggtactg<br>aggttccaga agaagtacgc aattcctttc atcggggcag tttgtttcgt<br>cttaccaaca ttgataccgg tttacggttg gggagaaacc tggactaatg<br>cctggcacgt cgccatgctg cggtacatta tgaaccttaa cgtcaccttc<br>ctggtcaaca gcgctgctca tatatatgga aagagacctt atgacaagaa<br>gatcctacca tctcaaaaca tagctgtgtc cattgcaacc tttggggaag<br>gtttccataa ttatcatcat gtatttccat gggattatcg cgcagctgaa<br>cttggaaata acagtttgaa tttccctacg aaattattg atttctttgc<br>gtgggatcgga tgggcgtatg acctaaagac tgtttcgaaa gaaatgataa<br>aacaaaggtc aaaaagaact ggtgatggaa ctaatctatg gggttagaa<br>gatgtggata ccccggagga tttaaaaaat acaaaaggcg aataggcaaa<br>cccttaaact caaacagtga ggtttaatgt gatatttaga attagaatta<br>atttatttga aattaaatga aggttttgga taactgtttt taataataaa<br>aatagttttt cgattaaatt ccttagatta ttttaaagga aatgtataag<br>gtactcgcgt ggttagcaac ccagcagtcc ctgtttatct gttttttatga |

SEQUENCE LISTING

```
                      atttattcta tgaatgtaga tgtcgcatga aattttaaaa tgttgcattt
                      gtataatttt acttatgaat aaataaattt atttttaaaa
                      aaaaaaaaaa aaaaaaaaaa aaaaaaaaaa SEQ ID NO: 46         Agrotis segetum desaturase from DTU WO 2016/207339_SEQ ID NO:
                      42
                      atg gct caa ggt gtc caa aca act acg ata ttg agg gag gaa gag
                      ccg tca ttg act ttc gtg gta cct caa gaa ccg aga aag tat caa
                      atc gtg tac cca aac ctt atc aca ttt ggg tac tgg cat ata gct
                      ggt tta tac ggg cta tat ttg tgc ttt act tcg gca aaa tgg caa
                      aca att tta ttc agt ttc atg ctc gtt gtg tta gca gag ttg gga
                      ata aca gcc ggc gct cac agg tta tgg gcc cac aaa aca tat aaa
                      gcg aag ctt ccc tta caa att atc ctg atg ata ctg aac tcc att
                      gcc ttc caa aat tcc gcc att gat tgg gtg agg gac cac cgt ctc
                      cat cat aag tac agt gac act gat gca gac cct cac aat gct act
                      cgt ggt ttc ttc tat tct cat gtt gga tgg ttg ctc gta aga aaa
                      cat cca gaa gtc aag aga cgt gga aag gaa ctt gac atg tct gat
                      att tac aac aat cca gtg ctg aga ttt caa aag aag tat gct ata
                      ccc ttc atc ggg gca atg tgc ttc gga tta cca act ttt atc cct
                      gtt tac ttc tgg gga gaa acc tgg agt aat gct tgg cat atc acc
                      atg ctt cgg tac atc ctc aac cta aac att act ttc ctg gtc aac
                      agt gct gct cat atc tgg gga tac aaa cct tat gac atc aaa ata
                      ttg cct gcc caa aat ata gca gtt tcc ata gta acc ggc ggc gaa
                      gtt tcc ata act acc acc acg ttt ttt cct tgg gat tat cgt gca
                      gca gaa ttg ggg aac aat tat ctt aat ttg acg act aag ttc ata
                      gat ttc ttc gct tgg atc gga tgg gct tac gat ctt aag acg gtg
                      tcc agt gat gtt ata aaa agt aag gcg gaa aga act ggt gat ggg
                      acg aat ctt tgg ggt tta gaa gac aaa ggt gaa gaa gat ttt ttg
                      aaa atc tgg aaa gac aat taa SEQ ID NO: 47         Trichoplusia ni desaturase from DTU WO 2016/207339_SEQ ID NO:
                      44
                      atg gct gtg atg gct caa aca gta caa gaa acg gct aca gtg ttg
                      gaa gag gaa gct cgc aca gtg act ctt gtg gct cca aag aca acg
                      cca agg aaa tat aaa tat ata tac acc aac ttt ctt aca ttt tca
                      tat gcg cat tta gct gca tta tac gga ctt tat ttg tgc ttc acc
                      tct gcg aaa tgg gaa aca ttg cta ttc tct ttc gta ctc ttc cac
                      atg tca aat ata ggc atc acc gca ggg gct cac cga ctc tgg act
                      cac aag act ttc aaa gcc aaa ttg cct ttg gaa att gtc ctc atg
                      ata ttc aac tct tta gcc ttt caa aac acg gct att aca tgg gct
                      aga gaa cat cgg cta cat cac aaa tac agc gat act gat gct gat
                      ccc cac aat gcg tca aga ggg ttc ttc tac tcg cat gtt ggc tgg
                      cta tta gta aaa aaa cat ccc gat gtc ctg aaa tat gga aaa act
                      ata gac atg tcg gat gta tac aat aat cct gtg tta aaa ttt cag
                      aaa aag tac gca gta ccc tta att gga aca gtt tgt ttt gct ctt
                      cca act ttg att cca gtc tac tgt tgg ggc gaa tcg tgg aac aac
                      gct tgg cac ata gcc tta ttt cga tac ata ttc aat ctt aac gtg
                      act ttc cta gtc aac agt gct gcg cat atc tgg ggg aat aag cct
                      tat gat aaa agc atc ttg ccc gct caa aac ctg ctg gtt tcc ttc
                      cta gca agt gga gaa ggc ttc cat aat tac cat cac gtc ttt cca
                      tgg gat tac cgc aca gca gaa tta ggg aat aac ttc ctg aat ttg
                      acg acg ctg ttc att gat ttt tgt gcc tgg ttt gga tgg gct tat
                      gac ttg aag tct gta tca gag gat att ata aaa cag aga gct aaa
                      cga aca ggt gac ggt tct tca ggg gtc att tgg gga tgg gac gac
                      aaa gac atg gac cgc gat ata aaa tct aaa gct aac att ttt tat
                      gct aaa aag gaa tga
```

The foregoing detailed description has been given for clearness of understanding only and no unnecessary limitations should be understood there from as modifications will be obvious to those skilled in the art.

While the disclosure has been described in connection with specific embodiments thereof, it will be understood that it is capable of further modifications and this application is intended to cover any variations, uses, or adaptations of the disclosure following, in general, the principles of the disclosure and including such departures from the present disclosure as come within known or customary practice within the art to which the disclosure pertains and as may be applied to the essential features hereinbefore set forth and as follows in the scope of the appended claims.

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

What is claimed is:

1. A method of producing a mono- or poly-unsaturated $C_6$-$C_{24}$ fatty acetate ester or aldehyde from a $C_6$-$C_{24}$ fatty acid, the method comprising the steps of:
   a) producing a mono- or poly-unsaturated $C_6$-$C_{24}$ fatty acid in a *Yarrowia lipolytica* microorganism manipulated to comprise at least one nucleic acid molecule encoding an exogenous fatty acyl desaturase having at least 95% sequence identity to the amino acid sequence of an insect fatty acyl desaturase selected from the group consisting of SEQ ID NOs: 1, 2, 32, 34, and 36-38;
   b) chemically esterifying and/or transesterifying the mono- or poly-unsaturated $C_6$-$C_{24}$ fatty acid to a $C_6$-$C_{24}$ fatty acid alkyl ester (FAAE) via Fischer esterification or acid or base catalyzed esterification or transesterification;
   c) chemically reducing the FAAE by contacting the FAAE with a reducing agent, a partial reducing agent, or a transition metal catalyst, wherein the reduction produces a mono- or poly-unsaturated $C_6$-$C_{24}$ fatty alcohol; and
   d) chemically converting the mono- or poly-unsaturated $C_6$-$C_{24}$ fatty alcohol to a corresponding $C_6$-$C_{24}$ fatty acetate ester by contacting the mono- or poly-unsaturated $C_6$-$C_{24}$ fatty alcohol with an acetylating agent, or chemically converting the mono- or poly-unsaturated $C_6$-$C_{24}$ fatty alcohol to a corresponding $C_6$-$C_{24}$ fatty aldehyde by contacting the mono- or poly-unsaturated $C_6$-$C_{24}$ fatty alcohol with an oxidizing agent.

2. The method of claim 1, wherein the *Yarrowia lipolytica* microorganism comprises a deletion, disruption, mutation, and/or reduction in the activity of one or more endogenous enzymes selected from the following:
   (i) one or more acyl-CoA oxidases encoded by a nucleic acid sequence selected from the group consisting of YALI0E32835g (POX1), YALI0F10857g (POX2), YALI0D24750g (POX3), YALI0E27654g (POX4), YALI0C23859g (POX5), and YALI0E06567g (POX6);
   (ii) one or more (fatty) alcohol dehydrogenases encoded by a nucleic acid sequence selected from the group consisting of YALI0F09603g (FADH), YALI0D25630g (ADH1), YALI0E17787g (ADH2), YALI0A16379g (ADH3), YALI0E15818g (ADH4), YALI0D02167g (ADH5), YALI0A15147g (ADH6), and YALI0E07766g (ADH7);
   (iii) a (fatty) alcohol oxidase encoded by YALI0B14014g (FAO1);
   (iv) a fatty acyl-CoA synthetase/fatty acid transporter encoded by YALI0E16016g (FAT1); and
   (v) an intracellular triacylglycerol lipase encoded by YALI0D17534g (TGL3).

3. The method of claim 1, wherein the step of chemically esterifying and/or transesterifying the mono- or poly-unsaturated $C_6$-$C_{24}$ fatty acid to the $C_6$-$C_{24}$ FAAE further comprises the steps of:
   isolating the mono- or poly-unsaturated $C_6$-$C_{24}$ fatty acid and/or enriching for a mono- or poly-unsaturated $C_6$-$C_{24}$ fatty acid having a specific chain length.

4. The method of claim 1, wherein the *Yarrowia lipolytica* microorganism comprises an exogenous elongase.

5. The method of claim 4, wherein the exogenous elongase is encoded by a gene selected from the group consisting of *Saccharomyces cerevisiae* ELO1, *Saccharomyces cerevisiae* ELO2 and *Saccharomyces cerevisiae* ELO3.

6. The method of claim 4, wherein the exogenous elongase is a fatty acid elongase.

7. The method of claim 1, wherein the *Yarrowia lipolytica* microorganism comprises a deletion, disruption, mutation, and/or reduction in the activity of one or more endogenous proteins involved in one or more fatty acid elongation pathways selected from the group consisting of a β-ketoacyl-CoA reductase, a β-hydroxyacyl-CoA dehydratase, an enoyl-CoA reductase, and any combination thereof.

8. The method of claim 1, wherein the *Yarrowia lipolytica* microorganism is MATA ura3-302::SUC2 Δpox1 Δpox2 Δpox3 Δpox4 Δpox5 Δpox6 Δfadh Δadh1 Δadh2 Δadh3 Δadh4 Δadh5 Δadh6 Δadh7 Δfao1.

9. The method of claim 1, wherein the *Yarrowia lipolytica* microorganism comprises one or more flavoprotein pyridine nucleotide cytochrome reductases selected from the group consisting of a cytochrome-b5 reductase and an NADPH-dependent cytochrome P450 reductase.

10. The method of claim 1, wherein the *Yarrowia lipolytica* microorganism comprises one or more thioesterases selected from the group consisting of an acyl-ACP thioesterase and an acyl-CoA thioesterase.

11. The method of claim 1, wherein the *Yarrowia lipolytica* microorganism does not comprise a nucleic acid molecule encoding an exogenous acyl-ACP thioesterase.

12. The method of claim 1, wherein the *Yarrowia lipolytica* microorganism has a lipid fraction of at least 30% w/w and the unsaturated fatty acid produced in step (a) is at least 10% g/g of the fatty acid species.

13. The method of claim 1, wherein step (a) has an unsaturated fatty acid yield of at least 3% g/g of the *Yarrowia lipolytica* dry cell weight.

* * * * *

SEQUENCE LISTING

<160> NUMBER OF SEQ ID NOS: 47

<210> SEQ ID NO 1
<211> LENGTH: 338
<212> TYPE: PRT
<213> ORGANISM: Helicoverpa zea

<400> SEQUENCE: 1

Met Ala Gln Ser Tyr Gln Ser Thr Thr Val Leu Ser Glu Glu Lys Glu
1               5                   10                  15

Leu Thr Leu Gln His Leu Val Pro Gln Ala Ser Pro Arg Lys Tyr Gln
            20                  25                  30

Ile Val Tyr Pro Asn Leu Ile Thr Phe Gly Tyr Trp His Ile Ala Gly
        35                  40                  45

Leu Tyr Gly Leu Tyr Leu Cys Phe Thr Ser Ala Lys Trp Ala Thr Ile
    50                  55                  60

Leu Phe Ser Tyr Ile Leu Phe Val Leu Ala Glu Ile Gly Ile Thr Ala
65                  70                  75                  80

Gly Ala His Arg Leu Trp Ala His Lys Thr Tyr Lys Ala Lys Leu Pro
                85                  90                  95

Leu Glu Ile Leu Leu Met Val Phe Asn Ser Ile Ala Phe Gln Asn Ser
            100                 105                 110

Ala Ile Asp Trp Val Arg Asp His Arg Leu His Lys Tyr Ser Asp
        115                 120                 125

Thr Asp Ala Asp Pro His Asn Ala Ser Arg Gly Phe Phe Tyr Ser His
130                 135                 140

Val Gly Trp Leu Leu Val Arg Lys His Pro Glu Val Lys Lys Arg Gly
145                 150                 155                 160

Lys Glu Leu Asn Met Ser Asp Ile Tyr Asn Asn Pro Val Leu Arg Phe
                165                 170                 175

Gln Lys Lys Tyr Ala Ile Pro Phe Ile Gly Ala Val Cys Phe Ala Leu
            180                 185                 190

Pro Thr Met Ile Pro Val Tyr Phe Trp Gly Glu Thr Trp Ser Asn Ala
        195                 200                 205

Trp His Ile Thr Met Leu Arg Tyr Ile Met Asn Leu Asn Val Thr Phe
    210                 215                 220

Leu Val Asn Ser Ala Ala His Ile Trp Gly Asn Lys Pro Tyr Asp Ala
225                 230                 235                 240

Lys Ile Leu Pro Ala Gln Asn Val Ala Val Ser Val Ala Thr Gly Gly
                245                 250                 255

Glu Gly Phe His Asn Tyr His His Val Phe Pro Trp Asp Tyr Arg Ala
            260                 265                 270

Ala Glu Leu Gly Asn Asn Ser Leu Asn Leu Thr Thr Lys Phe Ile Asp
        275                 280                 285

Leu Phe Ala Ala Ile Gly Trp Ala Tyr Asp Leu Lys Thr Val Ser Glu
    290                 295                 300

Asp Met Ile Lys Gln Arg Ile Lys Arg Thr Gly Asp Gly Thr Asp Leu
305                 310                 315                 320

Trp Gly His Glu Gln Asn Cys Asp Glu Val Trp Asp Val Lys Asp Lys
                325                 330                 335

Ser Ser

<210> SEQ ID NO 2
<211> LENGTH: 324
<212> TYPE: PRT

<213> ORGANISM: Sesamia inferens

<400> SEQUENCE: 2

```
Met Leu Ser Gln Glu Glu Pro Thr Asp Thr Ser Leu Val Pro Arg Ala
1               5                   10                  15

Ala Pro Arg Lys Tyr Gln Ile Val Tyr Pro Asn Leu Ile Thr Phe Gly
            20                  25                  30

Tyr Trp His Leu Ala Gly Leu Tyr Gly Leu Tyr Leu Cys Phe Thr Ser
        35                  40                  45

Ala Lys Trp Thr Thr Ile Leu Phe Ser Phe Ile Leu Cys Val Ile Ala
    50                  55                  60

Glu Ile Gly Val Thr Ala Gly Ala His Arg Leu Trp Ala His Lys Thr
65                  70                  75                  80

Tyr Lys Ala Asn Leu Pro Leu Gln Ile Leu Leu Met Val Met Asn Ser
                85                  90                  95

Ile Ala Phe Gln Asn Ser Ala Ile Asp Trp Val Arg Asp His Arg Leu
            100                 105                 110

His His Lys Tyr Ser Asp Thr Asp Ala Asp Pro His Asn Ala Ser Arg
        115                 120                 125

Gly Phe Phe Tyr Ser His Val Gly Trp Leu Leu Val Lys Lys His Pro
    130                 135                 140

Glu Val Lys Lys Arg Gly Lys Glu Leu Asp Met Ser Asp Ile Tyr Ser
145                 150                 155                 160

Asn Pro Val Leu Arg Phe Gln Lys Gln Tyr Ala Ile Pro Phe Ile Gly
                165                 170                 175

Ala Val Cys Phe Ile Leu Pro Thr Val Ile Pro Val Tyr Cys Trp Gly
            180                 185                 190

Glu Thr Trp Thr Asn Ala Trp His Ile Thr Met Leu Arg Tyr Ile Thr
        195                 200                 205

Asn Leu Asn Val Thr Phe Leu Val Asn Ser Ala Ala His Ile Trp Gly
    210                 215                 220

Tyr Lys Pro Tyr Asp Glu Asn Ile Leu Pro Ala Gln Asn Ile Ala Val
225                 230                 235                 240

Ser Ile Ala Thr Cys Gly Glu Gly Phe His Asn Tyr His His Val Phe
                245                 250                 255

Pro Trp Asp Tyr Arg Ala Ala Glu Leu Gly Asn Asn Asn Leu Asn Leu
            260                 265                 270

Thr Thr Lys Phe Ile Asp Phe Phe Ala Trp Leu Gly Trp Ala Tyr Asp
        275                 280                 285

Leu Lys Thr Val Ser Ser Asp Met Ile Lys Leu Arg Ala Lys Arg Thr
    290                 295                 300

Gly Asp Gly Thr Asn Leu Trp Gly Glu His Asn Asp Glu Leu Lys Glu
305                 310                 315                 320

Gly Lys Glu Asp
```

<210> SEQ ID NO 3
<211> LENGTH: 1050
<212> TYPE: DNA
<213> ORGANISM: Trichoplusia ni

<400> SEQUENCE: 3

```
atggctgtga tggctcaaac agtacaagaa acggctacag tgttggaaga ggaagctcgc      60
acagtgactc ttgtggctcc aaagacaacg ccaaggaaat ataaatatat atacaccaac     120
tttcttacat tttcatatgc gcatttagct gcattatacg gactttattt gtgcttcacc     180
```

```
tctgcgaaat gggaaacatt gctattctct ttcgtactct tccacatgtc aaatataggc    240
atcaccgcag gggctcaccg actctggact cacaagactt tcaaagccaa attgcctttg    300
gaaattgtcc tcatgatatt caactcttta gcctttcaaa acacggctat tacatgggct    360
agagaacatc ggctacatca caaatacagc gatactgatg ctgatcccca caatgcgtca    420
agagggttct tctactcgca tgttggctgg ctattagtaa aaaacatcc cgatgtcctg     480 aaatatggaa aaactataga catgtcggat gtatacaata tcctgtgtt aaaatttcag     540 aaaaagtacg cagtacccct aattggaaca gtttgttttg ctctgccaac tttgattcca    600
gtctactgtt ggggcgaatc gtggaacaac gcttggcaca tagccttatt tcgatacata    660
ttcaatctta acgtgacttt cctagtcaac agtgctgcgc atatctgggg gaataagcct    720
tatgataaaa gcatcttgcc cgctcaaaac ctgctggttt ccttcctagc aagtggagaa    780
ggcttccata attaccatca cgtctttcca tgggattacc gcacagcaga attagggaat    840
aacttcctga atttgacgac gctgttcatt gattttgtg cctggtttgg atgggcttat     900
gacttgaagt ctgtatcaga ggatattata aaacagagag ctaaacgaac aggtgacggt    960
tcttcagggg tcatttgggg atgggacgac aagacatgg accgcgatat aaaatctaaa    1020
gctaacattt tttatgctaa aaaggaatga                                     1050

<210> SEQ ID NO 4
<211> LENGTH: 1011
<212> TYPE: DNA
<213> ORGANISM: Agrotis segetum

<400> SEQUENCE: 4
atggctcaag gtgtccaaac aactacgata ttgagggagg aggagccgtc attgactttc     60
gtggtacctc aagaaccgag aaagtatcaa atcgtgtacc caaaccttat cacatttggg    120
tactggcata tagctggttt atacgggcta tatttgtgct ttacttcggc aaaatggcaa    180
acaattttat tcagtttcat gctcgttgtg ttagcagagt tgggaataac agccggcgct    240
cacaggttat gggcccacaa acatatataaa gcgaagcttc ccttacaaat tatcctgatg    300
atactgaact ccattgcctt ccaaaattcc gccattgatt gggtgaggga ccaccgtctc    360
catcataagt acagtgacac tgatgcagac cctcacaatg ctactcgtgg tttcttctat    420
tctcatgttg gatggttgct cgtaagaaaa catccagaag tcaagagacg tggaaaggaa    480
cttgacatgt ctgatattta caacaatcca gtgctgagat tcaaaagaa gtatgctata    540 ccttcatcg gggcaatgtg cttcggatta ccaactttta tccctgttta cttctgggga    600
gaaacctgga gtaatgcttg gcatatcacc atgcttcggt acatcctcaa cctaaacatt    660
actttcctgg tcaacagtgc tgctcatatc tggggataca aaccttatga catcaaaata    720
ttgcctgccc aaaatatagc agtttccata gtaaccggcg gcgaagtttc cataactacc    780
accacgtttt ttccttggga ttatcgtgca gcagaattgg ggaacaatta tcttaatttg    840
acgactaagt tcatagattt cttcgcttgg atcggatggg cttacgatct taagacggtg    900
tccagtgatg ttataaaaag taaggcggaa agaactggtg atgggacgaa tctttggggt    960
ttagaagaca aaggtgaaga agattttttg aaaatctgga aagacaatta a             1011

<210> SEQ ID NO 5
<211> LENGTH: 1440
<212> TYPE: DNA
<213> ORGANISM: Thalassiosira pseudonana
```

```
<400> SEQUENCE: 5
actagtatgg actttctctc cggcgatcct ttccggacac tcgtccttgc agcacttgtt      60
gtcatcggat ttgctgcggc gtggcaatgc ttctacccgc cgagcatcgt cggcaagcct     120
cgtacattaa gcaatggtaa actcaatacc agaatccatg gcaaattgta cgacctctca     180
tcgtttcagc atccaggagg ccccgtggct ctttctcttg ttcaaggtcg cgacggaaca     240
gctctatttg agtcacacca tcccttcata cctcgaaaga atctacttca gatcctctcc     300
aagtacgagg ttccgtcgac tgaagactct gtttccttca tcgccaccct agacgaactc     360
aatggtgaat ctccgtacga ttggaaggac attgaaaatg atgatttcgt atctgaccta     420
cgagctctcg taattgagca cttttctcct ctcgccaagg aaaggggagt ttcactcgtt     480
gagtcgtcga aggcaacacc tcagcggtgg atggtggttc tactgctcct tgcgtcgttc     540
ttcctcagca tcccattata tttgagtggt tcgtggactt tcgttgtcgt cactcccatc     600
ctcgcttggc tggcggttgt caattactgg cacgatgcta ctcactttgc attgagcagc     660
aactggattt tgaatgctgc gctcccatat ctcctccctc tcctatcgag tccgtcaatg     720
tggtatcatc atcacgtcat ggacatcac gcatacacca acatttccaa aagagatcca     780
gatcttgctc acgctccaca actcatgaga gaacacaaga gtatcaaatg gagaccatct     840
cacttaaatc aaacacagct tccgcggatt ctcttcatct ggtcgattgc agtcggtatt     900
gggttgaact tactgaacga cgtgagagca ctaaccaagc tttcatacaa caacgttgtt     960
cgggtggaga agatgtcatc gtcgcgaaca ttactccatt tccttggacg tatgttgcac    1020
atctttgtga ctacactttg gcccttttg gcgtttccgg tgtggaaggc catcgtttgg    1080
gcgactgtac cgaatgccat actgagtttg tgcttcatgc tgaatacgca aatcaatcac    1140
ctcatcaaca cgtgtgcaca tgcttccgat aacaactttt acaagcatca agttgtaact    1200
gctcagaact ttggccgatc aagtgccttt tgcttcatct tctcgggagg tctcaactac    1260
caaattgaac atcatttgtt gccgacggtg aaccattgcc attttgccagc tttggccccg    1320 ggtgtagagc gtttgtgtaa gaaacacggg gtgacataca actctgttga aggatacaga    1380
gaggccatca ttgcacactt tgcacatacc aaagatatgt cgacgaagcc tactgattga    1440

<210> SEQ ID NO 6
<211> LENGTH: 981
<212> TYPE: DNA
<213> ORGANISM: Amyelois transitella

<400> SEQUENCE: 6
atggtcccta caagggttc cagtgacgtt ttgtctgaac attctgagcc ccagttcact      60
aaactcatag ctccacaagc agggccgagg aaatacaaga tagtgtatcg aaatttgctc     120
acattcggct attggcactt atcagctgtt tatgggctct acttgtgctt tacttgtgcg     180
aaatgggcta ccatcttatt tgcatttttc ttatacgtga tcgcggaaat cggtataaca     240
ggtggcgctc ataggctatg ggcacatcgg acttataaag ccaagttgcc tttagagatt     300
ttgttactca taatgaactc tattgccttc aagacactg ctttcacctg gctcgtgat     360 caccgccttc atcacaaata tcggatact acgctgatc cccacaatgc taccagaggg     420 ttttttctatt cacatgtagg ctggcttttg gtgaagaaac accctgaagt caaagcaaga     480
ggaaaatact tgtcgttaga tgatcttaag aataatccat tgcttaaatt ccaaaagaaa     540
tacgctattc tagttatagg cacgttatgc ttccttatgc caacatttgt gcccgtatac     600
ttctggggcg agggcatcag cacggcctgg aacatcaatc tattgcgata cgtcatgaat     660
```

```
cttaacatga ctttcttagt taacagtgca gcgcatatct ttggcaacaa accatacgat      720
aagagcatag cctcagtcca aaatatttca gttagcttag ctacttttgg cgaaggattc      780
cataattacc atcacactta ccoctgggat tatcgtgcgg cagaattagg aaataatagg      840
ctaaatgatg ctactgcttt catagatttc ttcgcttgga tcggctgggc ttatgacttg      900
aagtctgtgc cacaagaggc cattgcaaaa aggtgtgcga aaactggcga tggaacggat      960
atgtggggtc gaaaaagata a                                               981

<210> SEQ ID NO 7
<211> LENGTH: 1017
<212> TYPE: DNA
<213> ORGANISM: Helicoverpa zea

<400> SEQUENCE: 7
atggcccaaa gctatcaatc aactacggtt ttgagtgagg agaaagaact aacactgcaa       60
catttggtgc cccaagcatc gcccaggaag tatcaaatag tgtatccgaa cctcattacg      120
tttggttact ggcacatagc cggactttat ggcctttact tgtgcttcac ttctgctaaa      180
tgggctacga ttttattcag ctacatcctc ttcgtgttag cagaaatagg aatcacggct      240
ggcgctcaca gactctgggc ccacaaaact tacaaagcga aactaccatt agaaatactc      300
ttaatggtat tcaactccat cgcttttcaa aactcagcca ttgactgggt gagggaccac      360
cgactccacc ataagtatag cgatacagat gctgatcccc acaatgccag ccgagggttc      420
ttttattccc atgtaggatg gctacttgtg agaaaacatc ctgaagtcaa aaagcgaggg      480
aaagaactca atatgtccga tatttacaac aatcctgtcc tgcggtttca gaaaaaatac      540 gccatacect tcattgggge tgttttgttte gccttaccta caatgatacc tgtttacttc      600
tggggagaaa cctggtccaa tgcttggcat atcaccatgc ttcgctacat catgaacctc      660
aatgtcacct ttttggtaaa cagcgctgct catatatggg aaacaagcc ttatgacgca      720 aaaatattac ctgcacaaaa tgtagctgtg tcggtcgcca ctggtggaga aggtttccat      780
aattaccacc atgtcttccc ctgggattat cgagcagcgg aactcggtaa caatagcctc      840
aatctgacga ctaaattcat agattttattc gcagcaatcg gatgggcata tgatctgaag      900
acggtttcgg aggatatgat aaaacaaagg attaaacgca ctggagatgg aacggatctt      960
tggggacacg aacaaaactg tgatgaagtg tgggatgtaa aagataaatc aagttaa       1017

<210> SEQ ID NO 8
<211> LENGTH: 1092
<212> TYPE: DNA
<213> ORGANISM: artificial
<220> FEATURE:
<223> OTHER INFORMATION: Candida albicans OLE1 leader sequence fused to
      Agrotis segetum desaturase

<400> SEQUENCE: 8
atgactacag ttgaacaact tgaaactgtt gatatcacta aattgaatgc cattgctgct       60
ggtactaata agaaggtgcc aatggctcaa ggtgtccaaa caactacgat attgagggag      120
gaagagccgt cattgacttt cgtggtacct caagaaccga aaagtatca aatcgtgtac       180 ccaaacctta tcacatttgg gtactggcat atagctggtt tatacgggct atatttgtgc      240
tttacttcgg caaaatggca acaattttta ttcagtttca tgctcgttgt gttagcagag      300 ttggaataa cagccggcgc tcacaggtta tgggcccaca aacatataa agcgaagctt       360 ccccttacaaa ttatcttaat gatattaaac tccattgcct tccaaaattc cgccattgat      420
```

```
tgggtgaggg accaccgtct ccatcataag tacagtgaca ctgatgcaga ccctcacaat      480
gctactcgtg gtttcttcta ttctcatgtt ggatggttgc tcgtaagaaa acatccagaa      540
gtcaagagac gtggaaagga acttgacatg tctgatattt acaacaatcc agtgttaaga      600
tttcaaaaga agtatgctat acccttcatc ggggcaatgt gcttcggatt accaactttt      660
atccctgttt acttctgggg agaaacctgg agtaatgctt ggcatatcac catgcttcgg      720
tacatcctca acctaaacat tacttttctta gtcaacagtg ctgctcatat ctggggatac      780
aaaccttatg acatcaaaat attgcctgcc caaaatatag cagtttccat agtaaccggc      840
ggcgaagttt ccataactac caccacgttt tttccttggg attatcgtgc agcagaattg      900
gggaacaatt atcttaattt gacgactaag ttcatagatt tcttcgcttg gatcggatgg      960
gcttacgatc ttaagacggt gtccagtgat gttataaaaa gtaaggcgga agaactggt      1020 gatgggacga atctttgggg tttagaagac aaaggtgaag aagatttttt gaaaatctgg      1080
aaagacaatt aa                                                          1092

<210> SEQ ID NO 9
<211> LENGTH: 1011
<212> TYPE: DNA
<213> ORGANISM: Agrotis segetum

<400> SEQUENCE: 9
atggctcaag gtgtccaaac aactacgata ttgagggagg aagagccgtc attgactttc       60
gtggtacctc aagaaccgag aaagtatcaa atcgtgtacc caaaccttat cacatttggg      120
tactggcata tagctggttt atacgggcta tatttgtgct ttacttcggc aaaatggcaa      180
acaattttat tcagtttcat gctcgttgtg ttagcagagt tgggaataac agccggcgct      240
cacaggttat gggcccacaa acatataaaa gcgaagcttc ccttacaaat tatcttaatg      300
atattaaact ccattgcctt ccaaaattcc gccattgatt gggtgaggga ccaccgtctc      360
catcataagt acagtgacac tgatgcagac cctcacaatg ctactcgtgg tttcttctat      420
tctcatgttg gatggttgct cgtaagaaaa catccagaag tcaagagacg tggaaaggaa      480
cttgacatgt ctgatattta caacaatcca gtgttaagat ttcaaaagaa gtatgctata      540
cccttcatcg gggcaatgtg cttcggatta ccaacttttta tccctgttta cttctgggga      600
gaaacctgga gtaatgcttg gcatatcacc atgcttcggt acatcctcaa cctaaacatt      660
actttcttag tcaacagtgc tgctcatatc tggggataca aaccttatga catcaaaata      720
ttgcctgccc aaaatatagc agtttccata gtaaccggcg gcgaagtttc cataactacc      780
accacgtttt ttccttggga ttatcgtgca gcagaattgg ggaacaatta tcttaatttg      840
acgactaagt tcatagattt cttcgcttgg atcggatggg cttacgatct taagacggtg      900
tccagtgatg ttataaaaag taaggcggaa agaactggtg atgggacgaa tctttgggt       960 ttagaagaca aaggtgaaga agatttttg aaaatctgga agacaatta a                 1011

<210> SEQ ID NO 10
<211> LENGTH: 981
<212> TYPE: DNA
<213> ORGANISM: Amyelois transitella

<400> SEQUENCE: 10
atggtcccta caagggttc cagtgacgtt ttgtctgaac attctgagcc ccagttcact       60
aaactcatag ctccacaagc agggccgagg aaatacaaga tagtgtatcg aaatttgctc      120
```

```
acattcggct attggcactt atcagctgtt tatgggctct acttgtgctt tacttgtgcg      180
aaatgggcta ccatcttatt tgcattttc ttatacgtga tcgcggaaat cggtataaca       240
ggtggcgctc ataggctatg gcacatcgg acttataaag ccaagttgcc tttagagatt       300
ttgttactca taatgaattc tattgccttc aagacactg ctttcacctg gctcgagat        360 caccgccttc atcacaaata ttcggatact gacgctgatc cccacaatgc taccagaggg     420
tttttctatt cacatgtagg ctggcttttg gtgaagaaac ccctgaagt caaagcaaga      480 ggaaaatact tgtcgttaga tgatcttaag aataatccat tgcttaaatt ccaaaagaaa    540
tacgctattc tagttatagg cacgttatgc ttccttatgc caacatttgt gcccgtatac    600
ttctggggcg agggcatcag cacggcctgg aacatcaatc tattgcgata cgtcatgaat   660
cttaacatga ctttcttagt taacagtgca gcgcatatct ttggcaacaa accatacgat   720
aagagcatag cctcagtcca aaatatttca gttagcttag ctactttgg cgaaggattc    780 cataattacc atcacactta cccctgggat tatcgtgcgg cagaattagg aaataatagg   840
ctaaatatga ctactgcttt catagatttc ttcgcttgga tcggctgggc ttatgacttg   900
aagtctgtgc cacaagaggc cattgcaaaa aggtgtgcga aaactggcga tggaacggat   960
atgtggggtc gaaaaagata a                                              981

<210> SEQ ID NO 11
<211> LENGTH: 1050
<212> TYPE: DNA
<213> ORGANISM: Trichoplusia ni

<400> SEQUENCE: 11
atggctgtga tggctcaaac agtacaagaa acggctacag tgttggaaga ggaagctcgc     60
acagtgactc ttgtggctcc aaagacaacg ccaaggaaat ataaatatat atacaccaac    120
tttcttacat tttcatatgc gcatttagct gcattatacg gactttattt gtgcttcacc    180
tctgcgaaat gggaaacatt gctattctct ttcgtactct tccacatgtc aaatataggc    240
atcaccgcag gggctcaccg actctggact cacaagactt tcaaagccaa attgcctttg   300
gaaattgtcc tcatgatatt caactcttta gcctttcaaa acacggctat acatgggct     360 agagaacatc ggctacatca caaatacagc gatactgatg ctgatcccca caatgcgtca    420
agagggttct tctactcgca tgttggctgg ctattagtaa aaaaacatcc cgatgtctta    480
aaatatggaa aaactataga catgtcggat gtatacaata atcctgtgtt aaaatttcag    540
aaaaagtacg cagtaccctt aattggaaca gtttgttttg ctcttccaac tttgattcca   600
gtctactgtt ggggcgaatc gtggaacaac gcttggcaca tagccttatt tcgatacata   660
ttcaatctta acgtgacttt cctagtcaac agtgctgcgc atatctgggg gaataagcct   720
tatgataaaa gcatcttgcc cgctcaaaac ttattagtttt ccttcctagc aagtggagaa  780
ggcttccata attaccatca cgtctttcca tgggattacc gcacagcaga attagggaat  840
aacttcttaa atttgacgac gttattcatt gattttgtg cctggtttgg atgggcttat    900
gacttgaagt ctgtatcaga ggatattata aaacagagag ctaaacgaac aggtgacggt   960
tcttcagggg tcatttgggg atgggacgac aagacatgg accgcgatat aaaatctaaa  1020
gctaacattt tttatgctaa aaaggaatga                                      1050

<210> SEQ ID NO 12
<211> LENGTH: 1017
<212> TYPE: DNA
<213> ORGANISM: Helicoverpa zea
```

<400> SEQUENCE: 12

```
atggcccaaa gctatcaatc aactacggtt ttgagtgagg agaaagaact aacattacaa      60
catttggtgc cccaagcatc gcccaggaag tatcaaatag tgtatccgaa cctcattacg     120
tttggttact ggcacatagc cggactttat ggcctttact tgtgcttcac ttctgctaaa     180
tgggctacga ttttattcag ctacatcctc ttcgtgttag cagaaatagg aatcacggct     240
ggcgctcaca gactctgggc ccacaaaact tacaaagcga aactaccatt agaaatactc     300
ttaatggtat tcaactccat cgcttttcaa aactcagcca ttgactgggt gagggaccac     360
cgactccacc ataagtatag cgatacagat gctgatcccc acaatgccag ccgagggttc     420
ttttattccc atgtaggatg gctacttgtg agaaaacatc ctgaagtcaa aaagcgaggg     480
aaagaactca atatgtccga tatttacaac aatcctgtct tacggtttca gaaaaaatac     540
gccatacccct tcattggggc tgtttgtttc gccttaccta caatgatacc tgtttacttc     600
tggggagaaa cctggtccaa tgcttggcat atcaccatgc ttcgctacat catgaacctc     660
aatgtcacct ttttggtaaa cagcgctgct catatatggg aaacaagcc ttatgacgca     720
aaaatattac ctgcacaaaa tgtagctgtg tcggtcgcca ctggtggaga aggttttccat    780
aattaccacc atgtcttccc ctgggattat cgagcagcgg aactcggtaa caatagcctc     840
aatttaacga ctaaattcat agatttattc gcagcaatcg gatgggcata tgatttaaag     900
acggtttcgg aggatatgat aaaacaaagg attaaacgca ctggagatgg aacggatctt     960
tggggacacg aacaaaactg tgatgaagtg tgggatgtaa aagataaatc aagttaa      1017
```

<210> SEQ ID NO 13
<211> LENGTH: 1068
<212> TYPE: DNA
<213> ORGANISM: Ostrinia furnacalis

<400> SEQUENCE: 13

```
atggctccta atattaagga cggagctgat ttgaacggag ttttatttga agatgacgct      60
agcaccccg attatgccct tgccacggcc ccagtccaga aagcagacaa ctatcccaga     120
aaactagtgt ggagaaacat catactcttt gcataccttc accttgccgc tgtgtatgga     180
gcatacctat tcttattttc agcgaaatgg cagacagata ttttgccta cattctttac     240
gtgatctcag gactcggcat cacagcggga gcccaccgcc tttgggcgca caagtcatac     300
aaggctaagt ggccacttag actcattctt attatcttca acactgtatc attccaggac     360
tctgctctcg actggtcacg tgaccaccgc atgcaccaca atactcgga gaccgacgcc     420
gacccgcaca cgcgactcg agggttcttc ttctctcata tcggctggtt attagtccgc     480
aagcacccg aattaaagag aaagggcaag ggattagact taagcgactt gtatgctgat     540
cccatcctcc gtttccagaa gaagtactat ttactattaa tgcctcttgg ctgcttcatc     600
atgccgacgg tggtcccggt gtacttctgg ggtgagactt ggactaacgc tttcttcgtc     660
gccgcgctct tccgatacac cttcatcctc aatgtcacct ggttggtcaa ctccgccgcg     720
cacaagtggg gccacaagcc ctatgacagc agcatcaagc cttccgagaa cctctcagtc     780
tccttattcg cgttgggcga aggattccac aactaccacc acacattccc ctgggactac     840
aaaactgccg agctcggcaa caacagactc aatttcacaa caaacttcat caacttcttc     900
gctaaaatcg gatgggctta cgacttgaaa acgtctccg acgagattat tcagaataga     960
gtcaagcgca caggagatgg ctcccaccac ttatgggtt ggggcgacaa ggatcaacct    1020
```

```
aaagaggagg taaacgcagc cattagaatt aatcctaaag acgagtaa            1068
```

<210> SEQ ID NO 14
<211> LENGTH: 1059
<212> TYPE: DNA
<213> ORGANISM: Lampronia capitella

<400> SEQUENCE: 14

```
atgccgccga acgtgacaga ggcgaacgga gtgttatttg agaatgacgt gcagactcct    60
gacatggggc tagaagtggc ccctgtgcag aaggctgacg agcgtaagat ccagctcgtt   120
tggaggaaca tcatcgcttt tgcatgtctt catttagcag ctgtgtatgg agcttattta   180
ttcttcacct cggctatatg gcagacagac atatttgcat acatccttta cgttatgtct   240
ggattaggaa tcacggcggg agcgcacaga ttatgggctc ataagtcata caaggcgaag   300
tggccgttaa gattaatcct cgtcgcattc aacactttgg cattccagga ttcggcaatc   360
gactgggcgc gcgaccaccg catgcaccac aagtactcgg agacggatgc ggacccacat   420
aacgccactc gcggcttctt cttttcgcac attggttggt tactctgccg aaaacacccg   480
gagctaaagc gcaagggcca gggcctcgac ttaagtgacc tctacgcaga tcctattatt   540
cgcttccaaa gaagtactac ttattgttaa tgccgttag cctgctttgt tcttcccacc   600
ataattccgg tctacctctg gggcgagtcc tggaaaaacg cgttcttcgt agctgcaatg   660
ttccgttaca cgttcatcct caacgtaaca tggctcgtca actccgccgc ccacaaatgg   720
ggaggcaagc cctatgataa gaacatccag cccgctcaga acatctctgt agctatcttc   780
gcattaggcg agggcttcca caactaccac cacacgttcc cctgggacta caagaccgct   840
gaattaggaa caacaggtt aaatttcaca acttcgttta tcaatttctt cgcaagcttc   900
ggatgggcct acgacttaaa gaccgtgtcg gacgagatta tacaacgcg cgttaagagg   960
acgggagatg ggagccatca cttacggggc tggggcgacc aggacatacc ggccgaagaa  1020
gctcaagctg ctttacgcat taaccgtaaa gatgattag                         1059
```

<210> SEQ ID NO 15
<211> LENGTH: 1062
<212> TYPE: DNA
<213> ORGANISM: Helicoverpa zea

<400> SEQUENCE: 15

```
atggctccaa atatatcgga ggatgtgaac ggggtgctct tcgagagtga tgcagcgacg    60
ccggacttag cgttatccac gccgcctgtg cagaaggctg acaacaggcc aagcaatta   120
gtgtggagga acatactatt attcgcgtat cttcacttag cggctcttta cggaggttat   180
ttattcctct tctcagctaa atggcagaca gacatatttg cctacatctt atatgtgatc   240
tccgggcttg gtatcacggc tggagcacat cgcttatggg cccacaagtc ctacaaagct   300
aaatggcctc tccgagttat cttagtcatc tttaacacag tggcattcca ggatgccgct   360
atggactggg cgcgcgacca ccgcatgcat cacaagtact cggaaccga tgctgatcct   420
cataatgcga cccgaggatt cttcttctct cacattggct ggttacttgt caggaaacat   480
cccgacctta aggagaaggg caagggactc gacatgagcg acttacttgc tgaccccatt   540
ctcaggttcc agaaaaaata ctacttaatc ttaatgccct tggcttgctt cgtgatgcct   600
accgtgattc ctgtgtactt ctggggtgaa acctggacca acgcattctt tgtggcggcc   660
atgttccgct acgcgttcat cctaaatgtg acgtggctcg tcaactctgc cgctcacaag   720
tggggagaca agccctacga caaaagcatt aagccttccg aaaacttgtc ggtcgccatg   780
```

```
ttcgctctcg gagaaggatt ccacaactac caccacactt tcccttggga ctacaaaact      840
gctgagttag gcaacaacaa actcaacttc actaccacct ttattaactt cttcgctaaa      900
attggctggg cttacgactt aaagacagtg tctgatgata tcgtcaagaa cagggtgaag      960
cgcactggtg acggctccca ccacttatgg ggctggggag acgaaaatca atccaaagaa     1020
gaaattgatg ccgctatcag aatcaatcct aaggacgatt aa                        1062
```

<210> SEQ ID NO 16
<211> LENGTH: 1434
<212> TYPE: DNA
<213> ORGANISM: Thalassiosira pseudonana

<400> SEQUENCE: 16

```
atggactttc tctccggcga tccttttccgg acactcgtcc ttgcagcact tgttgtcatc       60
ggatttgctg cggcgtggca atgcttctac ccgccgagca tcgtcggcaa gcctcgtaca      120
ttaagcaatg gtaaactcaa taccagaatc catggcaaat tgtacgacct ctcatcgttt      180
cagcatccag gaggccccgt ggctctttct cttgttcaag gtcgcgacgg aacagctcta      240
tttgagtcac accatccctt catacctcga aagaatctac ttcagatcct ctccaagtac      300
gaggttccgt cgactgaaga ctctgtttcc ttcatcgcca ccctagacga actcaatggt      360
gaatctccgt acgattggaa ggacattgaa aatgatgatt tcgtatctga cctacgagct      420
ctcgtaattg agcacttttc tcctctcgcc aaggaaaggg gagtttcact cgttgagtcg      480
tcgaaggcaa cacctcagcg gtggatggtg gttctattac tccttgcgtc gttcttcctc      540
agcatcccat tatatttgag tggttcgtgg actttcgttg tcgtcactcc catcctcgct      600
tggttagcgg ttgtcaatta ctggcacgat gctactcact ttgcattgag cagcaactgg      660
attttgaatg ctgcgctccc atatctcctc cctctcctat cgagtccgtc aatgtggtat      720
catcatcacg tcattggaca tcacgcatac accaacattt ccaaaagaga tccagatctt      780
gctcacgctc cacaactcat gagagaacac aagagtatca aatggagacc atctcactta      840
aatcaaacac agcttccgcg gattctcttc atctggtcga ttgcagtcgg tattgggttg      900
aacttattaa cgacgtgag agcactaacc aagctttcat acaacaacgt tgttcgggtg      960
gagaagatgt catcgtcgcg aacattactc catttccttg gacgtatgtt gcacatcttt     1020
gtgactacac tttggcccctt tttggcgttt ccggtgtgga aggccatcgt ttgggcgact     1080
gtaccgaatg ccatattaag tttgtgcttc atgttaaata cgcaaatcaa tcacctcatc     1140
aacacgtgtg cacatgcttc cgataacaac ttttacaagc atcaagttgt aactgctcag     1200
aactttggcc gatcaagtgc cttttgcttc atcttctcgg gaggtctcaa ctaccaaatt     1260
gaacatcatt tgttgccgac ggtgaaccat tgccatttgc cagctttggc cccgggtgta     1320
gagcgtttgt gtaagaaaca cggggtgaca tacaactctg ttgaaggata cagagaggcc     1380
atcattgcac actttgcaca taccaaagat atgtcgacga agcctactga ttga           1434
```

<210> SEQ ID NO 17
<211> LENGTH: 1050
<212> TYPE: DNA
<213> ORGANISM: Trichoplusia ni

<400> SEQUENCE: 17

```
atggctgtga ggctcaaaac agtcaagaa acggctacag tgttggaaga ggaagctcgc       60
acagtgactc ttgtggctcc aaagacaacg ccaaggaaat ataaatatat atacaccaac      120
```

| | |
|---|---|
| tttcttacat tttcatatgc gcatttagct gcattatacg gactttattt gtgcttcacc | 180 |
| tctgcgaaat gggaaacatt gctattctct ttcgtactct tccacatgtc aaatataggc | 240 |
| atcaccgcag gggctcaccg actctggact cacaagactt tcaaagccaa attgcctttg | 300 |
| gaaattgtcc tcatgatatt caactcttta gcctttcaaa acacggctat tacatgggct | 360 |
| agagaacatc ggctacatca caaatacagc gatactgatg ctgatcccca caatgcgtca | 420 |
| agagggttct tctactcgca tgttggctgg ctattagtaa aaaaacatcc cgatgtcctg | 480 |
| aaatatggaa aaactataga catgtcggat gtatacaata atcctgtgtt aaaatttcag | 540 |
| aaaaagtacg cagtacccct taattggaaca gtttgttttg ctctgccaac tttgattcca | 600 |
| gtctactgtt ggggcgaatc gtggaacaac gcttggcaca tagccttatt tcgatacata | 660 |
| ttcaatctta acgtgacttt cctagtcaac agtgctgcgc atatctgggg gaataagcct | 720 |
| tatgataaaa gcatcttgcc cgctcaaaac ctgctggttt ccttcctagc aagtggagaa | 780 |
| ggcttccata attaccatca cgtctttcca tgggattacc gcacagcaga attagggaat | 840 |
| aacttcctga atttgacgac gctgttcatt gattttgtg cctggtttgg atgggcttat | 900 |
| gacttgaagt ctgtatcaga ggatattata aaacagagag ctaaacgaac aggtgacggt | 960 |
| tcttcagggg tcatttgggg atgggacgac aaagacatgg accgcgatat aaaatctaaa | 1020 |
| gctaacattt tttatgctaa aaaggaatga | 1050 |

<210> SEQ ID NO 18
<211> LENGTH: 1017
<212> TYPE: DNA
<213> ORGANISM: Helicoverpa zea

<400> SEQUENCE: 18

| | |
|---|---|
| atggcccaaa gctatcaatc aactacggtt ttgagtgagg agaaagaact aacactgcaa | 60 |
| catttggtgc cccaagcatc gcccaggaag tatcaaatag tgtatccgaa cctcattacg | 120 |
| tttggttact ggcacatagc cggactttat ggcctttact tgtgcttcac ttctgctaaa | 180 |
| tgggctacga ttttattcag ctacatcctc ttcgtgttag cagaaatagg aatcacggct | 240 |
| ggcgctcaca gactctgggc ccacaaaact tacaaagcga aactaccatt agaaatactc | 300 |
| ttaatggtat tcaactccat cgcttttcaa aactcagcca ttgactgggt gagggaccac | 360 |
| cgactccacc ataagtatag cgatacagat gctgatcccc acaatgccag ccgagggttc | 420 |
| ttttattccc atgtaggatg gctacttgtg agaaaacatc ctgaagtcaa aaagcgaggg | 480 |
| aaagaactca atatgtccga tatttacaac aatcctgtcc tgcggtttca gaaaaaatac | 540 |
| gccatacccct tcattggggc tgtttgtttc gccttaccta caatgatacc tgtttacttc | 600 |
| tggggagaaa cctggtccaa tgcttggcat atcaccatgc ttcgctacat catgaacctc | 660 |
| aatgtcacct ttttggtaaa cagcgctgct catatatggg gaaacaagcc ttatgacgca | 720 |
| aaaatattac ctgcacaaaa tgtagctgtg tcggtcgcca ctggtggaga aggtttccat | 780 |
| aattaccacc atgtcttccc ctgggattat cgagcagcgg aactcggtaa caatagcctc | 840 |
| aatctgacga ctaaattcat agatttattc gcagcaatcg gatgggcata tgatctgaag | 900 |
| acggtttcgg aggatatgat aaaacaaagg attaaacgca ctgagatggg aacggatctt | 960 |
| tggggacacg aacaaaactg tgatgaagtg tgggatgtaa aagataaatc aagttaa | 1017 |

<210> SEQ ID NO 19
<211> LENGTH: 1050
<212> TYPE: DNA
<213> ORGANISM: artificial

```
<220> FEATURE:
<223> OTHER INFORMATION: Trichoplusia ni Z11 desaturase Homo sapiens
      codon optimized

<400> SEQUENCE: 19
atggccgtga tggcccagac cgtgcaggag accgcaacag tgctggagga ggaggcaagg      60
accgtgacac tggtggcacc caagaccaca cctagaaagt acaagtatat ctacaccaac     120
ttcctgacct tcagctacgc acacctggcc gccctgtatg gactgtacct gtgctttacc     180
tccgccaagt gggagacact gctgttctct tttgtgctgt ccacatgag caatatcgga      240 atcaccgcag gagcacacag gctgtggacc cacaagacat caaggccaa gctgcctctg      300 gagatcgtgc tgatgatctt caactctctg gcctttcaga ataccgccat cacatgggcc     360
cgggagcaca gactgcacca caagtatagc gacaccgatg cagacccaca caacgcaagc     420
aggggcttct tttactccca cgtgggctgg ctgctggtga gaagcaccc cgacgtgctg      480 aagtatggca agacaatcga catgtccgac gtgtacaaca atcccgtgct gaagtttcag     540
aagaagtatg ccgtgcctct gatcggcacc gtgtgcttcg ccctgccaac actgatcccc     600
gtgtattgtt ggggcgagtc ttggaacaat gcctggcaca tcgccctgtt ccggtacatc     660
tttaacctga atgtgacctt tctggtgaac tccgccgccc acatctgggg caataagcct     720
tacgacaagt ctatcctgcc agcccagaac ctgctggtgt ccttcctggc ctctggcgag     780
ggctttcaca attatcacca cgtgttccca tgggactaca ggaccgcaga gctgggcaac     840
aattttctga acctgaccac actgttcatc gattttgtg cctggttcgg ctgggcctat     900
gacctgaagt ctgtgagcga ggatatcatc aagcagaggg caaagaggac aggcgatggc     960
agctccggcg tgatctgggg atgggacgat aaggatatgg acagagatat caagagcaag    1020
gccaatatct ctacgccaa gaaggagtga                                       1050

<210> SEQ ID NO 20
<211> LENGTH: 1017
<212> TYPE: DNA
<213> ORGANISM: artificial
<220> FEATURE:
<223> OTHER INFORMATION: Helicoverpa zea Z11 desaturase Homo sapiens
      codon optimized

<400> SEQUENCE: 20
atggcacagt catatcagag cactaccgtc ctgagcgaag agaaggaact gacactgcag      60
cacctggtcc acaggcatc acctagaaag taccagatcg tgtatccaaa cctgatcacc     120
ttcggctact ggcacatcgc cggcctgtac ggcctgtatc tgtgctttac ctccgccaag     180
tgggccacaa tcctgttctc ttacatcctg tttgtgctgg cagagatcgg aatcaccgca     240
ggagcacaca gactgtgggc acacaagaca tataaggcca agctgcccct ggagatcctg     300
ctgatggtgt tcaacagcat cgccttcag aattccgcca tcgattgggt gcgggaccac     360
agactgcacc acaagtactc cgacaccgat gccgaccccc acaacgcctc tagggggcttc    420 ttttatagcc acgtgggatg gctgctggtg cggaagcacc ctgaggtgaa gagagaggc     480 aaggagctga atatgtctga tatctacaac aatcctgtgc tgcgcttcca gaagaagtat    540
gccatcccat tcatcggcgc cgtgtgcttt gccctgccca ccatgatccc cgtgtacttt    600
tggggcgaga catggagcaa cgcctggcac atcacaatgc tgcggtatat catgaacctg    660
aatgtgacat tcctggtgaa ctccgccgcc cacatctggg gcaataagcc atacgacgcc    720
aagatcctgc ccgcccagaa cgtggccgtg agcgtggcaa ccggaggaga gggcttccac    780
```

| aattaccacc acgtgtttcc ttgggattat cgggccgccg agctgggcaa caattctctg | 840 |
| aatctgacca caaagttcat cgacctgttt gccgccatcg gctgggccta tgatctgaag | 900 |
| acagtgagcg aggacatgat caagcagagg atcaagcgca ccggcgatgg cacagacctg | 960 |
| tgggggcacg agcagaactg tgatgaagtg tgggatgtga agacaagtc ctcctaa | 1017 |

<210> SEQ ID NO 21
<211> LENGTH: 1065
<212> TYPE: DNA
<213> ORGANISM: artificial
<220> FEATURE:
<223> OTHER INFORMATION: Trichoplusia ni Z11 desaturase Homo sapiens
      codon optimized with leader sequence replaced by Yarrowia
      lipolytica OLE1 leader

<400> SEQUENCE: 21

| atggtgaaga acgtggacca ggtggatctg tctcaggtgg acaccatcgc aagcggaagg | 60 |
| gatgtgaatt ataaggtgaa gtacacatct ggcgtgaaga ccacaccaag aaagtacaag | 120 |
| tatatctaca ccaacttcct gacattttct tacgcccacc tggccgccct gtatggcctg | 180 |
| tacctgtgct ttaccagcgc caagtgggag acactgctgt ctcctttgt gctgttccac | 240 |
| atgtctaata tcggaatcac cgcaggagca cacaggctgt ggacccacaa gacattcaag | 300 |
| gccaagctgc ccctggagat cgtgctgatg atcttcaact ccctggcctt tcagaatacc | 360 |
| gccatcacat gggcccggga gcacagactg caccacaagt attctgacac cgatgcagac | 420 |
| ccacacaacg caagcagggg cttctttac tcccacgtgg gctggctgct ggtgaagaag | 480 |
| caccctgacg tgctgaagta tgcaagaca atcgacatga gcgacgtgta caacaatcct | 540 |
| gtgctgaagt ttcagaagaa gtatgccgtg ccactgatcg gcaccgtgtg cttcgccctg | 600 |
| cccacactga tccccgtgta ctgttggggc gagtcctgga caatgcctg gcacatcgcc | 660 |
| ctgttccggt acatctttaa cctgaatgtg accttttctgg tgaacagcgc cgcccacatc | 720 |
| tggggcaata agccatacga caagtccatc ctgcccgccc agaacctgct ggtgtccttc | 780 |
| ctggcctctg gcgagggctt tcacaattat caccacgtgt ccccttggga ctacaggacc | 840 |
| gcagagctgg gcaacaattt tctgaacctg accacactgt tcatcgattt tgtgcctggg | 900 |
| ttcggctggg cctatgacct gaagtctgtg agcgaggata tcatcaagca gagggcaaag | 960 |
| aggacaggcg atgcagctc cggcgtgatc tggggatggg acgataagga tatggacaga | 1020 |
| gatatcaagt ccaaggccaa tatcttctac gccaagaagg agtga | 1065 |

<210> SEQ ID NO 22
<211> LENGTH: 1029
<212> TYPE: DNA
<213> ORGANISM: artificial
<220> FEATURE:
<223> OTHER INFORMATION: Helicoverpa zea Z11 desaturase Homo sapiens
      codon optimized with leader sequence replaced by Yarrowia
      lipolytica OLE1 leader

<400> SEQUENCE: 22

| atggtgaaaa acgtggacca agtggatctc tcgcaggtcg acaccattgc ctccggccga | 60 |
| gatgtcaact acaaggtcaa gtacacctcc ggcgttcgca agtatcagat cgtgtatcct | 120 |
| aacctgatca ccttcggcta ctggcatatc gctggactgt acggactgta tctgtgcttc | 180 |
| acttccgcca gtgggccac catcctgttc tcttacatcc tgtttgtgct ggcagagatc | 240 |
| ggaatcaccg caggagcaca cagactgtgg gcacacaaga catataaggc caagctgcca | 300 |
| ctggagatcc tgctgatggt gttcaacagc atcgcctttc agaattccgc catcgattgg | 360 |

| | |
|---|---|
| gtgcgggacc acagactgca ccacaagtac tccgacacag atgccgaccc ccacaacgcc | 420 |
| tctagggget tcttttatag ccacgtggga tggctgctgg tgcggaagca ccctgaggtg | 480 |
| aagaagagag gcaaggagct gaatatgtct gatatctaca acaatcctgt gctgcgcttc | 540 |
| cagaagaagt atgccatccc attcatcggc gccgtgtgct tgccctgcc caccatgatc | 600 |
| cccgtgtact tttggggcga gacatggagc aacgcctggc acatcacaat gctgcggtat | 660 |
| atcatgaacc tgaatgtgac attcctggtg aactccgccg cccacatctg ggcaataag | 720 |
| ccatacgacg ccaagatcct gcccgcccag aacgtggccg tgagcgtggc aaccggagga | 780 |
| gagggcttcc acaattacca ccacgtgttt ccatgggatt ataggcagc agagctggga | 840 |
| aacaattctc tgaatctgac cacaaagttc atcgacctgt tgccgccat cggctgggcc | 900 |
| tatgatctga agacagtgag cgaggacatg atcaagcaga ggatcaagcg caccggcgat | 960 |
| ggcacagacc tgtgggggca cgagcagaat tgtgatgaag tgtgggatgt gaaggataaa | 1020 |
| agcagttga | 1029 |

<210> SEQ ID NO 23
<211> LENGTH: 981
<212> TYPE: DNA
<213> ORGANISM: Amyelois transitella

<400> SEQUENCE: 23

| | |
|---|---|
| atggtcccta acaagggttc cagtgacgtt ttgtctgaac attctgagcc ccagttcact | 60 |
| aaactcatag ctccacaagc agggccgagg aaatacaaga tagtgtatcg aaatttgctc | 120 |
| acattcggct attggcactt atcagctgtt tatgggctct acttgtgctt tacttgtgcg | 180 |
| aaatgggcta ccatcttatt tgcattttc ttatacgtga tcgcggaaat cggtataaca | 240 |
| ggtggcgctc ataggctatg gcacatcgg acttataaag ccaagttgcc tttagagatt | 300 |
| ttgttactca taatgaattc tattgccttc aagacactg ctttcacctg ggctcgagat | 360 |
| caccgccttc atcacaaata ttcggatact gacgctgatc cccacaatgc taccagaggg | 420 |
| tttttctatt cacatgtagg ctggcttttg gtgaagaaac accctgaagt caaagcaaga | 480 |
| ggaaaatact tgtcgttaga tgatcttaag aataatccat tgcttaaatt ccaaaagaaa | 540 |
| tacgctattc tagttatagg cacgttatgc ttccttatgc caacatttgt gcccgtatac | 600 |
| ttctggggcg agggcatcag cacggcctgg aacatcaatc tattgcgata cgtcatgaat | 660 |
| cttaacatga ctttcttagt taacagtgca gcgcatatct tggcaacaa accatacgat | 720 |
| aagagcatag cctcagtcca aaatatttca gttagcttag ctactttgg cgaaggattc | 780 |
| cataattacc atcacactta ccctgggat tatcgtgcg cagaattagg aaataatagg | 840 |
| ctaaatatga ctactgcttt catagatttc ttcgcttgga tcggctgggc ttatgacttg | 900 |
| aagtctgtgc cacaagaggc cattgcaaaa ggtgtgcga aaactggcga tggaacggat | 960 |
| atgtggggtc gaaaaagata a | 981 |

<210> SEQ ID NO 24
<211> LENGTH: 1017
<212> TYPE: DNA
<213> ORGANISM: Helicoverpa zea

<400> SEQUENCE: 24

| | |
|---|---|
| atggcccaaa gctatcaatc aactacggtt ttgagtgagg agaaagaact aacattacaa | 60 |
| catttggtgc cccaagcatc gcccaggaag tatcaaatag tgtatccgaa cctcattacg | 120 |

```
tttggttact ggcacatagc cggactttat ggcctttact tgtgcttcac ttctgctaaa    180
tgggctacga ttttattcag ctacatcctc ttcgtgttag cagaaatagg aatcacggct    240
ggcgctcaca gactctgggc ccacaaaact acaaagcga aactaccatt agaaatactc    300
ttaatggtat tcaactccat cgcttttcaa aactcagcca ttgactgggt gagggaccac    360
cgactccacc ataagtatag cgatacagat gctgatcccc acaatgccag ccgagggttc    420
ttttattccc atgtaggatg gctacttgtg agaaaacatc ctgaagtcaa aagcgaggg     480 aaagaactca atatgtccga tatttacaac aatcctgtct tacggtttca gaaaaaatac    540
gccataccct tcattgggc tgtttgtttc gccttaccta caatgatacc tgtttacttc    600
tggggagaaa cctggtccaa tgcttggcat atcaccatgc ttcgctacat catgaacctc    660
aatgtcacct ttttggtaaa cagcgctgct catatatggg aaacaagcc ttatgacgca    720 aaaatattac ctgcacaaaa tgtagctgtg tcggtcgcca ctggtggaga aggtttccat    780
aattaccacc atgtcttccc ctgggattat cgagcagcgg aactcggtaa caatagcctc    840
aatttaacga ctaaattcat agattttatc gcagcaatcg gatgggcata tgatttaaag    900
acggtttcgg aggatatgat aaaacaaagg attaaacgca ctggagatgg aacggatctt    960
tggggacacg aacaaaactg tgatgaagtg tgggatgtaa aagataaatc aagttaa     1017
```

<210> SEQ ID NO 25
<211> LENGTH: 349
<212> TYPE: PRT
<213> ORGANISM: Trichoplusia ni

<400> SEQUENCE: 25

```
Met Ala Val Met Ala Gln Thr Val Gln Glu Thr Ala Thr Val Leu Glu
1               5                   10                  15

Glu Glu Ala Arg Thr Val Thr Leu Val Ala Pro Lys Thr Thr Pro Arg
            20                  25                  30

Lys Tyr Lys Tyr Ile Tyr Thr Asn Phe Leu Thr Phe Ser Tyr Ala His
        35                  40                  45

Leu Ala Ala Leu Tyr Gly Leu Tyr Leu Cys Phe Thr Ser Ala Lys Trp
    50                  55                  60

Glu Thr Leu Leu Phe Ser Phe Val Leu Phe His Met Ser Asn Ile Gly
65                  70                  75                  80

Ile Thr Ala Gly Ala His Arg Leu Trp Thr His Lys Thr Phe Lys Ala
                85                  90                  95

Lys Leu Pro Leu Glu Ile Val Leu Met Ile Phe Asn Ser Leu Ala Phe
            100                 105                 110

Gln Asn Thr Ala Ile Thr Trp Ala Arg Glu His Arg Leu His His Lys
        115                 120                 125

Tyr Ser Asp Thr Asp Ala Asp Pro His Asn Ala Ser Arg Gly Phe Phe
    130                 135                 140

Tyr Ser His Val Gly Trp Leu Leu Val Lys Lys His Pro Asp Val Leu
145                 150                 155                 160

Lys Tyr Gly Lys Thr Ile Asp Met Ser Asp Val Tyr Asn Asn Pro Val
                165                 170                 175

Leu Lys Phe Gln Lys Lys Tyr Ala Val Pro Leu Ile Gly Thr Val Cys
            180                 185                 190

Phe Ala Leu Pro Thr Leu Ile Pro Val Tyr Cys Trp Gly Glu Ser Trp
        195                 200                 205

Asn Asn Ala Trp His Ile Ala Leu Phe Arg Tyr Ile Phe Asn Leu Asn
    210                 215                 220
```

```
Val Thr Phe Leu Val Asn Ser Ala Ala His Ile Trp Gly Asn Lys Pro
225                 230                 235                 240

Tyr Asp Lys Ser Ile Leu Pro Ala Gln Asn Leu Leu Val Ser Phe Leu
                245                 250                 255

Ala Ser Gly Glu Gly Phe His Asn Tyr His His Val Phe Pro Trp Asp
            260                 265                 270

Tyr Arg Thr Ala Glu Leu Gly Asn Asn Phe Leu Asn Leu Thr Thr Leu
            275                 280                 285

Phe Ile Asp Phe Cys Ala Trp Phe Gly Trp Ala Tyr Asp Leu Lys Ser
            290                 295                 300

Val Ser Glu Asp Ile Ile Lys Gln Arg Ala Lys Arg Thr Gly Asp Gly
305                 310                 315                 320

Ser Ser Gly Val Ile Trp Gly Trp Asp Lys Asp Met Asp Arg Asp
                325                 330                 335

Ile Lys Ser Lys Ala Asn Ile Phe Tyr Ala Lys Lys Glu
                340                 345

<210> SEQ ID NO 26
<211> LENGTH: 479
<212> TYPE: PRT
<213> ORGANISM: halassiosira pseudonana

<400> SEQUENCE: 26

Thr Ser Met Asp Phe Leu Ser Gly Asp Pro Phe Arg Thr Leu Val Leu
1               5                   10                  15

Ala Ala Leu Val Val Ile Gly Phe Ala Ala Trp Gln Cys Phe Tyr
                20                  25                  30

Pro Pro Ser Ile Val Gly Lys Pro Arg Thr Leu Ser Asn Gly Lys Leu
                35                  40                  45

Asn Thr Arg Ile His Gly Lys Leu Tyr Asp Leu Ser Ser Phe Gln His
50                  55                  60

Pro Gly Gly Pro Val Ala Leu Ser Leu Val Gln Gly Arg Asp Gly Thr
65                  70                  75                  80

Ala Leu Phe Glu Ser His His Pro Phe Ile Pro Arg Lys Asn Leu Leu
                85                  90                  95

Gln Ile Leu Ser Lys Tyr Glu Val Pro Ser Thr Glu Asp Ser Val Ser
                100                 105                 110

Phe Ile Ala Thr Leu Asp Glu Leu Asn Gly Glu Ser Pro Tyr Asp Trp
                115                 120                 125

Lys Asp Ile Glu Asn Asp Asp Phe Val Ser Asp Leu Arg Ala Leu Val
130                 135                 140

Ile Glu His Phe Ser Pro Leu Ala Lys Glu Arg Gly Val Ser Leu Val
145                 150                 155                 160

Glu Ser Ser Lys Ala Thr Pro Gln Arg Trp Met Val Val Leu Leu Leu
                165                 170                 175

Leu Ala Ser Phe Phe Leu Ser Ile Pro Leu Tyr Leu Ser Gly Ser Trp
                180                 185                 190

Thr Phe Val Val Val Thr Pro Ile Leu Ala Trp Leu Ala Val Val Asn
                195                 200                 205

Tyr Trp His Asp Ala Thr His Phe Ala Leu Ser Ser Asn Trp Ile Leu
                210                 215                 220

Asn Ala Ala Leu Pro Tyr Leu Leu Pro Leu Leu Ser Ser Pro Ser Met
225                 230                 235                 240

Trp Tyr His His His Val Ile Gly His His Ala Tyr Thr Asn Ile Ser
```

```
                    245                 250                 255
Lys Arg Asp Pro Asp Leu Ala His Ala Pro Gln Leu Met Arg Glu His
                260                 265                 270

Lys Ser Ile Lys Trp Arg Pro Ser His Leu Asn Gln Thr Gln Leu Pro
            275                 280                 285

Arg Ile Leu Phe Ile Trp Ser Ile Ala Val Gly Ile Gly Leu Asn Leu
        290                 295                 300

Leu Asn Asp Val Arg Ala Leu Thr Lys Leu Ser Tyr Asn Asn Val Val
305                 310                 315                 320

Arg Val Glu Lys Met Ser Ser Ser Arg Thr Leu Leu His Phe Leu Gly
                325                 330                 335

Arg Met Leu His Ile Phe Val Thr Thr Leu Trp Pro Phe Leu Ala Phe
                340                 345                 350

Pro Val Trp Lys Ala Ile Val Trp Ala Thr Val Pro Asn Ala Ile Leu
            355                 360                 365

Ser Leu Cys Phe Met Leu Asn Thr Gln Ile Asn His Leu Ile Asn Thr
        370                 375                 380

Cys Ala His Ala Ser Asp Asn Phe Tyr Lys His Gln Val Val Thr
385                 390                 395                 400

Ala Gln Asn Phe Gly Arg Ser Ala Phe Cys Phe Ile Phe Ser Gly
                405                 410                 415

Gly Leu Asn Tyr Gln Ile Glu His His Leu Leu Pro Thr Val Asn His
                420                 425                 430

Cys His Leu Pro Ala Leu Ala Pro Gly Val Glu Arg Leu Cys Lys Lys
            435                 440                 445

His Gly Val Thr Tyr Asn Ser Val Glu Gly Tyr Arg Glu Ala Ile Ile
        450                 455                 460

Ala His Phe Ala His Thr Lys Asp Met Ser Thr Lys Pro Thr Asp
465                 470                 475

<210> SEQ ID NO 27
<211> LENGTH: 477
<212> TYPE: PRT
<213> ORGANISM: Thalassiosira pseudonana

<400> SEQUENCE: 27

Met Asp Phe Leu Ser Gly Asp Pro Phe Arg Thr Leu Val Leu Ala Ala
1               5                   10                  15

Leu Val Val Ile Gly Phe Ala Ala Trp Gln Cys Phe Tyr Pro Pro
            20                  25                  30

Ser Ile Val Gly Lys Pro Arg Thr Leu Ser Asn Gly Lys Leu Asn Thr
        35                  40                  45

Arg Ile His Gly Lys Leu Tyr Asp Leu Ser Ser Phe Gln His Pro Gly
    50                  55                  60

Gly Pro Val Ala Leu Ser Leu Val Gln Gly Arg Asp Gly Thr Ala Leu
65                  70                  75                  80

Phe Glu Ser His His Pro Phe Ile Pro Arg Lys Asn Leu Leu Gln Ile
                85                  90                  95

Leu Ser Lys Tyr Glu Val Pro Ser Thr Glu Asp Ser Val Ser Phe Ile
            100                 105                 110

Ala Thr Leu Asp Glu Leu Asn Gly Glu Ser Pro Tyr Asp Trp Lys Asp
        115                 120                 125

Ile Glu Asn Asp Asp Phe Val Ser Asp Leu Arg Ala Leu Val Ile Glu
    130                 135                 140
```

```
His Phe Ser Pro Leu Ala Lys Glu Arg Gly Val Ser Leu Val Glu Ser
145                 150                 155                 160

Ser Lys Ala Thr Pro Gln Arg Trp Met Val Val Leu Leu Leu Leu Ala
                165                 170                 175

Ser Phe Phe Leu Ser Ile Pro Leu Tyr Leu Ser Gly Ser Trp Thr Phe
            180                 185                 190

Val Val Val Thr Pro Ile Leu Ala Trp Leu Ala Val Val Asn Tyr Trp
        195                 200                 205

His Asp Ala Thr His Phe Ala Leu Ser Ser Asn Trp Ile Leu Asn Ala
    210                 215                 220

Ala Leu Pro Tyr Leu Leu Pro Leu Leu Ser Ser Pro Ser Met Trp Tyr
225                 230                 235                 240

His His His Val Ile Gly His Ala Tyr Thr Asn Ile Ser Lys Arg
                245                 250                 255

Asp Pro Asp Leu Ala His Ala Pro Gln Leu Met Arg Glu His Lys Ser
                260                 265                 270

Ile Lys Trp Arg Pro Ser His Leu Asn Gln Thr Gln Leu Pro Arg Ile
            275                 280                 285

Leu Phe Ile Trp Ser Ile Ala Val Gly Ile Gly Leu Asn Leu Leu Asn
        290                 295                 300

Asp Val Arg Ala Leu Thr Lys Leu Ser Tyr Asn Asn Val Val Arg Val
305                 310                 315                 320

Glu Lys Met Ser Ser Arg Thr Leu Leu His Phe Leu Gly Arg Met
                325                 330                 335

Leu His Ile Phe Val Thr Thr Leu Trp Pro Phe Leu Ala Phe Pro Val
                340                 345                 350

Trp Lys Ala Ile Val Trp Ala Thr Val Pro Asn Ala Ile Leu Ser Leu
            355                 360                 365

Cys Phe Met Leu Asn Thr Gln Ile Asn His Leu Ile Asn Thr Cys Ala
            370                 375                 380

His Ala Ser Asp Asn Asn Phe Tyr Lys His Gln Val Val Thr Ala Gln
385                 390                 395                 400

Asn Phe Gly Arg Ser Ser Ala Phe Cys Phe Ile Phe Ser Gly Gly Leu
                405                 410                 415

Asn Tyr Gln Ile Glu His His Leu Leu Pro Thr Val Asn His Cys His
            420                 425                 430

Leu Pro Ala Leu Ala Pro Gly Val Glu Arg Leu Cys Lys Lys His Gly
                435                 440                 445

Val Thr Tyr Asn Ser Val Glu Gly Tyr Arg Glu Ala Ile Ile Ala His
                450                 455                 460

Phe Ala His Thr Lys Asp Met Ser Thr Lys Pro Thr Asp
465                 470                 475

<210> SEQ ID NO 28
<211> LENGTH: 326
<212> TYPE: PRT
<213> ORGANISM: Amyelois transitella

<400> SEQUENCE: 28

Met Val Pro Asn Lys Gly Ser Ser Asp Val Leu Ser Glu His Ser Glu
1               5                   10                  15

Pro Gln Phe Thr Lys Leu Ile Ala Pro Gln Ala Gly Pro Arg Lys Tyr
                20                  25                  30

Lys Ile Val Tyr Arg Asn Leu Leu Thr Phe Gly Tyr Trp His Leu Ser
            35                  40                  45
```

Ala Val Tyr Gly Leu Tyr Leu Cys Phe Thr Cys Ala Lys Trp Ala Thr
            50                  55                  60

Ile Leu Phe Ala Phe Phe Leu Tyr Val Ile Ala Glu Ile Gly Ile Thr
 65                  70                  75                  80

Gly Gly Ala His Arg Leu Trp Ala His Arg Thr Tyr Lys Ala Lys Leu
                85                  90                  95

Pro Leu Glu Ile Leu Leu Ile Met Asn Ser Ile Ala Phe Gln Asp
            100                 105                 110

Thr Ala Phe Thr Trp Ala Arg Asp His Arg Leu His His Lys Tyr Ser
            115                 120                 125

Asp Thr Asp Ala Asp Pro His Asn Ala Thr Arg Gly Phe Phe Tyr Ser
130                 135                 140

His Val Gly Trp Leu Leu Val Lys Lys His Pro Glu Val Lys Ala Arg
145                 150                 155                 160

Gly Lys Tyr Leu Ser Leu Asp Asp Leu Lys Asn Asn Pro Leu Leu Lys
                165                 170                 175

Phe Gln Lys Lys Tyr Ala Ile Leu Val Ile Gly Thr Leu Cys Phe Leu
                180                 185                 190

Met Pro Thr Phe Val Pro Val Tyr Phe Trp Gly Glu Gly Ile Ser Thr
            195                 200                 205

Ala Trp Asn Ile Asn Leu Leu Arg Tyr Val Met Asn Leu Asn Met Thr
            210                 215                 220

Phe Leu Val Asn Ser Ala Ala His Ile Phe Gly Asn Lys Pro Tyr Asp
225                 230                 235                 240

Lys Ser Ile Ala Ser Val Gln Asn Ile Ser Val Ser Leu Ala Thr Phe
                245                 250                 255

Gly Glu Gly Phe His Asn Tyr His His Thr Tyr Pro Trp Asp Tyr Arg
            260                 265                 270

Ala Ala Glu Leu Gly Asn Asn Arg Leu Asn Met Thr Thr Ala Phe Ile
            275                 280                 285

Asp Phe Phe Ala Trp Ile Gly Trp Ala Tyr Asp Leu Lys Ser Val Pro
            290                 295                 300

Gln Glu Ala Ile Ala Lys Arg Cys Ala Lys Thr Gly Asp Gly Thr Asp
305                 310                 315                 320

Met Trp Gly Arg Lys Arg
                325

<210> SEQ ID NO 29
<211> LENGTH: 336
<212> TYPE: PRT
<213> ORGANISM: Agrotis segetum

<400> SEQUENCE: 29

Met Ala Gln Gly Val Gln Thr Thr Thr Ile Leu Arg Glu Glu Glu Pro
 1               5                  10                  15

Ser Leu Thr Phe Val Val Pro Gln Glu Pro Arg Lys Tyr Gln Ile Val
                20                  25                  30

Tyr Pro Asn Leu Ile Thr Phe Gly Tyr Trp His Ile Ala Gly Leu Tyr
                35                  40                  45

Gly Leu Tyr Leu Cys Phe Thr Ser Ala Lys Trp Gln Thr Ile Leu Phe
            50                  55                  60

Ser Phe Met Leu Val Val Leu Ala Glu Leu Gly Ile Thr Ala Gly Ala
 65                  70                  75                  80

His Arg Leu Trp Ala His Lys Thr Tyr Lys Ala Lys Leu Pro Leu Gln

```
                  85                  90                  95

Ile Ile Leu Met Ile Leu Asn Ser Ile Ala Phe Gln Asn Ser Ala Ile
                100                 105                 110

Asp Trp Val Arg Asp His Arg Leu His His Lys Tyr Ser Asp Thr Asp
            115                 120                 125

Ala Asp Pro His Asn Ala Thr Arg Gly Phe Phe Tyr Ser His Val Gly
        130                 135                 140

Trp Leu Leu Val Arg Lys His Pro Glu Val Lys Arg Arg Gly Lys Glu
145                 150                 155                 160

Leu Asp Met Ser Asp Ile Tyr Asn Asn Pro Val Leu Arg Phe Gln Lys
                165                 170                 175

Lys Tyr Ala Ile Pro Phe Ile Gly Ala Met Cys Phe Gly Leu Pro Thr
            180                 185                 190

Phe Ile Pro Val Tyr Phe Trp Gly Glu Thr Trp Ser Asn Ala Trp His
        195                 200                 205

Ile Thr Met Leu Arg Tyr Ile Leu Asn Leu Asn Ile Thr Phe Leu Val
    210                 215                 220

Asn Ser Ala Ala His Ile Trp Gly Tyr Lys Pro Tyr Asp Ile Lys Ile
225                 230                 235                 240

Leu Pro Ala Gln Asn Ile Ala Val Ser Ile Val Thr Gly Gly Glu Val
                245                 250                 255

Ser Ile Thr Thr Thr Thr Phe Phe Pro Trp Asp Tyr Arg Ala Ala Glu
            260                 265                 270

Leu Gly Asn Asn Tyr Leu Asn Leu Thr Thr Lys Phe Ile Asp Phe Phe
        275                 280                 285

Ala Trp Ile Gly Trp Ala Tyr Asp Leu Lys Thr Val Ser Ser Asp Val
    290                 295                 300

Ile Lys Ser Lys Ala Glu Arg Thr Gly Asp Gly Thr Asn Leu Trp Gly
305                 310                 315                 320

Leu Glu Asp Lys Gly Glu Glu Asp Phe Leu Lys Ile Trp Lys Asp Asn
                325                 330                 335

<210> SEQ ID NO 30
<211> LENGTH: 355
<212> TYPE: PRT
<213> ORGANISM: Ostrinia furnacalis

<400> SEQUENCE: 30

Met Ala Pro Asn Ile Lys Asp Gly Ala Asp Leu Asn Gly Val Leu Phe
1               5                   10                  15

Glu Asp Asp Ala Ser Thr Pro Asp Tyr Ala Leu Ala Thr Ala Pro Val
            20                  25                  30

Gln Lys Ala Asp Asn Tyr Pro Arg Lys Leu Val Trp Arg Asn Ile Ile
        35                  40                  45

Leu Phe Ala Tyr Leu His Leu Ala Ala Val Tyr Gly Ala Tyr Leu Phe
    50                  55                  60

Leu Phe Ser Ala Lys Trp Gln Thr Asp Ile Phe Ala Tyr Ile Leu Tyr
65                  70                  75                  80

Val Ile Ser Gly Leu Gly Ile Thr Ala Gly Ala His Arg Leu Trp Ala
                85                  90                  95

His Lys Ser Tyr Lys Ala Lys Trp Pro Leu Arg Leu Ile Leu Ile Ile
            100                 105                 110

Phe Asn Thr Val Ser Phe Gln Asp Ser Ala Leu Asp Trp Ser Arg Asp
        115                 120                 125
```

His Arg Met His His Lys Tyr Ser Glu Thr Asp Ala Asp Pro His Asn
    130                 135                 140
Ala Thr Arg Gly Phe Phe Phe Ser His Ile Gly Trp Leu Leu Val Arg
145                 150                 155                 160
Lys His Pro Glu Leu Lys Arg Lys Gly Lys Gly Leu Asp Leu Ser Asp
                165                 170                 175
Leu Tyr Ala Asp Pro Ile Leu Arg Phe Gln Lys Lys Tyr Tyr Leu Leu
            180                 185                 190
Leu Met Pro Leu Gly Cys Phe Ile Met Pro Thr Val Val Pro Val Tyr
        195                 200                 205
Phe Trp Gly Glu Thr Trp Thr Asn Ala Phe Val Ala Ala Leu Phe
    210                 215                 220
Arg Tyr Thr Phe Ile Leu Asn Val Thr Trp Leu Val Asn Ser Ala Ala
225                 230                 235                 240
His Lys Trp Gly His Lys Pro Tyr Asp Ser Ser Ile Lys Pro Ser Glu
                245                 250                 255
Asn Leu Ser Val Ser Leu Phe Ala Leu Gly Glu Gly Phe His Asn Tyr
            260                 265                 270
His His Thr Phe Pro Trp Asp Tyr Lys Thr Ala Glu Leu Gly Asn Asn
        275                 280                 285
Arg Leu Asn Phe Thr Thr Asn Phe Ile Asn Phe Phe Ala Lys Ile Gly
    290                 295                 300
Trp Ala Tyr Asp Leu Lys Thr Val Ser Asp Glu Ile Ile Gln Asn Arg
305                 310                 315                 320
Val Lys Arg Thr Gly Asp Gly Ser His His Leu Trp Gly Trp Gly Asp
                325                 330                 335
Lys Asp Gln Pro Lys Glu Glu Val Asn Ala Ala Ile Arg Ile Asn Pro
            340                 345                 350
Lys Asp Glu
        355

<210> SEQ ID NO 31
<211> LENGTH: 352
<212> TYPE: PRT
<213> ORGANISM: Lampronia capitella

<400> SEQUENCE: 31

Met Pro Pro Asn Val Thr Glu Ala Asn Gly Val Leu Phe Glu Asn Asp
1               5                   10                  15
Val Gln Thr Pro Asp Met Gly Leu Glu Val Ala Pro Val Gln Lys Ala
            20                  25                  30
Asp Glu Arg Lys Ile Gln Leu Val Trp Arg Asn Ile Ile Ala Phe Ala
        35                  40                  45
Cys Leu His Leu Ala Ala Val Tyr Gly Ala Tyr Leu Phe Phe Thr Ser
    50                  55                  60
Ala Ile Trp Gln Thr Asp Ile Phe Ala Tyr Ile Leu Tyr Val Met Ser
65                  70                  75                  80
Gly Leu Gly Ile Thr Ala Gly Ala His Arg Leu Trp Ala His Lys Ser
            85                  90                  95
Tyr Lys Ala Lys Trp Pro Leu Arg Leu Ile Leu Val Ala Phe Asn Thr
                100                 105                 110
Leu Ala Phe Gln Asp Ser Ala Ile Asp Trp Ala Arg Asp His Arg Met
            115                 120                 125
His His Lys Tyr Ser Glu Thr Asp Ala Asp Pro His Asn Ala Thr Arg
        130                 135                 140

```
Gly Phe Phe Phe Ser His Ile Gly Trp Leu Leu Cys Arg Lys His Pro
145                 150                 155                 160

Glu Leu Lys Arg Lys Gly Gln Gly Leu Asp Leu Ser Asp Leu Tyr Ala
                165                 170                 175

Asp Pro Ile Ile Arg Phe Gln Lys Lys Tyr Tyr Leu Leu Leu Met Pro
            180                 185                 190

Leu Ala Cys Phe Val Leu Pro Thr Ile Ile Pro Val Tyr Leu Trp Gly
        195                 200                 205

Glu Ser Trp Lys Asn Ala Phe Phe Val Ala Ala Met Phe Arg Tyr Thr
    210                 215                 220

Phe Ile Leu Asn Val Thr Trp Leu Val Asn Ser Ala Ala His Lys Trp
225                 230                 235                 240

Gly Gly Lys Pro Tyr Asp Lys Asn Ile Gln Pro Ala Gln Asn Ile Ser
                245                 250                 255

Val Ala Ile Phe Ala Leu Gly Glu Gly Phe His Asn Tyr His His Thr
            260                 265                 270

Phe Pro Trp Asp Tyr Lys Thr Ala Glu Leu Gly Asn Asn Arg Leu Asn
        275                 280                 285

Phe Thr Thr Ser Phe Ile Asn Phe Phe Ala Ser Phe Gly Trp Ala Tyr
    290                 295                 300

Asp Leu Lys Thr Val Ser Asp Glu Ile Ile Gln Gln Arg Val Lys Arg
305                 310                 315                 320

Thr Gly Asp Gly Ser His His Leu Arg Gly Trp Gly Asp Gln Asp Ile
                325                 330                 335

Pro Ala Glu Glu Ala Gln Ala Ala Leu Arg Ile Asn Arg Lys Asp Asp
                340                 345                 350

<210> SEQ ID NO 32
<211> LENGTH: 353
<212> TYPE: PRT
<213> ORGANISM: Helicoverpa zea

<400> SEQUENCE: 32

Met Ala Pro Asn Ile Ser Glu Asp Val Asn Gly Val Leu Phe Glu Ser
1               5                   10                  15

Asp Ala Ala Thr Pro Asp Leu Ala Leu Ser Thr Pro Val Gln Lys
                20                  25                  30

Ala Asp Asn Arg Pro Lys Gln Leu Val Trp Arg Asn Ile Leu Leu Phe
            35                  40                  45

Ala Tyr Leu His Leu Ala Ala Leu Tyr Gly Gly Tyr Leu Phe Leu Phe
        50                  55                  60

Ser Ala Lys Trp Gln Thr Asp Ile Phe Ala Tyr Ile Leu Tyr Val Ile
65                  70                  75                  80

Ser Gly Leu Gly Ile Thr Ala Gly Ala His Arg Leu Trp Ala His Lys
                85                  90                  95

Ser Tyr Lys Ala Lys Trp Pro Leu Arg Val Ile Leu Val Ile Phe Asn
                100                 105                 110

Thr Val Ala Phe Gln Asp Ala Ala Met Asp Trp Ala Arg Asp His Arg
            115                 120                 125

Met His His Lys Tyr Ser Glu Thr Asp Ala Asp Pro His Asn Ala Thr
        130                 135                 140

Arg Gly Phe Phe Phe Ser His Ile Gly Trp Leu Leu Val Arg Lys His
145                 150                 155                 160

Pro Asp Leu Lys Glu Lys Gly Lys Gly Leu Asp Met Ser Asp Leu Leu
```

```
            165                 170                 175
Ala Asp Pro Ile Leu Arg Phe Gln Lys Lys Tyr Tyr Leu Ile Leu Met
            180                 185                 190

Pro Leu Ala Cys Phe Val Met Pro Thr Val Ile Pro Val Tyr Phe Trp
            195                 200                 205

Gly Glu Thr Trp Thr Asn Ala Phe Phe Val Ala Ala Met Phe Arg Tyr
            210                 215                 220

Ala Phe Ile Leu Asn Val Thr Trp Leu Val Asn Ser Ala Ala His Lys
225                 230                 235                 240

Trp Gly Asp Lys Pro Tyr Asp Lys Ser Ile Lys Pro Ser Glu Asn Leu
            245                 250                 255

Ser Val Ala Met Phe Ala Leu Gly Glu Gly Phe His Asn Tyr His His
            260                 265                 270

Thr Phe Pro Trp Asp Tyr Lys Thr Ala Glu Leu Gly Asn Asn Lys Leu
            275                 280                 285

Asn Phe Thr Thr Thr Phe Ile Asn Phe Phe Ala Lys Ile Gly Trp Ala
            290                 295                 300

Tyr Asp Leu Lys Thr Val Ser Asp Asp Ile Val Lys Asn Arg Val Lys
305                 310                 315                 320

Arg Thr Gly Asp Gly Ser His His Leu Trp Gly Trp Gly Asp Glu Asn
            325                 330                 335

Gln Ser Lys Glu Glu Ile Asp Ala Ala Ile Arg Ile Asn Pro Lys Asp
            340                 345                 350

Asp
```

<210> SEQ ID NO 33
<211> LENGTH: 354
<212> TYPE: PRT
<213> ORGANISM: artificial
<220> FEATURE:
<223> OTHER INFORMATION: Trichoplusia ni desaturase with Yarrowia
      lipolytica OLE1 leader sequence encoded by SEQ ID NO: 21

<400> SEQUENCE: 33

```
Met Val Lys Asn Val Asp Gln Val Asp Leu Ser Gln Val Asp Thr Ile
1               5                   10                  15

Ala Ser Gly Arg Asp Val Asn Tyr Lys Val Lys Tyr Thr Ser Gly Val
            20                  25                  30

Lys Thr Thr Pro Arg Lys Tyr Lys Tyr Ile Tyr Thr Asn Phe Leu Thr
            35                  40                  45

Phe Ser Tyr Ala His Leu Ala Ala Leu Tyr Gly Leu Tyr Leu Cys Phe
        50                  55                  60

Thr Ser Ala Lys Trp Glu Thr Leu Leu Phe Ser Phe Val Leu Phe His
65                  70                  75                  80

Met Ser Asn Ile Gly Ile Thr Ala Gly Ala His Arg Leu Trp Thr His
            85                  90                  95

Lys Thr Phe Lys Ala Lys Leu Pro Leu Glu Ile Val Leu Met Ile Phe
            100                 105                 110

Asn Ser Leu Ala Phe Gln Asn Thr Ala Ile Thr Trp Ala Arg Glu His
            115                 120                 125

Arg Leu His His Lys Tyr Ser Asp Thr Asp Ala Asp Pro His Asn Ala
            130                 135                 140

Ser Arg Gly Phe Phe Tyr Ser His Val Gly Trp Leu Leu Val Lys Lys
145                 150                 155                 160

His Pro Asp Val Leu Lys Tyr Gly Lys Thr Ile Asp Met Ser Asp Val
```

```
                    165                 170                 175
Tyr Asn Asn Pro Val Leu Lys Phe Gln Lys Tyr Ala Val Pro Leu
                180                 185                 190

Ile Gly Thr Val Cys Phe Ala Leu Pro Thr Leu Ile Pro Val Tyr Cys
            195                 200                 205

Trp Gly Glu Ser Trp Asn Asn Ala Trp His Ile Ala Leu Phe Arg Tyr
        210                 215                 220

Ile Phe Asn Leu Asn Val Thr Phe Leu Val Asn Ser Ala Ala His Ile
225                 230                 235                 240

Trp Gly Asn Lys Pro Tyr Asp Lys Ser Ile Leu Pro Ala Gln Asn Leu
                245                 250                 255

Leu Val Ser Phe Leu Ala Ser Gly Glu Gly Phe His Asn Tyr His His
            260                 265                 270

Val Phe Pro Trp Asp Tyr Arg Thr Ala Glu Leu Gly Asn Asn Phe Leu
        275                 280                 285

Asn Leu Thr Thr Leu Phe Ile Asp Phe Cys Ala Trp Phe Gly Trp Ala
        290                 295                 300

Tyr Asp Leu Lys Ser Val Ser Glu Asp Ile Ile Lys Gln Arg Ala Lys
305                 310                 315                 320

Arg Thr Gly Asp Gly Ser Ser Gly Val Ile Trp Gly Trp Asp Asp Lys
                325                 330                 335

Asp Met Asp Arg Asp Ile Lys Ser Lys Ala Asn Ile Pro Tyr Ala Lys
                340                 345                 350

Lys Glu

<210> SEQ ID NO 34
<211> LENGTH: 342
<212> TYPE: PRT
<213> ORGANISM: artificial
<220> FEATURE:
<223> OTHER INFORMATION: Helicoverpa zea desaturase with Yarrowia
      lipolytica OLE1 leader sequence encoded by SEQ ID NO: 22

<400> SEQUENCE: 34

Met Val Lys Asn Val Asp Gln Val Asp Leu Ser Gln Val Asp Thr Ile
1               5                   10                  15

Ala Ser Gly Arg Asp Val Asn Tyr Lys Val Lys Tyr Thr Ser Gly Val
            20                  25                  30

Arg Lys Tyr Gln Ile Val Tyr Pro Asn Leu Ile Thr Phe Gly Tyr Trp
        35                  40                  45

His Ile Ala Gly Leu Tyr Gly Leu Tyr Leu Cys Phe Thr Ser Ala Lys
    50                  55                  60

Trp Ala Thr Ile Leu Phe Ser Tyr Ile Leu Phe Val Leu Ala Glu Ile
65                  70                  75                  80

Gly Ile Thr Ala Gly Ala His Arg Leu Trp Ala His Lys Thr Tyr Lys
                85                  90                  95

Ala Lys Leu Pro Leu Glu Ile Leu Leu Met Val Phe Asn Ser Ile Ala
            100                 105                 110

Phe Gln Asn Ser Ala Ile Asp Trp Val Arg Asp His Arg Leu His His
        115                 120                 125

Lys Tyr Ser Asp Thr Asp Ala Asp Pro His Asn Ala Ser Arg Gly Phe
    130                 135                 140

Phe Tyr Ser His Val Gly Trp Leu Leu Val Arg Lys His Pro Glu Val
145                 150                 155                 160

Lys Lys Arg Gly Lys Glu Leu Asn Met Ser Asp Ile Tyr Asn Asn Pro
```

165                 170                 175
Val Leu Arg Phe Gln Lys Lys Tyr Ala Ile Pro Phe Ile Gly Ala Val
            180                 185                 190

Cys Phe Ala Leu Pro Thr Met Ile Pro Val Tyr Phe Trp Gly Glu Thr
            195                 200                 205

Trp Ser Asn Ala Trp His Ile Thr Met Leu Arg Tyr Ile Met Asn Leu
210                 215                 220

Asn Val Thr Phe Leu Val Asn Ser Ala Ala His Ile Trp Gly Asn Lys
225                 230                 235                 240

Pro Tyr Asp Ala Lys Ile Leu Pro Ala Gln Asn Val Ala Val Ser Val
            245                 250                 255

Ala Thr Gly Gly Glu Gly Phe His Asn Tyr His His Val Phe Pro Trp
            260                 265                 270

Asp Tyr Arg Ala Ala Glu Leu Gly Asn Asn Ser Leu Asn Leu Thr Thr
            275                 280                 285

Lys Phe Ile Asp Leu Phe Ala Ala Ile Gly Trp Ala Tyr Asp Leu Lys
            290                 295                 300

Thr Val Ser Glu Asp Met Ile Lys Gln Arg Ile Lys Arg Thr Gly Asp
305                 310                 315                 320

Gly Thr Asp Leu Trp Gly His Glu Gln Asn Cys Asp Glu Val Trp Asp
            325                 330                 335

Val Lys Asp Lys Ser Ser
            340

<210> SEQ ID NO 35
<211> LENGTH: 363
<212> TYPE: PRT
<213> ORGANISM: artificial
<220> FEATURE:
<223> OTHER INFORMATION: Agrotis segetum desaturase with Candida
      albicans OLE1 leader sequence encoded by SEQ ID NO: 8

<400> SEQUENCE: 35

Met Thr Thr Val Glu Gln Leu Glu Thr Val Asp Ile Thr Lys Leu Asn
1               5                   10                  15

Ala Ile Ala Ala Gly Thr Asn Lys Lys Val Pro Met Ala Gln Gly Val
            20                  25                  30

Gln Thr Thr Thr Ile Leu Arg Glu Glu Glu Pro Ser Leu Thr Phe Val
            35                  40                  45

Val Pro Gln Glu Pro Arg Lys Tyr Gln Ile Val Tyr Pro Asn Leu Ile
        50                  55                  60

Thr Phe Gly Tyr Trp His Ile Ala Gly Leu Tyr Gly Leu Tyr Leu Cys
65                  70                  75                  80

Phe Thr Ser Ala Lys Trp Gln Thr Ile Leu Phe Ser Phe Met Leu Val
            85                  90                  95

Val Leu Ala Glu Leu Gly Ile Thr Ala Gly Ala His Arg Leu Trp Ala
            100                 105                 110

His Lys Thr Tyr Lys Ala Lys Leu Pro Leu Gln Ile Ile Leu Met Ile
            115                 120                 125

Leu Asn Ser Ile Ala Phe Gln Asn Ser Ala Ile Asp Trp Val Arg Asp
130                 135                 140

His Arg Leu His His Lys Tyr Ser Asp Thr Asp Ala Asp Pro His Asn
145                 150                 155                 160

Ala Thr Arg Gly Phe Phe Tyr Ser His Val Gly Trp Leu Leu Val Arg
            165                 170                 175

```
Lys His Pro Glu Val Lys Arg Arg Gly Lys Glu Leu Asp Met Ser Asp
            180                 185                 190

Ile Tyr Asn Asn Pro Val Leu Arg Phe Gln Lys Lys Tyr Ala Ile Pro
            195                 200                 205

Phe Ile Gly Ala Met Cys Phe Gly Leu Pro Thr Phe Ile Pro Val Tyr
            210                 215                 220

Phe Trp Gly Glu Thr Trp Ser Asn Ala Trp His Ile Thr Met Leu Arg
225                 230                 235                 240

Tyr Ile Leu Asn Leu Asn Ile Thr Phe Leu Val Asn Ser Ala Ala His
                245                 250                 255

Ile Trp Gly Tyr Lys Pro Tyr Asp Ile Lys Ile Leu Pro Ala Gln Asn
            260                 265                 270

Ile Ala Val Ser Ile Val Thr Gly Gly Glu Val Ser Ile Thr Thr Thr
            275                 280                 285

Thr Phe Phe Pro Trp Asp Tyr Arg Ala Ala Glu Leu Gly Asn Asn Tyr
            290                 295                 300

Leu Asn Leu Thr Thr Lys Phe Ile Asp Phe Phe Ala Trp Ile Gly Trp
305                 310                 315                 320

Ala Tyr Asp Leu Lys Thr Val Ser Ser Asp Val Ile Lys Ser Lys Ala
                325                 330                 335

Glu Arg Thr Gly Asp Gly Thr Asn Leu Trp Gly Leu Glu Asp Lys Gly
            340                 345                 350

Glu Glu Asp Phe Leu Lys Ile Trp Lys Asp Asn
            355                 360

<210> SEQ ID NO 36
<211> LENGTH: 361
<212> TYPE: PRT
<213> ORGANISM: Drosophila melanogaster

<400> SEQUENCE: 36

Met Ala Pro Tyr Ser Arg Ile Tyr His Gln Asp Lys Ser Arg Glu
1               5                   10                  15

Thr Gly Val Leu Phe Glu Asp Asp Ala Gln Thr Val Asp Ser Asp Leu
            20                  25                  30

Thr Thr Asp Arg Phe Gln Leu Lys Arg Ala Glu Lys Arg Arg Leu Pro
            35                  40                  45

Leu Val Trp Arg Asn Ile Ile Leu Phe Ala Leu Val His Leu Ala Ala
            50                  55                  60

Leu Tyr Gly Leu His Ser Ile Phe Thr Arg Ala Lys Leu Ala Thr Thr
65                  70                  75                  80

Leu Phe Ala Ala Gly Leu Tyr Ile Ile Gly Met Leu Gly Val Thr Ala
                85                  90                  95

Gly Ala His Arg Leu Trp Ala His Arg Thr Tyr Lys Ala Lys Trp Pro
            100                 105                 110

Leu Arg Leu Leu Leu Val Ile Phe Asn Thr Ile Ala Phe Gln Asp Ala
            115                 120                 125

Val Tyr His Trp Ala Arg Asp His Arg Val His His Lys Tyr Ser Glu
            130                 135                 140

Thr Asp Ala Asp Pro His Asn Ala Thr Arg Gly Phe Phe Phe Ser His
145                 150                 155                 160

Val Gly Trp Leu Leu Cys Lys Lys His Pro Asp Ile Lys Glu Lys Gly
                165                 170                 175

Arg Gly Leu Asp Leu Ser Asp Leu Arg Ala Asp Pro Ile Leu Met Phe
            180                 185                 190
```

Gln Arg Lys His Tyr Tyr Ile Leu Met Pro Leu Ala Cys Phe Val Leu
             195                 200                 205

Pro Thr Val Ile Pro Met Val Tyr Trp Asn Glu Thr Leu Ala Ser Ser
    210                 215                 220

Trp Phe Val Ala Thr Met Phe Arg Trp Cys Phe Gln Leu Asn Met Thr
225                 230                 235                 240

Trp Leu Val Asn Ser Ala Ala His Lys Phe Gly Asn Arg Pro Tyr Asp
             245                 250                 255

Lys Thr Met Asn Pro Thr Gln Asn Ala Phe Val Ser Ala Phe Thr Phe
             260                 265                 270

Gly Glu Gly Trp His Asn Tyr His His Ala Phe Pro Trp Asp Tyr Lys
             275                 280                 285

Thr Ala Glu Trp Gly Cys Tyr Ser Leu Asn Ile Thr Thr Ala Phe Ile
    290                 295                 300

Asp Leu Phe Ala Lys Ile Gly Trp Ala Tyr Asp Leu Lys Thr Val Ala
305                 310                 315                 320

Pro Asp Val Ile Gln Arg Arg Val Leu Arg Thr Gly Asp Gly Ser His
             325                 330                 335

Glu Leu Trp Gly Trp Gly Asp Lys Asp Leu Thr Ala Gly Asp Ala Arg
             340                 345                 350

Asn Val Leu Leu Val Asp Lys Ser Arg
             355                 360

<210> SEQ ID NO 37
<211> LENGTH: 359
<212> TYPE: PRT
<213> ORGANISM: Lampronia capitella

<400> SEQUENCE: 37

Met Pro Pro Tyr Pro Glu Glu Val Asp Thr Asn His Ile Phe Glu Glu
1               5                   10                  15

Asp Ile Ser His Glu Glu Ser Lys Pro Ala Leu Lys Pro Leu Val Ala
             20                  25                  30

Pro Gln Ala Asp Asn Arg Lys Pro Glu Ile Val Pro Leu Asn Leu Ile
         35                  40                  45

Thr Phe Gly Tyr Gly His Leu Ala Ala Ile Tyr Gly Ile Tyr Leu Cys
    50                  55                  60

Phe Thr Ser Ala Lys Trp Ala Thr Ile Val Phe Ala Phe Val Leu Tyr
65              70                  75                  80

Ile Cys Ala Glu Leu Gly Ile Thr Ala Gly Ala His Arg Leu Trp Ser
             85                  90                  95

His Arg Ser Tyr Lys Ala Lys Leu Pro Leu Arg Leu Ile Leu Leu Leu
            100                 105                 110

Phe Asn Thr Leu Ala Phe Gln Asn Thr Ala Ile Asp Trp Val Arg Asp
        115                 120                 125

His Arg Met His His Lys Tyr Ser Asp Thr Asp Ala Asp Pro His Asn
    130                 135                 140

Ala Thr Arg Gly Phe Phe Phe Ser His Val Gly Trp Leu Leu Thr Arg
145                 150                 155                 160

Lys His Pro Glu Val Lys Arg Arg Gly Lys Asp Ile Asp Met Met Asp
             165                 170                 175

Ile Tyr Asn Asp Ser Leu Leu Lys Phe Gln Lys Lys Tyr Ala Ile Pro
         180                 185                 190

Phe Val Gly Leu Val Cys Phe Val Ile Pro Thr Leu Met Pro Met Tyr

```
                195                 200                 205
Phe Trp Asn Glu Thr Leu Asn Asn Ser Trp His Ile Ala Thr Met Leu
210                 215                 220

Arg Tyr Ile Val Asn Leu Asn Met Thr Phe Leu Val Asn Ser Ala Ala
225                 230                 235                 240

His Ile Trp Gly Tyr Lys Pro Tyr Asp Lys Ser Ile Lys Pro Val Gln
                245                 250                 255

Asn Ile Thr Val Ser Ile Leu Ile Leu Gly Glu Gly Phe His Asn Tyr
                260                 265                 270

His His Val Phe Pro Trp Asp Tyr Arg Thr Ser Glu Leu Gly Asn Asp
                275                 280                 285

Phe Leu Asn Phe Thr Thr Leu Phe Ile Asn Leu Phe Ala Lys Ile Gly
290                 295                 300

Trp Ala Tyr Asp Leu Lys Thr Ala Ser Asp Lys Val Val Ala Ala Arg
305                 310                 315                 320

Arg Lys Arg Thr Gly Asp Gly Thr Asn Leu Trp Gly Trp Glu Asp Lys
                325                 330                 335

Ser Leu Asn Glu Glu Glu Arg Gln Ala Ala Thr Val Leu Tyr Pro Asn
                340                 345                 350

Lys Tyr Leu Asn Leu Lys Asp
                355

<210> SEQ ID NO 38
<211> LENGTH: 352
<212> TYPE: PRT
<213> ORGANISM: Cydia pomonella

<400> SEQUENCE: 38

Met Ala Pro Asn Val Thr Asp Val Asn Gly Val Leu Phe Glu Ser Asp
1               5                   10                  15

Ala Ala Thr Pro Asp Leu Ala Leu Ala Asn Ala Pro Val Gln Gln Ala
                20                  25                  30

Asp Asp Ser Pro Arg Ile Tyr Val Trp Arg Asn Ile Ile Leu Phe Ala
                35                  40                  45

Tyr Leu His Ile Ala Ala Leu Tyr Gly Gly Tyr Leu Phe Leu Val Ser
50                  55                  60

Ala Lys Trp Gln Thr Asp Ile Phe Ala Tyr Phe Leu Tyr Val Ala Ser
65                  70                  75                  80

Gly Leu Gly Ile Thr Ala Gly Ala His Arg Leu Trp Ala His Lys Ser
                85                  90                  95

Tyr Lys Ala Lys Trp Pro Leu Arg Leu Ile Leu Val Ile Phe Asn Thr
                100                 105                 110

Ile Ala Phe Gln Asp Ser Ala Ile Asp Trp Ala Arg Asp His Arg Met
                115                 120                 125

His His Lys Tyr Ser Glu Thr Asp Ala Asp Pro His Asn Ala Thr Arg
130                 135                 140

Gly Phe Phe Phe Ser His Ile Gly Trp Leu Leu Val Arg Lys His Pro
145                 150                 155                 160

Glu Leu Lys Arg Lys Gly Lys Gly Leu Asp Leu Ser Asp Leu Tyr Ala
                165                 170                 175

Asp Pro Ile Leu Arg Phe Gln Lys Lys Tyr Tyr Leu Ile Leu Met Pro
                180                 185                 190

Leu Ala Cys Phe Val Leu Pro Thr Val Ile Pro Val Tyr Leu Trp Asn
                195                 200                 205
```

Glu Thr Trp Thr Asn Ala Phe Phe Val Ala Ala Leu Phe Arg Tyr Ala
210                 215                 220

Phe Ile Leu Asn Val Thr Trp Leu Val Asn Ser Ala Ala His Lys Trp
225                 230                 235                 240

Gly Asp Lys Pro Tyr Asp Lys Ser Ile Lys Pro Ser Glu Asn Ile Ser
                245                 250                 255

Val Ser Leu Phe Ala Phe Gly Glu Gly Phe His Asn Tyr His His Thr
            260                 265                 270

Phe Pro Trp Asp Tyr Lys Thr Ala Glu Leu Ser Ser Asn Arg Leu Asn
                275                 280                 285

Phe Thr Thr Lys Phe Ile Asn Phe Phe Ala Lys Ile Gly Trp Ala Tyr
290                 295                 300

Asp Met Lys Thr Val Ser Asp Glu Ile Ile Gln Lys Arg Val Asn Arg
305                 310                 315                 320

Thr Gly Asp Gly Ser His His Leu Trp Gly Trp Asp Lys Asp His
                325                 330                 335

Ser Lys Glu Glu Val Asn Ala Ala Val Arg Ile Asn Pro Lys Asp Asp
                340                 345                 350

<210> SEQ ID NO 39
<211> LENGTH: 975
<212> TYPE: DNA
<213> ORGANISM: artificial
<220> FEATURE:
<223> OTHER INFORMATION: Sesamia inferens Z11 desaturase codon optimized

<400> SEQUENCE: 39

```
atgctgtctc aggaggagcc aaccgataca agcctggtgc aagggcagc acctagaaag      60
taccagatcg tgtatcccaa tctgatcacc ttcggctact ggcacctggc agggctgtac    120
ggcctgtatc tgtgctttac atccgccaag tggaccacaa tcctgttcag cttcatcctg    180
tgcgtgatcg ccgagatcgg agtgaccgca ggagcacaca ggctgtgggc ccacaagaca    240
tataaggcca acctgcccct gcagatcctg ctgatggtca tgaattccat cgccttccag    300
aactctgcca tcgattgggt gcgggaccac agactgcacc acaagtactc tgacaccgat    360
gccgaccctc acaatgccag cagaggcttc ttttattccc acgtgggctg gctgctggtg    420
aagaagcacc cagaggtgaa gaagaggggc aaggagctgg atatgtctga catctacagc    480
aaccccgtgc tgcgcttcca gaagcagtat gccatcccct tcatcggcgc cgtgtgctt    540
atcctgccaa ccgtgatccc cgtgtactgt ggggcgaga catggacaaa tgcctggcac    600
atcacaatgc tgaggtatat caccaatctg aacgtgacat ttctggtgaa cagcgccgcc    660
cacatctggg gctacaagcc ttatgatgag aatatcctgc agcccagaa catcgccgtg    720
tccatcgcaa cctgcggaga gggcttccac aattaccacc acgtgtttcc ttgggattat    780
cgggccgccg agctgggcaa caataacctg aacctgacca caaagtttat cgacttcttt    840
gcctggctgg gctgggccta cgatctgaag acagtgagct ccgacatgat caagctgagg    900
gcaaagagga ccggcgacgg aacaaatctg tggggcgagc acaacgatga gctgaaggag    960
ggcaaggagg actga                                                    975
```

<210> SEQ ID NO 40
<211> LENGTH: 326
<212> TYPE: PRT
<213> ORGANISM: Amyelois transitella

<400> SEQUENCE: 40

Met Val Pro Asn Lys Gly Ser Ser Asp Val Leu Ser Glu His Ser Glu
1               5                   10                  15

Pro Gln Phe Thr Lys Leu Ile Ala Pro Gln Ala Gly Pro Arg Lys Tyr
            20                  25                  30

Lys Ile Val Tyr Arg Asn Leu Leu Thr Phe Gly Tyr Trp His Leu Ser
            35                  40                  45

Ala Val Tyr Gly Leu Tyr Leu Cys Phe Thr Cys Ala Lys Trp Ala Thr
        50                  55                  60

Ile Leu Phe Ala Phe Phe Leu Tyr Val Ile Ala Glu Ile Gly Ile Thr
65                  70                  75                  80

Gly Gly Ala His Arg Leu Trp Ala His Arg Thr Tyr Lys Ala Lys Leu
                85                  90                  95

Pro Leu Glu Ile Leu Leu Leu Ile Met Asn Ser Ile Ala Phe Gln Asp
            100                 105                 110

Thr Ala Phe Thr Trp Ala Arg Asp His Arg Leu His His Lys Tyr Ser
            115                 120                 125

Asp Thr Asp Ala Asp Pro His Asn Ala Thr Arg Gly Phe Phe Tyr Ser
        130                 135                 140

His Val Gly Trp Leu Leu Val Lys Lys His Pro Glu Val Lys Ala Arg
145                 150                 155                 160

Gly Lys Tyr Leu Ser Leu Asp Asp Leu Lys Asn Asn Pro Leu Leu Lys
                165                 170                 175

Phe Gln Lys Lys Tyr Ala Ile Leu Val Ile Gly Thr Leu Cys Phe Leu
            180                 185                 190

Met Pro Thr Phe Val Pro Val Tyr Phe Trp Gly Glu Gly Ile Ser Thr
            195                 200                 205

Ala Trp Asn Ile Asn Leu Leu Arg Tyr Val Met Asn Leu Asn Met Thr
        210                 215                 220

Phe Leu Val Asn Ser Ala Ala His Ile Phe Gly Asn Lys Pro Tyr Asp
225                 230                 235                 240

Lys Ser Ile Ala Ser Val Gln Asn Ile Ser Val Ser Leu Ala Thr Phe
                245                 250                 255

Gly Glu Gly Phe His Asn Tyr His His Thr Tyr Pro Trp Asp Tyr Arg
            260                 265                 270

Ala Ala Glu Leu Gly Asn Asn Arg Leu Asn Met Thr Thr Ala Phe Ile
        275                 280                 285

Asp Phe Phe Ala Trp Ile Gly Trp Ala Tyr Asp Leu Lys Ser Val Pro
        290                 295                 300

Gln Glu Ala Ile Ala Lys Arg Cys Ala Lys Thr Gly Asp Gly Thr Asp
305                 310                 315                 320

Met Trp Gly Arg Lys Arg
                325

<210> SEQ ID NO 41
<211> LENGTH: 338
<212> TYPE: PRT
<213> ORGANISM: Spodoptera littoralis

<400> SEQUENCE: 41

Met Ala Gln Cys Val Gln Thr Thr Ile Leu Glu Gln Lys Glu Glu
1               5                   10                  15

Lys Thr Val Thr Leu Leu Val Pro Gln Ala Gly Lys Arg Lys Phe Glu
            20                  25                  30

Ile Val Tyr Phe Asn Ile Ile Thr Phe Ala Tyr Trp His Ile Ala Gly
            35                  40                  45

Leu Tyr Gly Leu Tyr Leu Cys Phe Thr Ser Thr Lys Trp Ala Thr Val
    50                  55                  60

Leu Phe Ser Phe Phe Leu Phe Val Val Ala Glu Val Gly Val Thr Ala
65                  70                  75                  80

Gly Ser His Arg Leu Trp Ser His Lys Thr Tyr Lys Ala Lys Leu Pro
                85                  90                  95

Leu Gln Ile Leu Leu Met Val Met Asn Ser Leu Ala Phe Gln Asn Thr
                100                 105                 110

Val Ile Asp Trp Val Arg Asp His Arg Leu His His Lys Tyr Ser Asp
                115                 120                 125

Thr Asp Ala Asp Pro His Asn Ala Ser Arg Gly Phe Phe Tyr Ser His
    130                 135                 140

Val Gly Trp Leu Leu Val Arg Lys His Pro Asp Val Lys Lys Arg Gly
145                 150                 155                 160

Lys Glu Ile Asp Ile Ser Asp Ile Tyr Asn Asn Pro Val Leu Arg Phe
                165                 170                 175

Gln Lys Lys Tyr Ala Ile Pro Phe Ile Gly Ala Val Cys Phe Val Leu
                180                 185                 190

Pro Thr Leu Ile Pro Val Tyr Gly Trp Gly Glu Thr Trp Thr Asn Ala
    195                 200                 205

Trp His Val Ala Met Leu Arg Tyr Ile Met Asn Leu Asn Val Thr Phe
    210                 215                 220

Leu Val Asn Ser Ala Ala His Ile Tyr Gly Lys Arg Pro Tyr Asp Lys
225                 230                 235                 240

Lys Ile Leu Pro Ser Gln Asn Ile Ala Val Ser Ile Ala Thr Phe Gly
                245                 250                 255

Glu Gly Phe His Asn Tyr His His Val Phe Pro Trp Asp Tyr Arg Ala
                260                 265                 270

Ala Glu Leu Gly Asn Asn Ser Leu Asn Phe Pro Thr Lys Phe Ile Asp
    275                 280                 285

Phe Phe Ala Trp Ile Gly Trp Ala Tyr Asp Leu Lys Thr Val Ser Lys
    290                 295                 300

Glu Met Ile Lys Gln Arg Ser Lys Arg Thr Gly Asp Gly Thr Asn Leu
305                 310                 315                 320

Trp Gly Leu Glu Asp Val Asp Thr Pro Glu Asp Leu Lys Asn Thr Lys
                325                 330                 335

Gly Glu

<210> SEQ ID NO 42
<211> LENGTH: 336
<212> TYPE: PRT
<213> ORGANISM: Agrotis segetum

<400> SEQUENCE: 42

Met Ala Gln Gly Val Gln Thr Thr Thr Ile Leu Arg Glu Glu Pro
1               5                   10                  15

Ser Leu Thr Phe Val Val Pro Gln Glu Pro Arg Lys Tyr Gln Ile Val
                20                  25                  30

Tyr Pro Asn Leu Ile Thr Phe Gly Tyr Trp His Ile Ala Gly Leu Tyr
                35                  40                  45

Gly Leu Tyr Leu Cys Phe Thr Ser Ala Lys Trp Gln Thr Ile Leu Phe
    50                  55                  60

Ser Phe Met Leu Val Val Leu Ala Glu Leu Gly Ile Thr Ala Gly Ala
65                  70                  75                  80

```
His Arg Leu Trp Ala His Lys Thr Tyr Lys Ala Lys Leu Pro Leu Gln
                85                  90                  95

Ile Ile Leu Met Ile Leu Asn Ser Ile Ala Phe Gln Asn Ser Ala Ile
            100                 105                 110

Asp Trp Val Arg Asp His Arg Leu His His Lys Tyr Ser Asp Thr Asp
        115                 120                 125

Ala Asp Pro His Asn Ala Thr Arg Gly Phe Phe Tyr Ser His Val Gly
    130                 135                 140

Trp Leu Leu Val Arg Lys His Pro Glu Val Lys Arg Gly Lys Glu
145                 150                 155                 160

Leu Asp Met Ser Asp Ile Tyr Asn Asn Pro Val Leu Arg Phe Gln Lys
                165                 170                 175

Lys Tyr Ala Ile Pro Phe Ile Gly Ala Met Cys Phe Gly Leu Pro Thr
            180                 185                 190

Phe Ile Pro Val Tyr Phe Trp Gly Glu Thr Trp Ser Asn Ala Trp His
        195                 200                 205

Ile Thr Met Leu Arg Tyr Ile Leu Asn Leu Asn Ile Thr Phe Leu Val
    210                 215                 220

Asn Ser Ala Ala His Ile Trp Gly Tyr Lys Pro Tyr Asp Ile Lys Ile
225                 230                 235                 240

Leu Pro Ala Gln Asn Ile Ala Val Ser Ile Val Thr Gly Gly Glu Val
                245                 250                 255

Ser Ile Thr Thr Thr Thr Phe Phe Pro Trp Asp Tyr Arg Ala Ala Glu
            260                 265                 270

Leu Gly Asn Asn Tyr Leu Asn Leu Thr Thr Lys Phe Ile Asp Phe Phe
        275                 280                 285

Ala Trp Ile Gly Trp Ala Tyr Asp Leu Lys Thr Val Ser Ser Asp Val
    290                 295                 300

Ile Lys Ser Lys Ala Glu Arg Thr Gly Asp Gly Thr Asn Leu Trp Gly
305                 310                 315                 320

Leu Glu Asp Lys Gly Glu Glu Asp Phe Leu Lys Ile Trp Lys Asp Asn
                325                 330                 335

<210> SEQ ID NO 43
<211> LENGTH: 349
<212> TYPE: PRT
<213> ORGANISM: Trichoplusia ni

<400> SEQUENCE: 43

Met Ala Val Met Ala Gln Thr Val Gln Glu Thr Ala Thr Val Leu Glu
1               5                   10                  15

Glu Glu Ala Arg Thr Val Thr Leu Val Ala Pro Lys Thr Thr Pro Arg
                20                  25                  30

Lys Tyr Lys Tyr Ile Tyr Thr Asn Phe Leu Thr Phe Ser Tyr Ala His
            35                  40                  45

Leu Ala Ala Leu Tyr Gly Leu Tyr Leu Cys Phe Thr Ser Ala Lys Trp
        50                  55                  60

Glu Thr Leu Leu Phe Ser Phe Val Leu Phe His Met Ser Asn Ile Gly
65                  70                  75                  80

Ile Thr Ala Gly Ala His Arg Leu Trp Thr His Lys Thr Phe Lys Ala
                85                  90                  95

Lys Leu Pro Leu Glu Ile Val Leu Met Ile Phe Asn Ser Leu Ala Phe
            100                 105                 110

Gln Asn Thr Ala Ile Thr Trp Ala Arg Glu His Arg Leu His His Lys
```

115                 120                 125
Tyr Ser Asp Thr Asp Ala Asp Pro His Asn Ala Ser Arg Gly Phe Phe
    130                 135                 140

Tyr Ser His Val Gly Trp Leu Leu Val Lys Lys His Pro Asp Val Leu
145                 150                 155                 160

Lys Tyr Gly Lys Thr Ile Asp Met Ser Asp Val Tyr Asn Asn Pro Val
                165                 170                 175

Leu Lys Phe Gln Lys Lys Tyr Ala Val Pro Leu Ile Gly Thr Val Cys
        180                 185                 190

Phe Ala Leu Pro Thr Leu Ile Pro Val Tyr Cys Trp Gly Glu Ser Trp
    195                 200                 205

Asn Asn Ala Trp His Ile Ala Leu Phe Arg Tyr Ile Phe Asn Leu Asn
    210                 215                 220

Val Thr Phe Leu Val Asn Ser Ala Ala His Ile Trp Gly Asn Lys Pro
225                 230                 235                 240

Tyr Asp Lys Ser Ile Leu Pro Ala Gln Asn Leu Leu Val Ser Phe Leu
                245                 250                 255

Ala Ser Gly Glu Gly Phe His Asn Tyr His His Val Phe Pro Trp Asp
        260                 265                 270

Tyr Arg Thr Ala Glu Leu Gly Asn Asn Phe Leu Asn Leu Thr Thr Leu
    275                 280                 285

Phe Ile Asp Phe Cys Ala Trp Phe Gly Trp Ala Tyr Asp Leu Lys Ser
    290                 295                 300

Val Ser Glu Asp Ile Ile Lys Gln Arg Ala Lys Arg Thr Gly Asp Gly
305                 310                 315                 320

Ser Ser Gly Val Ile Trp Gly Trp Asp Asp Lys Asp Met Asp Arg Asp
                325                 330                 335

Ile Lys Ser Lys Ala Asn Ile Phe Tyr Ala Lys Lys Glu
        340                 345

<210> SEQ ID NO 44
<211> LENGTH: 981
<212> TYPE: DNA
<213> ORGANISM: artificial
<220> FEATURE:
<223> OTHER INFORMATION: Amyelois transitella desaturase from DTU WO
      2016/207339_SEQ ID NO: 1 codon optimized

<400> SEQUENCE: 44
atggttccaa acaagggttc ctctgatgtt ttgtctgaac attctgaacc acaattcacc      60
aagttgattg ctccacaagc tggtccaaga agtacaaaa tcgtttacag aaacttgttg     120
accttcggtt actggcattt gtctgctgtt tatggtttgt acttgtgttt cacttgtgct     180
aagtgggcta ctattttgtt cgctttcttc ttgtacgtta tcgccgaaat tggtattact     240
ggtggtgctc atagattatg ggctcataga acttacaaag ccaagttgcc attggaaatc     300 tgttgttga tcatgaactc cattgccttc aagatactg cttttacttg gctagagat       360 catagattgc atcacaagta ctctgatact gatgctgatc cacataatgc tactagaggt     420
ttcttctact ctcatgttgg ttggttgttg gttaagaaac acccagaagt taaggctaga     480
ggtaagtact gtctttgga tgacttgaag acaaccctt tgttgaagtt ccaaaagaag      540
tacgccattt tggtcattgg actttgtgc ttttgatgc aactttcgt tccagtttac      600 ttttggggtg aagtattc tactgcctgg aacattaact tgttaagata cgtcatgaac     660
ttgaacatga ccttttggt taactccgct gctcatattt ttggtaacaa gccatacgat    720

| | |
|---|---|
| aagtctatcg cctctgttca aaacatctct gtttctttgg ctactttcgg tgaaggtttc | 780 |
| cataactacc atcatactta tccatgggat tacagagctg ctgaatttgg taacaataga | 840 |
| ttgaatatga ccaccgcctt cattgatttc tttgcttgga ttggttgggc ctacgatttg | 900 |
| aaatctgttc cacaagaagc tattgctaag agatgtgcta aaactggtga tggtactgat | 960 |
| atgtggggta gaaagagatg a | 981 |

<210> SEQ ID NO 45
<211> LENGTH: 1470
<212> TYPE: DNA
<213> ORGANISM: artificial
<220> FEATURE:
<223> OTHER INFORMATION: Spodoptera littoralis desaturase from DTU WO
     2016/207339_SEQ ID NO: 40 codon optimized

<400> SEQUENCE: 45

| | |
|---|---|
| ggacactgac atggactgaa ggagtagaga atcggcccgt ggagttggcc ttcatttca | 60 |
| gtcttatctc tcggtgttat ggtagtcact tatatcggta ttaaaataag tgaataaggc | 120 |
| ttgtaaaaat ggcgcaatgt gtacaaacaa caacgatttt ggaacaaaaa aagagaaaa | 180 |
| cagtaacttt gctggtacct caagcgggaa agaggaagtt tgaaattgtg tattttaata | 240 |
| tcatcacctt cgcttactgg catatagctg gactatatgg cctttatttg tgcttcactt | 300 |
| caacaaaatg ggcgacagtt ttattctcat tctttctatt cgtcgtagca gaagtagggg | 360 |
| tcacggctgg ctcccacaga cttggtcgc ataaaactta caagcaaaa ctacctttac | 420 |
| aaattctgct aatggtgatg aattcccttg catttcaaaa cacagtcatt gattgggtga | 480 |
| gagaccatcg actccatcat aagtatagcg acactgatgc cgatccccat aatgcctccc | 540 |
| gaggatttt ctattcgcac gtcggttggc tgcttgtgag aaaacaccct gatgtcaaga | 600 |
| aacgaggaaa ggaaattgat atatctgata tttacaacaa tccggtactg aggttccaga | 660 |
| agaagtacgc aattcctttc atcggggcag tttgttcgt cttaccaaca ttgataccgg | 720 |
| tttacggttg gggagaaacc tggactaatg cctggcacgt cgccatgctg cggtacatta | 780 |
| tgaaccttaa cgtcaccttc ctggtcaaca gcgctgctca tatatatgga aagagacctt | 840 |
| atgacaagaa gatcctacca tctcaaaaca tagctgtgtc cattgcaacc tttggggaag | 900 |
| gttccataa ttatcatcat gtatttccat gggattatcg cgcagctgaa cttggaaata | 960 |
| acagtttgaa tttccctacg aaattattg atttctttgc gtggatcgga tgggcgtatg | 1020 |
| acctaaagac tgtttcgaaa gaaatgataa aacaaggtc aaaagaact ggtgatggaa | 1080 |
| ctaatctatg gggttagaa gatgtggata ccccggagga tttaaaaat acaaaaggcg | 1140 |
| aataggcaaa cccttaaact caaacagtga ggtttaatgt gatatttaga attagaatta | 1200 |
| atttatttga aattaaatga aggttttgga taactgtttt taataataaa aatagttttt | 1260 |
| cgattaaatt ccttagatta ttttaaagga aatgtataag gtactcgcgt ggttagcaac | 1320 |
| ccagcagtcc ctgtttatct gttttttatga atttattcta tgaatgtaga tgtcgcatga | 1380 |
| aattttaaaa tgttgcattt gtataatttt acttatgaat aaataaattt atttttaaaa | 1440 |
| aaaaaaaaaa aaaaaaaaaa aaaaaaaaaa | 1470 |

<210> SEQ ID NO 46
<211> LENGTH: 1011
<212> TYPE: DNA
<213> ORGANISM: artificial
<220> FEATURE:
<223> OTHER INFORMATION: Agrotis segetum desaturase from DTU WO
     2016/207339_SEQ ID NO: 42 codon optimized

<400> SEQUENCE: 46

```
atggctcaag gtgtccaaac aactacgata ttgagggagg aagagccgtc attgactttc      60
gtggtacctc aagaaccgag aaagtatcaa atcgtgtacc caaaccttat cacatttggg     120
tactggcata tagctggttt atacgggcta tatttgtgct ttacttcggc aaaatggcaa     180
acaattttat tcagtttcat gctcgttgtg ttagcagagt tgggaataac agccggcgct     240
cacaggttat gggcccacaa acatatataa gcgaagcttc ccttacaaat tatcctgatg     300
atactgaact ccattgcctt ccaaaattcc gccattgatt gggtgaggga ccaccgtctc     360
catcataagt acagtgacac tgatgcagac cctcacaatg ctactcgtgg tttcttctat     420
tctcatgttg gatggttgct cgtaagaaaa catccagaag tcaagagacg tggaaaggaa     480
cttgacatgt ctgatattta caacaatcca gtgctgagat ttcaaaagaa gtatgctata     540
cccttcatcg ggcaatgtg cttcggatta ccaactttta tccctgttta cttctgggga      600
gaaacctgga gtaatgcttg gcatatcacc atgcttcggt acatcctcaa cctaaacatt     660
actttcctgg tcaacagtgc tgctcatatc tggggataca aaccttatga catcaaaata     720
ttgcctgccc aaaatatagc agtttccata gtaaccggcg gcgaagtttc ataactacc      780
accacgtttt ttccttggga ttatcgtgca gcagaattgg ggaacaatta tcttaatttg     840
acgactaagt tcatagattt cttcgcttgg atcggatggg cttacgatct taagacggtg     900
tccagtgatg ttataaaaag taaggcgaaa gaactggtg atgggacgaa tctttggggt      960
ttagaagaca aaggtgaaga agatttttg aaaatctgga aagacaatta a                1011
```

<210> SEQ ID NO 47
<211> LENGTH: 1050
<212> TYPE: DNA
<213> ORGANISM: artificial
<220> FEATURE:
<223> OTHER INFORMATION: Trichoplusia ni desaturase from DTU WO
      2016/207339_SEQ ID NO: 44 codon optimized

<400> SEQUENCE: 47

```
atggctgtga tggctcaaac agtacaagaa acggctacag tgttggaaga ggaagctcgc      60
acagtgactc ttgtggctcc aaagacaacg ccaaggaaat ataaatatat atacaccaac     120
tttcttacat tttcatatgc gcatttagct gcattatacg gactttatttt gtgcttcacc    180
tctgcgaaat gggaaacatt gctattctct ttcgtactct tccacatgtc aaatataggc     240
atcaccgcag gggctcaccg actctggact cacaagactt tcaaagccaa attgcctttg     300
gaaattgtcc tcatgatatt caactcttta gcctttcaaa acacggctat acatgggct      360
agagaacatc ggctacatca caaatacagc gatactgatg ctgatcccca caatgcgtca     420
agagggttct tctactcgca tgttggctgg ctattagtaa aaaacatcc cgatgtcctg      480
aaatatggaa aaactataga catgtcggat gtatacaata atcctgtgtt aaaatttcag     540
aaaaagtacg cagtacccct taattggaaca gtttgttttg ctcttccaac tttgattcca    600
gtctactgtt ggggcgaatc gtggaacaac gcttggcaca tagccttatt tcgatacata     660
ttcaatctta acgtgacttt cctagtcaac agtgctgcgc atatctgggg gaataagcct     720
tatgataaaa gcatcttgcc cgctcaaaac ctgctggttt ccttcctagc aagtggagaa     780
ggcttccata attaccatca cgtctcttcca tggattaccc gcacagcaga attagggaat    840
aacttcctga atttgacgac gctgttcatt gattttgtg cctggtttgg atgggcttat      900
gacttgaagt ctgtatcaga ggatattata aaacagagag ctaaacgaac aggtgacggt    960
```

```
tcttcagggg tcatttgggg atgggacgac aaagacatgg accgcgatat aaaatctaaa    1020
gctaacattt tttatgctaa aaaggaatga                                      1050
```